United States Patent
Hung et al.

(10) Patent No.: US 12,297,431 B2
(45) Date of Patent: **\*May 13, 2025**

(54) MODULATION OF HUNTINGTIN EXPRESSION

(71) Applicant: Ionis Pharmaceuticals, Inc., Carlsbad, CA (US)

(72) Inventors: Gene Hung, Carlsbad, CA (US); C. Frank Bennet, Carlsbad, CA (US); Susan M. Freier, San Diego, CA (US); Holly Kordasiewicz, San Diego, CA (US); Lisa Stanek, Cambridge, MA (US); Don W. Cleveland, Del Mar, CA (US); Seng H. Cheng, Natick, MA (US); Lamya Shihabuddin, Brighton, MA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/813,249

(22) Filed: Jul. 18, 2022

(65) Prior Publication Data

US 2023/0023015 A1    Jan. 26, 2023

Related U.S. Application Data

(60) Division of application No. 17/068,185, filed on Oct. 12, 2020, now Pat. No. 11,421,231, which is a division of application No. 16/801,431, filed on Feb. 26, 2020, now Pat. No. 10,837,016, which is a division of application No. 16/270,983, filed on Feb. 8, 2019, now Pat. No. 10,619,158, which is a continuation of application No. 15/596,249, filed on May 16, 2017, now Pat. No. 10,202,603, which is a continuation of application No. 15/005,712, filed on Jan. 25, 2016, now Pat. No. 9,683,236, which is a continuation of application No. 14/528,656, filed on Oct. 30, 2014, now Pat. No. 9,273,315, which is a continuation of application No. 13/395,188, filed as application No. PCT/US2010/048532 on Sep. 10, 2010, now Pat. No. 8,906,873.

(60) Provisional application No. 61/241,853, filed on Sep. 11, 2009.

(51) Int. Cl.
 *C07H 21/04* (2006.01)
 *C12N 15/113* (2010.01)

(52) U.S. Cl.
 CPC ........ *C12N 15/113* (2013.01); *C12N 2310/11* (2013.01); *C12N 2310/113* (2013.01); *C12N 2310/315* (2013.01); *C12N 2310/321* (2013.01); *C12N 2310/3341* (2013.01); *C12N 2310/341* (2013.01); *C12N 2310/345* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 5,595,756 | A | 1/1997 | Bally et al. |
| 5,686,288 | A | 11/1997 | MacDonald et al. |
| 5,700,922 | A | 12/1997 | Cook |
| 5,801,154 | A | 9/1998 | Baracchini et al. |
| 5,998,148 | A | 12/1999 | Bennett et al. |
| 6,043,060 | A | 3/2000 | Imanishi |
| 6,147,200 | A | 11/2000 | Manoharan et al. |
| 6,582,908 | B2 | 6/2003 | Fodor et al. |
| 6,670,461 | B1 | 12/2003 | Wengel et al. |
| 7,320,965 | B2 | 1/2008 | Sah et al. |
| 7,374,927 | B2 | 5/2008 | Palma et al. |
| 7,951,934 | B2 * | 5/2011 | Freier .................... A61P 25/00 435/375 |
| 8,658,608 | B2 | 2/2014 | Glazer |
| 8,906,873 | B2 | 12/2014 | Hung et al. |
| 9,273,315 | B2 | 3/2016 | Hung et al. |
| 10,202,603 | B2 | 2/2019 | Hung et al. |
| 10,619,158 | B2 | 4/2020 | Hung et al. |
| 10,837,016 | B2 | 11/2020 | Hung et al. |
| 11,421,231 | B2 | 8/2022 | Hung et al. |
| 2001/0053519 | A1 | 12/2001 | Fodor et al. |
| 2003/0109476 | A1 | 6/2003 | Kmiec |
| 2003/0144242 | A1 | 7/2003 | Ward et al. |
| 2003/0228597 | A1 | 12/2003 | Cowsert et al. |
| 2003/0232443 | A1 | 12/2003 | Bennett |

(Continued)

FOREIGN PATENT DOCUMENTS

| | | |
|---|---|---|
| CA | 2526893 | 11/2004 |
| JP | 2009-513144 | 4/2009 |

(Continued)

OTHER PUBLICATIONS

Van Roon-Mom et al. ("Dose-dependent lowering of mutant Huntingtin using antisense oligonucleotides in Huntington disease patients." nucleic acid therapeutics 28.2 (2018): 59-62).*

(Continued)

*Primary Examiner* — Kimberly Chong

(74) *Attorney, Agent, or Firm* — McDonnell Boehnen Hulbert & Berghoff LLP

(57) ABSTRACT

Provided herein are methods, compounds, and compositions for reducing expression of huntingtin mRNA and protein in an animal. Such methods, compounds, and compositions are useful to treat, prevent, delay, or ameliorate Huntington's disease, or a symptom thereof.

14 Claims, 10 Drawing Sheets

Specification includes a Sequence Listing.

(56) References Cited

U.S. PATENT DOCUMENTS

| | | |
|---|---|---|
| 2004/0092465 A1 | 5/2004 | Dobie |
| 2004/0096880 A1 | 5/2004 | Kmiec |
| 2004/0137471 A1 | 7/2004 | Vickers et al. |
| 2004/0146902 A1 | 7/2004 | Ecker et al. |
| 2005/0042646 A1 | 2/2005 | Davidson |
| 2005/0096284 A1 | 5/2005 | McSwiggen |
| 2005/0101013 A1 | 5/2005 | Freier et al. |
| 2005/0191638 A1 | 9/2005 | McSwiggen |
| 2005/0245475 A1 | 11/2005 | Khvorova et al. |
| 2005/0255086 A1 | 11/2005 | Davidson |
| 2005/0255487 A1 | 11/2005 | Khvorova et al. |
| 2006/0051769 A1 | 3/2006 | Barts |
| 2007/0031844 A1 | 2/2007 | Khvorova et al. |
| 2007/0099860 A1 | 5/2007 | Sah |
| 2007/0249551 A1* | 10/2007 | Teng ............... A61K 9/107 514/44 A |
| 2007/0299027 A1 | 12/2007 | Hung et al. |
| 2008/0015158 A1 | 1/2008 | Ichiro |
| 2008/0039415 A1 | 2/2008 | Stewart et al. |
| 2008/0039418 A1 | 2/2008 | Freier |
| 2008/0075720 A1 | 3/2008 | Holers |
| 2008/0274989 A1 | 11/2008 | Davidson et al. |
| 2009/0092981 A1 | 4/2009 | Swayze et al. |
| 2009/0275133 A1 | 11/2009 | Crooke |
| 2010/0120665 A1 | 5/2010 | Kaleko |
| 2011/0207797 A1 | 8/2011 | Monia |
| 2016/0222389 A1 | 8/2016 | Grossman |

FOREIGN PATENT DOCUMENTS

| | | |
|---|---|---|
| JP | 2009-524431 | 7/2009 |
| RU | 2297833 | 4/2007 |
| WO | WO 1994/026764 | 11/1994 |
| WO | WO 1999/050409 | 10/1999 |
| WO | WO 2000/003720 | 1/2000 |
| WO | 2001030395 | 5/2001 |
| WO | WO 2001/079283 | 10/2001 |
| WO | WO 2003/013437 | 2/2003 |
| WO | WO 2003/009835 | 8/2003 |
| WO | WO 2003/064625 | 8/2003 |
| WO | WO 2004/044123 | 5/2004 |
| WO | WO 2004/048601 | 6/2004 |
| WO | WO 2004/101787 | 11/2004 |
| WO | WO 2004/013280 | 12/2004 |
| WO | WO 2005/027980 | 3/2005 |
| WO | WO 2005/045032 | 5/2005 |
| WO | WO 2005/083436 | 9/2005 |
| WO | WO 2005/105995 | 11/2005 |
| WO | WO 2005/116204 | 12/2005 |
| WO | WO 2006/128141 | 11/2006 |
| WO | WO 2007/022470 | 2/2007 |
| WO | WO 2007/051045 | 5/2007 |
| WO | WO 2007/120883 | 10/2007 |
| WO | WO 2007089584 | 11/2007 |
| WO | WO 2008/005562 | 1/2008 |
| WO | WO 2008/018795 | 2/2008 |
| WO | WO 2009/008725 | 1/2009 |
| WO | 2010111522 | 9/2010 |
| WO | 2011008982 | 1/2011 |
| WO | 2011097388 | 8/2011 |
| WO | 2017081223 | 5/2017 |

OTHER PUBLICATIONS

Rook et al. ("Antisense oligonucleotide therapy: from design to the Huntington disease clinic." BioDrugs 36.2 (2022): 105-119).*

Anderson et al., "An Overview of Psychiatric Symptoms in Huntington's Disease" Current Psychiatry Reports (2001) 3:379-388.

Bennett et al., "Antisense oligonucleoties as a tool for gene functionalization and target validation" Biochimica Biophysica Acta (1999) 1489:19-30.

Boado et al., "Antisense-mediated down-regulation of the human huntington gene" Journal of Pharmacology and Experimental Therapeutics (2000) 295:239-243.

Boffa et al., "Isolation of active genes containing CAG repeats by DNA strands invasion by a peptide nucleic acid" PNAS (1995) 92:1901-5.

Borovecki et al., "Genome-wide expression profiling of human blood reveals biomarkers for Huntington's disease" Proc. Natl. Acad. Sci. USA (2005) 102:11023-11028.

Branch et al., "A good antisense molecule is hard to find," TIBS (1998) 23:45-50.

Caplen et al., "Rescue ofpolyglutamine-mediated cytotoxicity by double-stranded RNA-mediated RNA interference" Human Molecular Genetics (2002) II (2): 175-184.

Chang et al., "Structural Analysis of Complementary DNA and Amino Acid Sequences of Human and Rat Androgen Receptors" PNAS (1988) 85:7211-7215.

Chin "On the Preparation and Utilization oflsolated and Purififed Oligonucleotides." Document purportedly located on a CD-ROM and contributed to the public collection of the Katherine R. Everett Law Library of the University ofNorth Carolina on Mar. 14, 2002.

Crooke et al., "Basic Principles of Antisense Therapeutics" Antisense Research and Application (1998) Chapter 1:1-50.

Davidson et al., "Molecular medicine for the brain: silencing of disease genes with RNA interference" Lancet Neural. (2004) 3:145-149.

Diaz-Hernandez et al., "Full Motor Recovery Despite Striatal Neuron Loss and Formation of Irreversible Amyloid-Like Inclusions in a Conditional Mouse Model of Huntington's Disease" J Neurosci(2005) 25:9773-9781.

Drouet et al., "Sustained effects of nonallele-specific Huntingtin silencing" Ann Neural. (2009) 65(3): 276-285.

Eder et al., "Inhibition of LNCaP Prostate Cancer Cells by Means of Androgen Receptor Antisense Oligonucleotides" Cancer Gene Therapy (2000) 7(7):997-1007.

Gagnon et al., "HD Therapeutics—CHDI Fifth Annual Conference" IDrugs 13( 4): 219-223 (2010).

Gonzalez-Alegre et al., "Technology Insight: therapeutic RNA interference—how far from the neurology clinic?" Nature Clinical Practice 3:394-404.

Gryaznov et al., "Oligodeoxyribonucleotide N3'->P5' Phosphoramidates Synthesis and Hybridization Properties" JAm. Chern. Soc. (1994) 116:3143-3144.

Haque et al., "Antisense gene therapy for neurodegenerative disease" Experimental Neurology (1997) 144:139-146.

Harper et al., "Ten years ofpresymptomatic testing for Huntington's disease: the experience of the UK Huntington's Disease Prediction Consortium" J. Med. Genet. 37:567-571.

Harper et al., RNA interference improves motor and neuropathological abnormalities in a Huntington'sdisease mouse model PNAS (2005) I 02:5820-5825.

Hasholt et al., "Antisense downregulation of mutant huntingtin in a cell model" Journal of Gene Medicine (2003) 5:528-538.

Hersch et al., "Translating Therapies for Huntington's Disease from Genetic Animal Models to Clinical Trials" NeuroRX (2004) 1:298-306.

Hersch et al., "Neuroprotection for Huntington's disease: Ready, set, slow" Neurotherapeutics (2008) 5(2):226-236.

Liu et al., "Specific inhibition of Huntington's disease gene expression by siRNAs in cultures cells" Proceedings of the Japan Academy. Series B, Physical and Biological Sciences (2003) 79B:293-298.

MacDonald et al., "A novel gene containing a trinucleotide repeat that is expanded and unstable on Huntington's disease chromosomes" Cell (1993) 72(6):971-983.

Machida et al., "rAAV-mediated shRNA ameliorated neuropathology in Huntington disease model mouse" Biochem. Biophys. Res. Commun. (2006) 343:190-197.

MacMillan et al., "Molecular analysis and clinical correlations oftheHuntington's disease mutation" Lancet (1993) 342:954-958.

Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.

(56) References Cited

OTHER PUBLICATIONS

Martin et al., "38. Ein neuer Zugang zu 2'-0-Alkylribonucleosiden und Eigenschaften deren Oligonucleotide" Helv. Chim. Acta (1995) 78:486-504.

Nellemann et al., "Inhibition of Huntington synthesis by antisense oligonucleotides" Molecular and Cellular Neurosciences (2000) 16:313-323.

New England BioLabs, Inc. Catalogue (1998): 121, 284.

Nguyen et al., "Clioquinol down-regulates mutant huntingtin expression in vitro and mitigates pathology in a Huntington's disease mouse model" PNAS (2005) 102:11840-11845.

Nikiforov et al., "The Use of Phosphorothioate Primers and Exonuclease Hydrolysis for the Preparation of Single-stranded PCR Products and their Detection by Solid-phase Hybridization" PCR Methods and Applications (1994) 3:285-291.

Pakula et al., "Genetic analysis of protein stability and function" Annual review of genetics 23: 289-310 (1989).

Reynolds et al., "Rational siRNA design for RNA interference" Nature Biotechnology (2004) 22:326-330.

Sanghvi et al., "Heterocyclic Base Modifications in Nucleic Acids and Their Applications in Antisense Oligonucleotides" Antisense Research and Applications (1993) pp. 273-288.

Sewell et al., "Phase I Trial of ISIS 104838, a 2'-Methoxyethyl Modified Antisense Oligonucleotide Targeting Tumor Necrosis Factor-Alpha" The Journal of Pharmacology and Experimental Therapeutics (2002) 303(3):1334-1343.

Sheehan et al., "Biochemical properties of phosphonoacetate and thiophosphonoacetate oligodeoxyribonucleotides" Nucleic Acids Research (2003) 31 :4109-4118.

Uhlmann et al., "Antisense oligonucleotides: a new therapeutic principle" Chemical Reviews (1990) 90:543-584.

Vickers et al., "Efficient Reduction of Target RNAs by Small Interfering RNA and Rnase H-dependent Antisense Agents. A comparative analysis." J Biol. Chem. (2003) 278:7108-7118.

Wang et al., "Clinico-pathological rescue of a model mouse of Huntington's disease by siRNA" Neurosci. Res. (2005) 53:241-249.

Woolf et al., "Specificity of antisense oligonucleotides in vivo" Proc. Natl. Acad. Sci. USA (1992) 89:7305-7309.

Yen et al., "Sequence-specific cleavage of Huntingtin mRNA by catalytic DNA" Annals of Neurology (1999) 46(3):366-373.

International Search Report for Application No. PCT/US2007/002215 dated Nov. 16, 2007.

International Search Report for Application No. PCT/US2007/002171 dated Sep. 26, 2007.

International Search Report for Application # PCT /US2010/048532 dated Jan. 26, 2011.

Karaki S. et al., "Antisense Oligonucleotides, A Novel Developing Targeting Therapy" Antisense Therapy, pages (Jan. 19, 2019).

\* cited by examiner

MODULATION OF HUNTINGTIN EXPRESSION

SEQUENCE LISTING

The present application is being filed along with a Sequence Listing in electronic format. The Sequence Listing is provided as a file entitled BIOL0113USC3SEQ_ST25.txt created May 15, 2017, which is 488 Kb in size. The information in the electronic format of the sequence listing is incorporated herein by reference in its entirety.

FIELD OF THE INVENTION

Provided herein are methods, compounds, and compositions for reducing expression of huntingtin mRNA and protein in an animal. Such methods, compounds, and compositions are useful, for example, to treat, prevent, or ameliorate Huntington's disease.

BACKGROUND

Huntington's disease (HD) is a devastating autosomal dominant, neurodegenerative disease caused by a CAG trinucleotide repeat expansion encoding an abnormally long polyglutamine (PolyQ) tract in the huntingtin protein. The Huntington disease gene was first mapped in 1993 (The Huntington's Disease Collaborative Research Group. Cell. 1993, 72:971-83), consisting of a gene, IT15, which contained a polymorphic trinucleotide repeat that is expanded and unstable on HD chromosomes. Although CAG repeats in the normal size range are usually inherited as Mendelian alleles, expanded HD repeats are unstable through meiotic transmission and are found to be expanded beyond the normal size range (6-34 repeat units) in HD patients.

Both normal and variant huntingtin protein are localized chiefly in the cytoplasm of neurons (DiFiglia et al., Neuron 1995, 14:1075-81). As a result of excessive polyglutamine length, huntingtin protein forms aggregates in the cytoplasm and nucleus of CNS neurons (Davies et al., Cell 1997, 90:537-548). Both transgenic animals and genetically modified cell lines have been used to investigate the effects of expanded polyQ repeats on the localization and processing of huntingtin. However, it is still unclear whether the formation of aggregates per se is the essential cytotoxic step or a consequence of cellular dysfunction.

HD is characterized by progressive chorea, psychiatric changes and intellectual decline. This dominant disorder affects males and females equally, and occurs in all races (Gusella and MacDonald, Curr. Opin. Neurobiol. 1995 5:656-62). Symptoms of HD are due to the death of neurons in many brain regions, but is most apparent in the striatum, particularly in the caudate nucleus, which suffers a progressive gradient of cell loss that ultimately decimates the entire structure. Although the gene encoding huntingtin is expressed ubiquitously (Strong, T. V. et al., Nat. Genet. 1995, 5:259-263), selective cell loss and fibrillary astrocytosis is observed in the brain, particularly in the caudate and putamen of the striatum and in the cerebral cortex of HD patients (Vonsattel, J-P. et al., Neuropathol. Exp. Neurol. 1985, 44:559-577), and, to a lesser extent, in the hippocampus (Spargo, E. et al., J. Neurol. Neurosurg. Psychiatry 1993, 56:487-491) and the subthalamus (Byers, R. K. et al., Neurology 1973, 23:561-569).

Huntingtin is crucial for normal development and may be regarded as a cell survival gene (Nasir et al., Human Molecular Genetics, Vol 5, 1431-1435). The normal function of huntingtin remains incompletely characterized, but based upon protein-protein interactions, it appears to be associated with the cytoskeleton and required for neurogenesis (Walling et al., J. Neurosci Res. 1998, 54:301-8). Huntingtin is specifically cleaved during apoptosis by a key cysteine protease, apopain, known to play a pivotal role in apoptotic cell death. The rate of cleavage is enhanced by longer polyglutamine tracts, suggesting that inappropriate apoptosis underlies HD.

Antisense technology is emerging as an effective means for reducing the expression of specific gene products and may therefore prove to be uniquely useful in a number of therapeutic, diagnostic, and research applications for the modulation of huntingtin expression. (See U.S. Patent Publication Nos. 2008/0039418 and 2007/0299027)

Antisense compounds for modulating expression of huntingtin are disclosed in the aforementioned published patent applications. However, there remains a need for additional such compounds.

SUMMARY OF THE INVENTION

Provided herein are methods, compounds, and compositions for modulating expression of huntingtin and treating, preventing, delaying or ameliorating Huntington's disease and/or a symptom thereof.

Figure 1:
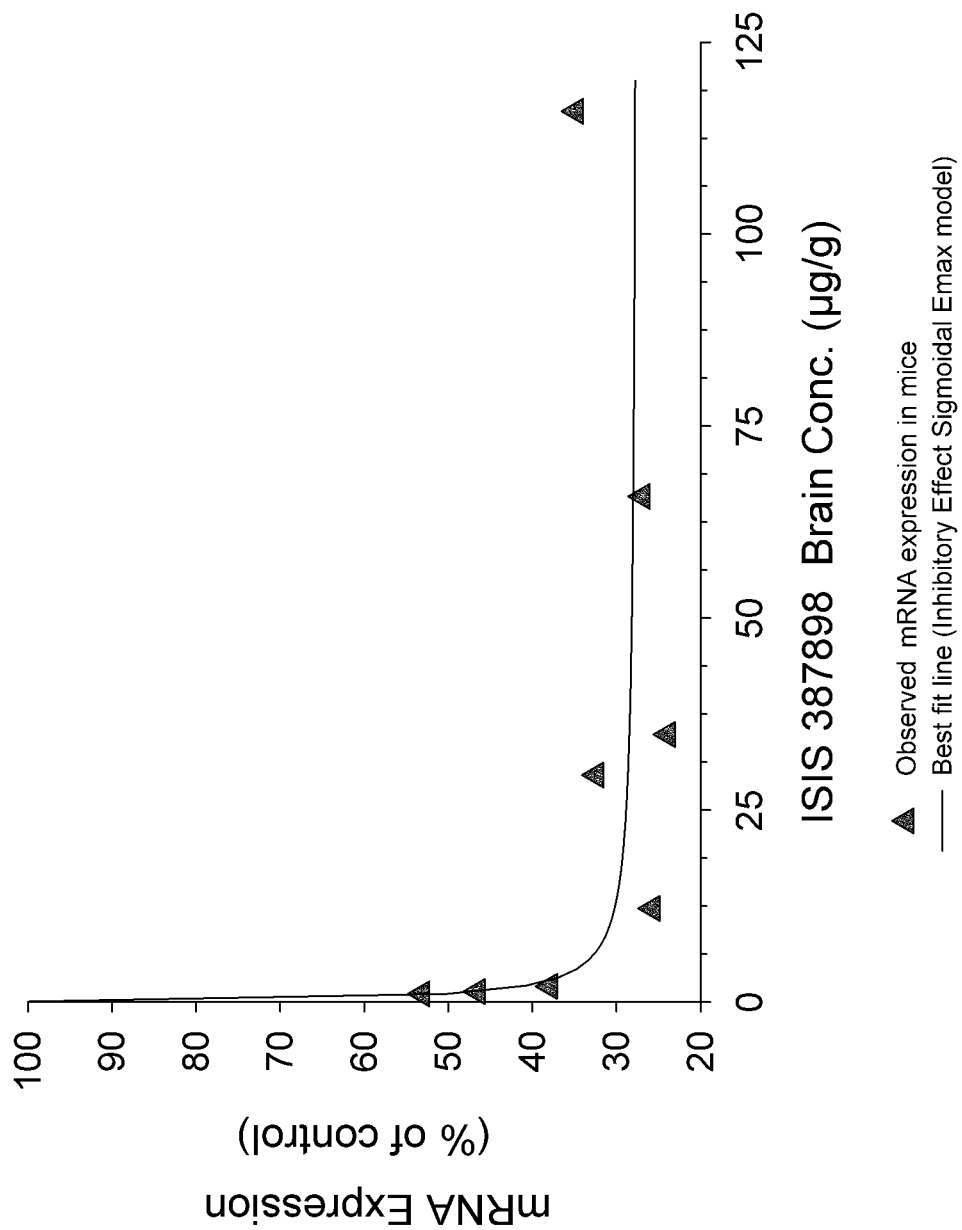
FIG. 1:
The PK/PD relationship of huntingtin mRNA expression in intrastriatal tissue with ISIS 387898 concentration in mouse brain. C57/BL6 mice were administered a single bolus of 50 µg of ISIS 387898 and huntingtin mRNA expression as well as the concentration of the antisense oligonucleotide in the tissue were measured. The $EC_{50}$ of ISIS 387898 was also calculated.

Comparison of huntingtin mRNA expression in posterior cortex tissue and ISIS 388241 concentrations at various time points. BACHD mice were administered intracerebroventricular infusion of 50 μg of ISIS 388241 for 2 weeks, and huntingtin mRNA expression as well as the concentration of the antisense oligonucleotide in the tissue were measured. The duration of action (as measured by htt mRNA expression) of ISIS 388241 (dashed line) was observed to be longer even after the concentration of the oligonucleotide (solid line) in the tissue.

FIG. 6:

Comparison of huntingtin mRNA expression in posterior cortex tissue and ISIS 443139 concentrations at various time points. BACHD mice were administered intracerebroventricular infusion of 50 μg of ISIS 443139 for 2 weeks, and huntingtin mRNA expression as well as the concentration of the antisense oligonucleotide in the tissue were measured. The duration of action (as measured by htt mRNA expression) of ISIS 443139 (dashed line) was observed to be longer even after the concentration of the oligonucleotide (solid line) in the tissue.

FIG. 7.

Effect of antisense oligonucleotide treatment on the motor performance of BACHD mice using the Rotarod assay. BACHD mice were treated with 50 μg/day ICV of ISIS 388241 or PBS for two weeks. Control groups of non-transgenic littermates were similarly treated with ISIS 388241 or PBS. The accelerating Rotarod assay was then performed. Animals were placed on the Rotarod at a speed of 2 RPM; the Rotarod accelerated to 40 RPM over 5 minutes. The duration to fall was recorded. Baseline values at 6 months age were taken before the treatment and the time points given are the age of the mice at which the assay was conducted. The bars represent the duration to fall in seconds by BACHD mice treated with ISIS 388241 (black); by BACHD mice treated with PBS (hashed); and by non-transgenic littermates treated with PBS (white). ISIS 388241-treated mice displayed increased duration of fall and, therefore, improved motor performance on the Rotarod, compared to the PBS control.

FIG. 8.

Effect of antisense oligonucleotide treatment on brain weight of R6/2 mice. Six-month old R6/2 mice were treated with 50 μg/day ICV of ISIS 388817 or control oligonucleotide ISIS 141923 or PBS for 4 weeks. Control groups of non-transgenic littermates were similarly treated with ISIS 388817 or PBS. A control group of eight-week old pre-symptomatic R6/2 mice were included in the study and not given any treatment. The bars represent the brain weights of eight-week old untreated R6/2 mice; R6/2 mice treated with ISIS 141923; R6/2 mice treated with PBS; R6/2 mice treated with ISIS 388817; non-transgenic littermates treated with PBS; and non-transgenic littermates treated with ISIS 388817. There was an increase in brain weight of R6/2 mice treated with ISIS 388817 compared to the PBS control.

FIG. 9

Behavioral characterization of antisense oligonucleotide-treated YAC128 mice using the Open Field assay. Five month old YAC128 mice were treated with 50 μg/day ICV of ISIS 388241 or control oligonucleotide ISIS 141923 or PBS for 14 days. A control group of non-transgenic FVB/NJ littermates were included in the study and not given any treatment. Mice were placed in an open field arena that uses photobeam breaks to measure horizontal and vertical movement over a 30 min test session. Data was analyzed using Activity Monitor software to examine total ambulatory movement within the arena and movement within the center of the arena as a measure of anxiety. The bars represent time in seconds spent at the center of the field by FVB/NJ mice, YAC128 treated with PBS, and, YAC128 mice treated with ISIS 388241. YAC128 mice treated with ISIS 388241 spent more time in the center and were therefore deemed less anxiety-prone than the PBS control.

FIG. 10

Behavioral characterization of antisense oligonucleotide-treated YAC128 mice using the Elevated Plus Maze assay. Five month old YAC128 mice were treated with 50 μg/day ICV of ISIS 388241 or control oligonucleotide ISIS 141923 or with PBS for 14 days. A control group of non-transgenic FVB/NJ littermates were included as untreated control. Mice were placed in the center of an apparatus which consisted of two open arms and two closed arms each measuring 65×6.25 cm and elevated 50 cm above the ground. The location of the mice on the apparatus and amount of time spent in the open arms was recorded over a 5 minute test session as a measure of anxiety. The bars represent the percentage of time spent in the open arms by FVB/NJ control, YAC128 treated with PBS, and YAC128 mice treated with ISIS 388241. YAC128 mice treated with ISIS 388241 spent more time in the open arms and were therefore deemed less anxiety-prone than the PBS control.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to huntingtin is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Huntingtin nucleic acid" means any nucleic acid encoding huntingtin. For example, in certain embodiments, a huntingtin nucleic acid includes a DNA sequence encoding huntingtin, an RNA sequence transcribed from DNA encoding huntingtin (including genomic DNA comprising introns and exons), and an mRNA sequence encoding huntingtin. "Huntingtin mRNA" means an mRNA encoding a huntingtin protein.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid may also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment.

"3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting huntingtin expression.

Certain embodiments provide antisense compounds targeted to a huntingtin nucleic acid. In certain embodiments, the huntingtin nucleic acid is any of the sequences set forth in GENBANK Accession No. NM 002111.6 (incorporated herein as SEQ ID NO: 1), GENBANK Accession No. NT_006081.17 truncated from nucleotides 462000 to 634000 (incorporated herein as SEQ ID NO: 2), GENBANK Accession No. NM 010414.1 (incorporated herein as SEQ ID NO: 3), the complement of GENBANK Accession No. NW 001109716.1 truncated at nucleotides 698000 to 866000 (incorporated herein as SEQ ID NO: 4), and GENBANK Accession No. NM 024357.2 (incorporated herein as SEQ ID NO: 5).

Certain embodiments provide compounds comprising a modified oligonucleotide consisting of 12 to 30 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, or at least 12 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, or at least 12 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 15 to 25 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 18 to 21 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, and 32. In certain embodiments, the modified oligonucleotide comprises at least 9, at least 10, at least 11, at least 12, at least 13, at least 14, at least 15, at least 16, at least 17 or at least 18 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14, at least 15, at least 16, at least 17, or at least 18 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 12-30 linked nucleosides wherein the linked nucleosides comprise at least an 8 contiguous nucleobase portion that is complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828, 4928-4947 of SEQ ID NO: 1. In certain embodiments the region is selected from 4384-4403, 4609-4628, 4610-4629, 4860-4877, 4862-4881, 4925-4944, 4928-4947, 4931-4950, 4955-4974, and 5809-5828 of SEQ ID NO: 1. In certain embodiments the region is selected from 4862-4881, 4609-4628, 5809-5828, 5809-5826, 5801-5820, and 4955-4974. In certain embodiments, the modified oligonucleotide has at least a 9, at least a 10, at least an 11, or at least a 12 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

In certain embodiments, the modified oligonucleotide consists of a single-stranded modified oligonucleotide.

In certain embodiments, the modified oligonucleotide consists of 20 linked nucleosides.

In certain embodiments, the nucleobase sequence of the modified oligonucleotide is at least 90% complementary over its entire length to a nucleobase sequence of SEQ ID NO: 1, 2, 3, 4 or 5. In certain embodiments, the nucleobase sequence of the modified oligonucleotide is at least 95% complementary over its entire length to a nucleobase sequence of SEQ ID NO: 1, 2, 3, 4 or 5. In certain embodiments, the modified oligonucleotide is at least 99% complementary over its entire length to SEQ ID NO: 1, 2, 3, 4 or 5. In certain embodiments, the nucleobase sequence of the modified oligonucleotide is 100% complementary over its entire length to a nucleobase sequence of SEQ ID NO: 1, 2, 3, 4 or 5.

In certain embodiments, the compound has at least one modified internucleoside linkage. In certain embodiments, the internucleoside linkage is a phosphorothioate internucleoside linkage.

In certain embodiments, the compound has at least one nucleoside comprising a modified sugar. In certain embodiments, the at least one modified sugar is a bicyclic sugar. In certain embodiments, the at least one bicyclic sugar comprises a 4'-CH(CH$_3$)—O-2' bridge. In certain embodiments, the at least one modified sugar comprises a 2'-O-methoxyethyl.

In certain embodiments, the compound comprises at least one at least one tetrahydropyran modified nucleoside wherein a tetrahydropyran ring replaces the furanose ring. In certain embodiments, the at least one tetrahydropyran modified nucleoside has the structure:

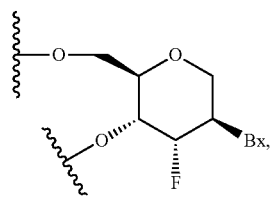

wherein Bx is an optionally protected heterocyclic base moiety.

In certain embodiments, the compound has at least one nucleoside comprising a modified nucleobase. In certain embodiments, the modified nucleobase is a 5-methylcytosine.

In certain embodiments, the modified oligonucleotide of the compound comprises:
 (i) a gap segment consisting of linked deoxynucleosides;
 (ii) a 5' wing segment consisting of linked nucleosides;
 (iii) a 3' wing segment consisting of linked nucleosides, wherein the gap segment is positioned between the 5' wing segment and the 3' wing segment and wherein each nucleoside of each wing segment comprises a modified sugar.

In certain embodiments, the modified oligonucleotide of the compound comprises:
 (i) a gap segment consisting of ten linked deoxynucleosides;
 (ii) a 5' wing segment consisting of five linked nucleosides;
 (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
 (i) a gap segment consisting of eight linked deoxynucleosides;
 (ii) a 5' wing segment consisting of six linked nucleosides;
 (iii) a 3' wing segment consisting of six linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
 (i) a gap segment consisting of eight linked deoxynucleosides;
 (ii) a 5' wing segment consisting of five linked nucleosides;
 (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32 or a salt thereof and a pharmaceutically acceptable carrier or diluent.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 12, 22, 28, 30, 32, and 33 or a salt thereof and a pharmaceutically acceptable carrier or diluent.

Certain embodiments provide methods of treating, preventing, or ameliorating Huntington's disease.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 12, 22, 28, 30, 32, and 33.

In certain embodiments, the animal is a human.

In certain embodiments, the administering prevents, treats, ameliorates, or slows progression Huntington's disease as described herein.

In certain embodiments, the compound is co-administered with a second agent.

In certain embodiments, the compound and the second agent are administered concomitantly.

In certain embodiments, the administering is parenteral administration. In certain embodiments, the parenteral administration is intracranial administration. In certain embodiments, the intracranial administration is intrathecal or intracerebroventricular administration.

Certain embodiments further provide a method to reduce huntingtin mRNA or protein expression in an animal comprising administering to the animal a compound or composition as described herein to reduce huntingtin mRNA or protein expression in the animal. In certain embodiments, the animal is a human. In certain embodiments, reducing huntingtin mRNA or protein expression prevents, treats, ameliorates, or slows progression of Huntington's disease.

Certain embodiments provide a method for treating a human with Huntington's disease comprising identifying the human with the disease and administering to the human a therapeutically effective amount of a compound or composition as described herein. In certain embodiments, the treatment reduces a symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, sleep disturbances, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination, dementia, a anxiety, depression, blunted affect, egocentrisms, aggression, compulsive behavior, irritability, suicidal ideation, reduced brain mass, muscle atrophy, cardiac failure, impaired glucose tolerance, weight loss, osteoporosis, and testicular atrophy.

Further provided is a method for reducing or preventing Huntington's disease comprising administering to a human a therapeutically effective amount compound or composition as described herein, thereby reducing or preventing Huntington's disease.

Further provided is a method for ameliorating a symptom of Huntington's disease, comprising administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby ameliorating a symptom of Huntington's disease in the human.

Further provided is a method for reducing the rate of progression of a symptom associated with Huntington's Disease, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reducing the rate of progression a symptom of Huntington's disease in the human.

Further provided is a method for reversing degeneration indicated by a symptom associated with Huntington's disease, administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby reversing degeneration indicated by a symptom of Huntington's disease in the human.

In certain embodiments, the symptom is a physical, cognitive, psychiatric, or peripheral symptom. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

Also provided are methods and compounds for the preparation of a medicament for the treatment, prevention, or amelioration of Huntington's disease.

Certain embodiments provide the use of a compound as described herein in the manufacture of a medicament for treating, ameliorating, or preventing Huntington's disease.

Certain embodiments provide a compound as described herein for use in treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein in a patient who is subsequently administered an additional agent or therapy as described herein.

Certain embodiments provide a kit for treating, preventing, or ameliorating Huntington's disease as described herein wherein the kit comprises:

(i) a compound as described herein; and alternatively
(ii) an additional agent or therapy as described herein.

A kit as described herein may further include instructions for using the kit to treat, prevent, or ameliorate Huntington's disease as described herein by combination therapy as described herein.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in treating an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12-30 linked nucleosides, wherein the linked nucleosides at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound so that expression of huntingtin is inhibited.

Certain embodiments provide compounds comprising a modified oligonucleotide consisting of 12-30 linked nucleosides, wherein the linked nucleosides comprise at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound to prevent, treat, ameliorate, or slow progression of Huntington's disease.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a huntingtin nucleic acid is 12 to 30 nucleotides in length. In other words, antisense compounds are from 12 to 30 linked nucleobases. In other embodiments, the antisense compound comprises a modified oligonucleotide consisting of 8 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a huntingtin nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6 or 5-8-5.

In certain embodiments, the antisense compound as a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to a huntingtin nucleic acid possess a 5-10-5 gapmer motif.

In certain embodiments, antisense compounds targeted to a huntingtin nucleic acid possess a 6-8-6 gapmer motif.

In certain embodiments, antisense compounds targeted to a huntingtin nucleic acid possess a 5-8-5 gapmer motif. In certain embodiments, an antisense compound targeted to a huntingtin nucleic acid has a gap-widened motif.

In certain embodiments, a gap-widened antisense oligonucleotide targeted to a huntingtin nucleic acid has a gap segment of ten 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of six chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode huntingtin include, without limitation, the following: GENBANK Accession No. NM 002111.6, first deposited with GENBANK® on May 31, 2006 incorporated herein as SEQ ID NO: 1; GENBANK Accession No. NT_006081.17 truncated from nucleotides 462000 to 634000, first deposited with GENBANK® on Aug. 19, 2004, and incorporated herein as SEQ ID NO: 2; GENBANK Accession No. NM 010414.1, first deposited with GENBANK® on Mar. 23, 2004, incorporated herein as SEQ ID NO: 3; the complement of GENBANK Accession No. NW 001109716.1 truncated at nucleotides 698000 to 866000, first deposited with GENBANK® on Jun. 14, 2006, incorporated herein as SEQ ID NO: 4, and GENBANK Accession No. NM 024357.2, first deposited with GENBANK® on Jun. 5, 2008, incorporated herein as SEQ ID NO: 5.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for huntingtin can be obtained by accession number from sequence databases such as NCBI and such information is incorporated herein by reference. In certain embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in huntingtin mRNA levels are indicative of inhibition of huntingtin expression. Reductions in levels of a huntingtin protein are also indicative of inhibition of target mRNA expression. Further, phenotypic changes are indicative of inhibition of huntingtin expression. For example, increase in brain size to normal, improvement in motor coordination, decrease in continual muscular spasms (dystonia), decrease in irritability and/or anxiety, improvement of memory, or an increase in energy, among other phenotypic changes that may be assayed. Other phenotypic indications, e.g., symptoms associated with Huntington's disease, may also be assessed as described below.

Hybridization

In some embodiments, hybridization occurs between an antisense compound disclosed herein and a huntingtin nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a huntingtin nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a huntingtin nucleic acid).

An antisense compound may hybridize over one or more segments of a huntingtin nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a huntingtin nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a huntingtin nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a huntingtin nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a huntingtin nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a huntingtin nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH3 and 2'-O(CH2) 2OCH3 substituent groups. The substituent at the 2' position can also be selected from allyl, amino, azido, thio, O-allyl, O-C1-C10 alkyl, OCF3, O(CH2)2SCH3, O(CH2)2-O—N(Rm)(Rn), and O—CH2-C(=O)—N(Rm)(Rn), where each Rm and Rn is, independently, H or substituted or unsubstituted C1-C10 alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH2)-O-2' (LNA); 4'-(CH2)-S-2; 4'-(CH2)-O-2' (LNA); 4'-(CH2)2-O-2' (ENA); 4'-C(CH3)2-O-2' (see PCT/US2008/068922); 4'-CH(CH3)-O-2' and 4'-C¬H(CH2OCH3)-O-2' (see U.S. Pat. No. 7,399,845, issued on Jul. 15, 2008); 4'-CH2-N(OCH3)-2' (see PCT/US2008/064591); 4'-CH2-O—N(CH$_3$)-2' (see published U.S. Patent Application US2004-0171570, published Sep. 2, 2004); 4'-CH2-N(R)—O-2' (see U.S. Pat. No. 7,427,672, issued on Sep. 23, 2008); 4'-CH2-C(CH3)-2' and 4'-CH2-C¬(=CH2)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

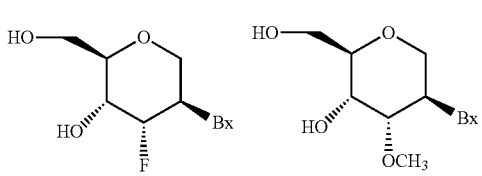

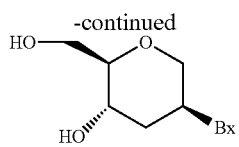

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854). Such ring systems can undergo various additional substitutions to enhance activity.

Methods for the preparations of modified sugars are well known to those skilled in the art. In nucleotides having modified sugar moieties, the nucleobase moieties (natural, modified or a combination thereof) are maintained for hybridization with an appropriate nucleic acid target. In certain embodiments, antisense compounds targeted to a huntingtin nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to a huntingtin nucleic acid comprise one or more modified nucleobases. In certain embodiments, gap-widened antisense oligonucleotides targeted to a huntingtin nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a huntingtin nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a huntingtin nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of huntingtin nucleic acids can be tested in vitro in a variety of cell types. Cell types used for such analyses are available from commercial vendors (e.g. American Type Culture Collection, Manassas, VA; Zen-Bio, Inc., Research Triangle Park, NC; Clonetics Corporation, Walkersville, MD) and cells are cultured according to the vendor's instructions using commercially available reagents (e.g. Invitrogen Life Technologies, Carlsbad, CA). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, CA). Antisense oligonucleotides are mixed with LIPOFECTIN® in OPTI-MEM® 1 (Invitrogen, Carlsbad, CA) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, CA). Antisense oligonucleotide is mixed with LIPOFECTAMINE 2000® in OPTI-MEM® 1 reduced serum medium (Invitrogen, Carlsbad, CA) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, CA). Antisense oligonucleotide is mixed with Cytofectin® in OPTI-MEM® 1 reduced serum medium (Invitrogen, Carlsbad, CA) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, CA) according to the manufacturer's recommended protocols.

Analysis of Inhibition of Target Levels or Expression

Inhibition of levels or expression of a huntingtin nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, CA). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, CA). Cyclophilin A expression is quantified by real time PCR, by being run simultaneously with the target, multiplexing, or separately. Total RNA is quantified using RIBOGREEN® RNA quantification reagent (Invitrogen, Inc. Eugene, OR). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a huntingtin nucleic acid. Methods for designing real-time PCR probes and primers are well known in the art, and may include the use of software such as PRIMER EXPRESS® Software (Applied Biosystems, Foster City, CA).

Analysis of Protein Levels

Antisense inhibition of huntingtin nucleic acids can be assessed by measuring huntingtin protein levels. Protein levels of huntingtin can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art. Antibodies useful for the detection of human and rat huntingtin are commercially available.

In Vivo Testing of Antisense Compounds

Antisense compounds, for example, antisense oligonucleotides, are tested in animals to assess their ability to inhibit expression of huntingtin and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in huntingtin nucleic acid expression are measured. Changes in huntingtin protein levels are also measured.

Certain Compounds

About seventeen hundred newly designed antisense compounds of various lengths, motifs and backbone composition were tested for their effect on human huntingtin mRNA in vitro in several cell types. The new compounds were compared with about two hundred and fifty previously designed compounds including ISIS 387916 which had previously been determined to be one of the most potent antisense compounds in vitro (see e.g., U.S. Patent Publication Nos. 2008/0039418 and 2007/0299027. Of the about seventeen hundred newly designed antisense compounds, about sixty compounds were selected for further study based on in vitro potency compared to ISIS 387916. The selected compounds were tested for systemic tolerability (see Example 3) and activity and tolerability in the brain of BACHD mice (see Example 4) compared to previously designed ISIS 388241 and ISIS 387916. From these studies, compounds having a nucleobase sequence of a sequence recited in SEQ ID NO: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 or 32 were selected as having high tolerability and high in vivo potency. By virtue of their complementary sequence, the compounds are complementary to the regions 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 or 4928-4947 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419628, ISIS 419637, ISIS 419640, ISIS 419641, ISIS 451541, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663.

Compounds described above as having high in vivo potency and tolerability were then tested by CNS bolus injection in rat to further assess neurotoxicity (see Example 5) along with several additional compounds having a nucleobase sequence of a sequence recited in SEQ ID NO: 7, 8, 11, 16, 17. Of these, ten compounds having a nucleobase sequence of a sequence recited in SEQ ID NO: 24, 25, 26, 6, 12, 28, 21, 22, 32 or 13 were selected as having high tolerability. By virtue of their complementary sequence, the compounds are complementary to the regions 4384-4403, 4609-4628, 4610-4629, 4860-4877, 4862-4881, 4925-4944, 4928-4947, 4931-4950, 4955-4974, or 5809-5829 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419640, ISIS 419641, ISIS 419642, ISIS 436665, ISIS 436671, ISIS 436689, ISIS 437507, ISIS 443139, ISIS 444591, and ISIS 444661. Selected compounds were compared with previously designed compound ISIS 388241 by ICV administration in BACHD mice.

Additional studies were then run on compounds described above as having high in vivo potency and tolerability. The additional studies were designed to further assess neurotoxicity. Studies included ICV administration in wild-type mouse (see Example 16) and bolus administration in rat (see Example 17). SEQ ID NOs: 12, 22, 28, 30, 32, and 33 were selected as having high neurotolerability. By virtue of their complementary sequence, the compounds are complementary to the regions 4862-4881, 4609-4628, 5809-5828, 5809-5826, 5801-5820, and 4955-4974 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by ISIS 388241, ISIS 443139, ISIS 436671, ISIS 444591, ISIS 437527, ISIS 444584, ISIS 444652, and ISIS 436689.

Accordingly, provided herein are antisense compounds with improved characteristics. In certain embodiments, provided herein are compounds comprising a modified oligonucleotide as further described herein targeted to or specifically hybridizable with the region of nucleotides of SEQ ID NO: 1.

In certain embodiments, the compounds as described herein are efficacious by virtue of having at least one of an in vitro IC50 of less than 7 uM, less than 6 uM, less than 5, uM, less than 4 uM, less than 3 uM, less than 2 uM, less than 1 uM when delivered to a human fibroblast cell line as described herein or an ED50 of less than 10 µg, less than 9 µg, less than 8 µg, less than 7.5 µg, less than 7.4 µg, less than 7.0 µg, less than 6 µg, less than 5 µg, less than 4 µg, less than 3 µg, or less than 2 µg by bolus injection. As described herein, ICV infusion can result in 3 to 4 fold higher ED50 values for the compounds described herein. In certain embodiments, the compounds as described herein are highly tolerable as demonstrated by having at least one of an increase an ALT or AST value of no more than 4 fold, 3 fold, or 2 fold over saline treated animals; an increase in liver, spleen or kidney weight of no more than 30%, 20%, 15%, 12%, 10%, 5% or 2%; or an increase AIF1 levels by no more than 350%, 300%, 275%, 250% 200%, 150% or 100% over control.

Certain Indications

In certain embodiments, provided herein are methods of treating an individual comprising administering one or more pharmaceutical compositions as described herein. In certain embodiments, the individual has Huntington's disease.

As shown in the examples below, compounds targeted to huntingtin as described herein have been shown to reduce the severity of physiological symptoms of Huntington's disease. In certain of the experiments, the compounds reduced rate of degeneration, e.g., the animals continued to experience symptoms, but the symptoms were less severe compared to untreated animals. In other of the experiments, however, the compounds appear to result in regeneration of function over time; e.g., animals treated for a longer period of time experienced less severe symptoms than those administered the compounds for a shorter period of time. As discussed above, Huntington's disease is a degenerative disease with a progression typified by increased severity of symptoms over time. The ability of the compounds exemplified below to restore function therefore demonstrates that symptoms of the disease may be reversed by treatment with a compound as described herein.

Accordingly, provided herein are methods for ameliorating a symptom associated with Huntington's disease in a subject in need thereof. In certain embodiments, provided is a method for reducing the rate of onset of a symptom associated with Huntington's disease. In certain embodiments, provided is a method for reducing the severity of a symptom associated with Huntington's disease. In certain embodiments, provided is a method for regenerating neurological function as shown by an improvement of a symptom associated with Huntington's disease. In such embodiments, the methods comprise administering to an individual in need thereof a therapeutically effective amount of a compound targeted to a huntingtin nucleic acid.

Huntington's disease is characterized by numerous physical, neurological, psychiatric, and/or peripheral symptoms. Any symptom known to one of skill in the art to be associated with Huntington's disease can be ameliorated or otherwise modulated as set forth above in the methods described above. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

In certain embodiments, the symptom is restlessness. In certain embodiments, the symptom is lack of coordination. In certain embodiments, the symptom is unintentionally initiated motions. In certain embodiments, the symptom is unintentionally uncompleted motions. In certain embodiments, the symptom is unsteady gait. In certain embodiments, the symptom is chorea. In certain embodiments, the symptom is rigidity. In certain embodiments, the symptom is writhing motions. In certain embodiments, the symptom is abnormal posturing. In certain embodiments, the symptom is instability. In certain embodiments, the symptom is abnormal facial expressions. In certain embodiments, the symptom is difficulty chewing. In certain embodiments, the symptom is difficulty swallowing. In certain embodiments, the symptom is difficulty speaking. In certain embodiments, the symptom is seizures. In certain embodiments, the symptom is sleep disturbances.

In certain embodiments, the symptom is impaired planning. In certain embodiments, the symptom is impaired flexibility. In certain embodiments, the symptom is impaired abstract thinking. In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is anxiety. In certain embodiments, the symptom is depression. In certain embodiments, the symptom is blunted affect. In certain embodiments, the symptom is egocentrism. In certain embodiments, the symptom is aggression. In certain embodiments, the symptom is compulsive behavior. In certain embodiments, the symptom is irritability. In certain embodiments, the symptom is suicidal ideation.

In certain embodiments, the symptom is reduced brain mass. In certain embodiments, the symptom is muscle atrophy. In certain embodiments, the symptom is cardiac failure. In certain embodiments, the symptom is impaired glucose tolerance. In certain embodiments, the symptom is weight loss. In certain embodiments, the symptom is osteoporosis. In certain embodiments, the symptom is testicular atrophy.

In certain embodiments, symptoms of Huntington's disease may be quantifiable. For example, osteoporosis may be measured and quantified by, for example, bone density scans. For such symptoms, in certain embodiments, the symptom may be reduced by about 15, 20, 25, 30, 35, 40, 45, 50, 55, 60, 65, 70, 75, 80, 85, 90, 95 or 99%, or a range defined by any two of these values.

In certain embodiments, provided are methods of treating an individual comprising administering one or more pharmaceutical compositions as described herein. In certain embodiments, the individual has Huntington's disease.

In certain embodiments, administration of an antisense compound targeted to a huningtin nucleic acid results in reduction of huntingtin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to huntingtin are used for the preparation of a medicament for treating a patient suffering or susceptible to Huntington's disease.

In certain embodiments, the methods described herein include administering a compound comprising a modified oligonucleotide having a contiguous nucleobases portion as described herein of a sequence recited in SEQ ID NO: 6, 9, 10, 11, 12, 13, 14, 15, 18, 19, 20, 21, 22, 23, 24, 25, 26, 27, 28, 29, 30, 32, 33, 35, 36, 10, 11, 12, 13, 18, 22 or 32. In certain embodiments, the methods described herein include administering a compound comprising a modified oligonucleotide having a contiguous nucleobases portion as described herein of a sequence recited in SEQ ID NOs: 12, 22, 28, 30, 32, and 33.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

The median effective concentration ($EC_{50}$) of an antisense compounds for inhibiting huntingtin mRNA expression was calculated after either ICV infusion or bolus injection (see Examples 9 and 10). The $EC_{50}$ for the compound after intrastriatal injection was determined to be 0.45 µg/g. The $EC_{50}$ after ICV administration was determined to be 26.4 µg/g.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

The half-life of MOE gapmer oligonucleotides in brain tissue is about 20 days (see Examples 9-11). The duration of action as measured by inhibition of huntingtin mRNA is prolonged in the brain (see Examples 9 and 10). Intracerebroventricular infusion of antisense oligonucleotides for 2 weeks results in inhibition of huntingtin mRNA by at least 50% in striatal tissue of BACHD mice for at least 91 days after termination of dosing. Administration by bolus injection resulted in a similar duration of action.

In certain embodiments, delivery of a compound or composition, as described herein, to the CNS results in 47% down-regulation of a target mRNA and/or target protein for at least 91 days. In certain embodiments, delivery of a compound or composition results in at least 25%, at least 30%, at least 35%, at least 40%, at least 45%, at least 50%, at least 55%, at least 60%, at least 65%, at least 70%, or at least 75% down-regulation of a target mRNA and/or target protein for at least 20 days, at least 30 days, at least 40 days, at least 50 days, at least 60 days, at least 70 days, at least 80 days, at least 85 days, at least 90 days, at least 95 days, at least 100 days, at least 110 days, at least 120 days.

In certain embodiments, delivery to the CNS is by intraparenchymal administration, intrathecal administration, or intracerebroventricular administration.

In certain embodiments, an antisense oligonucleotide is delivered by injection or infusion once every month, every two months, every 90 days, every 3 months, every 6 months, twice a year or once a year.

Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, coenzyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Oligonucleotides Targeted to Human Huntingtin Gene Sequences About seventeen hundred newly designed antisense compounds of various lengths, motifs and backbone composition targeting the human huntingtin gene sequence were tested for their effect on human huntingtin mRNA in vitro in several cell types. These gapmers were further designed with internucleoside linkages that are either only phosphorothioate linkages (described in Table 1) or that are phosphorothioate and phosphodiester linkages (described in Table 5). A number of the newly designed oligos and two benchmark oligonucleotides (previously designed and disclosed) are provided in Tables 1 and 5.

Gapmers with Fully Phosphorothioate Internucleoside Linkages

Certain of the compounds presented in Table 1 have a motif of 5-10-5 MOE, 6-8-6 MOE, or 5-8-5 MOE. The 5-10-5 gapmers have twenty linked nucleosides, wherein the central gap segment has ten 2'-deoxynucleosides and is flanked on both sides (in the 5' and 3' directions) by wings having five nucleosides each. The 6-8-6 gapmer has twenty linked nucleosides, wherein the central gap segment has eight 2'-deoxynucleosides and is flanked on both sides (in the 5' and 3' directions) by wings having six nucleosides each. The 5-8-5 gapmers have eighteen linked nucleosides, wherein the central gap segment has eight 2'-deoxynucleosides and is flanked on both sides (in the 5' and 3' directions) by wings having five nucleosides each. For all gapmers listed in Table 1, each nucleoside in the 5' wing segment and each nucleoside in the 3' wing segment has a 2'-MOE modification. The internucleoside linkages throughout each gapmer are phosphorothioate (P=S) internucleoside linkages. All cytosines throughout each gapmer are 5-methylcytosines. Each gapmer in Table 1 is targeted to SEQ ID NO: 1 (GENBANK Accession No. NM_002111.6) or SEQ ID NO: 2 (GENBANK Accession No. NT 006081.17 truncated from nucleotides 462000 to 634000). 'Start site' indicates the 5'-most nucleotide to which the gapmer is targeted in the human gene sequence. 'Stop site' indicates the 3'-most nucleotide to which the gapmer is targeted in the human gene sequence.

TABLE 1

Chimeric antisense oligonucleotides with phosphorothioate internucleoside linkages targeting human huntingtin gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4384 | 4403 | 1 | 436665 | TAGCATTCTTATCTGCACGG | 5-10-5 | 6 |
| 4511 | 4530 | 1 | 436668 | ACCCGTAACTGAACCAGCTG | 5-10-5 | 7 |
| 4599 | 4618 | 1 | 419627 | TTCCCTGAACTGGCCCACTT | 5-10-5 | 8 |
| 4605 | 4624 | 1 | 419628 | CTCTGATTCCCTGAACTGGC | 5-10-5 | 9 |
| 4607 | 4626 | 1 | 444607 | GCCTCTGATTCCCTGAACTG | 5-10-5 | 10 |
| 4608 | 4627 | 1 | 419629 | TGCCTCTGATTCCCTGAACT | 5-10-5 | 11 |
| 4608 | 4627 | 1 | 444578 | TGCCTCTGATTCCCTGAACT | 6-8-6 | 11 |
| 4609 | 4628 | 1 | 436671 | TTGCCTCTGATTCCCTGAAC | 5-10-5 | 12 |
| 4610 | 4629 | 1 | 444608 | ATTGCCTCTGATTCCCTGAA | 5-10-5 | 13 |
| 4617 | 4636 | 1 | 444615 | TGGAATGATTGCCTCTGATT | 5-10-5 | 14 |

TABLE 1-continued

Chimeric antisense oligonucleotides with phosphorothioate internucleoside linkages targeting human huntingtin gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4622 | 4639 | 1 | 437168 | GTTTGGAATGATTGCCTC | 5-8-5 | 15 |
| 4679 | 4698 | 1 | 419630 | CCAATGATCTGTTTTGAATG | 5-10-5 | 16 |
| 4733 | 4752 | 1 | 419636 | GCCTTCCTTCCACTGGCCAT | 5-10-5 | 17 |
| 4813 | 4832 | 1 | 444618 | CTGCATCAGCTTTATTTGTT | 5-10-5 | 18 |
| 4814 | 4833 | 1 | 419637 | CCTGCATCAGCTTTATTTGT | 5-10-5 | 19 |
| 4823 | 4842 | 1 | 444627 | AGCTCTTTTCCTGCATCAGC | 5-10-5 | 20 |
| 4860 | 4877 | 1 | 437507 | GTAACATTGACACCACCA | 5-8-5 | 21 |
| 4862 | 4881 | 1 | 388241 | CTCAGTAACATTGACACCAC | 5-10-5 | 22 |
| 4868 | 4887 | 1 | 436684 | ATGAGTCTCAGTAACATTGA | 5-10-5 | 23 |
| 4925 | 4944 | 1 | 419640 | TCCTTGTGGCACTGCTGCAG | 5-10-5 | 24 |
| 4928 | 4947 | 1 | 419641 | TTCTCCTTGTGGCACTGCTG | 5-10-5 | 25 |
| 4931 | 4950 | 1 | 419642 | TCATTCTCCTTGTGGCACTG | 5-10-5 | 26 |
| 4931 | 4948 | 1 | 437442 | ATTCTCCTTGTGGCACTG | 5-8-5 | 27 |
| 4955 | 4974 | 1 | 436689 | CGAGACAGTCGCTTCCACTT | 5-8-5 | 28 |
| 4960 | 4977 | 1 | 437175 | TGTCGAGACAGTCGCTTC | 5-8-5 | 29 |
| 5801 | 5820 | 1 | 444584 | TTGCACATTCCAAGTTTGGC | 5-10-5 | 30 |
| 5807 | 5826 | 1 | 387916 | TCTCTATTGCACATTCCAAG | 5-10-5 | 31 |
| 5809 | 5828 | 1 | 444591 | TTTCTCTATTGCACATTCCA | 5-10-5 | 32 |
| 5809 | 5826 | 1 | 437527 | TCTCTATTGCACATTCCA | 5-8-5 | 33 |
| 1446 | 1465 | 2 | 388817 | GCAGGGTTACCGCCATCCCC | 5-10-5 | 34 |
| 101088 | 101105 | 2 | 437441 | ACCTTATCTGCACGGTTC | 5-8-5 | 35 |
| 115066 | 115085 | 2 | 436754 | CTCTCTGTGTATCACCTTCC | 5-10-5 | 36 |

The complementarity of the gapmers in Table 1 with mouse, rhesus monkey and rat huntingtin gene sequences is further described in Tables 2, 3, and 4.

The gapmers of Table 2 are complementary with mouse huntingtin mRNA (GENBANK Accession No. NM_010414.1, designated herein as SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the mouse mRNA sequence.

TABLE 2

Complementarity of antisense oligonucleotides having phosphorothioate linkages with murine mRNA (SEQ ID NO: 3)

| Human Start Site | Human Stop Site | Human Target SEQ ID NO. | ISIS No. | Mouse Start Site | Mouse Stop Site | No. of mismatches | SEQ ID NO. |
|---|---|---|---|---|---|---|---|
| 4384 | 4403 | 1 | 436665 | 4343 | 4362 | 0 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |

TABLE 2-continued

Complementarity of antisense oligonucleotides having
phosphorothioate linkages with murine mRNA (SEQ ID NO: 3)

| Human Start Site | Human Stop Site | Human Target SEQ ID NO. | ISIS No. | Mouse Start Site | Mouse Stop Site | No. of mis-matches | SEQ ID NO. |
|---|---|---|---|---|---|---|---|
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 0 | 24 |
| 4928 | 4947 | 1 | 419641 | 4887 | 4906 | 0 | 25 |
| 4931 | 4950 | 1 | 419642 | 4890 | 4909 | 0 | 26 |
| 4931 | 4948 | 1 | 437442 | 4890 | 4907 | 0 | 27 |
| 4955 | 4974 | 1 | 436689 | 4914 | 4933 | 3 | 28 |
| 5807 | 5826 | 1 | 387916 | 5763 | 5782 | 1 | 31 |
| 5809 | 5826 | 1 | 437527 | 5765 | 5782 | 1 | 33 |
| 5809 | 5828 | 1 | 444591 | 5765 | 5784 | 1 | 32 |
| 101088 | 101105 | 2 | 437441 | 4340 | 4357 | 2 | 35 |

The gapmers of Table 3 are complementary with the rhesus monkey huntingtin genomic sequence (the complement of GENBANK Accession No. NW_001109716.1 truncated at nucleotides 698000 to 866000, designated herein as SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rhesus monkey gene sequence.

TABLE 3

Complementarity of antisense oligonucleotides
having phosphorothioate linkages with
rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mis-matches | SEQ ID NO. |
|---|---|---|---|---|---|---|---|
| 4511 | 4530 | 1 | 436665 | 98182 | 98201 | 0 | 6 |
| 4599 | 4618 | 1 | 419627 | 101353 | 101372 | 1 | 8 |
| 4609 | 4628 | 1 | 436671 | 102256 | 102275 | 3 | 12 |
| 4610 | 4629 | 1 | 444608 | 102257 | 102276 | 2 | 13 |
| 4617 | 4636 | 1 | 444615 | 102264 | 102283 | 0 | 14 |
| 4622 | 4639 | 1 | 437168 | 102269 | 102286 | 0 | 15 |
| 4679 | 4698 | 1 | 419630 | 102326 | 102345 | 0 | 16 |
| 4733 | 4752 | 1 | 419636 | 102380 | 102399 | 0 | 17 |
| 4813 | 4832 | 1 | 444618 | 105030 | 105049 | 0 | 18 |
| 4814 | 4833 | 1 | 419637 | 105031 | 105050 | 0 | 19 |
| 4823 | 4842 | 1 | 444627 | 105040 | 105059 | 0 | 20 |
| 4860 | 4877 | 1 | 437507 | 105077 | 105094 | 1 | 21 |
| 4862 | 4881 | 1 | 388241 | 105079 | 105098 | 1 | 22 |
| 4868 | 4887 | 1 | 436684 | 105085 | 105104 | 0 | 23 |
| 4925 | 4944 | 1 | 419640 | 106844 | 106863 | 0 | 24 |
| 4928 | 4947 | 1 | 419641 | 106847 | 106866 | 0 | 25 |
| 4931 | 4950 | 1 | 419642 | 106850 | 106869 | 0 | 26 |
| 4931 | 4948 | 1 | 437442 | 106850 | 106867 | 0 | 27 |
| 4955 | 4974 | 1 | 436689 | 106874 | 106893 | 0 | 28 |
| 4960 | 4977 | 1 | 437175 | 106879 | 106896 | 0 | 29 |
| 5801 | 5820 | 1 | 444584 | 125331 | 125350 | 0 | 30 |
| 5807 | 5826 | 1 | 387916 | 125337 | 125356 | 0 | 31 |
| 5809 | 5826 | 1 | 437527 | 125339 | 125356 | 0 | 33 |

TABLE 3-continued

Complementarity of antisense oligonucleotides
having phosphorothioate linkages with
rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mis-matches | SEQ ID NO. |
|---|---|---|---|---|---|---|---|
| 5809 | 5828 | 1 | 444591 | 125339 | 125358 | 0 | 32 |
| 101088 | 101105 | 2 | 437441 | 97904 | 97921 | 0 | 35 |
| 115066 | 115085 | 2 | 436754 | 110518 | 110537 | 0 | 36 |

The gapmers of Table 4 are complementary with rat huntingtin mRNA (GENBANK Accession No. NM_024357.2, designated herein as SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rat mRNA sequence.

TABLE 4

Complementarity of antisense oligonucleotides having
phosphorothioate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4384 | 4403 | 1 | 436665 | 4343 | 4362 | 1 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 1 | 24 |
| 4928 | 4947 | 1 | 419641 | 4887 | 4906 | 0 | 25 |
| 4931 | 4950 | 1 | 419642 | 4890 | 4909 | 1 | 26 |
| 4931 | 4948 | 1 | 437442 | 4890 | 4907 | 1 | 27 |
| 4955 | 4974 | 1 | 436689 | 4914 | 4933 | 3 | 28 |
| 5801 | 5820 | 1 | 444584 | 5757 | 5776 | 3 | 30 |
| 5807 | 5826 | 1 | 387916 | 5763 | 5782 | 0 | 31 |
| 5809 | 5826 | 1 | 437527 | 5765 | 5782 | 0 | 33 |
| 5809 | 5828 | 1 | 444591 | 5765 | 5784 | 0 | 32 |
| 101088 | 101105 | 2 | 437441 | 4340 | 4357 | 2 | 35 |

Gapmers with Mixed Phosphorothioate and Phosphodiester Internucleoside Linkages

The chimeric antisense oligonucleotides in Table 5 were designed as 5-10-5 MOE gapmers. The 5-10-5 gapmers have twenty linked nucleosides, wherein the central gap segment has ten 2'-deoxynucleotides and is flanked on both sides (in the 5' and 3' directions) by wings having five nucleosides each. Each nucleoside in the 5' wing segment and each nucleoside in the 3' wing segment has a 2'-MOE modification. The internucleoside linkages within the central gap segment, the linkages connecting the gap segment to the 5' or 3' wing segment, and the linkages for the 5'-most and 3'-most nucleosides of each wing segments are all phosphorothioate (P=S) linkages; the internucleoside linkages connecting the rest of the nucleosides of both the 5' and 3' wing segments are phosphodiester linkages; i.e. the gapmer has a mixed backbone. All cytosines throughout each gapmer are 5-methylcytosines. Each gapmer in Table 5 is targeted to the human mRNA sequence (GENBANK Accession No. NM_002111.6, designated herein as SEQ ID NO: 1). 'Start site' indicates the 5'-most nucleotide to which the gapmer is targeted in the human mRNA. 'Stop site' indicates the 3'-most nucleotide to which the gapmer is targeted in the human mRNA.

TABLE 5

Chimeric antisense oligonucleotides with phosphorothioate and phosphate internucleoside linkages targeting human huntingtin mRNA (SEQ ID NO: 1)

| Start Site | Stop Site | Target SEQ ID NO. | ISIS No. | Sequence (5' to 3') | Motif | SEQ ID NO. |
|---|---|---|---|---|---|---|
| 4607 | 4626 | 1 | 444658 | GCCTCTGATTCCCT GAACTG | 5-10-5 | 10 |
| 4608 | 4627 | 1 | 444659 | TGCCTCTGATTCCC TGAACT | 5-10-5 | 11 |
| 4609 | 4628 | 1 | 444660 | TTGCCTCTGATTCC CTGAAC | 5-10-5 | 12 |
| 4610 | 4629 | 1 | 444661 | ATTGCCTCTGATTC CCTGAA | 5-10-5 | 13 |
| 4813 | 4832 | 1 | 444663 | CTGCATCAGCTTTA TTTGTT | 5-10-5 | 18 |
| 4862 | 4881 | 1 | 443139 | CTCAGTAACATTGA CACCAC | 5-10-5 | 22 |
| 5809 | 5828 | 1 | 444652 | TTTCTCTATTGCAC ATTCCA | 5-10-5 | 32 |
| 4928 | 4947 | 1 | 451541 | TTCTCCTTGTGGCA CTGCTG | 5-10-5 | 25 |

The complementarity of the gapmers in Table 5 with mouse, rhesus monkey and rat huntingtin gene sequences are further described in Tables 6, 7, and 8.

The gapmers of Table 6 are complementary with mouse huntingtin mRNA (GENBANK Accession No. NM_010414.1; SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the mouse mRNA sequence.

TABLE 6

Complementarity of antisense oligonucleotides having mixed phosphorothioate and phosphate linkages with murine mRNA (SEQ ID NO: 3)

| Human Start Site | Human Stop Site | Human Target SEQ ID NO. | ISIS No. | Mouse Start Site | Mouse Stop Site | No. of mismatches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 1 | 32 |

The gapmers of Table 7 are complementary with the rhesus monkey huntingtin genomic sequence (the complement of GENBANK Accession No. NW_001109716.1 truncated at nucleotides 698000 to 866000; SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rhesus monkey gene sequence.

TABLE 7

Complementarity of antisense oligonucleotides having mixed phosphorothioate and phosphate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mismatches | SEQ ID NO. |
|---|---|---|---|---|---|---|---|
| 4609 | 4628 | 1 | 444660 | 102256 | 102275 | 3 | 12 |
| 4610 | 4629 | 1 | 444661 | 102257 | 102276 | 2 | 13 |
| 4813 | 4832 | 1 | 444663 | 105030 | 105049 | 0 | 18 |
| 4862 | 4881 | 1 | 443139 | 105079 | 105098 | 1 | 22 |
| 5809 | 5828 | 1 | 444652 | 125339 | 125358 | 0 | 32 |

The gapmers of Table 8 are complementary with rat huntingtin mRNA (GENBANK Accession No. NM_024357.2; SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rat mRNA sequence.

TABLE 8

Complementarity of antisense oligonucleotides having mixed phosphorothioate and phosphate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 0 | 32 |

Example 2: Dose-Dependent Antisense Inhibition of Human Huntingtin mRNA In Vitro About seventeen hundred newly designed antisense compounds of various lengths, motifs and backbone composition were tested for their effect on human huntingtin mRNA in vitro in several cell types. These compounds were compared to about two hundred and fifty previously designed compounds including the compound ISIS 387916 which was previously determined to be a compound of considerable potency in vivo. As shown in this example, ISIS 419640, ISIS 419641, ISIS 419642, ISIS 436665, ISIS 436671, ISIS 436689, ISIS 437507, ISIS 443139, ISIS 444591, ISIS 444661, ISIS 437527, ISIS 444584, and ISIS 444652 and previously designed ISIS 388241 were found to have similar or better potency than the benchmark compound ISIS 387916 in vitro.

A. GM04281 Fibroblasts

Cultured GM04281 fibroblasts at a density of 25,000 cells per well were transfected using electroporation with 500 nM, 1000 nM, 2000 nM, 4000 nM, or 8000 nM of antisense oligonucleotide. After a treatment period of approximately 16 hours, RNA was isolated from the cells and huntingtin mRNA levels were measured by quantitative real-time PCR. Human primer probe set RTS2617 (forward sequence CTCCGTCCGGTAGACATGCT, designated herein as SEQ ID NO: 37; reverse sequence GGAAATCAGAACCCT-CAAAATGG, designated herein as SEQ ID NO: 38; probe sequence TGAGCACTGTTCAACTGTGGATATCGG-GAX, designated herein as SEQ ID NO: 39) was used to measure mRNA levels. Huntingtin mRNA levels were adjusted according to total RNA content, as measured by RIBOGREEN®. Results are presented in Table 9 as percent inhibition of huntingtin mRNA, relative to untreated control cells and demonstrate antisense oligonucleotide-mediated dose-dependent reduction of huntingtin mRNA levels.

The half maximal inhibitory concentration ($IC_{50}$) of each oligonucleotide is also presented in Table 9 and was calculated by plotting the concentrations of oligonucleotides used versus the percent inhibition of huntingtin mRNA expression achieved at each concentration, and noting the concentration of oligonucleotide at which 50% inhibition of huntingtin mRNA expression was achieved compared to the control. The $IC_{50}$ is expressed in μM.

TABLE 9

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 33 | 73 | 90 | 96 | 97 | 1.00 |
| 388241 | 44 | 70 | 82 | 95 | 97 | 0.61 |
| 419641 | 26 | 32 | 71 | 90 | 93 | 1.06 |
| 436665 | 56 | 67 | 87 | 95 | 96 | 0.32 |
| 436671 | 12 | 35 | 68 | 82 | 91 | 1.55 |
| 436689 | 10 | 34 | 61 | 80 | 91 | 1.89 |

ISIS 387916, ISIS 388241, and ISIS 437507 were further tested for their effect on human huntingtin mRNA in vitro. Cultured GM04281 fibroblasts were tested in a similar procedure, as described above. The results are presented in Table 10 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 10 expressed in μM.

TABLE 10

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 56 | 84 | 94 | 98 | 99 | 0.34 |
| 388241 | 58 | 75 | 94 | 98 | 99 | 0.23 |
| 437507 | 61 | 74 | 85 | 93 | 93 | 0.22 |

ISIS 387916, ISIS 388241, and ISIS 437507 were further tested for their effect on human huntingtin mRNA in vitro. Cultured GM04281 fibroblasts were tested in a similar procedure as described above. The results are presented in Table 11 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 11 expressed in μM.

TABLE 11

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 40 | 61 | 85 | 94 | 97 | 0.70 |
| 388241 | 51 | 72 | 86 | 94 | 98 | 0.41 |
| 437507 | 30 | 55 | 71 | 79 | 82 | 1.07 |

ISIS 387916, ISIS 388241, ISIS 419641, and ISIS 436754 were further tested for their effect on human huntingtin mRNA in vitro. Cultured GM04281 fibroblasts were tested in a similar procedure as described above. The results are presented in Table 12 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 12 expressed in μM.

TABLE 12

Dose dependent reduction of huntingtin mRNA in GM04281 fibroblasts

| ISIS No. | 500 nM | 1000 nM | 2000 nM | 4000 nM | 8000 nM | IC$_{50}$ (μM) |
|---|---|---|---|---|---|---|
| 387916 | 58 | 75 | 93 | 98 | 98 | 0.22 |
| 388241 | 40 | 68 | 85 | 95 | 98 | 0.73 |
| 419641 | 37 | 58 | 86 | 92 | 95 | 0.80 |
| 436754 | 44 | 62 | 63 | 84 | 93 | 0.59 |

ISIS 387916, ISIS 388241, and ISIS 437507 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 13 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 13 expressed in μM.

TABLE 13

Dose dependent reduction of huntingtin mRNA in GM04281 fibroblasts

| ISIS No. | 250 nM | 500 nM | 1000 Nm | 2000 nM | 4000 nM | 8000 nM | IC$_{50}$ (μM) |
|---|---|---|---|---|---|---|---|
| 387916 | 10 | 9 | 61 | 85 | 97 | 99 | 0.79 |
| 388241 | 0 | 18 | 42 | 90 | 98 | 99 | 1.08 |
| 437507 | 1 | 0 | 32 | 71 | 92 | 98 | 1.30 |

ISIS 387916, ISIS 388241, ISIS 419628, ISIS 419629, ISIS 419637, ISIS 436684, ISIS 443139, ISIS 444584, ISIS 444615, ISIS 444627, ISIS 444652, ISIS 444658, ISIS 444659, ISIS 444660, and ISIS 444661 were further tested for their effect on human huntingtin mRNA in vitro. Cultured GM04281 fibroblasts at a density of 25,000 cells per well were transfected using electroporation with 156.25 nM, 312.5 nM, 625 nM, 1250 nM, or 2500 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 14 as percent inhibition of huntingtin mRNA, relative to untreated control cells, and demonstrate antisense oligonucleotide-mediated dose-dependent reduction of huntingtin mRNA levels. The data presented is the average of two experiments. The IC$_{50}$ of each antisense oligonucleotide is also presented in Table 14 expressed in μM.

TABLE 14

Dose dependent reduction of huntingtin mRNA in GM04281 fibroblasts

| ISIS No | 156.25 nM | 312.5 Nm | 625 nM | 1250 nM | 2500 nM | IC$_{50}$ (μM) |
|---|---|---|---|---|---|---|
| 387916 | 19 | 22 | 44 | 62 | 85 | 0.73 |
| 388241 | 3 | 13 | 24 | 42 | 71 | 1.42 |
| 419628 | 56 | 45 | 59 | 71 | 83 | 0.20 |
| 419629 | 42 | 38 | 67 | 70 | 89 | 0.33 |
| 419637 | 24 | 17 | 32 | 61 | 77 | 0.91 |
| 436684 | 15 | 28 | 55 | 73 | 85 | 0.59 |
| 443139 | 13 | 45 | 50 | 64 | 81 | 0.61 |
| 444584 | 0 | 0 | 25 | 50 | 74 | 1.28 |
| 444615 | 36 | 35 | 37 | 38 | 70 | 0.12 |
| 444627 | 40 | 38 | 48 | 73 | 87 | 0.43 |
| 444652 | 15 | 28 | 55 | 73 | 85 | 0.59 |
| 444658 | 50 | 54 | 75 | 84 | 96 | 0.18 |
| 444659 | 47 | 61 | 69 | 79 | 93 | 0.18 |
| 444660 | 41 | 61 | 65 | 84 | 95 | 0.22 |
| 444661 | 47 | 59 | 72 | 84 | 96 | 0.19 |

ISIS 387916, ISIS 436671, ISIS 444661, ISIS 419641, and ISIS 436665 were further tested for their effect on human huntingtin mRNA in vitro. Cultured GM04281 fibroblasts at a density of 25,000 cells per well were transfected using electroporation with 13.6719 nM, 27.3438 nM, 54.6875 nM, 109.375 nM, 218.75 nM, 437.5 nM, 875 nM, 1750 nM, 3500 nM, or 7000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 15 expressed in μM.

TABLE 15

Dose dependent reduction of huntingtin mRNA in GM04281 fibroblasts

| ISIS No. | 13.6719 nM | 27.3438 nM | 54.6875 nM | 109.375 nM | 218.75 nM | 437.5 nM | 875 nM | 1750 nM | 3500 nM | 7000 nM | IC$_{50}$ (μM) |
|---|---|---|---|---|---|---|---|---|---|---|---|
| 387916 | 0 | 31 | 14 | 43 | 44 | 68 | 86 | 89 | 97 | 97 | 0.31 |
| 436671 | 0 | 0 | 21 | 31 | 54 | 73 | 77 | 83 | 88 | 97 | 0.31 |
| 444661 | 0 | 10 | 25 | 53 | 66 | 73 | 87 | 96 | 99 | 99 | 0.16 |
| 419641 | 5 | 23 | 33 | 48 | 44 | 75 | 79 | 90 | 94 | 98 | 0.17 |
| 436665 | 26 | 37 | 47 | 44 | 65 | 83 | 89 | 94 | 98 | 98 | 0.07 |

ISIS 387916, ISIS 388241, ISIS 437168, and ISIS 437175 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM, and 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15.1 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.1 expressed in µM.

TABLE 15.1

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 22 | 63 | 70 | 83 | 95 | 96 | 0.62 |
| 388241 | 17 | 45 | 65 | 87 | 96 | 97 | 0.56 |
| 437175 | 47 | 31 | 56 | 60 | 79 | 91 | 1.19 |
| 437168 | 32 | 46 | 64 | 81 | 89 | 95 | 0.59 |

ISIS 387916, ISIS 388241, ISIS 437441, and ISIS 437442 were further tested for their effect on human huntingtin mRNA in vitro. Cultured GM04281 fibroblasts were tested in a similar procedure as described above. The results are presented in Table 15.2 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.2 expressed in µM.

TABLE 15.2

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 26 | 47 | 58 | 79 | 91 | 95 | 0.65 |
| 388241 | 30 | 52 | 60 | 81 | 94 | 97 | 0.55 |
| 437441 | 25 | 37 | 56 | 69 | 86 | 47 | 0.81 |
| 437442 | 39 | 43 | 47 | 70 | 85 | 50 | 0.59 |

ISIS 387916, ISIS 388241, ISIS 437175, and ISIS 437527 were further tested for their effect on human huntingtin mRNA in vitro. Cultured GM04281 fibroblasts were tested in a similar procedure as described above. The results are presented in Table 15.3 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.3 expressed in µM.

TABLE 15.3

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 40 | 45 | 47 | 76 | 92 | 96 | 0.50 |
| 388241 | 40 | 37 | 50 | 90 | 96 | 97 | 0.80 |
| 437175 | 48 | 55 | 55 | 63 | 80 | 93 | 0.37 |
| 437527 | 33 | 52 | 61 | 80 | 86 | 95 | 0.52 |

B. A549 Cells

Some of the antisense oligonucleotides described in Example 1 were tested for their effect on human huntingtin mRNA in vitro. Cultured A549 cells at a density of 4,000 cells per well were transfected using lipofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 16 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 16 expressed in nM.

TABLE 16

Dose dependent reduction of huntingtin mRNA in A549 cells

| ISIS No. | 7.4074 nM | 22.222 nM | 66.667 nM | 200.00 nM | $IC_{50}$ (nM) |
|---|---|---|---|---|---|
| 387916 | 12 | 37 | 76 | 92 | 33 |
| 419640 | 21 | 45 | 73 | 93 | 27 |
| 419641 | 34 | 60 | 83 | 96 | 15 |
| 419642 | 30 | 58 | 85 | 95 | 16 |

ISIS 387916, ISIS 388241, and ISIS 437507 were further tested for their effect on human huntingtin mRNA in vitro. Cultured A549 cells at a density of 20,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 17 expressed as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 17 expressed in µM.

TABLE 17

Dose dependent reduction of huntingtin mRNA in A549 cells

| ISIS No. | 250 nM | 500 nM | 1000 nM | 2000 nM | 4000 nM | 8000 nM | $IC_{50}$ (µM) |
|---|---|---|---|---|---|---|---|
| 387916 | 15 | 17 | 25 | 36 | 52 | 75 | 3.09 |
| 388241 | 12 | 22 | 38 | 58 | 77 | 91 | 1.43 |
| 437507 | 25 | 28 | 38 | 57 | 58 | 76 | 1.84 |

C. LLC-MK2 Cells

Some of the antisense oligonucleotides described in Example 1 and targeted to a human huntingtin nucleic acid were tested for their effect on rhesus monkey huntingtin mRNA in vitro. Cultured LLC-MK2 cells at a density of 25,000 cells per well were transfected using electroporation with 625 nM, 1250 nM, 2500 nM, 5000 nM, 10,000 nM, or 20,000 nM of antisense oligonucleotide. After a treatment period of approximately 16 hours, RNA was isolated from the cells and huntingtin mRNA levels were measured by quantitative real-time PCR. Human primer probe set RTS2686 (forward sequence GTCTGAGCCTCTCTCGGT-CAA, designated herein as SEQ ID NO: 40; reverse sequence AAGGGATGCTGGGCTCTGT, designated herein as SEQ ID NO: 41; probe sequence AGCAAAGCTTGGTGTCTTGGCACTGTTAGTX, designated herein as SEQ ID NO: 42) was used to measure mRNA levels. Huntingtin mRNA levels were adjusted according to total RNA content, as measured by RIBOGREEN®. Results are presented in Table 18 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 18 expressed in µM.

TABLE 18

Dose dependent reduction of huntingtin mRNA in LLC-MK2 cells

| ISIS No. | 625 nM | 1250 nM | 2500 nM | 5000 nM | 10000 nM | 20000 nM | $IC_{50}$ (MM) |
|---|---|---|---|---|---|---|---|
| 388241 | 21 | 12 | 35 | 46 | 46 | 94 | 4.1 |
| 444591 | 37 | 46 | 51 | 52 | 82 | 96 | 1.9 |
| 419641 | 32 | 52 | 69 | 87 | 94 | 97 | 1.2 |
| 444661 | 45 | 59 | 66 | 85 | 91 | 95 | 0.8 |
| 419642 | 6 | 3 | 56 | 81 | 91 | 98 | 2.9 |
| 436665 | 40 | 43 | 70 | 73 | 84 | 89 | 1.2 |
| 436671 | 31 | 51 | 68 | 82 | 90 | 97 | 1.2 |
| 436689 | 24 | 37 | 59 | 74 | 89 | 98 | 1.9 |
| 437507 | 21 | 15 | 11 | 33 | 55 | 92 | 6.4 |
| 443139 | 31 | 36 | 37 | 56 | 76 | 97 | 2.6 |

ISIS 387916, ISIS 388241, ISIS 436684, ISIS 437168, ISIS 437175, ISIS 437441, ISIS 437507, ISIS 437527, ISIS 444578, ISIS 444584, ISIS 444591, and ISIS 444607 were further tested for their effect on rhesus monkey huntingtin mRNA in vitro. Cultured LLC-MK2 cells were tested in a similar procedure as described above. The results are presented in Table 19 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 19 expressed in µM.

TABLE 19

Dose dependent reduction of huntingtin mRNA in LLC-MK2 cells

| ISIS No. | 625.0 nM | 1250.0 nM | 2500.0 nM | 5000.0 nM | 10000.0 nM | 20000.0 nM | $IC_{50}$ |
|---|---|---|---|---|---|---|---|
| 387916 | 23 | 42 | 57 | 81 | 88 | 96 | 1.95 |
| 388241 | 6 | 12 | 37 | 43 | 62 | 84 | 5.32 |
| 437168 | 72 | 47 | 60 | 78 | 83 | 92 | 1.43 |
| 437175 | 27 | 48 | 36 | 56 | 68 | 78 | 3.58 |
| 437441 | 29 | 34 | 50 | 67 | 56 | 85 | 2.43 |
| 437507 | 18 | 29 | 18 | 33 | 45 | 66 | 6.12 |
| 437527 | 36 | 36 | 48 | 57 | 81 | 90 | 2.71 |
| 436684 | 0 | 12 | 24 | 29 | 36 | 49 | n.d. |
| 444578 | 34 | 40 | 65 | 74 | 82 | 87 | 1.70 |
| 444584 | 28 | 38 | 68 | 75 | 90 | 94 | 1.69 |
| 444591 | 25 | 45 | 55 | 74 | 85 | 94 | 1.84 |
| 444607 | 41 | 54 | 76 | 87 | 92 | 94 | 0.96 | n.d = $IC_{50}$ could not be measured for that compound

ISIS 387916, ISIS 388241, ISIS 444608, ISIS 444615, ISIS 444618, ISIS 444627, ISIS 444652, ISIS 444658, ISIS 444659, ISIS 444660, and ISIS 444661 were further tested for their effect on rhesus monkey huntingtin mRNA in vitro. Cultured LLC-MK2 cells were tested in a similar procedure as described above. The results are presented in Table 20 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 20 expressed in µM.

TABLE 20

Dose dependent reduction of huntingtin mRNA in LLC-MK2 cells

| ISIS No | 625.0 nM | 1250.0 nM | 2500.0 nM | 5000.0 nM | 10000.0 nM | 20000.0 nM | $IC_{50}$ |
|---|---|---|---|---|---|---|---|
| 387916 | 35 | 44 | 68 | 74 | 90 | 96 | 1.35 |
| 388241 | 23 | 37 | 54 | 56 | 68 | 89 | 2.64 |
| 444608 | 43 | 50 | 64 | 83 | 90 | 95 | 1.07 |
| 444615 | 29 | 45 | 55 | 76 | 90 | 97 | 1.67 |
| 444618 | 30 | 34 | 57 | 73 | 89 | 95 | 1.66 |
| 444627 | 35 | 56 | 76 | 90 | 97 | 98 | 1.00 |
| 444652 | 32 | 55 | 66 | 55 | 92 | 98 | 1.23 |
| 444658 | 50 | 62 | 80 | 90 | 95 | 97 | 0.55 |
| 444659 | 31 | 56 | 68 | 86 | 95 | 97 | 1.17 |
| 444660 | 38 | 49 | 62 | 86 | 89 | 96 | 1.26 |
| 444661 | 41 | 50 | 75 | 68 | 95 | 97 | 0.95 |

ISIS 387916, ISIS 419627, ISIS 419628, ISIS 419629, ISIS 419630, ISIS 419636, ISIS 419637, ISIS 419640, ISIS 419641, and ISIS 419642 were further tested for their effect on rhesus monkey huntingtin mRNA in vitro. Cultured LLC-MK2 cells at a density of 3,000 cells per well were transfected using lipofectin transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 21 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 21 expressed in nM.

TABLE 21

Dose dependent reduction of huntingtin mRNA in LLC-MK2 cells

| ISIS No. | 6.25 nM | 12.5 nM | 25.0 nM | 50.0 nM | 100.0 nM | 200.0 nM | IC$_{50}$ |
|---|---|---|---|---|---|---|---|
| 387916 | 1 | 37 | 37 | 53 | 84 | 90 | 35 |
| 419627 | 0 | 9 | 18 | 45 | 58 | 72 | 75 |
| 419628 | 9 | 30 | 49 | 63 | 73 | 77 | 31 |
| 419629 | 9 | 16 | 40 | 56 | 80 | 85 | 36 |
| 419630 | 17 | 8 | 43 | 58 | 71 | 81 | 40 |
| 419636 | 23 | 25 | 38 | 55 | 72 | 78 | 37 |
| 419637 | 10 | 35 | 31 | 62 | 78 | 76 | 33 |
| 419640 | 3 | 28 | 39 | 59 | 74 | 87 | 36 |
| 419641 | 11 | 34 | 51 | 65 | 85 | 87 | 26 |
| 419642 | 25 | 30 | 49 | 65 | 85 | 88 | 24 |

ISIS 387916, ISIS 419641, and ISIS 436689 were further tested for their effect on rhesus monkey huntingtin mRNA in vitro. Cultured LLC-MK2 cells at a density of 3,000 cells per well were transfected using LipofectAMINE2000 transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 22 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 22 expressed in nM.

TABLE 22

Dose dependent reduction of huntingtin mRNA in LLC-MK2 cells

| ISIS No | 6.25 nM | 12.5 nM | 25 nM | 50 nM | 100 nM | 200 nM | IC$_{50}$ (nM) |
|---|---|---|---|---|---|---|---|
| 387916 | 0 | 50 | 31 | 68 | 83 | 90 | 47 |
| 419641 | 28 | 23 | 28 | 51 | 65 | 81 | 74 |
| 436689 | 16 | 30 | 29 | 48 | 67 | 83 | 69 |

ISIS 387916, ISIS 388241, ISIS 436665, ISIS 436671, and ISIS 436689 were further tested for their effect on rhesus monkey huntingtin mRNA in vitro. Cultured LLC-MK2 cells at a density of 3,000 cells per well were transfected using lipofectin transfection reagent with 4.6875 nM, 9.375 nM, 18.75 nM, 37.5 nM, 75 nM, or 150 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 23 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 23 expressed in nM.

TABLE 23

Dose dependent reduction of huntingtin mRNA in LLC-MK2 cells

| ISIS No. | 4.6875 nM | 9.375 nM | 18.75 nM | 37.5 nM | 75.0 nM | 150.0 nM | IC$_{50}$ (nM) |
|---|---|---|---|---|---|---|---|
| 387916 | 7 | 6 | 38 | 59 | 82 | 91 | 32 |
| 388241 | 0 | 0 | 5 | 35 | 62 | 81 | 60 |
| 436665 | 7 | 0 | 36 | 59 | 64 | 69 | 37 |
| 436671 | 21 | 7 | 35 | 59 | 80 | 86 | 31 |
| 436689 | 38 | 45 | 45 | 59 | 76 | 86 | 15 |

D. BACHD Transgenic Mouse Hepatocyes

Some of the antisense oligonucleotides described in Example 1 and targeted to a human huntingtin nucleic acid were tested for their effect on human huntingtin mRNA in vitro. Cultured BACHD mouse hepatocytes at a density of 10,000 cells per well were transfected using cytofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 24 as percent inhibition of huntingtin mRNA, relative to untreated control cells, and demonstrate antisense oligonucleotide-mediated dose-dependent reduction of huntingtin mRNA levels. The data presented is the average of two experiments. The IC$_{50}$ of each antisense oligonucleotide is also presented in Table 24 expressed in nM.

TABLE 24

Dose dependent reduction of huntingtin mRNA in BACHD transgenic murine hepatocytes

| ISIS No. | 7.4074 nM | 22.222 nM | 66.667 nM | 200.00 nM | IC$_{50}$ (nM) |
|---|---|---|---|---|---|
| 387916 | 8 | 19 | 58 | 89 | 40 |
| 419640 | 15 | 30 | 64 | 93 | 33 |
| 419641 | 20 | 35 | 73 | 97 | 31 |
| 419642 | 3 | 29 | 70 | 96 | 43 |

ISIS 387916, ISIS 388241, and ISIS 419641 were further tested for their effect on human huntingtin mRNA in vitro. Cultured BACHD mouse hepatocytes at a density of 10,000 cells per well were transfected using cytofectin transfection reagent with 12.5 nM, 25 nM, 50 nM, 100 nM or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 25 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 25 expressed in nM.

TABLE 25

Dose dependent reduction of huntingtin mRNA in
BACHD transgenic murine hepatocytes

| ISIS No. | 12.5 nM | 25 nM | 50 Nm | 100 nM | 200 nM | IC$_{50}$ (nM) |
|---|---|---|---|---|---|---|
| 387916 | 0 | 37 | 51 | 78 | 91 | 51 |
| 388241 | 0 | 10 | 45 | 70 | 92 | 68 |
| 419641 | 17 | 38 | 70 | 88 | 96 | 34 |

ISIS 387916, ISIS 388241, ISIS 419641, ISIS 436665, ISIS 436671, and ISIS 436689 were further tested for their effect on human huntingtin mRNA in vitro. Cultured BACHD mouse hepatocytes were tested in an identical manner as described above. The results are presented in Table 26 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 26 expressed in nM.

TABLE 26

Dose dependent reduction of huntingtin mRNA
in BACHD transgenic murine hepatocytes

| ISIS No. | 12.5 nM | 25 nM | 50 nM | 100 nM | 200 nM | IC$_{50}$ (nM) |
|---|---|---|---|---|---|---|
| 387916 | 19 | 48 | 64 | 86 | 93 | 32 |
| 388241 | 20 | 34 | 54 | 81 | 93 | 38 |
| 419641 | 38 | 54 | 70 | 85 | 95 | 21 |
| 436665 | 32 | 40 | 67 | 84 | 93 | 29 |
| 436671 | 32 | 42 | 58 | 78 | 91 | 32 |
| 436689 | 35 | 44 | 70 | 88 | 96 | 25 |

ISIS 387916, ISIS 419640, ISIS 419641, and ISIS 419642 were further tested for their effect on mouse huntingtin mRNA in vitro. Cultured BACHD mouse hepatocytes at a density of 20,000 cells per well were transfected using cytofectin transfection reagent with 6.667 nM, 20 nM, 60 nM, or 180 nM of antisense oligonucleotide. After a treatment period of approximately 16 hours, RNA was isolated from the cells and huntingtin mRNA levels were measured by quantitative real-time PCR. Murine primer probe set RTS2633 (forward sequence CAGAGCTGGTCAACCGTATCC, designated herein as SEQ ID NO: 43; reverse sequence GGCTTAAACAGGGAGCCAAAA, designated herein as SEQ ID NO: 44; probe sequence ACTTCATGATGAGCTCGGAGTTCAACX, designated herein as SEQ ID NO: 45) was used to measure mRNA levels. Huntingtin mRNA levels were adjusted according to total RNA content, as measured by RIBOGREEN®. Results are presented in Table 27 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 27 expressed in nM.

TABLE 27

Dose dependent reduction of huntingtin mRNA
in BACHD transgenic murine hepatocytes

| ISIS No. | 6.667 nM | 20 nM | 60 nM | 180 nM | IC$_{50}$ (nM) |
|---|---|---|---|---|---|
| 387916 | 15 | 15 | 68 | 94 | 37 |
| 419640 | 4 | 39 | 73 | 94 | 32 |
| 419641 | 16 | 45 | 81 | 96 | 24 |
| 419642 | 23 | 39 | 75 | 93 | 25 |

Example 3: Systemic Administration of Antisense Oligonucleotides Against Huntingtin mRNA in BACHD Mice Of the about seventeen hundred newly designed antisense compounds, sixty six compounds were selected based on in vitro potency compared to ISIS 387916 for testing in systemic tolerability screens.

BACHD mice were treated with ISIS oligonucleotides and evaluated for changes in the levels of various metabolic markers as well as inhibition of huntingtin mRNA in the liver. Antisense oligonucleotides which caused adverse changes in body weight, organ weight or in the levels of metabolic markers were deemed unsuitable for utilization in further studies.

Study 1.

Treatment

Nineteen groups of four BACHD mice each were injected intraperitoneally with 12.5 mg/kg of ISIS 387916, ISIS 388241, ISIS 419629, ISIS 419637, ISIS 436684, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 28 and 29 and were calculated as percent inhibition of human and murine huntingtin expression levels respectively, relative to the PBS control. All the antisense oligonucleotides effect significant inhibition of human huntingtin mRNA levels. ISIS 388241 has more than three mismatches with the murine huntingtin mRNA (SEQ ID NO: 3) and therefore did not show significant inhibition of murine mRNA levels compared to the control.

TABLE 28

Percent inhibition of human huntingtin
mRNA in BACHD mice

| ISIS No. | % inhibition |
|---|---|
| 387916 | 82 |
| 388241 | 52 |
| 419629 | 80 |

TABLE 28-continued

Percent inhibition of human huntingtin mRNA in BACHD mice

| ISIS No. | % inhibition |
|---|---|
| 419637 | 83 |
| 436684 | 55 |
| 444578 | 70 |
| 444584 | 62 |
| 444591 | 54 |
| 444607 | 76 |
| 444608 | 61 |
| 444615 | 89 |
| 444618 | 91 |
| 444627 | 92 |
| 444652 | 79 |
| 444658 | 62 |
| 444659 | 74 |
| 444660 | 66 |
| 444661 | 72 |
| 444663 | 77 |

TABLE 29

Percent inhibition of murine huntingtin mRNA in BACHD mice

| ISIS No. | % inhibition |
|---|---|
| 387916 | 77 |
| 419629 | 75 |
| 419637 | 87 |
| 436684 | 32 |
| 444578 | 64 |
| 444584 | 20 |
| 444591 | 32 |
| 444607 | 76 |
| 444608 | 66 |
| 444615 | 60 |
| 444618 | 88 |
| 444627 | 58 |
| 444652 | 66 |
| 444658 | 53 |
| 444659 | 62 |
| 444660 | 47 |
| 444661 | 67 |
| 444663 | 60 |

Organ Weight Measurements

Liver, spleen and kidney weights were measured at the end of the study, and are presented in Table 30 as a percent of the saline control normalized to body weight.

TABLE 30

Percent change in organ weight of BACHD mice after antisense oligonucleotide treatment

| ISIS No. | Liver | Spleen | Kidney |
|---|---|---|---|
| 387916 | −5 | −13 | +6 |
| 388241 | −1 | +14 | −5 |
| 419629 | +5 | +13 | −12 |
| 419637 | −6 | −17 | −25 |
| 436684 | −2 | −3 | +6 |
| 444578 | +11 | +18 | +1 |
| 444584 | +8 | +54 | +1 |
| 444591 | +4 | −4 | −3 |
| 444607 | +3 | +22 | −8 |
| 444608 | +6 | +18 | −3 |
| 444615 | +6 | +1 | +3 |
| 444618 | +11 | +0 | −2 |
| 444627 | +3 | −14 | +14 |
| 444652 | −11 | −4 | −18 |
| 444658 | −1 | 0 | −16 |
| 444659 | +1 | +15 | −2 |
| 444660 | −5 | +4 | −6 |
| 444661 | −1 | +7 | −1 |
| 444663 | +7 | +10 | +8 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, NY). Measurements of alanine transaminase (ALT) and aspartate transaminase (AST) are expressed in IU/L and the results are presented in Table 31.

TABLE 31

Effect of antisense oligonucleotide treatment on markers of liver function

| | ALT | AST |
|---|---|---|
| PBS | 40 | 69 |
| 387916 | 69 | 84 |
| 388241 | 42 | 76 |
| 419629 | 51 | 71 |
| 419637 | 59 | 86 |
| 436684 | 60 | 87 |
| 444578 | 62 | 93 |
| 444584 | 48 | 76 |
| 444591 | 39 | 53 |
| 444607 | 51 | 111 |
| 444608 | 48 | 75 |
| 444615 | 74 | 95 |
| 444618 | 687 | 908 |
| 444627 | 105 | 127 |
| 444652 | 54 | 64 |
| 444658 | 46 | 59 |
| 444659 | 90 | 138 |
| 444660 | 34 | 64 |
| 444661 | 49 | 99 |
| 444663 | 90 | 164 |

Study 2

Treatment

Fourteen groups of four BACHD mice each were injected intraperitoneally with 12.5 mg/kg or 50 mg/kg of ISIS 419581, ISIS 419602, ISIS 419628, ISIS 419629, ISIS 419640, ISIS 419641, or ISIS 419642 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 32 and 33 and were calculated as percent inhibition of human and murine huntingtin expression levels respectively, relative to the PBS control.

TABLE 32

Percent inhibition of human huntingtin mRNA in BACHD mice

| ISIS No. | Dose (mg/kg) | % inhibition |
|---|---|---|
| 387916 | 12.5 | 71 |
| 419581 | 12.5 | 54 |
|  | 50 | 68 |
| 419602 | 12.5 | 72 |
|  | 50 | 77 |
| 419628 | 12.5 | 65 |
|  | 50 | 76 |
| 419629 | 12.5 | 87 |
|  | 50 | 93 |
| 419640 | 12.5 | 69 |
|  | 50 | 79 |
| 419641 | 12.5 | 61 |
|  | 50 | 80 |
| 419642 | 12.5 | 76 |
|  | 50 | 83 |

TABLE 33

Percent inhibition of murine huntingtin mRNA in BACHD mice

| ISIS No. | Dose (mg/kg) | % inhibition |
|---|---|---|
| 387916 | 12.5 | 70 |
| 419581 | 12.5 | 42 |
|  | 50 | 86 |
| 419602 | 12.5 | 77 |
|  | 50 | 85 |
| 419628 | 12.5 | 67 |
|  | 50 | 86 |
| 419629 | 12.5 | 90 |
|  | 50 | 93 |
| 419640 | 12.5 | 63 |
|  | 50 | 84 |
| 419641 | 12.5 | 52 |
|  | 50 | 81 |
| 419642 | 12.5 | 56 |
|  | 50 | 83 |

Organ Weight Measurements

Liver, spleen and kidney weights were measured at the end of the study, and are presented in Table 34 as a percent of the saline control normalized to body weight.

TABLE 34

Percent change in organ weight of BACHD mice after antisense oligonucleotide treatment

| ISIS No. | Dose (mg/kg) | Liver | Spleen | Kidney |
|---|---|---|---|---|
| 387916 | 12.5 | −9 | 3 | −4 |
| 419581 | 12.5 | −2 | −6 | −1 |
|  | 50 | 14 | −1 | −11 |
| 419602 | 12.5 | 10 | 1 | −2 |
|  | 50 | 28 | 9 | −3 |
| 419628 | 12.5 | −2 | −7 | −2 |
|  | 50 | −3 | 7 | −9 |
| 419629 | 12.5 | −7 | −5 | −10 |
|  | 50 | 16 | 0 | −8 |
| 419640 | 12.5 | −5 | −2 | −8 |
|  | 50 | 1 | −20 | −4 |
| 419641 | 12.5 | −7 | −10 | −11 |
|  | 50 | −2 | −13 | −9 |
| 419642 | 12.5 | −11 | −21 | −19 |
|  | 50 | −1 | −8 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, NY). Measurements of ALT and AST are expressed in IU/L and the results are presented in Table 35.

TABLE 35

Effect of antisense oligonucleotide treatment on markers of liver function

| | Dose (mg/kg) | ALT | AST |
|---|---|---|---|
| PBS |  | 44 | 80 |
| 387916 | 12.5 | 44 | 75 |
| 419581 | 12.5 | 56 | 101 |
|  | 50 | 390 | 281 |
| 419602 | 12.5 | 86 | 108 |
|  | 50 | 240 | 229 |
| 419628 | 12.5 | 52 | 110 |
|  | 50 | 51 | 73 |
| 419629 | 12.5 | 104 | 118 |
|  | 50 | 1262 | 1150 |
| 419640 | 12.5 | 36 | 65 |
|  | 50 | 38 | 55 |
| 419641 | 12.5 | 56 | 103 |
|  | 50 | 57 | 172 |
| 419642 | 12.5 | 40 | 64 |
|  | 50 | 47 | 101 |

Study 3

Treatment

Eighteen groups of four BACHD mice each were injected intraperitoneally with 12.5 mg/kg or 50 mg/kg of ISIS 388250, ISIS 388251, ISIS 388263, ISIS 388264, ISIS 419641, ISIS 436645, ISIS 436649, ISIS 436668, or ISIS 436689 twice a week for 2 weeks. A group of four BACHD mice was injected intraperitoneally with 12.5 mg/kg of ISIS 388241 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 36 and 37 and were calculated as percent inhibition of human and murine huntingtin expression levels respectively, relative to the PBS control. All the antisense oligonucleotides effect significant inhibition of human huntingtin mRNA levels. ISIS 388241, ISIS 388250, ISIS 388251, ISIS 388263, ISIS 388264, and ISIS 436645 have more than three mismatches with the murine huntingtin mRNA (SEQ ID NO: 3) and therefore did not show significant inhibition of murine mRNA levels compared to the control. ISIS 436649 and ISIS 436689 have three mismatches with the murine huntingtin mRNA (SEQ ID NO: 3) and therefore did not show significant inhibition of murine mRNA levels compared to the control.

TABLE 36

Percent inhibition of human huntingtin mRNA in BACHD mice

| ISIS No. | Dose (mg/kg) | % inhibition |
|---|---|---|
| 388241 | 12.5 | 32 |
| 388250 | 12.5 | 21 |
|  | 50 | 45 |
| 388251 | 12.5 | 30 |
|  | 50 | 34 |
| 388263 | 12.5 | 29 |
|  | 50 | 35 |
| 388264 | 12.5 | 35 |
|  | 50 | 42 |
| 419641 | 12.5 | 71 |
|  | 50 | 73 |
| 436645 | 12.5 | 43 |
|  | 50 | 48 |
| 436649 | 12.5 | 40 |
|  | 50 | 38 |
| 436668 | 12.5 | 45 |
|  | 50 | 69 |
| 436689 | 12.5 | 62 |
|  | 50 | 78 |

TABLE 37

Percent inhibition of murine huntingtin mRNA in BACHD mice

| ISIS No. | Dose (mg/kg) | % inhibition |
|---|---|---|
| 419641 | 12.5 | 68 |
|  | 50 | 77 |
| 436668 | 12.5 | 41 |
|  | 50 | 62 |

Organ Weight Measurements

Liver, spleen and kidney weights were measured at the end of the study, and are presented in Table 38 as a percent of the saline control normalized to body weight. Mice treated with ISIS 388263 and ISIS 436645 suffered increases in liver weight at the 50 mg/kg dose compared to the PBS control.

TABLE 38

Percent change in organ weight of BACHD mice after antisense oligonucleotide treatment

| ISIS No. | Dose (mg/kg) | Liver | Spleen | Kidney |
|---|---|---|---|---|
| 388241 | 12.5 | 1 | 6 | 9 |
| 388250 | 12.5 | 2 | 1 | -2 |
|  | 50 | 1 | 30 | 3 |
| 388251 | 12.5 | 4 | -8 | 1 |
|  | 50 | 19 | 19 | 2 |
| 388263 | 12.5 | 4 | 8 | 9 |
|  | 50 | 23 | 52 | 1 |
| 388264 | 12.5 | 2 | -2 | 3 |
|  | 50 | 12 | 9 | 6 |
| 419641 | 12.5 | -1 | -9 | 3 |
|  | 50 | 2 | -4 | 3 |
| 436645 | 12.5 | 8 | 6 | 5 |
|  | 50 | 26 | 25 | 9 |
| 436649 | 12.5 | 1 | 0 | 6 |
|  | 50 | 0 | 1 | 3 |
| 436668 | 12.5 | 1 | 5 | 10 |
|  | 50 | -2 | 3 | 11 |
| 436689 | 12.5 | -3 | -5 | 4 |
|  | 50 | 6 | 11 | 5 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, NY). Measurements of alanine transaminase (ALT) and aspartate transaminase (AST) are expressed in IU/L and the results are presented in Table 39.

TABLE 39

Effect of antisense oligonucleotide treatment on markers of liver function

| | Dose (mg/kg) | ALT | AST |
|---|---|---|---|
| PBS |  | 43 | 76 |
| 388241 | 12.5 | 43 | 88 |
| 388250 | 12.5 | 37 | 55 |
|  | 50 | 44 | 89 |
| 388251 | 12.5 | 42 | 98 |
|  | 50 | 67 | 91 |
| 388263 | 12.5 | 51 | 90 |
|  | 50 | 55 | 93 |
| 388264 | 12.5 | 31 | 59 |
|  | 50 | 65 | 90 |
| 419641 | 12.5 | 39 | 70 |
|  | 50 | 42 | 83 |
| 436645 | 12.5 | 43 | 82 |
|  | 50 | 179 | 143 |
| 436649 | 12.5 | 35 | 47 |
|  | 50 | 38 | 76 |
| 436668 | 12.5 | 36 | 73 |
|  | 50 | 28 | 57 |
| 436689 | 12.5 | 31 | 52 |
|  | 50 | 49 | 164 |

Study 4

Treatment

Eighteen groups of four BACHD mice each were injected intraperitoneally with 12.5 mg/kg or 50 mg/kg of ISIS 388241, ISIS 437123, ISIS 437132, ISIS 437140, ISIS 437442, ISIS 437446, ISIS 437477, ISIS 437478, or ISIS 437490 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 40 and 41 and were calculated as percent inhibition of human and murine huntingtin expression levels respectively, relative to the PBS control. ISIS 388241 and ISIS 437490 have more than three mismatches with the murine huntingtin mRNA (SEQ ID NO: 3) and therefore did not show significant inhibition of murine mRNA levels compared to the control. ISIS 437132 has three mismatches with the murine huntingtin mRNA (SEQ ID NO: 3) and therefore did not show significant inhibition of murine mRNA levels compared to the control. ISIS 437123 and ISIS 437140 have two mismatches with the murine huntingtin mRNA (SEQ ID NO: 3) and do not show significant inhibition of murine mRNA levels compared to the control.

TABLE 40

Percent inhibition of human huntingtin mRNA in BACHD mice

| ISIS No. | Dose (mg/kg) | % inhibition |
|---|---|---|
| 387916 | 12.5 | 51 |
| 388241 | 12.5 | 47 |
|  | 50 | 67 |
| 437123 | 12.5 | 0 |
|  | 50 | 21 |
| 437132 | 12.5 | 31 |
|  | 50 | 33 |
| 437140 | 12.5 | 7 |
|  | 50 | 32 |
| 437442 | 12.5 | 42 |
|  | 50 | 85 |
| 437446 | 12.5 | 39 |
|  | 50 | 70 |
| 437477 | 12.5 | 52 |
|  | 50 | 75 |
| 437478 | 12.5 | 54 |
|  | 50 | 78 |
| 437490 | 12.5 | 42 |
|  | 50 | 44 |

TABLE 41

Percent inhibition of murine huntingtin mRNA in BACHD mice

| ISIS No. | Dose (mg/kg) | % inhibition |
|---|---|---|
| 387916 | 12.5 | 48 |
| 437442 | 12.5 | 27 |
|  | 50 | 76 |
| 437446 | 12.5 | 38 |
|  | 50 | 71 |
| 437477 | 12.5 | 63 |
|  | 50 | 87 |
| 437478 | 12.5 | 60 |
|  | 50 | 89 |

Organ Weight Measurements

Liver, spleen and kidney weights were measured at the end of the study, and are presented in Table 42 as a percent of the saline control normalized to body weight.

TABLE 42

Percent change in organ weight of BACHD mice after antisense oligonucleotide treatment

| ISIS No. | Dose (mg/kg) | Liver | Spleen | Kidney |
|---|---|---|---|---|
| 387916 | 12.5 | 1 | 6 | 12 |
| 388241 | 12.5 | −3 | 16 | −2 |
|  | 50 | −6 | 10 | 0 |
| 437123 | 12.5 | −4 | 0 | 4 |
|  | 50 | 4 | 0 | −4 |
| 437132 | 12.5 | −2 | −3 | −5 |
|  | 50 | 2 | −6 | −2 |
| 437140 | 12.5 | −4 | 11 | −3 |
|  | 50 | 4 | 5 | −5 |
| 437442 | 12.5 | −10 | 9 | 3 |
|  | 50 | −3 | −20 | −10 |
| 437446 | 12.5 | −6 | 7 | 2 |
|  | 50 | −4 | 1 | −1 |
| 437477 | 12.5 | 1 | −2 | 0 |
|  | 50 | 25 | −9 | −6 |
| 437478 | 12.5 | −7 | −4 | −9 |
|  | 50 | 22 | 4 | 3 |
| 437490 | 12.5 | −5 | 0 | −5 |
|  | 50 | −7 | 3 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, NY). Measurements of alanine transaminase (ALT) and aspartate transaminase (AST) are expressed in IU/L and the results are presented in Table 43.

TABLE 43

Effect of antisense oligonucleotide treatment on markers of liver function

|  | Dose (mg/kg) | ALT | AST |
|---|---|---|---|
| PBS |  | 32 | 58 |
| 387916 | 12.5 | 40 | 122 |
| 388241 | 12.5 | 39 | 93 |
|  | 50 | 28 | 62 |
| 437123 | 12.5 | 38 | 88 |
|  | 50 | 34 | 66 |
| 437132 | 12.5 | 34 | 52 |
|  | 50 | 30 | 52 |
| 437140 | 12.5 | 30 | 62 |
|  | 50 | 40 | 63 |
| 437442 | 12.5 | 40 | 106 |
|  | 50 | 63 | 119 |
| 437446 | 12.5 | 35 | 119 |
|  | 50 | 35 | 89 |
| 437477 | 12.5 | 39 | 68 |
|  | 50 | 52 | 162 |
| 437478 | 12.5 | 37 | 53 |
|  | 50 | 55 | 71 |
| 437490 | 12.5 | 48 | 71 |
|  | 50 | 34 | 59 |

Study 5

Treatment

Eleven groups of four BACHD mice each were injected intraperitoneally with 12.5 mg/kg of ISIS 388241, ISIS 419640, ISIS 419641, ISIS 419642, ISIS 436665, ISIS 436671, ISIS 436689, ISIS 437507, ISIS 443139, ISIS 444591, or ISIS 444661 twice a week for 2 weeks. A control group of four mice was injected intraperitoneally with phosphate buffered saline (PBS) twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 44 and 45 and were calculated as percent inhibition of human and murine huntingtin expression levels respectively, relative to the PBS control.

All the antisense oligonucleotides effect significant inhibition of human huntingtin mRNA levels. ISIS 388241, ISIS 437507, and ISIS 443139 have more than three mismatches with the murine huntingtin mRNA (SEQ ID NO: 3) and therefore do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 44

Percent inhibition of human huntingtin mRNA in BACHD mice

| ISIS No. | % inhibition |
|---|---|
| 388241 | 53 |
| 419640 | 34 |
| 419641 | 63 |
| 419642 | 55 |
| 436665 | 63 |
| 436671 | 66 |
| 436689 | 57 |
| 437507 | 54 |
| 443139 | 39 |
| 444591 | 48 |
| 444661 | 50 |

TABLE 45

Percent inhibition of murine huntingtin mRNA in BACHD mice

| ISIS No. | % inhibition |
|---|---|
| 419640 | 24 |
| 419641 | 51 |
| 419642 | 34 |
| 436665 | 49 |
| 436671 | 63 |
| 444591 | 41 |
| 444661 | 46 |

Body Weight and Organ Weight Measurements

The body weights of the mice were measured at the onset of the study and subsequently twice a week. The body weights of the mice are presented in Table 46 and are expressed as a percent change over the weights taken at the start of the study. The results indicate that treatment with these oligonucleotides did not cause any adverse change in body weight of the mice throughout the study.

TABLE 46

Percent change in body weight of BACHD mice after antisense oligonucleotide treatment

| | day 4 | day 7 | day 10 | day 12 |
|---|---|---|---|---|
| PBS | −3 | 0 | +2 | +1 |
| ISIS 388241 | −2 | −1 | −1 | +1 |
| ISIS 419640 | +1 | 0 | +3 | +4 |
| ISIS 419641 | +1 | +1 | +2 | 0 |
| ISIS 419642 | −3 | −2 | +1 | −5 |

TABLE 46-continued

Percent change in body weight of BACHD mice after antisense oligonucleotide treatment

| | day 4 | day 7 | day 10 | day 12 |
|---|---|---|---|---|
| ISIS 436665 | +1 | +4 | +5 | +1 |
| ISIS 436671 | +1 | +2 | +5 | +4 |
| ISIS 436689 | +1 | +3 | 0 | −1 |
| ISIS 437507 | −1 | −2 | +2 | −2 |
| ISIS 443139 | −2 | +6 | +4 | +1 |
| ISIS 444591 | −1 | +1 | +2 | 0 |
| ISIS 444661 | +1 | +3 | +2 | 0 |

Liver, spleen and kidney weights were measured at the end of the study, and are presented in Table 47 as a percent of the saline control normalized to body weight.

TABLE 47

Percent change in organ weight of BACHD mice after antisense oligonucleotide treatment

| ISIS No. | Liver | Spleen | Kidney |
|---|---|---|---|
| 388241 | +2 | +13 | −7 |
| 419640 | −2 | +12 | −12 |
| 419641 | +4 | +3 | −13 |
| 419642 | +5 | +19 | −8 |
| 436665 | −3 | +3 | −13 |
| 436671 | 0 | +1 | −18 |
| 436689 | −6 | −10 | −12 |
| 437507 | −5 | −5 | −14 |
| 443139 | −2 | −9 | −13 |
| 444591 | −2 | −10 | −12 |
| 444661 | 0 | −16 | −12 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, NY). Measurements of ALT and AST are expressed in IU/L. Plasma levels of bilirubin and albumin were also measured using the same clinical chemistry analyzer and expressed in g/dL. The results are presented in Table 48.

TABLE 48

Effect of antisense oligonucleotide treatment on markers of liver function

| | ALT | AST | Bilirubin | Albumin |
|---|---|---|---|---|
| PBS | 42.5 | 86.5 | 0.2 | 3.1 |
| ISIS 388241 | 39.3 | 54.5 | 0.3 | 3.0 |
| ISIS 419640 | 36.8 | 85.8 | 0.2 | 2.9 |
| ISIS 419641 | 50.0 | 71.8 | 0.2 | 3.0 |
| ISIS 419642 | 42.8 | 77.0 | 0.1 | 3.0 |
| ISIS 436665 | 51.5 | 123.0 | 0.2 | 3.0 |
| ISIS 436671 | 52.0 | 71.0 | 0.1 | 3.0 |
| ISIS 436689 | 38.3 | 75.3 | 0.2 | 3.1 |
| ISIS 437507 | 37.0 | 77.5 | 0.1 | 3.0 |
| ISIS 443139 | 41.3 | 124.8 | 0.2 | 3.0 |
| ISIS 444591 | 46.5 | 61.3 | 0.2 | 3.0 |
| ISIS 444661 | 67.5 | 109.8 | 0.2 | 3.1 |

Measurement of Kidney Function

To evaluate the impact of ISIS oligonucleotides on the kidney function of mice described above, plasma concentrations of blood urea nitrogen (BUN) and creatinine were measured using an automated clinical chemistry analyzer (Hitachi Olympus AU400e, Melville, NY). Results are presented in Table 49 expressed in mg/dL.

TABLE 49

Effect of antisense oligonucleotide treatment on markers of kidney function

|  | BUN | Creatinine |
|---|---|---|
| PBS | 24.0 | 0.17 |
| ISIS 388241 | 22.6 | 0.17 |
| ISIS 419640 | 21.4 | 0.16 |
| ISIS 419641 | 19.9 | 0.16 |
| ISIS 419642 | 23.6 | 0.18 |
| ISIS 436665 | 20.2 | 0.17 |
| ISIS 436671 | 22.6 | 0.17 |
| ISIS 436689 | 19.2 | 0.18 |
| ISIS 437507 | 19.9 | 0.16 |
| ISIS 443139 | 23.3 | 0.16 |
| ISIS 444591 | 23.5 | 0.18 |
| ISIS 444661 | 25.4 | 0.18 |

Measurement of Other Metabolic Parameters

To evaluate the impact of ISIS oligonucleotides on other metabolic functions in mice described above, plasma concentrations of glucose, cholesterol and triglycerides were measured using an automated clinical chemistry analyzer (Hitachi Olympus AU400e, Melville, NY). Results are presented in Table 50 expressed in mg/dL and demonstrate that treatment with these oligonucleotides did not cause any adverse changes in the levels of these metabolic markers between the control and treatment groups.

TABLE 50

Effect of antisense oligonucleotide treatment on metabolic markers

|  | Glucose | Cholesterol | Triglycerides |
|---|---|---|---|
| PBS | 198 | 142 | 225 |
| ISIS 388241 | 197 | 133 | 185 |
| ISIS 419640 | 198 | 132 | 189 |
| ISIS 419641 | 188 | 140 | 219 |
| ISIS 419642 | 184 | 128 | 192 |
| ISIS 436665 | 199 | 134 | 152 |
| ISIS 436671 | 196 | 148 | 174 |
| ISIS 436689 | 194 | 132 | 174 |
| ISIS 437507 | 198 | 139 | 155 |
| ISIS 443139 | 178 | 122 | 239 |
| ISIS 444591 | 202 | 145 | 263 |
| ISIS 444661 | 180 | 140 | 247 |

Example 4: Bolus Administration of Antisense Oligonucleotides Against Huntingtin mRNA to the Striatum of BACHD Mice BACHD mice were treated with ISIS oligonucleotides via bolus administration to a defined mouse brain area, the striatum, for the purpose of screening the activity of the oligonucleotides in brain tissue against human and mouse huntingtin mRNA expression.

Treatment and Surgery

Groups of four BACHD mice each were administered with ISIS 388241, ISIS 419628, ISIS 419637, ISIS 419640, ISIS 419641, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661 or ISIS 444663 delivered as a single bolus injection at 3 µg, 10 µg or 25 µg concentrations into the striatum.

A control group of 4 BACHD mice were similarly treated with PBS. ISIS 388241 was administered in seven groups of 4 mice each and the results presented are the average of the data derived from the 28 mice. ISIS 419628 was administered in 2 groups of 4 BACHD mice each and the results presented are the average of the data derived from the 8 mice. Seven days after the bolus administration, the mice were euthanized using isoflurane and the organs were removed. The animals were decapitated and the brain was removed for dissection of the striatal tissue.

RNA Analysis

RNA was extracted from striatal tissue for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. The results for human huntingtin mRNA levels are presented in Table 51 and are expressed as percent inhibition compared to the PBS control group. All the antisense oligonucleotides effect dose-dependent inhibition of human huntingtin mRNA levels. The results for murine huntingtin mRNA levels are presented in Table 52 and are expressed as percent inhibition compared to the PBS control group.

The effective doses ($ED_{50}$) of each oligonucleotide for human huntingtin mRNA and mouse huntingtin mRNA were calculated by plotting the concentrations of oligonucleotides used versus the percent inhibition of huntingtin mRNA expression levels of either species and noting the concentrations at which 50% inhibition of huntingtin mRNA expression was achieved for each species compared to the corresponding controls. The $ED_{50}$ (µg) for each antisense oligonucleotide is also presented in Tables 51 and 52 for human and murine huntingtin mRNA respectively.

ISIS 388241, ISIS 436684, ISIS 436754, ISIS 437175, ISIS 437507, ISIS 443139, and ISIS 444584 are each mismatched by 8 base pairs or more with murine huntingtin mRNA (SEQ ID NO: 3) and therefore do not show significant inhibition of murine mRNA levels compared to the control. ISIS 437168 and ISIS 437441 have 2 mismatches each with the murine huntingtin mRNA (SEQ ID NO: 3) and do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 51

Percent inhibition of human huntingtin mRNA levels in vivo and $ED_{50}$ of the antisense oligonucleotides

| ISIS No. | 3 mg | 10 mg | 25 mg | $ED_{50}$ |
|---|---|---|---|---|
| 388241 | 33 | 55 | 68 | 7.4 |
| 419628 | 49 | 58 | 83 | 5.1 |
| 419637 | 40 | 62 | 79 | 6.1 |
| 419640 | 52 | 64 | 77 | 4.8 |
| 419641 | 71 | 77 | 89 | 2.2 |
| 419642 | 67 | 70 | 83 | 3.0 |
| 436665 | 52 | 71 | 60 | 5.8 |
| 436671 | 68 | 80 | 84 | 2.4 |
| 436684 | 2 | 18 | 37 | 36.9 |

TABLE 51-continued

Percent inhibition of human huntingtin mRNA levels in vivo and ED$_{50}$ of the antisense oligonucleotides

| ISIS No. | 3 mg | 10 mg | 25 mg | ED$_{50}$ |
|---|---|---|---|---|
| 436689 | 27 | 63 | 81 | 7.0 |
| 436754 | 31 | 54 | 61 | 10.5 |
| 437168 | 2 | 49 | 60 | 15.2 |
| 437175 | 0 | 53 | 64 | 12.9 |
| 437441 | 3 | 32 | 38 | 35.3 |
| 437442 | 38 | 50 | 56 | 11.9 |
| 437507 | 38 | 59 | 79 | 6.6 |
| 437527 | 37 | 47 | 59 | 11.9 |
| 443139 | 39 | 61 | 70 | 6.7 |
| 444578 | 51 | 66 | 75 | 4.6 |
| 444584 | 30 | 63 | 71 | 7.8 |
| 444591 | 60 | 54 | 70 | 5.6 |
| 444607 | 57 | 69 | 75 | 3.2 |
| 444608 | 67 | 68 | 82 | 3.1 |
| 444615 | 47 | 55 | 91 | 5.2 |
| 444618 | 57 | 64 | 83 | 4.0 |
| 444627 | 47 | 70 | 61 | 5.0 |
| 444652 | 36 | 62 | 66 | 7.8 |
| 444658 | 60 | 66 | 79 | 3.6 |
| 444659 | 61 | 67 | 84 | 3.4 |
| 444660 | 55 | 62 | 66 | 4.2 |
| 444661 | 48 | 57 | 70 | 6.4 |
| 444663 | 42 | 60 | 80 | 5.5 |

TABLE 52

Percent inhibition of murine huntingtin mRNA levels in vivo and ED$_{50}$ of the antisense oligonucleotides

| ISIS No. | 3 mg | 10 mg | 25 mg | ED$_{50}$ |
|---|---|---|---|---|
| 419628 | 50 | 55 | 83 | 5.1 |
| 419637 | 63 | 79 | 86 | 2.6 |
| 419640 | 51 | 60 | 86 | 4.9 |
| 419641 | 65 | 80 | 87 | 2.7 |
| 419642 | 69 | 73 | 88 | 2.5 |
| 436665 | 68 | 82 | 66 | 2.7 |
| 436671 | 75 | 87 | 90 | 2 |
| 437442 | 30 | 53 | 82 | 9 |
| 437527 | 67 | 73 | 90 | 2.7 |
| 444578 | 50 | 65 | 74 | 4.9 |
| 444591 | 69 | 69 | 81 | 2.8 |
| 444607 | 57 | 70 | 75 | 3.8 |
| 444608 | 70 | 72 | 90 | 2.5 |
| 444615 | 30 | 37 | 88 | 9.5 |
| 444618 | 66 | 71 | 90 | 2.8 |
| 444627 | 41 | 60 | 57 | 8.8 |
| 444652 | 47 | 62 | 66 | 4.7 |
| 444658 | 60 | 62 | 85 | 3.9 |
| 444659 | 54 | 62 | 85 | 4.2 |
| 444660 | 42 | 48 | 64 | 9.5 |
| 444661 | 49 | 57 | 74 | 5.9 |
| 444663 | 42 | 65 | 84 | 5.1 |

The ten compounds marked with an asterisk had an improved ED$_{50}$ over ISIS 388241.

Example 5: Assay for Neurotoxic Effects of Bolus Administration of Antisense Oligonucleotides in the Striatal Tissue of Rats About 30 compounds were selected as having high tolerability and high potency. Compounds were then tested by CNS bolus injection in rat to further assess neurotoxicity.

Sprague-Dawley rats each were treated with ISIS oligonucleotides via bolus administration to a defined brain area, the striatum, for the purpose of screening for the induction of the microglial marker AIF1 as a measure of CNS toxicity.

Treatment and Surgery

Groups of four Sprague-Dawley rats were administered with ISIS 387916, ISIS 388241, ISIS 419627, ISIS 419628, ISIS 419629, ISIS 419630, ISIS 419636, ISIS 419637, ISIS 419640, ISIS 419641, ISIS 419642, ISIS 436665, ISIS 436668, ISIS 4196671, ISIS 436684, ISIS 436689, ISIS 436754, ISIS 443168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 delivered as a single bolus injection at 50 µg concentration into the striatum.

A control group of 4 rats were similarly treated with PBS. A group of 4 rats were similarly treated with ISIS 104838, an antisense oligonucleotide against TNF-α, as a negative control group. ISIS 387916 was administered in four groups of 4 rats each and the results presented are an average of the data derived from the 16 rats. ISIS 419628 was administered in two groups of 4 rats each and the results presented are the average of the data from the 8 rats. ISIS 419629, ISIS 444584 and ISIS 444618, which had toxic indicators in the systemic administration study (Example 3) were also tested in this study. Seven days after bolus administration, the rats were euthanized using isoflurane and the organs were removed. The animals were decapitated and the brain was removed for dissection of the striatal tissue.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219 (forward sequence AGGAGAAAAACAAAGAACACCAGAA, designated herein as SEQ ID NO: 46; reverse sequence CAATT-AGGGCAACTCAGAAATAGCT, designated herein as SEQ ID NO: 47; probe sequence CCAACTGGTCCCCCAGCCAAGAX, designated herein as SEQ ID NO: 48). Results were calculated as the percentage of AIF1 expression over that of the PBS control and are presented in Table 53. ISIS 419629, ISIS 444584, and ISIS 444618, which had toxic indicators in the systemic administration study (in Example 3), also had toxic indicators in this study (greater than 300% above saline control). Later studies showed that ISIS 444584 is neurotolerable and exhibits negligible toxic indicators (see Example 16 and 17).

TABLE 53

Percent expression of AIF1 mRNA levels in vivo as a measure of neurotoxicity

| ISIS No. | % expression |
|---|---|
| 104838 | 111 |
| 387916 | 870 |
| 388241 | 236 |
| 419627 | 168 |
| 419628 | 497 |
| 419629 | 247 |
| 419630 | 227 |
| 419636 | 464 |
| 419637 | 275 |
| 419640 | 305 |
| 419641 | 206 |
| 419642 | 173 |
| 436665 | 217 |

TABLE 53-continued

Percent expression of AIF1 mRNA levels in vivo as a measure of neurotoxicity

| ISIS No. | % expression |
|---|---|
| 436668 | 447 |
| 436671 | 239 |
| 436684 | 700 |
| 436689 | 149 |
| 436754 | 125 |
| 437168 | 130 |
| 437175 | 131 |
| 437441 | 158 |
| 437442 | 157 |
| 437507 | 133 |
| 437527 | 184 |
| 443139 | 143 |
| 444578 | 352 |
| 444584 | 317 |
| 444591 | 194 |
| 444607 | 362 |
| 444608 | 476 |
| 444615 | 645 |
| 444618 | 547 |
| 444627 | 377 |
| 444652 | 336 |
| 444658 | 364 |
| 444659 | 319 |
| 444660 | 411 |
| 444661 | 249 |
| 444663 | 448 |

RNA Analysis of Huntingtin Expression Levels

RNA was extracted from striatal tissue for real-time PCR analysis of huntingtin mRNA levels. Rat huntingtin mRNA levels were measured using the rat primer probe set rHt-t_LTS00343 (forward sequence CAGAGCTGGT-GAACCGTATCC, designated herein as SEQ ID NO: 49; reverse sequence GGCTTAAGCAGGGAGCCAAAA, designated herein as SEQ ID NO: 50; probe sequence ACTT-CATGATGAGCTCGGAGTTCAACX, designated herein as SEQ ID NO: 51). Results were calculated as the percentage reduction of huntingtin expression over that of the PBS control and are presented in Table 54. ISIS 388241, ISIS 436684, ISIS 436754, ISIS 437175, ISIS 437507, and ISIS 443139 are each mismatched by 6 base pairs or more with the rat gene sequence (SEQ ID NO: 5) and therefore do not show significant inhibition of rat mRNA levels compared to the control. ISIS 419640, ISIS 419641, ISIS 419642, ISIS 436665, ISIS 436668, ISIS 437442, ISIS 444615, and ISIS 444627 have 1 mismatch each with the rat gene sequence (SEQ ID NO: 5) and do not show significant inhibition of rat mRNA levels compared to the control. ISIS 437168 and ISIS 437441 have 2 mismatches each with the rat gene sequence (SEQ ID NO: 5) and do not show significant inhibition of rat mRNA levels compared to the control. ISIS 436689 and ISIS 444584 have 3 mismatches each with the rat gene sequence (SEQ ID NO: 5) and do not show significant inhibition of rat mRNA levels compared to the control.

TABLE 54

Percent reduction of rat huntingtin mRNA levels in rats

| ISIS No. | % reduction |
|---|---|
| 387916 | 70 |
| 419627 | 67 |
| 419628 | 57 |
| 419629 | 85 |
| 419630 | 11 |
| 419636 | 53 |
| 419637 | 84 |
| 436671 | 77 |
| 437521 | 86 |
| 444578 | 72 |
| 444591 | 35 |
| 444607 | 57 |
| 444608 | 68 |
| 444618 | 56 |
| 444652 | 75 |
| 444658 | 61 |
| 444659 | 55 |
| 444660 | 63 |
| 444661 | 52 |
| 444663 | 59 |

Example 6: Intracerebroventricular Administration of Antisense Oligonucleotides Against Huntingtin mRNA-Tolerability Study in BACHD Mice Selected compounds were compared with previously designed compound ISIS 388241 by ICV administration in BACHD mice.

Selected compounds plus the benchmark 388241 were selected based on in vitro and systemic potency and systemic tolerability as well as CNS potency and tolerability.

BACHD mice were treated with ISIS oligonucleotides via intracerebroventricular (ICV) administration to a defined mouse brain area, the right lateral ventricle, for the purpose of evaluating the tolerability of ICV dosing in mice.

Treatment and Surgery

Groups of five BACHD mice each were administered ISIS 388241, ISIS 437507, ISIS 443139, ISIS 419640, ISIS 419641, ISIS 419642, ISIS 444591, ISIS 436665, ISIS 436671, ISIS 444661, or ISIS 436689 at 150 µg/day delivered ICV with Alzet 2002 pumps at the rate of 12 µL/day for 2 weeks. A control group of 4 BACHD mice were similarly treated with PBS. The mice were surgically implanted with the pumps in the following manner: Mice were individually anaesthetized with 3% isoflurane for pump implantation. After two weeks, the mice were anesthetized again and the pump was surgically removed. The animals were then allowed to recover for two more weeks before being euthanized.

The body weights of the mice were taken weekly during the treatment and recovery periods. After 4 weeks, the mice were euthanized using isoflurane and decapitated. The brain was removed for tissue acquisition from the anterior and posterior sections.

RNA Analysis

RNA was extracted from the right hemisphere of the anterior cortex and the posterior cerebellar section of the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Results were calculated as percent inhibition of human and murine huntingtin mRNA expression compared to the control and are presented in Tables 56 and 57 respectively. All the antisense oligonucleotides effect significant inhibition of human huntingtin mRNA levels. ISIS 388241, ISIS 437507, and ISIS 443139 are each mismatched by 8 base pairs or more with the murine huntingtin mRNA (SEQ ID NO: 3) and therefore do not show significant inhibition of murine mRNA levels compared to the control. ISIS 444591 has 1 mismatch with the murine huntingtin mRNA (SEQ ID NO: 3) and does not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 56

Percent reduction of human huntingtin mRNA levels in BACHD mice via ICV administration of antisense oligonucleotides

| ISIS No. | Number of mice | Anterior cortex | Posterior cortex |
|---|---|---|---|
| 388241 | 3 | 82 | 70 |
| 419640 | 1 | 60 | 46 |
| 419641 | 2 | 75 | 66 |
| 419642 | 3 | 29 | 42 |
| 436665 | 5 | 62 | 38 |
| 436671 | 3 | 69 | 77 |
| 436689 | 3 | 49 | 40 |
| 437507 | 3 | 77 | 66 |
| 443139 | 5 | 93 | 90 |
| 444591 | 5 | 79 | 78 |

TABLE 57

Percent reduction of murine huntingtin mRNA levels in BACHD mice via ICV administration of antisense oligonucleotides

| ISIS No. | Number of mice | Anterior cortex | Posterior cortex |
|---|---|---|---|
| 419640 | 1 | 22 | 34 |
| 419641 | 2 | 40 | 26 |
| 419642 | 3 | 63 | 71 |
| 436665 | 5 | 72 | 56 |
| 436671 | 3 | 80 | 71 |

Body Weight Measurement

The body weights of the mice were measured at the onset of the study and subsequently once a week. The body weights of the mice are presented in Table 58 and are expressed as a percent change over the weights taken at the start of the study. The body weights were considered a measure of the tolerability of the mice to the ICV administration of antisense oligonucleotide. 'n.d.' means that there was no data available for that time period.

TABLE 58

Percent change in body weight of BACHD mice during antisense oligonucleotide treatment

|  | week 1 | week 2 | week 3 | week 4 |
|---|---|---|---|---|
| PBS | −1 | +2 | +6 | +6 |
| ISIS 388241 | +3 | +11 | +15 | +7 |
| ISIS 437507 | +21 | +10 | +13 | −4 |
| ISIS 443139 | +10 | +10 | +16 | +12 |
| ISIS 419640 | +21 | +11 | −10 | +9 |
| ISIS 419641 | +24 | +3 | −5 | −12 |
| ISIS 419642 | +45 | +39 | +12 | +1 |
| ISIS 444591 | +18 | +38 | +27 | +17 |
| ISIS 436665 | +34 | +43 | +23 | +9 |
| ISIS 436671 | +19 | +17 | +11 | 0 |
| ISIS 444661 | +19 | −10 | −21 | n.d. |
| ISIS 436689 | +49 | +40 | +2 | −17 |

Survival of the Mice

The survival of the mice was assessed throughout the entire study period. Table 59 below shows the survival pattern in the groups of mice treated with ISIS oligonucleotides as well as the control.

TABLE 59

Number of survivals during antisense oligonucleotide treatment

|  | week 1 | week 2 | week 3 | week 4 |
|---|---|---|---|---|
| PBS | 5 | 5 | 5 | 5 |
| ISIS 388241 | 4 | 3 | 3 | 3 |
| ISIS 437507 | 5 | 5 | 4 | 4 |
| ISIS 443139 | 5 | 5 | 5 | 5 |
| ISIS 419640 | 5 | 5 | 4 | 1 |
| ISIS 419641 | 5 | 5 | 4 | 2 |
| ISIS 419642 | 5 | 5 | 4 | 2 |
| ISIS 444591 | 5 | 5 | 5 | 5 |
| ISIS 436665 | 5 | 5 | 5 | 5 |
| ISIS 436671 | 4 | 4 | 3 | 3 |
| ISIS 444661 | 5 | 5 | 1 | 0 |
| ISIS 436689 | 4 | 4 | 4 | 3 |

Example 7: Intracerebroventricular Administration of Antisense Oligonucleotides Against Huntingtin in C57/BL6 Mice Wild-type C57/BL6 mice were treated with ISIS oligonucleotides via intracerebroventricular (ICV) administration to a defined mouse brain area, the right lateral ventricle, for the purpose of evaluating the potency of the oligonucleotides against mouse huntingtin in these mice.

Treatment and Surgery

Groups of ten C57/BL6 mice each were administered ISIS 408737 (5' TCCTAGTGTTACATTACCGC 3' (SEQ ID NO: 52), start site 5263 of SEQ ID NO: 3) at 50 µg/day delivered ICV with Alzet 2002 pumps at the rate of 0.5 µL/day for 7 days or 14 days. A control group of six C57/BL6 mice were similarly treated with PBS. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 7 or 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely into five sections (51, S2, S3, S4, and S5) using a mouse brain matrix. Sections 1 to 5 were approximately 2 mm apart from each other with 51 being most rostral and S5 most caudal.

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Mouse huntingtin mRNA levels were measured using the murine primer probe set ABI #Mm01213820 ml (Applied Biosystems) and normalized to peptidylprolyl isomerase A mRNA levels. Protein lysates were prepared from mouse brain slabs as described previously (Li S. H. and Li X. J., *Methods in Molecular Biology* (2008), 217:1940-6029). Lysates were run on 3-8% tris-acetate gel and transferred using the iBlot dry blotting system (Invitrogen). Blots were probed with anti-beta tubulin (Chemicon) and monoclonal MAB2166 antibody (Millipore) that reacts specifically with murine huntingtin protein. Immunoblots were quantified using Odyssey V3.0 software.

The results are presented in Table 60 as percent reduction compared to the PBS control and demonstrate significant inhibition of huntingtin mRNA and protein levels by the antisense oligonucleotide both at day 7 and day 14.

TABLE 60

Percent inhibition of murine huntingtin mRNA in C57/BL6 mice

|  | day 7 | day 14 |
|---|---|---|
| mRNA | 66 | 68 |
| protein | 21 | 49 |

Example 8: Intracerebroventricular Administration of Antisense Oligonucleotides Against Huntingtin mRNA in Cynomologous Monkeys Cynomologous monkeys were treated with ISIS oligonucleotides via intracerebroventricular (ICV) administration to a defined brain area, the lateral ventricles, for the purpose of screening the activity of the oligonucleotides in brain tissue against huntingtin mRNA expression. Treatment and surgery Two groups of 3 cynomologous monkeys each were administered either 0.635 mg/ml (1.5 mg/day) or 1.67 mg/ml (4 mg/day) of ISIS 436689 delivered ICV with individual ambulatory pumps (Pegasus Vario) at the rate of 0.05 ml/hr for 4 weeks. A control group of 2 cynomologous monkeys were administered with PBS in a similar manner. The groups were administered ISIS 436689 bilaterally. One animal was administered ISIS 436689 at the 4 mg/day dose unilaterally to the right ventricle.

Animals were allowed 10 days to recover from surgery prior to infusion being performed. During the post surgery recovery period, the animals were maintained on PBS ICV infusion at a flow rate of 0.05 mL/h using one ambulatory infusion pump per ventricle. At the end of the recovery period, each cannula was connected to an individual ambulatory pump (Pegasus Vario) placed within a primate jacket (Lomir, PJ-02NB). The pumps remained connected until completion of the infusion period. After 4 weeks administration, the animals were euthanized and the brain, liver and kidney were harvested.

RNA Analysis of Htt mRNA

RNA was extracted from the anterior caudate, posterior caudate, temporal cortex, parietal cortex, hypothalamus, mid-brain, hippocampus, and spinal cords, as well as the liver and kidney for real-time PCR analysis of huntingtin mRNA levels. Huntingtin mRNA levels were measured using the human primer probe set RTS2617 and normalized to monkey cyclophilin A levels. Results were calculated as percent inhibition of huntingtin mRNA expression compared to the PBS control and are presented in Table 61. ISIS 436689 effected significant inhibition of human huntingtin mRNA levels in the CNS.

TABLE 61

Percent reduction of huntingtin mRNA levels in cynomologous monkeys via ICV administration of antisense oligonucleotides

| Tissue | Dose (mg/day) | | | |
|---|---|---|---|---|
|  | 1.5 (bilateral) | 4 (bilateral) | 4 (right unilateral) | 4 (left unilateral) |
| Anterior caudate | 59 | 49 | 85 | 12 |
| Posterior caudate | 52 | 81 | 63 | 0 |
| Temporal cortex | 10 | 34 | 41 | 31 |
| Parietal cortex | 22 | 38 | 46 | 24 |
| Hypothalamus | 59 | 71 | 35 | 100 |
| Mid-brain | 32 | 38 | 2 | 0 |
| Hippocampus | 18 | 18 | 28 | 10 |
| Cervical cord | 58 | 65 | n.d. | n.d. |
| Thoracic cord | 50 | 67 | n.d. | n.d. |
| Lumbar cord | 49 | 62 | n.d. | n.d. |
| Liver | 0 | 13 | n.d. | n.d. |
| Kidney | 0 | 13 | n.d. | n.d. | n.d.= no data

Example 9: Measurement of Half-Life of ISIS 387898 in the Striatum of C57/BL6 Mice Via Single Bolus Administration C57/BL6 mice were administered ISIS 387898 as a single bolus to the striatum for the purpose of measuring half-life and duration of action of the antisense oligonucleotide against huntingtin mRNA expression in that tissue.

Treatment

Forty C57/BL6 mice were treated with ISIS 387898 (5' CTCGACTAAAGCAGGATTC 3' (SEQ ID NO: 53); start position 4042 of SEQ ID NO: 1 and start position 4001 of SEQ ID NO: 3) delivered as a single bolus of 50 µg in a procedure similar to that described in Example 5. Eight control C57/BL6 mice were treated with PBS in a similar procedure. Groups of 4 mice each were euthanized at various time points and striatal tissue extracted in a procedure similar to that described in Example 5.

RNA Analysis

RNA was extracted from striatal tissue for real-time PCR analysis of huntingtin mRNA levels. Mouse normal huntingtin mRNA levels were measured using the murine primer probe set RTS2633. The results are presented in Table 62 and are expressed as percent inhibition compared to the PBS control group at day 7. The inhibitory effect of ISIS 387898 was observed to be prolonged for at least 91 days.

TABLE 62

Effect of ISIS 387898 as a single bolus administration on murine huntingtin mRNA expression at various time points in C57/BL6 striatum

| Treatment | Days after dosing | % inhibition |
|---|---|---|
| ISIS 387898 | 1 | 66 |
| | 7 | 74 |
| | 14 | 68 |
| | 21 | 77 |
| | 28 | 75 |
| | 50 | 63 |
| | 73 | 55 |
| | 91 | 48 |
| PBS | 50 | 5 |

Analysis of Antisense Oligonucleotide Concentration in the Brain:

Brain tissues were minced, weighed, homogenized, and extracted using a phenol/chloroform liquid-liquid extraction method. This was followed by solid phase extraction of the supernatant on a phenyl-bonded column before capillary gel eletrophoresis electrokinetic injection. A P/ACE MDQ capillary electrophoresis instrument (Beckman Coulter, Fullerton, CA) was used for gel-filled capillary electrophoretic analysis. Oligonucleotide peaks were detected by UV absorbance at 260 nm.

Figure 2:
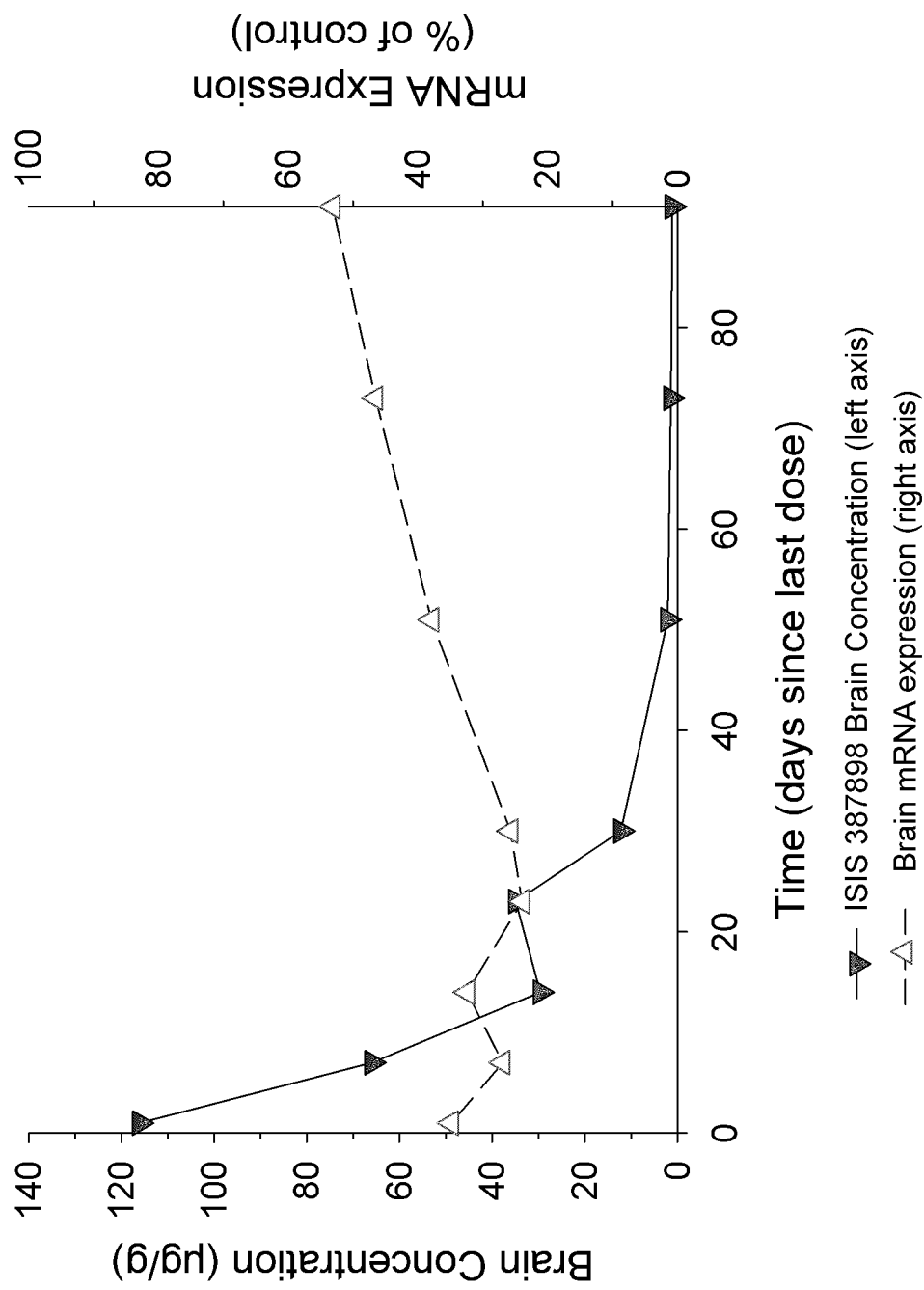
FIG. 2:
Comparison of huntingtin mRNA expression in intrastriatal tissue and ISIS 387898 concentrations at various time points. C57/BL6 mice were administered a single bolus of 50 µg of ISIS 387898 and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

The concentration of ISIS 387898 in the brain (µg/g) was plotted against the expression of human huntingtin as a percentage of the PBS control (Table 63 and FIG. 1). The concentration of ISIS 387898 which achieves 50% inhibition of huntingtin mRNA expression ($EC_{50}$) was calculated. The $EC_{50}$ was determined to be 0.45 µg/g. The time-dependent concentration of ISIS 387898 in the brain tissue and corresponding percentage huntingtin mRNA expression was also plotted (Table 64 and FIG. 2) and the half-life of the oligonucleotide was calculated as 21 days.

TABLE 63

Concentration of ISIS 387898 in brain tissue and its effect on htt mRNA expression as a percentage of the control

| concentration (µg/g) | % mRNA expression |
|---|---|
| 0 | 105.0 |
| 25 | 28.8 |
| 50 | 28.2 |
| 75 | 27.9 |
| 100 | 27.8 |
| 125 | 27.8 |

TABLE 64

Time-dependent concentration of ISIS 387898 in brain tissue and its effect on htt mRNA expression as a percentage of the control

| Time (day) | Conc (µg/g) | mRNA % expression |
|---|---|---|
| 1 | 116 | 35 |
| 7 | 65.7 | 27 |
| 14 | 30 | 32 |
| 23 | 34.9 | 24 |
| 30 | 12.2 | 26 |
| 51 | 2.1 | 38 |
| 73 | 1.4 | 47 |
| 92 | 1.1 | 53 |

Example 10: Measurement of Half-Life of ISIS 387898 in the Lateral Ventricles of BACHD Mice Via ICV Administration BACHD mice were administered ISIS 387898 by ICV to the lateral ventricles of the brain for the purpose of measuring half-life and duration of action of the antisense oligonucleotide against huntingtin mRNA expression in that tissue.

Treatment

Twenty eight BACHD mice were treated with ISIS 387898 delivered by ICV administration at 75 µg/day for 2 weeks in a procedure similar to that described in Example 9. Twenty eight control BACHD mice were treated with PBS in a procedure similar to that described in Example 9. Groups of 4 mice each from both the treatment and control groups were euthanized at biweekly time points and anterior cortical tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Human mutant huntingtin mRNA expression levels are presented in Table 65 and are expressed as percent inhibition compared to the average of that measured in the PBS control groups. Murine normal huntingtin mRNA expression levels are presented in Table 66 and are expressed as percent inhibition compared to the average of that measured in the PBS control groups. The inhibitory effect of ISIS 387898 was observed to be prolonged for 91 days.

TABLE 65

Effect of ISIS 387898 administered ICV on human huntingtin mRNA expression at various time points

| Treatment | Days after dosage | anterior | posterior |
|---|---|---|---|
| ISIS 387898 | 14 | 74 | 65 |
| | 28 | 67 | 61 |
| | 42 | 70 | 61 |
| | 56 | 57 | 52 |
| | 70 | 57 | 43 |
| | 91 | 41 | 61 |
| | 127 | 28 | 16 |

TABLE 65-continued

Effect of ISIS 387898 administered ICV on human huntingtin mRNA expression at various time points

| Treatment | Days after dosage | anterior | posterior |
|---|---|---|---|
| PBS | 14 | 0 | 0 |
|  | 28 | 0 | 0 |
|  | 42 | 1 | 0 |
|  | 56 | 9 | 10 |
|  | 70 | 13 | 10 |
|  | 91 | 13 | 25 |
|  | 127 | 11 | 0 |

TABLE 66

Effect of ISIS 387898 administered ICV on murine huntingtin mRNA expression at various time points

| Treatment | Days after dosage | anterior | posterior |
|---|---|---|---|
| ISIS 387898 | 14 | 85 | 81 |
|  | 28 | 81 | 69 |
|  | 42 | 86 | 79 |
|  | 56 | 74 | 69 |
|  | 70 | 73 | 58 |
|  | 91 | 39 | 63 |
|  | 127 | 39 | 0 |
| PBS | 14 | 0 | 0 |
|  | 28 | 0 | 0 |
|  | 42 | 0 | 0 |
|  | 56 | 17 | 14 |
|  | 70 | 5 | 24 |
|  | 91 | 9 | 17 |
|  | 127 | 32 | 0 |

Figure 3:
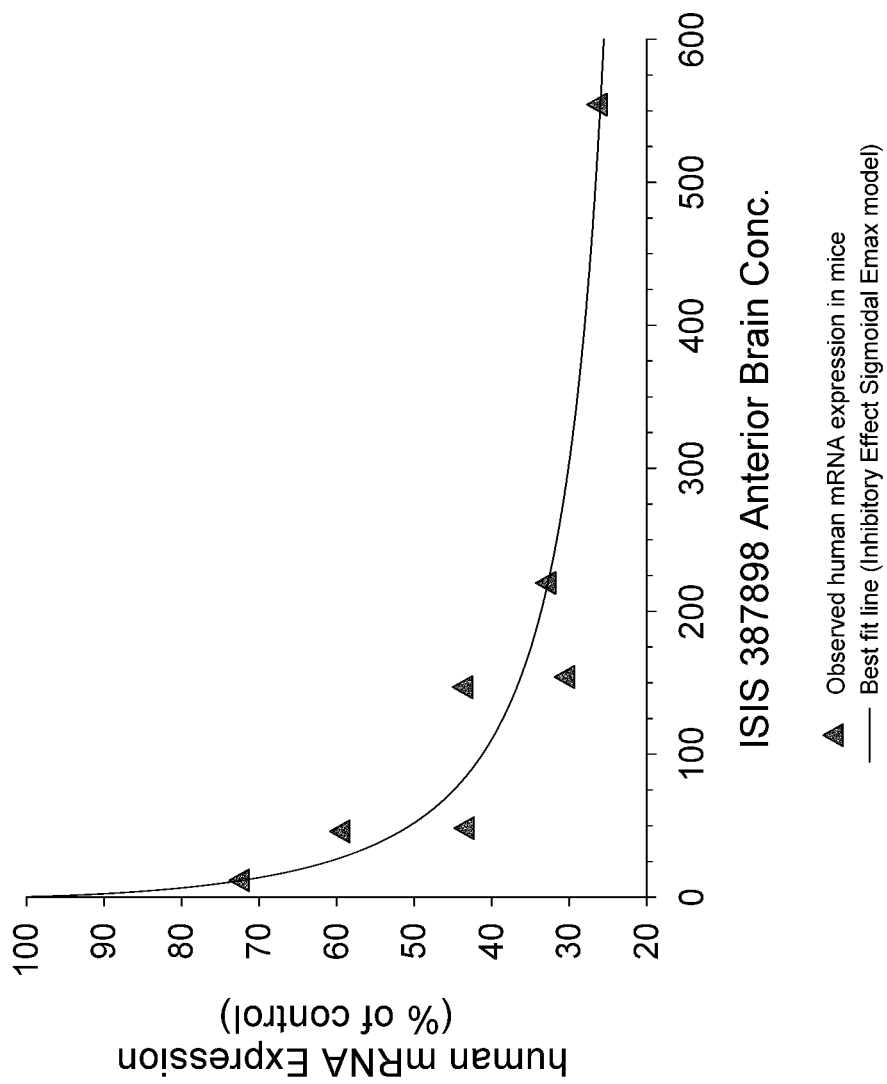
FIG. 3:
The PK/PD relationship of huntingtin mRNA expression in the anterior cortex tissue with ISIS 387898 concentration in mouse brain. BACHD mice were administered an intracerebroventricular infusion of 75 µg of ISIS 387898 for 2 weeks and huntingtin mRNA expression as well as the concentration of the antisense oligonucleotide in the tissue were measured. The $EC_{50}$ of ISIS 387898 was also calculated.
Figure 4:
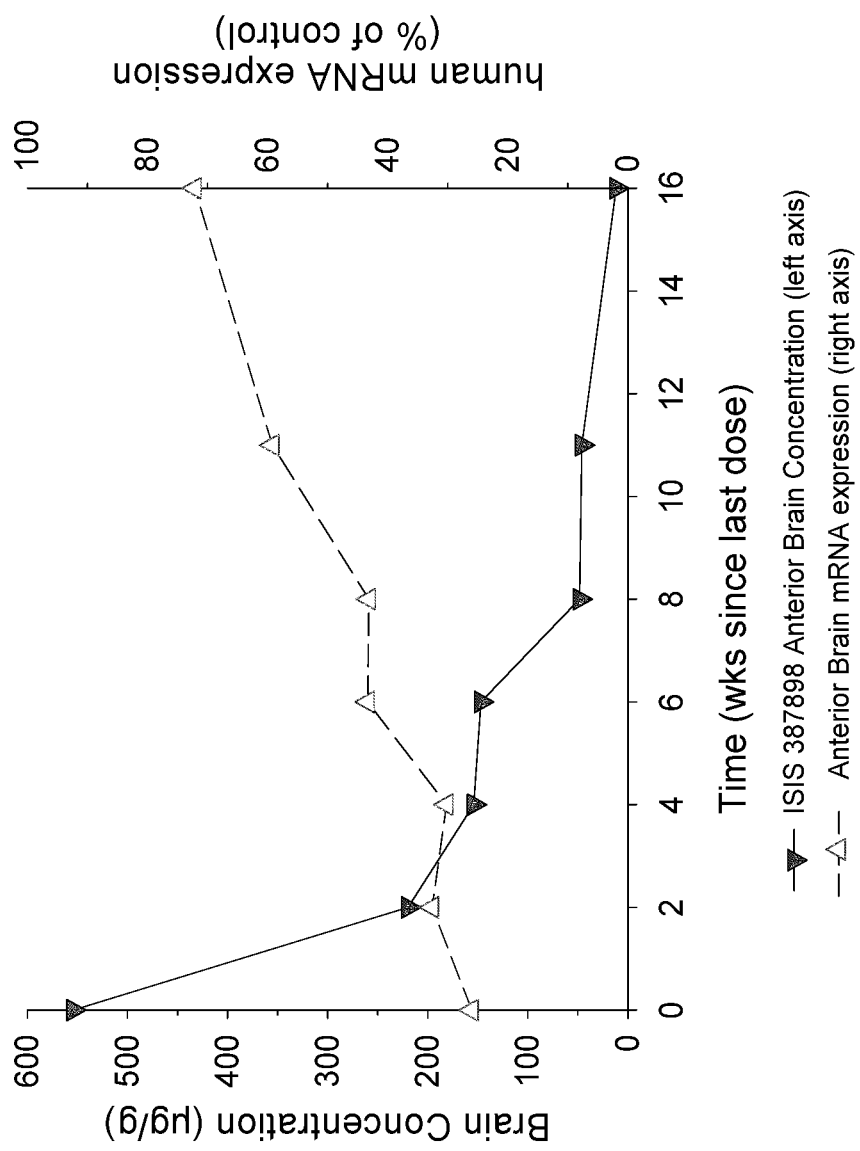
FIG. 4:
Comparison of huntingtin mRNA expression in anterior cortex tissue and ISIS 387898 concentrations at various time points. BACHD mice were administered intracerebroventricular infusion of 75 µg of ISIS 387898 for 2 weeks, and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

Analysis of Antisense Oligonucleotide Concentration in the Brain:

Brain tissue was processed in a procedure similar to that described in Example 9. The concentration of ISIS 387898 in the anterior cortex of the brain (µg/g) was plotted against the inhibition of human huntingtin as a percentage of the PBS control (Table 67 and FIG. 3), and the $EC_{50}$ was calculated to be 26.4 µg/g. The time-dependent concentration of ISIS 387898 in the brain tissue was also plotted (Table 68 and FIG. 4) and the half-life of the oligonucleotide was calculated as 21 days.

TABLE 67

Concentration of ISIS 387898 in brain tissue and its effect on htt mRNA expression as a percentage of the control

| Concentration (µg/g) | % mRNA expression |
|---|---|
| 0 | 105 |
| 10 | 90.7 |
| 100 | 19.3 |
| 200 | 14.3 |
| 300 | 13.2 |
| 400 | 12.7 |
| 500 | 12.5 |
| 600 | 12.4 |

TABLE 68

Time-dependent concentration of ISIS 387898 in brain tissue and its effect on htt mRNA expression as a percentage of the control

| Days after last dose | Conc (mg/g) | % mRNA expression |
|---|---|---|
| 14 | 554.3 | 12 |
| 28 | 219.8 | 15 |
| 42 | 154 | 13 |
| 56 | 146.9 | 32 |
| 70 | 48.3 | 28 |
| 91 | 46.1 | 66 |
| 127 | 11.8 | 90 |

Example 11: Measurement of Half-Life of ISIS 388241 and ISIS 443139 in the Lateral Ventricles of BACHD Mice Via ICV Administration BACHD mice were administered ISIS 388241 or ISIS 443139 by ICV to the lateral ventricles of the brain for the purpose of measuring half-life and duration of action of the antisense oligonucleotide against huntingtin mRNA expression in that tissue.

Treatment

Twenty BACHD mice were treated with ISIS 38241 delivered by ICV administration at 50 µg/day for 2 weeks in a procedure similar to that described in Example 9. Twenty BACHD mice were treated with ISIS 443139 delivered by ICV administration at 50 µg/day for 2 weeks in a procedure similar to that described in Example 9. Twenty control BACHD mice were treated with PBS in a procedure similar to that described in Example 9. Groups of 4 mice each from both the treatment groups and control group were euthanized at biweekly time points and tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. The results are presented in Table 69 and are expressed as percent inhibition compared to the average of that measured in the PBS control groups. The inhibitory effects of both ISIS 388241 and ISIS 443139 were observed to be prolonged for at least 16 weeks.

Both ISIS 388241 and its mixed backbone equivalent, ISIS 443139, have more than 3 mismatches with murine huntingtin mRNA (SEQ ID NO: 5) and therefore did not show significant inhibition of murine mRNA levels compared to the control.

TABLE 69

Effect of ISIS 388241 and ISIS 443139 administered ICV on human huntingtin mRNA expression at various time points

| Treatment | Weeks after dosage | anterior | posterior |
|---|---|---|---|
| ISIS 388241 | 0 | 63 | 64 |
|  | 4 | 79 | 56 |
|  | 8 | 67 | 51 |
|  | 12 | 76 | 68 |
|  | 16 | 35 | 34 |

TABLE 69-continued

Effect of ISIS 388241 and ISIS 443139 administered
ICV on human huntingtin mRNA
expression at various time points

| Treatment | Weeks after dosage | anterior | posterior |
|---|---|---|---|
| ISIS 443139 | 0 | 35 | 55 |
|  | 4 | 20 | 62 |
|  | 8 | 61 | 59 |
|  | 12 | 67 | 53 |
|  | 16 | 46 | 37 |
| PBS | 0 | 15 | 10 |
|  | 4 | 0 | 2 |
|  | 8 | 5 | 0 |
|  | 12 | 32 | 4 |
|  | 16 | 6 | 2 |

Figure 5:
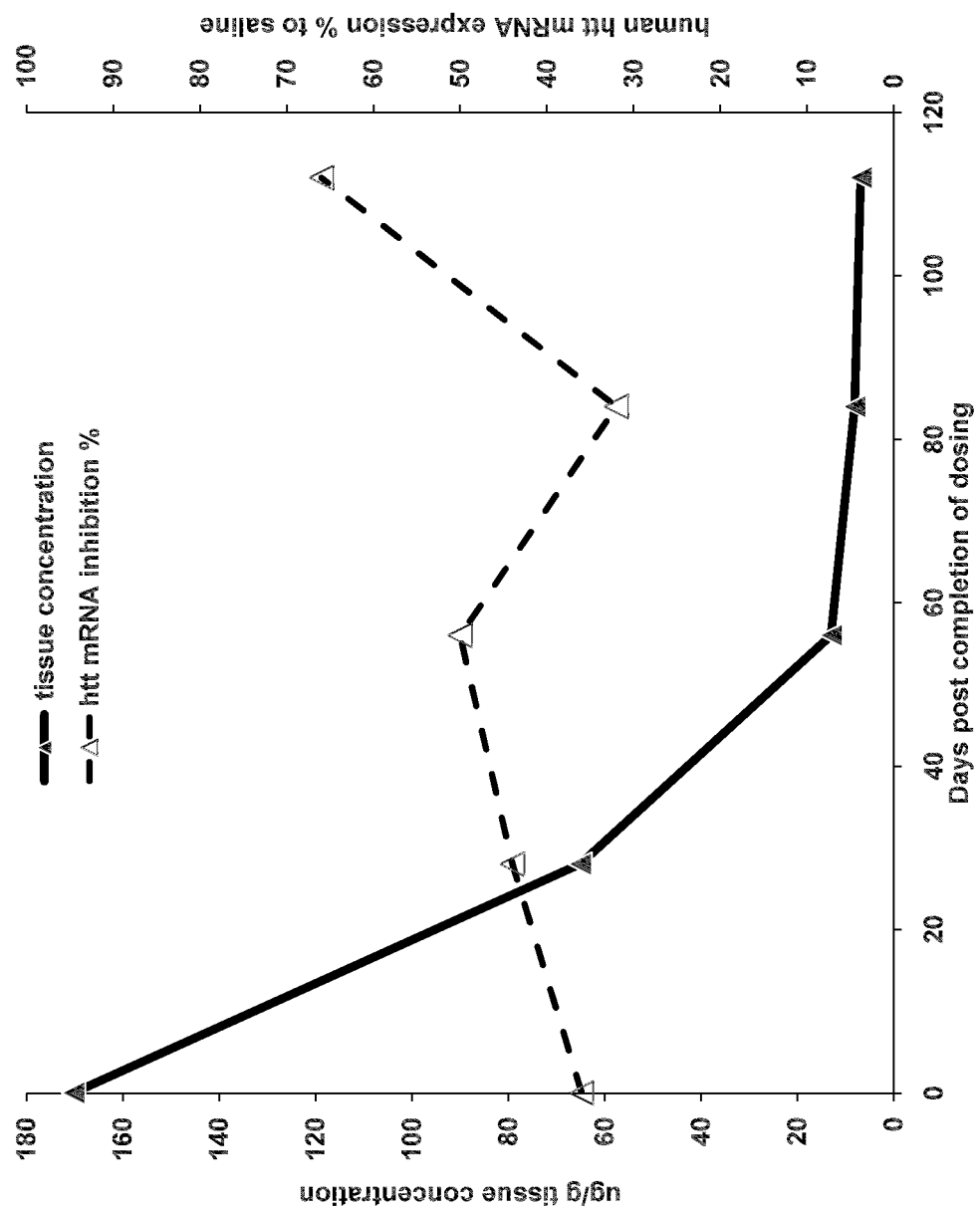
FIG. 5.
Figure 6:
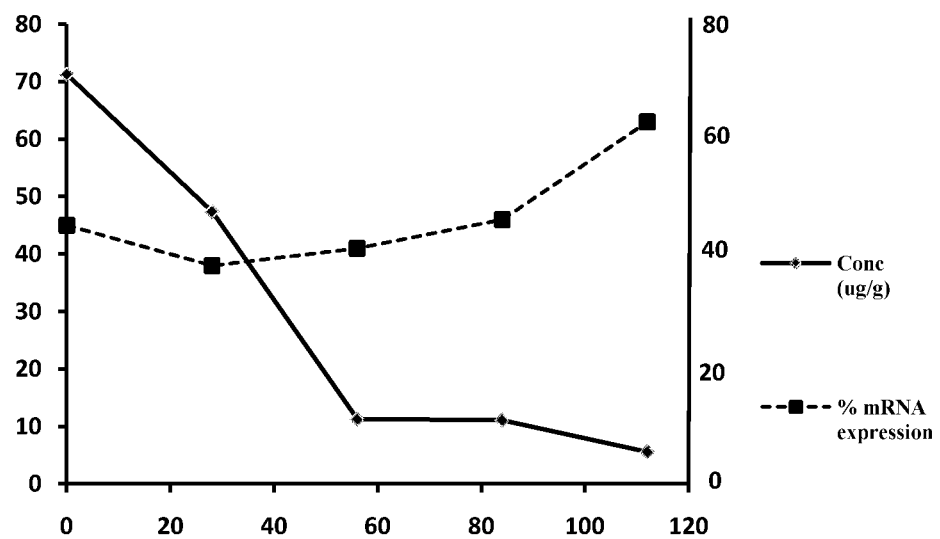

Analysis of Antisense Oligonucleotide Concentration in the Brain:

Brain tissue was processed in a procedure similar to that described in Example 9. The time-dependent concentration of ISIS 388241 in the posterior brain tissue was plotted (Table 70 and FIG. 5) and the half-life of the oligonucleotide was calculated as 20 days. The time-dependent concentration of ISIS 443139 in the posterior brain tissue was plotted (Table 71 and FIG. 6) and the half-life of the oligonucleotide was calculated as 20 days.

TABLE 70

Concentration of ISIS 384241 in brain tissue and
its effect on htt mRNA expression as a
percentage of the control

| Days after last dose | Conc (ug/g) | % mRNA expression |
|---|---|---|
| 0 | 170.3 | 36 |
| 28 | 65.2 | 43 |
| 56 | 13 | 49 |
| 84 | 8.2 | 32 |
| 112 | 6.9 | 66 |

TABLE 71

Concentration of ISIS 443139 in brain tissue and
its effect on htt mRNA expression as a
percentage of the control

| Days after last dose | Conc (ug/g) | % mRNA expression |
|---|---|---|
| 0 | 71.3 | 45 |
| 28 | 47.4 | 38 |
| 56 | 11.3 | 41 |
| 84 | 11.1 | 46 |
| 112 | 5.6 | 63 |

Example 12: Effect of Antisense Inhibition of Mutant Human Huntingtin on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Six month old BACHD mice and their non-transgenic littermates were trained to run on the rotarod for one week prior to treatment. This consisted of three consecutive trials of 5 minutes each, with a 20 minute rest period between trials. A group of 15 BACHD mice were then treated with ISIS 388241 at 50 µg/day delivered ICV with Alzet 2002 pumps at the rate of 12 µL/day for 2 weeks. The mice were surgically implanted with the pumps in a similar procedure as that described in Example 6. A control group of 14 BACHD mice were treated with PBS in a similar manner. A control group of 9 non-transgenic littermates were treated with PBS in a similar manner.

Rotarod Performance Assay

Figure 7:
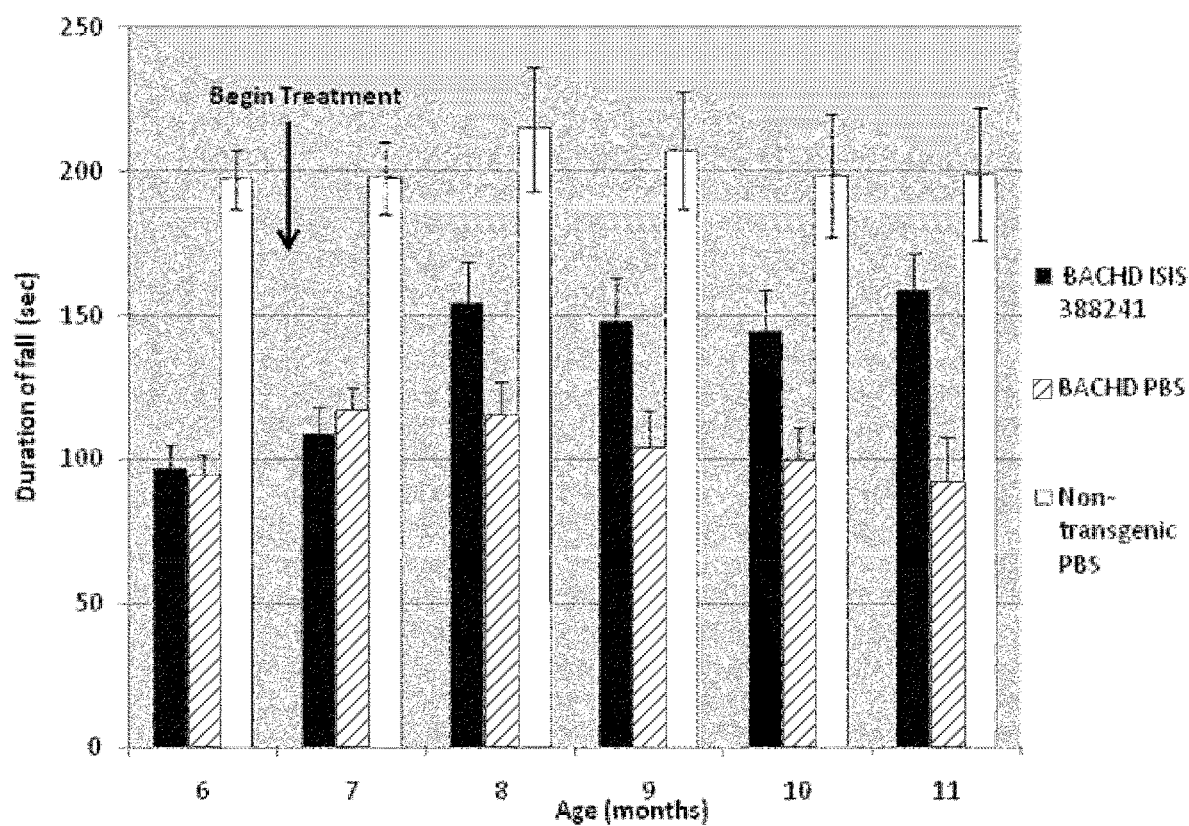

At the end of the treatment period, the pumps were removed and two weeks later, the first post-treatment rotarod assay was conducted. Rotarod behavior was analyzed monthly till the mice were 11 months of age. Each month, the animals were placed on the rotarod for three trial runs a day for 2 days. The results are presented in FIG. 7, as well as in Table 72 expressed as duration to fall in seconds. Baseline values at 6 months age were taken before the treatment and the time points given are the age of the mice at which the assay was conducted. The data indicates that treatment of BACHD mice with ISIS 388241 increased the duration to fall compared to that observed in untreated BACHD mice.

TABLE 72

Effect of antisense inhibition of mutant huntingtin
mRNA on duration to fall (sec)

| | 6 months | 7 month | 8 months | 9 months | 10 months | 11 months |
|---|---|---|---|---|---|---|
| ISIS 388241 | 97 | 108 | 154 | 148 | 144 | 159 |
| PBS control | 94 | 117 | 115 | 104 | 99 | 92 |
| Non-transgenic control | 197 | 198 | 215 | 207 | 198 | 199 |

Example 13: Effect of Antisense Inhibition of Mutant Human Huntingtin and Wild Type Murine Huntingtin mRNA on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Two month old BACHD mice and their non-transgenic littermates were trained to run on the rotarod for one week prior to treatment. This consisted of three consecutive trials of 5 minutes each, with a 20 minute rest period between trials. Groups of 17-21 BACHD mice each were then treated with ISIS 388241 at 50 μg/day, ISIS 408737 at 75 μg/day, or ISIS 387898 at 75 μg/day, delivered ICV with Alzet 2002 pumps at the rate of 0.5 μL/hour for 2 weeks. The mice were surgically implanted with the pumps in a similar procedure as that described in Example 6. A control group of 20 BACHD mice were treated with PBS in a similar manner. Groups of non-transgenic control mice were also similarly treated with ISIS oligonucleotides or PBS in a similar manner.

Rotarod Performance Assay

At the end of the treatment period, the pumps were removed and two weeks later, the first post-treatment rotarod assay was conducted. Rotarod behavior was analyzed monthly till the mice were 10 months of age. Each month, the animals were placed on the rotarod for 3-5 trial runs a day for 3 consecutive days. The results are presented in Table 73 expressed as duration to fall in seconds. Baseline values at 2 months age were taken before the treatment and the time points given are the age of the mice at which the assay was conducted. ISIS 387898 (designated in the table as Human-mouse ASO) is cross-reactive for both mouse and human huntingtin mRNA and therefore would inhibit both human mutant huntingtin mRNA and wild-type murine huntingtin mRNA in the mice. ISIS 388241 (designated in the table as Human ASO) specifically targets human huntingtin mRNA and is mismatched by 8 base pairs with murine huntingtin mRNA. Therefore, ISIS 388241 would specifically inhibit only human mutant huntingtin mRNA and not wild-type murine huntingtin mRNA in the mice. ISIS 408737 (designated in the table as Mouse ASO) specifically targets murine huntingtin mRNA and is mismatched by 7 base pairs with human huntingtin mRNA. Therefore, ISIS 408737 would specifically inhibit only wild-type murine huntingtin mRNA and not human mutant huntingtin mRNA in the mice. 'Tg' indicates the BACHD mice and 'Non-Tg' indicates the non-transgenic control mice.

The results of the study indicate that inhibition of human mutant huntingtin mRNA by ISIS 388241 (Tg-Human ASO) significantly improved the performance of the mice in the rotarod assay compared to the control (Tg-PBS). The results also indicate that treatment of mice with ISIS 387898 (Tg-Human-mouse ASO), which targets both mutant and wild-type huntingtin mRNA in the mice, did not cause any deleterious effects on the motor performance of the mice and, in fact, also significantly improved rotarod performance compared to the control (Tg-PBS). The mice treated with ISIS 408737 (Tg-Mouse ASO) did not show improved rotarod performance compared to the PBS control, as expected, since the oligonucleotide does not target the mutant huntingtin mRNA. The non-transgenic controls were utilized as positive controls in this assay.

TABLE 73

Effect of antisense inhibition of huntingtin mRNA on duration to fall (sec)

|  | 2 months | 3 months | 4 months | 5 months | 6 months | 7 months | 8 months | 9 months | 10 months |
|---|---|---|---|---|---|---|---|---|---|
| Tg-Human ASO | 146 | 167 | 190 | 192 | 190 | 188 | 181 | 191 | 191 |
| Tg-mouse ASO | 151 | 142 | 152 | 143 | 139 | 144 | 139 | 123 | 130 |
| Tg-Human-mouse ASO | 149 | 187 | 203 | 199 | 196 | 194 | 189 | 194 | 171 |
| Tg-PBS | 152 | 164 | 169 | 160 | 159 | 155 | 148 | 135 | 136 |
| Non-Tg-Human ASO | 212 | 223 | 234 | 236 | 247 | 248 | 245 | 247 | 235 |
| Non-Tg-Mouse ASO | 201 | 212 | 215 | 213 | 231 | 243 | 244 | 250 | 247 |
| Non-Tg-Human-mouse ASO | 220 | 240 | 239 | 224 | 243 | 244 | 246 | 229 | 235 |
| Non-Tg-PBS | 193 | 220 | 228 | 227 | 228 | 216 | 220 | 208 | 208 |

Example 14: Effect of Antisense Inhibition of Huntingtin mRNA on the Brain Mass of R6/2 Mice R6/2 mice were treated with ISIS oligonucleotides via intracerebroventricular (ICV) administration for the purpose of evaluating the effect of the oligonucleotides against huntingtin mRNA expression on brain weight and volume.

Treatment

R6/2 mice were housed in groups of up to 5 per cage (mixed genotypes, single sex), All mice were housed in shoe-box cages with sterile wood bedding covering the ground that were changed as frequently as needed to provide the animals with dry bedding. This basic environment was enriched with the addition of play tunnels, shredded nestlet, and plastic bones for all mice; i.e. an environmentally-enriched cage containing a Mouse Tunnel, (amber color, certified, transparent, BioSery Product #K3323), a Petite Green Gumabone (BioSery Product #K3214) and a nestlet (Hockley et al., Ann Neurol. 2002, 51: 235-242). Food and water were available ad libitum to the mice in their home cages.

A group of ten six month old R6/2 mice was administered 50 μg/day of ISIS 388817 delivered ICV with Alzet 1004 pumps at the rate of 0.12 μl/hr for 4 weeks. A group of two non-transgenic littermates was administered 50 μg/day of ISIS 388817 delivered in a similar manner. A control group of five R6/2 mice was administered 50 μg/day of ISIS 141923 delivered in a similar manner. A control group of nine R6/2 mice was administered PBS delivered in a similar manner. A group of eight non-transgenic littermates was administered PBS delivered in a similar manner. A group of four untreated eight-week old pre-symptomatic R6/2 were also included in the study.

Brain Weight Measurement

Figure 8:
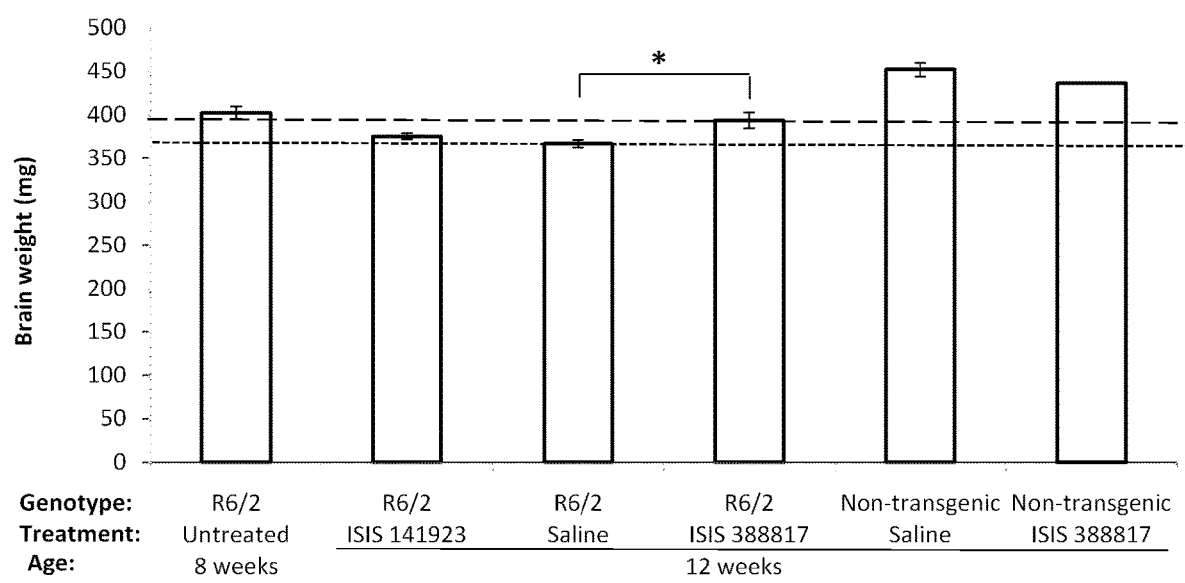

Animals were anaesthetized with isofluorane and then subjected to transcardial perfusion with ice-cold Sorenson's phosphate buffer (SPB), and fixed with 4% paraformaldyhyde in SPB. Brains were removed, and trimmed with coronal cuts immediately rostral to the forebrain (removing the olfactory bulbs) and immediately caudal to the cerebellum (removing the spinal cord). The remaining brain was weighed in mg. The results are presented in FIG. 8 and Table 74 and demonstrate the increase in brain weight in R6/2 mice treated with ISIS 388817 compared to the PBS control

TABLE 74

Effect of antisense inhibition of mutant
huntingtin mRNA on brain weight (mg)

| Mouse model | Treatment | Brain weight |
|---|---|---|
| R6/2 | PBS | 367 |
| | ISIS 141923 | 375 |
| | ISIS 388817 | 394 |
| R6/2 (8 weeks old) | None | 402 |
| Non-transgenic | ISIS 141923 | 452 |
| | ISIS 388817 | 436 |

Example 15: Effect of Antisense Inhibition of Huntingtin mRNA on Anxiety Performance of YAC128 Mice YAC128 mice were treated with ISIS oligonucleotides via intracerebroventricular (ICV) administration for the purpose of evaluating the effect of the oligonucleotides against huntingtin mRNA expression on anxiety in these mice as measured by their performance in the open field and elevated plus maze assays.

Treatment

A group of seven five-month old YAC128 mice was administered 50 µg/day of ISIS 388241 delivered ICV with Alzet 1004 pumps at the rate of 0.5 µl/hr for 14 days. A control group of four YAC128 mice were similarly treated with PBS. A control group of eight non-transgenic FVB/NJ littermates were included in the study and did not receive any treatment. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 14 days, after which the pumps were removed. The animals were allowed to recover for 2 weeks after which behavioral analysis was done and the mice were finally euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being most rostral and S5 most caudal.

Open Field Assay

Figure 9:
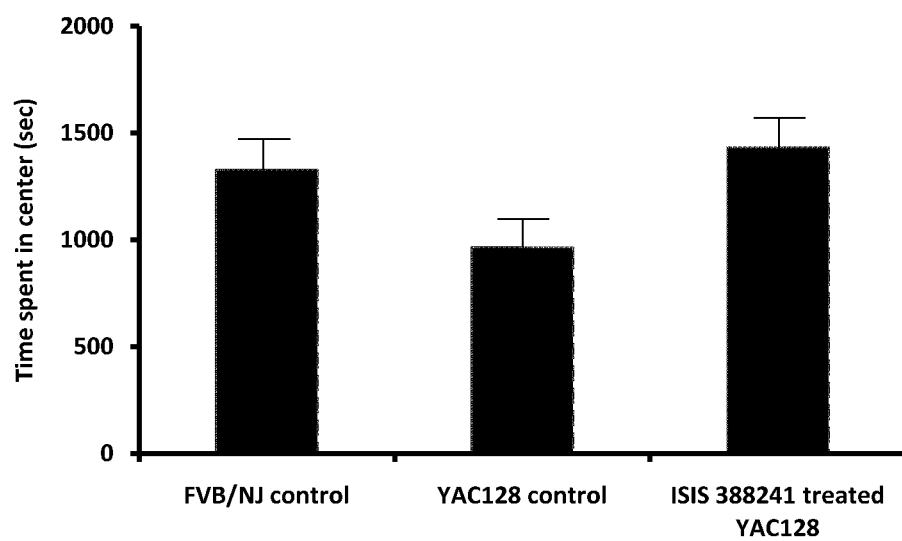

Mice were placed in an open field arena (Med Associates) that uses photobeam breaks to measure horizontal and vertical movement over a 30 min test session. Data was analyzed using Activity Monitor software to examine total ambulatory movement within the arena and movement within the center of the arena as a measure of anxiety. YAC128 control mice were expected to spend less time at the centre of the arena compared to their non-transgenic, less anxiety-prone FVB/NJ littermates. The results are presented in FIG. 9 and Table 75 and indicate that treatment of YAC128 mice with antisense oligonucleotide decreased anxiety in these mice, according to the parameters of the open field assay.

TABLE 75

Effect of antisense inhibition of mutant htt mRNA
on open field performance of YAC128 mice

| Mice model | Time in center (sec) |
|---|---|
| FVB control | 1326 |
| YAC128 control | 964 |
| ISIS 388241 treated YAC128 | 1433 |

Elevated Plus Maze Assay

Figure 10:
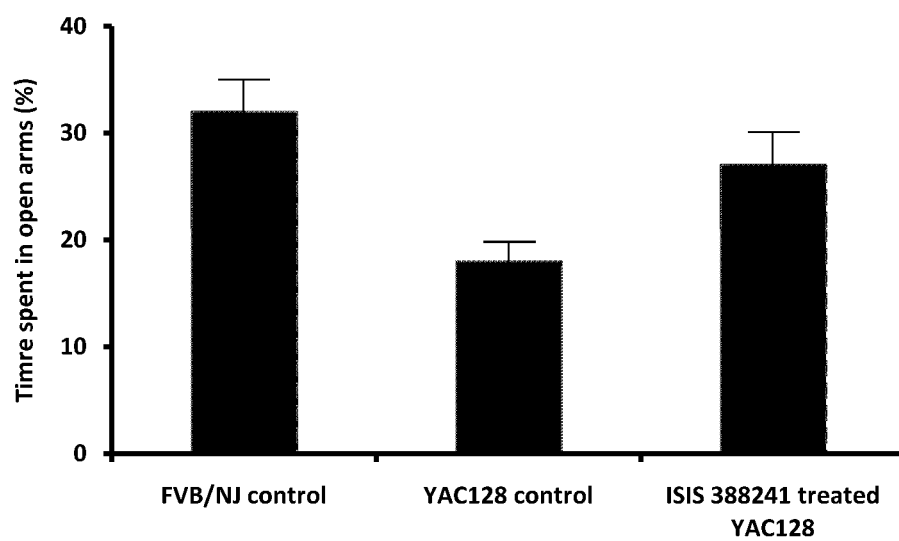

The apparatus consisted of two open arms and two closed arms each measuring 65×6.25 cm and elevated 50 cm above the ground. Mice were placed in the center of the apparatus and their location was recorded over a 5 minute test session. YAC128 control mice were expected to spend less time at the open arms of the apparatus compared to their non-transgenic, less anxiety-prone FVB/NJ littermates. The results are presented in FIG. 10 and Table 76 and indicate that treatment of YAC128 mice with antisense oligonucleotide decreased anxiety in these mice, according to the parameters of the elevated plus maze assay.

TABLE 76

Effect of antisense inhibition of mutant htt mRNA
on elevated plus maze performance of
YAC128 mice

| Mice model | % time in open arms |
|---|---|
| FVB control | 32 |
| YAC128 control | 18 |
| ISIS 388241 treated YAC128 | 27 |

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Human huntingtin mRNA levels were measured using the human primer probe set RTS2686 and normalized to peptidylprolyl isomerase A mRNA levels.

Protein lysates were prepared from mouse brain slabs as described previously (Li S. H. and Li X. J., *Methods in Molecular Biology* (2008), 217:1940-6029). Lysates were run on 3-8% tris-acetate gel and transferred using the iBlot dry blotting system (Invitrogen). Blots were probed with anti-beta tubulin (Chemicon) and mouse monoclonal EM48 antibody that reacts specifically with human huntingtin protein (Millipore). Immunoblots were quantified using Odyssey V3.0 software.

The results are presented in Table 77 as percent reduction compared to the PBS control and demonstrate significant inhibition of huntingtin mRNA and protein levels by the antisense oligonucleotide.

TABLE 77

Percent inhibition of huntingtin mRNA in YAC128 mice

|  | % inhibition |
|---|---|
| mRNA | 85 |
| protein | 86 |

Example 16: Intracerebroventricular Administration of Antisense Oligonucleotides Against Huntingtin in C57/BL6 Mice C57/BL6 mice were treated with ISIS oligonucleotides via intracerebroventricular (ICV) administration to the right lateral ventricle, for the purpose of evaluating the tolerability of the oligonucleotides in these mice.

Treatment and Surgery

Groups of five C57/BL6 mice each were administered ISIS 387916, ISIS 437527, ISIS 444578, ISIS 444584, ISIS 444607, ISIS 444608, ISIS 444627, ISIS 444652, ISIS 444659, ISIS 444660, or ISIS 444661 at 150 µg/day delivered ICV with Alzet 2002 pumps at the rate of 0.5 µL/day for 2 weeks. A control group of six C57/BL6 mice were similarly treated with PBS. The procedure for implanting the pumps and oligonucleotide administration is described in Example 6.

The animals were allowed to recover for two weeks before being euthanized using isoflurane. Brain and spinal cord tissue were harvested and snap frozen in liquid nitrogen. Prior to freezing, brain tissue was cut transversely into five sections (51, S2, S3, S4, and S5) using a mouse brain matrix. Sections 1 to 5 were approximately 2 mm apart from each other with 51 being the most rostral and S5 the most caudal.

RNA Analysis

Total RNA was extracted from anterior and posterior cortices of the brain for real-time PCR analysis of huntingtin mRNA levels using an RNeasy Mini prep kit (Qiagen). RT-PCR reactions were conducted on an ABI Prism 7700 Sequence Detector (Applied Biosystems). Mouse huntingtin mRNA levels were measured using a murine primer probe set RTS2633 and normalized to cyclophilin mRNA levels. The results are presented in Table 78 as percent reduction compared to the PBS control. ISIS 387916, ISIS 437527, ISIS 444627, and ISIS 444652 all have one mismatch with the murine huntingtin mRNA (SEQ ID NO: 3) and therefore did not show significant inhibition of murine mRNA levels compared to the control.

The microglial marker, AIF1 was also measured by RT-PCR analysis using murine primer probe set mAIF1_LTS00328 (forward sequence TGGTCCCCCAGC-CAAGA, designated herein as SEQ ID NO: 54; reverse sequence CCCACCGTGTGACATCCA, designated herein as SEQ ID NO: 55; probe sequence AGC-TATCTCCGAGCTGCCCTGATTGG, designated herein as SEQ ID NO: 56). The results are presented in Table 79 and indicate that the tested ISIS oligonucleotides did not induce an inflammatory response.

TABLE 78

Percent inhibition of murine huntingtin mRNA compared to the control in C57/BL6 mice

| ISIS No | anterior | posterior |
|---|---|---|
| 387916 | 72 | 74 |
| 437527 | 59 | 62 |
| 444578 | 69 | 69 |
| 444584 | 0 | 9 |
| 444607 | 59 | 79 |
| 444608 | 41 | 66 |
| 444627 | 41 | 45 |
| 444652 | 61 | 64 |
| 444660 | 35 | 33 |
| 444661 | 72 | 69 |

TABLE 79

Percent increase in AIF1 mRNA expression compared to the control in C57/BL6 mice

| ISIS No | anterior | posterior |
|---|---|---|
| 387916 | 159 | 67 |
| 437527 | 102 | 77 |
| 444578 | 22 | 7 |
| 444584 | 33 | 37 |
| 444607 | 34 | 58 |
| 444608 | 29 | 1 |
| 444627 | 46 | 22 |
| 444652 | 59 | 50 |
| 444660 | −3 | 11 |
| 444661 | 67 | 62 |

Body Weight Measurements

Body weights were measured at regular intervals throughout the study period, and are presented in Table 80. These weights were utilized as an indicator of tolerability. Mice treated with ISIS 437527, ISIS 444584, and ISIS 444652 had consistent body weight throughout the study period and were deemed the most tolerable of all the ISIS oligonucleotides included in the study. 'n/a' indicates no data for that group of mice.

TABLE 80

Body weights of C57/BL6 mice after antisense oligonucleotide treatment

|  | Day 0 | Day 4 | Day 8 | Day 12 | Day 16 | Day 19 | Day 23 | Day 26 | Day 28 |
|---|---|---|---|---|---|---|---|---|---|
| PBS | 105 | 108 | 111 | 114 | 111 | 111 | 113 | 114 | 112 |
| ISIS 387916 | 107 | 108 | 106 | 111 | 106 | 104 | 101 | 101 | 97 |
| ISIS 437527 | 105 | 116 | 116 | 120 | 111 | 112 | 112 | 108 | 108 |
| ISIS 444578 | 105 | 116 | 112 | 115 | 103 | 98 | 83 | 81 | 87 |
| ISIS 444584 | 105 | 117 | 115 | 111 | 105 | 105 | 103 | 104 | 102 |
| ISIS 444607 | 105 | 115 | 112 | 110 | 101 | 98 | 106 | 109 | 106 |
| ISIS 444608 | 102 | 111 | 112 | 112 | 97 | 91 | 78 | 75 | 87 |
| ISIS 444627 | 105 | 116 | 124 | 126 | 105 | 104 | 93 | 94 | 91 |

TABLE 80-continued

Body weights of C57/BL6 mice after antisense oligonucleotide treatment

| | Day 0 | Day 4 | Day 8 | Day 12 | Day 16 | Day 19 | Day 23 | Day 26 | Day 28 |
|---|---|---|---|---|---|---|---|---|---|
| ISIS 444652 | 106 | 122 | 124 | 126 | 119 | 113 | 111 | 111 | 108 |
| ISIS 444659 | 105 | 118 | 123 | 116 | 92 | 89 | 68 | n/a | n/a |
| ISIS 444660 | 104 | 115 | 120 | 118 | 103 | 93 | 89 | 84 | 90 |
| ISIS 444661 | 107 | 125 | 120 | 106 | 76 | 86 | 89 | 86 | 91 |

Example 17: Assay for Neurotoxic Effects of Bolus Administration of Antisense Oligonucleotides in the Striatal Tissue of Rats Sprague-Dawley rats were treated with ISIS oligonucleotides via bolus administration to the striatum, for the purpose of screening for the induction of the microglial marker AIF1 as a measure of CNS toxicity.

Treatment and Surgery

Groups of four Sprague-Dawley rats were administered ISIS 388241, ISIS 443139, ISIS 436671, ISIS 437527, ISIS 444584, ISIS 444591, or ISIS 444652 delivered as a single bolus at a concentration of 25 µg, 50 µg, 75 µg, or 100 µg.

A group of 4 rats were similarly treated with ISIS 387916, delivered as a single bolus at 10 µg, 25 µg, 50 µg, or 75 µg concentrations. A control group of 4 rats were similarly treated with PBS. Seven days after bolus administration, the rats were euthanized using isoflurane and the organs were removed. The animals were decapitated and the brain was removed for dissection of the striatal tissue. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 81. The results indicate that ISIS 388241, ISIS 443139, ISIS 436671, ISIS 444591, ISIS 437527, ISIS 444584, and ISIS 444652 were well tolerated in rat brain.

TABLE 81

Percent expression of AIF1 mRNA levels in vivo as a measure of neurotoxicity

| ISIS No | Dose (µg) | % increase |
|---|---|---|
| 387916 | 10 | 145 |
| | 25 | 157 |
| | 50 | 247 |
| | 75 | 316 |

TABLE 81-continued

Percent expression of AIF1 mRNA levels in vivo as a measure of neurotoxicity

| ISIS No | Dose (µg) | % increase |
|---|---|---|
| 388241 | 25 | 29 |
| | 50 | 12 |
| | 75 | 30 |
| | 100 | 41 |
| 436671 | 25 | 37 |
| | 50 | 2 |
| | 75 | 13 |
| | 100 | 50 |
| 443139 | 25 | 0 |
| | 50 | 7 |
| | 75 | 167 |
| | 100 | 26 |
| 444591 | 25 | 18 |
| | 50 | 80 |
| | 75 | 50 |
| | 100 | 207 |
| 437527 | 25 | 98 |
| | 50 | 45 |
| | 75 | 23 |
| | 100 | 126 |
| 444584 | 25 | -1 |
| | 50 | 10 |
| | 75 | 35 |
| | 100 | 31 |
| 444652 | 25 | 17 |
| | 50 | 46 |
| | 75 | 39 |
| | 100 | 48 |

RNA Analysis of Huntingtin Expression Levels

RNA was extracted from striatal tissue for real-time PCR analysis of huntingtin mRNA levels. Rat huntingtin mRNA levels were measured using the rat primer probe set rHtt_LTS00343. Results were calculated as the percentage reduction of huntingtin expression over that of the PBS control and are presented in Table 82. ISIS 388241 and ISIS 443139 are each mismatched by 6 base pairs or more with the rat gene sequence (SEQ ID NO: 5) and therefore do not show significant inhibition of rat mRNA levels compared to the control. ISIS 444584 has 3 mismatches with the rat gene sequence (SEQ ID NO: 5) and therefore does not show significant inhibition of rat mRNA levels compared to the control.

TABLE 82

Percent reduction of rat huntingtin mRNA levels in rats

| ISIS No | Dose (µg) | % inhibition |
|---|---|---|
| 387916 | 10 | 6 |
| | 25 | 39 |
| | 50 | 55 |
| | 75 | 60 |

TABLE 82-continued

Percent reduction of rat huntingtin mRNA levels in rats

| ISIS No | Dose (µg) | % inhibition |
|---|---|---|
| 388241 | 25 | 8 |
|  | 50 | 23 |
|  | 75 | 27 |
|  | 100 | 19 |
| 436671 | 25 | 52 |
|  | 50 | 57 |
|  | 75 | 57 |
|  | 100 | 70 |
| 443139 | 25 | 35 |
|  | 50 | 29 |
|  | 75 | 28 |
|  | 100 | 27 |

TABLE 82-continued

Percent reduction of rat huntingtin mRNA levels in rats

| ISIS No | Dose (µg) | % inhibition |
|---|---|---|
| 444591 | 25 | 26 |
|  | 50 | 57 |
|  | 75 | 68 |
|  | 100 | 69 |
| 437527 | 25 | 40 |
|  | 50 | 55 |
|  | 75 | 60 |
|  | 100 | 74 |
| 444584 | 25 | 43 |
|  | 50 | 38 |
|  | 75 | 38 |
|  | 100 | 41 |
| 444652 | 25 | 49 |
|  | 50 | 70 |
|  | 75 | 55 |
|  | 100 | 59 |

Example 18: Dose-Dependent Antisense Inhibition of Huntingtin mRNA in Cynomolgous Primary Hepatocytes ISIS 437527, ISIS 444584, and ISIS 444652 were tested in cynomolgous primary hepatocytes at various doses. The benchmark oligonucleotides, ISIS 387916 and ISIS 388241 were also included for comparison. Cells were plated at a density of 35,000 cells per well and transfected using electroporation with 39.0625 nM, 78.125 nM, 156.25 nM, 312.5 nM, 625 nM, 1,250 nM, 2,500 nM, 5,000 nM, 10,000 nM, and 20,000 nM concentrations of each antisense oligonucleotide. After approximately 16 hours, RNA was isolated from the cells and huntingtin mRNA transcript levels were measured by quantitative real-time PCR using primer probe set RTS2686. Huntingtin mRNA transcript levels were normalized to total RNA content, as measured by RIBOGREEN®. Results are presented in Table 83 as percent inhibition of huntingtin, relative to untreated control cells. Control oligonucleotide, ISIS 141923 was included in this assay and did not demonstrate inhibition of huntingtin mRNA, as expected.

ISIS 437527, ISIS 444584, and ISIS 444652 had lower $IC_{50}$ values than the benchmark oligonucleotide, ISIS 388241. ISIS 437527 and ISIS 444652 had as low or lower $IC_{50}$ values than the benchmark oligonucleotide, ISIS 387916.

TABLE 83

Dose-dependent antisense inhibition of huntingtin mRNA in cynomolgous primary hepatocytes

|  | ISIS 387916 | ISIS 388241 | ISIS 437527 | ISIS 444584 | ISIS 444652 | ISIS 141923 |
|---|---|---|---|---|---|---|
| 39.0625 nM | 0 | 6 | 0 | 0 | 0 | 0 |
| 78.125 nM | 17 | 4 | 19 | 0 | 16 | 0 |
| 156.25 nM | 6 | 0 | 27 | 11 | 12 | 3 |
| 312.5 nM | 19 | 0 | 23 | 16 | 35 | 0 |
| 625.0 nM | 31 | 0 | 37 | 30 | 50 | 0 |
| 1250.0 nM | 45 | 0 | 28 | 23 | 52 | 0 |
| 2500.0 nM | 62 | 4 | 33 | 47 | 74 | 0 |
| 5000.0 nM | 78 | 54 | 55 | 42 | 86 | 0 |
| 10000.0 nM | 82 | 80 | 68 | 77 | 91 | 0 |
| 20000.0 nM | 84 | 75 | 70 | 69 | 92 | 0 |
| $IC_{50}$ (µM) | 1.4 | 5.4 | 2.0 | 4.0 | 0.8 | >20 |

Example 19: Measurement of Half-Life of ISIS Oligonucleotides in BACHD Mice Via Single Intrastriatal Bolus Administration BACHD mice were administered ISIS oligonucleotides as a single bolus to the striatum for the purpose of measuring the duration of action of the antisense oligonucleotides against huntingtin mRNA expression, or its half-life, in that tissue.

Treatment and Surgery

Groups of 25 BACD mice each were treated with ISIS 388241, ISIS 436689, ISIS 436671, or ISIS 444591, delivered as a single bolus of 40 µg in a procedure similar to that described in Example 4. A control group of 25 BACHD mice were treated with PBS in a similar procedure. At various time points, 5 mice from each group were euthanized and striatal tissue was extracted. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis

RNA was extracted from anterior and posterior sections of the striatal tissue for real-time PCR analysis of huntingtin mRNA levels. Human mutant huntingtin mRNA levels were measured using RTS2617. Mouse normal huntingtin mRNA levels were measured using the murine primer probe set RTS2633. The results are presented in Tables 84 and 85 and are expressed as percent inhibition compared to the average of the PBS control group at week 1, week 10, and week 20. The half-life of the ISIS oligonucleotides in the anterior section of the brain was calculated from the inhibition data and is presented in Table 86.

TABLE 84

Percent inhibition of human huntingtin mRNA expression at various time points

| ISIS No | Time (weeks) | Posterior | Anterior |
|---|---|---|---|
| 388241 | 1 | 72 | 91 |
| | 5 | 65 | 86 |
| | 10 | 52 | 73 |
| | 15 | 26 | 56 |
| | 20 | 14 | 53 |
| 436671 | 1 | 82 | 92 |
| | 5 | 78 | 89 |
| | 10 | 68 | 82 |
| | 15 | 61 | 77 |
| | 20 | 30 | 77 |
| 444591 | 1 | 60 | 85 |
| | 5 | 58 | 76 |
| | 10 | 48 | 60 |
| | 15 | 27 | 43 |
| | 20 | 27 | 36 |
| 436689 | 1 | 72 | 83 |
| | 5 | 72 | 87 |
| | 10 | 60 | 74 |
| | 15 | 50 | 74 |
| | 20 | 44 | 59 |

TABLE 85

Percent inhibition of mouse huntingtin mRNA expression at various time points

| ISIS No | Time (weeks) | Posterior | Anterior |
|---|---|---|---|
| 388241 | 1 | 1 | 12 |
| | 5 | 22 | 36 |
| | 10 | 17 | 14 |
| | 15 | 7 | 18 |
| | 20 | 9 | 38 |
| 436671 | 1 | 84 | 96 |
| | 5 | 77 | 80 |
| | 10 | 64 | 86 |
| | 15 | 51 | 78 |
| | 20 | 19 | 75 |
| 444591 | 1 | 74 | 95 |
| | 5 | 70 | 90 |
| | 10 | 57 | 67 |
| | 15 | 34 | 47 |
| | 20 | 33 | 38 |
| 436689 | 1 | 40 | 32 |
| | 5 | 47 | 40 |
| | 10 | 35 | 18 |
| | 15 | 34 | 22 |
| | 20 | 36 | 5 |

TABLE 86

Half-life of ISIS oligonucleotides in the anterior section of the brain in BACHD mice after intrastriatal bolus injection

| ISIS No | Half-life (days) |
|---|---|
| 436671 | 46.6 |
| 436689 | 39.4 |
| 444591 | 24.3 |
| 388241 | 25.8 |

Body Weight Measurements

Body weights were measured at regular intervals, and are presented in Table 87 as a percent of the weight of the mice at the start of the study. These weights were utilized as an indicator of tolerability. There were no adverse changes in body weight in any of the mice treated with ISIS oligonucleotides.

TABLE 87

Percent change in body weight of BACHD mice after antisense oligonucleotide treatment

| | Week 5 | Week 10 | Week 15 | Week 20 |
|---|---|---|---|---|
| PBS | 8 | 19 | 26 | 28 |
| ISIS 388241 | 9 | 22 | 29 | 26 |
| ISIS 436671 | 5 | 19 | 35 | 38 |
| ISIS 444591 | 7 | 21 | 30 | 43 |
| ISIS 436689 | 3 | 18 | 31 | 38 |

Example 20: Effect of Intrathecal Administration of ISIS 437527 in Sprague Dawley Rats Sprague Dawley rats were dosed with ISIS 437527 by intrathecal (IT) administration either as a single dose, repeated doses, or continuous infusion.

Treatment and Surgery

Rats were anesthetized with isoflurane and a 28-gauge polyurethane catheter was placed into the IT lumbar space of each rat. The proximal end of the catheter was attached to a dosing pedestal that was extended through the skin for animals in groups receiving bolus injections. The catheter for animals in the group receiving continuous infusion was attached to an ALZET pump (Model 2ML1) which was placed in a subcutaneous pocket on the dorsal aspect of each animal. Post-surgically the animals received a single intramuscular dose of ceftiofur sodium (5 mg/kg) and butorphanol tartrate (0.05 mg/kg). The rats receiving continuous infusion began receiving the oligonucleotide dose immediately. The animals that would receive bolus injections were allowed a surgical recovery period of at least five days after which the patency of the catheter was evaluated.

A group of 5 Sprague Dawley rats was administered a single bolus injection of 350 µg of ISIS 437527 delivered intrathecally. Another group of 5 Sprague Dawley rats was administered bolus injections of 120 µg of ISIS 437527 delivered intrathecally three times over the course of 1 week. Another group of 5 Sprague Dawley rats was administered bolus injections of 350 µg of ISIS 437527 delivered intrathecally three times over the course of 1 week. Another group of 5 Sprague Dawley rats was administered 50 µg/day of ISIS 437527 delivered by continuous infusion at a rate of 0.01 mL/hr for 7 days. A control group of 5 Sprague Dawley rats was administered bolus injections of PBS delivered intrathecally three times over the course of 1 week. Each group was given a recovery period of 7 days, after which the rats were euthanized. The brain and spinal cord from all groups were harvested and analyzed.

RNA Analysis of Huntingtin Expression Levels

RNA was extracted from the frontal cortex, temporal cortex, and the cervical cord for real-time PCR analysis of huntingtin mRNA levels. Rat huntingtin mRNA levels were measured using the primer probe set rHtt_LTS00343 normalized to Cyclophilin levels. The results are presented in Table 88 and are expressed as percent inhibition compared to the average of the PBS control groups.

TABLE 88

Percent inhibition of huntingtin mRNA expression in Sprague Dawley rats

| Tissue | Dose schedule | Dose | % inhibition |
|---|---|---|---|
| Frontal Cortex | IT Infusion | 50 μg/day | 11 |
| | Single IT Bolus | 350 μg | 28 |
| | Repeated IT Bolus | 120 μg × 3 | 21 |
| | Repeated IT Bolus | 350 μg × 3 | 0 |
| Temporal Cortex | IT Infusion | 50 pg/day | 0 |
| | Single IT Bolus | 350 μg | 34 |
| | Repeated IT Bolus | 120 μg × 3 | 44 |
| | Repeated IT Bolus | 350 μg × 3 | 48 |
| Cervical Cord | IT Infusion | 50 μg/day | 22 |
| | Single IT Bolus | 350 μg | 45 |
| | Repeated IT Bolus | 120 μg × 3 | 58 |
| | Repeated IT Bolus | 350 μg × 3 | 46 |

RNA Analysis of AIF1 Expression Levels

RNA was extracted from frontal cortex, temporal cortex, and the cervical cord for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 89. The results indicate that repeated IT bolus administrations lead to inflammation at the cervical cord tissues. Continuous IT administration and single IT bolus administrations were well tolerated in the rats.

TABLE 89

Percent expression of AIF1 mRNA levels in Sprague Dawley rats as a measure of neurotoxicity

| Tissue | Dose schedule | Dose | % inhibition |
|---|---|---|---|
| Frontal Cortex | IT Infusion | 50 μg/day | −36 |
| | Single IT Bolus | 350 μg | −4 |
| | Repeated IT Bolus | 120 μg × 3 | 41 |
| | Repeated IT Bolus | 350 μg × 3 | −7 |
| Temporal Cortex | IT Infusion | 50 μg/day | 15 |
| | Single IT Bolus | 350 μg | 22 |
| | Repeated IT Bolus | 120 μg × 3 | 25 |
| | Repeated IT Bolus | 350 μg × 3 | 76 |
| Cervical Cord | IT Infusion | 50 μg/day | 108 |
| | Single IT Bolus | 350 μg | 72 |
| | Repeated IT Bolus | 120 μg × 3 | 473 |
| | Repeated IT Bolus | 350 μg × 3 | 268 |

Example 21: Measurement of Half-Life of ISIS 436689 in the CNS Tissues of Cynomolgous Monkeys Via Intrathecal Administration Cynomolgous monkeys were administered ISIS 436689 intrathecally (IT) for the purpose of measuring the half-life and duration of action of the antisense oligonucleotide against huntingtin mRNA expression in various CNS tissues.

Treatment

The study was conducted at Northern Biomedical Research, MI. Prior to the start of the treatment, the monkeys were kept in quarantine for a 4-week time period, during which standard panels of serum chemistry and hematology, examination of fecal samples for ova and parasites, and a tuberculosis test, were conducted to screen out abnormal or ailing monkeys. The monkeys were implanted with intrathecal lumbar catheters using polyurethane catheters connected to a subcutaneous titanium access port (P.A.S. PORT® Elite Plastic/Titanium portal with Ultra lock connector). For continuous infusion using an external pump, the animals were anesthetized to attach the dosing apparatus to the port. The animals were pretreated with atropine sulfate by subcutaneous injection at a dose of 0.04 mg/kg. Approximately 15 minutes later, an intramuscular dose of 8 mg/kg of ketamine HCl was administered to induce sedation. The animals were masked to a surgical plane of anesthesia, intubated and maintained on approximately 1 L/min of oxygen and 2% halothane or isoflurane. The animals received a single intramuscular dose of 5 mg/kg ceftiofur sodium antibiotic. An incision was made near the port for placement of the modified needle support. The modified needle was placed in the port and secured with sutures. Upon recovery from surgery, a jacket was placed on the animal.

Fifteen male cynomolgus monkeys were administered 4 mg/day of ISIS 436689 at a concentration of 1.67 mg/mL and at a flow rate of 2.4 mL/day for 21 days. A control group of 3 cynomolgus monkeys was administered with PBS in a similar manner for the same time period. Groups of 3 monkeys each were allowed recovery periods of 1 day, 2 weeks, 4 weeks, or 8 weeks, after which they were euthanized. During the study period, the monkeys were observed daily for signs of illness or distress.

All animals were sedated with an intramuscular injection of 8.0 mg/kg of ketamine HCl, maintained on a halothane or isoflurane/oxygen mixture, and provided with an intravenous bolus of heparin Na at 200 IU/kg. The animals were perfused via the left cardiac ventricle with 0.001% sodium nitrite in saline.

At the time of sacrifice, the brain was cut in a brain matrix at 3 mm coronal slice thickness. Several brain structures were sampled using a 4 mm biopsy punch. One 4 mm diameter sample from each structure was placed in 2 mL screw capped tubes containing 1.0 mL of RN Alater RNA stabilization solution (Qiagen, CA), incubated for 1 hour at ambient temperature and then frozen. Adjacent 6 mm diameter samples were placed in 2 mL screw capped tubes and frozen for pharmacokinetic analysis.

The spinal cord was sectioned into cervical, thoracic and lumbar sections, and approximately 3 mm thick sections of each area of the spinal cord were taken for RNA and pharmacokinetic analysis. These samples were processed in a manner similar to those of the brain samples.

Samples of the liver were harvested for RNA and pharmacokinetic analyses. These samples were processed in a manner similar to those of the brain and spinal cord described above.

RNA Analysis

RNA was extracted from the lumbar spinal cord, thoracic spinal cord, cervical spinal cord, frontal cortex, occipital cortex, cerebellar cortex, caudate tissue, hippocampus, middle brain, and pons for real-time PCR analysis of huntingtin mRNA levels with primer probe set RTS2617. The results measured in the various sections of the spinal cord are presented in Table 90 and are expressed as percent inhibition compared to that measured in the PBS control group at 8 weeks. The results measured in the various sections of the brain are presented in Table 91 and are expressed as percent inhibition compared to that measured in the PBS control group at 8 weeks.

Oligonucleotide Concentration Measurement by ELISA

Tissues (20 mg) were minced, weighed, and homogenized prior to liquid/liquid extraction using phenol/chloroform. The supernatant was removed, lyophilized, and reconstituted in human EDTA plasma (1 mL) before being analyzed using a hybridization ELISA procedure.

ISIS 436689 was detected in the tissues by hybridization to a labeled complementary cutting probe (digoxigenin at the 5' end and a C18 spacer and BioTEG at the 3' end). The complex was then captured on a neutravidin-coated plate and S1 nuclease was added to digest the unhybridized cutting probes. Since ISIS 436689 protected the cutting probe from digestion, the undigested cutting probe was used as a measure of the oligonucleotide concentration. The undigested cutting probe was detected using an anti-digoxigenin antibody conjugated to alkaline phosphatase followed by fluorogenic substrate readout. Oligonucleotide concentrations were measured in the cervical, thoracic, and lumbar sections of the spinal cord and in the liver on days 7, 20, 34, and 62 of the recovery period, and are presented in Table 92. The half-life of ISIS 436689 in these tissues was calculated from this data, and is presented in Table 93. The data indicates that the oligonucleotide was mainly concentrated in the CNS with negligible concentrations in the systemic tissues.

TABLE 92

Concentrations (μg/g tissue) of ISIS 436689 administered IT on huntingtin mRNA expression in various tissues at various time points

| Organ | Day 7 | Day 20 | Day 34 | Day 62 |
|---|---|---|---|---|
| Cervical cord | 118.9 | 78.7 | 79.8 | 42.8 |
| Thoracic cord | 503.5 | 215.8 | 101.6 | 61.4 |
| Lumbar cord | 557.1 | 409.5 | 143.3 | 49.5 |
| Liver | 33.6 | 10.3 | 2.0 | 0.2 |

TABLE 90

Effect of ISIS 436689 administered IT on huntingtin mRNA expression in the spinal cord at various time points

| Recovery period | Lumbar spinal cord | Thoracic spinal cord | Cervical spinal cord |
|---|---|---|---|
| 1 Day | 36 | 66 | 65 |
| 2 Weeks | 56 | 55 | 54 |
| 4 Weeks | 0 | 63 | 65 |
| 8 Weeks | 48 | 48 | 44 |

TABLE 93

Half-life of ISIS 436689 administered IT on huntingtin mRNA expression in various tissues

| Organ | Half-life |
|---|---|
| Cervical cord | 4.0 |
| Thoracic cord | 15.1 |
| Lumbar cord | 18.7 |
| Liver | 7.6 |

TABLE 91

Effect of ISIS 436689 administered IT on huntingtin mRNA expression in various brain tissues at various time points

| Recovery period | Frontal cortex | Occipital cortex | Cerebellar cortex | Caudate | Hippocampus | Middle brain | Pons |
|---|---|---|---|---|---|---|---|
| 1 Day | 53 | 37 | 8 | 21 | 19 | 24 | 22 |
| 2 Weeks | 42 | 28 | 16 | 3 | 28 | 0 | 32 |
| 4 Weeks | 47 | 32 | 25 | 7 | 22 | 2 | 43 |
| 8 Weeks | 33 | 34 | 11 | 17 | 27 | 5 | 22 |

The invention claimed is:

1. A compound comprising a single-stranded modified oligonucleotide, wherein the single-stranded modified oligonucleotide is a gapmer consisting of a 5' wing segment, a central gap segment, and a 3' wing segment, wherein:
the 5' wing segment consists of five linked nucleosides, the central gap segment consists of ten linked deoxynucleosides, and the 3' wing segment consists of five linked nucleosides,
wherein each nucleoside of each wing segment comprises a 2'-O-methoxyethyl sugar, wherein the single-stranded modified oligonucleotide has the nucleobase sequence of 5'-CTCAGTAACATTGACACCAC-3' (SEQ ID NO: 22), wherein each cytosine is a 5-methylcytosine, and wherein each internucleoside linkage of the single-stranded modified oligonucleotide is either a phosphorothioate internucleoside linkage or a phosphodiester internucleoside linkage; and
wherein each internucleoside linkage within the gap segment is a phosphorothioate linkage, the internucleoside linkage connecting the central gap segment to the 5' wing segment is a phosphorothioate linkage, the internucleoside linkage connecting the central gap segment to the 3' wing segment is a phosphorothioate linkage, the 5'-most internucleoside linkage of the 5' wing segment is a phosphorothioate linkage, and the 3'-most internucleoside linkage of the 3' wing segment is a phosphorothioate linkage; and the remaining internucleoside linkages are phosphodiester linkages.

2. The compound of claim 1, consisting of the single-stranded modified oligonucleotide.

3. The compound of claim 1, consisting of the single-stranded modified oligonucleotide covalently linked to a conjugate group.

4. The compound of claim 1, wherein the compound is a pharmaceutically acceptable salt.

5. The compound of claim 4, wherein the pharmaceutically acceptable salt is a sodium salt or a potassium salt.

6. A pharmaceutical composition comprising the compound of claim 1 and a pharmaceutically acceptable carrier or diluent.

7. The pharmaceutical composition of claim 6, wherein the compound consists of the single-stranded modified oligonucleotide.

8. The pharmaceutical composition of claim 6, wherein the compound consists of the single-stranded modified oligonucleotide covalently linked to a conjugate group.

9. The pharmaceutical composition of claim 6, wherein the compound is a pharmaceutically acceptable salt.

10. A pharmaceutical composition consisting essentially of the compound of claim 1 and PBS.

11. A method for reducing huntingtin mRNA levels in an animal, the method comprising administering to the animal a therapeutically effective amount of the pharmaceutical composition of claim 6.

12. The method of claim 11, wherein the single-stranded modified oligonucleotide covalently linked to a conjugate group.

13. The method of claim 11, wherein the compound is a pharmaceutically acceptable salt.

14. The method of claim 13, wherein the pharmaceutically acceptable salt is a sodium salt or a potassium salt.

* * * * *

SEQUENCE LISTING

```
Sequence total quantity: 56
SEQ ID NO: 1              moltype = DNA   length = 13481
FEATURE                   Location/Qualifiers
source                    1..13481
                          mol_type = genomic DNA
                          organism = Homo sapiens
SEQUENCE: 1
gctgccggga cgggtccaag atggacggcc gctcaggttc tgcttttacc tgcggcccag   60
agccccattc attgcccccgg tgctgagcgg cgccgcgagt cggcccgagg cctccgggga  120
ctgccgtgcc gggcgggaga ccgccatggc gaccctggaa aagctgatga aggccttcga  180
gtccctcaag tccttccagc agcagcagca gcagcagcag cagcagcagc agcagcagca  240
gcagcagcag cagcagcagc aacagccgcc accgccgccg ccgccgccgc cgcctcctca  300
gcttcctcag ccgccgccgc aggcacagcc gctgctgcct cagccgcagc cgcccccgcc  360
gccgccccccg ccgccacccg gcccggctgt ggctgaggag ccgctgcacc gaccaaagaa  420
agaactttca gctaccaaga aagaccgtgt gaatcattgt ctgacaatat gtgaaaacat  480
agtggcacag tctgtcagaa attctccaga atttcagaaa cttctgggca tcgctatgga  540
acttttctg ctgtgcagtg atgacgcaga gtcagatgtc aggatggtgg ctgacgaatg  600
cctcaacaaa gttatcaaag ctttgatgga ttctaatctt ccaaggttac agctcgagct  660
ctataaggaa attaaaaaga atggtgcccc tcggagtttg cgtgctgccc tgtggaggtt  720
tgctgagctg gctcacctgg ttcggcctca gaaatgcagg ccttacctgg tgaaccttct  780
gccgtgcctg actcgaacaa gcaagagacc cgaagaatca gtccaggaga ccttggctgc  840
agctgttccc aaaattatgg cttctttttgg caattttgca aatgacaatg aaattaaggt  900
tttgttaaag gccttcatag cgaacctgaa gtcaagctcc cccaccattc ggcggacagc  960
ggctggatca gcagtgagca tctgccagca ctcaagaagg acacaatatt tctatagttg 1020
gctactaaat gtgctcttag gcttactcgt tcctgtcgag gatgaacact ccactctgct 1080
gattcttggc gtgctgctca ccctgaggta tttggtgccc ttgctgcagc agcaggtcaa 1140
ggacacaagc ctgaaaggca gcttcggagt gacaaggaaa gaaatggaag tctctccttc 1200
tgcagagcag cttgtccagg tttatgaact gacgttacat catacacagc accaagacca 1260
caatgttgtg accggagccc tggagctgtt gcagcagctc ttcagaacgc ctccacccga 1320
gcttctgcaa accctgaccg cagtcggggg cattgggcag ctcaccgctg ctaaggagga 1380
gtctggtggc cgaagccgta gtgggagtat tgtggaactt atagctggag ggggttcctc 1440
atgcagccct gtcctttcaa gaaaacaaaa aggcaaagtg tcttaggag aagaagaagc 1500
cttggaggat gactctgaat cgagatcgga tgtcagcagc tctgccttaa cagcctcagt 1560
gaaggatgag atcagtggag agctggctgc ttcttcaggg gtttccactc cagggtcagc 1620
aggtcatgac atcatcacag aacagccacg gtcacagcac acactgcagg cggactcagt 1680
ggatctggcc agctgtgact tgacaagctc tgccactgat ggggatgagg aggatatcctt 1740
gagccacagc tccagccagg tcagcgccgt cccatctgac cctgcatgg acctgaatga 1800
tgggacccag gcctcgtcgc ccatcagcga cagctcccag accaccaccg aagggcctga 1860
ttcagctgtt accccttcag acagttctga aattgtgtta gacggtaccg acaaccagta 1920
tttgggcctg cagattggac agcccccagga tgaagatgga gaagccacag gtattccttcc 1980
tgatgaagcc tcggaggcct tcaggaactc ttccatggcc cttcaacagg cacatttatt 2040
gaaaaacatg agtcactgca ggcagccttc tgacagcagt gttgataaat ttgtgttgag 2100
agatgaagct actgaaccgg gtgatcaaga aaacaagcct tgccgcatca aaggtgacat 2160
tggacagtcc actgatgatg actctgcacc tcttgtccat tgtgtccgcc ttttatctgc 2220
ttcgtttttg ctaacagggg gaaaaaatgt gctggttccg gacagggatg tgagggtcag 2280
cgtgaaggcc ctgccctca gctgtgtggg agcagctgtg gccctccacc cggaatcttt 2340
cttcagcaaa ctctataaag ttcctcttga caccacggaa taccctgagg aacagtatgt 2400
ctcagacatc ttgaactaca tcgatcatgg agacccacag gttcgaggag ccactgccat 2460
tctctgtggg accctcatct gctccatcct cagcaggtcc cgcttccacg tgggagattg 2520
gatgggcacc attagaaccc tcacaggaaa tacattttct ttggcggatt gcattccttt 2580
gctgcggaaa acactgaagg atgagtcttc tgttacttgc aagttagctt gtacagctgt 2640
gaggaactgt gtcatgagtc tctgcagcag cagctacagt gagttaggac tgcagccagt 2700
catcgatgtg ctgactctga ggaacagttc ctattgctg gtgaggacag agcttctgga 2760
aaccccttgca gagattgact tcaggctggt gagcttttg gaggcaaaag cagaaaactt 2820
acacagaggg gctcatcatt atacagggct tttaaaactg caagaacgag tgctcaataa 2880
tgttgtcatc catttgcttg gagatgaaga ccccagggtg cgacatgttg ccgcagcatc 2940
actaattagg cttgtcccaa agctgttta taaatgtgac caaggacaag ctgatccagt 3000
agtggccgtg gcaagagatc aaagcagtgt ttacctgaaa cttctcatgc atgagacgca 3060
gcctccatct catttctccg tcagcacaat aaccagaata tatagaggct ataacctact 3120
accaagcata acagacgtca ctatggaaaa taacctttca agattattg cagcagtttc 3180
tcatgaacta atcacatcaa ccaccagagc actcacattc ggatgctgtg aagctttgt 3240
tcttctttcc actgccttcc cagtttgcat ttggagttta ggttggcact gtggagtgcc 3300
tccactgagt gcctcagatg agtctaggaa gagctgtacc gttgggatgg ccacaatgat 3360
tctgaccctg ctctcgtcag cttggttccc attggatctc tcagcccatc aagatgcttt 3420
gattttggcc ggaaacttgc ttgcagccag tgctcccaaa tctctgagaa gttcatgggc 3480
ctctgaagaa gaagccaacc cagcagccac caagcaagag gaggtctggc cagccctggg 3540
ggaccggggcc ctggtgccca tggtggagca gctcttctct cacctgctga aggtgattaa 3600
catttgtgcc cacgtcctgg atgacgtggc tcctggaccc gcaataaagg cagccttgcc 3660
ttctctaaca aaccccccttt ctctaagtcc catccgacga aagggggaagg agaaagaacc 3720
aggagaacaa gcatctgtac cgttgagtcc caagaaaggc agtgaggcca gtgcagcttc 3780
tagacaatct gataccttcag gtccgttac aacaagtaaa tcctcatcac tggggagttt 3840
ctatcatctt ccttcatacc tcaaactgca tgatgtcctg aaagctacac acgctaacta 3900
caaggtcacg ctggatcttc agaacagcac ggaaaagttt ggaggggttc tccgctcagc 3960
cttggatgtt ctttctcaga tactagagct ggccacactg caggacattg ggaagtgtgt 4020
tgaagagatc ctaggatacc tgaaatcctc ctttagtcga gaaccaatga tggcaactgt 4080
ttgtgttcaa caattgttga agactctctt tggcacaaac ttggcctccc agttgatgg 4140
cttatcttcc aaccccagca gtcacaagg ccgagcacac gccttggct cctccagtgt 4200
gaggccaggc ttgtaccact actgcttcat ggccccgtac acccacttca cccaggccct 4260
```

```
cgctgacgcc agcctgagga acatggtgca ggcggagcag gagaacgaca cctcgggatg   4320
gtttgatgtc ctccagaaag tgtctaccca gttgaagaca aacctcacga gtgtcacaaa   4380
gaaccgtgca gataagaatg ctattcataa tcacattcgt ttgtttgaac ctcttgttat   4440
aaaagcttta aaacagtaca cgactacaac atgtgtgcag ttacagaagc aggttttaga   4500
tttgctggcg cagctggttc agttacgggt taattactgt cttctggatt cagatcaggt   4560
gtttattggc tttgtattga aacagtttga atacattgaa gtgggccagt tcagggaatc   4620
agaggcaatc attccaaaca tcttttttctt cttggtatta ctatcttatg aacgctatca   4680
ttcaaaacag atcattggaa ttcctaaaat cattcagctc tgtgatggca tcatggccag   4740
tggaaggaag gctgtgacac atgccatacc ggctctgcag cccatagtcc acgacctctt   4800
tgtattaaga ggaacaaata aagctgatgc aggaaaagag cttgaaaccc aaaaagaggt   4860
ggtggtgtca atgttactga gactcatcca gtaccatcag gtgttggaga tgttcattct   4920
tgtcctgcag cagtgccaca aggagaatga agacaagtgg aagcgactgt ctcgacagat   4980
agctgacatc atcctcccaa tgttagccaa acagcagatg cacattgact ctcatgaagc   5040
ccttggagtg ttaaatacat tatttgagat tttggccctt tcctccctcc gtccggtaga   5100
catgcttta cggagtatgt tcgtcactcc aaacacaatg gcgtccgtga gcactgttca   5160
actgtggata tcgggaattc tggccatttt gagggttctg atttcccagt caactgaaga   5220
tattgttctt tctcgtattc aggagctctc cttctctccg tatttaatct cctgtacagt   5280
aattaatagg ttaagagatg gggacagtac ttcaacgcta gaagaaccac gtgaagggaa   5340
acaaataaag aatttgccag aagaaacatt ttcaaggttt ctattacaac tggttggtat   5400
tctttagaa gacattgtta caaaacagct gaaggtggaa atgagtgagc agcaacatac   5460
tttctattgc caggaactag gcacactgct aatgtgtctg atccacatct tcaagtctgg   5520
aatgttccgg agaatcacag cagctgccac taggctgttc cgcagtgatg gctgtggcgg   5580
cagtttctac accctggaca gcttgaactt gcgggctcgt tccatgatca ccacccaccc   5640
ggccctggtg ctgctctggt gtcagatact gctgcttgtc aaccacaccg actaccgctg   5700
gtgggcagaa gtgcagcaga ccccgaaaag acacagtctg tccagcacaa agttacttag   5760
tccccagatg tctggagaag aggaggattc tgacttggca gccaaacttg gaatgtgcaa   5820
tagagaaata gtacgaagag gggctctcat tctcttctgt gattatgtct gtcagaacct   5880
ccatgactcc gagcacttaa cgtggctcat tgtaaatcac attcaagatc tgatcagcct   5940
ttcccacgag cctccagtac aggacttcat cagtgccgtt catcggaact ctgctgccag   6000
cggcctgttc atccaggcaa ttcagtctcg ttgtgaaaac ctttcaactc caaccatgct   6060
gaagaaaact cttcagtgct tggaggggat ccatctcagc cagtcgggag ctgtgctcac   6120
gctgtatgtg gacaggcttc tgtgcacccc tttccgtgtg ctggctcgca tggtcgacat   6180
ccttgcttgt cgccgggtag aaatgcttct ggctgcaaat ttacagagca gcatggccca   6240
gttgccaatg gaagaactca acagaatcca ggaataccct cagagcagcg ggctcgctca   6300
gagacaccaa aggctctatt ccctgctgga caggtttcgt ctctccacca tgcaagactc   6360
acttagtccc tctcctccag tctcttccca cccgctggac ggggatgggc acgtgtcact   6420
ggaaacagtg agtccggaca aagactggta cgttcatctt gtcaaatccc agtgttggac   6480
caggtcagat tctgcactgc tggaaggtgc agagctggtg aatcggattc ctgctgaaga   6540
tatgaatgcc ttcatgatga actcggagtt caacctaagc tgctagctc catgcttaag   6600
cctagggatg agtgaaattt ctggtggcca gaagagtgcc ctttttgaag cagcccgtga   6660
ggtgactctg gcccgtgtga gcggcaccgt gcagcagctc cctgctgtcc atcatgtctt   6720
ccagcccgag ctgcctgcag agccggcggc ctactgagc aagttgaatg atctgttttgg   6780
ggatgctgca ctgtatcagt ccctgcccac tctggcccgg gcctggcac agtacctggt   6840
ggtggtctcc aaaactgccca gtcatttgca ccttcctcct gagaaagaga aggacattgt   6900
gaaattcgtg gtggcaaccc ttgaggccct gtcctggcat ttgatccatg agcagatccc   6960
gctgagtctg gatctccagg cagggctgga ctgctgctgc ctggccctgc agctgcctgg   7020
cctctggagc gtggtctcct ccacagagtt tgtgacccac gcctgctccc tcatctactg   7080
tgtgcacttc atcctggagg ccgttgcagt gcagcctgga gagcagcttc ttagtccaga   7140
aagaaggaca aataccccaa aagccatcag cgaggaggag gaggaagtag atccaaacac   7200
acagaatcct aagtatatca ctgcagcctg tgagatggtg gcagaaatgg tggagtctct   7260
gcagtcggtg ttggccttgg gtcataaaag gaatagcgac gtgccggcct ttctcacgcc   7320
attgctaagg aacatcatca tcagcctggc ccgcctgccc cttgtcaaca gctacacacg   7380
tgtgccccca ctggtgtgga agcttggatg gtcacccaaa ccgggagggg attttggcac   7440
agcattccct gagatccccg tggagttcct ccaggaaaag gaagtctta aggagttcat   7500
ctaccgcatc aacacactag gctggaccag tcgtactcag ttggaagaaa cttgggccac   7560
cctccttggt gtcctggtga gcgcagcccc cgtgatggga caggaggaga gccaccagaa   7620
agaagcacag gagaggaccc agatcaacgt cctggccgtg caggccatca cctcactggt   7680
gctcagtgca atgactgtgc ctgtggcggg caacccagct gtaagctgct ggagcagca   7740
gccccggaac aagcctctga aagctctcga caccaggttt gggaggaagc tgagcattat   7800
cagagggatt gtggagcaag agattcaagc aatggtttca aagagagaga atattgccac   7860
ccatcattta tatcaggcat gggatcctgt cccttctctg tctccggcta ctacaggtgc   7920
cctcatcagc cacgagaagc tgctgctaca gatcaacccc gagcgggagc tggggagcat   7980
gagctacaaa ctcggccagg tgtccataca ctccgtgtgg ctggggaaca gcatcacacc   8040
cctgagggag gaggaatggg acgaggaaga ggaggaggag gacgcgccc ctgcaccttc   8100
gtcaccaccc acgtctccag tcaactccag gaaacaccgg gctggagttg acatccactc   8160
ctgttcgcag ttttttgcttg agttgtacag ccgctggatc ctgccgtcca gctcagcag   8220
gaggacccccg gccatcctga tcagtgaggt ggtcagatcc cttctagtgg tctcagactt   8280
gttcaccgag cgcaaccagt ttgagctgat gtatgtgacg ctgacagaac tgcgaagggt   8340
gcacccttca gaagacgaga tcctcgctca gtacctggtg cctgccacct gcaaggcagc   8400
tgccgtcctt gggatggaca aggccgtggc ggagcctgtc agccgcctgc tggagagcac   8460
gctcaggagc agccacctgc ccagcagggt tggagccctg cacggcgtcc tctatgtgct   8520
ggagtgcgac ctgctggacg acactgccaa gcagctcatc ccggtcatca gcgactatct   8580
cctctccaac ctgaaaggga tcgccctctg cgtgaacatt cacagccagc agcacgtact   8640
ggtcatgtgt gccactgcgt tttacctcat tgagaactgt taggccagga   8700
attttcagca tcaataatac agatgtgtgg ggtgatgctg tctggaagtg aggagtccac   8760
cccctccatc atttaccact gtgccctcag aggcctggag cgcctcctgc tctctgagca   8820
gctctcccgc ctgatgcag aatcgctggt caagctgagt gtggacagag tgaacgtgca   8880
cagcccgcac cgggccatgg cggctctggg cctgatgctc acctgcatgt acacaggaaa   8940
ggagaaagtc agtccgggta gaacttcaga ccctaatcct gcagcccccg acagcgagtc   9000
```

```
agtgattgtt gctatggagc gggtatctgt tcttttgat aggatcagga aaggctttcc    9060
ttgtgaagcc agagtggtgg ccaggatcct gccccagttt ctagacgact tcttcccacc    9120
ccaggacatc atgaacaaag tcatcggaga gtttctgtcc aaccagcagc catacccca    9180
gttcatggcc accgtggtgt ataaggtgtt tcagactctg cacagcaccg ggcagtcgtc    9240
catggtccgg gactgggtca tgctgtccct ctccaacttc acgcaggagg ccccggtcgc    9300
catggccacg tggagcctct cctgcttctt tgtcagcgcg tccaccagcc cgtgggtcgc    9360
ggcgatcctc ccacatgtca tcagcaggat gggcaagctg gagcaggtgg acgtgaacct    9420
tttctgcctg gtcgccacag acttctacag acaccagata gaggaggagc tcgaccgcag    9480
ggccttccag tctgtgcttg aggtggttgc agccccagga agcccatatc accggctgtc    9540
gacttgttta cgaaatgtcc acaaggtcac cacctgctga gcgccatggt gggagagact    9600
gtgaggcggc agctggggcc ggagcctttg gaagtctgcg cccttgtgcc ctgcctccac    9660
cgagccagct tggtccctat gggcttccgc acatgccgcg ggcggccagg caacgtgcgt    9720
gtctctgcca tgtggcagaa gtgctctttg tggcagtggc caggcaggga gtgtctgcag    9780
tcctggtggg gctgagcctg aggccttcca gaaagcagga cagctgtgc tgcaccccat    9840
gtgggtgacc aggtccttc tcctgatagt cacctgctgg ttgttgccag gttgcagctg    9900
ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg   10020
ggtgtgcatg ccacgcccg tgtctggatg cacagatgcc atggcctgtg ctgggccagt   10080
ggctgggggt gctagacacc cggcaccatt ctcccttctc tcttttcttc tcaggatttta   10140
aaatttaatt atatcagtaa agagattaat tttaacgtaa ctctttctat gcccgtgtaa   10200
agtatgtgaa tcgcaaggcc tgtgctgcat gcgacagcgt ccggggtggt ggacagggcc   10260
cccggccacg ctccctctcc tgtagccact ggcatagccc tcctgagcac ccgctgacat   10320
ttccgttgta catgttcctg tttatgcatt cacaaggtga ctgggatgta gagaggcgtt   10380
agtgggcagg tggccacagc aggactgagg acaggccccc attatcctag gggtgcgctc   10440
acctgcagcc cctcctcctc gggcacagac gactgtcgtt ctccacccac cagtcaggga   10500
cagcagcctc cctgtcactc agctgagaag gccagccctc cctggctgtg gctcccaccc   10560
actgtgtcca gagacatggg cctcccactc ctgttccttg ctagccctgg ggtggcgtct   10620
gcctaggagc tggctggcag gtgttgggac ctgctgctcc atggatgcat gccctaagag   10680
tgtcactgag ctgtgttttg tctgagcctc tctcggtcaa cagcaaagct tggtgtcttg   10740
gcactgttag tgacagagcc cagcatccct cctgcccccg ttccagctga catcttgcac   10800
ggtgacccct tttagtcagg agagtgcaga tctgtgctca tcggagactg ccccacgcc   10860
ctgtcagagc cgccactcct atccccaggc caggtccctg gaccagcctc ctgtttgcag   10920
gcccagagga gccaagtcat taaaatgaaa gtggattctg gatggccggg ctgctgctga   10980
tgtaggaggt ggatttggga gctctgcttg ccgactggct gtgagacgag gcaggggcca   11040
tgcttcctca gcccctagagg cgagccaggc aaggttgcg actgtcatgt ggcttggttt   11100
ggtcatgccc gtcgatgttt tgggtattga atgtggtaag tggaggaaat gttgaactc   11160
tgtgcaggtc ctgccttgag acccccaagc ttccacctgt ccctctccta tgtggcagct   11220
ggggagcagc tgagatgtgg acttgtatgc tgcccacata cgtgagggg agctgaaagg   11280
gagccctcc tctgagcagc ctctgccagg cctgtatgag gcttttccca ccagctccca   11340
acagaggcct cccccagcca ggaccactc gtcctcgtgg cggggcagca ggagcggtag   11400
aaaggggtcc gatgtttgag gaggcccta agggaagcta ctgaattata acacgtaaga   11460
aaatcaccat tccgtattgg ttgggggctc ctgtttctca tcctagcttt ttcctggaaa   11520
gcccgctaga aggtttggga acgagggga agttctcaga actgttggct gctccccacc   11580
cgcctcccgc ctcccccgca ggttatgtca gcagctctga gacagcagta tcacaggcca   11640
gatgttgttc ctggctagat gtttacattt gtaagaaata acactgtgaa tgtaaaacag   11700
agccattccc ttggaatgca tatcgctggg ctcaacatag agtttgtctt cctcttgttt   11760
acgacgtgat ctaaaccagt ccttagcaag gggctcagaa caccccgctc tggcagtagg   11820
tgtcccccac ccccaaagac ctgcctgtgt gctccggaga tgaatatgag ctcattagta   11880
aaaatgactt cacccacgca tatacataaa gtatccatgc atgtgcatat agacacatct   11940
ataatttcct acacacacct ctcaagacgg agatgcatgg cctctaagag tgcccgtgtc   12000
ggttcttcct ggaagttgac tttccttaga cccgccaggt caagttagcc gcgtgacgga   12060
catccaggcg tgggacgtgg tcagggcagg gctcattcat tgcccactag gatcccactg   12120
gcgaagatgg tctccatatc agctctctgc agaagggagg aagactttat catgttccta   12180
aaaatctgtg gcaagcaccc atcgtattat ccaaatttg ttgcaaatgt gattaatttg   12240
gttgtcaagt tttgggggtg ggctgtgggg agattgcttt tgtttcctg ctggtaatat   12300
cgggaaagat tttaatgaaa ccagggtaga attgttggc aatgcactga agcgtgtttc   12360
tttcccaaaa tgtgcctccc ttccgctgcg ggcccagctg agtctatgta ggtgatgttt   12420
ccagctgcca agtgctcttt gttactgtcc accctcattt ctgccagcgc atgtgtcctt   12480
tcaagggga aatgtgaagc tgaaccccct ccagacaccc agaatgtagc atctgagaag   12540
gccctgtgcc ctaaaggaca ccctcgccc ccatcttcat ggagggggtc atttcagagc   12600
cctcggagcc aatgaacagc tcctcctctt ggagctgaga tgagcccac gtggagctcg   12660
ggacggatag tagacagcaa taactcggtg tgtggccgcc tggcaggtgg aacttcctcc   12720
cgttgcgggg tggagtgagg ttagttctgt gtgtctggtg ggtggagtca ggcttctctt   12780
gctacctgtg agcatcctt ccagcagaca tcctcatcgg gctttgtccc tcccccgctt   12840
cctccctctg cggggaggac ccgggaccac agctgctggg cagggtagac ttggagctgt   12900
cctccagagg ggtcacgtgt aggagtgaga agaaggaaga tcttgagagc tgctgaggga   12960
ccttggagag ctcaggatgg ctcagacgag gacactcgct tgccgggcct gggcctcctg   13020
ggaaggaggg agctgctcag aatgccgcat gacaactgaa ggcaacctgg aaggttcagg   13080
ggccgctctt cccccatgtg cctgtcacgc tctggtgcag tcaaaggaac gcttcccctt   13140
cagttgtttc taagagcaga gtctcccgct gcaatctggg tggtaactgc cagccttgga   13200
ggatcgtggc caacgtggac ctgcctacgg agggtgggct ctgacccaag tggggcctcc   13260
ttgtccaggt ctcactgctt tgcaccgtgg tcagagggac tgtcagctga gcttgagctc   13320
ccctggagcc agcagggctg tgatgggcga gtccggagc ccacccaga cctgaatgct   13380
tctgagagca aagggaagga ctgacgagag atgtatattt aatttttaa ctgctgcaaa   13440
cattgtacat ccaaattaaa ggaaaaaaat ggaaaccatc a                       13481

SEQ ID NO: 2         moltype = DNA   length = 172001
FEATURE              Location/Qualifiers
source               1..172001
```

```
                    mol_type = genomic DNA
                    organism = Homo sapiens
SEQUENCE: 2
cctgcagggg cctctccagc tcactggggg tggggtgggg gtcacacttg gggtcctcag   60
gtcgtgccga ccacgcgcat tctctgcgct ctgcgcagga gctcgcccac cctctcccg   120
tgcagagagc cccgcagctg gctcccgca gggctgtccg ggtgagtatg gctctggcca   180
cgggccagtg tggcgggagg gcaaacccca aggccacctc ggctcagagt ccacggccgg   240
ctgtcgcccc gctccaggcg tcggcggggg atcctttccg catgggcctg cgcccgcgct   300
cggcgccccc tccacggccc cgccccgtcc atggcccccgt ccttcatggg cgagcccctc   360
catgccctg cccctccgcg cccacccct ccctcgcccc acctctcacc ttcctgcccc   420
gcccccagcc tccccaaccc tcaccggcca gtccctccc ctatcccgtc cgcccctcag   480
ccgccccgcc cctcagccgg cctgcctaat gtccccgtcc ccagcatcgc cccgccccgc   540
ccccgtctcg ccccgcccct caggcggcct ccctgctgtg ccccgcccg gctcgccac    600
gcccctacct caccacgccc cccgcatcgc cacgcccccc gcatcgccac gcctcccta   660
ccatgcagtc ccgcccgtc ccttcctcgt cccgcctcgc cgcgacactt cacacacagc   720
ttcgcctcac cccattacag tctcaccacg ccccgtcccc tctccgttga gccccgcgcc   780
ttcgcccggg tggggcgctg cgctgtcagc ggccttgctg tgtgaggcag aacctgcggg   840
ggcagggggcg ggctggttcc ctggcagcc attggcagag tccgcaggct agggctgtca   900
atcatgctgg ccggcgtggc cccgcctccg ccggcgcgcg cccgcctccg ccggcgcagc   960
gtctgggacg caaggcgccg tggggggctgc cgggacgggt ccaagatgga cggccgctca  1020
ggttctgctt ttacctgcgg cccagagccc cattcattgc cccggtgctg agcggcgccg  1080
cgagtcggcc cgaggcctcc gggactgcc gtgccggggcg ggagaccgcc atggcgaccc  1140
tggaaaagct gatgaaggcc ttcgagtccc tcaagtcctt ccagcagcag cagcagcagc  1200
agcagcagca gcagcagcag cagcagcagc agcagcagca acagccgcca ccgccgccgc  1260
cgccgccgcc gcctcctcag cttcctcagc cgccgccgca ggcacagccg ctgctgcctc  1320
agccgcagcc gccccccgcg ccgccccgc gccaccgg cccggctgtg gctgaggagc  1380
cgctgcaccg accgtgagtt tgggcccgct gcagctccct gtcccggcgg gtcccaggct  1440
acggcgggga tggcggtaac cctgcagcct gcgggccggc gacacgaacc cccggccccg  1500
cagagacaga gtgacccagc aacccagagc ccatgaggga caccccgccccc ctcctggggc  1560
gaggccttcc cccacttcag ccccgctccc tcacttgggt cttcccttgt gcaggcgttt gaatgagttg  1620
ggggaggcag agccttgttg gggcctgtcc tgaattcacc gaggggagtc acggcctcag  1680
ccctctcgcc cttcgcagga tgcgaagagt tggggcgaga acttgtttct ttttattgc  1740
gagaaaccag ggcgggggtt cttttaactg cgttgtgaag agaacttgga ggagccgaga  1800
tttgctcagt gccacttccc tcttctagtc tgagagggaa gagggctggg ggcgcgggac  1860
acttcgagag gaggcggggt ttggagctgg agagatgtgg gggcagtgga tgacataatg  1920
cttttaggac gcctcggcgg gagtggcggg gcagggggg ggcggggagt gagggcgcgt  1980
ccaatgggag atttctttc ctagtggcac ttaaaacagc ctgagatttg aggctcttcc  2040
tacattgtca ggacatttca tttagttcat gatcacggtg gtagtaacac gattttaagc  2100
accaccctaag agatctgctc atctaagcct aagttggtct gcaggcgttt gaatgagttg  2160
tggttgccaa gtaaagtggt gaacttacg ggtgattaat gaaattatct taaatattag  2220
gaagagttga ttgaagttttt ttgcctatgt gtgttgggaa taaaaccaac acgttgctga  2280
tggggaggtt aattgccgag ggatgaatga ggtgtacatt ttaccagtat tccagtcagg  2340
cttgccagaa tacgggggt ccgcagactc cgtgggcatc tcagatgtgc cagtgaaagg  2400
gtttctgttt gcttcattgc tgacagcttg ttacttttttg gaagctaggg gtttctgttg  2460
cttgttcttg gggagaattt ttgaaacagg aaaagagaga ccattaaaac atctagcgga  2520
accccaggac tttccctgga agtctgtgtg tcgagtgtac agtaggagtt aggaagtact  2580
ctggtgcagt tcaggccttt ctcttaccct tcagtattct atttccgatc tggatgtgtc  2640
ccagatggca tttggtaaga atatctctgt taagactgat taattttag taatattct   2700
tgttcttgt ttctgttatg atccttgtct cgtcttcaaa gttaattag aaaatgattc   2760
ggagagcagt gttagcttat ttgttggaat aaaatttagg aataaattat tctaaaggat  2820
ggaaaaactt tttggatatt tggagaaatt ttaaaacaat ttggctttatc tcttcagtaa  2880
gtaatttctc atccagaaat ttactgtagt gcttttctag gaggtaggtg tcataaagt   2940
tcacacattg catgtatctt gtgtaaacac taaacagggc tcctgatggg aaggaagacc  3000
tttctgctgg gctgcttcag acacttgatc attctaaaaa tatgccttct ctttcttatg  3060
ctgattttgac agaacctgca tttgcttatc ttcaaaatat gggtatcaag aaattttcctt 3120
tgctgccttg acaaaggaga tagattttgt ttcattactt taaggtaata tatgattacc  3180
ttatttaaaa aatttaatca ggactggcaa ggtggcttac acctttaatc cgagcacttt  3240
gggaggccta ggtggacgaa tcacctgagg tcaggagttt gagaccagcc tggctaacat  3300
ggtgaaaccc tgtctctact aaaaatacaa aaattagtc gtcatggtgg cacgtgcctg  3360
taatccaagc tacctggag gctgaggcag gaaatcgct tgaacccggg aggcagagtc  3420
tgcagtgagt tgagatcacg ccactgcact ccagcctggg tgacagagcg agactctatc  3480
tcaaaaaaaa tttttttaa tgtattattt ttgcataagt aatacattga catgatacaa  3540
attctgtaat tacaaaaggg caataattaa aatatcttcc ttccacccct ttcctctgag  3600
tacctaactt tgtccccaag aacaagcact atttcagttc ctcatgtatc ctgccagata  3660
taacctgttc atattgtaag atagatttaa aatgctctaa aaacaaaagt agtttagaat  3720
aatatatatc tatatatttt tgagatgta gtctcacatt gtcacccagg ctggagtgca  3780
gtgatacaat ctcggctcac tgcagtctct gcctccaggg ttcaaatgct tctcctgcct  3840
cagccttctg agtagctggg attacaggcg cccaccaca tgtccagcta atttttgtat  3900
ttttagtaga gatggggttt caccatgttg gccaggctgg tcttgaactc ctgacccttgt  3960
gatctgtcca cctcggcctc ccaaagtgct gggattacag gtgtgagcca ccatgcctgg  4020
ctagaataat aactttaaa ggttcttagc atgctctgaa atcaactgca ttaggtttat  4080
ttatagtttt atagttattt taaataaat gcatatttgt catatttctc tgtatttgc   4140
tgttgagaaa ggaggtattc actaattttg agtaacaaac actgctcaca aagtttggat  4200
tttggcagtt ctgttcacgt gcttcagcca aaaatctct ttctcaaagt aagattgatg  4260
aaagcaattt agaaagtatc tgttctgttt ttatggctct tgctctttgg tgtggaactg  4320
tggtgtcacg ccatgcatgg gcctcagttt atgagtgttt gtgctctgct cagcatacag  4380
gatgcaggag ttccttatgg ggctggctgc aggctcagca aatctagcat gcttgggagg  4440
gtcctcacag taattaggag gcaattaata cttgcttctg gcagtttctt attctccttc  4500
agattccat ctggtgtttc cctgactta ttcattcatc agtaaatatt tactaaacat   4560
```

```
gtactatgtg cctggcactg ttataggtgc agggctcagc agtgagcaga caaagctctg  4620
ccctcgtgaa gctttcattc taatgaagga catagacagt aagcaagata gataagtaaa  4680
atatacagta cgttaatacg tggaggaact tcaaagcagg gaaggggata gggaaatgtc  4740
agggttaatc gagtgttaac ttatttttat ttttaaaaaa attgttaagg gctttccagc  4800
aaaacccaga aagcctgcta gacaaattcc aaaagagctg tagcactaag tgttgacatt  4860
tttattttat tttgttttgt tttgttttttt ttgagacagt tcttgctcta tcagccaggc  4920
tggagtgcac tagtgtgatc ttggctcact gcaacctctg cctcttgggt tcaagtgatt  4980
ctcatgcctc agcctcctgt ttagctggga ttatagacat gcactgccat gcctgggtaa  5040
ttttttttt ttccccgag acggagtctt gctctgtcgc ccaggctgga gtgcagtggc  5100
gcgatctcag ctcactgcaa gctccgcttc ccgagttcac gccattctcc tgcctcagtc  5160
tcccaagtag ctgggactac aggcgcctgc caccacgtcc agctaatttt tttgtatttt  5220
taatagagac ggggtttcac cgtgttagcc aggatgatct tgatctcctg acctcgtcat  5280
ccgccgacct tgtgatccgc ccacctcggc ctcccaaagt gctgggatta caggcatgag  5340
ccactgtgcc cggccacgcc tgggtaattt ttgtattttt agtagagatg gggtttttgc  5400
atgatgagca ggctggtctc gaactcccgg cctcatgtga tctgcctgcc ttggcctccc  5460
aaagtgctag gattacaggc atgagccacc atacctggcc agtgttgata ttttaaatac  5520
ggtgttcagg gaaggtccac tgagaagaca gcttttttt ttttttttt tggggttggg  5580
gggcaaggtc ttgctcttta acccaggctg gaatgcagta tcactatcgt agctcacttc  5640
agccttgaac tcctgggctc aagtgatcct cccacctcaa cctcacaatg tgttgggact  5700
ataggtgtga gccatcacac ctggccagat gatggctttt gagtaaagac ctcaagcgag  5760
ttaagagtct agtgtaaggg tgtatgaagt agtggtattc cagatggggg gaacaggtcc  5820
aaaatcttcc tgtttcagga atagcaagga tgtcattttg gttgggtgaa ttgagtgagg  5880
gggacatttg tagtaagaag taaggtccaa gaggtcaagg gagtgccata tcagaccaat  5940
actacttgcc ttgtagatgg aataaagata ttggcatttta tgtgagtgag atgggatgtc  6000
actgaggat tagagcagag gagtagcatg atctgaattt caatcttaag tgaactctgg  6060
ctgacaacag agtgaagggg aacaccggca aaagcagaaa ccagttagga agccactgca  6120
gtgctcagat aagcatggtg ggttctgtca gggtaccggc tgtcggctgt gggcagtgtg  6180
aggaatgact gactggattt tgaatgcgga accaactgca cttgttgaac tctgctaagt  6240
ataacaattt agcagtagct tgcgttatca ggtttgtatt cagctgcaag taacagaaaa  6300
tcctgctgca atagcttaaa ctggtaacaa gcaagagctt atcagaagac aaaaataagt  6360
ctggggaaat tcaacaataa gttaaggaac ccaggctctt tcttttttt tttttgaaa  6420
cggagtttcg ctcttgtcac ccgggctgga gtgcaatgat gtgatctcag ctcactaaaa  6480
cctctacctc ctgggttcaa gtgattcttc tgcctcagcc tcccaagtaa ctgggattac  6540
aggcgtatac caccatgccc agctaatttt tgtgtttttta gtagagatgg ggtttcacca  6600
tgttggccag gctggtctcg aacttctgac ctcaggtgat ccactcgcct cagcctgcca  6660
aagtgctggg attacaggtt tgggccactg caccggtca gaacccaggc tctttcttat  6720
acttaccttg caaaccttg ttctcatttt ttccctttgt attttattg ttgaattgta  6780
atagttcttt atatattctg gatactggat tcttatcaga tagatgattt gtaaaaactc  6840
tcccttcctt tggattgtct ttttacttc ttgatagtgt cttttgaagt gtaaaagttt  6900
ttaattttga tgaagtcgag tttatctatt ttgtctttgg ttgctgtgct tcaagtgtca  6960
tatctaagaa atcattgtct aatccaaagt caaaaaggtt tactcctatg ttttcttcta  7020
agaatttag agttttacat ttaagtctga tccattttga gttaattttt atatatggtt  7080
caggtagaag tccaacttta ttcttttcca tgtggttatt cagttgtccc agcactgttt  7140
gttgaagaga ctattctttc cccatggaat tatcttagta cccttgttga aaattaatcg  7200
tccttaattg tataaattta tttctagact gtcagttcta cctgttggtc tttatgtcga  7260
tcctgtgcca gtaccataca gtcttgatta ctgaagtttg tgtcacagtt taaattcatg  7320
aaatgtgagt tctccaactt tgttccttt caagattgat ttggccatgc tgggtccctt  7380
gcatttccgt acgaattgta ggatcagctt gtcagtttca acaaagaagc caagtaggat  7440
tctgagaggt attgtgttga atctgtagat caacttgggg agtattgcca tcttaacaat  7500
attgtcttcc acctatgaac atgggcaaac tttgtgtaaa tggtcagatt gtaagtattt  7560
cgggctgtgt gggcacagtg tctctgtcac agctacgcgg ctctgccatt gtagcatgaa  7620
agtagccata agcaatatgt atgagtgtct gtgttccaat agaatttttat taatgacaag  7680
gaagtttgaa tttcatataa ttttcacctg tcatgagata gtatttgatt attttggtca  7740
accattttaaa aatgtaaaaa catttcttag cttgtgaact agccaaaaat atgcaggtta  7800
tagttttccc actcctaggt taaaatatga taggaccaca ttttgaaagc atttcttttt  7860
tttttttttt tttttttttt gagacggagt tcactcttg ttgcccaggc tggagtgcag  7920
tggcgcgatc tcggctcact gcaacctctg cctcccaggt tcaagacatt ctcctgcacg  7980
gcctccctag tagctgggat tacaggcatg cgccaccaca cccagctaat tttgtatttt  8040
tagtagagac ggggtttctc catgttggtc aggctggtct tgaactcctg acctcaggtg  8100
atccacccgc ctcagcctcc caaagtgctg ggattacagg tgtgagcca ccacacccctg  8160
ctggaaagca tttctttttt ggctgttttt gtttttttt taaactagtt ttgaaaatta  8220
taaaagttac acatatacat tataaaaata tcttcaagca gcacagatga aaaacaaagc  8280
ccttcttgca agtctgtcat ctttgtctaa cttcctaaga acaaaagtgt ttcttgtgtc  8340
ttcttcccag atttttaatat gcatatacaa gcatttaaat gtgtcatttt ttgtttgctt  8400
gactgagatc acattacata tgtatttttt tacttaacaa tgtgtcatag atattgttcc  8460
atagcagtac ctgtaattct tattaattgc tatgtaatat tttagaattt cttttttaaa  8520
gaggactttt ggagatgtaa aggcaaaggt ctcacatttt tgtggctgta gaatgtgctg  8580
gtgacatatt ctctctacct tgagaagtcc ccatccccat cacctccatt tcctgtaaat  8640
aagtcaacca cttgataaac taccttttga tggatccaca ctcaaaacat ttagtcttat  8700
tcagacaaca aggaggaaaa ataaaatacc ttataaagca ctgtttaata ttgtattaaa  8760
ttggatcaat ttgggggcta aatgtatgt tagagacatg atatgtccat aggtccttgc  8820
tatcacagtg aggtctcagg gacagtcgtt tggtatcatt tgggatctca taagcagact  8880
ctctctgctt gacctgacaa atcagagtct gtgttttaac aggttcagtg agtgacttac  8940
atgcacatgt gagtttggga agctccactg taggtgctta gccttacct ttgttgttgc  9000
taataacaat gcaagcattt gggaggaaga cctgtgttgc tcatatgtgt ccaggtgtag  9060
ctgaggtggc cttgcttatc tgctgtaggg ccgttgagca tttctgtagc tgtgatgagt  9120
gagctgaggt gagcctgcgg agagctccca gccattggta gtgggactcg cttagatgaa  9180
ctggaaggac cctttcatct gagcagccac tatgcagaaa acaaccgaa tgaggggaga  9240
gacaatgtgc aatttattt agggcacaaa ggagagctgt ggttagaagg tgacatttga  9300
```

```
gtggaaaggg ggcaagccat gtgtatagcg ggagaagaga ggtccaggca gagttaacag   9360
aaggcagaaa tgctttccat gtttgagaac cagtaaggag gccagtggct gaagtaaggt   9420
gaagggcaga aataaggatg aggctgcgag agatgagagg ttagagacga gcgtcttgtg   9480
caccaagata agcttgtgtg gtcaaaacaa gtagtttaat ttatgttttt aaaagatcat   9540
tttggctggg cacaatggtt catgcctgta ataccagtag tttgagacgg tgtggtggga   9600
ggattgcctg aggccagacg accagcatag ccaacatagc agcacctata aggtctctac   9660
aaaaaacttt aaaaaattag ctgggcatag tggtgtgtgc ctgtagtccc agctactcag   9720
gaggctgagg aggctggagg attgcttgag tccaggagtt tgaggctgca gtgagctatg   9780
attatgccac tacactacaa cctgggcaag agagtgagac cctgtctcta aatatacaca  9840
cacacacaca cacacacaca cacacacaca cacacacaca catatatatg   9900
tatatatatg catttagatg aaaagatcac tttgacaata ccacatgctg gtgaggattt   9960
agaaaaacta ggtcacttat tgctggtggg aatataatat agtacggcca ctctggaaaa  10020
cagtttggca gtttgtcata aaactgaaca taccgttagt atacagccca gcagcaacta  10080
caatcctggg cattaatcct agagaaatga aaccttaatg ttcacataaa aacctatact  10140
caagtatgca tagcagcttt acccataata tctaagaact ggaatcagct cagatgtcct  10200
tcaacaggtg aatggttaaa ctactcagta ataaaaagga atgagctact gatagcatgc  10260
aacagtttag gtgaagttat gctaatgaaa aaagccaatc ccaaaaggtt atacatactg  10320
tatgattcta tgtttttttg caatggcaca gttttaggga tggagaatag attagtggtt  10380
gcctggggtt agagatgggg tagtagagta ggttagtggt ggcagaggag agaaaagaga  10440
gggaggtgaa tgtggttata aaggacaac acagggggaat acttgtaatg gaaatgcttt  10500
gtcttttttt ttttttttt tttttggcg acagagtctt gctctgttgc ccaggctgga  10560
gtgcagtggc atgatctttt ctcactgcaa cctctgcctc ctgggttcaa gtgatacttg  10620
tgtctcagtc tcccatgttc agagtgaaac aaaccagaga taatgttcat ccaaataatc  10680
caacacacat gacattaaaa catcaagatc aggtcggacg tggtggctca tgcctgtaat  10740
cccagcactt tgggaggcc aaggtgggca gatcacttga ggtcaggagt cgagaccag  10800
ccgggccaac atgatgaaac cccatccttga ctaaaaatac aaaaattagc cgggcatggt  10860
ggtgtgcacc tgtagtccca gctacttggg aggctgaggc aagagaactg cttgaacccg  10920
aggggcagag gttgcagtga gctgagagtg cgccattgca cttcagcctg tgtgacagag  10980
taagactcca tctccaaaaa aaaaaaacca agatcaatta aaatacagca ttactgggcc  11040
gggtgtggtg gctcacacct gtaatcccag cactttgggg ggccgagatg ggcagatcac  11100
gaggtcagga gatccagacc atcccggcta acacggtgaa accccgtctc tactaaaaaa  11160
tacaaaaaat tagccgggta tagtggtggg tgcctgtagt cccagctact gggaggctg  11220
aagcaggaga atggtgtgaa cccgggaggc agagctggca gtgagctgag atcgcgccac  11280
tgcactccag cctgggcgac agagcaagac tccgtctccgg gggaaaaaaa aaataaata  11340
aatagaatgc tgtagtgtcc ttgagtttac atgccctcc ttacgcttgt gtgcccgtgc  11400
agattgcttg attacacaat tagaggaggc tggcggagga ttgttttaat ttttttttt  11460
ttgagacagt ctggctctgt tccccaggct agagtgcaat ggcgcaatct tggtgcactg  11520
caacctctgc ctcctgggtt caagcagttc ttctgccgca gcctcccgag tagctgggat  11580
tataggcgcc cgccaccacg cccaactatt ttttgtattt ttagtagagac agcgttttcac  11640
catgctggcc aggctggtct cgaactcctg acctcagatg atctgctgcc ccagcctccc  11700
aaagtgctgg gattacaggc gtgagccaca cctggccgtt tgttttaatt ttgaaggtga  11760
agtgaaagtg actacattta ccaaaagtga ttgaaaagcc aggactgttc ttaccctgtt  11820
tttccagttc ttgctcagag caaggtggtt tctttttcaa ttaatcacca tacttacttt  11880
tcatgtagaa caagtcagtt tgagttatca gttcatcatc ttaactaaat tccatggggg  11940
aaggaattag ttttagtttc ttaaacttcc aggtttgctt attggacaaa atgagatagc  12000
aaggcagtgt ttttaagtta gattttttat ttctttggta atacaattt ctcagaaact  12060
tagtagtctt ttagtttagt tgtttttagt tggtcctata ttttggatca cccctctcta  12120
ctttatttg atagtgccaa ctgtgaagac atctgaagcc ataggtttgg atgggaagga  12180
ggcatcttta gcctgatcat cttcgccagg ctgtttatct cctttgctt ggctgagaag  12240
tcttaatagg aggcttattc ccagctattt ggggacatag aagcagttag ccattgctta  12300
tattttactg aggtctgtgt ggtatgttga ttgtagtcag ttaacgattt tgagaactga  12360
aggcagcctg gtatatatag agtaggtatt agactgtgtt tcttctaatt gaatttccca  12420
tctcttgtaa tctatgccat catcttctgt actgctgaga aagaaagaaa gtttctaatc  12480
aaactatacc actggttgta agatgcagtt tggctttagt gatgttaaca catgattcaa  12540
acgtgaaatt gattgagtat tggtgaaata cagaggagat ttaaagccag aagacctggg  12600
tttaaatgct ggctgtatga cttcatatct gtgtgatctt gggcatgtca tggttggcac  12660
ttcaatttct tctctctata atgggggaag tgaggcagt catggtggct catacctata  12720
atcccagtgc tttgggaggc caagatggga agatcgcttg aggccaggag tttgagcaat  12780
tgggcaacat cgtgaggccc cgtctctaca aaatattttg aaaaaattag ccaggccgag  12840
tggtgcgtgc ctgtggtccg cgccactcag gaggctgaga cgggaggatc ctttcagcct  12900
aggagtttaa ggctaaagtg agccatgatt gtgctatcgt actccagcct gggcagcaga  12960
gcaagatcct gactctaaaa aaaagtaaaa taaagtaaaa tgggggaaat gaactgcttt  13020
agtaacatca tctgttttt ctgtgagcag cgtagcttga cagccattgg tgaactcgtg  13080
ctgtgcttt ccctgtccag atccccattc tgcccgcaac atggagtata acggttatt  13140
catagtagtc gagaaacact cactgaatga atgaatgagg tgtagaacta agtggagtgg  13200
gtaattcaac acatattaat ttccttcttt ttttattttt tagaaagaaa gaactttcag  13260
ctaccaagaa agaccgtgtg aatcattgtc tgacaatatg tgaaaacata gtggcacagt  13320
ctgtcaggta attgcacttt gaactgtcta gagaaaataa gaactttgta tatttcagt  13380
cttaatgggc tagaatattc tttgtgtccc agctatttta aatgcattca gaaatcagtt  13440
taagatgaag aaggacccctt tcccatatt tctggctata tacaaggata tccagacact  13500
gaaatgaata atgttccctt tttgtaatct tttatgcaaa aattaaaacc attatggtaa  13560
ttgaacaaca tgtttatgtt tagttaacac ccttagcaac tatagttatt ttaaaaccat  13620
ctatggtttg ataatttttgc atttgttgca atagtaggaa cagcacaaga cagttcagtt  13680
tgtctctctt attttgtttt tcttggcagt ttgctgtcct attgtacctc tgctcctagc  13740
agtggctgga gcccactcct ctgtgcttcg ggattagtgg ggatcgtggg gcattgactg  13800
taggtcagct ttccttgctt gatctttctc actgggatga actagcagca ccttcttttg  13860
tagctgcttt gcttttgact atctttctga ccgttgttcc tagtagctgt agatggtaaa  13920
tatatttagg cctgtttcca atggctcagt aggagacata ttcacctatg atatctgaat  13980
tctgttaccc acatgggcat gcgtgaaata gttgccttgc cttactttcc cttggaataa  14040
```

```
ataattcatg ttattctcct ggtagaagct agaaaaagcc tttatagtca gtcagaaaaa    14100
aatttttaga caaataatct tgattttagt actgacaaaa acgtgtggtg attcttttt     14160
taatttttt ttgagacgga gtttcactct tgttgcccag gctggagtgc aatggcgtga     14220
tctcggctca ctgcaacctc tgcctcctgg gttcaagtga ttctcctgcc tcagcctccc    14280
aagtagctgg agttacaggc atgtgctact gtgcccagct aattttgtat ttttagtaga    14340
gatgttggtc aggctgatct cgaactccca accttaggtg atctgcccgc ctcagcctcc    14400
caaagtgctg ggattacagg cgtgagccag ggcgcccggt gattcatttg tttttttcaaa   14460
aaatttcctc ttggccattg cttttcactt ttgttttttt tttttttttg agacggagtc    14520
acgatctgtc acccaggctg gagtgcagtg gcatgatctt ggcttactgc aagctctgcc    14580
tcccaggttc acgccattct cctgcttcag cctggcgagt agctgggact acaggtgctc    14640
gccaccacac ccggctaatt ttttgtattt ttagtagaga tggggtttca ccgtggtctt    14700
gatctcctga cctcatgacc cgctcaactc agcctcccaa agtgctggga ttacaggcgt    14760
gagccaccgc gcccggccct ctcttgtctt tttattgtgg taaaatgcac ataaaattga    14820
ctgtcttaac cattttagg ggtacagttc agtatatata ttcgtaatgt tgtacagcca     14880
tcactgccat ctacttcata agttttttctt ctgtcaaaac tgaacatctg tcttcattaa   14940
actccctatc atccattctt tcctgtagtc ccttttctact ttctgtctgt atgagtgtaa   15000
ctgctctgga gacctcatgt aagtggattc ctacaggatt tgtgttttt ttttggtgat     15060
ctgcttattt ttaatgcctc tgtgcatttg tattatatac tttcaaagtg atttcacaaa    15120
accgtttcat tttaggttaa ctcatttctg ttgtttgtga aatactgtgt atgattctgt    15180
tctgtttctg tctaatttgt ggaaatgttg tgggaagaaa atgaaataac aaatgagcat    15240
atgtcctgaa aataaaata taaaaattct aagttagcat gctattgtag aatacaacgc     15300
tatgataaaa gtaggaaaaa aaaaggtttg aattctatct ctgctacctg tgtaagctgg    15360
gtgactttag ataagctgta acgtgtttga gccttactgg ctcattttg aaatgtaatc     15420
cctagttaca cagttcttgt gggatcagat ggtacatgtg aaacactgtg aaaaagcaac    15480
tgcatagata tgttcattag ccacctgagc gggaagcgta tcccattgcg atgcccatca    15540
tccaaagcta tatgttatct ttacttttt tttttgaga cagagtctg ctctgttgcc       15600
caggctagag tgcagtggtg caatctcagc tcactgcaag ctccacctcc cgggttcacg    15660
ctattctcct gccccagcct cccaagtagc tgggactaca ggcacccgcc accatgcctg    15720
gctaaatttt tgtatttta gtagagatgg ggtttcaccg tgttagccag gatggtcttg     15780
atctcctgac ctcgtgatcc gcccgcctcg gcctcccaaa gtgctgggat tacaggcgtg    15840
agccactgcc cctggccatc tttacttttt ttgtgaaatg actttaaata cttggcaaac    15900
atttggtcat tgttcatctg atctccacca tccaggtctc agagaacata atttctctct    15960
gaaagcttat tgacccagga aataagatct ctttcaatct gagtgcgtca ggctttattc    16020
ttgtcatttt gtcttttgat aattttcaaa tggaattcat ggaatgttgg cttatattca    16080
tatattagta aagtatgttg agacatctta agattgattt gtggttctat atgccatatt    16140
aaatcaaaat aatagctgtt aatggttttc acattagtct gtctcttgtt tttatggagt    16200
aatgctgaga gttcattatg cttgttctac agaagagcat gttaaaagga gttttttggag  16260
tcagagaggt tattcttggt ttcataggat acactctata ctttttaggg atttcagagt    16320
atatagctga aggtgatatt ttatgtaaat atgttttatg gaaacttatt gctcatcgct    16380
gtttcctgtt aactctccta aaatataatt aaactttttgg aactttttta tagcttttgt   16440
gctagactaa ttttttgtctc taatgaggtt atataaatgg cagcttctga cgttttcaat   16500
gtaggaagtc atttaaaact tcatgtatat tgtgaaaatg tagtctgctt taagctctct    16560
aaagtgtct aagttactgg ttcctaagta tggatgagca tcaaaatcat ctggaaaatt     16620
tgttaaaaat acagtaatga aggcacctca ctgtcctttt tcccaaacat acttctgcat    16680
tctgtttgag taggtaggga ctacacattt ttcacaagta tcctcttggg aatacccagg    16740
aatgcttact tgagcaacct cttactaata tgtaccttga taagtggct aggtaaacat     16800
aaatatacaa aaatccatag atctcccata tattagcata aatcagctag aaaataac     16860
gtttaaagat ctagttcaca gtagcaccaa tatatcgaac tctaaggaat cgataaatat    16920
gcaaaaactt tataaaaact tctgttaatg ttttctgaaag ataggtgaa ccactttcta    16980
gataggaaga ttttatatta ctaagttgaa ttttctctaa attaacacag aaatttaaaa    17040
taatcttgat caaaattcta gtagaggtat ttttgaactt gttcactgca agaataaata    17100
cataattgca aagaatatct caaaatcatc accaggcctg gtgtggtggc ccatgcctgt    17160
aatcccagca ctttgggagg ctgaggcagg cagatcacct gaggtcaaga gtttgagacc    17220
agctggacca gtgcggtgaa acactgcctc tactaaaaat acaaaaatta gctgggtgtg    17280
gtggtgcatg cctgtagtcc cagctacttg ggaggctgag gcaggagat tgcttgaacc     17340
caggaggtac aggttgcggt gagcctagat cgcaccactg cattccagcc tgggcgacaa    17400
gagcaaaatt ctgtctcaag aaaaaagaga aaaagaaaa agaaatcaac actaatatgg     17460
tgagacttaa tgtatgtgac attaaaatag tgattggatg ttaaaacagg tatagaacag    17520
aaagaagagt gtatgtgtgt atctgtatga attttatgatg ggtgtaacat atatgtatta   17580
gggaaatgag ggaaatgata catttctctg actttgggag aacattatat ctctacctca    17640
tattgcaaac aaacataaag ttcagattaa ttacctaaat gtgaaaaaat gaataatttt    17700
cttaaaaaaa tgtaatctta gtttgaggaa ggttaacatt ataaggaaa aaactgtttt     17760
gagtggaata tagttcaata tgtcaaaatc caccttcaac aaaattgaaa gtaaattgaa    17820
cttggggaaa gtattgacag catatagatc aaaggttact agcctgtgta aagagcagtt    17880
ataaatatcg ttaagaaaaa cactgtcgac ctgtcggcac cttgttctcc gactcccagc    17940
ctccagaact gtgacgagta agtgcttatt gtttaaacca cccagtctgt atgtggtatt    18000
ttgttataga aactcaagct gattaggaca ctagtaatca gtagactgaa actgaaacaa    18060
aataagaac cttttttacc tgtcaaattg gcaaacatta agaatattca gatttttgtc     18120
agaggtgata caaccttcta agaaggcaat ttgggaaaat ataaagcttt agattattat    18180
atgtctgacc tagcagtttt acctctaggg tgcttacccc taggaaagtg tgtaatgata    18240
ttggtcagt gcccttcatc ccattagaaa attaaaaata accttaatgg cctaccacta     18300
aaaggggatt gaaatttaa gatatattta tttatgtgtt tattgagatg gagtcttgca     18360
ctgtccgcct gggccagagt gcaatggtgc gatctcggct cactgcaacc tctgcttccc    18420
gggttcatgt gattcctctg ctcagcctcc tgagtagct gggattacag gctcacacca     18480
ccgcacccgg ctaattttt tgtattttag tagagatggg gtttcactgt gttggccaga    18540
ctggtctcga actcctgacc tcatgatccg cgccctcgg cctcccagtg ttgggattac      18600
aggtgtgagc cactgcgcct ggccagatac atttatacaa gagaatgtta gttaacattc    18660
atagatattt atattttgtt tacttttat taaaaaaatt tttttagag acaggatctt       18720
actctgtcac ccaggcagga tgcagttgca caatcatagc ccactgcagc ctgaactcct    18780
```

```
gggcttaagt gatccttctg cctcagcctt ttgagtacct gggggacttt aggcagtgct  18840
actatacctg gctaattttt aaatgtttta tagatgagat cttgctgtat tgcccaggct  18900
ggtctagaat tcctgggccc aagtgatcct cccaccttgg cctcccaaag cgctgagatt  18960
acaggcatga gccaccactt ctgaccaata gatatttata tttgtgactg gaaaatatat  19020
taacaatgtg ttaaaaaatt cagttaaaaa ataatgaaga ttttttgctt ctggctaaga  19080
tagaataaca aggacagcat ttatcttctt gccttgaaat agttgaaaac ggaagaaata  19140
tatgtaacag tggttttcaa gttattgggc atcaggcaaa gaagaatagt tatcccagga  19200
aaatgaatgt ggagagccct acaatttcct tacattactg cctggtcatg gcaagaggaa  19260
aaactgagag gagactgagg ctgagccagt ggtttgctgg gttgaggagg cagagctggg  19320
agtgcagaga tgcaaggtgg tgagagccca tatggaagaa taccagggaa gagagctgca  19380
gagggagctc cggagacctg caccctgccc tctcagtacc ctgtcatgtg tgtagctgag  19440
tactgacgag cacttgcttg tgcggaaatg acccagggct ggaggtagag ccacctgaaa  19500
ggattagaag gaacagttgc tgaaagtcac acagggccag gaagaatttc taatcacacc  19560
agttggagtg gaaaacctca gctctcatag agcaggtagg gtactcagaa gggtttgccc  19620
acctagcccc agactaagtt tcgttactct gaccctacct aatattaaaa agagattaat  19680
taaattgttc gcaacaaaaa taatatattt cagtgttgt aacacgtaga agtgaattgt  19740
atgacaatag cataaaggct ggaagagcag aaattgacat gtatttgcgc tgggcagaat  19800
aatgctcccc tctttcccca aaagatatca agtcctaatc cctggagcct gtaaatatta  19860
ctttatatgg aaaattgttt tatgatgtga ttaaattcag gatcttgaga tgaggggct  19920
atcttggatg atctgggtag gcactaaatg caatcacata tatataaaaa ggaggcagag  19980
ggagatttta cacacagaga gaaggccctg tgaagatgga acagaaagat ttgaaggtgc  20040
tggccttgaa aattggagtg atgaagctat aagccaagga atgcagcagc caccaaagct  20100
ggaagaggca cggagcagtt ctcatttaga gcctactcca gagggaatgt ggtgctgcca  20160
attccttttt ttttttttt tttaagatat catttacccc tttaagttgg tttttttttt  20220
tttttttttt ttttagtatt tattgatcat tcttgggtgt ttcttggaga gggggattg  20280
gcagggtcat aggacaatag tggagggaag gtcagcagat aaacatgtaa acaaaggtct  20340
ctggttttcc taggcagagg gccctgccac gttctgcagt gtttgtgtcc ctgggtactt  20400
gagattaggg agtggtgatg actcttaacg agtatgctgc cttcaagcat ctgtttaaca  20460
aagcacatct tgcaccgccc ttaatccatt taacccttag tggacacagc acatgtttca  20520
gagagcacgg ggttgggggt aaggttatag attaacagca tcccaaggca gaagaatttt  20580
tcttagtaca gaacaaaatg gagtgtccta tgtctactc tttctacgca gacacagtaa  20640
caatctgatc tctctttctt ttcccacatt tcctcctttt ctattcgaca aaactgccac  20700
cgtcatcatg gactgttctc aatgagctat tgggtacacc tcccagatgg ggtggcggcc  20760
gggcagaggg gctcctcact tcccagatgg ggcggccggg cagaggcgcc cccaacctc  20820
ccagacgggg cggcggctgg cggggggctg ccccccaccc cccgagcggg gcgggtggcc  20880
gggcggggc tgcccaccac ctcccggacg gggcggctgg ccgggcgggg gctgccccc  20940
acctcccgga cggggcgggt ggccgggcgg ggctgccc ccacctcccg gacggggcgg  21000
ctggccggc gggggctgcc cccaccctcc cggacggagc ggctgccggg cggaggggct  21060
cctcacttcc cggacggggc ggctgctggg cggaggggcg cctcacttct cagacggggc  21120
ggctggtcag agacgctcct cacctcccag acggggtggc agtggggcag agacattctt  21180
aagttcccag acggagtcac ggccgggcag aggtgctctt cacatctcag acggggcggc  21240
ggggcagagg tgctccccac ttcccagacg atgggcggcc gggcagagat gctcctcact  21300
tcctagatgg gatgacagcc gggaagaggc gctcctcact tcccagacgg gacgagccagg  21360
cagaggggct cctcacatcc cagacgatgg gcggccaggc agaaacgctc ctcacttcct  21420
agacggggtg gcggctgggc agaggccgca atcttggcac tttgggaggc caaggcaggc  21480
ggctggggagg tgaaggttgt agtgaccga gatcacgcca ctgcactcca gcctgggcaa  21540
cactgagcac tgagtgagcg agactccgtc tgcaatcccg gcacctgggg aggccgaggc  21600
tggcagatca cttgcagtca ggagctggag accagcccgg ccaacacggc gaaaccccgt  21660
ctccaccaaa aaacacgaaa accagtcaga catggcggtg cgtgcctgca atcccaggca  21720
cttggcaggc tgaggcagga gaatcaggta gggaggttgc agtgagtaga gatggtggca  21780
gtacagtcca gccttggctc ggcatcagag ggagactgtg cgagggcgag ggcgagggcg  21840
agggaattcc ttaatttcag tttagtgata ctaattttgg actctggcct ctaaaactgt  21900
gaaagaaaaa atttttgtt tgttgtttc ttttaagcca catagtttgt ggtaatttgt  21960
tacagcagct gcaggaaact aatttatgct gcatgtgaaa tggtgtaata aggtagattg  22020
tgatgaagat acatagtata aacaattaag caacaactaa aagcacaaca aggaattata  22080
gctaatgaac caaaaagga gattagaata ataaaaatgg tgaatcccaa agaagccaga  22140
aatagggaa gaggcaaata aaggaagaa agagcttgat ggtagatttc aacctaacta  22200
tgtcaaaaag gacattacat gtaaaaggca gcgattttc agattgaatg gaaagtaag  22260
actcggtta tgctgctgcc tgcaagaaac acattctaaa tataaaggca aaaataacct  22320
acaggtaaca gaacggaaag aagttcactg tgcttacaag aattagatgc aagctagact  22380
ggttctgtta atatcagaca aagtggattt caaagcaaag gctcttgccc aggatgagat  22440
ggtcatttca taatgatgaa ggggattcgt tcatcagcct ggcatagcaa gctgaaatgt  22500
ttatgcaccg gactacagag ctaaaataca tgaagcaaag cctgacagaa ctacaagtag  22560
aaacagacaa atccacagtg atagagattt cagtagccgc tctcaatgat ttgtagaaca  22620
cgtagccata atatctggat ctagaacact tgaccaacac tgtcccctgt gcaacctcat  22680
tggcatttac aggacactcc acccagcacc agcagaagag acactctctc aagtgctcac  22740
agaatgtttt ccaagataga gcagatgctg gccataaaa caagtctcta aattaaaagc  22800
attcaaatta ttcagagtat gttttctgac ctcagtatca ttaagttgga atatattata  22860
ggaagataac ctggaaaagc ctcagatatg tggaaaaacc catttccaca tggcccatgg  22920
gtcagaagtg aagtcaaaag ggaaatttga aagtcttttg gattgactga tataaaaaca  22980
atagatttct aaacttgtgg ggtgctgtta cagcatagta aatggaaatt tctagcatta  23040
aatgcctgtt ttaggaaaga aagatttcaa atcaatgacc tcagcttcta cctttggaaa  23100
cttgaaaatg acaagcaaat ggaatccaga gttaccagaa gggccaggta cggtggctta  23160
tgcctgcagt tctgccactt tgggaggccg aggcaggtgg attgtttgag actggcagtt  23220
gaagaccagc ctgggcagcc tagggagacc ccatatctac aaaaaacaaa aaattagcc  23280
aggtgtggtg gcatgtgcct gtagtcccag ctaaccagga gtctaaggtg gaggattgc  23340
ttgagtctgg gaggttgagg ctgcagtgaa ctgtgattgt gccactgtgt tccatcctgg  23400
gcaacagaat gagaccctgt ctcaaaaaca aaaacagtta ctagaagaat ggacatcata  23460
aagataggag cagaagtcag taaaatagaa aacaaaaata cataggaaat caataaaacc  23520
```

```
aaaagctggt tcatcaagaa catcaataaa ttggtaaagc tgataggaaa aacagtgaag   23580
tcacaaatta gcaatatcag gaatgaggga gatgacagta gtatagatta tatagatatt   23640
aaaaggactg tatgaggcag gtgtggtggt tcacgcctgt aatcccagca ccttgggagg   23700
ccgaggtgga cagatcacct gaggtcagga gtttgggacc agcctggcca acatggtgaa   23760
actctgtctc tactaaaaat acaaaaatta gttggtcgtg gtgctgtgtg cctgtaatcc   23820
cagctacttg ggaggctgag gcaggagaat tgcttgaacc tgggaggcgg aggttgcagt   23880
gagctgagat tgtgccgttg cactccagcc tgggtgacag agcaagactc catctcaaaa   23940
caaataaata aataaaaagg actatatggt aatattatga acaactttat gccaataaat   24000
ttgacaactt atagatgaaa tggatgagtt ccttgaaaga cacagaaact attaaagctc   24060
tctcaagaag atatagataa gctgattagc cctatatcta ttttattgaa tttaaatgtt   24120
aaaatcaata tttagttact ggaaaacttt taagtgtggt tggaaatggt atacgaactt   24180
tttcaactga attttatgaa gtctaatcac aggtaaaggt tttctgatga aaatttagtg   24240
tctgaattga gatatactgt aaaaaatgtt atatatctta attatttctt cacattaatt   24300
acatgttgaa ataatacttt gggtgtattg ggttaaatta aatattatga aaatcttgcc   24360
tgttttcttt ttacttttga tgcgtcagct aggaaatata aaagtgtagc tcacattctg   24420
tttctgttga cagtactgct ttggagcaca gtgtttgaat gatctatcat ttcaaagacc   24480
tttcctcagt tcgttattca tggctgtctg tattccacat agataaggtc tgaaatactg   24540
ctaagtggca tgttttgttt tatgcttta taagttttgtt gatcattact gatgtggact   24600
tttggtgcct cttaggctca ttgctatctt ccaaccattg tttgcaattt ttacctagag   24660
ataaagagaa agagacattt ggtttcagag tagttagatt gggatcatga aagagcaacc   24720
tcattttgat gcttcaaaaa tagcacatcc cccgtattac tgggatttgc tattcttggg   24780
attacttcaa gaacatcctt gtgttactgg tttggatgct tctgaatgct gtgaagtcag   24840
tttcatgtac atggctcatc agtttagctc tctcttggct ttgtttagac agttggagca   24900
tgatggccta aacagcttct ttcaattaaa catttaaaaa tagtttacaa atagtaaaca   24960
aactccagtt tttgtgactc tttgtctcgc acaacaaaaa cacaatctga ccatgatcat   25020
ctggcatctt agggtgaaat atggttatac tttggcccat accgaaagca agattaaaaa   25080
ggggcaggag agatagactg ctgaactgat tttcaaggtt ccaagaatat tgtaggttaa   25140
gagtaaaagt aaactttgg tagaaagcag tgggttgtct aggattgaag tatctgaagt   25200
tttaaacga aaatttaaaa agaaaaatga gaattgcctt acaagtacaa tctcttcttt   25260
tttaaaaaat aaacttttat ttgaaatagt tttagattta tagaaaaaaa ttagataggg   25320
taggaagttt tcatatagccc tacatccagt taccccagtt attatcatcc taatttagtg   25380
tgagacattt tcatgtttaa tgaatcaata ttgatatgct attaacttaa gtccagactt   25440
tattcagatt ttcttaattt ctatgtaatg tcctttttct gttccagaat tccatgcagg   25500
acaccggata cctcattaca tttcattgtc atgtcaccatt aggctcctct tgacagttttc   25560
tcttcttttt ttgcttagaa attctccaga atttcagaaa ccttctgggca tcgctatgga   25620
actttttctg ctgtgcagtg atgacgcaga gtcagatgtc aggatggtgg ctgacgaatg   25680
cctcaacaaa gttatcaaag taagaaccgt gtggatgatg ttctcctcag agctatcatt   25740
gttgtaggct gagagaagaa gcgatcattg agtgttcttc tgttttgagt ccctgaggat   25800
gtctgacttt ttttcctttc tgatgtatgg tttggaggtg ctctgttgta tggtttggag   25860
gtgctctgtt gtatggtttg gaggtgctct attgtatggt ttggaggtgc tctgttgtat   25920
ggtttggagg tgctcttgta tggtttggag gtgctcttgt atggtttgga ggtgctctgt   25980
tgtatggtt ggaggtggtc ttgtatggtt tgcaggtgct ctattgcatg gtttgcaggt   26040
gctctattgt atggtttgga agtgctcttg tatggttgga ggtgctcttg tatggtttgga   26100
gagatgctct attgtatggt ttgcaggtgc tctattgtat ggtttggaag tgctcttgta   26160
tggtttggag gtgctcttgt atggtttgga ggtgctctgt tgtatggttt ggaggtgctc   26220
tgttgtatgg tttggaggtg ctcttgtatg gtttggaggt gctctattgt atggtttgga   26280
gatgctctgg tatctgcctg cattgcttgc cacacctgcc cggtcagaag gcgctatgtt   26340
gacaattgtg cctgcacggt gcctaggtca atgaagggaa ccgatggtag ccactgatg   26400
ctcctgggaa aatgtcacta caggcaccag agaagccaga gctatgccca aatttctatg   26460
agtctcagtt ttcttaacca taaaatggga tcaatgtttt tgtggcatgt gtatgagtgt   26520
gtgtctgtgt atgtgtgagg attaaattgt gtatgtgtga ggactaattg ccactactgg   26580
atcctcaaag tggtaagaag tgttcttatt aataatgaca tccttacact cttacccagc   26640
aagattgatg ggtgtggcac tgcttctctt tttccatcac atggttttcca tggtatcctt   26700
ttgcccaggg aatctttgct ttgtggctag cactttgttg tttggctaat cacgctttct   26760
ggtgtcagga cgctggcttc tctggagcca tgggattcta gctccctgtc ttgtccctag   26820
agtggtcact gtcttctctc tccgcttgca attcctgctt tgctcgcatc tcacttatgc   26880
agtgacgtat atcagtttca ccttgttctc cgtgcctgct gatcattggc accacttgca   26940
tggtgccatt tagggcctgc ttccagttaa gcttgcttct ccacaggcct aaatatcctt   27000
gcttgcttct tttattctca ctggcaggac cagggcggtc tgtctttgca tgagacaggg   27060
tctcgctcag tcacccaggc tggagtgcag tggctgatca cggctcattg cagccttgag   27120
ctaccgggct caagcatatcc tcctggcttg gcccctttgag tagctgggac tacaggcgtg   27180
caccaccatg cccagctaat ttttaaaatt atttgtagag atgggatctc gccaggttgc   27240
ccaggctggt cttgaacgcc tgggctcaag tgatcctccc tccttggttt cccaaagtgc   27300
tgggatcaca ggtgtgagcc actgtgcctg gcccttgatg tttcagttct tgatatttga   27360
tcctcagagt cagaaaatct aaaaagaggg ctatcccagg ttgccttggt tcatggcaaa   27420
tgggacgtta agagggcaga gagaaatatga acagaaactg ttctaatatt ggtcattaa   27480
tgtgtaagta ttgttctttt ttaaacctcc ttcattttt ttccaggaat tgctggacac   27540
agtggcttgg tgtgtgtctg aggactgtag gccatggcc taggttgtgg tttaggtcagc   27600
caggtgctct tcctggctgt ctccttgctt cttttcccatg tcctcttctt tgttccagc   27660
catttctccc ttatgcttaa gtttggtgca gcagggtttg gctgctctca gattcctgct   27720
tcctcagatg ctgtagttgt caggcccagc ggggtggcag cgggatcagg atctggctag   27780
gtttgctctc actgtggcag agtaggggga ggcgtgggag agcacgtgtg accccaggcc   27840
agctgtaggg agcataggca tggtcacgta gccttcaggt cctagacttt gtcttctcat   27900
gagtatgct gtgtgtgtat ggtgaaaact aggttctact tagcccaaga aaatgggcac   27960
attttgcatg tggtttctgt agagaaatgc actgggtatc tgacatagcc tggcagcatg   28020
cctccctcag gtaggttagt ctcaggcggt gaagcacgtg tgtccagcaa gaacttcata   28080
tgtggcataa agtctccgtt ctgtgaggtg ctggcaaatc accaccaccg tcaagaggct   28140
gaagtgattt ttgtctaggg aggcaggaaa ggcttcctgg agtcagcagc cagtaggtga   28200
aagagtagat tggagacctt cttaatcatc accgcctctt gtctcaaggg gtgccaggaa   28260
```

-continued

```
gctgtggagg ctgaacccat cttatgctgc cagagagtgg gacaccatga gggtcaggtc 28320
aaggggttgt accttgtttg gtagagaatt aggggctctt gaagactttg gatgtggtca 28380
ggggagtgta tcatttagga agagtgaccc ggtgaggacg tggggtagag gaggacaggt 28440
gggagggagt ccaggtggga gtgagtagac ccagcaggag tgcagggcct cgagccagga 28500
tggtggcagg gctgtgagga gaggcagcca cctgtgtgtc tgccgaagca ggggcaaagag 28560
ggaagaggcc agcagcgtgc tgccatcacc cagcgactgg cgtagattgt gagagaccat 28620
tccctgctct taggaggggc tgagttttag ttttctcttg ttatacaata agcttggtat 28680
ttgtttacaa aacattgta aagctaaatc aaggtttgat aaggcttcta gttttattta 28740
agaagtaatg ttgaaataaa tgtttgtcca attcgctttg ctcatttaag gactttcagt 28800
acaaactgca acaacaggat taggatttaa acgtttctga gatgttttta ctcctcagaa 28860
tttcccagaa tgtgatctgg ttttgatttt caagcttgct gacccaatag gttaacccac 28920
aagttttacg aagaccatct cagtccactt acatcaactg cccatgccac ggttaaagag 28980
atcatcgact gatgtttggc acagcttcct ccctcttggg tgggcaagca tttggaagag 29040
aaggctccta tgggtgagag tggggcacca aagtcttccc tgtcccatcc cctagcttg 29100
gaagcccttc tctaatgtgg actttgtgcc gttagcatcg ttactagctt gaagttgacc 29160
atctggacgt actttctggt ttagcctcac aagtgagcaa ggagggttga gagatgtgct 29220
gtgaggaatg tggggcccca gctggcagca ggctctgggt caggggggca gggaccacgg 29280
gcatacctga cagtgaggag gggccacacc tgcagaaaag gatgcaggac tccgcctgg 29340
gaagtgttct aggccagagc gagggtctgt ggtttataag tacacccaca gtgctcggga 29400
ccctgcagat gtccagggtg ccgtctgagc ccgtatcatc caacagaatg ttctgctagt 29460
gaagattaaa gatttactcc aggggcttta ggatttatta tatatatata aatcctatat 29520
ataaatttt ttttttttt tttttgaga tggagtttcg ctcttgttgc ccaggctgga 29580
gtgcaatggc gtgatcttgg ctcactgcaa cctccgcctc ccgggttcaa actattctcc 29640
tgcctcagcc tctcgagtag ctgggattac aggcgcccac caccacccc ggctaatttt 29700
tgtattttt agtagagacg gagtttctcc atgttggtca ggctggtctt gaactcctga 29760
cctcaggtga tctgcccgcc ttggctccc aaagtgctgg gattacaggc atgagccgcc 29820
ccacctggcc aggattattt gtatttgaac catctaccat tttaattttg atgttatgta 29880
gtatttgatg ataatgaaag ttaaattgtt tttctttcca tttttctgtt taagtgaatg 29940
acctgtatct agtttattca gtaacttcct gcatatattt gtttctttca ttcttaatga 30000
atatattctt aatttagttg ctattatgtt ttgctttgcc ccaaaattga aatcttagtt 30060
tccttttagc tcgttttaga actagtgatg ggatgtgtct tccataaatc tcttgtgatt 30120
tgttgtaggc tttgatggat tctaatcttc caaggttaca gctcgagctc tataaggaaa 30180
ttaaaaaggt gggccttgct tttcttttt aaaaatgttt taaattttaa attttatag 30240
gtacacgtat tttgtaggta catgtaaatg tatatatta tggggtacat gagatatttt 30300
gatacaggta tacaatacat aataatcaca ccatgaaag ttggatatcc atgccctcaa 30360
gcatttatcc tttgtgttac aaacaatcca gttacatgct ttacttattt tattttattt 30420
ttgagacaga gtcttgctt cacccatgct agagtacagt ggcatgacct tggctcactg 30480
caacctccgc ctcccgggtt caaccgaact ttgggctggt ctcgaactcc tgacctcagg 30540
tgatccgccc gcctcggcct cccaaagtgt tgggattaca tagctgggtt actgtgccgg 30600
gcctgattgt acattttaaa ataactaaaa cagtcagggc acagtggctc atgcctgtaa 30660
tcccagcatt ttgggaggct gaggcaggtg atcacctgag atcaggagtt cgagaccagc 30720
ctggccaaca tggagaaacc ctgtctctac taaaaataca aaaattagcc aagtgtggtg 30780
gcgggcgcct gtaatcctgg ctactcggga ggctgaggta ggggaatggc ttgaacctgg 30840
gggtggaggt tgcagtgagc cgagatcacg ccactgcatt ccagcctgag cgacagagtg 30900
agactttgtc tcaaaaaata aaatgaaat aaaattgggc cgggtgtggt ggctcacacc 30960
ttagtcccag cactttggga acctgaggca ggtggatgct tgagaccagg agtttgagac 31020
cagcatgggc aacatggcaa aacgcgtgtct gtacagaaat tgctgggtg tggtggtgca 31080
caactatagt ctcagctact gggagattga aggtgggagg attaattgag cctggaaggt 31140
tgaatctata ggtagctgag attgtgccac tgcccttcag cctgggcgac caagtgagac 31200
cctgtctcaa aagaaaaaca aaaaacaaa aacaaacca ctattatcga ctatatatta 31260
ttgtctatga tccctctgct gtgctgtcga ataccaggtc ttgggcccttt atttccatca 31320
ctgagcaaac ttcactctgt taagcagcag gtgtgggatt tcatcgttat tcagtaattc 31380
acaatgttag aaggaaatgc tgtttggtag acgattgctt tactttcctt caaaaggtta 31440
ctctttatta gatgagatga gaattaaaaa tggtaactta cttttatatct ttataattga 31500
agccactag accttaaagt agttaccaga tgttttatgc atttaaatgg cctttctct 31560
aaaaattagaa agtaacaagg aaagaaaatg cttcgtttct atgcaaccct cttggtgact 31620
agtatgtgac tcttaatgca acccctcatg cacccctca gaatggtgcc cctcggagtt 31680
tgcgtgctgc cctgtggagg tttgctgagc tggctcacct ggttcggcct cagaaatgca 31740
ggtaagttgt acactctgga tgttggtttt tgtcggggc cagctgctac tgatccttta 31800
tgtctcagct cagatgtcat ttcaaaagtc tgctctgccc tctccaaatt gcagtcgacc 31860
ttgccctgtt tatgtttccc tcatagcact aatccatgtc agaaattgtc acgtacagtc 31920
tatctgtgtg cttgttatt ttctatccca cccttccgca agagactat gggatgtgtg 31980
ccccaggaca gcagggtct tactgtctta tgctctgttg cagcccagca gcgataacag 32040
tgtctgcaca tagtacttgc ttaaaagata cttgccaaat tgttgaagt tgaggtacca 32100
atttcattat tgctgactat aggagttata gcaaaatatc catttgtctg ttacatgagt 32160
taaaaatatg gttgttgcac tgtgaatagt ttggtttagt caaaacagtt gtatcttaac 32220
ggattgagaa acaaaagcag gaccacttt catcagctcc ctccttctcc ttaaccagca 32280
atacatgctg atgctgatat cccatagacc ctcagctcca tcctgagtca ctgggaatgt 32340
ggtctaaacc ctcactttg atatgagactg agtttcaata agaatcttat atgggtcggg 32400
catagtggct catacctttg atcccagcac ttcaggaggc caaggcaggt ggattgcttg 32460
acccagacta ggcaacatgg tgaaacgccg cctctacaaa aaatacaaaa cttagccagg 32520
catggtggtg cgtgcctgtg gtcacagcca ctcgagaggc tgaggtggga ggatcacttg 32580
agcctgggag gtggaggtcg tgttgagcca agatcgcacc actgcactcc agcctgggca 32640
acagagtgag acctgtctca aaaaaaccaa aatccagaaa agaacttata tggctgcagg 32700
ggtataatca ctaaggaaat ttccttttgt ataatctttt ttcttttact atcattttaaa 32760
aaaatgtgtt atatttctga agcaacacat ccaggttctg cacatagcag ccaaagtgac 32820
cttaagaat ataactgggt cttgtcattc ccttatttaa actcttgtac ccatttccca 32880
gtgccgttta gatagagatt ccagactcgt caatggctct gtcacctcag acaccctgca 32940
ttgactcatt agtctgatta gagtcaggtt tttcttcctc ctgatggttt ttttttcccc 33000
```

```
cttagttctc agcggaacag tcacttcctt agggaggttt ccccagccac cctctgaggc  33060
cgtgcttgtt gccagactct gccactagag ggcagggctg caccactcct ggcacctcgc  33120
acccggcctg ccctgtcact ctgtgtgttg ggtgaattcc tgtgatcgt gactcactgc   33180
tctgtgtcct acacattcgg cttttcttct ctccccacaa ccccatttta taattctcct  33240
ttttcaggaa agctttattc ccatttaaaa attttgttt ttaaaatggt attttcttac   33300
acttattttc taattaaaaa tgagtgtttt aagaagtatt atgatttact gcaaataatt  33360
tttaaaccca gccttttaga tcctctgtga tcataagaga aatgaaggat gtctcccaac  33420
acttgagctt catccacatt tcatcctcct gttctttcag ctgagttttc cccatcccat  33480
tagggactgt tggaatataa aactggcttt tccctaacag ggaatgaatt gcttctgttt  33540
ctcctgaagg agagctggaa gaatgacttg cgttcttttg catacacagg ccttacctgg  33600
tgaaccttct gccgtgcctg actcgaacaa gcaagagacc cgaagaatca gtccaggaga  33660
ccttggctgc agctgttccc aaaattatgg cttcttttgg caattttgca aatgacaatg  33720
aaattaaggt atgattgttg cctcaggtca caaacatgcg agtgatgctg tgagtgagtc  33780
tgtggagggt gagggcttct gaacagggag tcctgtggga gtgcttcttg gggtatgttg  33840
tatgtcgtaa tttagactac catcatttgt gttattttg aggcacctaa ggacttcttt   33900
ccacttctca tttcttactg tggggtgaag agttgaattg ggagatggtt tctagatgca  33960
aattgaaaag gcattttcc agagcagatt tgttttcggc gtactagagt gactctttaa   34020
cctagctgcg ggaagatgac tgtgccaaga ctgcaggtag gagaaagctc actgacgagg  34080
ccttgtgggt ctgaacgtcc tgcagctatc agagcctgtt ggcttcctgt tgtgcattcc  34140
aacaaatcat cttcaaaccc actttagtgt tttgttata atgtccagaa atagtgaccc   34200
tgtcacatgc tctacagatt acaggattct tagcctcttc ctttttggta ggtcagtcct  34260
gggtttgagc ccaagtgacc ctcctgggag gtgatgatac acactgggta gagtggaatc  34320
agatggactt ggattagaat tctgtcctct ttactagtta ttttcctcta ggcaaactgg  34380
ccaacagctc taagctattt ccttcgtatt ctgaaaaata agcctaatg ggacccatat   34440
agggcaactc tgagagtaaa ataaaggaat atgtgttaga gtgtagcata gtcacccacg  34500
ggaagggctt aggttagc tgctactgct cttattagct gaatgatttg gaataaactg    34560
ttagcctctc tcatgttttt tctcttgagc ttcgaagttt tcttgttaat actaaggaga  34620
tattcaaact agtcatgggg ttttggaatg acgaagggag atgatgaatc taagaatt    34680
agtgtaatat ttcttcatgc tcagtaaatg gtagtttctg ctgctgttat ttttattacc  34740
atctctttgg aatgggagta ggtgctcctt tgtggtcaga ggctgtgaga gctccacagc  34800
gccagtttgc ccatctgtac actggggtct gttgaaggca gtccctctg tgatatctct   34860
ggctgtcaga gctcagatga tagatggtat ttttgtactc ttagttctca tcattttcat  34920
gatttcgatc accatttgag tatgatgatg ctaacacttt gttgaacgta gaatccgtta  34980
attacttcct tcctgaacct ttggcattaa aaaaaatca ttctgctactc tctctgctca   35040
tttatggtta ttcaaattta ttatcaagag cctggtacag tggcttgtgc ctataattgt  35100
agctactgg gaggctgagg taggaggatt gcttgaggcc aggagtttga ccagcctg     35160
ggcaagatag tgagaccta tctctaaaaa aactgaaaaa aaattagctg gacatgatgg   35220
catgtgcctg tggtcctagc tactcaggag gctgagacag gaggctcggt tgagcccagg  35280
agttggagtt cgaggctaca ctgagctgtg attgtgccac cacactccag catgggtgtg  35340
aaaacaagat gccatttctt aaaaaaaaaa aatatatata tatatattat caatgaaatt  35400
cagtagtacc aacaggatta taaacaaaga tagtagttcc cttcctactt tttctcttaa  35460
tccttgtgtc tcacaggcaa acataactct tagtatttct tccaatattt actttcatgt  35520
ttctttcttt ctttcttttt ttttcttttga gatggagttt tgctcttgtt gccaaggctg  35580
gagtgcaatg acgcaatctt ggctcaccac aacctctgtc tcccgggttc aagcgattct  35640
cctgcctcag cctcctagta gctgggatta caggcatgca tcaccacgct cggctaattt  35700
tgtacttta gtagagatgg ggtttctccg ggttggtcag gctggtctcg aactcctgac   35760
ctcaggtgat cctcccacct cagcctccca aagtgctggg attacaggcg tgagccactg  35820
cgcccagcaa cttccacatt tctaaataac atgcttctac tgctatttt ttttcaatt    35880
ttagacattt ttttactttc actatagttc tatcagaatt cagtgtgtac gttattatgc  35940
ctaagtaaat agtcatggtt gcttacgtat tatatttctt tgattgtgtt tcttatttga  36000
tgagaagagt gtgttttttg ctctgggttg aaactggaga gaggacctgg ggaggaggag  36060
gaggacagat gaagttggtg actgtaccct catggccata gctgggttct cagccaccgg  36120
ggatctgctg atcacctact cataggccag gccctatcg aagttctagg tgacccagtg   36180
ctggggacgg ggggccacc tgcaaggtct aatcatggag gtgggggcta cagtgttggc   36240
ttgtcgtggg gccagcatcc ttaggaaggc atcttggagg tggaggagac agccgcccac  36300
ttcttgattg gggccttcag cagcaccagc ttcttgggca ggctggtgct ggctttcatc  36360
accatgtcgt gttcaatctt cttccagatc ctgacttcta ggttcagctt tcctcagacc  36420
ctggttcctt tcagaggcca ttgctgctgc cttgctcttt gctggcttgt gccttgatta  36480
tatgtctttg tacaacttttt tgttttcctg gagttaatct tcacatctgt tttcttggag  36540
ttaatcgtta cctctatatc gcttgcttat tattctttgg ccttttttgtc ttctcacacc  36600
ttccaacttc tttgtaatat gtgtttagta caatttttca tgacaggtag tttactgaat  36660
cagttttcc ccagtgtggt catccaactt gagttatcca gctctctgcc ccagtctggg   36720
caggttgatc ttcaggtctg tagtacactt gtatcctagg acttctcttt gccattagcc  36780
tggaatttcc tttgcagttc tcccgttgga tgcccagtc ctagatgcca tatgtttttc   36840
tatcgtctag tagcttcctg agagaagatg aatgggaggg aaattgtatg aggttttgca  36900
ttcataaaaa tgccatttt tttcctgtac acttggctgg gtatggtgtt ctggggtaga   36960
aatcattttc cctcagaaat gcaaagtctt tgccctgttg tcttaaaatc tccaacgtga  37020
cccgattcct taacctatga atgtacttt cttttggaagc tttccatttt tgggaggtg    37080
aagtgctagg tacttagtag gcctttaat tggaaactt acatcccttc agttctgggga  37140
aaattttctt aacatttctc tgagaagttc ttgccttta ttttctgtgt tctctcctga   37200
aattggttag ttggatgttg gtcctcctag attgactcac atcttacctt tttcttttct  37260
ttttctggta cttttagat atccatctca aactcttcta ttcattgtta tgttttaac    37320
ttctttcttt tctttgtctc ttgatggggt cttgccctgt gcccaggtt gtggtgcagt   37380
ggtgcatca tagctcactg cagcctcaaa ttcctgacc caagcagctg ttctgcctca   37440
ccctcccaag tagttgggac tacaggtatg caccaccacg tccagctatt ttctttactt  37500
tttttttttt tttttgaga tggagtccta ctctgtcgcc caggctagag tgcggtggtg   37560
ggattttggc tcacttaagc ctctgcctcc caggttcaag cagttctcct gcctcagcct  37620
ctcaagtagc tgggattaca ggtgtgcacc accatgcccg gctaattttt gtattttag   37680
tagagccaga gtttcaccat gttggccagg ctggtctcga acgcctgacc tcaggtgatc  37740
```

```
cgcctgcctt ggcctccgaa agtgccggga ttacaggcgt gagcccatca ttagatcttt   37800
aaataccagt atctataagt cttttcctct tgagtcagct agtatccctg gaaggaaatt   37860
actcattttc ctgcttggag gctataagct tggctatgtt tatcctgcaa ccggggactg   37920
gaagggaggg gactgacagt gttgctggtc agggtgccct cttactttt gttttctgtg    37980
tgcatctcac gtctgtcctc agcctatgta aacacctcct gagattatcc ctctcaatct   38040
ttgccggagg tggggagggg gctgcttcct gggctgcctt ggattggagg gaagacctca   38100
ggtgagtggg tgggaatttg cccaaggagc catgagacca gccactattt caccctctcc   38160
atccctccac tttcagatgt atgtggcgcc tccaaagccc gagctcttct tggcgtctgt   38220
ggcttcaata agcttgcttt ttgctggtat ccctcctacc ctcccctgtc cccagcaaag   38280
cttgcatttg aacttcttcc tacgggctaa caaatcagtc agttatgtag ctcttgttac   38340
tttttagctt ccgaagtttt gttgacaccc gtagtctgct aatgtccctg ttctgttctt   38400
tctgttcgtg taaatatatg ctttatacaa cttctttaca tgattttgt ggggtttctg     38460
ggtagcagag cttcacaagt tcaatccagc gtgttggatt agaaatctcc caccctctgg   38520
tttattctta ttctcaaaat tacctgccaa acactgattc tcccttgttt ttccttttcc   38580
tgacaggaaa tgtacatacc atacaggaca gaaatcatta gtgtatcct tggtgaataa     38640
ccacaaagtg aacttaaccc ttgtaaccgc cacccaggtc aagacagaat attaccaagc   38700
actcagaagc ctctccccta ttccccgtc actgctcctg ccttcctccc caaggtcatg     38760
actgctggct tctaattcca gagtctgttt ttaaattctg tgtacataga ccatggatta   38820
agtgttcttt ttgtctggtt tattttggtc gacattaagt tcatgagagt cttctatatt   38880
atcgtgtgta ttagtattcc tgtagtttta ggagcttcat agcattccat tgtagggata   38940
taccacagtt tattcattgt attatcactg ggttgtttct agttcttggc tattgcgagc   39000
agtgctactg tgaccactct taggtgtgtc ttttggagta catgtgcagg tttccatctt   39060
gcacagctag aggtggagtt gttgggtgat agggtgtgtg catctcagct gcagtagaaa   39120
ctgccaaata gctttccttg agtgcttgta ccagctcacc cttttgccac tgtgtatggg   39180
gattccagga gctctggtcc tcgctagcac ttggaattgc tgatgcttt actcttagcc      39240
ttcctgatgg gtgttttctg gaatcacatt atgattttaa tttccattcc ttaaagtacc   39300
cttggctctg aagtttaatg attcatgcat ctcttccctt ttgaagtact cttacggta     39360
tgttgtgcat gtgttgaaaa gtggcactat ctattctaaa atacagtatg cctcctctgt   39420
gtttgaacag ttgtagcgtg gccttggggc ctcctgttag ctggcttgga gaagggattc   39480
ttgggattgt agagattaga cctgaggagg ccccttggag ctctctgact aaatttttatt  39540
ctttattatt ccaaactatt taagctcacc gtgtgctgac tcatcataat aatgagtagc   39600
tctcattgtg cttgtctatt tggactcata caatgatttt ttttttttct ttgagacaga   39660
gtcttgctct gttgcctagg ctggagtgca gtggcacaat ctcggctcac tgcagcctcc   39720
acctcccagg ttcaagtgat tcttgtgcct cagcttctca agtacgtgag actgcaggtg   39780
cgtaccacca tgcctggcta atgtttgtat ttttagtaga gacggggttt caccatgttg   39840
gccaggttgg tctcaaactc ctgacctcaa gtgatctgcc ttcttcagcc tcccaaagtg   39900
ctgggattac aggtgtgagc cactgagctt ggccaaagta gttttttaag atgttagtat   39960
cttttcttgc agctaaaaaa gtttgtcaga gatgattcta ctttgttctc caggtgtttt   40020
ctcagggaga aattggaggc agtaagccac tgggggagtc ctgtggctgg ggggtgggtt   40080
agtcctgtgg ctccttgtca gggagtcctg tggctggcaa ggagagaagt cctgtggctg    40140
ggttgggagg gagtcctgtg gctggggtct catcctgtgc ctaacagtgt ccagaggtgc   40200
cgagaccagc tcagtcgggg agaccctaac ccagcagcgc tagaggaatt aaagacacac   40260
acacagaaat ataggggtgt gaagtgagaa atcagggggtc tcacagcctt tagagctagg   40320
agccctgaac agagatttac ccacatattt attaatagca aaccagtcat tagcattgtt    40380
tctatagatg ttaaattaac taaaagtatc ccttatggga aacagagggga tgggccgaat   40440
taaaagaaga ggttgggcta gttaaccgca gcaggagcat gtccttaagg cacagatcgc   40500
tcatgctatt gtttgtggct taagaatgcc tttaagcggt tttccacctt gggtgggcca   40560
ggtgttcctt gccctcattc ctgtcaaccc acaaccttcc agtgtgggca ttagggccat   40620
tatgaacatg ttacagtgct tcagagattt tgtttatggc cagttttggg gccagtttat   40680
ggccagattt tgggggcct gctcccaata cagaggtctc gtgtaaattc cctgggaggc     40740
gataagcctc tgagaaacag actatgctaa ccacgccatg aaagagaaac ttatttataa   40800
atcagatgcc agttactagt ttactgctta tttgcccagg cgtagctctg acagagtccc   40860
cgactcatag tgcttgctca gtgcatgctg aacaatgatt ggaatcaagt catggctcag   40920
agcatagttt tgaataatgg gaaatggatg ttcttaagta acatagtcac caagataatg   40980
cgactagctg ggtcacccct tttcaatttt aggatatttt tatcaagatt taaatggcca   41040
tcattagagt tatagcactt tctccttttgg attgtcctag aggcccatga gaaagtattc    41100
cctaattct taggagaaca gttttgtgggt agtatgcggt catgtccagt taaattgcag    41160
atatttccga tcgaagatgt tccagtcctg agaacttcgt gacattagca ggacttctac   41220
aagccatctc ttagggtggg gcatttactg cagttggcta gtactctttt ctccttaact   41280
ttgtcatttg ttgattttttt tttaactgtc cccaaatact gtgggcagag tgtatctaga   41340
attgaggcct ccaccattgc ggagaggaca tggatgctga gcagtccct gagtgaaggt      41400
tataaagaag caaatagact acacatgtct gtaaactgct cttgagtgtc ccaaatttgg    41460
ggtacttcag ttcagctgta ggaaaagcct caaactgttt atactttgca agaattggaa   41520
acttctaatt cacgttaagt tttatgtaat acatgataag cttcataggg gcttcatctt   41580
ttatctactt ggacttttgc ttccgtaggt tttgttaaag gccttcatag cgaacctgaa   41640
gtcaagctcc cccaccattc ggcggacagc ggctggatca gcagtgagca tctgccagca   41700
ctcaagaagg acacaatatt tctatagttg gctactaaat gtgctcttag gtaaggtgga   41760
ggcatatgag tggaagagtc tccagcatgt actcaagata gacctttgaa ataaataaaa   41820
ccagatgatc cctcagcttc tagaccaggc tatttggcac tggttgattg aatgtgaact   41880
gcactgggc tgctgtgagc ccgcatgggt ctctgtgacc ctgcagatgc agccgtgccc     41940
agggactggg cagtgggtgt gggcggtgt gagccctgtc tgccacccag ggcctggccc     42000
tctgtctgtg tcggccatga ctatggtgag tcttgtaggc ttgagactgt gcctcggaggtt    42060
cctgcgggtt ctctgtaggt cagttgacag tttctcctgt tgtgtggta actgtggaaa     42120
cgaacactgg caagtgctga agcgacatg tggacgtggac atatgaaata acgacctggc    42180
tttcaaaggc agtgaggctc tctgaaaagg accttgctga gctagggatg tgggtgtgta   42240
gccattccca gtgggcctca tggcgtactc gttcatgatc atgtttgtgc catcttgatc   42300
tctcaggatc tcttcttttt taacagatta agccgggaat ctccaaacag tgagtcagat   42360
gttaagatgt cttgcttcca cccccacagg cttactcgtt cctgtcgagg atgaacactc   42420
cactctgctg attcttggcg tgctgctcac cctgaggtat ttggtgccct tgctgcagca   42480
```

-continued

```
gcaggtcaag gacacaagcc tgaaaggcag cttcggagtg acaaggaaag aaatggaagt   42540
ctctccttct gcagagcagc ttgtccaggt aggagcacag ggtttactct aggccctgca   42600
tgtgaatgac tgacattcaa agaaccgatt aatttggaag agaagcggca gaaccgagag   42660
ttagaggtgt ggactctgga gctgcgctgc tcgtttccaa ccctaggtgc tgacctctag   42720
ctgtcttccc tctgtatgtc cctgtcaccg tgagtcaaat gcgggtgatg cctcctcagg   42780
tgccgtgtta cctaagcctc tcagagacca ctgctaccct gtttctaaaa ccagaggtca   42840
cgatatgtgt tcatccaccc agtaaatact gattgagcac ccactgtgtg ctaggctctg   42900
ggataggggc tgggtataca atggtgagta tttcagctgc agcttctgcc ccgtggaggc   42960
tgtggcctag cacactggtc taggcacggt ggtatatgct cactcaagga gatagggacg   43020
tggtcgtttg gggtgtcgga acaaaatgtc ggaacttctc tttccaatgc agagaaacct   43080
tgcagtaatt ctaatgtact gtgattggca gttgacttca gttctttgta gcacgcttac   43140
tcaggttatt tcactaacta tgtaaccatg cagcctcatt ttaagcaatt ggattttttg   43200
aacttttactt aaaatgttat gtcagggttt ttattgtgct taatgtgtgc catttagcta   43260
agttttgtag gatacgaaat tgtaagtggc ttaaaatgat tcttaataga atcatgaatt   43320
gaagataatg ctaataattt aagcactgag ttaggtagta tttgtaaaat gcttagaatg   43380
cttcctggca catgttaagg ccatgtaagt gctgcgtgtt gataaacagc tgagcaaaag   43440
tggactctta agaaagtatt ggggctgaga gttctgttcc aaccagctgc cctttggtta   43500
tttttcagaa taaaagcaga gtctcatggg atatgacatt tatatttcct tcacaaaaaa   43560
cactgctgag tgttttgttg agtaaaaagg gtgtagccat ggtaataata catttaaaat   43620
atagtttatt tcatctttac cttgccttgt ttttttttta agctagcttt ttattgagaa   43680
ttccacacat acaaaagtat caactcatga ccagttatat ttcatttata atcctacttc   43740
tccctttttt tattatttga aagcaaaccc caattactct cttatttcat ctataagtat   43800
ttcagtatct ctatagatga ggactcttct ttattttttaa aacttttattt ttaaaatgat   43860
ggtcagatgc agtgttcatg cctgtaatcc cagaactttg ggaggccaag ctgggcggat   43920
cacttgaacc tgggagtttg agaccagccc gggaaacatg gcgaaacccc atgtcttaaa   43980
gaaaaaaatc agccaagtgt ggtgatgcat gcctgtagtc ccagctactt gggaggctga   44040
gatgggaggg tcacatgagc ctggaagatc aaggctgcag tgatccatga ttgtaccact   44100
gcactccatc ctgggtgatg gagcaagatt ctgtctcaaa aaaacaaaac tgcaaaacaa   44160
cgtcacaaaa cagtgccatt gttagacctg aaaatattaa acatttccta catcaaatac   44220
ccaccaactc attatcaatt tttctctcta ctcttttgga atcagcatct aaataaaatt   44280
ggtcgataag gattgtaaat ctctttgatg aactggttcc cctccatccc agttttttttc   44340
ccttagagtt catttattga gaaccagat tgtttgtctt ctaagttttc ctgtggtctg    44400
atatactgct tccatctcca ctgtgtaaat taacaccttt ttctcttctc tgtatttcct   44460
gtaaatcaat aattggagga aaagccttgt cagatttagt gtatatttta tatctgagtc   44520
cagtatttct tatatatat tttaagataa gtgtactctt ttaaaagta ttgaaactat    44580
atgctcaatt tttttttaact gatgctttta agaaggctgc ttgatcataa aagtttagag   44640
atcattggtc tgatgggaaa agcaaataat tactaaaccg tttagcaagg ttgaggtgca   44700
catggtgggg cctggagaag ttcagtcatg agccgtcact tatgggcacg tggaatctga   44760
cccggcacag agttgggaga agacaggagc tttatagaca gaaaatgtgg tctttgctaa   44820
gtcccaggag tgaaagggtg agacagtgct cacagcacac gagtgtgggt gcgtagacag   44880
agcaagggtg ggtcctgaaa aggcctgcag gcttttctcat agattagcaa gagtgctggt   44940
tacggaggtt tctaacattt gtgaacagat cgaaactgtg ttaaattggg attgcagtaa   45000
tcctggaagg acagggatag agggtgaagg ggaaaaaagg gggatgat gagacttaat    45060
tgctgatttt cttaagacct ttctccaaag taaataaatg atgtggcaca ttttttgaact   45120
ggcaaattct aaactctaga tatgattatc tctataacat atcttactcc atcttctttt    45180
gactaaaaac tgttcttaat taaattacca tgagacgttc aattcagcaa atgtagtttg    45240
gctaaccata tttaattaga atttaatata atcctaggcc tggccaaact attaagcaag    45300
tgtgggcaaa atattgataa ttttagatat gcaggaactt agtttgcttt ccatgtgtgc    45360
ttttcgaaaa aggaataaat tgaaaatag aggaagccct gaaatccaag aagcaaactc    45420
tctcacctag gcatgcagta aaagcaattc taggatgatt gctgtttggc gcgtagttcg    45480
tattagaaac cattcttctt gaataaataa tatgtttaag aagctgggca gagggaaggc   45540
atatgcatat attatcaaca aggagggaga aaaaggcaat tagtaaccat ccataggagg    45600
gtcagcaaga tttataaagg aaatttgtga tccaagtatg aagcaaaata aggtgcagaa    45660
taaattttaa gcaagtaata gattagagta agagaaccca tttgaccatt aaccttggga    45720
cattctttt caaatgacat ggagtagtac tgaaatcttt ctttctttct gagtctaggt    45780
tattgtgact ggactcagaa agaaatattt cattattgca gtgaataaca tttgtgaaca    45840
ttattgttca taaattatgc agtgaataac atttatgaac acgtgatgtg taagatacat    45900
actgtttatt tttagttaag ttttttggct caacttctag gcagagaaca ttaaatgtaa    45960
atagtgttac ctaggagcat gtaaatgaa atctccatag tatgaaagca gtgctgttgc    46020
taacagaatt taggagggg cagatgaggt gaaggaaatg tgggtgctga tttccttatt    46080
acattgagag gagccaggag attctttgtt caaaatggat ggcttaagaa gtcaaagtat    46140
aagctgatta cgtagagcag gtacccaaaa atgttttgtg taaggggcca gatagtaaat    46200
attttcagtc ttgcaggcca tcccaagtct gtggcagcta ctcaacacta cctttgtagc    46260
atgaaagcag ccacaggcag cccataaatg tggctctgtt ccggtgaaac tttaggtaca    46320
aaagcaggtg caggccagac ctgacctgtg cactgtggtt tgctgacctg ggattcaggg    46380
gtatagaagt taccatcaga agagctaaaa gtgagctttt ttactttata ctcttctaca    46440
ctgtctgatt ttgaaaaaaa gaaacatgta ttttataata ttaaagatag ggttggcaaa    46500
tagcaaataa aaatacagaa taccagtgaa atttgaactt cagatacatt atgagtaatt    46560
ttatggtgta agtatattcc aaatcatgtg ggacatactt acactacaaa attatttgtt    46620
gtttgtttac agtttaaatt tgagtgcctt gtattttatc tggcaactgt aattaaaggg    46680
aaaaagaata aattcattat gttcatataa tgtgatatag caggggtccc caaccccag     46740
gctgcagagt ggtactggtc catgggtccc caaccccag gctgcagagc ggtattggtc    46800
catggcctgt taggaaccag gctgcccagc aggaagtgag cagcaggtga gctggcattc   46860
ccacctgagc accgcctcct gtcagatcag tggcagcatt agattcccat aggagtgcaa    46920
accctattgt gaactgcaca tgtgaggggt ctaggttgtg cgctccttat gagaatctaa    46980
tgcctgatga tctgaggtgg aacagtctcg tcttgaaacc atccctggcc cctgtggaaa    47040
aattgtctcc catgaaacca gtctctggtg ccagaaaggt tgggtagcac tgtgatatag    47100
tattaaaagt gctaataaat atggcatact gcctttaaaa tgtctggtag ctcttctca    47160
gtggcactca taatagtgtt ttttgatttt taaatgtgtg tcaagctgac tctcccctcc   47220
```

```
gtgtatgctg ggctttattt tcccttttcct agtcaccagt ttttgggaaat agagatcttc  47280
attctcatgc tgctcctcta gtgcaagtgc tccattatt ttttaaggaat taatataaca  47340
aaaaatcatg ggaatttaga aaacaacatg gaagctaatg atcacattgg tggaagtgat  47400
agggaaatat ttaggggag aagttaaggt ataaactttg tcaatgaagt cctattaaaa  47460
acaacaaaaa agtgaagctt aggatgcatt ttataaactc tgaccagaac acctgtgttt  47520
ctctgtttct aggtttatga actgacgtta catcatacac agcaccaaga ccacaatgtt  47580
gtgaccggag ccctgagct gttgcagcag ctcttcagaa cgcctccacc cgagcttctg  47640
caaaccctga ccgcagtcgg gggcattggg cagctcaccg ctgctaagga ggagtctggt  47700
ggccgaagcc gtagtgggag tattgtggaa cttataggca agttattagc aaggtctact  47760
cttacaatta actttgcagt aatactagtt acactctatt gattatgggc ctgccctgtg  47820
ctaagcagtc tgcattccat cttccttgcc aaaacttata atacaaattt catctttatt  47880
ttataaatag gggagttggg ctgggtgtgg tggctcacgc ctgtaatttc agcacttttgg  47940
aaggatcgct tcagcccagg agtttgagac aacctggcca agtgagaccc tgtctctaca  48000
aaaaaaaaaa aaaaaaaaaa attagctggg catggtggca catgcctgta gtcccagctg  48060
ctttggaggc tgaggtggta ggattgctta agcccaagag gttgaggctg cagtgaatct  48120
tgatggcagc tgcactgagc ctggtgacag agcaagatgc tgtctcaaaa taaatttaaa  48180
aataaaataa gagaattaaa gtttagcagg ttgggtggca aaatgaggcc acacatttaa  48240
agcccctcct cctgattctt ttctctgcct tggctgccat ttaggtgctg  48300
agaaatgaaa acagtaggga aaatagttcc aggatcctca tgttaatttg ccagaaatgt  48360
catcttcaag tcgtcagagg gatctgagag ttccttcctg gcctgacttg agaaaatccg  48420
tctgtcccca gctctgcgtc tgcctccact gcccagtcac ctcctctcca tgctcttggg  48480
gctgggccct accccaccat gcagtgctgc cctggacgag tgagcttgag gggtcctgtc  48540
tggcatgaga gctgcctttg ggagctggat cccagcctct accactgggt ctggtgccta  48600
gcaggctatg gataaacttc tgctgactcc ggcctctcct aagccactgc aacgtggtcg  48660
gtgtagtgca cagtgtgtgt gcagcgtggc cttactcaca gcctccacat tagagagaat  48720
ctgactgaag tcttactgct gcctcgtgtg aacataaatg tttgccagaa ccatgagcag  48780
gaaatgttaa tctgccttgt ttcctgtcct ttacacggaa gaatttttttt ctgtatggaa  48840
tgcgtgcctt acaaataatg agtggaaata cccatcgcta atgaaaagtt atacttgact  48900
gttagtcagc taaataatct gagatttcta atactttaa tttggctttt acaatgcaat  48960
ttatcttagc tttttttgatt tcttaggtca tatcttttaga actatatatt tgaatgttaa  49020
tgtaatttttc atattgaaat taaaatgttg aactgcgatg ttaagtgttt cctgtgaaa  49080
aacgttcaca ttttctctag ttttaaagtt gaatcaagct gtttgaagat tttcacatttt  49140
cttctagatt ttatcagctt gttactttat ctgtcacttt ctgtgatttg cagctggagg  49200
gggttcctca tgcagccctg tccttttcaag aaaacaaaaa gggtgattatt tcagaaatca  49260
gagtcttgtg ttgaatctta ctgattttct tgtatttctg taatgtaatg tatcttgtat  49320
ttcttgtaat actgtattgg actctgtgta tatctcttct cagatgagtg attatatgtg  49380
tgaatgttgc tggaatctga taaccaggcc tgaatagttt tgtagggtgg cttttaaaaa  49440
ttactttcat atcagaattg ctttgtcata aattttgaac gcatcataaa tttctaatgt  49500
tcggggtcag cagactttt ttgtaaaggg acagttgta aacatcttag ctttatggc  49560
catatggtct ctttttgcaac attcagctct gcccctgtgac aggaatgcag ttgtaaagac  49620
atgagctact ggccagctat gttccagtag aactttactt acagaaacag acaggctgta  49680
gttttgccaat acctgcctta gggaatgtgt tgttatattt tgtgagttac cttctcagta  49740
aattttattt agtattagtc aggaatatta ttaagtagct tcttttccag tctgtcaac  49800
atagtgagac ccggtctcta ccaaaacaaa acaaaacaa aaaacagcca cgcatgtggc  49860
atgtgcctgt agcctcagct gctgctcagg gggctgaggc aagaggattg tttgagccca  49920
ggagtttgag gtcacagtga gctgtagtca tgccactgca ctccagccta ggcaacagaa  49980
tgagacttg tgtcttaaaa aaaaaagtt tcctttgttg ggttattta atttgacct  50040
ggttatcatt tttcagccat attttaactttt gtacatatca gaatgttctg ataaaacttta  50100
actttattta aagtgtttgt gatatatct gctagttttg gtacacatta tctttttgcaa  50160
tgccagttat tttcttttcc agtgtgggtt tgcataggaa aagaattgct gtcactttct  50220
attttgaaat cttaaaagac tgatcctttt ttgtgtcatg atttgagtat ttaattgaga  50280
gcctaatgcc taatattatt tgcagtatta aatgggatct taacaggaat agcattctag  50340
ccttcattga attaagtaaa cattctttaa gagaacttgg aatctataat atttgcgtca  50400
tcatagtatg agatacttaa tcaagtttga gattttagtg aaacattgtt tagaagccaa  50460
aaggattcta ggaaaaatta atgtctatat tcttgaatta ggagagattt tgggacgtgt  50520
gactaagtta cgctgacact tgtttgtttc ttagtcgctt tttccagtgg cggtgagaac  50580
gaagatgact gattcacatt gctcagatga gttttatcctc ttctggctgg gacatgggat  50640
atatcctgtc tcttttaagc cttttttggta tttttccccc attgagagct gtgtcttcaa  50700
actcttctgt tatagctgga aaatccttttt taagtgaaat ctgcccaaat tataagacag  50760
atgaaggtag agttgtgttg gatataggat tagggtgaaa gtagtgggggg tgtcctggag  50820
cctctcttct ggtggcagcc tagctcttgt gcctttgagg aaattaccct ggggacggct  50880
ctgtggaaca tatttgcaaa ccactgatttt ggaagataga gatggctttt gttaagatct  50940
gaattcacct tttttggcatt ttatttgatt tctcaaggta aagaacttat tttgtaataa  51000
agtttcctat tatttagtag ataggccaag ttgctgtgtt aattccatgt agatttttgag  51060
tttcctttgc tcattttttc actcttaatc tcacatcatt gtaagtttat ggaagttatc  51120
atacttctga ctttttcttt gaagagcaga aattagaaat tcccaataat tatttttgata  51180
gtgtcattta atgacactca catgtgatgt agccacaaag atttaatgag ttcagttttaa  51240
aatcatatta agactgttg tttcattttgt tctcattaat taattctga agataacaa  51300
taaaatgtat tttagaact ttcaaatgaa aatattttttc atccttccag atcatataat  51360
gcttaagttc tgattgttaa tcataaagtc tagaaaatta aaagataata aaatgaaagt  51420
gactttaagg tattagagtt ttattataaa ttctggtgtg tcattggagc tatgacatga  51480
atatttcaaa ggccaatagc attggatctt tacagttata acttaccatt tttaagttta  51540
agtagtaata tagattattt aatatcaaa tcaataaat attaattatt aaaatgttttt  51600
gtggtatagt ttgagaatca ttgcttttaa cttttttccat ataggtttat tgactttaat  51660
agcattctaa acataacatc tctacattct ttgtgtttaa tactgtggag gtataaaaat  51720
acttatatat gatgataaac tatattgag taaattaaat attcttatga gtttcatttt  51780
agagtgcatt tacttaattt tgaagtcctt attttttagca aactaaaagg aatgttggta  51840
cattatttac taggcaaagt gctcttagga gaagaagaag ccttggagga tgactctgaa  51900
tcgagatcgg atgtcagcag ctctgcctta acaggtagtt ctcactagtt agccgctggt  51960
```

```
gtggaccttc actgtctgcc ttccacccct tgcccttcct gctcgtcccc ctgcacctgg   52020
tggacagcac gactgggggc agcagtggag ccaggttgct taaatggggc atattcgggc   52080
ttcttttata atacttactc tgaagcttgt gtgtctgtgg tgtttgcatc atatatttgt   52140
tgttttccat ggtttaggct gttttaaaat taggtttatg gcttgagcat agggctttgt   52200
gagtagggga tggcaggtcg aaacatctca tgagttggat gggttatgct ggggttggg   52260
aaatgggatg aaaaattatg ggatgaaaaa ttgcctatgg atagtttaac ttgaaagaat   52320
ctgcctttgt ttacagatag ttatctttt tcttttttga gatagagtct cacactgtca   52380
cccagtgcag atacccagtg tcactggagt gcagtggtgt gctcttggtg cactgcagcc   52440
tccgccttct gggttccagc gattctcctg cctcagcctc ccaagtagct gggactacag   52500
gtgcccgcca ccacgcttgg ctaattttg tattttttg tggagacggg ttttgccat   52560
gttggtcagg ctggtcttga actcctgacc tcaagtgatc tgcctgcctc agcctcccac   52620
agtgccggga ttacaggagt gagccactgt gcccggccag ttacagatac ttatctaatg   52680
aaattctctg tgtactttat aaaagatgag gattaactga aggtactaat aactggatta   52740
tatgagggtg gtttggttg tataatccta tctaaaagaa tattttagct ataactgaaa   52800
gtaagactta aatatttaga gaggaaaatc tgaataattc tagtagtaat tatttattta   52860
caaaataaaa atagatttt ttttgattac acaaattaaa caacaataaa acatcacagc   52920
aatccggata ctataaagct cacatgctta ccgacccaac tgcccagga gtgaccactg   52980
ccaacagctt catgtcgacc tttttgccat aattttata tagccttttt tgttttaaa   53040
tggtaattta gaaagtcaac taggaaaatg tgttacaggt ttatcttcca ggagaatagg   53100
actgagtcg gatcttgaa tgtggcttgg aagaaggcaa gcccaccca gagagatgag   53160
ttgacagttg tttctgacca ctgcttgctt agagggcctg cgtgtctgtg accgcctagc   53220
tttgcgcccc tgactaggct gccccttaat tacaaatgtc tttatatatt gctccagcta   53280
aggcttggag tagtcggtta agaacttgaa cttcggtttt tgcagtgaaa cagcatttga   53340
gaatatcacc ttctgataag ccttattta taaggtgggt actgtagtgg gaggcagtgt   53400
gagagatgct tgaaggatgc actgctgtcc tgcatttcag catcttcagg atgctgtgca   53460
gctgaaacat ttgataacgg tggaactgtt cgttattttg caagcctgtg attccctatt   53520
gaatgttttc tctcgccatt tgacaaatga gtgtttctct gtcttcagcc tcagtgaagg   53580
atgagatcag tggagagctg gctgcttctt caggggtttc cactccaggg tcagcaggtc   53640
atgacatcat cacagaacag ccacggtcac agcacacact gcaggcggac tcagtggatc   53700
tggccagctg tgacttgaca agctctgcca ctgatgggga tgaggaggat atcttgagcc   53760
acagctccag ccaggtcagc gccgtcccat ctgaccctgc catggacctg aatgatggga   53820
cccaggcctc gtcgcccatc agcgacagct cccagaccac caccgaaggg cctgattcag   53880
ctgttacccc ttcagacagt tctgaaattg taagtgggca gaggggcctg acatcttttt   53940
ttttatttt tatttgagac agagtctcac tccatagtgc agtggaggcc gggcacaggg   54000
gctcatgcct gtaatcccag cactttggga gactgaggca ggcggatcac ttgaggtcag   54060
gagttcgaga ccagcctggc caacatggtg aaaccctgtc tctactaaaa atacaaaaat   54120
tagttgggcg tggtggcaca tgtctgtagt cccagctgtt agggaggctg aggcaggaga   54180
attgcttgag cctgggaggc agaggttgca atgagccgag atcgtgacac tgcactccag   54240
cccgggcaac agagcaagac tccatttcaa aaaaaataaa aaataaagt gcagtggctc   54300
gttctcagcc cactgcaact tctgcctccc aggctcgagc gattctcccg cctcagcctc   54360
ctgagtaggt gggattacag gtgggcacca ccacactcag ctaatgtttg tattttcagt   54420
agagacaggg tttcaccatg ttggccaggc tggtctcaaa ctcctgacct tagatgatcc   54480
acccaccttg gcctcctaaa gtattgggat tatagttgtg agccaccatg cccggccctg   54540
ccacctgcca tcttttgagt tcttccctgg agacctagac ctgaaccctc ctgcttgttc   54600
tcttgttatc taatacccct attgacagcg cagcttagat cattaatgga gagcttgacc   54660
tcatctgata ccttcactga aggaaacaac ttagtgtctt tgtgttgaa cactgaggta   54720
aaaaattgga atagttgatt atatgaactc tgctaaaatt ggagtgcattt tacatttttt   54780
aaggccttgt tgggccctgg ttaaataatt atttttaaaa atccttaagg agcctattat   54840
aaacagatct gtggtcttaa tgaaatgtga ttaaatactgt gcattatttt aagaactttt   54900
gacttttcaa aaaactttta caacatttcc catttgatag cggcataggt ttaagcactt   54960
ctcatctcta agttagtgga caaaaaaccc tcatggatag tctaataatg tttgctacaa   55020
gtccatgttg agttttatac tccatttat tttcagtttt aaaaactgtg gttaaatatg   55080
tgtaacataa aatttatgtt cttaaccatt ttttgcgtat acagttcgct ggtattaaat   55140
acatttaaat aatgtcatgg aatcattgct accacccatc tctgtaacct tttgatcatg   55200
taacactgaa gctctgttcc cattgaactc tattcctcct ttcccgccaa gtccctggca   55260
accacgattc ttctttctgt cttctgaatt tgactacttt ggggttctcat atactttagg   55320
agtcacacag tatttgtttt acttagcata atgtccccaa agctcatgca tgttgtagcc   55380
tatgttagaa cttcctaatg tttcaggcca aatactattc cattgtatgg ataggccaca   55440
ttttgctttt ccattcctct gtccatggac acttgtattg cttcatgttt tagccattgt   55500
gaatcatgct gttatgaacg tgggtgtaca gatagctcct ggagactctg ctttcatttt   55560
ttttggctaa atacccagaa atggagttgc ttttacattc aatttttaat ttaaaacatt   55620
catatcattg agtgttttac ttaatagtat agtagttaac aaacttaata aaatagtatt   55680
ttggtaataa tttgctggta gtccattgtt cagttttttt aggtaaatta cacaggacat   55740
ttcaagtgga catgaaacat cttgtgatgt ggaatcaatgc cccaagctga tggctaaaca   55800
tatgaaatac catacccctaa atttagtaga tttagtctttt gcaatttagg agataacctg   55860
ttatattgtt aggttttgt cgaaaagctt tgtcctcata tttccaactt gctgtaaaat   55920
ttgtttgtga agacaaatat ttttgtatgg gtttttctt tttcatatta aaaagaaatg   55980
tccacattgg aatttttttg gagttttag agctaataga gcttttcata atgtagtggg   56040
aatgagtgat cagtaagctc ttagcagttt ccatgcgtgc atttctgtgc cttgaaataa   56100
atgacagatg agtacatttg tgttctgtgt gtaaaatgtg ctctttcctc attgcacttc   56160
catgttggag ggcttgtctc ttggtgatca cacttcaaaa ttctcacagc ccccccttgaa   56220
ccgtttaggt gttagacggt accgacaacc agtatttggg cctgcagatt ggacagcccc   56280
aggatgaaga tgaggaagcc acaggtattc ttcctgatga agctcggag gccttcagga   56340
actcttccat gggtatgtgg actacaggtg atgcgctaca aagtggtttg tattcagacc   56400
tggacatctt aattatatct ttgcttccaa gaagaagtcc tttgatactg ttttctgagt   56460
tctgaatagc tgatgaaaat gaccaattga ggaataatca tacttttct tgatctaaat   56520
cttatacttt tgagttatct tagcataaat gtataattgt attttaagtg gaaatttgtc   56580
acttaatctt gatttctctg tttttaaagc ccttcaacag gcacatttat tgaaaaacat   56640
gagtcactgc aggcagcctt ctgacagcag tgttgataaa tttgtgttga gagatgaagc   56700
```

```
tactgaaccg ggtgatcaag aaaacaaggt gagggacata ggcttgagac gacttggtgt   56760
ttctgagctt gtgtgaggat ttaaaatcgc cctggctact gtctacttta ttgctttccc   56820
atccctgggc ctttaaattt cccctttaaa taccagctct tcccaggcct gttgttttct   56880
gcctttccag gtactaccca cagccttgag aattgcctga gttctgcctc ctttgagagt   56940
gtgccccaga caaatctatt ctgtactgaa tgtttccttg tctgatttct tggatcattc   57000
atttgatggt tgcgtatggc ctgcaacgtt tcttgttttg gttctactga actgttctaa   57060
aagtctctct tcatattatc ttttacatg taaatgtaac tgtcttcact tttaattcct   57120
caaggacaag gaatagcgtt tcacagttcg tcccatcaat cagaattata gcctttggca   57180
tctccctatc taccaggccc acttcctctt agatttgggc ttccccaggc tgttgccttt   57240
ccccaagtag cttctgcttg tcctgtagaa gacctttcat gctttgcttc tgcagcagcc   57300
gttcctgaat gcctagtgtc aactgccttc ttaccacgcc caccctcct gcatgctgca   57360
tttatcccct gccacagccc tgtgaccctg tgtcctgctg cctctgactt gtctgtttct   57420
gcttggccat ggtctctgtg aggtcaggtg tgcatatggg cacaaaccag ggcatctctt   57480
tatcccagc acctggctta agtgctgctc tggaactatc tgttgaatga actaatgcat   57540
gaatgtattg ttgagtatga gacaaacaag tgtcattgtc tcctttctag ccttgccgca   57600
tcaaaggtga cattggacag tccactgatg atgactctgc acctcttgtc cattgtgtcc   57660
gcctttatc tgcttcgttt ttgctaacag ggggaaaaaa tggtgagtac aaaaggggat   57720
gtgcacagtt gaaggaaata actaggtttc agaggtcggc ttggtggcct gttttttgcct  57780
tgcgtgcagc agaggaagta gaatctgagg atgagtttgg ttttcactag ccgaggggag   57840
ggaggaaatg atgggagcag gtaggttatt gggtctggtt ttgttcattt gaaacaatc   57900
tgttgtttga ggctgaaggt ggcttgggtg atttcttggc agtgctggtt ccggacaggg   57960
atgtgagggt cagcgtgaag gccctggccc tcagctgtgg gggagcagct gtggccctcc   58020
acccggaatc tttcttcagc aaactctata aagttcctct tgacaccacg gaataccctg   58080
gtatgttaaa agttcacatc ttattttctc agatttaatc attattgtaa aaactatttc   58140
agtattgact attttagttt tagagcagta agtgttttga gttcatttgg gatatttgac   58200
ctgcgttgta gctcttcaga aaacacatga atagtgaagt tctttgtttc atgggtttcc   58260
tttagatgaa acccatagag gagaaaagta gaaacctcag cacgtaagag ccaacatata   58320
tacacatcgg atttaaacct aaagcacaaa ttgtgcctgg tcgcagtggc gctgagtcgc   58380
actcagccag gccaggcatt cacactcagg gtgagtggga accaggactg gctgaggcag   58440
cagtggaccc aagtctccat cgcgcccatg cttactatga agccttctcg ttctctcttt   58500
ttctttgggt gagaggtac acttgtgttt ttgaatttat atgaggtaag tgtgtaatag   58560
ggttttttct aatctttttt aagtggaatc tggaattta atcagattta ttatctgaca   58620
acctagaatt ataatccaga aagtctgtgg tattgaggac atattggcaa tatgatgaat   58680
ctctaattct taaatcctga aacttttttt tttttaatca cttaggggtta ttatagtgaa   58740
gtcatttctg aatttggatc ttctcttcac acctcttttt ctctttcctg agaattaagc   58800
ttttgtttcg agttagaaag ttgatagtag ggaattgttc catggctgag caatttatct   58860
ccacagagga acagtatgtc tcagacatct tgaactacat cgatcatgga gacccacagg   58920
ttcgaggagc cactgccatt ctctgtggga ccctcatctg ctccatcctc agcaggtccc   58980
gcttccacgt gggagattgg atgggcacca ttagaaccct cacaggtaac ggccagtttt   59040
tcagctgtgt tttttctagt tatgcttact aaggtttaag tttagatgat gatgtttgtt   59100
gcttgttctt ctggttagga aatacatttt cctttggcgga ttgcattcct ttgctgcgga   59160
aaacactgaa ggatgagtct tctgttactt gcaagttagc ttgtacagct gtgagggtga   59220
gcataatctt ctgtggaacc atttcttcac ttagtgcaat tttatcatt gctacaatta   59280
aaattggagc ttaataggaa atatttccat gcactctaaa gctgtaacca gtaatacccca  59340
ccatgtatcc atctctcagc tttagaaaga aaacgttgcc agtaaagtta atgcttcata   59400
aacttcagtt taagttctaa ttctcagaat atttgtttga aatagacctc ttcctaaagg   59460
atatatttag aaataaccta tcattaagtg taaagtctgt tgaatatgct gggcacggtg   59520
actcacacct gtaatctgac cactttggga ggccaaggtg gaaggattgc ttgagcccag   59580
gagttcaaga ctatgggcaa catagttgac cctgtcccta cagaaaatta aaaaaaaaa   59640
aaaaaaagt agctgggtat ggtggtgcat acctgtagtc tcagctactc gggaagctga   59700
ggtggaggg ggattgcttg agccccagag gcaaggcgtg cagtaaggcg tggttacacc   59760
actgccctct agcctgggca acagagtgag actgtctcaa aataatagt aataataatc   59820
agttgaatta aaaaaaaaaa aaaaaaacc actgtgctag gcccatagta tggtaagagt   59880
taaagtgagc cttagggatt atttactcaa cctctgtttc tgtataaagt ggaataggct   59940
caattcttta agtgatagca tgttgaacct ttccatacca actggctcat aagtcacaac   60000
tggccagtca acaagagtaa aaattaactg gtaaaaatca aagcaaaaaa cctacaattg   60060
tcaaatttgt gggataactc cccctttttaa aatgtcatgc ctgacagtaa ttctctctcta   60120
gtttccaggt tttcagtcag ttgtgtcttt tttgagcaga aggaagcatg ctaagagctc   60180
aatcttgtgg ctagctgggg gtcttttgtgt cagccatgca tgtgatggtg ccctgggtg   60240
cttggggctg cagggagg gtacagcagt aggggcctgt tctgttctct cgtgctgtgg   60300
agtacatagt gacatagtgg ggtggtcctt ggtgtaggtc ccttgttcct accctggg   60360
ctgagattta tttagaagtg gtgttgggc tgtcggcag gccctctgt aactgatcaa   60420
tgtttgtgaa gttgctgttt gagagttgaa accatgacat aagcagaaat ggaaggaaga   60480
aagaaccagt tatgtgaaag ggacacattt acttttaaag ttgtatttac tgagatgaaa   60540
tattcttaat caatgttctt gagaggtgtg ggaaaaatgc aacatcctgg ttgcagttaa   60600
acccagaaca ttgtgtgttg aagagtgacg gttctcaaac cgtcaagacg cgggtactga   60660
gtgggactaa cctgctgtcc tcttgccttg gaccttgtgt tccagaactg tgtcatgagt   60720
ctctgcagca gcagctacag tgagttagga ctgcagctga tcatcgatgt gctgactctg   60780
aggaacagtt cctattggct ggtgaggaca gagcttctgg aaaccctttgc agagattgac   60840
ttcaggtaag tgagtcacat ccattagatt tcatgaacta agctcaattg aaagttctgg   60900
gatcacttga tgcaaggaat gatgttatca agtaccctgt ccatcagaaa tccgagtggt   60960
ttaggtagat gacagtgatt ttctcctccc agtggctttt tgctgaactt tgccctatgc   61020
ttggaatttt attttatttt attatttatt tagagacaag atcttgctct gtcgcccagg   61080
cttgaatgca gtagcacaat catgctcac tgcagctgtg aactctagga ctcaagtggt   61140
cctcctgcct cagcctcccg attagctagg agaataggtg tgtgccgtca cactggctaa   61200
tattttttgt agaaatgggg tcttgctatg ttcccaggc tggtctcaaa ctcctgggct   61260
tgattgatcc tccatcttgg cctcccaaag tgctgggatt acaggcatga gccactgtgc   61320
ctggcctaga attttaaaat ataagtagaa gagtagattt ttttttttgg tagtcctcgt   61380
catttaagta ttctggatag tgggaataaa agagcttaga attttttcatc tttgtcttaa   61440
```

```
acttttaaaa aaatgtagct tatattaatt ctgcttgttt aaaaagaata tactcttcat   61500
tatactgaac ctaggtaaga cagctggttt atattttgtt gcaattaaaa aacgtgagct   61560
gtggttgcag tgagccaaga ttgtggccat tgcacttcag cctggcaaca gagtgagact   61620
tggcctcaaa aaaaaaaaaa taacatgagc tgtgttggca ctttcatttt ctaagagtag   61680
ttttggctgg agaagttttc tttcagtact ttcttttaga agggaaattt tccttttataa  61740
tttagggttt gttttttttt tttccaagcc acctttttata gagccttgt gggttatttc   61800
atttaatcct tagaatgttt ataaatctgg gcttgttctc ggctccaccc acagataggg   61860
acgctgagcg tgcatgagtg ggcagcaaga tagcaggtta tggagggccc agctcacccc   61920
ttctgtggct tgagccaatt ttataggggca cttacagagt cttttgaaat agtatttatt  61980
ttgaagaaaa agaaaaacag tttactgagt actgtcttat tgagtctgga attgtgagag   62040
gaatgccacc tctatttatt taaagccatt ggccttttt gttgttttga gtaagtgctg    62100
cccaaggtcc ttccagggca cctgatgag cctgctctgg agcaagctgg cggtaagtgt    62160
ttactgagta actaaatgat ttcattgtta aatgtgctct tttgttaggc tggtgagctt   62220
tttggaggca aaagcagaaa acttacacag aggggctcat cattatacag gggtaagcgg   62280
tttattttg tgagatgctg ttttaccttc aagaaggtga aagtgaggct ttccttgtgg    62340
aatttctcta aatgcattcg tcatgtttta gatgtttatt tcacagttta tatcatgaaa   62400
gttataatct tgtcatatgg atttaagtct agtaatgttg agttcttttct cactagcttt  62460
ccaaaatatc ttacctaaaa tttagtcaaa tacaagatta tgtttatttt tattatccctt  62520
ctctctaaag cttttaaaac tgcaagaacg agtgctcaat aatgttgtca tccatttgct   62580
tggagatgaa gaccccaggg tgcgacatgt tgccgcagca tcactaatta ggtatttacc   62640
aatattttat ctctttttcct tttttggttg aagtactaaa agatacgaga atggaaagag  62700
agggaagaat tcaaaggatg tagagcagta ttcctgaatc tgagctcatt tcagccattc   62760
tattcttaaa ctataatgaa aaaaaaatcc aaaaaagtct aaaattataa ttaaaaaaac   62820
aacaaaatac taactgtcca ttgtaaaaag taatgcactt tcattgtaaa aattttggac   62880
tatagagaat agtactaaga agaaaaaaaaa aatcaccttc aattctgctg ccacctggag  62940
gtaatcactg ttaatttttt gctatatact ctatgatttt cttgttcaaa atcaggtcaa   63000
aattacatgc aattttgtaa tctgacaatt tccacttaat attttattag catttttcctg  63060
ttatgaaaca gtaattttag ttatgggtcg ttgttttgct atgcggttgg gataaaattt   63120
tatatacttt ttttggcaat tacttattat acataaatgt ttgtgtatag ttttcttttt   63180
ctgaaattc ctggaagttg agttaccagg cccggctttg aattttttt tttatttttt     63240
ttttgagaca gagtcctgct ctattgtcca ggtgctatct cggctcactg caacctctgt   63300
ctccctggtt caagcgattc tcctgcctca gcctcccgag tagctgggat tacaggggca   63360
caccaccacg cccaattaat ttttgtattt ttagtagaga cagggtttca cgatattggc   63420
caggctggtc tcgaacttct gaccccgtga tccacctgca ttggcctccc aaagtgctgg   63480
gattacaggc gtgagccatg gcgcctggcc aggctttaaa tttaaaacaa atcttctaat   63540
agctttatgg aggttataat ttacatttct tgaaatgtac tcactttgag tgtatagtaa   63600
actccaattt tatcacattt ctgtcacccc aaatgtatcc ttgtgcccat ttgctgtaac   63660
ctccggttcc tgccccaact cctaggcagc cactcatcta ttttctgtcc cttaagattt   63720
gtgttttcgc caggcgctca tgcctgtaat cccagcactt tgggaggccg aggttggtgg   63780
atcacttgag gtcaggagtt cgagaccagc ctggccaaca tggtgaaacc ttgtctctac   63840
taaaaataca aaaattagtc ggatgtggtg gcacacgcct gtaatcccag ctactcggga   63900
ggctgaggca ggagaatcac ttgaacctgg gaggcggagg ttgcagtgag cagagatcgc   63960
gccactgcct tccaacctgg gcaacagaga gagctgtct caaaacaaac aaagatttgt    64020
attttctgga cattttatag tactgggtc atagtataga tggactttg catttggctt     64080
cttttactta attgtgagat tggttcttgt tgtagcatgt atcagtagtt tgttcatttt    64140
tattggcgaa agtattctat tatatgaata ataccatatt ttatctatcc atcagatgga   64200
tattatagag ttcatgtttt ggctaattta tgaattatga tactgtgaac atttgcctgc   64260
aagattttgt gtagacatgt cttcatttct cttgagtaga tcacctagaa gtggattttt   64320
aaataatttt ggtacttact gtgaaactgc tcttcaaaaa cataccattg ttccttcctt   64380
ccttccttcc ttccttcctt ccttctttcc ttcctcccctt cctcccctccc ttccctactt  64440
ccctctcccct ttccctttcc cttccccttt tccttcccct ttcccgcctg cctgcctgcc   64500
tgccttcctt ccttccttcc ttcgtttctt tctacatata cacattttt taaatttcaa    64560
tggttttttgg ggtacaagtg gttttttgtt acatggctga atttggtta catggtgaag    64620
tctgagattt tagtacacct gtcacccgag tagtgtacct tgtacccaat atgtagtttt   64680
ttgtccctca ccttccagcc ttccgccttg tgagtctcca atgtccatta taccacactg   64740
tatgcccttg cgtacccaca gctcagctcc cacttctgag aacatatagc agaaacatgc   64800
caaagtatac tcccactacc agaatgtgat tgtgcctgat tcttctcacc agtacaaata   64860
tttcaaaaaa agttaaatat gtatcagttt tttgggcaga agttgatact tctcttttatt  64920
tatttatttt ttttgagata gggtctcatt ctatgatgcc caggctggag tgtggtggtg   64980
cgatctcggc tcactgcagt ctctgcctcc caggttcaag tgattcccac gtcagcctcc   65040
caggaagctg gaattacagg cgagggccac cactgccagc taattttttgt attttttggt   65100
agagatgggg tttcaccatg ttggccgagc tggtctcaag ctcctgacct caagtgatcc   65160
acctgccttg gccttccaaa gtgctgggat tacaggcgtg agctaccaca cccggctgat   65220
atttctttt aaaataactt accttcttt gaaagtaata catgtttaat gaacagaatt      65280
taaggaaaat ataaaaaaac gaaataatct ttgtaatcaa actactgaaa agaaaaccaa   65340
agttacattt tggtgcatat tcttttttcat tttcatcatt gtaatttgca tttctttgat   65400
tacttgtgag acactccttt catttactta ataggtttat atgacttgcc tattcagaga   65460
ttgtcagct ttaccatttt ctgcaaatga tagcaacttc tttttgttg tttgtttgtg      65520
gagacagagt ctcgctctgt cactcaggca ggaatgcagt ggtggaatct tggctcattg   65580
caactattgc ctcctgggtt caagcgattc tcctgcctca gcctcccaag tagctgggat   65640
tacaggagtg tgccaccatg cccggctaat ttttgtatct ttagtagaga tggggttttg   65700
ccatgttggc cgggctgatc ttgaactcct ggcctcaagc ggtcccctg tctcggcctc    65760
ccaaagtgct gggattacag gcgtgagcac cgtacccagc cagtagttac ttcttatatt   65820
ctagaaaaaa ttctactcat gatcaagtct ccatgaggaa agagacttta attgaagatc   65880
atgggggcttg cagaccaata tgataaaata gttcattgtt tctaaaagta ttactgagtg   65940
ttgatgcag atatgaaccc tttttgtttttt gtaggaaaat gttacccgta ttctccattt   66000
gaattcagtt tagatttgtt aggaatcgca gcttaagctt tgccatctgg gagtgtttgg   66060
gacagttttg cagacaaaat tgcaaagtg cctaaggaat gcagctggca ttcagacctg    66120
ctctgtgctc agtactctgt ggacagacac tgttcagcac ttgttgatca gaaggtttag   66180
```

```
aaagagaact ttcaaagttg gttttaatt aaagcattta atagtgtaaa tagaaaggga  66240
ttaaatttta tgacagacaa aagaaagtac agcacccagc tgggcgtggg ggctcacgcc  66300
tgtaatccag cactatgggg ggctgaggtg ggtggatcac gaggtcagga gttcaagagt  66360
tcaagaacag cctggccaag gtgatgaaac cctgtctcta ctaaaactac aaaaattagc  66420
cgggcgcggt ggcaggcgcc tgtaatccca gctactcagg aggctgaggc aggagaatca  66480
cttgaacctg gacggcagag gttgcagtga gccaagattg caccattgta ctccggcctg  66540
ggccacagag tgacattctg tctcaaaaaa aaaaaaaaaa gaaaaaaaga aagtacagca  66600
cccagttatg tccgagtggg tgcatgagag tgaccctgag attggagaca cgctgtcac   66660
gtgcttgaag aacgccacct gagaaagggg gcgagaagtg gtgtccgctg gtaaccagag  66720
gtgttggctt agccatctgc agggaggagg gtggtcatca acaggtgagt ttcatctact  66780
ttcttaagca aattaacctt acttttgtgt taggcttgtc ccaaagctgt tttataaatg  66840
tgaccaagga caagctgatc cagtagtggc cgtggcaaga gatcaaagca gtgtttacct  66900
gaaacttctc atgcatgaga cgcagcctcc atctcatttc tccgtcagca caataaccag  66960
gtatgctgac ccagtggcat cttcacattg tcgggaaaat gcccttcct gatgcctttc   67020
tttaggcttt aattgaaaac attttatttt ctagaaaaaa gcttcagctc aggatgtttg  67080
agtgtaggtc agtcctttga taggatatta tcattttgag gattgaccac accacctctg  67140
tatttaagct ctgccacaat cactcagctg tgacactgta aatctcttaa tagttttatta 67200
cattccatgt gctgacagtt gtatttttgt ttgtgacact tacgtattat ctgttaaaac  67260
attttcactt tagttgtgtt acctttaaag aggattgtat tctatcatgc ctgttgattt  67320
tttggtgagc gggctattaa agtcagtgtt atttagggtt atccactagt tcagtgattt  67380
gcgagattat cattcacatt tattgtggag cttttgaata tcgtgtcaaa tggccacata  67440
tatcccattc ttatctgctt cttaggtgag tgggacacag tgcttttaatg aagctataat 67500
cttcagaatt ctagcttgca gagaagattg cagaagtgat aagacttgtg cttttttaatt 67560
ttgtctttta aatgttattt taaaaattgg ctttatatga tactcttttt ttctgctgag  67620
taacagtgtt ttacaaaact tggactaaat gacttctaag cttaaatgat cacttgatgc  67680
ttttttctg aatataggaac tcagcttatc aaatatcaaa gtcataattc ctgaataaat   67740
aacgtctttt ttcatgtaaa gactgcttta aaaaacacat ggaaggctgg gtgcggtggc  67800
tcacgcctgt aatcctaaca ctttgggagg cccaggtggg caggtcgctt gagctcaggg  67860
gttcaagacc acccagggca acatggcaaa acccacctct actcaaatac aaaaaattag  67920
ccaggcgtgg tggcgggccc ctgtaatccc agctactcgg gaggctgagg gatgagaatc  67980
acttgagccc cggaggcaga ggttgcagtg agccaagatt gtgccattga actccagct   68040
tgggctacag agtgagactc tgtctcaaaa aaagacacac acacaaacaa aaaaaacatg  68100
gagacatttt tttggccacc ttaatatttc ccctcagata atttccttttg tttaaactca 68160
gaactggcat tttctctctt ggagaagatt caggacaaat actccttttaa gataagtaga 68220
agcagtgaaa gaggatttga ttatcaggaa tttgataagc ttagaataaa ttgttgcttc  68280
ttaatgtcat ttcagaagat gaatatttat taatagatgc caactgagat atcattaaaa  68340
ttgattacta actactactt ggaaagtct cccagttcca aacttcagca ggcctcttga   68400
caattcagct gtggtcaatt gggtcttgcg tgatagataa atgaccaat tgtgcagcag   68460
agtgtgctgc ttagctgcct attctgttag cattcatgtg ttaacttaaa atcataatct  68520
ccttagtttt gttgagtgtc tccgtgacca agacactgtg agggatacaa aatcagattg  68580
gctttattca aaccactggg gtattataat tcatttataa tttattttat tttttgcctt  68640
tttccatgt gttctaaagg aattagagtt tgtatataac tataatgggg gatagaaatt   68700
gacatgtgcc atgaagggaa tgcaaaaag tgccgtggga gatgagagt gagagaagga   68760
atttctttt tcttggaagc aggaataact tcatgaagca tgtatttcaa cttaaacaga   68820
tagtaggcaa cgctgtaagg ggagtatggc tgcagcaaaa gtgttcgggg cagactggga  68880
ggaagggagg gaataaaattc agccattgtt atggaataat gatcaaaatt tattttcagc 68940
ccgtttcact taaaagttga gactgcttaa cttttttaaa tatatatct taaactttta   69000
aatgccattt gatctttaaa aatatatgtt ttaatagtgt attttaaatc tctatatttt  69060
tgttattaga atatatagag gctataacct actaccaagc ataacagacg tcactatgga  69120
aaataaccctt tcaagagtta ttgcagcagt ttctcatgaa ctaatcacat caaccaccag 69180
agcactcaca gtaagtctct ttcttgatcg gtcttactga cattgtaata gtttttgcta  69240
gcttgtatgg ccagttagtt gtatggtcat cttacggtga ggtgcttgtc ttacagctct  69300
tacttatcca tgaggcttgc taagaaattg tgcttctgtg aaaagaatct cagcttactc  69360
caggaatgta aatgactatg ttttttctga ttattaaagt aatacacgcc caaaataaaa  69420
aaattcagcc aatttaggaa gacacaacaa ttaaaataag ccaggcatgg tggctcatgc  69480
ctgtaatccc agcactttgg gaggccaagg ttggggctc acttgaggtg aggagtcgga   69540
taccagcctg gccaacgtgg tgaaacccca tctctactaa aaatacaaaa attagctggg  69600
cgtggtggcg ggcgcctgta atcccagcta ctcaggaggc tgaggcagga gaatcgcttg  69660
aacctgggag gtagaggttg cagtgagctg aggtcaagcc actgcactcc agcctgtgca  69720
atagagcgag actctgtctc aaaaaaaaaa aaaagaaaaa agtaaactac              69780
tgtcacctgc attggtaatg tatcagaagt ttaaaatgtc tagattataa ttaactcagt  69840
gacctggtaa tatatactaa gggaaaaata tttataattt acatttttac atttttattt  69900
ttttaatttt attattttt tttgagaca gagttttgct cttgttgccc aggctggagt   69960
gcaatggcat gatctcagct caccacaacc tccacctccc gggttcaagc aattctcctg  70020
cctcagcctc ctgagtagct gggattacag gcatgcacca ccatgcccgg ctaatttgt   70080
attttagta gagacagggt ttctccatgt tggtcaggct ggtctcaaac tcccaacctc   70140
aggtgatccg cctcctcga cccccaaag tgctgggatt acaggtgtga gccaccatgc    70200
ctggccttac atttttataa ttgaaattta tgttgctgac attagaaaag aaccataata  70260
tccaagaatc caagaataat taaattatgt acatatgcta gtatatagtg tgatgctttg  70320
gagaattttt aacaatatgg agatgtataa tctggattgt aatattgagt gaaaaaggc   70380
agaatacaaa cctggtgggg gtatagtcgg atttcagtta agaaaaataa tatttacata  70440
tatacatttc tcacactggc agataatcac caagataaat tttgggattg tggatgattt  70500
ttttcttctt tatatttttc agatattctc aaattttcta aaatgagcaa gtataacttt  70560
tgttatcaga aaaaaataat atacaaaagt tagtttaaat tgctggtgac caggttaaac  70620
ctttttattt ttattttttg agatggaatc tcactctgtt gcccaggcta gagcacagtg  70680
gcatgatctt ggctcactgc agcctccgct tcctgggttc aaatgattct ctggcccag   70740
cctcctgagt ggctggaatt acaggcgtgt ggcaccacac ctggctaatt tttgtattttt 70800
tagtagaggt agggtttcac caggttggtc aggctggtct cgaactcctg acctcgtgat  70860
ccaccccacct cggcctccca aagtgctggg attacaggcg tgagctactg cgcccagcca  70920
```

```
gacctttta ttttatttga caaaagaaat acttccatgt tatagaagac taaatattgt  70980
ttgggctgtc tgcagtatgg tcttcccttg atttgttcaa aatatcgtaa actttgctta  71040
tttatttta ttgtggccga ctgtgtcggg cactgttgta ggcttgggat ggaaaaacag  71100
gattcctgcc cttagggttt ctgcaggctg gtcaggggaga cgatgtggta agctggagct  71160
cagctcctaa ggatgtgcag gggcagttga gaggcggaag ggtgggagat cattccaggg  71220
tgtgggcagc acaggaacct ctcttcattg ggatataatt gccattctga taacacgtgg  71280
ttgaggtgtc taaagtagga agttgtacca tggtgggaca gatatcctgt ggttatcata  71340
cacagatctc agttttcttc tcattgtttg tactttttat aaagggtaac aggagatata  71400
attcaataaa cctttgtggt gtttgggtgt gattttattg tttctttctt ctcagtttgg  71460
atgctgtgaa gctttgtgtc ttcttccac tgccttccca gtttgcattt ggagtttagg  71520
ttggcactgt gggtatgtat tttcctcagt atatattaat agttgtctac aacagtatga  71580
cataaacata gttattagga tgccctttt cttttctttt aagtcttta tcaatttggc  71640
tttttggaaa aatatctgat ggaatacttg tttctgctat attagctgtg tgagactagt  71700
gacaggagct gtgggaaatg aatgccaaat gttcttaggc attgatggga atttcagggt  71760
gtggtcttca agttcattta agggaatttt catatgctgg caaaaggctt ttctcattag  71820
cttgactctt tccaaaatta tttgctgtga attagaagtt taggaacctt ttttcactta  71880
attgtgacct agcatacgaa atggtgatga tttaggaact actgttcttg tattaacagc  71940
ttttatttaa aaatgatttt cctccagtag atggccctac tagcatctgg gaaataattt  72000
caagtcttct ccagcattca ggaataggct ttcattttgt gtatcaatta ctgagaatga  72060
ttttggtgac tcacatcaca tttgagaagt aaacctgcag atttcttgtg tgtgtcagca  72120
aatgaccaac tgatatttgc ttgaagtgga ttacattatc tgctctagaa tgattgcttt  72180
cccaccttcc tcacatacag actgagcagc tacggtttct aatcataggt ctggcactag  72240
acttcacttc tgggcaactt tggcattgga gtaaaatgta ttaattaaa gaaagttaaa  72300
aatccgttca agtaaacata cagttctaat acttttaca atttaaaata tagatttaaa  72360
tgataaaata aaaagaaaa tatgggtaga caccataatc ctcgtttctg catctgttca  72420
caagggttg atatttatga gttctattct ccatatccat tctatgttct cttaatgctc  72480
agtcagcacc tcaggtggtt ggagttcaat gcttggtagt ttgacttaca ctgtcttttc  72540
taggggattg agccctgggt agtcctgctt atttgaggtt gcaatttgtc tttcaataac  72600
ttttactaca agatatggcg tgttaaagga taccattggg gaaccaacat aataatca  72660
ggaaaactaa ccacgtcaga cctgccccat tgtgtatcaa gtacactatt tttccatagt  72720
aataaagagt tcaccccagc caattctctt ttattttgtg cctgtttact caatggcatt  72780
aacatgccca aatgtctggg tagctgtctc atctccagtt cagcagaacc attgtcatat  72840
gccctagtaa aagcattcct tcattggaca cttaggcccc aatactttca ttcagatcta  72900
ctacctgatt tcatttctca aatgattttt atggagctct gatttatagg aaagatgtta  72960
gttgattaaa aataaaacaa tttctgagct ggtataaaat gtattgtgac atgccttcct  73020
cttggaattg caagagaaag gaagactgtt gtttgcttaa aaattgtcta taatttgact  73080
ttgcaaatgt ctgcttccag agtgcctcca ctgagtgcct cagatgagtc taggaagagc  73140
tgtaccgttg ggatggccac aatgattctg accctgctct cgtcagcttg gttcccattg  73200
gatctctcag cccatcaaga tgctttgatt ttggccggaa acttgcttgc aggtactggt  73260
actgagttga aacagggact ccaggacttg gattttgatt tccttagggg gaatgggggt  73320
ggtgagcata tgaggggaaa atactataag gtcattgcca gtgatggctt gtcccttag  73380
tcaaatttca gatgttacct atatgcataa acacatgcag ttggcagctg ttctgtgctg  73440
agtattttaa agtagcctct tcccaatata gcccctcagt taactacaag taaactcatt  73500
ttgaatttca ttttaatggg caccatatgc cagtactccc tcgggcactg ggatgttaag  73560
aaagtataat gtatggactt cattctcaag ttagttttag attagagggg gatacacgta  73620
aacaaaagtg cagtggtcac acagagtggc cctaatcact ctccttgggc agatttatgg  73680
gctggtagga aagagcacaa cacggagagg gtgtagcacc ttggcgatga taatggagga  73740
tgtggccagc aaggaagacg gagtccattg aaattgattt tgggagaagt tgccaatctc  73800
catgaaagaa ttggggcctg tgctatttgc ttcaggggc tataggagag tttcgtgaaa  73860
gggactaaaa gatgagtatt ttaataagat cattcatcca acttgaacat gggctggagg  73920
agaaggtagg agagactcagg agattaatgt tgatgctaag gcaagataat ggcttttggga  73980
ctgtagggaa gacactgatt gtaagagaat gaaggaggca gaattgccag gcctggttca  74040
ccaactgaac ttcggttgtg aagacaaaga aacctgggat gacttacat cctgggcagg  74100
tgtgtggtgg tgacagtcat ggaaattggg aacacagatt tgtgcgggaa acatcagttt  74160
cagtttgagt ttggcttatc agttgaatat caggcacaga tgtctggcca actctcaaca  74220
tagggtctta aatgacttca gttcccaag caatttgtcc ttcccatgct attggggtgg  74280
agaggtaatg tctgtgccca tatcacagcc agtgctccca aatctctgag aagttcatgg  74340
gcctctgaag aagaagccaa cccagcagcc accaagcaag aggaggtctg gccagccctg  74400
ggggaccggg ccctggtgcc catggtggag cagctcttct ctcacctgct gaaggtgatt  74460
aacatttgtg cccacgtcct ggatgacgtg gctcctggac ccgcaataaa ggtaatgtcc  74520
cacttgggtg ctggattcat acagccttaa tgactatggg tttccagact acctttgttt  74580
agtaatctgt cccttcttta ttctcttttt gctttaaatg aacaaaattg ctcagattgt  74640
gacactaaat ttaacatcaa aatgtgacca tgtggatggg tgcagtggct cgtgcctgtt  74700
attccagcac tttgggagac tgaggcaagt ggatcacttg aggccaagag ttcgagacca  74760
gcctgggcaa catcacgaaa ccccctctct actaaaaata caaaaaatta gatgggttgg  74820
gccgggcgtg tgggctcaag cctgtaatcc cagcactttg ggaggccgag gtgggcggat  74880
cacgaggtca agagatcaag accatcctgg ctaacacagt gaaaccccgt ctctactaaa  74940
aatacaaaaa aattatctga gcatggtggc gggcgcctgt agtcccagct gctcgggagg  75000
ctgaggcagg agaatggcag gcgggagctt gcagtgagcc gagatcgtgc  75060
cactgcactc cagcctgggt gacagagcga gactccgtct caaaaaaaaa attagatggg  75120
catggtggtg cgtgcctgta atcccagcta cttgggaggc tgaggcaaga gagttcttg  75180
aacctgggag gcggagttgg cagtaagcct tgattgtgcc gctgcactcc agcctgggtg  75240
acagagtcag actctttcca aaagaagaaa aaaatgtgac catgtgtttt atagctcttt  75300
tagtatcatc agtcactgtt atccctaaga gggaaatacc tagctttagt ttaggtttc  75360
cagcattagc caagaaagct cagaattgat gttcctggcc aagtacctca ttgctgtctc  75420
cttaaatctt ggttaatggc tactgtcctg gctagcatag ttatggagca tttccatggt  75480
tgtagaatgt tctgccaatc tcaggacag ttttgctttt ctgtgaagca ataaaatcaa  75540
cttcaaaaca aatgttaact atttgtacaa tggatttaag atagaccagt tcacatactt  75600
tttttttttt tttttttga gatggagttt cattcttgtt gcctgggctg gagtgcaatg  75660
```

```
gtgtgatctc agctcactgc aacttctgcc tcctgggttc aaacgattct tctgcctcag   75720
cctctcgagg cagattacag ctgggattac aggcatgcac caccacaccc agctaatttt   75780
tttgtagttt tagtagagac gggggtttca catgttggtc aggttggtct caaactcctg   75840
acctgaagtg atctatccgc ttcggcctcc aaagtgttg ggattacggg catgagccac    75900
cacgcccagc ctaagataga ccagttcact tactgtttat atctgattac tctctctttg   75960
ccttgtcttc tacctttaaa aatctcccta ctaacttccc attctccttt agctgccatc   76020
agtcttctcc cttctctgca aacatctctg gagagtccca gcctcagccc acagagcttc   76080
ccactgctct gaggtggacc ttgtttgcaa ggcttctttg gctctcttgg cctggaccct   76140
gtctactact tcagccatcc ttccttaacc cctgctggtg gtttctgttg ccacactcca   76200
tagcagcgtt tcccgcccag atcatgtctt tacatctctg ggcactgctc tggtcctgcc   76260
tgcctttccc tctttgtatc ctgcaggctg ctaccccat cttgagtgtc ctcttcagtt    76320
ggctttcaga gggcctcctg ggtgttccct tacccacttg ccactcccca gtcactgggt   76380
tcagtcctc ctgcccacca gcacatgctt tctaggctct gtcctaggcc gtcttctctc    76440
tttgtagtct ctgggccagt gctgttctag agagtggcag aattttctat aaccatggca   76500
gtgctccata gctatgccag gcaagacagt agccactaaa cacatatagc tgttgagccc   76560
ttgaaatgca gctagtgtga ctgaagaact gaaccccgat tcggtttaat tttcattaaa   76620
tttaaattta aataacctta tgtgggtagt ggctccagta ttgggcaggg cagcctgaga   76680
gtcggggctg ttctcctgtc ttcagtgtct agatgaggga cctcagagga cctgtctctg   76740
gagctgcagt tcaatgtagc cagctgcccc gtgacactta catatagctg atttgtggat   76800
atgtcagaca cggtgtgatg agctcagctt tctgtcctcc tccccacatc tgcccctgcc   76860
ccatttaccc cactttgtgt cttatcaagc tagaaacagg tcaccacaag tcttcatttc   76920
cactcaccaa gtcttttgtt tcccctacta aatatttgc gagaagaaag tgtgtaccctt   76980
tgtattcaca tacatgtaca tgcacatata catgcacata tgcagggtc cccaacctct    77040
gttaaaaacc ggactgcagg ccgtgcgtgg tggctcacgc ctgtaattcc agaactttgg   77100
gaggccgaga ccagtgcatc acaaggtcag gagatcgaga ccattccggc tcacacggtg   77160
aaaccccgtc tctactaaaa atacaaaaaa aaattagccg ggtgtggtgg cgggcgccca   77220
tagtcccagc tacctgggag gctgatgcag gagaacgcg tgaacctggg aggcggagct    77280
tgcagtgagc cgagattgtg ccattgcact ccagcctggg cgacagagcg agactctgtc   77340
tcaaaaacaa aacaaaacaa aaaaaaaaaa aaccaggctg cacaggaaga agtgagcaag   77400
cattaccatc tgagctctat ctcctctcag gccagtggtg gcattagatt ctcataggag   77460
cgtgtatgag ttcgttctca cacttctgta aagacatacc tgagacatat aaagaaaaga   77520
ggtttaattg gctcacagtt ctgcaggctg tacaggcttc tgtttctggg aaggcctcag   77580
gaaacttgca gtcatggcag aaggtgaagg ggaagtaggc acatcttcac atggcccaca   77640
ggaaaaagag agaaggagag agagagagag acagagagag agagagaaaa agaaagattg   77700
agaggggagag aggagggaga aaggagagtg cctgtagggg gagttgctac acaaaggagc   77760
accaggggga tggtgctcaa ccattagaaa ctacccccat gatccaatca cctcccacca   77820
ggccccacct ccgacactgg agattacaat tcagcatgag atttgggtgg ggacacagag   77880
ccaaaccata tcagagcatg aaccctattg tgaactcac atttgaggga tctaggttgc    77940
atgctcctta tgagaatcta atgcctgatg atgatttgag gtggaacagt ttcatcccga   78000
aaccatcccc cgccaaccct ggtttgtgga aaaattgtct tccacagaac cggtccctga   78060
tgccaaaaag tttgggggacc tctgcacata tgcatgcacc tgtacatgga cacataatac   78120
atgtacatat gcatacttta tattctctgc cacttctggt ccagactgat atactatctc   78180
atttggatta ctgcactagc cttttggttt ggaaacagca tttttaaaaa aattaattt    78240
aattttttg agataggggtg tcattctgtt gcccagcttg gagtgcagtg tcatgatcat   78300
agctcactgc ggcctcgatc tcccaggctc aagtgatcct tctgcctcag ccttctcagt   78360
agttgggact acaggcatac ccaccatgcc cagctaattt tttgattttt tttttttttt   78420
gagacagagt ctcagcctgt cgcccaggct ggagtggtt ggcgcgatct cagctcactg    78480
caacttctgc ctcccaggtt caagtgattc tcctgcctca gcctcccgag tagttgggat   78540
tacaggcgcc tgccaccaca cccagctaac ttttttgtatt tttagtagag acgggggttt   78600
accatgttgg ccaggctggt ctcgaacttg tgacctcgtg attagcccgc ctcggcctcc   78660
caaagtgctg ggattacagg cgtgagctac cgctcccagc caggaaacag cattcttgag   78720
ataattcata taattcaccc atttaaagta tataattcat tctctttagt atgcccacag   78780
agttgtacag ccatcaccag aatcagtttt agaacccata aaggaactct gtactcttta   78840
cccaaaacct ccatgcctcc agctgcaggc agccactaac ctgccttctg tctctgtgac   78900
tctacgtctt ctggacatta ctgtggatgg gctcatacag tcagtgagct tgtgactggt   78960
gccttctacc aagcagggtt ttcagtgtag cagcctctct gtttttcttt ttttttttaaa   79020
ttgtgacgga acttctgcct cccggggttca agcgattctc ctgcctcagc ctcccgagtg   79080
gctgggacta caggccccatg tcaccatgcc tggctaattt tttttttttt ttttttagt   79140
agagatgggt ttcaacatgt tagccagggt ggtctcgatc tcctgacttc atgatccgcc   79200
tgcctcggcc tcccaaagtg ctgggattac aggcgtgagc caccatgccc ggctaaccct   79260
tcatttactg tctgcatttc ttccctgatg ccttccagtc catgcacccg attgtagcca   79320
ttcatcctat tatggtttaa ggtgactgtc ttagtcagca tgggttgcca taacaaaata   79380
ccatagcctg ggtggcttca acaacagaat ttacttctca cacttctgga ggttgggaag   79440
tccaagatcc aggactttcg ccttgccctc atgtggtgag ggggtgagga agctcctggg   79500
ggcctcttat atatggatgc taatctcatt catgaggggt ctgccctcat gacccagtca   79560
cctcccaaag gccccacctc ctaataccat caccctggta attaagtttc agtgtataaa   79620
tttgggggac tatagacatt gaaccataa caagcacttt tctaagatca gggagtgagt    79680
aagtagcaga gctaggacct caattccaca tgtcagtcat cttgccttca ctctgctcca   79740
tgatggctgc ctcctagagc attgggagtc tcgatgttct atatgctctc atgtgttgtg   79800
tattggagat agttgaggct ttatgaatac atctggattt ttgacttct agctttgctg    79860
gtaaccagct gtgaccttga ataagttact tcatctctga gcctgtttcc tcttttagaa   79920
acaggagttt aaaatgctgc ttgggttgg gcacggtggc tcatgcctgt aattccagca   79980
ctttgggagg ctgagatggg aggatcactg gagcttggag ttcgagacca gctgggcat    80040
catagtgtga gatcctgtct cctcaagaaa ttaaaaaatt agctgggtga tgtggcgtgt   80100
gcctgtggtc ccatcactc tggaggctga ggtgggagga ttgcttgagc ccaggaggtt    80160
gaggctacaa tgaaatatga ttgcacccca tcctgggtga cgagtgagac cctgtctcaa   80220
aaaagaaaaa aaaatgctg ctttgtaccc ctttcatgtc atggcgtcat ggccaacata    80280
gaatgccctg gttgtttgct gttggagggc atgggcctgg gggctccctg agggctcctt   80340
ccatcttcaa ctcattctct gtgcacctgt taggaagttg tgggccagtc cctaccatgt   80400
```

-continued

```
atcattgtgt gggtaaaagt aaataaaatg tgtacagtgt ctgaactgta catatcaggg  80460
tccaagaaca aaatgagtga catgggttag ctcttttaa taaatggtaa aaccaaatat   80520
tctaattttc agttttgtta tacttccatc acatgttttt gttttttgt tttttgtttt    80580
tgttttcta ttttaggcag ccttgccttc tctaacaaac cccccttctc taagtcccat    80640
ccgacgaaag gggaaggaga aagaaccagg agaacagtca tctgtaccgt tgagtcccaa   80700
gaaaggcagt gaggccagtg caggtaggaa acagcgtggg gaagggaggg acatgagtgc   80760
agcatctgtc atgtagaaac ataggattta agtaacttgg tgttttagag aaataaaatat  80820
aatacacatc agtaaagtga gagaaagttt ctccaggtgc ggttcaagat attagaaact   80880
aatgactgat gtacacagac caccttttgg tctgaagcat ttctaagtgc cactggctga   80940
catgcagccc ctacagcctc caggcttcca gccctagcat ggagcatcac tctcctatgc   81000
ttccctggtt gcaggtgatg gctggagagg cctcctgatt ttcagtaagg gaagtggtgt   81060
agatgcttag gaatagatgt agtgagtgaa aaaactgatt ctgatatgtc aaaaattctg   81120
attggaaatg gaatatttac atttggaaga gctaaaggcg agagaaagtg gggataaagt   81180
catctgagtt ggaggagctt aaaccattca caagtttgga gacctttttt ttacccatga   81240
aaaggtcaga acagaagggg ctaggattta ggtgtgactg cagttattg aattcccatc    81300
catactgctc tcggtgggca gtggcagggg caggagagga gcctggcaaa gcatgaagtg   81360
actgctgctg cctctgctat ctgggacgcc tggccacctg tctgtacagt ctccctccag   81420
acccattctc acgctgtctc ttggcaccca ggggccagtg atggttctcc catttgtttt   81480
gtgtatatag catttatatc aaggctattt atttatttat ttattttatt tatttatttt    81540
tttgagacag agtctcactc tgtcacccag gctggagtgc agtggtgcaa tctcggctca   81600
gtgcaagctc tgcctcctgg gttcaagcaa ttctcctgcc tcagcctcct gagtagctgg   81660
gactacaggt gtgcaccacc acacctggct aattttttatt atttttatt agtggagacg   81720
gggtttcacc ttgttggcca ggatggtctt gatctcctga cctcgtgatc cgtccacctc   81780
agcctctcaa agtgctggga ttacaggcat gagtcactgt acccggccta tttatttatt    81840
tttaattgac aaaattgtat atatctgtaa tatacaacat gatgtttgaa atatgtgtac   81900
attggccagg cgtggtggct cacaccttt atcccagcac tttgggaggc tgaggtgggc    81960
ggattacgag gtcgggggtt taaggccaaa ctgccagca tggtgaagag gtgcccctac    82020
taaaaatacc ccaaaaaaaa aaaaaaaaa aaaagccgg gcatggtggc tcgcgccagt     82080
cgtcccagct acttgggagg ctgaggcagg agaattgctt gaatctggca ggtggaggtt   82140
gcagtgagct gagttcatgc cactgcactc tagcctggcg atagagcga gactccgtct    82200
caaaaaaaaa aaaaaagaa gaaatacata tgcattgtgg aatggctaat taacctgtgc    82260
atcacctcac gtatcattgt tttgtggtga gaacacttaa aatctactct ttcagtgatt    82320
ttcttgcata tggtacattg ctattaactg cagtcaccat gctatacagt agatctcttg    82380
aactcattcc tcctgtctat aaatgaaatt ttgtatcctt gaccaacaca ttcaaggttt    82440
tttttgagat ggagtcttct tcacccaggc tggagtacca tggcacgatc tcatctcact   82500
gcaacctccg cctcccaggt tcaagcaatt ctcctgcctc agcctcctga gtagctggga   82560
ttacaggcac atgctactgc acctggctaa ttttgtatt tttagtagaa gtggagtttc     82620
accatgttgg ccaggctggt ctcgaactcc tgacctcaag tgatccgcct gccttggcct    82680
gccaaagtgc tgggattaca ggtgtgagcc actgcacccg gcctcaagcg ttttaaaaga   82740
tgctctttc taaggattga ctgtagtaca ggaggaagat tgacctgttg aaaagcctca    82800
gcctttacaa gtgtaaaatt atcagtatat tactatcatc tttctgatga attaaataaa    82860
ctaaggactc caagtcaaaa gtcttcaaac tgaagtagaa tagttgtata tagtgcttgg    82920
cactttaata tttagtatcg gttttaatgat aatgtttgtg ccttttgccgt cttaaaaca   82980
ttttttacatc atccctgttt gattacttgg tgtgctcatg aagttgttgg ccactaagga    83040
atcttaggct cagagaggtt ctggaattgg ccagtggtcc ttgaatcagc tgctcctatg    83100
attctctaac tgatttctca caaagcaaac aagcaatcat aacaaaacaa ctgtgcacac    83160
tgctcttctt attttgttat ttaaaaagta cttaggctct acttatgttt gttagtcaat    83220
ttctcattac ttctagttaa tcaaaaggtc agaggaaata cttgaatatt ttcatactag    83280
aatactttaa aaaatcatga tttccagtaa tctctttaaa acttggcaag ttattttgat    83340
ctaaagtttt atcttttgtg tgcatatttt taaagcttct agacaatctg atacctcagg    83400
tcctgttaca acaagtaaat cctcatcact ggggagtttc tatcatcttc cttcatacct    83460
caaactgcat gatgtcctga aagctacaca cgctaactac aaggtatggg cctctgcatc    83520
tttttaaaaat atatatgcac acatacttac gtctaatgga tagttgatgt ttttcttatg    83580
atttgtagga tgtataagcc ctttgagata tgagttacat ttagttttt caagtttgtt     83640
tgtctttcag cttttgtttat gatagcttct atcatacagg tgttttggat tttcatattg    83700
tttgtactca cagctaagat tgattacagt gacagagcta ggatgtgcag ccaggttata    83760
ggggaagtg gccctggtgg agtctggagg gatccgtgta caggcttcct tccctcccgt      83820
gaggctcaca caaaaataca gcaacatgct ggtcctgcag gtaccctctg cctaacatga    83880
gccacaattc cagactcaca gaagaaaagc aggtgttcaa cataaaccat gtgtttcaaa    83940
tagtctgggc atggtgagcc acttgttatc agctagggaa agtttatgtc agcgtaagaa    84000
actgttcacc agatacccc aagagccagc ctttctgtct agggatgttt tagttttta      84060
gttcattttt ttttttaact ttaaaatttt ctgttcatct gcaatttgtt agatatgaag    84120
tatgtgtcta atttaatttt tgttttggt tgtcccaat aatgtttaca gaagaattt         84180
tctgcactaa ttggcttgag ttacttacat tctcatagtt ctctagtttc agtagtttca   84240
tttattattt tgttatatca atctatctgt ctgctcatct attagaagca tccttgtttt   84300
tttttttct ttttagaca gagtcttgct ctgtccccag gttggagtgc agtggtgcaa   84360
ccatgcctcc ctgcagtctc agggctcaag tgatcctccc acctcagctc tgagtacct    84420
gggactaccg gcatgtgcca ccacacccag ctaattttta catttttttgt agagacaggg  84480
tctcccta ag ttgcctgggc tggtctcaag ctcctggctt aagtaatcct ccctccttgg    84540
cctcccaaag tgctgggatt acaggtgtga gcaactgcac ccggctacaa gtatacttct    84600
taattattgt agcttaatgg tatttatgag gggatcagtt ccctgttgt tctttagaat     84660
tttctgata ttcttcttta ttgatttgg gatgtgaaca atagaatcaa cttctacttg     84720
tagattgatt tagggagaac ttatacctca gatgttaagt caccctgtcc agaatgtggg    84780
atgcttttcc atttgttcag aacttttaa attacctcag aagcacatga aattaaagg      84840
atttttaaaaa aaacttaaag attatttcac atagctcttg cacatttctt gataaatgaa    84900
tcctcaggta ttcctctgtt tttgttacta atagttactt cttatgggtt ttttttcccc     84960
tgaaaatcat ttatcaaacg tatgtggctt attttctgaa ggatgtttga aattttgga    85020
agatatgaaa gtcttcatat tttacaaggt ttgaggtctc tttaagctgc atggttctca   85080
tgtcagctcc caaagcagaa gacggcatgt tgaaaaatgc cgtagagaag atacttcttt   85140
```

```
tccacctgtt ttcaactcat atcatcttga atttcagggc acctttccat gctcctagtg   85200
cttgctatct gtttattatt ttccttcctg aatacccctga actccagcat gttctgctgt   85260
aattctggcc tccctggcat cttggactcc tgtttccttt gctctgtcat ccccgcggtc   85320
agctcctgct gcgcagcttc tcagctgaag tgcgtttgga gtgcctggcg tgtcttgctg   85380
gatctttgag tattgcctct ggtttccttg gttccttctg ctgagttgct cagcgtctcc   85440
actccccatt tcttgtgtgg cccttcctgc actcctctga ttccttttgt cttccctggt   85500
ttcttgcttt ggtttcgagt ctccacagaa cttttgcagc tcttctgaag acctggaagc   85560
tttttcatct taattctcat ctcatgacct cttttccctt ctttgagagc tagaacttcc   85620
catggtgaac ttctctttcc agaattccat gccttctttt ccctcccact tacctgttgt   85680
ccaggagagg tcagattgct gtgcatattg gaggagaacc cttcttccc tgggctcttc   85740
atctcacatg acatcaccac atcacctcgt tccttggacc ctcagtggtg tcactgctgg   85800
attttcttt cctttggctg gccttagggc acacccaggt tgactagcgt agtcatggta   85860
tttagatcca ctcacatttt cagttctgt gtctgtctct tgcctgcttc tgacttcgcc   85920
cagagaaagc ttctcttca caagggttct tagatttatg ttcactgagc accttctttt   85980
ctgaggcagt gttttaccaa tatttatttt cctagtcagt ctcgccttac ctttcttgtt   86040
atgcatgtct ttggtcctga cccattctct gagtctgtaa aatagaattg ctgtataatt   86100
taattacatg aaatccttta gaatcttaac acatcttaca cctgatttaa tattttattg   86160
tatccaaatt gaaccaaccc tatgtgaatt tgacagtgat ttctcccagg gatcctagtg   86220
tataaggaat aggacttagt attttctatt ttttgatata ccacatacca gatactgatt   86280
atgatggaca tttaacccctt ttttctcatt atgaaagaaa gttaggaatt attctcttcca   86340
gtagcgccaa tgtaacctga aagcctttga aagagtagtt tttgtatagc tatctgaaag   86400
gaatttcttt ccaaaaatatt tttccagtgc tgacaacaaa cacgcagaca caccctgcaa   86460
ggtgagtgta cggcgccgca cagtggaggc atctgctgca gccgtcgatg tttgtgtctt   86520
tggttgtaca ttatgagatc gtgacagggc cagtaaccgt gtgttctctc cttcaccttc   86580
ccaaggtcac gctggatctt cagaacagca cggaaaagtt tggagggttt ctccgctcag   86640
ccttggatgt tctttctcag atactagagc tggccacact gcaggacatt gggaaggttt   86700
gtgtcttgtt ttttctcctt gggttgtggc tggcacactt gatgtgcgtc ttctgggctg   86760
agttcatcta ggatggagcc tggttctcca gggtgcctcc gggagactcc tccctgcccc   86820
acgtgcttgc gtcacaggac ccaagtctga ctctgcctta gccatgaagt ttaggggaa   86880
gtttctattt gtattctatt tttgtctgtt atcatgtatt agcttagacc cagtttagtt   86940
tggaaaatca gtgggtttca aaatgtgttt gtagagtcct ttatttcta acttgacctt   87000
ttcaagtgga aaggggcaaa acagacgggg aaggggcgg ggcgggaggt gtgacttgct   87060
ctttttgtgcc tgaggaagta acagagctgg ggttgacagt catattctct gacacagata   87120
gtctctgact tatctcacag aaagtcagcg gcagagcctg agttaaaagt ctcgtagatt   87180
ttctttttct ttttttttggt ggctaatttc agttttattt atatttgttt atttatttat   87240
tatactttaa gttctgggtt acatgtgcag aatgtgcagt tttgttacat aggtatacac   87300
gtgccatgat ggtttgctgc acccatcaac ccatcaccta cattaggtat ttctcctaat   87360
gttatccctc ccccagtccc ctcactcccc atgggcccccg gtgtgtgatg ttctcctccc   87420
tgtgcccatg tgttctcatt gttcaatttc cacttgtgag tgagaacatg cggtgttgg   87480
ttttctgatc ttgtgatagt ttgctgagaa tgatggtttc cagcatcatc catgtgcctg   87540
caaaggacat gaactcatcc ttttttatgg ctgtatagta ttccatggtg tatatgtgcc   87600
acattttctt aatccagtct atcattgatg gacattcggg ttggttccaa gtcttttgcta   87660
ttgtgactag tgccacaata aacatacatg tgcatgtgtc tttatcgtag aatgatttat   87720
aatcctttgg gtatatgccc agtaatggga ttgctgggtc aaatggtatt tctagttcta   87780
gacctttgag gaatcgccag actgtcttcc acaatagttg aactaattta cactcccacc   87840
aacagtgtaa aagtgttcct attttccac aacctctccaa gcatctgttg tttcgtgact   87900
ttttaacgat cgccatccta actggcgtga gatggtatct cattgtgatt ttgatctgca   87960
tttctctaat gaccagtggt gatgagcatt ttttcgtatg tctgttggct gcataaatgt   88020
cttcttttgc gaagtgtctg ttcatatcct ttgtccattt tttgatgggg ttgtttgctt   88080
tttttcgta aatttgttta agttcttgt agattctgga tgttaatctt ttgtcagatg   88140
ggtagattgc aaaaattta tcccattctg taggttgcct gttcactctg atgatagttt   88200
cttttgctat gcagaagctc tttagtttaa ttagatcccg tttgtcaatt ttggcttttg   88260
ttgccattgc ttttggtgtt ttagacatga agtctttgcc tatgcctatg tcctgaatgt   88320
tatgcccag gttttcttct aggattttta tggtcctagg tcttatgttt aagtctttga   88380
tccatcttga gttgatttt gtgtaaggta taaggaaggg gtccagttc agttttctgc   88440
atgtggctag ccagttttcc caacaccatt tattaaatag gaatctttt cccccattgct   88500
tatgtgtgtc aggtttgtca aagatcagat gattgtagat gtgtggtggt atttctgagg   88560
cctctgttct gttccattgg tctatatatc tgttttggta ccagtaccat gcagttttgg   88620
ttactgtagt gttgtagtat agtttgaagt caggtagtgt gatgcctcca gctttgttct   88680
tctagcccag gattgtcttg gctatgcagg ctctttttg gttccatatg aagtttaaaa   88740
tagttttttc caattctgtg aagaaagtca gtgatagctt gatggggga tagcattgaa   88800
tctataaatt actttgggca gcaaggccat tttcacgata ttgattcgtc ctatccatga   88860
acatggaatg tttttctatt tgtttgtgtc ctctcttatt tccttgagca gtggtttgta   88920
gttctccttg aagaggtcct tcacatccct tgtaagttgt cttcctaggt gtttcattcc   88980
cttagtagca tttgtgaatg ggagttcact catgattgtg ctctctgttt gtctgttatt   89040
ggtgtatagg aatgcttgtg atttttgcac attgattttg tatcctgaga ctttgctgaa   89100
gttgctaatc agcttaagga gatttgagc tgaaccaata gggttttcta aatatacaat   89160
catgtcatct gcaaacaggg acagttttac ttcctctctt cctattttgaa taccctttat   89220
tgctttctct tgcctgattg cgctggccag aacttccaat actatgttga ataggagtgg   89280
tgagagaggg catccttgtc ttgtgccggt ttcgaaggg aatgcttcca gttttttgccc   89340
attcagtatg atattagctg tgggtttgtc ataaatagct cttactatgt tgagatacgt   89400
tccatcgata cctagtttat tgagagtttt tagcatgaaa ggctgttgaa ttttgtcaaa   89460
ggcctttct gcatctgttg agataatcat atggttttgt tgttggttc tgtttatgtg   89520
atggattacg tttattgatt tgcgtatgtt gaaccagtgt tgcattccag ggatgaagct   89580
gacttgattg tggtggataa gctttttgat gtgctgctgg attcagtttg ccagtatttt   89640
attgaggatt ttcacatcga tgttcatcag ggatattggc ctaaaattct cttttttgt   89700
tgtgtctctg ccaggctttg gtatcaggat gatgctggcc tcataaaatg agttaggag   89760
gattctctct ttttctattg attggaatag tttcagaagg aatggtacca tctcctcttt   89820
gtacctctgg tagaattcgg ctgtgaatcc atcctggact ttttttggtt agtaggctat   89880
```

```
taactattgc ctcaagttta gaacctgtta tcagtctatt cagagattca gcttttttct   89940
ggtttagtct tgggagggtg tatgtgtcca ggaatttatc catttcttct agattttcta   90000
gtttatttgg gtagagatgt ttatagtatt ctctgatggt agtttgtatt tctgtgggat   90060
cggtggtgat atcccctttta tcgtttttat tgagtctatt tgattcttct ctcttttctt   90120
ctttattagt cttgctagcg gtctacctat tttattgatc ttttcaaaaa accagcacct   90180
ggattcattg atttttttg gagggttttt tttcgtgtct ctatctcctt cagttctgct   90240
ctgatcttag ttattttttg tcttctgcta gcttttgaat ttgtttgctc ttgcttttct   90300
agttctttta attgtgatgt tagggtgtta attttagatc ttttctgctt tctcttgtgg   90360
gcatttagtg ctataaattt ccctctacac actgctttaa atgtgtccca gagattctgg   90420
tatgttgtgt cttcgttctc attggttttcc aagaaaattt ttatttctgc cttcatttcg   90480
ttatttaccc agtagtcatt caagagcagg ttgttcagtt tccatgtagt tgtgtggttt   90540
tgagtgagat tctcaatcct gagttctaat ttgattgcac tgtggtctga cagacagttt   90600
gttgtgattt ctgttctttt acatttgctg aggagtgttt tacttccaac tatgtggtca   90660
gttttagaat aagtgcaatg tggtgctgag aagaatgtat gttctgttga tttggggtgc   90720
agagttctgt agatgtctat taggtccgct tggtccagtg ctgagttcaa gtcctgggata   90780
tccttgttaa ttttctggct cattgatctg cctaatattg acagtggggt gttaaagtct   90840
cccactatta ccgggtggga gtctcttttgt aggtctctaa gaacttgctt catgaatctg   90900
ggtgctcctg tattggggc gtgtatattt aggatagtta gctcttcttg ttgaattgat   90960
cccctttacca ttatgtaatg gccttctttg tctccttttga actttgttga tttaaagtct   91020
gttttatcag agactaggat tgcaatccct gcttttttttt tgctttccat ttgcttgtta   91080
gatcttcctc catcccttta ttttgagcca atgagtgtct ttgcatgtga gatgggtctc   91140
ctgaatacag cacaccaaatg ggtcttgact cttttatccaa tttgccagtc tgtgtctttt   91200
aattggggca tttagcccat ttacatttaa ggttaatatt gctatgtgtg aatttgatct   91260
tgtcattatg atcctagttg gttatttgc ccgttaactg atgcagtttc ttcatagcgt   91320
cagtagtctt tacaatttgg catgttttg cagtggctgg tactggttgt tccttttccat   91380
gtttagtgct tccttcagga gctcttgtaa ggcaggcctg gtggtgacaa aatctctgca   91440
tttgcttgtc tgtaaaggat tttatttctc gttcacttat gaagcttagt ttggctggat   91500
atgaaattct gggttgaaaa tacttttttt aaagaatgtt gaatattggc tcccactctt   91560
ttctggcttg taggatttct gcagagagat ctgctgttag tctgatgggc ttccctttgt   91620
gggtaacccg acctttctct ctggctgccc tttccttcat ttcaatcttg gtggatctga   91680
tgattatgtg tcttggggtt gctcttctcg aggagtatct ttgtggtgtt ctctgtattt   91740
cctgaatttg aatgttggtc tgccttgcta ggttggggaa gttctcctgg ataatatcct   91800
gaagagtgtt ttcaacttg gttctattct ccccatcact ttcaggtaca ccaatcaaac   91860
gtagatttgg tcttttcaca tagtcccata tttctttggag gcttggttca tttcttttca   91920
ctctttttttc tctaatcttg tcttctcgct ttattctcatt aatttgatct tcaatcactg   91980
atatcctttc ttctgcttga ttgaatcggc tgtcgaagct tgtgtatact tcacaaaatt   92040
ctcgttctgt ggtttttagc tccatcaggt catttaagct cttctctaca ctggttattc   92100
tagccattag tctaacattt ttttcaaggt ttttagcttc cttgtgatgg gttagaacat   92160
gctcctttag ctcggagaag tttgttatta ccgaccttct gaagcctact tctgtcaatt   92220
catcaaactc attctccatc cagttttgtt cccttgctgg tgaggagttg tgatcctttg   92280
gaggagaaga ggtgttctgg tttttggaat tttcagcctt tctgctatgg tttctccca   92340
tcattgtggt tttatctacc tttggtcttt gatgttggtg acctacgggat ggggttttgg   92400
tgtgggtgtc cttttttgtg atgttgatgc tattccttc tgtttgttag ttttccttct   92460
aacagacagg ccccctcagct gcaggtctgt tggagtttgc tggaggtcca ctccaggccc   92520
tgtttgcctg ggcatcacca gcagaggctg cagaacagca aatattgctg cctgatcctt   92580
cctctggaaa catcgtccca gagcacgaag gtgtctgcct gtatgaggtg tttgttggcc   92640
cctactggga ggtgtctccc agtcaggcta catgggggtc agggacccac ttgaggcagt   92700
ctgttcatta tcggagcttg aatgccgtac cgggagaacc actgctctct tcagagctgt   92760
caggcacgta tgtttaaatc tggagaagct gtctgctgcc ttttgttcag atgtgccctt   92820
cccccagagg tggaatctag agaggcagta ggccttgctg agctgcagtg ggctctgccc   92880
agttcagct tccctgctgc tttgtttaca ctgtgagcat agaaccacct actctagcct   92940
cagcagtggt ggacacccct cccccagcca agctcctgca tcccaggtcg atttcagagt   93000
gctgcgctag cagtgagcaa ggccccatgg gcgtgggacc cgctgagcca ggcacaggag   93060
agaatctcct ggtctgctgg ttgtgaagac tgtgggaaaa gtgcagtatt tgggcaggag   93120
tgtactgctc cttcaggtac agtcactcat ggcttccttt ggcttggaaa gggaagtccc   93180
ccgaccccctt gtgcttccca ggtgaggcaa caccccgccc tgcttcggct tgccctccgt   93240
gggctgcacc cactgtccag caagtcccag tgagatgaac taggtacctc agttggaaat   93300
gcagaaatca cctgtcttct gtgtcgatct cactgggagc tgtagactgg agctgttcct   93360
attcggccat tttggaagca tcccttgttt tttgaggtgg agtcttgctc tgtcgcccag   93420
gctgacgtgc atcggcacaa tctcggccca ctgcctcctg tgcctcaagcga   93480
ttctcctacc tcagcctccg gagtagctgg gattacaggc acctgccacc atgcctggct   93540
aatttttttgt attttagtg gagatggggt ttcaccacat tggccaggct agtctcgaac   93600
tcctgacctt gtgatccacc cacctcagcc tcctagagtg ctgggatcac aggtgtcagc   93660
caccacgccc agccatattt tcagatctcc ctctcttttgc cctaaaccac tgtgcttaat   93720
aagtagtttt tagtggccag cagtctccat gtataacaca ttttagcaaa atggaaaata   93780
ctatatgttt taaatttgaa cgtgagatta tactgaaata aaaatcatct aactgggatt   93840
ctttaaatag taagatttc tttttgtat gtgggttttt tttaacctt attattgatga   93900
ctgtcatata tagaaatggc tgtttttcag ttacagtcag tgaatgtatc aaatgctgtc   93960
ttatccaaat aataaaagta aattattaat aagtcacaat ttaatgaaga ttgatgttag   94020
ttgatcttta tattcttgaa atcagccata tggttgtgtg tgtatgtata tatttttaaa   94080
ggtacataaa gataataagc tcatctctga aaatttttac atttggcata agaataactg   94140
gataattaag catcttattc tctggcctgt gtctttacag ttaaaggtag atttactcac   94200
ctctccttttt ttgttttctt aagttcatct ttttttgctgt ttcaagacag aggcccattt   94260
tagctttctc gcatatccttt ttgtttgtac tttggaagcc tcacctgctt aattgttgag   94320
ttttttatccg tggtcttta gagggggata tgtagggtag aagctttcac aggttcttgt   94380
ttgcacttgg cccctgactg ttttgaggaa tctccctcac tgactcacag catggcaagg   94440
tttcagatct ctttctgcca cacagcagtt ctgaggcagc tggaaagata tccagatgct   94500
tagattgtca ggcaggcttt gagatataca aactattgag ccttatctgt gaccttgctt   94560
aggtgaaggc atcagagccc ctgcaccaac atgcataggc ctctgcatgt gtgcggggct   94620
```

```
gggtgttgag gtctgagcac aagtgtagct ggagaggtga gcttgatgtg gcgacgggta    94680
tgagcaggtt ttcttcagac ttctgtgagt ttacctagtt ccaggattta aaggcacaga    94740
gactttagaa ttaaaataga atcattttct ttttctaaat agcaacacta ggaataaaaa    94800
ataataattc cacattcttg acaggtaatg ttttttcttg tcttctaatc cttatttatt    94860
ccatactcat ttttatacat aattgaaatg tattatgcat tggattttto ttttgcatta    94920
tattatagac gattttttcat gtaactcctt actgttccat tttatatgtt ttgtctggtt    94980
taagacttta tctgcaaacc gggaaactgt ctctacaaaa agaaaaacaa aaatagttgg    95040
ccgcagtggc atgcgtctgt ggtcccagct actcggggct gaggtgggag gattgcttga    95100
gccttgggag gttgaggctg caaagagcca tgatcatgcc attgcactcc agcatgggtg    95160
acagactta tactgtctgt tttgggtgat ttgataatga tatgccctga tgtagttttt    95220
ttatatcttg tgtttcttgt gcctgggttt attgaggttg ggtctgtggc ttcatagtat    95280
ttttaaagtt tggaaaattt taggccattc tttctttctt tctttctttt tttttttttt    95340
gagacagtgt ctcgctctgt cgcctgcgtt ggagtgcagt gacactatct tggctcactg    95400
caagctctgc ctcctgggtt cacgccattc tcctgcctca gcctcctgag tagctgggac    95460
tacaggcgcc tgccaccacg cctggctaat ttttttgtat tttagtagag acgaggtttc    95520
actgtgttag ccaggatggt ctcaatctcc tgacctcgtg atctgcccgc ctgggcctcc    95580
caaagtgctg ggattacagg cgtgagccac tgcacccagc taggccatta tttcttcaaa    95640
gatttttttt ctgccctgcc tccctccttt tttccctctc ttaaagggc tgtgatttcc    95700
tgaatgattg cttagtgttg tcccatagct tactgatgct cttttcagtg tttgattgtt    95760
ttatgtgttt tctgtttgt atagtttcta ttattgtgtt ttcaagttct ctgatccttt    95820
cttctacagt gtctactctg ttgttaatct gttaatctgt tgttaatcct gtccagcgta    95880
tttttttttt tgtttttgaa acagtctcac tctgttgccc aggctgagt ttagtggtgc    95940
gatatcagct cactgcaacc tccacctccc aggctcaagc aattcttctg cctcagcctc    96000
ccgagtagct gggactatag gcacgtgcca ccacacctgg ctaatttgtg tatttttatt    96060
agagatgggg tttcaccatg ttggccaaac tggccttgaa ctcctgacct caggtgattc    96120
atccgcctcg gctctcccaaa gtgttgggat tataggcatg agccaccgtg tctgccccct    96180
gttcagtgta tatcactaat tttgttttta tctctagaag tttgatttag gtcttttaaa    96240
aatgtctccc tgtgttttctg tttagcttg tgaacacaat tgtaataact gttttaatat    96300
ccttctctgc tagttctaag atcttctaat aacttcccag ttcttggtgt ttctcattgg    96360
ttgattgata ctcctcgttt tgggttgtat tttcctgcct ctttgtatgg ctgccaattt    96420
tttattggat gcccaacctt gtgaatttta ctttgttgga tgctatatat ttttgtgttc    96480
ccatagatct tcttgagctt tgtctgagg ttagttgagt tacatataga tggttttactc    96540
ttttgggtct tgctttataa tttgtcagat gggttggagc agtgcttagt ttaggactaa    96600
tttttttttt ggactaatta ttcctctta ggaataatta ggtaccatgc ttaggaggca    96660
agaccatcct gagtactcta cctaatgaac cagaaagttt ggggtttcca gtccgcctgc    96720
tgagaacagt gactttctag ccctgtgtga gcgctgagct ctgctccttc taatcctttc    96780
caatgcttcc ttccctggcc tcagggagtt ttctcacaca catatctctg ctgagtactc    96840
gagagggacc ttccccagat ctccagagct ctctctgtct tgttttctct tctctggtgc    96900
tctgtcttat gaactgtggc tgtcttggtc tcctagatt ctcagcacct cttcaattca    96960
gagggttgcc tgtccctcct ccttgtgcca cagcctagga actctctcaa agcagcgagt    97020
tggggcagcc atagggctga cttagtctct cgtctcccag ggatcactgt ccttcattgc    97080
tcatgtccag tgtcttgagg actctgggtt ttgtctgttt tgttttttgg tttgctttgg    97140
ttgtctcagg caggagggta aacccagtcc ctcaccctca ttgtgctcag tagtggaagt    97200
ctcactctat tacattagat attagtattt gtagcagagc cctggttccc tggtacttgg    97260
ggagctcttg aaaggccaga aacagcatgc tttctcacct tttccagggc ttcagtttct    97320
ggtgcacatc aagcattcca tacacatttg ttaaagtcct tgttagaca agtagtgatt    97380
cacaggttct atttgtaatt ttttcagtta acatgtattg ggtatctgct gggagctagt    97440
aaaaacaaaa agtggtgtgt gacaaattca attctgacaa gaacaacctt aaacacttag    97500
aatatacttt gagcatatca gaatttttaaa aatgtgtggc ccttgagtat ttgaaaccaa    97560
caagaatcta ttgcttatta gtagaggata ttttgttaaa caagtggaga gagaggcatt    97620
ttcagtctaa ttggtgttgg cttttagcag ctgatggaaa ccagttcgtg attagccagg    97680
cagtggtgaa acaggctgtg cattctgaat gcctaggtat ctaggcattc agaatggtga    97740
cgctctttga gttagcatct tcttcttct tgattctttt tttttttttt ttgagatgga    97800
ctttcgctct tgttgcccag gtaacaactc cagtgcaatg gcgccatctc ggctcactgt    97860
aacctctgcc tccctggttc aagcgattct cctgcctcag cctctcaagt agctgggatt    97920
acaggtgtgc gccaccacgc ctggctaatt ttgtattttt ggtagagatg ggtttcact    97980
atattggtca ggctggtctt gaactcctga cctcaagtga tgcacctgcc tcgatctccc    98040
aaaatgctgg gattacaggc gtgagccacc actcccagcc ccttcttgat tcttgaaaag    98100
gacattgggt gctgtacatc tcgttataga tgttgataaa aatgcttgtg agaagagtaa    98160
cattaaggta gttattttgg cattttttgca gattatttta agacaattgt aggactgatt    98220
tgtggtaaat cacacattgc tgtatcatag ttgtgttcac tgaacatatt caggggctct    98280
acagatgcag ggctcttagc tgctttgcac acttctgaat tcctgccctg cgaacaggac    98340
tggataccta atagacaaca ggtacttgat aacagtttat tgaattaatg agtgaatgaa    98400
cagatacata aatgcatgaa agaatggttg taatgtatat aacttggatt tcaagacttt    98460
ttactgactg ttcaaaataa gaaattgaaa actttcctct gattttccte tactatttac    98520
acaatttaaa tggaagttat cttgtacctt caatttctgt ctaggattcg tacaataacg    98580
ggtcatctct gagtcgctta atgtctcact tgtcttcta cagtgtgttg aagagatcct    98640
aggataccctg aaatcctgct ttagtcgaga accaatgatg gcaactgttt gtgttcaaca    98700
agtaagagct tcattctttt cctcttctgt taagacgttc aggtgatgaca gcaaaacgt    98760
gctactcctt aagaggcagg cgctgttggc ataatcagct gggaggattg tggggtccag    98820
cgcagcactt tttggctcag tccatgattg agccaagagg ccatccttcc cttcactccc    98880
caggaggacg aggtctgtca ctgtggaggg cagaggacac cagaagctcc tctgcaacct    98940
cgctagttaa cttccagtcc ctcggagttt ctgtttagaa tgctcaatct catttagaat    99000
tgcaaggaaa ccacaaaacgc ctatttaagg tacaaacagc acttcatcaa atatctcatg    99060
aggtattaat agtgattcac aggaagaatt tcacgctgtg agtctttgct aacatatcca    99120
gttatttaca gatggatttg atatttgtgt gggagattct taaaagtgtt gttcacgcca    99180
cattgttgat gcctcatttt tttcactgta gttgttgaag actctctttg gcacaaactt    99240
ggcctcccag tttgatggct tatcttccaa ccccagcaag tcacaaggcc gagcacacg    99300
ccttggctcc tccagtgtga ggccaggctt gtaccactac tgcttcatgg cccgtacac    99360
```

```
ccacttcacc caggccctcg ctgacgccag cctgaggaac atggtgcagg cggagcagga   99420
gaacgacacc tcggggtaac agttgtggca agaatgctgt cgttggtgga agcacgaaag   99480
agcaagcagg aaatactttg taaaagaata aaaacgaaaa atgttagcga acatcttcta   99540
atagtctgct gtattcagag aactctagga gatatatatg gttgatgcaa agatgattta   99600
aggcatagcc cggccttcca agaagtgtgt ggccagtgag tgagatgggc ttgggactta   99660
cacatctcag aggtggggt agaggaggag gaacactgag tgggctgaga agcagccagc    99720
tctcattgcc aaagtgtgtc agcaaaccag aatgcagttc ataatgtccc cacccattca   99780
aagcacagga cctgtagagt ggtgtggcat gtgttggtgg cacttttcag gcctgtaaca   99840
aggatgaaag aacagcttca tagcagcaca gtagtgctgg tgttcagagg tgtgtgaagg   99900
ccatagaagc atcttggata tattaccttg tgttttgtca gctttatgac tagaagtctc   99960
ttttcactta aatttgtttt ttttttttt gagacggagt cttgctctgt cgcccaggct   100020
ggagtgcagt ggtgcaatct cagctcactg caagctctgc atcctgggtt catgccattc   100080
tcctgcctca gcctcccgag tagctgggac tacaggcgcc tgccatcacg cctggctaac   100140
tttttttgt attttttagta gagacggggt ttcaccatgt tagccaggat ggtctcgatc   100200
tcctgacctc gtgatctgcc cgtcccggcc tcccaaagtg ctgggattac aggcgtgagc   100260
caccgcgccc ggcctctttt cacttaaatt tatgtttgtg tttttaatgc ctagtataca   100320
ggacttctta aattgcctta agtatgaaca ggtatttgag ttgctaatct gtatagtagc   100380
aataatagaa tcccttgttt ttcctttat aaatttagcg attaaatagc tacaattaaa    100440
acactagagt caggagtcaa ggaaaatacc catgttccag gctgtatgtt agtgatgtac   100500
ttactatata ttggagtttc aggagtaagt ctgtttcaat gcttctgta accatttggg    100560
gtattaataa gcatgtgagt gtgtgcatgt ttgggttaat ttcatatatg tttcttagaa   100620
gggatatcat tgatgtaaat atttaaagg ctttgtcctcc aaaaaaatca tgtaatttct   100680
tctaaattac tgatcttta aatgaccttc acctttctct caaatctcac ttaagactgg    100740
gctgagtagt cagtttcctg tagcagaaaa aagctcagac ttgagtagcc ttctgcgagt   100800
gaggagactt gatggctgtc aggcagctgt aaactctaaa tagagtgtca ttatctgaag   100860
agggcgatgc tgccacactg agtggccttt caagttgttt ctcaatctga cacgttctga   100920
tcgtgtgaat gtgaaattgg tttgagcagg agtatatctg agtgcagagg agattattta   100980
aagatattct cattctctgc ttcccttta ttcccatttg gcagatggtt tgatgtcctc    101040
cagaaagtgt ctacccagtt gaagacaaac ctcacgagtg tcacaaagaa ccgtgcagat   101100
aaggtaaatg gtgccgtttg tggcatgtga actcaggcgt gtcagtgcta gagaggaaac   101160
tggagctgag actttccagg tattttgctt gaagctttta gttgaaggct tacttatgga   101220
ttctttcttt cttttttct ttttttataga atgctattca taatcacatt cgtttgtttg    101280
aacctcttgt tataaaagct ttaaaacagt acacgactac aacatgtgtg cagttacaga   101340
agcaggtttt agatttgctg gcgcaactgg ttcagttacg ggttaattac tgtcttctgg   101400
attcagatca ggtttgtcac ttttatcttt catccatcat acctgttcct aatttagtac   101460
aaattacccct aaaagacact gaaatctact ttaaagaaat gtggtctgca tgtttccctc   101520
atcagttgct gctgcttatc tttttcatgc acctagctgg tgcagaaggc ctggggcata   101580
gccagcctca gcaagtcagc atccttgccc cagctcccctg gactcaaggc taacctgggg   101640
ttggctgtta gggatttcca aaggtttgtc ccatccactt gcctccccctc caaaataagt   101700
ttgaatttaa attgtgagat acaattaaga tttattgttt ggggaacatt tttgcaaaat    101760
ctagagttag tttaaacaga ttatcaatta ttaccataat tgatcatctg cagtttcaag    101820
ctatctaaca ggttcactta cctctcttaaa aaggaatgga atttagcagg acagtaactg   101880
agaccgtgc tcctggagtc catgtgggag ctgtgtggct ctgcacaagc atttgcacgc    101940
ttccctctt gactgcatta ccttcctcct atagttgctg tgggcaccag attctggcta   102000
gtcctgtccc ttcatgatgc acatttcct caagattcgt cccagttaaa tcactgcaga    102060
tgaaactgcc ttttcatcgt caaaatttaa ctgtcatttt tgagccgtga tcttgggcta   102120
ctttcttatg tgggagga atatttgtga gttagaaata ttacacttct ctattttcctt    102180
ctagacgtaa atctgttaat cctgtcagca ctgttactca cctgaaaggg tctgtttccc   102240
taggagaact gagggcactc ggtcaacact gattttccac agtgggtatt ggggtggtat   102300
ctgcttgttt ttttgttgt tgttgttgt tttttttgt ttttttttg agatgggagtc     102360
tcgctctgtc acccaggctg gagtgcaggg gtgcgatctc ggctcactgc cagctccgcc   102420
tcagaggttc acgccattct cctgcctcag cctcccgagt agctgggact acaggcaccc   102480
accactacgc caggctaatt ttttgtattt ttagtagaga cgaggtttca ctgtgttagc   102540
caggatggtc tccatctcct gacctcgtga tctgcccgcc tcggcctccc aaagtgctgg   102600
gatgacaggc gtgagccacc gcgcccggcc tgggtctgc ttttaatgaa ggaggcatca    102660
aggggtgggc tttgcgttgg cctgatgctt tcatctttct ttcacaaaac ctgtccgaag   102720
aaaatccgtc taaatgggcc attgctctcc tcaggaaata gtcattggga acttctttc    102780
ctttcctttg acactaggag gctgactggg gagaagccct ggtctatggc tgtgggcagc   102840
aggggctgag aggagcaggc tctcagggg gcacgggtac cccaagggaa gccagagccc    102900
tgatttgttc cattctagta agaacaaaga ctgctctggt ttcatgtttg ttctgattgc   102960
ctttcatcaa ccgggtcccct ttctcccagt tcttaagatt cagtacagtg acagttttat   103020
gaacaagaat agaacactag aacagacaaa ccattgaact ctatgctgat aaagatttat   103080
tgagctcctg ctgtatgttt gcattctgcc cagaggctct gagaaaacca ggccatatgc   103140
tccatgcttt atccatggaa gctccccgtc aggttgggaa agctgacagc tgcaggggaat   103200
acagtgtgac acaaaactgg ctcccatgca gcccttacgt gtcgcctctc agatggttgg   103260
gggacgaagg tcgactcctt tgggtatctt attactaaac cagtttcagg gaatctgtgc   103320
caccctatct gccattaacg tgaacagatg agtcccaag gtgtaatttt gggtattgtc    103380
tgatgtctct tggaattta tatttgtttt tccaatgaga tttcacctca gggtatagta   103440
aagttgttga ggggattcct ggatgtgttc tgcaattatc taggctgatt tcagaataga   103500
gttatgctta tagtcaaatt tatcagctgt caagaatttt atttaaaatt tatgcagata   103560
agcaggagga aaagaagcct ggttttaca tttaatcct attattgatg tgaaattta     103620
ttttccttcc tgtaggtgtt tattggctt gtattgaaac agtttgaata cattgaagtg   103680
ggccagttca ggtaatagca ttttattatt ttagatttttt ttcttcttct tgtgtactta  103740
catgtaattt aggttattaa gtgaatgttt aaactactgt taggcattt tgctgtttca    103800
tttaaatgga aatctgacta acatactgtg catttttgct tctcttaaaa attaatgtat   103860
atctcaagac ttgttttggaa gtagttatgt atctgaaaat tccatatgtt gtcagtattc   103920
attgcacatt tcaaagcatt taattgtgtt gacagatggt ggaatgaaat cttggtggg    103980
agcactagtg ttttaaatctt cttagagaaa gcagtttat ataatgttgt ctttagtaat    104040
tattatgcat ttgtattctc tgcagctttt tcttgctaga tgttgaggtt ttaatacttc   104100
```

```
ttgctagtcc attacaggtt tataattatt aaaagttaaa attcttttag tacctaaaat    104160
gcttaataaa cattgtaatt aggaaaattt agtgcagaag gaaagtgttc ccagattccc    104220
tggggtctgg aaacatagtg tttattctaa ttacatgaca cctccactgt gttttggggc    104280
aagttactgt ttctcttttg agtttcaatt tcttcaagag caaagaggca gaggagagct    104340
aggaagatcg tagctgctgt gccctgtgc cgtcgggtgc cttctacctg ctgcctccga    104400
acctttacac atgtccctgc tctgcgcgag ggcacagatg ggatgcactg tggcaggggt    104460
ggggttagag tagatcacgg acacctgtta gcttgatgtg tgcttgctgt caaggttgaa    104520
tcatgaatta ttttatgttg cttatattga tatgtatctt aattttaaaa gaaaggtcta    104580
aatggatgtt tttgttttta gggaatcaga ggcaatcatt ccaaacatct ttttcttctt    104640
ggtattacta tcttatgaac gctatcattc aaaacagatc attggaattc ctaaaatcat    104700
tcagctctgt gatggcatca tggccagtgg aaggaaggct gtgacacatg gtaacgggac    104760
acacctttca ctgtcgtctt cggtgtcgtg atgtgcttgg cagtgttcgt tttcatatac    104820
ccactttgaa cgttgtcagt ggcagccatg tgcttctcag gctctgcatg tgtgtctgtg    104880
tatgtgaagg tactggttag agacgtttca aaagagaaga gagcatattc tttactctca    104940
gcaatttgta atcttctcag ggaaaaaaat tcaagaaaca gtaagataac ctaaggtaca    105000
gatagattct gaatataaag ttcctgttca ttcacatgaa acgctaaaag ttcttcactt    105060
gatcttagcc aaaaggccaa gaagcgatgc aacactaaaa attcttaaat cgaacttgcc    105120
gtgaattaaa ttttgatctc tcatccagtg gtattggaga tatagtttga cttgggttca    105180
gggctttctg ttttgcctga tgattttgct ggagcttaaa taaggaaccc aggagatggc    105240
cagctgtgca agcccccagc ctgtggaagg agctagtgtg gttttatgaa tgagttgcaa    105300
atctttcttt gagcttttg aactgatctt ccagcattgc cctattgacc cctccctgac    105360
tcctttgctg gaatctgtag gcttttgaac tttgacaggg acacatccta agacccttgc    105420
aaactcccag atgtgagaat ggcactacta cttagagtct tttcgactca gcgtgtgtgc    105480
agaagagcat caaccgggct gtgttgcgag gcagggcctt ggctgacctc tcagtgttta    105540
catagctaag ccagttagtg tttgccacgg cctcacaagg gcttcagatt cacacagcca    105600
aagtatagat tattaaaggc ataggtgttt ggtttcctgg acttggaggg tctttggaca    105660
gaaaatcagt aggcaaccac acccagtact ttgtgctggg aagcttggtc atctgtgaga    105720
gggtcagaga gtatacccat gcgtgcatgc caccgaaggg tcagtgagta ttcctgtgtg    105780
tgcatgtctc agggccggag agagtatgtg tcactgagag gtcagagtgt ttgtgtgtgt    105840
gtcaaagagg gttgcattgt gcccttcact gaggggtcag aggggtcctc gcgtgtgtgt    105900
gtgtgtacgt gtgtgtgtgt cactgagggg tcagagtgtg cctgtgtgtg tgcttgtgtg    105960
tgcgtacatg tcactgaggg gtcagagtgt gcctctgtgt gtgtgctcat gtgtgtgcat    106020
acgtgtcact gaggggtcag agtgtgcctc tgtgtgtgct catttgtgag cgtatgtgtc    106080
actgaggggg tcagagtgtg cctctgtgtg tgtgctcatg tgtgagcgta tgtgtcactg    106140
aggggtgcag agtgtgcctc tgtgtgtgtg ctcatgtgtg agcgtatgtg tcactgaggg    106200
gtcagtgttc ctatgctctc atgacattga gggtcagagt gtgcctgtgt gccaatgaaa    106260
ggcatttctt atatttttt atatgtggtc atagtagacc agttaattta ttttgactcc    106320
tgtgttagac caaaataaga cttgggggaa agtcccttat ctatctaatg acagagtgag    106380
tttacttaaa aaagcataat aatccagtgg cttttgactaa atgtattatg tggaagtctt    106440
tattgtcttt tcagatgaat caagtagatt attcttgaga ccaggaatgt tgctgttttg    106500
gttatttgga aagttttatc attttcaaat tgacttttga atttgagtca ccttttttca    106560
gaagtggtgt taaattatag gagccctagg tttttttttct tttttttagaa gtcatcacaa    106620
aatgatcagt gttcagagga agagctttga ccttccacat ggtataatga ttgataacct    106680
taattcatct cttaccataa accaagtatg tgtaagggtt ttcttatttt cttgaaagca    106740
ttttgtagat gttgagagca gttttccaaa tgtaatttcc atgaaatgcc tgataagggt    106800
accctttgt ccccacagcc ataccggctc tgcagcccat agtccacgac ctctttgtat    106860
taagaggaac aaataaagct gatgcaggaa aagagcttga aacccaaaaa gaggtggtgg    106920
tgtcaatgtt actgagactc atccagtacc atcaggtaag aggaatgtat gttggaactg    106980
tcgtggatac tttattgacc cgtgcagatg gaaggaagtg ccatgtggta acgctcactg    107040
ttaactgtgt tactttgaac caggtttggg ctttctgggg cctgggtaga tgccggtgca    107100
gggggatggg gaggggaggcg ggggggtgggg gggtgtgggg gagttggtgga gagtgcagtgg  107160
caggaggtgt tgttggtgtg tatccttttt tttttttga gatggagtct ctctccgtcg    107220
cccaggctgg agtgtggtgg cacgatcttg gctcattgca agctccacct cccgggttta    107280
agcaattctc ctgcctccac ctcccgagta gctgggatta caggcatgca ccaccatgcc    107340
cagcaaattt tttttttttgt attttttagta gagatggggt ttcaccatga tggccaagct    107400
gtttcgaact cctgacctca agtgatcctc ctgccttggc ctcccaaagt gctaggatta    107460
caggcgtgag ccaccatgcc cagcctggtg tttatcttta aagtgggcac agccacagga    107520
gttcacctga ctcctggtct gagagtcacg agatcgttca agatagtgag gccctctttt    107580
ccaaaacgag gaccaaaaat caattgacag tgttggtcaa gatggtagaa acctaaaat    107640
gatagaaatc tcaactctga aataaaaact ttatttgtat atttatttac cactatttttg   107700
acatagggct aaggtctttt tctttgagct gatttctggt tttgttttct taaagtggca    107760
taagaattca aagacatttt gaggaaggct gagtgcagaa atctctcttt ttaaatgact    107820
tctccttct tttaacttgc actgttgtct agccctcact tattttgtca attcttttta    107880
gctgtttgtc tttgaatctt cataaagcca tagctttttct cataagaagc agcactttct    107940
ttgttcattc atatttttaat gaacccctgt agtatttaat taaatactta atgcctaattt   108000
aaatcacata attgcaatgc aaaagtacat gtatcataaa gaggtctgaa aatgagcaac    108060
tggcaagcag gtggtggcag gcagagctgc ttgggtgggt gggtgtcatg gagaggagtt    108120
catcagccac atgttcagtg agctctggat atgtctgttt agaaatgatc actaatarac    108180
ttgtgctcaa ccatgtatac ctctgggaag caggtgctct tcagtagatt gcctctgcag    108240
agaacacaga attgaagtga atgtccacaa aggcaatgag ccacctgcag aatagtttag    108300
tcaaggctgt gtttgaagtt tgccaaagat taatatacat ttgattttca tgttgtgcct    108360
tttctctgat tgtgaaatat tacaaattct atacaaataa caatgatggc aaatcctcct    108420
gagcaaagtg tgcaccttgt atgtgcccta gaggaacttg tgtttcgttc tgattcccct    108480
acatttctca tgtcatagag tgggggttgc attagtgctc cctcgtcctc gctgggata    108540
catctgtttg gatcctagag tcttccagct gaactgggac aagtataaca gacggacacg    108600
tagggtggga aaggcgtctc ttggcagcag actttctaat tgtgcacgct cttataggtg    108660
ttggagatgt tcattcttgt cctgcagcag tgccacaagg agaatgaaga caagtggaag    108720
cgactgtctc gacagatagc tgacatcatc ctcccaatgt tagccaaaca gcaggtttgt    108780
ccccgcagcc ttggcttgtt gttgcatagt gatggtagct taaggtcctt gtgaaaggtg    108840
```

```
ggtggctgga atcagctctt ccttcagtcc taatctgtgc cttgatagca gttctccgtg   108900
ctagtcatgg gacagctgac ttcatttctt ctcacaatgc catctcaggt tggtattgcc   108960
cacctacttt acagggggga tcccacagct ccgagaggtt atggaggtga tcaggcagca   109020
cacagcttta gagtgctggg gtgagggcgg gccaaggcta actctaaagc ccgaaccctt   109080
acctcctaca ctgcctcctg cattctggtc aacccagtgt tttatttggt ggttagattt   109140
ttgtttttgt taccttactg cttgtaattt agcagttttc cttccttttc ccttccttc   109200
ctttccgaca gggtctcact ctgtcaccca ggctagagtg cagtcgtgta atctcactgc   109260
aacaacctct gcctcccagg ttcaaccaat tctcccacct cagcctcctg agtagcaagg   109320
accacaggtg tgcaccacta cgcctggcta gttttttgta ttttagtag agatgaggtc   109380
tcgctgtgtt gcccaggctg gttttaaact cctgggcgca agtgatccac caaccttggc   109440
ctgccaaagt gctggcatta caggtgtgag ccacctcgcc tggcctattc atcactaatc   109500
agaatttcta tgatcaaatg acatgaatca ttgtttccac aactgcagtg gaaggaaatg   109560
gcctggcagt gccagtttca gaagcagcct gcccccagtc aggcacaggc cactgtgccc   109620
ccagtgtagc agcacctctg tagctcacag agaagggtgg tggggacctc cttgaggcag   109680
ctctgccaga aaatctcatg agctgcctgg cacagcttga ggttgccttt taagtggact   109740
cagcaaatac atgtttgttc atcttgatta tacacaataa caactactc tgtatagtac   109800
gagtagtccg tggttttttgg catttgattt aaacttagag gcatgtgata ttgatgttac   109860
tgccttcatg actgcacccc cattctgatt tcataatgaa atgttatctt gagaccagtt   109920
agacaacagg acaggatct tggcttctgg tgagattgac agcagttta gtgtggtcag   109980
ggtctccctg cctacagatg gttttagaat ggtgccctgg aagctttatc ccattctttt   110040
ctgtgcgtaa tctgagtaga gtggagatcg aaggcctgaa tacatagtaa atacctgact   110100
taatatctgc cgcaatggaa attgtgtgat acaacattta tgaaacgctt agtgcagcac   110160
ctgccaggta gctcaccaca ggtgcatgtt gcattcagaa gtagtgctag atactatcct   110220
gttactggca gtgcatacat cagtgatcaa agcagattaa agaaagaccc cctgccttct   110280
tggagtgaag attttgttgg gatgcgggta agggacaga caatagaaaa gcaagtgagt   110340
gaagtctata ccatggcggc tgatcaggaa caccgtacag agaaatccag gaggggaagag   110400
agttaggtgg tgtctgcggt gggagtggca ttgttcagct ggtgatgaga agaagctttg   110460
gtgatctggt gacatttgag tgaatttgca gaaaggaaag atacaagcct aggagatacc   110520
tggggaagga acattccagg cagagcaaat agcagtgcaa aggccctggc gggggcgga   110580
catgctgtta gggtacaagc aatgagggtg gaggagtggg gcagccatgg ggagggaagg   110640
gagtgaggcc tggtgggtg aggccagtgt ggaggagcct tgagagggtt tgcgctgatg   110700
tggtgtaggt tttagcagga tcattcttat tcctgagttg agaatagcct tgaggggag   110760
gtgagggcag agcagggcca cccatgtgag acccggcact ggagtggaat ggcccaagtc   110820
agcatccctt ggcagcatga aagcaaaacc agcaaggttt gctggtggct tagatgtggc   110880
atgtgagaga gagcagggct ttgggggtga tttcagggtg aggacaggt ggctgtggac   110940
aaggtagggc agacattggg ggcagcagga ggtcagagcc tgtctggatg tagcagttga   111000
gacccccatag gtgcctaatg aggtgaggcc agcatcaggt gtatgagcct ggagttgtcg   111060
agagactgtg gggcaggggg tcagcatctg agatgtccac tcacagtgga cccagactgg   111120
ctggagagga ggaggagctt gaataccgag cctgctgagt cccagctcca aggtcaggta   111180
ggtgagggga gccagtgctg gggcagggg agtaggcagg tgtgggggttc ctaaagccaa   111240
gatttttttt aaggcatttt gtgcaggagg gcgacatctg ctgtcagcac cttgggaact   111300
tggcccaggt ttggcagcac cgagggcact gatgagtgct tttggaggag caaagggagc   111360
caaaccctaa tgggaatgtg ttcctgaaag gacaggagag agacttggga aaaggtttta   111420
cttgaagagg gaacgagaa atagggcagt agccagagga ggagaggagt cggcaatggg   111480
ttaagttggc agaaatgaag gcctgtttac gcactgaggg cagaagcaac agggaggatc   111540
agttcatgac acaggagaca caaatcgccg ttgtggtgtt cacagacatg ggttaggatt   111600
ggctgcatgg atgacagagc actgtgggtt ctcccagagt tgctggggag gaggcagagt   111660
tggtgagcac aggcgagggt ccaggatgca ggaatcctgg agctcaagtc agttgttccc   111720
ttgttgtaag atgtggccag tgttgtgagc ttcacatctg tgccttgaaa acaccacat   111780
ctgtttgcag agttgtttac tatgtataca cactcagtag aaacaaaaat tggaaacagt   111840
cagtgcccac catcaataag taatggttga acacactgtg gtataagctt agactatttt   111900
agcttgggct attttgcatg attaaaaatg ttctggccag gtgtggtggc tcatgcctgt   111960
aatcccagca ctttgggagg ccaaggcagg cagattgctt gagctcagga gtttgagacc   112020
agcctgggca acatggtgaa accctgtctc tactagaaat acaaaaagta gctgggtgtg   112080
gtggtgtgcg cctgtagtcc tggctaactc aggaggctga ggtgggagga tcacttgagc   112140
ccattcgtgc gccactgcac tcctgggca cagagtgaga ctctgttaga aagagagaga   112200
gagaaagaag agaggggag ggaggaagga aggaagaaa taaatggaag aaatggaagg   112260
gaggaaggg agggaggaag gaagaagga agttcagcca gttgccttgg gagttctcca   112320
ttgcactggg ttaagtgaga agagcagaga cgtttatgat ttttcaaaac aactaaaaca   112380
aaacctctgt gggtgagggg gcaaggatat ggctatagga acatgggca gattaagaaa   112440
gggatataca cacaccactt agcatttgtt acaactgttg tgggagggat ggagtgcaga   112500
aaaagaaaaa aaaagtgca caccatccca tgtatgtgta tacaaaggga cgcttggaag   112560
actggtcccc aaaatgttgg taatgattgt gtcagggtgc tgcagtgcta gttgattttt   112620
tttcacactt ttgtatattt gagtcttta cagaaagcat ttattattta tgtaataaa   112680
atctaaatga caagatttct gttatggaa aaatgtagct atacagtgtt gttgtaaaaa   112740
tgtttgcttg gttcaccact gaacttaaaa tgctttaaa tgagggaagg tgacgatgag   112800
atgattatga tgatttgccc ttgagttaca tagctggtgt acaggaagct gtcgtttctt   112860
ttggcttacg tagaaatgtt tgtggtgtct aattccacag atgcacattg actctcatga   112920
agccctgga gtgttaaata cattatttga gattttgaa ccttcctccc tccgtccgt   112980
agacatgctt ttacggagta tgttcgtcac tccaaacaca atggtgagtc tctcgcctgg   113040
ctcagcagat gaatctggac ggcttgttca ggctctgatt actgggacca ccccagaat   113100
gtctgagtca gtcagtttgg gtagggcttc ttgagagttt gcttttttt tttttttt   113160
ttttggtgtg gggtggtgc ggaacagagt ctcactctgt cgcccaggct ggagtacagt   113220
gtcatgatct cggctcactg caagctctgc cttccagctt cacaccattc tcctgcctca   113280
gcctcccgag ttgctgggac tacaagcgcc caccaccacg cccggctaat tttttttgtat   113340
ttttagtaga gatgggggttt caccgtgtta gccaggatgg tcttgatctc ctgacctcgt   113400
gacccgccca tctcagcctc ccaaagtgct gggattacag gcgtgagcca ccgcacccgg   113460
ccttttattt tttttggag atggagcctt gctctgtcac ccaggctgga gtacagtggc   113520
gctacctcga ctcactgcaa cctccgcctc ccgggttcaa gcaattttcc tgcctcagcc   113580
```

```
tcccgagtag ctgggactac aggtgcgtgc cactgtgccc ggctaatttt ttgtattttt   113640
agtagagacg gggtttcact gtgttagcca ggatggtcgc gatctcctga ccttgtgatc   113700
cgcccgcctc ggcctcccaa agtgttggga ttacaggtgg ctctcgcacc aagccaagag   113760
tttgcattt  tagcaaattc ccaggtgaaa ctaatgcctg cttttctggg agcacacttt   113820
gggactcagt gatagagagg tttattggta ggatagtaaa ataggagtta ttttctttca   113880
caaaattggc aattggggga aatttaatct tcctttttc  ttcagctgtg acttatgtat   113940
tatgtttatt ttaggcgtcc gtgagcactg ttcaactgtg gatatcggga attctggcca   114000
ttttgagggt tctgatttcc cagtcaactg aagatattgt tctttctcgt attcaggagc   114060
tctccttctc tccgtattta atctcctgta cagtaattaa taggttaaga gatggggaca   114120
gtacttcaac gctagaagaa cacagtgaag ggaaacaaat aaggaatttg ccagaagaaa   114180
cattttcaag gtatgctttc tatctgagcc tataactaac ccatgccttt tgggaagtca   114240
cgtgatgttt cacagtcagt aagtctgaaa taatacctgg tcttgcttca cttctgagtt   114300
gggtaaagaa gtctgtatca gtgtaatttt ctaatccgtc ctgcattatc tatggctctt   114360
ggttcatacc tgtcttgaag ttctgtcatg ttctgtctct tgtcctcagt agagatgcta   114420
cagcagtggc tcgcctcagg cagggcaggg cagtggggtg gctgtcctgg gggcaggcag   114480
taggggcacg ctgacgtcag ggaagttgaa acccaagaga agccagtaaa agtgagtctc   114540
agattgtcac catgtgctgg cagttttaca cgctgtcagt aataaaagtc ttctccctgc   114600
agggcagcct gcctccaata aatacgtgta gtatcaaatc ctgtcttccc tcataaattg   114660
tttggaagct ccccaaggac agtgatgagg cactcgtaag tgcttgctgc ctagatgggg   114720
ccctctccac ctttgctaga ttctgagcat tcactgagtt agagctgctt ctgcaaatgt   114780
gctgcttctg ctaagtggct gtgacttcat gcagccttca cttggtttgt catcagtgga   114840
gatgccctgt gttgtcgaag gagataagcc cagtaagcct gctgggcacc ttttggtttg   114900
caggttcagc aggcagccca tggctttccc tgtgtcgcat tgaagcagcc ggctaaaatt   114960
gatgatacat taaattcctg tgacagatga tcagcttgta tttgtgtaat ggtgtacagt   115020
tcacaaagct taaaaaatg  ctacctgcca tttcatcctc agtgaggaag gtgatacaca   115080
gagagaccaa gtgactgtgt ccacggcgac ggcgctctgc atttcacttt agccggttaat   115140
gtactctacc tatatttta  ctttatattt accatatatc ttttcatgta tacttggcgt   115200
aagtgcttta tagtagtcac ctaattcact gtcatctttt ttgtttcttg gaaggtttct   115260
attacaactg gttggtattc ttttagaaga cattgttaca aaacagctga aggtggaaat   115320
gagtgagcag caacatactt tctattgcca ggaactaggc acactgctaa tgtgtctgat   115380
ccacatcttc aagtctggta ggtgaatcac attagtcttc ctggagtgtc tcgttcccca   115440
ttctgcacta tacactctca gagtgtagga gctgtgctgc ccggtagaaa ctctgccttg   115500
cccagtgtgc cagttgaaaa tatttgttgc tgtaagagta cacctgatac catgtgaccc   115560
agcagttcca ctcttggga  tatacccaaa agaatgaaaa gcagggtggt gaaaagatat   115620
ttgcatgcca gcattcatag cagcattatt cacgatagct aaaatgtgga accaactgaa   115680
gtgtccctcg atggatgaat ggataagcaa aatctggtgt atatttacag tggaatatta   115740
ttcagcctta aaaaaaggac attctgacac atgctacaac atgggtgacc cttaaggaca   115800
ttatgctaaa tgaaataagc cagtcacaaa aggacaaata ctatgtgatt ccacttacat   115860
gagggacctg gagtagttaa ttcatagata tagaaagtag aatggtggtt gccaggggct   115920
gcaggggagg ggagttattt ttacaagatg aagagagtta ttctagaaat gaatggtggt   115980
gatggttgta taacattatg aatgtactta atgctactga actgtacagt taaaaatagt   116040
taagaggacc aggtgtcatg gctcatgcct gaaatccaag cactttgaga ggccaaggca   116100
ggaggattgc ttgagccaag gagtttgaga ccagcctcag caacatggta ggaccccatc   116160
tgtacaaaca aactagccgg ggatagtggt gtgcatgtgg tcccagctac tcaggagact   116220
gaggctggag gatcgcttga gcccaggagg ttaagtctct agtgagatgt gttcatgcca   116280
ctgcactcca gcctcggcta tagagtaaga ccctgcctca aaaaaacaaa acaaacaag   116340
acaagagcca aaaatggtta agatgggcca atcacagtgg cttatgcctg taatcccaac   116400
actttgggag gtcaaggtaa aaggatcact tgaagccagg agcttgggac cagcctgagc   116460
aacatatcga gaccectatc tctacaaaga aaatcaaaaa ctagctagat atggtgggca   116520
catgcctgta gtcccagcta cttgggaggc tgaggtggga ggatctcttg agctcaggag   116580
ttcgaggctg cagggagcta ttattgcact ccagcctggg ctacagaatg ataccctgct   116640
tcttattaaa aaaaaatcca aaaaaaaaaa aaagtaaacc tgagagcttc ctcctcctgt   116700
gttaaatttg gaggccaaga tgttttttgtt acttttacaa atgatcaagg acggtgaagg   116760
ttgggcatgg tagctcacac ctgaaatccc agcactttgg gaggctgagg cgggtgatc   116820
gcttgagctt gagaccagcc tggacaacat agcaagagac cccatctcca caaaaataaa   116880
aaaataaaaa aaaatagcca ggagtagtgg catgagcctg agcccaggag gtcaagctgt   116940
agtgagccat gatcatgcca ctgcactcca gcctgggcga gatcgagacc atgtctctag   117000
agaaagaaaa tgacaaggac agtgaaccca agaaagtcat aagatgccag ctgtgcagca   117060
agcatggaaa gcagccagtc caaattagga cagtgtgttt tccaagaaga acgatcgttt   117120
gtaatgagaa tgctttgctt taaataaatg actaaatagc tagaagccta gttctagggg   117180
ataggcacgt ctttcttctc tcaagaaaat agaaaggcaa ttctaatttc tagtaacagc   117240
aaacagcatt aagtcatggt ccaaatatga ggcaaaccaa aatgtggctt gattgttcag   117300
cagttgatct gttggaagcc cttgatatta aaaaggttct cctttaagcg gcttaggagt   117360
cacgatcaaa gacctataga aagagatgcc atccttctag gatccttggc tctcttggga   117420
actagattca gatagtcata atgtaaatac tgcttgagct ttcttttcttt cttttctttct   117480
ttcttttttt ttttgagaca gagtttcact cttgttgccc atcctggagt gcaatggtgc   117540
catctcggct caccgcaacc tctgcctccc aggttcaagc aattctcctg cctcagcctc   117600
ccgagtagct gggattacgg gcatgccacca ccacgcctgg ctaattttt  gtatttttag   117660
tagagacagg gtttctccat gttgaggctg gtctcgaact cctgacctca ggtgatccac   117720
ccgcctcggc ctcccaaagt gtgggatta caggtgtgag ccaccgcacc ggcccgagc    117780
tttcattttt gaaatcaatg tatgactgaa acactgaaga cttactgact taattatggt   117840
ttcagaacag aatgaaaatg tcttcggttc tgatgaatat aaaaggaaaa ctaaccaagt   117900
taatttggca agtagatggt agagatagag gtggggagtg gaagggaac  taaaatcttc   117960
aacttgcatt gttgggatta tatggttaca tcatctgaga ttgacagacc aaaatataga   118020
ggcttcagag gtctccaaat agaactaaac atgtaattca gattgttagg aggtagtata   118080
aatgagctaa atctcatctt tattacggta gagttaatgg gtgatgtcta aagttgtctg   118140
aagtctataa atcatgacaa attatgatgt ggtgattgta ttcaacagtc tttcagttgc   118200
agggataaaa ccccagttta aactagagta agagaaagaa tgtgttggtt taagctcctg   118260
gaaagtgcag gcaagggtag ttggtaggac tgcatctagt gttgtaattc tgtggtctgc   118320
```

```
attgtatatt tatgcatctc agctctgctt tcttctttc atttatataa tttttaaatt    118380
ttatttaaa  dataggtct  cactttgtcg cctaggctga agtgcagtgg catgaagtgc   118440
agtgcgaggc tcactctagc ctcgaactcc tgggctctag agttcttcct gcctcagcct   118500
tctaagtagc tgagacaata ggcatgtacc aacatgcctg gataggtttt aaaattttt   118560
tgtagaaatg gaagtcttgc tgtgttgccc aggcgggtct ttaactctta gcttcaggcg   118620
atcctcctgc ctctgcctcc caaaatgctg aggttatagg tgtcacccac cacgcccagt   118680
ctcatctctg cttcctgtgt tagttttgtt ctctggtggg ctgttttcac atgaccgaag   118740
atgacctcta gcaggctgtg ttctcagccc tcaagtaggg cctatgtgat tggccttgca   118800
tgagtaatat gggtgaccat aaaccctga atgctctggt ccacatgggc caaatgggag    118860
actggacagc attccattga tgaggaggtg gggctggtct ccgggagtaa gggagaggag   118920
cacatgcagt aactgatggt ctgctgcaag ggatagcagc acagcagtta gaatttggaa    118980
ggtaactacc agaactgaaa acagaaatga taacaagtag ttgcccttaaa aagggatggg   119040
agcagggtgc ttttgtgatc aaagctcctt tctcttactg gattttgta cactttgc      119100
atacatatct tagagtaaaa gatagcattt tcagcgtttg tccatttgag gatactcttg   119160
gcgtggcccg cctccatgct agcaggctct ggttgtgcca agttcagttg agcatcctgg   119220
ctcttgcctg cacggaactt ccagtcagtg cgtcagtatc acaagtcttg atattccta    119280
tgaagaagaa cagtagtgca gtgacagacg aaatgggtgg gcaggcagag gcaggatttc    119340
tgagggagag aagtagctag cttttttgcag agaagagttc cggcacccaa gagagcagct   119400
gagagtacag gcaggcaggc aggatgccgg tagggcccgg ccgcacggcg ccacagaatc    119460
ctggagaaag gggcctcttc atgggcctctg cattcagctg ctgtcaccct ccgcacaggc   119520
catggccaaa atttaatttt catagtggac tctagttttt gagccttact tgctattatt    119580
gaaataattt tcttgtttct ttttaaagat cttcggatta tgcttcactg accactgtaa   119640
taagtttaaa gttgagaaaa tatgcttgt taatgaatga taggtcaatt ttagtatgtt     119700
ggtcatttta atattttgcc accagttggt ttggatttga tgccaggagg agacagcctc    119760
atttctaagg actagtcttg cctttgtggg ataagggtgg tgtgttctgt gtccttctac    119820
atgtccgagc gatctctgtg cagctcaaat gtggtcactg tcttattgcg ctgatttcct   119880
ctccttccat ctcacaattg aggcaaaata ttgttactgt tgaagtgttg tccaatagga    119940
cttccagcag agacaggatg tctgcactgt ctaatttagt tgcctttagc cacatgtggt    120000
gttctgtacc tgaaatgtgg ctggtctgat tggatagctt aatttataat tttatttaat   120060
tttaattaac ttaaatttaa acagctctgt gtggatagtg gctcctgtat gagacagtga    120120
aggtctgttg agaagcagct ttactggtgg gagtggaggg cttggagagg gcacgtgggt   120180
ttcctgctgg tatcttttga cctttatttaa tctgcccaac atttgcaagt aagttgtgtg   120240
tgtgtgtata tataaatgtg tgtttctgtc ttcttgtttc ctttgactgc atttatttga    120300
aagacactag gtggcagaat tactgtattt gattggttc aagataagag ttgaaataat      120360
tcatctcgtg ttttttatata agtaaggtgt gtttagcatg taaaattggt aatatgtatt    120420
cacgtactgc ttaaacaaag gctatgaatt ccacccataa accgaaaatg aagaccttta    120480
aatttgtcca tttcaggcgt gggtacttct taaataatac ctggttcagg aactagtcag    120540
aatggcaccc ttgactttt gtttcctgct tttcctcttg ttgggagagg agggtattca    120600
tcccaaagtg gtttgcctat ttcacattcc atctaggata agcagaatag ccaagaaaga   120660
tagctgtcct cctgtttaca acatttgggg taaccagcat ccctctcttt tggtccaaga    120720
tagactggtt tagaaacaga tgatggcacc agaggcccag gaggtggaaa catcagcttt    120780
gtttgttgtc catgtggctg aattagagct gtctggcctt gtagcctcaa cacggccttc    120840
cagcttttgct caccgtgatt ttcaaggaca catcttgtc tcttccctgc ctgccatcca     120900
gactataccc agtcagggtg gcaggagctg ctgcccttc ctccctgagt cctggtcgtg     120960
ggtggtggag atgtgccatg acgctcacgg aggcatgctc accccttcct ctgtggcaga    121020
ggggatggct gcacgacagc tcttccctgt cctttccaaa gcgtctgtgg ttccacttttt    121080
tggggcaaag caggaatact ggaagagaga gaaagtgctc ctttctatag taataaagtt    121140
gacattgatt caagttcatg cttgggaaa ggacagggct actaacaatt ataatgctgag     121200
gagcaatgga attttctcat gggtatgtgg taggtttaat tttaattatc ccagttaatt    121260
cttagaactg ctctgtgaag tatttcccgc tttgtgctta agttctaaaa gatcctgtgc    121320
caaaaccaag aatgaaaacc caagcattct ttcttgccca tcgatctttc tctcatcagg    121380
ccacttcttg ggttgatagt ggtgagtgta gccgctgcca cttttcagaat acccaccatg    121440
ggccccagtc actgtgtggc gtggagaaga gatggttctc tctgtgtcat agctgaacaa    121500
gcccagccca gagaggttc tgccctagga gctctcgatg tgggaattgg gatgcgatcc     121560
cacatcctgc ctgttttgaa aacagcattc tttattttca attcctgctt ccattgttcc    121620
ttttaatat tctttgttta gctcacaaaa acacggcttg cggagctgct gcgtgcagct     121680
gtagctgttt ctctgggtgc agcctgcatc cgccttcctg cccgcctcct ttcctgcact     121740
gccatcgtgt tctccgggca cttggtcctt ttctcttccc ctgagtcct ttggctcccc     121800
tgtgccaccc ttgtgatcca caggctctgc cttctttctg tctcagactg ctgctcatca    121860
ctactcggga ccctaggaag ggaggttcca ccgagaagca tcttctcatc tcagccacgt    121920
tctcagtgcc actgttgtct ttgttaggta atggtagcta ctgtaacaaa taaaccaaca    121980
tttccatggc ttcacaccag agaaggttgt ttccttggttt tatgacaatg tattgagggt    122040
gttcttggtt cacggatggt tttcctccat gtgggaattc ggggacccag gctcctttcc    122100
ttcttttggt tctgttctcc aggccttcac atccctctgtc tctggttggg gacaaggaga    122160
gggaaggtaa agaaggcttt gtggccttgg ataagtgaca ggcatggcctt tgctggtgtt    122220
ctctcgtggt gacaggtcac agccccaccc tgtaaagggg gactgagaga cgtcgtcctg    122280
ctgcttccca gcagcagcac tgtggtctct gatgtgtttt ctgtgaggat aaaaacaggt   122340
gattccagga tgaggaaagt cagggaaacc cttgaagga ggggaccagg cgggtgtcac     122400
catgggatta gtggtggctt cagaatgagc tgcagcgcct ctaaagcttt                122460
tgctattctg atatgcccac accatgccca gcaggtgtct gccttgctct ccgcagagag    122520
agtgatgaat cctcctcatg agcctctgtc cagttgttcc tccctccacc tggaagggac    122580
cctgggttcc tcataacatc ccagcggaac aggggaccttt ctatcctgtc cccaagttca    122640
tcctcatcct cctgccggct tcctggcccc tcttatgtct gcttcctgac gccacatcct   122700
tctgcattct ctgaattga attttgcctt tgatgctttat ttaaaaatat ccattgcagg   122760
ccaggtgtgg tggctcacac ctgtaatcct gtgcactttg ggaagccaag gtgggcagat    122820
tgcttgagcc caggagtttg agattagcct gagcaacatg ttgaaatcct gtttctatag    122880
aaaatacaaa aattagctgg gcatggtggc gcacacctat actcccagct actcaggaac    122940
ctgagacagg aggatcaatt gagccccgga ggccaaagct acagtgggct gtgatcgtgc    123000
cactgtactc cagtctggtc aaacagagtg agaccctgtc tgaaaaaaaa aaaaaaatcc    123060
```

```
attgcatact tcaccgtagc gaaacatgta tgtcttacct ttcctttcct gcctgtagct   123120
gctcttttac acttaacagc cacactaagc cagccttaaa tgaaaaacaa accagcactt   123180
cctgtgccct cctgcttcct tcatgagggg tccctccctc tgtgtacact ccattctcat   123240
tgcccatggt ggtttgtttc cctcttgttt ctcaagccat ggcagcctgc ctcttgccct   123300
ctttactaaa aaggcctttg cagaggctgc ctgtgttctt tcttctgagg tctctctcat   123360
cctaggccct ccagcttgat tctgtggagc tgccctcttg tcactcagta gcttgtgggg   123420
tcttctctgt ctagccactt aattgattgt gttcctcgag ttgctgtcca tggtctctcg   123480
ttactgtttt ctctgtgttt ctgcctctct ccttggcctt ggtaggtcca tccccttgt   123540
gaccttggct gttgctctca tggacaactt tctcttgctg gtccttgtag tcctggcatc   123600
cagcttctcg acacgggact tgtcctgcca gtacctcaga cttgcactta aaattgaact   123660
agcaccactg tcactctcca gggcctcttc ttgttaatta gatcattagg gatgttcaga   123720
atcccagcat catagtatgt tcctcctccc gctaccccag gaaccctaac cttacctcct   123780
cctctctatc tactaggagg tggccctcag agtccgtctc atcttccacc tgaacttccc   123840
taataggctc cagcagctgc caccccgggg gctgagtact tcctccatgc cttgtgcagt   123900
gctgagccct ttacctgggt tctcctgttt gctccttatt acagccctgc gaacagatac   123960
tgctcttaat tccatcttac acctaaggaa gctgaggccc caggtaaggt gcatccaagg   124020
tcacccaggt agtagacagt agagccacga tctgaaccag gcagtctgat tcagagcctg   124080
tgttgacact cagccaccta gaacacagct tggattgtgg gtttctatta cctgttcaaa   124140
accccctacat cccgggtctg tccctgcacg tgctctgtgg cctggctgca tcttccttga   124200
aggcagtgca tgcctcttca ctcagggggc ccatgcagga acagagggcc ccacagaagg   124260
atgaggccag tgcagaatgg gctggagggg acaatgctga ccaggaagca agtgtagaga   124320
aatcccagga aacctggagg agccagagac aaggcattag aactcctcgt cgtgacctgg   124380
tctgcattct ctgagtgtgc tgcttctgtt agctcgcttc cttggtctca ggttatagtt   124440
taaggcattg tggagcccta aaaagcctgt actctgtttt tacctgtttt aggacccttt   124500
cactttgggg atgtgttgat tttttttttt tttttttttt tttttttgag atagagtctc   124560
gctccattgc ccaggctaga gtgcagtggc acgatcctgg ccactgctgc ccctgcctcc   124620
tgggttcaag caattcttgt gctcccgcct cccaaatacc tgggattaca ggcacccgcc   124680
accacactcg gccaatttt tgtattttag tggagacagg gttttaccat gttggtcagg   124740
ctggtctcga actcctgacc tcaagtgatc tgcccacctt ggcctcccaa agtgctgtga   124800
ttataggcgt gagccaccac acccggcctg aaatttaaat cagaaataaa attttgatcc   124860
caacagtgat gccaggcagc ccagatctgt gggagagggt ggccttggcc agctgggcct   124920
ttctctgttt cccaagtctt gctgcctctc cctgctgggc tttgcagcct gtgcatgtct   124980
ctgtgccttt gaccttgttt atccaaagga gaggatagaa tgaagtcatg attcctggag   125040
ccctgagaag gatgctgtgg agaaatttgc cggtagaatc tagctgagtg tgttgctgag   125100
gtgccagcat tgtgtgtggg gaggctgacc gcttggcctg cctaggccca ggatgctcca   125160
tggccgggca cagaggccac ttggctgtca ggtgtcagga gcctgcagag ggcacacaga   125220
gcctggaccg caggggggtc ctgctttctc acctggcctc cttcagcatt tctgtccctc   125280
agtccttagc aagcccagga gctgttgagt ttggcaggtg ccgagtgctg ttcctgcctg   125340
tgtagctgtg gctcagtcct gtgggggccc cgctgtggcc cgagtgcagt gattcgaggc   125400
gctgagtgtt ccctgactcc ttctccagga gctgtgttca gactttcgca gctcttggct   125460
tggagctcct ggagggcttg gcattgccga ccaatgtgga ggtcgacagt gagagaggag   125520
gaatgctagc tttcttgacc agtccattaa ataagtggga tattggccag gcacggcggc   125580
tcacgcctta atcccagcac tttgggaggc tgaggcgggt ggatcacgag ctcaggagtt   125640
caagaccagc ctggccaaca tggtgaaacc ccctctatac taaaaataca aatattagct   125700
gggcgtggtg gcaggcgcct gtaatcctag ctacttggga ggctgaggca ggagaacagc   125760
ttgaaaccgg aaggtggagt ttgcagtgag ccaagattgc gccactgcac tccaacctgg   125820
gcaacaagag caaaactcta tctcaaaaaa aaaaaaaaaa ataggatatc tgtttctgct   125880
tagaaaaatc agaattttct aaatgccagg tgttctgaat acgtaagtat gggagacgac   125940
tcagcctgtt tcattttat gtaaaatctt cgcgtagcca tgtggcactg gaccgagatg   126000
aaaagcaaaga catttctcct taactttgtt tctaggaatg ttccgagaaa tcacagcagc   126060
tgccactagg ctgttccgca gtgatggctg tggcggcagt ttctacaccc tggacagctt   126120
gaacttgcgg gctcgttcca tgatcaccac ccacccggcc ctggtgctgc tctggtgtca   126180
gatactgctg cttgtcaacc acaccgacta ccgctggtgg cagaagtgc agcagacccc   126240
gaagtaggtt cataatgccc cacagcccag ggcgccagcc cagcaccctg tcctgagact   126300
cccagtaacc tgagctttgg ccaccgttaa agcattttca ttttccattt tttgtgaggg   126360
cttgtgaaat ttctgctgca tattaatatt ccttttcatg acagcatatt attgggacaa   126420
acatgcggtc cagctaaagg cattcaaaat agcagttgct ttctaaatgc gatttttcttt   126480
ggcaggttct ttgacaccat tgcatcttgt gggatatgct tgtcatgctc tgtggctcct   126540
actaagttct agtccttaaa ttggttccat agccagacat gttgcaatgt cttaacctca   126600
ttataaagta aatgtggttc tggttatcct tagataatga agtaacagtg tagcaaattt   126660
caaaacctct tggaaatgtt attttaccat tcaaaaaggc ttactaaggt tctcgttatg   126720
ggtggccctc tttttgcaaa aggttttcag gcttaagctc catttctagg tgctccaaca   126780
ctccattatt tgtatatgta tggaaataaa agctgtgacc accccaacc ctggcccccg   126840
cccagctgaa tcctcagcac agtatttctg gaaggctcaa gatcccacgc tggggaaaag   126900
aagtctgga gacaaaagag ggcaggtgct gccgtgcctc tctgctcagt atggatactg   126960
gaccttgtgc tgccagggct cccagtaggg ccagttcatg gcactcagct ggaaagtcca   127020
ctgttgggag gcattcttaa ccatccactc tgtgccgtat gtagtggggt ctggtcattc   127080
tgttggagga gacagaccag tgacgacatt tgaaatgctt ggtggatgtc ttaggcctgt   127140
tacgatgact gacactgtg ggggcaggag acagaaagtc agtgctcct agttctgttg   127200
tgctttaacg tgcatagaaa tcagctgcgg attcagcaga tcactccttt tctgacagat   127260
gggcctgctt actctgatgt tatatcagaa agctctgaat ctgggaattg tgtccctga   127320
attggagtaa cagaaatgct tagatgatga gtgtttaaaa gaaataaacc aaaggtaaat   127380
ttagtttgga attcagcaag cgtcttcatt cagccctctg agggcaaact acagcttttt   127440
gtaaatgtag gtaaattctg tgactgtttc gtgacccct ctgatccagt tttccttttat   127500
aaccttctgt attgttcctt ctattatcct gaaataacat taatagatta ggctgggcgt   127560
ggtggctcat gcctataatc ccagcacctt gggaagccaa ggcgggcaga tcacctgagg   127620
ccaggacttc gagaccagcc tggccaacat gatgaaatgc tgtctctact gaaataacaa   127680
aaaattagcc gagcatggtg acaggtgcct gtagtccctg ctactcagaa ggctgaggcg   127740
ggagaatcgc ttgaacctag gaggaaaagg ttgcagtgag ctgagatcgc gccactgcac   127800
```

```
tctagcctgg gtgacagagt gagactccat ctcaaaaaaa aaaaaaaaaa aaaaaaatta   127860
atggatcaat ggattttttaa cctaataatt aaatttcaaa aaatatcgtt ctttaatggt   127920
aatgtaaagg taaaattaag ataatatgta acaagcatgt gagtgtctaa ggtgtccccg   127980
tggtggaagg aaaaaataaa tccccataag tgtccaagat gcccatagag agcagagctg   128040
ttctggttta aaccctgct cttagcactg tgttttttca gctgtggggtg gtgggggatg   128100
agtatctttt tatttccatg agatgagaaa aatgaattac tagaagtgtg aaatacaaaa   128160
cacagctgct ctttttttag ccatagactc agcagccata aaattgctgt atccagttgc   128220
agaaattcct gctgcttact cttgaccctc tctcggtttg tgtgcatctc ctctcaggct   128280
ggctcccaga tgggagctgg ctccaggcga cactgggtgc tctgctccag gaggtcctta   128340
tgtgggtcct gccctagcct agccccctctc ttatgactc tgtcactgtg ggtttatgat   128400
tcactctcaa tctgtcttac ctcttggtga actgttagag tcctgcctat actttggcgc   128460
ttgtgggtgt gttgtggtac acatgatgtg ttggtcactt cccagctcat cttgttctga   128520
gtcaccctag atttgggaca ttcattcgcc accagtaccg ggcggtgtat ggcctgagat   128580
tggggggggc ttgtgctgct acaaattggg gctgaatttg agttgacagt ggaccttctt   128640
tatgtctact gctcatattt gaattgcaaa tactgcctct tctctttcag aggctcatta   128700
ccctatagct gtattattgc aaagtgcaca attacagctt gagtgtaagt cacactgcgc   128760
tggcaggacg gcccactgag aaagggcacg tttcctgttc gttagttttc acattgacac   128820
ataatttaca atacagtaaa atgtactttt ctatcaactg tagtcagtaa cagcccccct   128880
ccccccaacca catcaagata tagaggagtg ctgtcacttc aaacagttcc ctcttcctct   128940
gccacatcct gcccctcccc aggtctaacc accaatccgt gctctgtccc tctgttcagc   129000
ccattgcaga aggccataga aatagaatct ataggctagg tgtggtggct catgcctgta   129060
atcccagtat tttgagaggc tgaagtggga ggatgacttg gggctgggag ttcaagacta   129120
gcctgggctg cctagcaaga ccccatctcc agaaaaaaaa aatttaaaaa ttacaatcac   129180
gtccctgtag ttcagctgct tgggaggctg aggcaggagg atcacttgag ctcaggagtt   129240
agaggttaca gtgagctatg atcgtgccac tgtgctccag cctaggtgac acagcaagac   129300
gttgtctctg gggaaaaaag aaagaaacgg aaccacgcgg tgtgcagcct tctgagtctg   129360
gcccctttcg gtgagcagtg tctaaagttc tgtcgcgtgt tgcccacgcg tcggtggctc   129420
gctccttgca actgctgagc attgtatggc taggctgtag tttgttttca cttcaccagt   129480
tgggaaacag agaaaaggca cttttttaaa agtttaaatc tgtagaattt tggttttttac   129540
cagttctctt ctaaatcctg agggattaca ggaaaagttg ttgtatttca gaatattctt   129600
agcttgatgt gacctctgtc cccgttaagg ccctttgccg caatgggaag gacgtcgctc   129660
ggtcagaccc tgaaggtcag aggggcagtt tgggagtgtg tcaacatttt aactgtatgg   129720
actagagcca agagtctcaa ggtttataat tcccacgtat tcaaaagaa aaaaacaata   129780
aagtgagaag tcagtgtaga gtgaaataac ctgtgttagt ggggaagaag tgttttttaaa   129840
caggatttcc ataacgtata acatcaacat gtttagagtg ggtgatgttc attgggaaac   129900
gaacagtaaa acatgaaagc agggaggttt tcattctggc agttggcaac tttcacggca   129960
gatggagaat ttcaaaagca attgctcaat tatcaaacat agccagtgtg agttctgaaa   130020
taaaggtgct gattgaatgt gcagctttat ggtggatttt gctattcagg caagcatttt   130080
aattttctgc ctgttaaatt ctgtttttctt tagttttttca tatgtggttt atttgtagctt   130140
aggaatagat aactgagagt atatattaca catacaacat tctgatatgg caatatttaa   130200
aacaactgtc ctgttttaga actagaatta aacataatca tcttcagtat tttgcaaata   130260
agctcactgc catccagaaa cattgtcaat gcatctgttg ctccttctag aagacacagt   130320
ctgtccagca caaagttact tagtccccag atgtctggag agaggagga ttctgacttg   130380
gcagccaaac ttggaatgtg caatagaaaa atagtacgaa gaggggctct cattctcttc   130440
tgtgattatg tcgtaagttt gaaatgcctg taaacgggt tgagggaggt ggggaccagg   130500
agaacatcct gtgtagatga cacttgcatg gaccctctgg aacccagacc gcccggtgtc   130560
ctgccaagct ccatcgaaac taaatctaga atgaatgttt acttctgctg tgacatataa   130620
ttggagacca ggcctggcct tccagtcact ggattctaag ttggactgtg agagtttttg   130680
cagctgactc atttatcaaa tgcccggcta ttggctcacg cctacatgat gctgggtatg   130740
tttgttaatt tgagggaagc aatggaataa taataactaa tgatttaaaa aacaaagtaa   130800
gtgcattgac tgtagtgggg ttctgatttt aaatttttt aaaaattaat accaggagca   130860
gtggcttatg cctaaattcc agcaactcga gaggctgagg taggaagatc acttgagccc   130920
aggagtttga gacaagcctg ggctatggtg tgagacaccc atctctaaaa aaataaaaaa   130980
taaaaaatta tccaagtgtg gtggctcgtg cctgtaatca cagctctttg agaagctgag   131040
ggcggaggat ggcttgagcc tgggagttcg agaccagcct ggcaacacag agaaaccctg   131100
cctctaccaa aaaaagaaag agaggaagaa agaaaaatta gcctggcgtg gtggtgcatg   131160
cctgtggtcc cagccacctg agagactgag aagggaggat tgcttgagcc cagaagtttg   131220
aggctgcagt gagctgtgac tgtgtcactg cactccggcc tgggtgacaa ggcgagaccc   131280
ctgtctaaaa ataatttttt taagttaatt tgtagaaaag gtgttagatg ttctttgtca   131340
cattttatga tggattcctg tttaaatgcc gttctcttta aagaaaaaaa aataacttgg   131400
gggagttttt aaccataaaaa ctagcatcac atatttacca tggagaattt acaaaaaaac   131460
aaataaacgg aggaaaataa aacctcctgt aatcatacta ctcagagata acttgctgtt   131520
agatttttggt ctagatttaa tacttttttct atatttatat taaaaatatt taaaacatat   131580
gcatttcttt gtcacaaaca tggtatctta tagatactac ttcacatag caaaacagtg   131640
ttaaatattc tgaatcagaa aaggaagccg actctccaac tgaaagaggt gttatcctag   131700
agactttttc tggtgatgac aatttattaa tagtcacttt ttgctttact ttctctattg   131760
aagtagtttt tctattttgt tctacttta aggataataa aatttataat gctgtttttc   131820
acagaaatat aagaaaaaag ataactaattt tataagttaa taaagtttga tcatcccaaa   131880
tccaaaaatc tgaaatccaa aatgctccaa attctgaagc tttttgagtg ctgacattat   131940
gttcaaagga aatgttcatt ggaaggtttc agatttcgg atttagggag ctcaacaaat   132000
aagtataatg cacatatttc aaaacctgaa aaaaatccta aattcagaat acttctgatc   132060
ccaaacattt cagataaggg ttattcaacc tgtactgtca gatgatccca aatgaaaaat   132120
attaatcgtt aaccaaatat caaggaattg atcacatttt acagtttctg cctaggatta   132180
tgaatcaaga tgaaaaggct ctgcatgttt aaaaatatat attttttattt tcttataaat   132240
cttaaatatc tacacttaag atttatttga tatgtgggat ccattcatat tttggattca   132300
acagttctgt caaaactgtg gcagtgatag gggattcttt ttttccccact gaactatcac   132360
aaaattggaa aaagagtaat tggagaaccc cactggctta gccggcccga gcccggggag   132420
agggcaggca gtgctgtgga tggggtcatc ccagcgcaac gctgccccctg ctacctgcgg   132480
atctcgctga ggcctgcctt tgtccttttga cccttggcca tttgttagtg tctctgagag   132540
```

```
ctggactgct gtaccctact tccccagggg gcctaacttc acacagcctc tgccgcagtg  132600
cgtggttgga ggtgacggcc ttggtaaatc gagtttccta cctcctcaat tatttgtgct  132660
catacactgt atattttag tgaggtttat atttgggatg tgttttctcc ttcttaccct   132720
ttctggcctt tctatggcat taatacctgg tctcttcttg tgtacttgaa aatgaatctc  132780
tcatcatatt tttccttagt gtcagaacct ccatgactcc gagcacttaa cgtggctcat  132840
tgtaaatcac attcaagatc tgatcagcct ttcccacgag cctccagtac aggacttcat  132900
cagtgccgtt catcggaact ctgctgccag cggcctgttc atccaggcaa ttcagtctcg  132960
ttgtgaaaac ctttcaactg tacgtcttca tcctgccgac tattgccagt tgcagttttc  133020
cctgccttaa aaatggagta ttgaaatttt taactttaat ttctgatttg caaaatagtc  133080
atcttttgtt cttttccttc ttgctgttag ccaaccatgc tgaagaaaac tcttcagtgc  133140
ttggagggga tccatctcag ccagtcggga gctgtgctca cgctgtatgt ggacaggctt  133200
ctgtgcaccc ctttccgtgt gctggctcgc atggtcgaca tccttgcttg tcgccgggta  133260
gaaatgcttc tggctgcaaa tttacaggta ttgggaagaa aaaccctgat attgatttat  133320
attgaaaatt tagcaggcca agcaaaacag gtggctggct ttttcctccg taagtatggt  133380
cttgacatgg tcaccgatag aaacatgaaa acatctgcaa acttgccgtt actcgtgtgt  133440
ccgatctgac tgtttcttgt attttttcct agtctgccct tactaggatg aactgtacac  133500
atcagttcat cctttttaaa tgagcatgag gttattttgg gttgttaggt gttacaaaca  133560
cactaatgtg ttttgtcta ttagagcagc atggcccagt tgccaatgga agaactcaac  133620
agaatccagg aataccttca gagcagcggg ctcgctcaga ggtaatgctg gaaacacagg  133680
tcgtccttgt gttaggacaa cccaggatat aaaggatata gatttgtacg ggaataaatt  133740
cacaggacaa gaaatcgatg tgccttatag gtgggttac tgcagaagtg ccataataga   133800
accttcctac ttttaaaaca accagatctc actttctaaa gagtaaagga tgaccggcag  133860
gatcacgtct gtgacgtgag tggaggcagt ttgcactcct ggtggctgtt tgagaggtag  133920
catttagaat gcctgtattc actgtcctgt gatgagtggg aaaataggtt atcaggttta  133980
tcttagcaaa atcaaagcat gtcatctaat tgctaaacaa gagttggcaa atctgagaga  134040
cattactcaa tccttggcat gcaggactta catctgcatc ctgttgccat tttatgtctt  134100
caaagcattt aatcatttag ttgtgtttgc aaagtctttg agaagccttt gtcagaaatc  134160
cctacatctc ctatgtgagt gtatttccat gactgcagaa taagttaaac tttaccttt   134220
ttccttccct tgcggggcgg ggtggggggc agggattgtg tgtgtgagag ggagagagag  134280
acagcagaga aggagaatat aattatcatg tctgtgtatt tgagctgaaa ctgcaaaaaa  134340
ggaaaaacac acaaaaatta ttatgctttt cagtctttag agtaccttgt ctattatgct  134400
tttcagtctt tagagtacct tgttgatggt gtttttaaat gggattgggc acaattaggt  134460
ggacagtttg ggatgatttt tcagtctgta gggccaagct cttttgtaat ttgcattatg  134520
aagttgtcac tctcatagca gatggcggga gataaactat tattacttt tgaccctaga   134580
cttagtcttc agtccagatg agggagatta aaagtattata aatatcttgt gccagatgag  134640
gtgattttat tttgaaatga ccatgaattc ctatcagttg tcttactggg atatttgata  134700
gtggaatttg tgcatttgag tcttagatga tctgtttac atttattaag aaagccttta  134760
ttagcttta tactgtgtat tgcctgttgc agtgtttgag tataaatgaa atttctggaa   134820
aatattaatg gagtacaaac tgtgatactt aaaagtaaac tagggcctgc atttgtatca  134880
tgacctgttt gagtattgat gagaagatag ctgtgaagaa aaaggtttaa acaagtgtat  134940
tttcctttaa gaagccacta atagtgcatc tccttagagt gtatatttct agaatcctag  135000
tgtgcagagt ttagactaag actaaaaaaa aaaaaaaaca aattatactg taatttcatt  135060
tttatttgta ttttagacac caaaggtctc atttccctgct ggacaggttt cgtctctcca  135120
ccatgcaaga ctcacttagt ccctctcctc cagtctcttc ccacccgctg gacggggatg  135180
ggcacgtgtc actggaaaca gtgagtccgg acaaagtaag tgtccagcgt gtctgcatgg  135240
gaggcacagg gcgctgagtg cctctgtcac ctgtggcaga tacagagagt gcagaggagg  135300
tgccgtggac ccaaggagtt ctggcgctcg gctcggctca gtgaagctgt ggttagagac  135360
gtggggggcc atcaaggtct gagggagcca agcagtgctg atgtgggacc cttttgtag   135420
gagtgtgggg tgagtagtta gtgggtgaat caaggaatag tcggccgtgg cctgcaggcc  135480
cctgactgca caggccttca agcacatgtc aatgccgtta gcctccctcc atctcctcat  135540
accttctggc cacctgtgag ttgcactgcc actgccagcc attctggtat gttgtcagca  135600
cctccactgc tcatacctca tggttaggga ccacctggag ccttggtaga gccttgctag  135660
agccttggta ctctacttc ctggacaaag ttcagcttat gaatatgaat ttagatttca   135720
aaaccagca gcccaagtat aagaaagcga aggttcagtc ctgccttctt aggctctatt   135780
cgctaagcac ctgccctgcc ctggttgctg gggagagatg agtaaagcag acaacccagg  135840
agaggatgc aaaggggccg ctaacccta gtggtttagc tatatttgga aggcctattg   135900
gaagttcacc aggtgaaggg ggaggctgtg agggtgccca ggcaggtaac agaagtccaa  135960
aggggaaaac ctgtggtgtg gtgagccgta tagccacagc ctgccggccg gcagccctct  136020
cagcctagtg cggtgttccc aagcactggc ctaggcctgt agctccaggg atgtgaagtc  136080
cccttgaacg ccgcccatca tgttcccctt atccattttt ttcttcccag gactggtacg  136140
ttcatcttgt caaatcccag tgttggacca ggtcagattc tgcactgctg gaaggtgcag  136200
agctggtgaa tcgattcct gctgaagata tgaatgcctt catgatgaac tcggtacggg   136260
gggagcagtg gaggcaagga atcctcagct tttcttgtga cttccaagtg ggatttgtct  136320
catcatcatg tgacccactt gttgacaaca catgttgggg actccagtct gggcaggcag  136380
gggatgtcgg agagactcca ctctgaatgg ggcggaagt tggggaggac tccatttcag   136440
atggggtcgg gacatggggg ttatgctgat cgagacagaa aagcacattg tttcagccac  136500
attagaatcc acgaggtgt tgttttgaaa tccagctggc cccaaggctg ggtgtatggt   136560
ttgggatgag aactatctgg cctccactgg aggaacaaac acagatgct atcatctaag   136620
ctccatggcc aagacagaat ggaagtcaag gttgcgtatt tgccgtagac ttcaacacag  136680
tgtcgtaatg cgtgacgtca ataacttgtt tctagtgtct tggaagttga tctttagtcg  136740
taaaagagac ccttcgatgc agcgagattt cctctactca cacctctgtt agatgtagtg  136800
aggttcttca ccccccaacc ccagatgtca gagggcaccc tgcgcagagc taggaggcca  136860
tgcaaagcct tggtgtccct gtccctcacc cgtgggcagg tcctgtgagc agtggggggg  136920
ccacctcttg ggtatggtgc agccatggcc caagcaggtc ttcttctcag acctactagg  136980
acgggagaaa cctcctggtg ctttagccct gcgttgatat gcagcaaatg ggagggaagt  137040
gggcacctgg gaggacaaat gcctgtgagg gccgggagtg acgcaggtg ttcatgaaaa   137100
gagaccttgt ggggagggca acacaacagt gtgttctgat gtactgaaga gctcaactga  137160
aaacaacagg agaattagcc caaaatccat ttactaaat tgtttatctt ttttttttt    137220
tttgagacaa agtctcgctg ttgtccccca ggctggagtg caatgcgcgt atcttggctc  137280
```

```
actgcaacct ccgcctcctg ggttcatacg attctcctgc ctcagcctcc caaatagctg   137340
gtattaacag gcatgcacca ccacgcccgg ctaattttg tattttagt agagacggga   137400
tttcaccatg ttggccaggc tggtctcaaa ctcctgacct caggtgatcc gcccacctcg   137460
gcctcccaaa gtgctgggat tataggcctg agccaccacg cccggcctaa aattgtttat   137520
cttaagattc atgcagtgaa agctaactta ctgagtgata aatttgctta ctgatctgtt   137580
tattaggttt tccaaatttg ctaattgggc tttgaacagc tgtaaaagtt ctgactgtaa   137640
aagaaagctt caacttttgg cattcatgat gcttttctga gtattaaact aagatagatg   137700
ttttacctga aggatcggcc accaatcttt aaatggctaa acaaagggt tgctaaaaca   137760
taatccaaat tgacataaga aataccattt ttccaaccaa aatttggca ttcatatgc   137820
tacttttacg tatttcagct gcatttgaac atctttttca aactttaggg tggttggtgt   137880
atcactgagg tcttggatga cactttagct ttgattttgt ttttatgaat taaaattgtc   137940
ataccaaaat ttttatttca agcaaatcca agagcataaa aaattaaaat attacttaaa   138000
atactaagag agaacagata tatattttac taagcatatg ttgaatgaaa ttgttcaaat   138060
atttataaca ggcatagagt agaattttct taaaaatatt tttgatggta taccaatttg   138120
tattttctca gaaacatttg ccttattctt ttttctgttg tgttttctt acctgattga   138180
aagctcataa tctgttgtta ttgtttgtta acctttaatg ctctgatttc aggagttcaa   138240
cctaagcctg ctagctccat gcttaagcct agggatgagt gaaatttctg gtggccagaa   138300
gagtgccctt tttgaagcag cccgtgaggt gactctggcc cgtgtgagcg gcaccgtgca   138360
gcagctccct gctgtccatc atgtcttcca gcccgagctg cctgcagagc cggcggccta   138420
ctggagcaag ttgaatgatc tgtttggtaa ttaaaattaa aatttatctt atttttaaaa   138480
agcattccag ggccagtata gtactttgca ccaagtaaat gtacaataaa ggcagtggat   138540
ctaatacatt gaaagcgttt acagaggtag ctaaagacga ctaaagcga gggtgt cctcggctca   138600
gaatttcttc ctgtgtgttt gccactttgc cattcattga catggtcatg gacataggc   138660
tctaagcct tgaggaaggc tgggccagac ctcaggggag atgcagcccc aaaccacgtg   138720
cagtcctgtg gacggatgtg tagatgtgcc actgaggaac aatgtcttga gctttcatca   138780
gattctcaga gaattgcttg actgcctttc gaagttgatc catctgtgct cacgtttgca   138840
cccacccacg aggtccttct gtttcagggg atgctgcact gtatcagtcc ctgcccactc   138900
tggcccgggc cctggcacag tacctggtgg tggtctccaa actgcccagt catttgcacc   138960
ttcctcctga gaaagagaag gacattgtga aattcgtggt ggcaacccct gaggtaagag   139020
gcagctcggg agctcagtgt tgctgtgggg aggggcatg gggctgacac tgaagagggt   139080
aaagcagttt tatttgaaaa gcaagatctc tgaccagtcc agtcacttt ccatctcagc   139140
ctggcagtaa gtcttgtcac cgtcaagtta ttgtagccat ccttccccct cacctcgcca   139200
ctcctcatgt tggcctgtga ggtcagccag gtccccttct catctgcacc taccatgtta   139260
ggtggatcct aatttagag acatgaaaaa taatcatctg gaagtacttt atgtcttaag   139320
ttggcctgga catgtcagcc aaggaatact tacttggttt gtgttagtgc ttgtaattgc   139380
cccccagaat gtgtacacgt tctgatgca ttaaagtctg gcctgtatcc ttaaagggcc   139440
atcgctgtgc tgcctgccct cagcaaggac acactttgca gacccacaga ggctccgcct   139500
ccacctcaca ccaaagaaag ggaggagtcc aaagggcatc agtgccatta ctcgtccttc   139560
gataaataca cccttattct gaaccacgtg gagtcatatg gtttgtgatc ctgtccttc   139620
aggtttcagc ttagtgggga agtgggaaag tcagcgtgtg atcacagcac agggtggattg   139680
ctgctgatta tattatgtgc ctgctgtatg caggatgaaa tactttatat gcgtcatctt   139740
atttgactct cacaaccccc tgtgagatag gctctgttac tcccatttga caggtgagga   139800
aagcaaggct tagagaattt cagtgacttg cccaggtcct ctgagctagg aagtagccat   139860
tctggcattt gaaccccaagg cctgctatcc ctagaaccca cgctctcaaa ttcaacctat   139920
gacagaggca agccctggtg ctgtgggagc cccaaggaag agcctctggc ctggtggcca   139980
cgtagcccag gagagatttc tacaggagcc cacacgcgct aaggagagag aggcagcaga   140040
gtaagggggc tttgtggcag agaggggact ggcactttgg ggaataggtg ggtcaggact   140100
gaatgtaatg gagccatgtc agagctgtcc ttctggaagg gcaagggcac ctggacgcgc   140160
tgcccctcag tgctttggac ggttccacaa ctgtgattca cacggcttcc ccaaacgaag   140220
gtacacgagt gggcattctg tgactcggta cttccctta ggccctgtcc tggcatttga   140280
tccatgagca gatcccgctg agtctgatc tccaggcagg gctggactgc tgctgcctga   140340
ccctgcagct gcctggcctc tggagctgtgg tctcctccac agagtttgtg acccacgcct   140400
gctccctcat ctactgtgtg cacttcatcc tggaggccgg tgagtccccg tccatgaacg   140460
gtgggttcct atcatagttc ctgtctgctt caccatgttt ttattttgtg ctgcctgttt   140520
gccaggtact aagctaggaa ttggggatgg agaggtagat aaaatatgca tcaggaaggg   140580
ctgggcccca tctcttactc tccaatatat tggagtctac actggaattt aactggaatt   140640
tgcttttta gtcatttat ttagattttg aagtttcagc tttcatcaaa aatacctcta   140700
aactttatgt ctctgtgatc tttggtctta gctgttttat gtatttagtc ttatatgatc   140760
ataagattaa taacattaca ttcagaagat tatttgttt ctgtcagagt taaaatgttt   140820
gttttttatac tgcattgtaa tattaacgta ctgtaaaata aaagtggctt gttctttca   140880
aggaacagta tcctcaacaa gggtcattag ccacaatttt taaaaaattg gacgtcatag   140940
tttacatgtt agagggcgtt ttgaagcttt gtatttttaa attaaatgtt atagagtgat   141000
gttttcatgt ttcataattg ttttcatctg tgcatttgta gccaacttga aaacaaagat   141060
ccagggatta ctacttaaaa gccagacttc ttggaggtta tagtgatgat tttaggaggt   141120
tcttgagccg tctcataata acctcagggt gagagatggc caacaggaga cagtcgaggg   141180
acttagaaat ctgaatgaaa tctgaagttc aaatcttcag acatatacca ctaaccaaga   141240
gattggtacc tcagtctagt attgtctgtt tgtctaaaat tggttctaag aatctaggc   141300
tagtctgtct atcccttca actttttgtga ggctgcacaa atgtaaaatg ttgaataaaa   141360
agcactgatg gaagtgtgta gaaattcttc tctttgttct gttgtaattt tagttgcagt   141420
gcagcctgga gagcagcttc ttagtccaga aagaaggaca aatacccaa aagccatcag   141480
cgaggaggag gaggaagtag atccaaacac acagagtaag tctcaggacc cattttttc   141540
ttacatgttg ttcctccagg acttaaaaat cattcacaga gacgtgcacc gcggtgagtg   141600
tggactcctg gaagcgcacc gtagctccgc tgtgtcctgc tgctcctccc tagctgtcag   141660
ggaggctgga gtccattgct ttgccagctc ttgtttttcc gagtgaacac tttatccgta   141720
cacatgcggc tgtctctgac cctacagacc agctgggatg ccactggggg agcgctccct   141780
tccccccgca cttcccacac tctgcagtta ttctgagatc cttgagggca gggaacaggt   141840
ttgtcttctt tgtgttctca gaaattaatg ctcggcctct ggtcagcaag caacaacctt   141900
ttgttgagtg ataatgaata aataaatgtt cccacatga gtattcagta acctcagtgt   141960
caggttcagc catctgtttt ggtggatatt taaagaaaaa ttccgcttt cctacagaaa   142020
```

```
aaaaaaaaaa tccaaatccc agtgattta a gccagttata gacttagaca tatactacgg   142080
cttttcatgc actttcctcc caattctaga gtaggtattt tactaggaaa atggtggcag   142140
tgcctgttgg gaggaagatt ctttggccaa gtgtctttg ttcttgccag ggcccctagg    142200
ctgctggggt gcttcagctt ctttagccca gtgtctggtg gggaatggcc cctgttgcct   142260
gtcccacaga ggtggggtg cctcacctgg agcctgtcca cacattttac acagcacgct    142320
tacctggagc atcaggcatc ttttccatgc tctgtggctc aggaaacacg ccttttcaat   142380
catgagtgca ccagtgcttt tgggcttttt ctccccgctt ttgtgcaatc ctggttgtgg   142440
atggagtttt cctgtcttta gtcttctgca tagtactttt ctcttctggt tccggttca    142500
aggttttgta attagagaat gacccagaag caatggcatt ttaatgcaca gccaaggact   142560
tctctgaatt tgtatctcaa acctctgtgg gtccttcagg cttcagtttg tgattcatg    142620
atttcttgtt gctacctaag gaatatgaaa acacccacct ccctactctg catcttccag   142680
ccgagtggca cctcaggctg tggatcctgt gcttctgtgg tgaggataag aatagtgcca   142740
accgtgtgga ttgaaatcaa tcagttaatc cctccatgta aagcacctgg aacggatgac   142800
agtcttgtta tgaatactca acaaatgcta tcatgatttt tagttagctt tccattgctt   142860
taaaacagtt gagacatctt ggcggtttga gttagagcaa cgggccctga agtgggttct   142920
gtttgggtga agatgattat gcttattccc catggccctc tttaggcaag agtgggaagc   142980
tttctttgtt tttttaatca cctcgatagg acgttacttc ttaaaggtca tccaataaat   143040
attaataggc cgggcgcggt ggctcacgcc tgtaatccca gcactttggg aggccgaggc   143100
gggcggatca cgaggtcagg agatcgagac catcccagct aaaacggtga aaccccgtct   143160
ctactaaaaa tacaaaaaat tagccgggcg tagtggcggg cgcctgtagt cccagctact   143220
tgggaggctg aggcaggaga atggcgtgaa cccgggaggc ggagcttgca gtgagccgag   143280
atcccgccac tgcactccag cctgggcgac agagcaagac tccgtctcaa aaaaaaaaaa   143340
aaatattaat aaagccaact cgttagcgtg gggcttaatt gcttaagtcc aatgagaagt   143400
ccttctctat cctaggaagt tgcccaaact gtagaatctc gtggcctgtg ggtaatagcc   143460
acgtaataca cactcactgc ctcaacaaat catattttag taggtatgat attctagact   143520
caagacacca ttctgtggat cttcccaagg gtgtgaagtg tccacagcct ctgccttggg   143580
agtttccatg cccaccagaa ccatgcccca agcccctcaa gcactctgac ctaggaaagc   143640
cagtgaagca aggatgacaa catggccctt tgatactagc tgagggacag acacaggtcc   143700
tgggagacca gagaaagacg aggggcagag gaggtgtcct aaaggaagtc tgaggctgag   143760
gagccacagg atggcttcca gctgtcacag gctgctgctg gccttatcac agagagtggg   143820
ccagagggct gggaaccaag gccagagctc aggttcagga ccattccagc aatcccagca   143880
gaaaatgggg agaattgtat ggtataggc gatatgaagg tagaatctgc aggccttcag   143940
tggccaactc agagtctaag tggattccac agttacagct tgagcagctg gttgtaggtc   144000
atgcttttcta cactgggcat ataggatgtg ttttttaaaa agtcctctct taaccgttgc   144060
ttgtttagat cctaagtata tcactgcagc ctgtgagatg gtggcagaaa tggtgggagtc   144120
tctgcagtcg gtgttggcct tgggtcataa aaggaatagc ggcgtgccgg cgtttctcac   144180
gccattgcta aggaacatca tcatcagcct ggcccgcctg cccttgtca acagctacac    144240
acgtgtgccc ccactggtga gtctgctcgt tccttgcaga agaccaagta cggtgaaagg   144300
caccggtagg ccctgggctg ggcacacgtg agagggcagg acagaatccc cgcagcccag   144360
aggctgcctg ctgtggttct ggtgcccact gtggttctgg tgccaggctg ctttcctcag   144420
gcaccacgtg tggaggtcgc tagtagaaat actgggtttt ctaaaatgaa ctgaggccct   144480
acatccctaa gagattagtg ttagacctga ttctagagca actagaccac tttgcttaat   144540
agcagaccag aaaccacacc ccctcgagtg agtgagattt tccttttggag ataattcatg   144600
tttttctaca cagttttgca gttgtcttca gaattggttt aaagtaggtg ttattgccag   144660
gcgcagtagc tcatgcctgt aatcccagca ctttgggaag ccaaggtggg cggatcactt   144720
gaggtcagga tttcgagacc agcctggcca acatggtgaa accccatctc tactaaaaat   144780
ataaaaatta gccaggtgtg gtggtatacg cctgtaatcc cagctactca ggagactgag   144840
acaggagaat cgcttgaacc caggaggcga aggttgcagt aagccgagat cgcgccactg   144900
cactctagcc tgggcaacag agcaagactc cgtctcaaaa aaaaaaaagg taggtgttat   144960
tgatcagaac ccttgtttca gataacatga ggagcttagc ttgaggagag tgagggtgga   145020
tggagggga ctgacttctg cccagtgaaa tggcatcatc tcccaccagc ccgctgaaat   145080
aagatgatgg ggcctgttcc ttagggcctg cagcatcctc aggcaggaaa gaaaggccga   145140
cctgcaggg tgtgagccag caggtgtagg tcagggagaa tggagccagg tcccagggaa    145200
gaggcttgtg gctgcctgag aagggtgcgt gcctgcctgt gtgtgtgtgt gcacgtgtgt   145260
gtatgtatgc tggagagtct agggaggctt gctccaagga cgcagtattg tttgatcctg   145320
agagataagg attctgccgc agggaatgaa ggtattccag atggcgggct tattccgaag   145380
aagaggccag tgcctggcgg tgctggaagc agttgcagaa cagggagttg taggctttcc   145440
tgggaagaga gcagcagggg tgctggagaa gcaggccaca cttgctgcat ggggttgctc   145500
tcggccccac tcttggtgca cagcgagtca ctgtgggttc attagcatct ggttatgaga   145560
cagtaactgc tccttttgag gggctcgtgg agaccatgca ggagggcacg gtcttgaggt   145620
catgccgtcc agagcacacc tgaggatagg ccaggacggg ctgcacgctg taggtaaaat   145680
tcctccagca agctcttcac tggcattgag gagttccctg agtgcggtca tctgaaggc    145740
agctgtaaca ggcactgcag tctctccctg ggtgggtacc agagaggagc ataggggagc   145800
ataaccgatt taaagagagg gcttttcctgt ggtgaggtaa gagattagct ggtcattatc   145860
atagagcccc ctctgccttt gtgcagatgg gctgtgggaa tcctggggtt ccgttgggtc   145920
ctttgtcacc tcactgaagg catgtaagct gagctggcca gacccgtgagc tgatcctgcc    145980
acttgaacag catcaagcct gcctctggat tcttctgtgc atggcacttg tctgagcacc   146040
tcacgcacag agaactggac ttcagagttt acagaaataa gctgtatgt tcattttcat    146100
gcctgcttgc caataaacat atctgagctg aacctcattg aacgcctgcc tttattctag   146160
cacagcacct gctgtttgtg ggcgaggggt gctgtctcta actcctgcct gcttctccca   146220
gcactccctg agtgggtgt gccagcagcc tcaggatgag gacaggaagt gggagggcag    146280
agcagatttg gagggccac ttgatgggga aggaagtccc aggaagcagt tggagctgtt    146340
ttctggggga gaaggtgcca gctctgggac agtgttgggg tagtgaggag ggagcccagt   146400
ggagagaagt cgggcttcct gcttcctcac agtatgtcctg tcctgactca actcggatga   146460
tgtcacttcc ttttcatctt ctcaggtgtg gaagcttgga tggtcaccca accgggagg    146520
ggattttggc acagcattcc ctgagatccc cgtggagttc ctccaggaaa aggaagtctt   146580
taaggagttc atctaccgca tcaacacact aggtactctt ggggcctctc cttcaggtca   146640
ccattgtcgg acatctaccg ggaggaaatc cagagccccc agtactggga tcttctcatt   146700
tgactccaga aaagatttaa gcatgataat aatacaaacc tatgtgaata cattttgcag   146760
```

```
tgttggcaaa actccttta tactgagaaa atagatccca gttcctgtgt tttgtggctt    146820
gaatcccagc tttgtgtatt ccgggcttgt ttgaagtcag gaaaggttca tgtgtagtgg    146880
acaacgtgag accaaattct gccttagatt ttgcatttag gctaaacagt ggcagcactt    146940
gtctcagaat gttttcttgt gttcaccagt ctgatcctgt tgtgtctcag tggtccattt    147000
tctcatatgg gaacaagcag acgggagcag atggagtcag gtttcttggc actcgccttc    147060
cccagagcct agaggcagca tggggagaaa gcaggcttgg ggctcagaca gtcctggtct    147120
gcttccagcc ctcctacctg agcagcgcag ggcaagtccg tctaacctct agagaccctc    147180
agttttgtca tatgtaaaat gggggtcgtg tctatttcat agaattgttg cagatttaga    147240
aattacattt ctaaacaaat gttacccctt atttctaaat aagtgtctaa atgaataagt    147300
caccactttt gccccctattt gatggcaaga ggtgtgatct tgtggtggga ctgtaatcag    147360
tcagttctca gtgactgtgc cctgctgtgg tgtttcctgg aatgttcctg tcttgtccta    147420
gaaagtctgg caggggcacc ctgactccac tgtccagtcc tctccccagt ccctcgggct    147480
tctgcagatt tgaggcttgt ttggatccca gaaggttgtg gcaggagaca ccttgcctct    147540
actttcccct ttataattca atgtccaaag agagccctga gcaggtacct cacgccagct    147600
gcctcacgga gctcctcctc ttcctggctg tgaggatcgg tatcagtggc ctcctgctct    147660
ctccccttg cctaacacga gcacctttgc ttacttgggt gcccttgctc ttgaactgcc    147720
catcggacgt gcgtgaccca agactgtgcc gcagtccttg ccttgtctgt gctcattttc    147780
tttgttcatt tttttccctg taacgtaaat tgttatattt gtctgtatct gtgtctgaat    147840
cagtcctgca cgctctcctt ctctctgtct cttgttcttt cttaccccg tttatcacgg    147900
ggaccccgat gtccattgct ctagttctcc tgtcctaagc accccatccc gtctctctgg    147960
ccttaccaca agtggcgtgg ctgcctcaga catcatgatg gggacatgaa gcacagctgt    148020
cagaaacaac tgttcgttag atacactcga atgcagctca tcaatggggaa tggagggtct    148080
gtcggatgta ttttcactga atccccgttc ctaccttgat acactctttt taatctattc    148140
ttctagacag tcagaggaa ccattacttt gacttttaaa ttttttagcag ctttattgag    148200
gtagaattca catactacag atttcaccca ctctaagcgg acagcttggt ggccattagt    148260
tttatccaca gagttgtgca gccagctgca cagtctcagg gctggactcc agggaagatt    148320
ttagcccatt tagtgagtgg ggcagaagtg gccctggccc tgcacgaggt tgcctgcatg    148380
ggcgtccctg ccctgtccct gtgtctgctc cactgggggt tgaccaggct gccagggccg    148440
acttgggcct gtgccacctg cctctcatgt gtctcggaca gtgcagccga tgtctatact    148500
tcggtttcct caatgatgaa atggagggga tagtgttccc cgcatcatag aactgtgtga    148560
ggtttaaggg actcactgcc cttggcgtgg agccttctcc aggggccgtg ctgtgtcggc    148620
gtagctgtca gctctccgtt acaggcttga gaagggttga cactctctca tgtaacattt    148680
atatttctag gctggaccag tcgtactcag tttgaagaaa cttgggccac cctccttggt    148740
gtcctggtga cgcagcccct cgtgatggag caggaggaga gcccaccaga agtaaggcca    148800
caccctgtgc tggttggcac atgggcagtt atggccgctt gcaggccttt ggtggggaat    148860
aaaataaggc agcaagctgg tgttcttttt ttctcttacc ttattttttga aagagtagct    148920
gaatggtgtc ttgactgata ttccagagca gggacaaagc ctgctgaggt ctgggggctg    148980
cgattaccaa tggctggaat gcattttatt acggtgcatt ccatgttaag gatcaatacg    149040
attgtgccct ttctggaaaa tatcttttag tttatcaata ttcagaggag tgtaggttga    149100
attaaaaatga aaaggcactt tataaaggcc atgagtagta cctggtttca tttttctaat    149160
gtcttgcaga gattttatca ggcttcttga agtgttcacg tacattacgc taacacgata    149220
ttaataataa ctgtgctctg gtacagcgga gccagcagaa tgggaagttg tggaatgcag    149280
gcccttgatt ctgatagaag gtgtggtttg aactcacaga aatgacagtt tggaggggtag    149340
acatatgtca caagtcatca agattgtctt taaattcatg catagaagct aacagggtgt    149400
cataagcaag gcctgtaaaa tgtatgaggg aattcaaaga taatttatta aaaagtaatt    149460
catgtttgga gttttgtgcc caaggagtc cttgatttga aaaatgggct tttgcccatc    149520
agattgtttc aggggccgtg tgtgcggagg ccctgccttg tgccccgtga gctcagcctg    149580
acagaaatcc tttggtagca cttaaggctc ctcttcctcc cattgaggcg gggaagactc    149640
tgggttctgc aggcagaggt ggttgtgggt gtcttgctgc tcttgttgac atgtgggctc    149700
tccttccagg aagacacaga gaggacccag atcaacgtcc tggccgtgca ggccatcacc    149760
tcactggtgc tcagtgcaat gactgtgcct gtggccggca acccagctgt aagctgcttg    149820
gagcagcagc cccggaacaa gcctctgaaa gctctcgaca ccaggtttgc ttgagttccc    149880
acgtgtctct gggacatagc aggtgctggg gacagtgggt tccccgctga agcgtccagc    149940
agcttcaacc aggccgtttt ccttcattgc tagaattgaa acaccgtcc gtgtggcctg    150000
tgcaggagat gcagacccaa aggtggcctc ctggtcagtg agaagctgga aacgtgacag    150060
gaactgacgt ggggttattg agcatttagg ggaagacgtt agcagagcag gaatgagcag    150120
gcaactagta gaacacccac ttaagggctc acggacaggt gctcacttag gaagtgagtt    150180
tcatttggta ttacaccagg ttcctttagg caaagcggag ggaaagttct ggtgttttc    150240
acttgtaaga tttgaagga aacaaaacac tctttacctt ttttctaaaa tgtaggtttg    150300
ggaggaagct gagcattatc agagggattg tggagcaaga gattcaagca atggtttcaa    150360
agagagagaa tattgccacc catcatttat atcaggcatg ggatcctgtc ccttctctgt    150420
ctccggctac tacaggtacc tgagggaaag ggtgcggggg agcggttgta cttgggctag    150480
aatgagagaa gactggcatg ctcaccacac cagtgatgcg ggaagacctg agtgtggtct    150540
gagttggaga ctgtggtgct aaatacgctg cccctttcat aagcaggagt cttagtcagg    150600
cccagggagg aagtaaaatc tggaaatgaa tgagaagcat tctctcctgc cagtcaagaa    150660
atgagaagcg aaagaattct cacgggctgt aagaccagca ggatttaaaa gttgaattag    150720
ttgcttatgt taagaactca accaagttca tctacacaag ctgaatctcc agcttttcct    150780
aagaaaccat gtgtggcagt ggctgcaggg cagggcacag ctgggcctga gcaccccgct    150840
ccctgccacct ctcccctccc tgggccctgc ctgtcactgc ccactcctcc accaagcgct    150900
ccggttgtgt gcctgcccta tcacaggcat cggagcttgt cacctggttt aaaagaagag    150960
agttgtgtgg ggatttggga tgcacgtttt tcactcaaaa gtattttagc gtagagctct    151020
gtgattccgt agctatttag gagtttaagc accttgaagg ctttaattgc agaaagttcc    151080
atgtggacgt gcaatgtgtt atacgcagtg tctatgagac tcaaatgttt attagggcgt    151140
tgaagtaaac tgagcacttg caggggccatg gatccagcct tcaaggagct cataagtcag    151200
gaggacccag gagcaatgac ctgtcataga aggcagaaaa gaggggcaca gaggtgggtg    151260
ggaggcatac acaggcagct cctgagctc caagggagc aagtgcttcc agggaagggg    151320
gcgtggaggc ccctttggag gaggcaagtt gatctgggt ctggcagagg gttagctggg    151380
gacatttagc gggaggctgg tgcccgggaa ttggggggat gcccagcaga aagacatgag    151440
gaggctggcc tggggcgtgg gggggtgtga aaggttaagt gggggcatta tcctgctccc    151500
```

```
gctcctgccg gctgtatctg gtcagcctgg gcaccgaggt gggggttctgg aaggcactgt  151560
tcaccaaaat gcttatctgg gtcccccaga gagcttgcct gcctggactg tcggctcgcc  151620
tgcaactgct gactcctaag cttttgcagc tcagcccaca accagttcct attcacagag  151680
gtgggagctg aggggtgaca agtgactgct gcagtcttat ttgtcataga gaaaaagtga  151740
cagagtccag cttgcccact ggcccctgcca gcttaactgg ttataaagtg acaaatcccc  151800
aagacccaca gggctctgca caacctgggc cctcctgcca gtggcggcga gggcaggtgg  151860
ctcacggctg ggtgcctgtc tgggcaggag ctgggctggt atggggtggg cctgcggccc  151920
tgcccccctg tgcagatcaa gactcagggt gctggtgttc acaggtgccc tcatcagcca  151980
cgagaagctg ctgctacaga tcaaccccga gcgggagctg gggagcatga gctacaaact  152040
cggccaggtc agtctcgcgc ccccgccgcc tggcctctgt ccgtttctgt cctcagactt  152100
tggcgcttga cacacccagg agaaaagctc agtgcacttt ttaaatgaaa ggaagttttc  152160
cttttttta aaaaaaatt taatgttcat tgttttatc tgttttattc ctaggtcccg  152220
caagcagagg aagcattagt tttgttttta tttatgttct gtattccaga aagtagttaa  152280
gagacctcac atgtagcgat agagatgtgt gtaagagaca gtgagaggc gtgacttgga  152340
cttaagcaag gaccgtgaga cacaaaaagg ggggtgagga cagagtggag tcagctgaaa  152400
tgctcaggag gaagtagacg ccatgaaggg ccatggtatg ggggccgca ggcgtggccg  152460
tgagtgtccc tggggccagc tcttgggggg ctccctgagt gtccctgtcc ctgtggccag  152520
ttctgggtgg gagcccgtg tgcaggcaga cagctcggcc acttcctagc aggtcacatt  152580
ggtctgtgct tctgtttcct cctcagataa gtgaagggat tcaagggtct gggtgtggtg  152640
gctaacacct gtaatctata acattttagg aggctgaggc aggaggctta cctgagctca  152700
ggaggttgag gctgcagtga gccatgattg caccactgca ctccagcctg ggcaacagac  152760
cagtactctg tcccttaaaa aaaaatgtaa acagaaacgt agggcattt gcatatgatg  152820
gcacatggcc tggagcccta caggtgtatg ctgggcgggg cccggctgtg ctggccgact  152880
tgcacctttc cctccacccc ggtgctgtgt ctttcgctca ccgggttcct gatttagtga  152940
aagcagttgt gcaggacagt tctctttgta gcttttgttt ctgtgaaat gggtcagaat  153000
atggtgttta gaaacactta tgagctctga gagtttcctc ttctgagttc ctggcctgga  153060
gccttcacag cagaaaccct gtgatgtcac aagcctgttt ctgttccctg ctctctgcct  153120
gtactgtcct gttttgtgcc tgccggtttc agtgacagga agcagggagc tactggacca  153180
gcctgtattt ttctagacat agttggaaaa agaagtccca ctcttctgtc ctttcacctt  153240
tgacagatgt ttccaccca agataagtga aaatgaccaa taggatgcac tgtattttc  153300
atgaaagtgt ttctgaaggg caggctgaga gtgagaggcc tggggctcac tgggtgcctc  153360
tggcctttgtc ctgggcccag ggacactggt ctgtgcccga ggtattccct atccccccaa  153420
ccccgctgca tttggccaca tccttcaatg tttgcgttgt gtccagcgtc cgcaaaccaa  153480
ctgtcatggg atcatactgg ggctgaagta cggtcccacc cctgccctgt ctggggctga  153540
agtacagtgc cacccctgcc ctgtctgggg ctgaaggaca gtgccacccc tgccctgtct  153600
ggggctgaag tacagtgcca cccctgccct gtctggggct gaaggacagt gccacccctt  153660
ccctgtctgg ggctgaagga cagtgccacc cctgccctgt ctgggctga aggacagtgc  153720
cacccctgcc ctgtctgggg ctgaaggaca gtgccacccc tgccctgtct ggggctgaag  153780
gacagtgcca cccctgccct gtctggggct gaaggacagt gccacccctg ccctgtctgg  153840
ggctgaagga cagtgccacc cctgccctgt ctggggctga aggacagtgc caccctgcc  153900
ctgtctgggg ctgaaggaca gtgccacccc tgccctgtct ggggctgaag gacagtgcca  153960
ccctgccct gtctgggct gaaggacagt gccaccctg cctgtctgg gctgaagga  154020
cagtgccacc cctgccctgt ctggggctga aggacagtgc caccctgcc ctgtctggg  154080
ctgaaggaca gtgccacccc tgccctgtct gggatgttta gccctagat gccactggac  154140
tgagccgcta cttgcttttg ggaaagaggg gtgggggtta ggggtctggg cgaggggagt  154200
gcaggggctc ctccttggcc tgagagctgt tcatacagac tcctcgccca ctccctgcag  154260
ggtgctgggt cccagggggg aaatggccct tggtgccaag aacgtgagtt gggcgtagtg  154320
ccagtgatga tggagaacag ctttttatgg gcacacagcc cacagcactg tgccaagtgc  154380
tcgaggcttc ccgagaacca ggcagaaagg aggacagtcg aggtgtgctg actgcgtggt  154440
ggctgcgtga tctagagcgc gggtcacaaa ggcgcgaggg agctctggcc ttgggtttac  154500
cgcaatgact gccagtgcgg gagactgaa aaggaatcct acgtattggt tccgtgtgtt  154560
ggggactcca ttcagatgtc acttaggagt gaaagcatcc cttcgtagag cctctttctg  154620
tgtcaccctc ctcagctgct cctggggttg actggccct gattcatgcc tttagcatgt  154680
gctggagctt cccagcagct gtccagcccc tgcccaccc tctctgtggg ctcccttgcc  154740
cgtaacctgg ggtgtctgaa cgaccctggc taaggggcag actgttagac ggtaggcatg  154800
tgctgagtcc cagtgccac acccaccac caggagcctg gcactggtc cgcagcactg  154860
agcagtgccc cgtttctgtg gcaggtgtcc atacactccg tgtggctggg aacagcatc  154920
acccctga gggaggagga atgggacgag gaagaggagg aggaggccga cgcccctgca  154980
cctcgtcac cacccacgtc tccagtcaac tccaggtttt tcaatggcct ttttctttt  155040
aacagaaatt tgaaatttct tatcagtcat ttgatttgtt tgaggtgctt cttgaaatga  155100
gcctctcatc tcatgtactt ggaaaatacc catctcgcat attccacagg aaacaccggg  155160
ctggagttga catccactcc tgttcgcagt ttttgcttga gttgtacagc cgctggatcc  155220
tgccgtccag ctcagccagg aggaccccgg ccatcctgat cagtgaggtg gtcagatccg  155280
taagtgagcc ttcccattcc cctcacacct gcacgtgcca cacgcaccac acacaacaca  155340
caccccacac acacacaccg cccacacaca tgccacttgc acacacaccc ctcatgcatg  155400
caacacacac acaggccaca cgcaccatag acaccacaca cacatgccac atgcacacac  155460
atacacggca tgcaccatac acacaacaca cacagcacac atgccacaca cacacgccac  155520
accacatgca ccacacacat gccacacgca cacactcca acatgcatgc accacacaca  155580
cacacacaca ccacacacac cacatgccac acaccacaca ggttacatgc acacaacaca  155640
cacatgccac gtcacacac cccacacacc acatgtatgt gccacacaca gcacacaacc  155700
acacacatgc accacacaca tgccacatgt gcatgcacca gacacatggc acacactaca  155760
cacgccac gtgcacacac cccacacaca tgtacgcacc acacatgc cacacacaca  155820
tgcaccacac acatgccaca tgtacacaca tgtatatca caccacac acacacaca  155880
ccacttgcac caccgcaca cacacacat gcgcacacac cacacatgt acacaccata  155940
acacaccata cacacaccat acatgccaca cgtgtaccac gcacccacac agacacagca  156000
cacgcataca ccacacacac acgcacacat gcgtcccgca cagtaatgtc tcttgggtgt  156060
aagaacacga cttgccagta gtagcgttct ggatgcgttg cctggattct aacagcgcga  156120
ttctcccctt gccctcctgg ttttccacat ctccagcttc tagtggtctc agacttgttc  156180
accgagcgca accagtttga gctgatgtat gtgacgctga cagaactgcg aagggtgcac  156240
```

```
ccttcagaag acgagatcct cgctcagtac ctggtgcctg ccacctgcaa ggcagctgcc   156300
gtccttggga tggtaagtga caggtggcac agaggtttct gtgctgaagc cacggggggcc  156360
catctgcctt gggacctggt gttggccaga ggtgccgggt gcggctgcct ccttccaaga   156420
gttgacccga accggactcc acggcccacg tgagctgcag tgcttctcag atggagggggg  156480
ttcagcgacg gtcagtgcca ttcacaggtc actgtgatgt gggttgtggc ggcaagcca   156540
tggtttgggg tcccgtatcc ctgggcttat gacatcattg tagtagccca tccccacaga  156600
accacggtgt gtggtggcgc tgaggcatcg tagatggtgg aaatgctact ggcttcccca   156660
tgctctgccc tgaggcctga ctgcctcact ccccttctca gttatgttcc aggcccccg    156720
agcttcctgg ctggacagct tctctctctgg gggccgtttt gtcacagtga ccctgtgtt   156780
ctagtcccaa atctgggtgc tatagtctct ttttagcgtg gtggttgtct tagtcttttt   156840
tggctgctac cacaagttac cttagactgg gtaatttata aacagtggaa atttacttct   156900
caccgttctg ggggctggaa gttttcatgg tcaaggtgcc agcagatttg tgtgtgatg    156960
agggctgctc tctgcttcat agatggcatc ttctggctgg tcctcacgg tggaaggagt    157020
gaacaagctc cctcaggcct tttagaaggg ccccaatcca caagggctct cccatcatga   157080
cctcatcacc tcccaaggcc ccaccttctt gtactgtggc actgcaaatt aggtgtcagt   157140
gtaggagttt caggagggat agaaacattc agaccatccc agcggtcaag tgttcatcct   157200
cttgagttcc tccttattct gcttctggtt tatcaggatt cagccagtgc agcatggtac    157260
ctgtattctg tggcacatca ccacatggta tttgccaagt atccatcacc tgcacacgtg   157320
aaatcattgc ccgtgggtcc cgacatctgg cgaagcatat tcaaggatgg cagaactgtc   157380
agagctggca cctctggttc cttgtcatgt ggcattacct agtaatccat tttatgatag    157440
caatggaaac tcatttcttc aacaaacacc tgagtggctg ccgtgtgcca gccgtctggg   157500
gcccttggtg agaatggcat ggtggtgccc atcagggcct gcctagcccg tgctctggac   157560
gggctcctgt gtgtcaggaa cgacaatgct gtcatgacgg tgaatgattt ttttttttgc   157620
catcactcca gccgctaaca tttgcggagc tcttcctccc gcaccccac ctgacaaggc    157680
caagggtgac cttggcccca ccctaggcgg ccaaggtcag aggttagctg gcttgtctgg   157740
gtcacacaaa atgcagcaga ggttgaggtg agcacatgtc cgtgacctgg agcctgactc    157800
cctctctgcg agtcttgact gctcttgcct agactctgtc ctccccgagc ccaaacgcca   157860
gtcatcttcc cttgtgggtg tccttcagcc tggtgccatg ctggtgactc agcagccgtc   157920
cagggagtgg aaacaattga gtgtgtgggt tccctgtgtg ggcatctctc ttcacggcga   157980
acaccctctg ggtgttgccc acacgatgtc aaagcgcctc ttggaagggg tccttctcct  158040
ttgtgggaag tttcagctgc tgggctaact tgaattgtaa ctgtggtttt gtgctcaggc   158100
ccagatcccc ctaggcaagt gttgtgccat cagtaatcaa atgagaaata atcatttga    158160
aaagcagatc ctaaggcagg atggtcatgg acactcactc ccagctcttt gtgcactcat   158220
gctttctgga agatggccat cctctgtgaa ggtttcagc gcgtcattct tggtacccac    158280
gtatccagag catgtcgttt tgaggtattt gcccaccgtt gtgaaatccg tgccacccga   158340
gagcaggtcc tgatgtgggg ctttcagaag tgggacctgg ggccgtacgc agtccttagg   158400
gaggggccgt gtggcgttgt gcgtgtgagg ggatagcaca gggtgaggtg ggggcccaag   158460
aaggaagtga cccacaaaga acagcctcct cttttggtcc ttgttcctgg gatggctggg   158520
agtggcttct gtgtcgtccg gccatttccc ctgcggagag gctcctacca ctgccgagaa   158580
cctcatcatt ccacaaaaac aagaggccgc ctgccatcc agcgctccat gggaattctg    158640
tgtccccata gtcttgggct gaaggagggt gacattcctt gctgacttct gcaggggtct   158700
cctcactgtt aaagagcaga ttgaaagtga agaacgtggg ctaagtgttt aggtcgatat    158760
ttaacctgc taggttttgg atactaagtg aaattgaagc cattttgttt gaagttgaca   158820
gaaaccacta tcaggggatcc ccaagactac cccaggctttt tctagaaaga ctctcagcta   158880
agatgtgtta tggtaaaagc acacaaaaca aaatcagcaa agaaaattag caagggcaga   158940
ggcccatggg gcgatgtccc gaggacacca ggcttgagct tccagaatcc tctcccagcg   159000
gggtcgtgca ggacgcactt aactccccgc acagtgacgc gtgacagcg gtgtgcagtg    159060
tcgtcgccag gaaagcacac tagagactcg gtgccagggt ttttactggg ggctgggcac    159120
atgggcaccc tctgcctgcc tcgtcccag actctggact cccggaggga aggcaagttc    159180
tcagcaccaa ccctggtgcc cacacaagca gctgagcaca gggagcccct cctcagtgag   159240
gatggtgggc accgtcccaa caccagccag gggccagcct tgcacacagg cctctcagga   159300
tggtctccgg cctgctgtgt agtctcttct gcacacaagc gtgagggcag cgccccgcc    159360
tcggctgtgg ggaggagcca ctgggacgtg agctctggtg gcatgcagca gcttttgtct    159420
gtgtgtgcct aggacaaggc cgtggcgag cctgtcagcc gctgctgga gagcacgctc    159480
aggagcagcc acctgcccag caggggttgga gccctgcagg gcgtcctcta tgtgctggag   159540
tgcgacctgc tggacgacac tgccaagcag ctcatcccgg tcatcagcga ctatctcctc   159600
tccaacctga aagggatcgc ccagtgagtg ggagcctggc tggggctggg gcggggtct    159660
cagaatgagc tgtgaaggaa gcagcatcac cctctccaag tgcccaggct cctggccaga   159720
tggcaggcca ggtatcagtg ggaacccagg tgggtgccat ggctgaggtc agtgagacgc    159780
aagagcacag gtgcgtccta gaggcttcct cgggccacctc cagcgagctg gagctctcgc   159840
ctctgctgct gtctcatgtg gcgcttagca cactctccca cgtgcccatt cctgactctg    159900
ctctcgaggc catcggctct cattctctgc tcccagaacc ctgttattac ccaggctagc   159960
ctcctctctg caccttcccc gccctggccc agtacctccc tcttgtttcc actgtgattc   160020
cgacctcacc ttatcttaaa gctgctggac ggcaggttct gtacacgt gtccttgaca   160080
aagcacggct ggtgccgcaa ccccccagcg agcaagtcaa gctcttcaca gcgatgtctt   160140
acaagccag agggctctgt gacacccggg tctcaccgcc actcttccaa agtcgcagag   160200
gcttagcag agatgggccc agcctctctg agtcataggc ttctgcacac gggagctgtc   160260
tttagaggga gggtggaatt tcatcagcca cccacatggg ggagttgagg gcaaaatta    160320
ggagcaaaga tgggaagggg tctgggagga atggccaggt atccccttg acaagtgggc   160380
aggaaacggg ggctaggtca aagttgagtg gaagacctgg agggagacgg gaaggtctct   160440
gtaggcacag ttcagacagg agggaggtgt gagccaggc acatgccggt ggccgtctgg    160500
caggatttgg gacatgctgg agcagggaca gcggctcatc aggggccatt gcctcatcc    160560
aggccagagt gtcacaagcc cgtggggagg cccttctcgc ctgtcatcct tgctgggcag   160620
tgggtgtgt gctagcagga caggcggacg gctggcaact gtctctgcat ccctggagcc   160680
tggcataggg ccaagtcaca cggggcacag gcctgcaaat caggcacata tgttggtgca   160740
gtgacgtgat tttgggggc agccccagaa caggcccagg acacaggcca aagccctgcc   160800
tgtgctggtg tgttgggctg ttctatggct cttgctgtgg gcatggagga ctcagggaag   160860
gagagttgag gtggtccagg agttgcgttt gggatgcaga gagcttgtgg catccaggta   160920
gaaatggtgc gtggggctga cctcagcacc atgggcagag gggccgtgtc acgtgcctcc    160980
```

```
gaggtggagg tgggaccacg tggtgacaga tatacgcatc actgggcacg tttttgtggg  161040
tgttgggggg catcgtattg gctcctctgt tcacagtggc cactcattca gtccctggct  161100
accaggtcct cactgtgcca tggggaaggc cggcgctgtc gggggatcac agaaggcagc  161160
acgtcatgat ggcatgtgcc atgaaggaaa agcacagggc actcaggaag tagagggac   161220
tggcctgggg tgtgggaatc tagggcctcg ttgagggaca gagagaggaa gtgtgtggtg  161280
gccagcatgg aggtggccac aggggaggct gagttaggcc gagagggcag ggcgttgggg  161340
aggtagacgg gctcagccac tcagggagtg gtcaagcaga ggctgaaggg tcaggccagg  161400
ttgcaggggc ctggggagc cactcagggt aggcgctccc gggagcccgc ctggcccata   161460
gctctacact cccgcgtggg gccggacatg ctgtgaagcc ctctccacgt tggatggggg  161520
tggctgagcc tggatgctgt ctcccgtttt cagctgcgtg aacattcaca gccagcagca  161580
cgtactggtc atgtgtgcca ctgcgtttta cctcattgag aactatcctc tggacgtagg  161640
gccgaatttt tcagcatcaa taatacaggt gagtgggccc tggctgtctt cctctgcaca  161700
cggggagtgg gcttcccttc tcttttcctt gcaggatcat accagtgggc cagttttgac  161760
ttggtcggga ggaggcatga acacctgaga ctgtgcagcg attctttgac acagaggcct  161820
ttctccctgt gcagatgtgt gggg1gatgc tgtctgcaag tgaggagtcc accccctcca  161880
tcatttacca ctgtgccctc agaggcctgg agcgcctcct gctctctgag cagctctccc  161940
gcctggatgc agaatcgctg gtcaagctga gtgtggacag agtgaacgtg cacagcccgc  162000
accgggccat ggcggctctg ggcctgatgc tcacctgcat gtacacaggt gagcatgtac  162060
acggtgccca taaggccagc ccaagtcctg ttcaagggag gcaggagcat gctcactcaa  162120
gggacctcga ctaggtgccc tctgatttca cacttctggt gttgcccaa gccggcccca   162180
tcaccttgca agaaaggctc tggagccccc agggctggag tacctggtca gggttgaccg  162240
tccctgtggt cactcatccc atgtggctga gctgggctgg gtcctgggca agcaagggc   162300
tgatatcacc tgcttttcaga tctccaggga ctcactggaa ccctgtgtac aaagcactgt  162360
ctacagagcc tattggggttg tatagaggta accttcgtac tgaacacttt tgttacagga  162420
aaggagaaag tcagtccggg tagaacttca gaccctaatc ctgcagcccc cgacagcgag  162480
tcagtgattg ttgctatgga gcgggtatct gttcttttg ataggtaaga agcgaagccc   162540
catccctcag ccgttagctt ccctagaact ttggcctgaa gctgtgcttt tgtgtgtgtc  162600
tgctgatccc ctgcgctgt tgctggagtc ctgccagtga ttccccacca cagcctgacc   162660
atgggctgcc ttggctcagg gttccactgg cgagctggtg gtccttggac cccagcactc  162720
aggtgtagcg ttgaccagtt ccaaggttgt cccagtgcct gcccatctct cctgagggct  162780
cagggacagt acctggcagt tgggggtgtg gcaggggca ggaatgacca gcctctggga   162840
gggtggggca gaagcctgta cagtgaggag gagctggctc agcctggctg cctatcgtga  162900
gaggggagcc cacggggctg tgggagggg gccgtggtgc ctgtgagcag ggtgaggagc   162960
agccgcagga ggatgaaggt ggaacccaca catgcatctt tgagaccgt gtggtcagtg    163020
gcttctgccc cccaccaccc cccactgctg tgcgtgcata gaattggctt ccctccacctg  163080
ctctggaagt gggttaggag cttggtaggg ctttttctca aggacaaggg ccctgatttt   163140
gctctcaggc ctcagtcctg gcgacatggt ggatctggag cctgttgca ctgccttgcc   163200
tgtgctctc aatcagggtg gccagtgggg agccatttgg cttttctcaa gagcatactc    163260
aggtggacct tgctccactg tttgaccaga tgaggcattc tgaacagcca agcctgtgct  163320
ggtctgtttt catgttgatt tttttttttc ttttctttt gagatggagt ttttcccttg    163380
tcacccaggc tggagtgcaa tggtgtgatc tcggctcact gcaacctccg cctcccgggt  163440
tcaagtgatt ctcctgcctc agcctccta gtagctggga ttacaggcac acaccaccat   163500
gcccagctaa ttttttgtgtt tttagtagag acggggtttg accgtgttgg ccggctggt   163560
ctcgaactcc tgaactcaag tgatccaccc tccttggcct cccaaagtgc tgggattgca  163620
ggcgtgagcc actgcgcccg gcccccatgt cgatttttaa atgcacctct gcatcgttct   163680
tcagtcccca tatgctcact gagcaccact gcgactggca gacgggcaca gggaggcgcc  163740
acgaccagtc ctggccttca aggggcttgt ggtctagtgg gcccaatgct aggtggcgag  163800
tgctccaaag agtgtggtgc acgccttccg cttgaccgct ctccagacgc cacagggagg  163860
caccctcgcag ctgaccacag atttctctct gtggagcagt gtcttcagag cggctgccat  163920
gccactgctg ggcgagggtc tgcgggcggg tagagccagg agcacctgtg aggaagtgca  163980
ctgccatttt cgtagctgct tcccgtgtgt ctcagttaca cacggctggc atgtgtgca   164040
tgatgagacg ggaacgtgat ggttgctttt cagcactgaa agggatactg ctcaggggc   164100
gtgtttcagg atctggttag ggaagaagca gcgagagcac agatgggcc ctgtgtggta    164160
acaagaaaaa agtcctggtt gacaacagtg ccacgaagcg ttagaacaca tagggatgtt  164220
tgtggagcat ttgcatgtgg aaagcagcaa aaacataatg ggaacggttt cttttgttat   164280
gattttaaa aatctcttttt gtaacatcct tcccgctgcg ccgtttctgc atattccttt   164340
atgtagcttt caaactcctc ttaggagttc tggtccctac agggcgtggg agcccaggct   164400
ttacgtagct ttcaaactcc tcttaggagt tctggtccct acagggtgtg ggagcccagg   164460
gcctgtgccg agcagcctgc ctccacgagc tagacagagg aaaggctggg gttttgcct    164520
tttagtctca aaattcgtac tccagttgct taggctctga cttttcccac ttggaaagtc  164580
cctcacggcc gagggtccct cccagccctg atttcacatc ggcatttttcc ccagtattag  164640
agccaaggcc ctccgcgggc aggtggggca gctgtgggag ctggtgccag tctctgacct  164700
gcgtccctcc tcccaggatc aggaaaggct tccttgtga agcagagtg gtggccagga     164760
tcctgcccca gtttctagac gacttcttcc caccccagga catcatgaac aaagtcatcg  164820
gagagttttct gtccaaccag cagccatacc cccagttcat ggccaccgtg gtgtataagg  164880
tgaggttgca tgtgggatgg ggatggagtg ggaaagcctg gaggtggagt tgcctccgac  164940
ttcccagcag attcgccagc agagcccagc tcctccgctt taaagcagca atgcctctgg  165000
cccccacccc accccgcca cccaggcgca gcaggtgctt cccgtccccc cagccctgac  165060
actcaggcac ctgcttgctc cttgcaggtg tttcagactc tgcacagcac cggcagtcg   165120
tccatggtcc gggactgggt catgctgtcc ctctccaact tcacgcagag ggccccggtc  165180
gccatggcca cgtggagcct ctcctgcttc tttgtcagcg cgtccaccag cccgtgggtc  165240
gcggcgatgt atcctctctg ggtccctggt gctggcccg tttcccttgt caacaccgag   165300
gctcatgttt catgataagg tttttgaaacc taacctttgc aaaaacccca cagatgccag  165360
ggtgacaggc cctcagcccc agggaagtaa aatgctgaca aggagacaga aaggagcag    165420
tccagacatt tgctgaccag ggcctctcag aggggccggt gtatgcagg agggtcgcag   165480
ctgaggggca tttctgtgga gggcctgggt gaggggagcg agggtgggcg gtggtctctg  165540
cagacgtccc gcccactcgc gggctctgtg tggctggct tctcctgaca ctgcttctca   165600
ttagctttgg tcattgtgcc tcgatcgccc tctcgggaa aggcttaagt aaagatccag    165660
ttcccacccc cagatgctgg ctgccaggag tttccctttc cacagccctt ccccaagaca  165720
```

```
gaccacaaga gcctccaagc agcacagttg tcctggtgct gacagcacag ccttgcccgg   165780
cgtgcctggc acggctctgc cctcactgca ttggagcagg gctagtggag gccagcggaa   165840
gcaccggcca ccagcgctgc acaggagcca ggcaggtga gtgctgccga gtgggtgccc    165900
tgcctgcagg gcatccagcc agccaagggt tgcaggaatg gaggtggagg cgctgatgca   165960
gctgcaggca tccaggtggc cctttccgggg ctctgctcgc tctccaggct ccctggaccc  166020
ctttgtagac tgtttcagga gaggaactcc caggtgagga cagggaggca gcattcccct   166080
catttgccgg ccttttcct taactcctgc accagcctcc cacatgtcat cagcaggatg    166140
ggcaagctgg agcaggtgga cgtgaacctt ttctgcctgg tcgccacaga cttctacaga   166200
caccagatag aggaggagct cgaccgcagg gccttccagt ctgtgcttga ggtggttgca   166260
gccccaggaa gcccatatca ccggctgctg acttgtttac gaaatgtcca caaggtcacc   166320
acctgctgag cgccatggtg ggagagactg tgaggcggca gctggggccg gagcctttgg   166380
aagtctgcgc ccttgtgccc tgcctccacc gagccagctt ggtccctatg ggcttccgca   166440
catgccgcgg gcggccaggc aacgtgcgtg tctctgccat gtggcagaag tgctctttgt   166500
ggcagtggcc aggcagggag tgtctgcagt cctggtgggg ctgagcctga ggccttccag   166560
aaagcaggag cagctgtgct gcaccccatg tgggtgacca ggtcctttct cctgatagtc   166620
acctgctggt tgttgccagg ttgcagctgc tcttgcatct gggccagaag tcctccctcc   166680
tgcaggctgg ctgttggccc ctctgctgtc ctgcagtaga aggtgccgtg agcaggcttt   166740
gggaacactg gcctgggtct ccctgggtgg gtgtgcatgc cacgccccgt gtctggatgc   166800
acagatgcca tggcctgtgc tgggccagtg gctgggggtg ctagacaccc ggcaccattc   166860
tcccttctct cttttcttct caggatttaa aatttaatta tatcagtaaa gagattaatt   166920
ttaacgtaac tctttctatg cccgtgtaaa gtatgtgaat cgcaaggcct gtgctgcatg   166980
cgacagcgtc cggggtggtg gacagggccc ccggccaagc tccctctcct gtagccactg   167040
gcatagccct cctgagcacc cgctgacatt tccgttgtac atgttcctcc ttatgcattc   167100
acaaggtgac tgggatgtag agaggcgtta gtgggcaggg ggccacagca ggactgagga   167160
caggcccca ttatcctagg ggtgcgctca cctgcagccc ctcctcctcg ggcacagacg    167220
actgtcgttc tccacccacc agtcagggac agcagcctcc ctgtcactca gctgagaagg   167280
ccagccctcc ctggctgtga cagcctcca ctgtgtccag agacatgggc ctcccactcc    167340
tgttccttgc tagccctggg gtggcgtctg cctaggagct ggctggcagg tgttgggacc   167400
tgctgctcca tggatgcatg ccctaagagt gtcactgagc tgtgttttgt ctgagcctct   167460
ctcggtcaac agcaaagctt ggtgtcttgg cactgttagt gacagagcca agcatccctt   167520
ctgcccccgt tccagctgac atcttgcacg gtgacccctt ttagtcagga gagtgcagat   167580
ctgtgctcat cggagactgc cccacggcc tgtcagagcc gccactccta tccccaggcc    167640
aggtccctgg accagcctcc tgtttgcagg cccagaggag ccaagtcatt aaaatggaag   167700
tggattctgg atggccgggc tgctgctgat gtaggagctg gatttgggag ctctgcttgt   167760
cgactggctg tgagacgagg caggggctct gcttcctcag ccctagaggc gagccaggca   167820
aggttggcga ctgtcatgtg gcttggtttg gtcatgcccg tcgatgtttt gggtattgaa   167880
tgtggtaagt ggaggaaatg ttggaactct gtgcaggtgc tgccttgaga cccccaagct   167940
tccacctgtc cctctcctat gtggcagctg gggagcagct gagatgtgga cttgtatgct   168000
gcccacatac gtgagggga gctgaaaggg agccctcct ctgagcagcc tctgccaggc    168060
ctgtatgagg ctttttcccac cagctcccaa cagaggcctc cccagccag gaccacctcg    168120
tcctcgtggc gggcagcag gagcggtaga aaggggtccg atgtttgagg aggcccttaa    168180
gggaagctac tgaattataa cacgtaagaa aatcaccatt ccgtattggt tggggctcc    168240
tgtttctcat cctagctttt tcctggaaag cccgctaaga ggtttgggaa cgaggggaaa   168300
gttctcagaa ctgttggctg ctccccaccc gcctcccgcc tccccgcag gttatgtcag    168360
cagctctgag acagcagtat cacaggccag atgttgttcc tggctagatg tttacatttg   168420
taagaaataa cactgtgaat gtaaaacaga gccattccct tggaatgcat atcgctgggc   168480
tcaacataga gtttgtcttc ctcttgttta cgacgtgatc taaaccagtc cttagcaagg   168540
ggctcagaac acccccgctct ggcagtaggg gtcccccacc cccaaagacc tgcctgtgtg   168600
ctccggagat gaatatgagc tcattagtaa aaatgacttc acccacgcat atacataaag   168660
tatccatgca tgtgcatata gacacatcta taattttaca cacacacctc tcaagacgga   168720
gatgcatggc ctctaagagt gcccgtgtcg gttcttcctg gaagttgact ttccttagac   168780
ccgccaggtc aagttagccg cgtgacggac atccaggcgt gggacgtggt cagggcaggg   168840
ctcattcatt gcccactagg atcccactgg cgaagatggt ctccatatca gctctctgca   168900
gaagggagga agactttatc atgttcctaa aaatctgtgg caagcaccca tcgtattatc   168960
caaatttttgt tgcaaatgtg attaatttgg ttgtcaagtt ttgggggtgg gctgtgggga   169020
gattgctttt gttttcctgc tggtaatatc gggaaagatt ttaatgaaac cagggtagaa   169080
ttgtttggca atgcactgaa gcgtgtttct ttcccaaaat gtgcctccct tccgctgcgg   169140
gcccagctga gtctatgtag gtgatgtttc cagctgccaa gtgctctttg ttactgtcca   169200
ccctcatttc tgccagcgca tgtgtccttt caagggaaa atgtgaagct gaaccccctc    169260
cagacacccca gaatgtagca tctgagaagg ccctgtgccc taaaggacac ccctcgcccc   169320
catcttcatg gaggggtca tttcagagcc ctcggagcca atgaacagct cctcctcttg    169380
gagctgagat gagccccacg tggagctcgg gacggatagt agacagcaat aactcggtgt   169440
gtggccgcct ggcaggtgga acttcctccc gttgcgggt ggagtgaggt tagttctgtg    169500
tgtctggtgg gtggagtcag gcttctcttg ctacctgtga gcatccttcc cagcagacat   169560
cctcatcggg ctttgtccct ccccccgcttc ctccctctgc ggggaggacc cgggaccaca   169620
gctgctggcc agggtagact tggagctgtc ctccagaggg gtcacgtgta ggagtgagaa   169680
gaaggaagat cttgagagct gctgagggac cttgagagc tcaggatggc tcagacgagg    169740
acactcgctt gccgggcctg ggcctcctgg gaaggaggga gctgctcaga atgccgatgg   169800
acaactgaag gcaacctgga aggttcaggg gccgctcttc cccatgtgc ctgtcacgct    169860
ctggtgcagt caaaggaacg ccttcccctc agttgtttct aagagcagag tctcccgctg   169920
caatctgggt ggtaactgcc agccttggag gatcgtggcc aacgtggacc tgcctacgga   169980
gggtgggctc tgacccaagt ggggcctcct tgtccaggtc tcactgcttt gcaccgtggt   170040
cagagggact gtcagctgag cttgagctcc cctggagcca gcagggctgt gatgggcgag   170100
tcccggacca cacccagaca ctgaatgctt ctgagacgaa agggaaggac tgacgagga    170160
tgtatattta attttttaac tgctgcaaac attgtacatc caaattaaag gaaaaaaatg   170220
gaaaccatca gttgttgctg tgtgaggctt gctttgcttc atgagaacct agaccttgct   170280
gagctggagt cttaggaagc agtctcctaa gtgcttctcc agcaggggca gaaactgtcc   170340
caccagctaa catctggcat tatggagggt ccccaggca gctgccagca gggacaggcc    170400
ccgtgttttc tgtagccagg gatgaggaag tggcccagg gcatgggcct ggctgggtgc    170460
```

-continued

```
ttctgcaagg gccttcccaa accacagtac aggtggtctt cctgccctgc agatgggagc   170520
tgtgggagct gctggagctg ctggagcctt catggtcaag tgacatcata agcttatatg   170580
acatacacaa gcctcaggac ttggcccatg gcactgaagc aggtcatcag gcccagcaca   170640
gagactagag ctgtgttctc acagggccca ccacccttcc acctccttgg ccattgacac   170700
ctgcgtccct ggcccagctg ctcccaggta accccaaaga cagctggcac atccacctc   170760
tggtgtggcc ggggctgctg tgtgccgca gggcctgccc cgtctattct agcttgtttg   170820
tcctgtctga accagcgcct actccaagaa gcctctgctc agcccagcgg ggatgcttct   170880
aagctccgga cgagcctctc ggaagccttg gtgattggtg gtgtagtcat cttgggatgc   170940
agatgtctta ccaacctgca agaacaaaaa ccctgtggct tcctctggtg cagggtattt   171000
agtcaatgtt tgctgaggtc ccgtctggtt ctggctaatt ggcagggggtc gtccacccat   171060
tctttccctg ctctgctgtc tgtgccagga gagacggggg ccagtcggcc aaggggccag   171120
ctcctgctgc ctgctcctct tgggcacgtg cgggggcccc ctttctctga gcagggatag   171180
ggatcagtct gccggaggga tgtggtggac aggcctaaag catttgggc ggggcatggc   171240
acttgagctc cctaaatctg tctcctcata ggtgacaccg ctccaggcc ccccagtggc   171300
ctctcctttc agagctacct aaattctggt cacttcagag aaatggagca cccccttctc   171360
cctggtccag gtgtggacag cctgcacac tgagcacacc tggcatggct ggtaatttca   171420
gaaagaagag gggccgggt ccagtgggaa gcagcggtga acccctcgtg agtgggcttt   171480
gcagtccctc cccatgccac ggcagagctg ccctcaacac agccttcctc ttcctcatcg   171540
gagagcacac cctgtcccct tgccgagctg tgccctgtgc cttcggtggt atttgatttt   171600
ggctgctact ggctttgttg ggatctgaaa gtcgcttccc ctgcgtgtg cgtggagcac   171660
tgtaagtcag atgagggaag tagccagggt gaggtgagta ccgggtggag ccgccactga   171720
agggactggg tagggggggcc ttgcctctac atgatgtgac acagccaacc gaggacagag   171780
gaagccccgt tcctggggt gtggggtgca cccctcaggg aagcctgcag tggggcctga   171840
ggaaaggcat cctccgcgag cccacgagtc tggtccatga gcaccgtgac agtgtctgtg   171900
ggtagaggtg gacccggcct tgtgtcatca ccaggacctc ttttgggaaa ccatgtggac   171960
atcgcttgcg ggtcccccag gctctgcagc cccagcagcc t                       172001

SEQ ID NO: 3          moltype = DNA   length = 10081
FEATURE               Location/Qualifiers
source                1..10081
                      mol_type = genomic DNA
                      organism = Mus musculus
SEQUENCE: 3
gcactcgccg cgagggttgc cgggacgggc ccaagatggc tgagcgcctt ggttccgctt   60
ctgcctgccg cgcagagccc cattcattgc cttgctgcta agtggcgccg cgtagtgcca   120
gtaggctcca agtcttcagg gtctgtccca tcgggcagga agccgtcatg gcaaccctgg   180
aaaagctgat gaaggctttc gagtcgctca agtcgtttca gcagcaacag cagcagcagc   240
caccgccgca ggcgccgccg ccaccgccgc cgccgcctcc gcctcaaccc cctcagccgc   300
cgcctcaggg gcagccgccg ccgccaccac cgccgctgcc aggtccggca gaggaaccgc   360
tgcaccgacc aaagaaggaa ctctcagcca ccaagaaaga ccgtgtgaat cattgtctaa   420
caatatgtga aaacattgtg gcacagtctc tcagaaattc tccagaattt cagaaactct   480
tgggcatcgc tatggaactg tttctgctgt gcagtgacga tgcggagtca gatgtcagaa   540
tggtggctga tgagtgcctc aacaaagtca tcaaagcttt gatggattct aatcttccaa   600
ggctacagtt agaactctat aaggaaatta aaagaatgg tgctcctcga agtttgcgtg   660
ctgcctgtg gaggtttgct gagctggctc acctggttcg acctcagaag tgcaggcctt   720
acctggtgaa tcttcttcca tgcctgaccc gaacaagcaa aagaccggag gaatcagttc   780
aggagacctt ggctgcagct gttcctaaaa ttatggctcc ttttggcaat ttcgcaaatg   840
acaatgaaat taaggttctg ttgaaagctt tcatagcaaa tctgaagtca agctctccca   900
ccgtgcggcg gacagcagcc ggctcagccg tgagcatctg ccaacattct aggaggacac   960
agtacttcta caactggctc cttaatgtcc tctaggtct gctggttccc atggaagaag   1020
agcactccac tctcctgatc ctcggtgtgt tgctcacatt gaggtgtcta gtgccccttgc   1080
tccagcagca ggtcaaggac acaagtctaa aaggcagctt tggggtgaca cggaaagaaa   1140
tggaagtctc tccttctaca gagcagcttg tccaggttta tgaactgact ttgcatcata   1200
ctcagcacca agaccacaat gtggtgacag ggcactggac gctcctgcag cagctcttcc   1260
gtacccctcc acctgaactc ctgcaagcac tgaccacacc aggagggctt gggcagctca   1320
ctctggttca agaagaggcc cggggccgag gccgcagcgg gagcatcgtg gagcttttag   1380
ctggaggggg ttcctcgtgc agccctgtcc tctcaagaaa gcagaaaggc aaagtgctct   1440
taggagagga agaagccttg gaagatgact cggagtccag gtcagatgtc agcagctcag   1500
cctttgcagc ctctgtgaag agtgagattg gtggagagct cgctcgttct tcaggtgttt   1560
ccactcctgg ttctgttggt cacgacatca tcactgagca gcctagatcc cagcacacac   1620
ttcaagcaga ctctgtggat ttgtccggct gtgacctgac cagtgctgct actgatgggg   1680
atgaggagga catcttgagc cacagctcca gccagttcag tgctgtccca tccgaccctg   1740
ccatggacct gaatgatggg acccaggcct cctcacccat cagtgacagt tctcagacca   1800
ccactgaagg acctgattca gctgtgactc cttcggacag ttctgaaatt gtgttagatg   1860
gtgccgatag ccagtattta ggcatgcaga taggacagcc acaggaggac gatgaggagg   1920
gagctgcagg tgttctttct ggtgaagtct cagatgtttt cagaaactct tctctggccc   1980
ttcaacaggc acacttgttg gaaagaatgg gccatagcag gcagccttcc gacagcagta   2040
tagataagta tgtaacaaga gatgaggttg ctgaagccag tgatccagaa agcaagcctt   2100
gccgaatcaa aggtgacata ggacagccta atgatgagta ttctgctcct ctggtacatt   2160
gtgtccgtct tttatctgct tccttttttgt taactggtga aaagaaagca ctggttccag   2220
acagagacgt gagagtcagt gtgaaggcc tggccctcag ctgcattggt gcggctgtgg   2280
cccttcatcc agagtcgttc ttcagcagac tgtacaaagt acctcttaat accacgaaa   2340
gtactgagga acagtatgtt tctgacatct gaactacat cgatcatgga gacccacagg   2400
tccgaggaga tactgccatt ctctctgtca cccttgtcta ctccatcctc agtaggtcca   2460
gtctccgtgt tggtgactgg ctgggcaaca tcagaaccct gacaggaaat acattttctc   2520
tggtggactg cattccttta ctgcagaaaa cgttgaagga tgaatcttct gttacttgca   2580
agttggcttg tacagctgtg aggcactgtg tcctgagtct ttgcagcagc agctacagtg   2640
acttgggatt acaactgctt attgatatgc tgcctctgaa aacagctcc tactggctgg   2700
tgaggaccga actgctggac actctggcag agattgactt caggctcgtg agttttttgg   2760
```

```
aggcaaaagc agaaagttta caccgagggg ctcatcatta tacagggttt ctaaaactac  2820
aagaacgagt actcaataat gtggtcattt atttgcttgg agatgaagac cccagggttc  2880
gacatgttgc tgcaacatca ttaacaaggc ttgtcccaaa gctgttttac aagtgtgacc  2940
aaggacaagc tgatccagtt gtggctgtag cgagggatca gagcagtgtc tacctgaagc  3000
tcctcatgca tgagacccag ccaccatcac acttttctgt cagcaccatc accagaatct  3060
atagaggcta tagcttactg ccaagtataa cagatgtcac catggaaaac aatctctcaa  3120
gagttgttgc cgcagtttct catgaactca ttacgtcaac aacacgggca ctcacatttg  3180
gatgctgtga agccttgtgt cttctctcag cagcctttcc agtttgcact ggagtttag  3240
gatggcactg tggagtgccc ccactgagtg cctctgatga gtccaggaag agctgcactg  3300
ttgggatggc ctccatgatt ctccaccttg ctttcatcag cttggttccca ctggatctct  3360
cagcccatca ggatgccttg attttggctg gaaacttgct agcagcgagt gcccccaagt  3420
ctctgagaag ttcatggacc tctgaagaag aagccaactc agcagccacc agacaggagg  3480
aaatctggcc tgctctgggg gatcggactc tagtgccctt ggtggagcag cttttctccc  3540
acctgctgaa ggtgatcaat atctgtgctc atgtcttgga cgatgtgact cctggaccag  3600
caatcaaggc agccttgcct tctctaacaa accccccttc tctaagtcct attcgacgga  3660
aagggaagga gaaagaacct ggagaacaag cttctactcc aatgagtccc aagaaagttg  3720
gtgaggccag tgcagcctct cgacaatcag acacctcagg acctgtcaca gcaagtaaat  3780
catcctcact ggggagtttc taccatctcc cctcctacct caaactgcat gatgtcctga  3840
aagccactca cgccaactat aaggtcacct tagatcttca gaacagcact gaaaagtttg  3900
gggggttcct gcgctctgcc ttggacgtcc tttctcagat tctagagctg gcgacactgc  3960
aggacattgg aaagtgtgtt gaagaggtcc ttggatacct gaaatcctgc tttagtcgag  4020
aaccaatgat ggcaactgtc tgtgtgcagc agctattgaa gactctcttt gggacaaact  4080
tagcctcaca gtttgatggc ttatcttcca accccagcaa gtctcagtgc cgagctcagc  4140
gccttggctc ttcaagtgtg aggcccggct tatatcacta ctgcttcatg gcaccataca  4200
cgcacttcac acaggcctttg gctgacgcaa gcctgaggaa catggtgcag gcggagcagg  4260
agcgtgatgc ctcggggtgg tttgatgtac tccagaaagt gtctgcccaa ttgaagacga  4320
acctaacaag cgtcacaaag aaccgtgcag ataagaatgc tattcataat cacattaggt  4380
tatttgagcc tcttgttata aaagcattga agcagtacac cacgacaaca tctgtacaat  4440
tgcagaagca ggttttggat ttgctggcac agctggttca gctacgggtc aattactgtc  4500
tactggattc agaccaggtg ttcatcgggt ttgtgctgaa gcagtttgag tacattgaag  4560
tgggccagtt cagggaatca gaggcaatta ttccaaatat attttcttc ctggtattac  4620
tgtcttatga gcgctaccat tcaaaacaga tcattggaat tcctaaaatc atccagctgt  4680
gtgatgcat catggccagt ggaaggaagg ccgttacaca tgctatacct gctctgcagc  4740
ccattgtcca tgacctcttt gtgttacgag gaacaaataa agctgatgca gggaaagagc  4800
ttgagacaca gaaggaggtg gtggtctcca tgctgttacg actcatccag taccatcagg  4860
tgctggagat gttcatcctt gtcctgcagc agtgccacaa ggagaatgag gacaagtgga  4920
aacggctctc tcggcaggtc gcagacatca tcctgcccat gttggccaag cagcagatgc  4980
atattgactc tcatgaagcc cttggagtgt taaatacctt gtttgagatt ttggctcctt  5040
cctccctacg tcctgtggac atgcttttgc ggagtatgtt catcactccca agcacaatgg  5100
catctgtaag cactgtgcag ctgtggatat ctggaatcct cgccattctg agggttctca  5160
tttcccagtc aaccgaggac attgttcttt gtcgtattca ggagctctcc ttctctccac  5220
acttgctctc ctgtccagtg attaacaggt taagggggtgg aggcggtaat gtaacactag  5280
gagaatgcag cgaagggaaa caaaagagtt tgccagaaga tacattctca aggttttctt  5340
tacagctggt tggtattctt ctagaagaca tcgttacaaa acagctcaaa gtggacatga  5400
gtgaacagca gcatacgttc tactgccaag agctaggcac actgctcatg tgtctgatcc  5460
acatattcaa atctggaatg ttccgagaaa tcacagcagc tgccactaga ctcttcacca  5520
gtgatggctg tgaaggcagc ttctatactc tagagagcct gaatgcacgg gtccgatcca  5580
tggtgcccac gcaccagcc ctggtactgc tctggtgtca gatcctactt ctcatcaacc  5640
acactgacca ccggtggtgg gcagaggtgc agcagacacc caagagacac agtctgtcct  5700
gcacgaagtc acttaacccc cagaagtctg gcgaagagga ggattctggc tcggcagctc  5760
agctgggaat gtgcaataga gaaatagtgc gaagagggcc ccttattctc ttctgtgatt  5820
atgtctgtca gaatctccat gactcagaac acttaacatg gctcattgtg aatcacattc  5880
aagatctgat cagcttgtct catgagcctc cagtacaaga ctttattagt gccattcatc  5940
gtaattctgc agctagtggt ctttttatcc aggcaattca gtctcgctgt gaaaatcttt  6000
caacgccaac cactctgaag aaaacacttc agtgcttgga aggcatccat ctcagccagt  6060
ctggtgctgt gctcacacta tatgtggaca ggctcctggg cacccccttc cgtgcgctgt  6120
ctcgcatggt cgacaccctg gcctgtcgcc gggtagaaat gcttttggct gcaaatttac  6180
agagcagcat ggcccagttg ccagaggagg aactaaacag aatccaagaa cacctccaga  6240
acagtgggct tgcacaaaga caccaaaggc tctattcact gctggacaga ttccagctct  6300
ctactgtgca ggactcactt agcccttgc ccccagtcac ttcccaccca ctggatgggg  6360
atgggcacac atctctggaa acagtgagtc cagacaaaga ctggtacctc cagcttgtca  6420
gatcccagtg ttggaccaga tcagattctg cactgctgga aggtgcagag ctggtcaacc  6480
gtatccctgc tgaagatatg aatgacttca tgatgagctc ggagttcaac ctaagccttt  6540
tggctccctg tttaagcctt ggcatgagcg agattgctaa tgcccaaaag agtccccacc  6600
ttgaagcagc ccgtgggtg attctgaacc gggtgaccag tgttgttcag cagcttcctg  6660
ctgtccatca agtcttccag cccttcctgc ctatagagcc cacggcctac tggaacaagt  6720
tgaatgatct gcttggtgat accacatcat accagtctct gaccatactt gcccgtgccc  6780
tggcacagta cctggtggtg ctctccaaag tgcctgctca tttgcacctt cctcctgaga  6840
aggagggga cacggtgaag tttgtggtaa tgacagtgga ggccctgtca tggcatttga  6900
tccatgagca gatcccactg agtctggacc tccaagccgg gctagactgc tgctgcctgg  6960
cactacaggt gcctggcctc tggggggtgc tgtcctcccc agagtacgtg actcatgcct  7020
gctccctcat ccattgtgtg cgattcatcc tggaagccat tgcagtacaa cctggagacc  7080
agcttctcgg tcctgaaagc aggtcacata ctccaagagc tgtcagaaag gaggaagtag  7140
actcagatat acaaaaacctc atcatgtca cttcggcctg cggagatgtg gcagacatgg  7200
tggaatccct gcagtcagtg ctggcttgg gccacaagag gaacagcacc ctgccttcat  7260
ttctcacagc tgtgctgaag aacattgtta tcagtctggc ccgactcccc ctagttaaca  7320
gctatactcg tgtgcctcct ctggtatgga aactcgggtg gtcacccaag cctggagggg  7380
attttggcac agtgtttcct gagatccctg tagagttcct ccaggagaag gagatcctca  7440
aggagttcat ctaccgcatc aacaccctag ggtggaccaa tcgtacccag ttcgaagaaa  7500
```

```
cttgggccac cctccttggt gtcctggtga ctcagcccct ggtgatggaa caggaagaga 7560
gcccaccaga ggaagacaca gaaagaaccc agatccatgt cctggctgtg caggccatca 7620
cctctctagt gctcagtgca atgaccgtgc ctgtggctgg caatccagct gtaagctgct 7680
tggagcaaca gccccggaac aagccactga aggctctcga taccagattt ggaagaaagc 7740
tgagcatgat cagagggatt gtagaacaag aaatccaaga gatggttttcc cagagagaga 7800
atactgccac tcaccattct caccaggcgt gggatcctgt cccttctctg ttaccagcta 7860
ctacaggtgc tcttatcagc catgacaagc tgctgctgca gatcaaccca gagcgggagc 7920
caggcaacat gagctacaag ctgggccagg tgtccataca ctccgtgtgg ctgggaaata 7980
acatcacacc cctgagagag gaggaatggg atgaggaaga agaggaagaa agtgatgtcc 8040
ctgcaccaac gtcaccacct gtgtctccag tcaattccag aaaacaccgt gccggggttg 8100
atattcactc ctgttcgcag tttctgcttt aattgtacag ccgatggatc ctgccatcca 8160
gtgcagccag aaggaccccc gtcatcctga tcagtgaagt ggttcgatct cttcttgtag 8220
tgtcagactt attcaccgaa cgtacccagt ttgaaatgat gtatctgacg ctgacagaac 8280
tacggagagt gcacccttca gaagatgaga tcctcattca gtacctggtg cctgccacct 8340
gtaaggcagc tgctgtcctt ggaatggaca aaactgtggc agagccagtc agccgcctac 8400
tggagagcac actgaggagc agccacctgc ccagccagat cggagccctg cacggcatcc 8460
tctatgtgtt ggagtgtgac ctcttggatg acactgcaaa gcagctcatt ccagttgtta 8520
gtgactatct gctgtccaac ctcaaaggaa tagcccactg cgtgaacatt cacagccagc 8580
agcatgtgct ggtaatgtgt gccactgctt tctacctgat ggaaaactac cctctggatg 8640
tgggaccaga attttcagca tctgtgatac agatgtgtgg agtaatgctg tctgaagtg 8700
aggagtccac ccctccatc atttaccact gtgccctccg gggtctggag cggctcctgc 8760
tgtctgagca gctatctcgg ctagacacag agtccttggt caagctaagt gtggacagag 8820
tgaatgtaca aagcccacac agggccatgg cagcccctagg cctgatgctc acctgcatgt 8880
acacaggaaa ggaaaaagcc agtccaggca gagcttctga ccccagccct gctacacctg 8940
acagcgagtc tgtgattgta gctatggagc gagtgtctgt tctctttgat aggatccgca 9000
agggatttcc ctgtgaagcc agggttgtgg caaggatcct gcctcagttc ctagatgact 9060
tctttccacc tcaagatgtc atgaacaaag tcattggaga gttcctgtcc aatcagcagc 9120
catacccaca gttcatggcc actgtagttt acaaggtttt tcagactctg cacagtgctg 9180
ggcagtcatc catggtccgg gactgggtca tgctgtccct gtccaacttc acacaaagaa 9240
ctccagttgc catggccatg tggagcctct cctgcttcct tgttagcgca tctaccagcc 9300
catgggtttc tgcgatcctt ccacatgtca tcagcaggat gggcaaactg gaacaggtgg 9360
atgtgaacct tttctgcctg gttgccacag acttctacag acaccagata gaggaggaat 9420
tcgaccgcag ggctttccag tctgtgtttg aggtggtggc tgcaccagga agtccatacc 9480
acaggctgct tgcttgtttg caaaatgttc acaaggtcac cacctgctga gtagtgcctg 9540
tgggacaaaa ggctgaaaga aggcagctgc tggggcctga gcctccagga gcctgctcca 9600
agcttctgct ggggctgcct tggccgtgca ggcttccact tgtgtcaagt ggacagccag 9660
gcaatggcag gagtgctttg caatgagggc tatgcaggga acatgcacta tgttggggtt 9720
gagcctgagt cctgggtcct ggcctcgctg cagtggtga cagtgctagg ttgaccaggt 9780
gttttgtcttt ttcctagtgt tcccctggcc atagtcgcca ggttgcagct gccctggtat 9840
gtggatcaga agtcctagct cttgccagat ggttctgagc ccgcctgctc cactgggctg 9900
gagagctccc tcccacattt acccagtagg catacctgcc acaccagtgt ctggacacaa 9960
aatgaatggt gtgtggggct gggaactggg gctgccaggt gtccagcacc attttccttt 10020
ctgtgttttc ttctccaggag ttaaaattta attatatcag taaagagatt aatttaatg 10080
t                                                                10081
```

| | | |
|---|---|---|
| SEQ ID NO: 4 | moltype = DNA length = 168002 | |
| FEATURE | Location/Qualifiers | |
| misc_feature | 8794..8848 | |
| | note = n is a, c, g, or t | |
| misc_feature | 11952..12155 | |
| | note = n is a, c, g, or t | |
| misc_feature | 13733..14137 | |
| | note = n is a, c, g, or t | |
| misc_feature | 17299..17497 | |
| | note = n is a, c, g, or t | |
| misc_feature | 18993..19355 | |
| | note = n is a, c, g, or t | |
| misc_feature | 30628..32144 | |
| | note = n is a, c, g, or t | |
| misc_feature | 37234..37641 | |
| | note = n is a, c, g, or t | |
| misc_feature | 56357..56602 | |
| | note = n is a, c, g, or t | |
| misc_feature | 66208..66275 | |
| | note = n is a, c, g, or t | |
| misc_feature | 72472..72756 | |
| | note = n is a, c, g, or t | |
| misc_feature | 82608..83314 | |
| | note = n is a, c, g, or t | |
| misc_feature | 108856..108875 | |
| | note = n is a, c, g, or t | |
| misc_feature | 131686..132275 | |
| | note = n is a, c, g, or t | |
| misc_feature | 143992..145163 | |
| | note = n is a, c, g, or t | |
| misc_feature | 147895..148388 | |
| | note = n is a, c, g, or t | |
| source | 1..168002 | |
| | mol_type = genomic DNA | | organism = Macaca mulatta
SEQUENCE: 4

```
atacaggcgt gagccaccgc acccagctgg aacttaattt tttttaaagat cgtgttgctc    60
tatcgcccaa gctggagtgc agtggtgcaa ccatagctca cttgcagcca caaattcctg   120
gtttcaggtg atcctcctac atcagcctcc caagaactgg gaactaacgg ctgtttctct   180
gctgtccttc tcaagagaag ggagggagac aatgctgggt ttcccttttgg gacaggctct  240
gagacaaggt ggaggtgctg cttgtggcca cagagcaggg gactctgggt tgcaggtgtg   300
gcctggcttg agtaggcttt agtgggcttc tctctgcctg caccacccc gggctgggtg    360
gttgtctctg aggccaaccc tactccctaa tgggcaggct ggacagctgc cctctctgtt   420
tgccctcta ccacccaaaa ggcgggaggc tctggagacc aggaccctgc ctgcgccggc    480
ctgtgcccca ggcgtgaggg ggtgcccac agatctctgc tgagctgagg ctgaatggca    540
ccccttgggg gtcctgccag gtcagagcag ggtgctttcc catacagaaa cgcccccagg   600
tcgggactca ttcctgtggg aggcgtcttg tggccacaac tgcttctcgc tgcactaatc   660
acagtgcctc tgtgggcagc gggcgctgac catccggggc tgcctcagac cctctcctcc   720
cttccggggc gctgcgctgg gaccgatggg gggcgccagg cctgtgggca ccgcccctgca  780
ggggccgctc cagctcactg gggggtgggg agggtcacac ttgggggtctt cagatggcgc  840
cgaccacgcg caatctctgc gctctgcgca ggggctcgcc caccctctcc ccgtgcagcg   900
agtccccagc aggctccccg cagggcgtc caggtgaggc tggctctggc cgcggggcag    960
tgtggcgggc gggcaagccc cgaggccacc tcggctcaga gcccacggcc ggctctcgcc  1020
cagctccaga cgtctgcgag ggttccattc cgcttgggcc ggcgcccgc gcgccgcgcc   1080
ctggccccgc ccctccctca tcccgccccc tctgcacccc acccctccct ggccccgccc  1140
tccgcgcccc acctctcatc ttcccgcccc gcccccagcc acgccccctca cggtcagccc 1200
cctcccctat ccgccccgcc tctcatcgtc tcgcctcgct ccgcccctca gccgtcccgc  1260
ccctcagccg ccctgcctaa tgtccccgcc cccagcctcg ccccgctccg ccccagcctc  1320
gccccgcccc gccccctcagg cgccctgcct gctgtgcccc gccccagcct cgccacgccc 1380
ctcgttacca tgtagtcccg ccccgtccct tccgcgtccc gcctcgcccc taccccttca  1440
cagcttcgcc ccaccccatt acagtcttgc cacgcccccgt ccctgtccg ttgagccctg   1500
ctccttcgcc caggtggggc gctgcgctgt cagaggcttt ggtggctctg tgaggcagaa   1560
catgcgggcg cagggactgg ctggctccct ggccagtcat tggcagagtc cgcaggctag   1620
ggctgtcaat catgctggcc ggcgtggccc cgcctccagc gcctgagacgc ttgagacgc   1680
aaggcgccgc ggggctgcc gggacgggtc caagatggac ggccgcttcg gttccgcttt   1740
tacccgcggc ccagagcccc attcattgcc ccggtgctga gcggcgctgc gagtcggccc   1800
gaggcctccg gggactgcct agccgggcgg gagaccgcca tggcgaccct ggaaaagctg   1860
atgaaggcct tcgagtctct caagtccttc cagcagcagc agcagcagca gcagcaagca   1920
ccgccgccgc cgccgccgcc gcctcctcct cctcctcagc ttcctcagcc gccgcaggca   1980
cagccgatgc tgcctcagcc gcagccgccc ccgccgccgc cccgccacc acccggcccg   2040
gctgtggctg aggagccgct gcaccgaccg tgagtttggg cccgctgcag ctccctgtcc   2100
cggcgggtcc cagcctacgg cggggatggc ggaatcctgc agcctgcggg ccggcgacac   2160
gaaccccccc ggccccgcag cgacagagtg accagcaac ccagagccaa tgagggacac   2220
ccgcccccctc ctgcggcgag accttccccc acttcagccc cggtcccgca cttgggtctt  2280
gtcctcccgc gaggggaggc agaacctcgt tgggaccgtgt cctgaattca cggaggggag  2340
tcacggcctc agccctctcg ccctttcag ggtgcgaaga gttggggcga aaacttgttt   2400
cttttattt gcgagaaact agggcgggg tttaactggg tttctgaagag aacttggaag   2460
agccgagatt tgctcagggc cacttccctc atctagtcag agagggaaga gggctggggg   2520
cgcgggacac ctcgagagga ggcggggttt ggagctagag agatgtgggg gcagtgggatg  2580
acataatgct tttaggacgc ctcggcggga gtggctgag tggggggcgg ggagtgaggg    2640
cgcgtccaat gggagattta ttttccaagt ggcattttaaa acagcctgag atttgaggct  2700
cttcctacat tctcagggca tttcatttag ttcatgatcg cggtggtagt aacacgattt   2760
taagcaccac ctaagagacc tgctcatcta agccgcaagtt agtgtgcagg catttgaatg  2820
agttgtggtc gccaaataag tggtgaactt acgtggtatt aataaaatta tcttaaatat  2880
taggaagagt tgattgaagt ttattgcctg ttttgtgttgg gaataaaact aacacgttgc  2940
tgaggggggag gttaattgcc gagggatgaa tgaggtatac attttaccag tattgcagtc   3000
aggcttgcca gaatatggga ggtgcagaca tccgtggac atctcatgt ccagtgaaag    3060
ggtttctgtt cgcctcattg ctgacagctt gttacttttt ggaagctaga ggtctctgtt  3120
gcttgttctt gggggagaatt tttgaaacag aaaaagagac cattaaaaca tctagcggaa 3180
ccccaggacg tgggagtgtg tgctgagtgt ttagcaggat ttaggaagta ctccgctgca  3240
gttcaggcct ttctcttacc tctcagtgtt ctatttccga tctggacgtg tatcagatgg  3300
catttgataa gaatatctct attaagactg attaatttt agtaatattt cttgttcttt   3360
gtttctgtta tgatccttgc cttgtcttga aagtttaatt agaagaggag gattttggaa  3420
gcagtgttag cttatttgtt agagtaaaat ttaggaataa attcttctaa aggatggaaa  3480
aactttttgg atattagag aaatttttaa acaattggc ttatctcttc agtaagtaat    3540
ttctcatcct tccagaaatt taatgtagtg cctttctagg aggtaggtgt catagaagtt  3600
cacacattgc atgtatcttg tgtaaacact aaactgggct cctgatggga aggaagacct   3660
ttctgctggg ctgcttcaga cacttgatca ttcctgaaat atgccgtctc tttcctgtgc  3720
tgatttgata gaacctgcgt ttgcttatct tcaaatatg ggtatcaaga aatttccttt    3780
gctgccttta caaggagat agattttgtt tcattacttt attttaaggt aatatatgat   3840
taccttattt taaaaattta atcaggcctg gcaaggtggc tcatgccttt aatccgagca   3900
ctttgggagg cttaggcgga tgaatcacct gaggtcagga gttcgagacc agtctggcta  3960
acatggtgaa accccatctc tactaaaagt acaaaaatta gttggtcatg gtggcacgtg  4020
cctgtaatgc cagctacctg ggaggctgag gcaggaaaat cgctggaacc cgggaggcag  4080
aggctgcagt gagctgagac tgcgccactg cactccagcc tgggtgacag agcgagactc  4140
ttgtctcaaa aaaaaaaaa ttattatttt tgcataagta atacattaac atgacacaaa    4200
ttccgtaatt acaaagagc aatacttaaa atatcttcct tccaccccttt tcatctgagt  4260
acctaacttt gtccccaaga acaagcacta ttacagttcc tcctgtatcc tgccagatat   4320
aatctatgca tattgtaaga tagatttaaa atgctgtaaa aataaaagta gtttacagta   4380
ataatttttt ttcttttattt ttttttgagat gtagtctcac attgtcaccc aggctggagt  4440
gcggtggtat gatcttggct cactgcaacc tccacctccc aggttcaaac gattctcctg   4500
cctcagcctc cagagtagct gggattacag gtgctcacca ccatgtccag ctgatttttg  4560
tattttagt agagatgggg tttcaccatg ttggccaggc tggtcttgaa ctcctgacct  4620
```

```
cggaatccat ccacctcggc ctcccaaagt gctggggtta caggtgtgag ccactgcccc  4680
tggctagaat aataactttt aaaggttctt agcattctct gaaatcaact gcattaggtt  4740
tatttatagt tattttaaat aaaatgcata tttgtcatat ttgtatgtat tttgctgttg  4800
agaaaggagg tattcgctaa ttttgagtaa caaacactgc tcacaaagtt tggattttgg  4860
catttctgtt catgtgcttc agccaaaaaa tcctcttctc aaagtaagat tgactaaagc  4920
aatttagaaa gtatctgttt ttatggctct tgctcttttg tgtggaactg tggtgtcatg  4980
ccatgcatgg gcctcagtct aagtatgagc gtatgtgctc tgctcagcat acaggatgtg  5040
ggagttccgt gtggggctgg ccacagtctc agcaaatcta gcatgcttgg gagggtcctc  5100
acagtaatta ggaggcaact gatacttgct tctggcaatt ccttattctc cttcagattc  5160
ctatccggtg tttccctgac tttattcatt catcagtaaa tatttactaa acatgtacta  5220
tgtacctagc actgttctag atgcagggct cagcagtgag cagacaaagc tgtgccctca  5280
tgaagctttc attctaatga aggacataga caataagcaa gatagataag taaaatatac  5340
agtatgttaa taagtggagg aatgtcaaag cagggaaggg gatagggaaa tgtcagggtt  5400
aatcaattgt taacttattt ttattaaaaa aaaattttt taagggcttt ccagcaaaac  5460
ccagaaagcc tgctggacaa cttccaaaaa aactgtagca ctaagtgttg acatttttat  5520
tttattttat tttattttgt tttgttttgt ttttgaggc agtcttgctt tgtcagccag  5580
gctgcagtgc actggtgtga tcttagctca ctgcaacctc tgcctgttgg gttcaagcga  5640
ttcttatgcc tcagcctcct gattagtgg gattatagac atgcaccgtc ccgcctgggt  5700
aatttttttt ttttccccct gagacagagt cttgctctgt cgcccaggct ggagtgcagt  5760
ggcacaatct ggctcactg caagctccgc ctcccaggtt catgccattc tcctgcctca  5820
gcctcccagg tagctgggac tacaggcgcc tgccaccacg cccagctaat ttttgtatt  5880
tttagtagag atggggtttc actgtgtcag ccaggatggt cttgatctcc tcacctcgta  5940
gtccgccccc cttggcctcc caaagtgctg ggattacagg cgtgagccac cgcgcccggc  6000
ctgtaatttt tttttttttt ttttgagaca gagtcttgct ttgttgctag gctggactgc  6060
agtggtgtga tcttggcaca ctgcaacctc tgcctcccgg gttcaagcga ttctcctgcc  6120
tcagcttccc gagtagctgg gactacaggc acgtgccatc acgcttggct acttttttgta  6180
tatttagtag aaacggggtt tcaccatgtt agctgagatg atctcgatct cttgacctcg  6240
tgatccgccc gcctcggcct cccagagtgc tgggattaca ggtgtgagcc actgtgcctg  6300
accacgcctg gtaattttt gtattttag tagagacggg atttcaccac gatggccaga  6360
ctggtctcga actcccagcc tcatgtgatc tgcctgccta ggcctcccaa agtgctagga  6420
ttacaggcat gagccaccat gactggccag tgttgatatt ttaaataggg tgttcaggga  6480
aggtccactg aggtgacagc tgttttttg ggggagtgg tgggacaggg ccttgctctt  6540
taacccaggc tggaatacag catcacaatc gtagcttact gcagccttga actcctaggc  6600
tcaagtgatc ttcccacctt gacctcacaa cgtgttggga ctgtaggtgt gagtcaccat  6660
gcctgccag atgatggctt tgagtaaaga cctcaggcga gttaagagtc tagcgtaaag  6720
gtgtatggag tagggtatt ccagataggg ggaacaggtc caaagtcttc ctgtttgagg  6780
aatagcaagg gtgccatttt agttgggtga attgagtgag ggcgacattt gtagtaagag  6840
gtaaagtcca agaggtcaag ggagtgccat atcagaccaa tactacttgc cttgtagatg  6900
gaataaagat attggcattt atgtgagtga gatgggatgt cactggagga ttagaggaaa  6960
ggagtagcat gatctgaatt tcattcttaa gtgaactctg gctgacaaca gagtgaaggg  7020
gaacatggac aaaagcagaa accagttagg aagccactgc agtgctcaga taagcgtggt  7080
gggttctgtc agggtaccgg ctgtgggcag tgtgaggaat gactggattt tgaatgcaga  7140
agcaactgta cttgttgaac tctgctaagt ataactattt agcagtagct ggcattatca  7200
gttaggtttg tattcagctg caagtaacag aaaaattctgc tgcaatagct taaactggta  7260
acaagaaaga gcttatcaga agacaaaaat aagtctgttt ggggaaattc aacaataagt  7320
taaggaaccc aggctctttc tttttttttt tgaaatggag ttttgctctt gtcacccagg  7380
ccggagtgca atgatgcgat cttggctcac tataacctcc gcctcctagg ttccagtgat  7440
tcttctgcct cagccttcca ggtatctggg attagaggcg cacgcacacc accatgccca  7500
gctaattttt gtattttag taggcacggg gtttcatcat gttggccagg ctggtctcga  7560
actcctgacc ttaggtgatc aacccgcctc agcctgccaa agtgctgaga ttacaggtgt  7620
gagccactgc actcggtcag aacccaggct cttttttaca cttagcttgc aaaccctgt  7680
tctcattctt ttccctttgt attttttattg tcgaattgta acagttcttt gtgtattctg  7740
gatactggat tcttatcaga tagatgattt gtgaaaacat tctctcttcc tttggattgt  7800
ctttttactt tcttgatcat gtcttttgaa gtgtgaaagt ttttaatttt gatgaagtct  7860
agtttatcta gtttgtcctt ggttgctatg ctttgagtgt catatctaag aaatcattgt  7920
ctaatccaaa gtcaaaaagg tttacccgta tgttttcttc taagaatttt agagtttac  7980
atttaggtct gatccatttt gagttaattt ttatatgtgg ttcaggtaga agtccaactt  8040
cattcttttg catgtggtta ttcagttgtc ccagcacagt ttgttgaaga gactgtactt  8100
tcccatgga attgtcttag catccttgtt gaaaattcat tgtccttgat tgtatagatt  8160
tatttcttga ctctcagttc tacctattgg tctttatgtt gatcctgtgc cagtaccata  8220
cagtcttgat tactgaagtt tgtgtcacaa tttaaattca tgaaatgtga gttctccaac  8280
tttgttcttt ctcaagattg atttggccat gctgggtccc ttgcatttcc atatggattg  8340
taggatcaac ttgtcagttt ctacaaagaa gccaaggagg attctgagag ggattgtgtt  8400
gaatctgtag atcaacttgg ggagtattac catcttcaga gtattgtctt ccatctctga  8460
actgggcaaa ctttgtgtaa atggtcagat ttaggtattt caggctgtgt gggcacaatg  8520
tctctgtcac agctactcag ctctgccatt gtagcgtgaa atagccataa gcaatatgta  8580
tgagtgtctg tgttccagta taattttatt aatgacaagg aaatttgaat tcgtgtaat  8640
tttcacctgt catgaaatat tatttggttt ttttggtcaa tcatttaaaa atgtaaaaac  8700
ttttcttgae ttttgaactg gccaaacata tgcaggttat aattttccca ctcctagatt  8760
aaaatatgat aggaccacct ttgaaaagca tgtnnnnnnn nnnnnnnnnn nnnnnnnnnn  8820
nnnnnnnnnn nnnnnnnnnn nnnnnnnnaa cactttggga ggccgagcca ggtggatcac  8880
ttgaggccag gagttcgaga ccagcctaac caacatggtg aaaccccatc tctactaaaa  8940
ataaaaaaat tagctggggg tggtggtggg tgtagggtcc agccctatgg ggcttagcgg  9000
gtgttctccc cgtgcgggga gacgagagat cttaagaaat aaagacacgg ccgggcgcgg  9060
tggctcacgc ctgtaatccc agcactttg gaggccgagg cgggcggatc acaaggtcag  9120
gagatcgaga ccacggtgaa accccgtctt tactaaaaat acaaaaaatt agcggggcgc  9180
ggttgtgggc gcctgtagtc ccagctactc gggaggctga ggcaggagaa tggcgtgaac  9240
ccgggaggag gagcttgcag tgagccgaga tcgcgccact gcactccaga cggggcgaca  9300
gagcgagact cctgtctcaa aaaaaaaaaa aaaaaaaaa agaaaagcat gttttttttt  9360
```

```
ttttgagatg gagtttcgct tttgttgccc aggctggagt gcagtggcgc gatctcggt     9420
caccacaacc tctgcctccc aggttcaagc gattctcctg cctcagcctc ccttgtagct    9480
gggattacag gcatgtgcca ccatgcccgg ctaattttgt attttagta gagacggggt     9540
ttctccaggt tggtcaggct ggtctcgaac tcctgacctc aggtgatctg cctgcctcgg    9600
cctcccgaag tgctgggatt acaggcgtga gccactctgc ccagccagaa agcattttctt  9660
ttttggctgt ttttttgttg tttttttaa ttaactagtt ttgaaaatta tagaagttac    9720
acatatatgt tataaaaaca tctccaagca gcacagaaga tgaaaaacaa agcccttctt   9780
gcaagtctgt catctttgtc taacttccta agaacaaaag tatttcttgt gtcttcttcc   9840
cagattttaa tatgcatata caagcatttta aatatgtcat tttttgttgg cttgactgag  9900
atcacattac atacgtattt ttttacttaa caatttgagt acaatgtgtc atggaaattg   9960
ttccatagca gtatctgtaa ttcttattaa ttgctgtgta atattgtaga atttctttt   10020
aaaagaggac ttttggagat gtaaaggcaa aggtctccca ttattctggc tgtacaacgt  10080
tctggtgaca tattctctct accctgagag gtccccatac ccatcacctc catttcctgt  10140
aaataagtca accacttggt aaactacctt tgaatggatc cacactcaaa acatttagtc  10200
ttattcagac aacaaggagg aaaaataaaa taccttataa agcactgttt catatgtatt  10260
aaattggatc aatttgcgtg ctagaatgta tgttagagac atgatatgcc cataggtcct  10320
tgctatcacg gtgaggtctc agggacagca gtttggtatc atttggtatc tcataagcag  10380
actctgtctg cctgacttaa caaatcagag tctgcgtttt aacaggttca gtgagtgact  10440
tacatgcaca ttggagtttg ggaagctcca ctataggtgc ttagacctta cctttgttgt  10500
tgctaataac aatgcaagca tttgggagga agacctgtgt tgctcgtatg tgtccaggtg  10560
tagctgaggt ggccttgctt gtctgctgta gggccattga gcatttgcgt agctgtgatg  10620
aatgagctga ggtgagcctg cggagagctc ccagccattg gtagtgggac ttgcttagat  10680
gaactagaag gacctgagca tccacttttgg ggaaaaacaa ccgaatgaag ggagaggcaa  10740
catgcagttt tatttagggt acgaaggaga gctgtggtta gaaggtgaca tttgagtgga  10800
aagggggcaa cccatgtgtg gagcgggaga agagcggtcc aggcagagtt aacagaaggc  10860
agaaatgctt tccatctttg aaaactagga aggatgcctga tggctgaagt aagatgaagg  10920
acagaaatag gggatgaggc ttcgagagat gagaggttag agacgagggt cttgtgcacc  10980
aagataagct tgtgtggtca aaacaagtag tttcgttttt gttttaaaa gatcactttg   11040
gctgggtgca atggttcatg cctgtaatac cagtactttg agaggctgtg gtgggaggat  11100
tgcctgaagc caggggacca gcgtagccaa catgcagccc cctataaggt ctctacaaaa  11160
aacttttaaa aagtagctgg gtgtagtggt gtgtgcctgt agtcccagcc acccaggagg  11220
ctgaggaggc tggagggttg cttgagtcca gcagtttgag gctgcagcga gcaatgattg  11280
tgccactgca ctacagcctg ggcatgagag tgagacctcg tctctaaata tatgtgtata  11340
tataaaagaa aagatcactt tgacaacacc acatgctggt gaggatttag aaaaactagg  11400
tcacttattg ctggtgggaa tataatatag tacggccact ctggaaaaca gtttggcagt  11460
ttctcataaa actgaatgta caattagtat acaacccagc aactcctgca atcctgcgca  11520
ttaatcctag agaatgaag ccttcatgtt cacataaaaa cctatactca agcgtgcata  11580
gcagctttac ccataatatc taagaactgg aatcagctca gatgtcctcc tgcaggtgaa  11640
tggttaaact actcagtaat aaaaaggaat gatctactga tgacatgcaa cagtgtaggt  11700
gaagttatgc taatgaaaaa agccaatccc aaaaggttac atattatatg attctatgta  11760
tataacgttt tggcagtgac acagttttag ggatggagaa tagattagtg gttgcctggg  11820
gttagagatg gggttgtaga gtaggttagg ggtggcagag gagagaaaag agagggaggc  11880
gagtggtgtt ataaaggac aacacagggg gatacttgta acagaaatgc tttgtcttt   11940
tttttttttt tnnnnnnnnn nnnnnnnnnn nnnnnnnnnn nnnnnnnnnn nnnnnnnnnn  12000
nnnnnnnnnn nnnnnnnnnn nnnnnnnnnn nnnnnnnnnn nnnnnnnnnn nnnnnnnnnn  12060
nnnnnnnnnn nnnnnnnnnn nnnnnnnnnn nnnnnnnnnn nnnnnnnnnn nnnnnnnnnn  12120
nnnnnnnnnn nnnnnnnnnn nnnnnnnnnn nnnnngctca ctgcagcctc tgcctctggg  12180
gttcaagcga ttcttctgcc tcagcctcct gagtagctgg gactacaggt gcacgccacc  12240
atgcccggct aatttttgta tttttagtag agacagggtt tcatcatgtt ggccaggctg  12300
gtcttgatct cctcacctca tgatccgccc acctcgccca cctcggcctc ccagagtgct  12360
gggattacag gcttgagcca ccgcgtccgg cctattttat ttttttttgag acagagtctc  12420
actctgtatc ccagactgga gtacagtggc gcgatcttgg ctcactgcag cctctgcctc  12480
tggggttcaa gcgattctcc tgcctcagcc tcctgagtag ctgggactac aggtgcacgc  12540
caccatgccc ggctaatttt tgtattttta gtagagacgg ggtttcacca tgttggccag  12600
ggtggtcttg atctcctcac ctcatgatcc gcccacctcg gcctcccaaa gtgctgggat  12660
tacagggatt tttgtgtttt tcgtagagac agggtttcat tatgatggcc aggttggttt  12720
tgaactcctg acctcctgtg atctgctggc ctcgcctccc aaagtgttgg gattatagac  12780
gttgagccac tgcactcggc caaggaaaga gatgctttgt cttgagtgtg gtggtgtata  12840
gaaattgtat agaactaagg ctgggacacgg tggctcactc ctgtaatccc agcattttgg  12900
gagaacgagg tgggcagatc gtgagttcag gagattgaga ccatcctggc taacatggtg  12960
aaaccctgtc cctgctaaaa ataccaaaaa ttggccgggc gtggtggctc acgcctataa  13020
tcccagcact ttgggaggct gaggcgggtg gatcacgagg tcaggagatc gagaccatcc  13080
tggctaacac agtgaaaccc tgtctctact aaaaatacaa aagcaaaatt agccgggcgt  13140
ggtggcgggc gcctgtagtc ccagctactt gggaggctga gacaggagaa tggcgtgaac  13200
ctggaggtg gaggttgcag tgagctgaga tcgcgccact gcactccagc ctgggcaaca  13260
gagtgagact ctgtctcaaa aaaaaaaaaa aaaagaaat tgtatagaac taaatacaca  13320
aatgaacaac aataaaactt gaaactctaa gtaagatcac tggattgtat cagtgtcaat  13380
attctggttg tgataatgta gtatattaaa tagttttgca aagtgttacc attgggaaa   13440
actggataaa gggcacactg gatctctgtt atttcttaca actgcacgtg aaccaataat  13500
tatcttaaaa aaacttcaat tcaaaaaagt ctgcccctgat ccagttggga ggctactgaa  13560
gtaatcaaag ctagacatgc tggtgtcttg tgactggtag cagtggtgat ggtaagtggt  13620
cagattctgg atctcttgga gaaagatctg acaagatttg cagattcttt aaaaaaaatg  13680
agattaggct gggcacggtg gctcacgctt gggaggctga ggagggcgga tcnnnnnnnn  13740
nnnnnnnnnn nnnnnnnnnn nnnnnnnnnn nnnnnnnnnn nnnnnnnnnn nnnnnnnnnn  13800
nnnnnnnnnn nnnnnnnnnn nnnnnnnnnn nnnnnnnnnn nnnnnnnnnn nnnnnnnnnn  13860
nnnnnnnnnn nnnnnnnnnn nnnnnnnnnn nnnnnnnnnn nnnnnnnnnn nnnnnnnnnn  13920
nnnnnnnnnn nnnnnnnnnn nnnnnnnnnn nnnnnnnnnn nnnnnnnnnn nnnnnnnnnn  13980
nnnnnnnnnn nnnnnnnnnn nnnnnnnnnn nnnnnnnnnn nnnnnnnnnn nnnnnnnnnn  14040
nnnnnnnnnn nnnnnnnnnn nnnnnnnnnn nnnnnnnnnn nnnnnnnnnn nnnnnnnnnn  14100
```

```
nnnnnnnnnn nnnnnnnnnn nnnnnnnnnn nnnnnnnttg ataatttata aaatgtgatt   14160
atagaatgct gtagtgtcct tgagtttaca tgcccttcct tacacttgtg tgcctgtgca   14220
gatgccttga tttcacaatt agaggaggct gactgagatt tgtttaattt tttttttttt   14280
tgaggcagag tcttgttatg tcccccaggc tagagtacag tagcgcaatc ttggtgcact   14340
gcaacatccg cctcctgggt tcaagcaatt cctctgcctc agcctcccga gtgcctggga   14400
taacaggtgc cagcccccac gcccagctat tttttgtatt tttagtagag acgggatttc   14460
accatgttga ctgggctggt ctcaaactcc tgacctcaga tatctgccgc cccagcctcc   14520
caaagtgctg ggattacagg cgtagccaca cctggccgtt tgttttaatt tttaaggtga   14580
cgttaaagtg actgcattta ccaaaagtgg ttgagaagcc aggactgttc ttatcctgct   14640
tttccagttc ttgctcagag caaggtggtt tatttttcac ttaattacca tacttacttt   14700
tcatgtagaa caagtcagtt tgagttatca gttcatcatc taactaaatt ccatggggga   14760
aggaatagtt ttagtttctt aaacttccaa ggttgcttat tggacaaaat gagatagcaa   14820
ggcggtgttt ttaagttaga ttttttattt ctttggtaat ataattttct caaaaactta   14880
gtagtctttt agtttagttg tttttagttg gtcctatgtt ttgcatcccc cctctctact   14940
tttattttga tagtgccaat tgcgaagaca tctgaagcca taggtttggg tgggaaggcg   15000
gcacctttag cctgattatc tttgccaggc tgtttatctc cttttgcttg gctgagaagt   15060
cttaatagga ggcttattcc cagctacttg gggacataga agcggttagc tattgttcat   15120
gttttactga ggtctgtgtg gtatgttgac tgcagtcagt tactggtttt gagaattgaa   15180
ggcagcctgg tatatagagt aggtattata ttgtgtttct ttgaattgaa tttcctatct   15240
cttgtaatct ttgccatcat cttctgtgaa agaaaaaaag tttctatcaa actataccat   15300
tggttgtaag atgcagttcg gctttagtga tgctaacaca tgatccaaac gtgaaactga   15360
gtattggtga aatacagagg agatttaaag ccagaagacc tgggtttaaa tgctggctct   15420
atgacttcaa atctgtgtgt tcttgggcac gtcatggttg gcacttcaat ttcttctctc   15480
tgtaatgggg gaaatgaggc cagtcatggt ggctcatacc tatgatccca gcactttggg   15540
ggccaagatg ggaagatcgc ttgaggccag gaggttgagc aattgggcaa catagtgagg   15600
ccccgtctct acaaaacatt taaaaaaaat tagccaggcc cagtggtgca tgcctgtggt   15660
ccccaccact caggaggctg agatgggagg atcctttcag cccaggagtt taaggctaaa   15720
gtgagccatg attgtgctac tgtactctag cctgggcagt agagcaagat cctgactcta   15780
aaaaaaagta aaatgaaata aaatggggga aatgaactgc tttagtaaca tcatctgttt   15840
tttctgtgag cagtgtagct tgaaagccat tggtgaactc atgcactgtg cttccctgtc   15900
cagatcccca ttctgccccc agcatggagt ataacagttt attagtagta gtcgagaaac   15960
cctcattgaa tgaatgaatg agatgtagaa gtaagtggag tgggtaattg aacacatatt   16020
catttccttt tctttttctt tattttaga aagaaagaac tttcagctac caagaaagac   16080
cgtgtgaatc attgtctgac aatatgtgaa aacatagtgg cacagtctgt caggtaattg   16140
cactttgaac tgtctagaga aaataagaac tttgtatatt ttcagtctta atgggctaga   16200
atattctgtg tccagttat tttaaatgga ttcaaaaatc cttgaagaag gacccttttc   16260
ccatatttct ggctatatac aaggatatcc agacactaaa atgaataatg ttcccttttc   16320
gtaatctttt atgcaaaaat taaaaccatt atggtaattg aacaacatgt ttatgtttag   16380
ttaacaccct tagcaactat agttatttta aaatcctgtg tggtttgata tttttgcgtt   16440
tattgtaaca gtgggaacag cacaaggcgg tccactttgt ctctctcatt ttgcagtttg   16500
ctgtcctgtt gtgctggtgc tcctagcagt ggctggagcc cacttctctg tgctttggga   16560
ttagtggggt catgggcat tgactggagg tcagcttttcc ttgcttgatc tttctcactg   16620
gggtaaacta gcagccactt cttttgtagc tgctttgctt ttggctatct ttctgaccgt   16680
tgttcctagc agctgtagat ggtaaatatg tttaggcctg tttccaatgg ctgagtagga   16740
gacatatgca cctatgatat ctgaattctg ttacccagat gggcgtgtgt gaaatagtta   16800
ccttgcttta cttttccttg gaataaataa ttcatgttat tctcctggta gaagctgaaa   16860
aaagtctttt atagtcagtc agaaaaaaat ttttagacaa ataatcttga ttttagtact   16920
gacaaaaatg tgtggtgatt cttttttttta gtttttttg agatggagtt tcactcttgt   16980
tgcccaggct ggagtgcaat ggtgcgatct cggctcactg caacctccgc ctcctgggtt   17040
caagcgattc tcctgcctta gtcctcgag tagctgggt tacaggcatg tgccaccacg   17100
cccagctaat tttgtatttt tagtagagac agggttttcc catgttggtc ggctgatct   17160
caaactccca acctcaggtg atccgcccgc ctcagcctct caaagtgctg ggattacagg   17220
cgtgagccat ggcaccggtt gattcatttg tttttttaaa aatttcctct tggccattgc   17280
ttttcactgt tttcttttnn nnnnnnnnnn nnnnnnnnnn nnnnnnnnnn nnnnnnnnnn   17340
nnnnnnnnnn nnnnnnnnnn nnnnnnnnnn nnnnnnnnnn nnnnnnnnnn nnnnnnnnnn   17400
nnnnnnnnnn nnnnnnnnnn nnnnnnnnnn nnnnnnnnnn nnnnnnnnnn nnnnnnnnnn   17460
nnnnnnnnnn nnnnnnnnnn nnnnnnnnnn nnnnnnntgt agaaatattg tgggaagaaa   17520
atgaaataac aaatgagcat gtgtcctgaa aataaaaata taaaaattct aagttagcat   17580
gctattgtag aatacaacac tatgataaaa gtagggaaaa aaaagtttga attccacgtc   17640
tgctgcctgt gtaagctggg tgactttaga taagctttaa cgtgtttgag ccttactggc   17700
tcatgtttga agtgtaatcc ctcgttacac agttcttgtg ggatcagacg atgcatgtga   17760
aacactgtga agaagtaact gcgatagatg tgttcattag ccgcctgaac gggaagcaca   17820
tcccattgcg atgcccatca tccaaagcta tatgttatct ttacttttttt tgttttttg   17880
agacagagtc tcactctgtc gcccagactg gagtgcagtg gcgcatctc ggctccactg   17940
agttctgcc tcctgggttc acgccattct cctgcctcag cctcccaagt agctgggact   18000
acaggtgccc gccaccacac ctggccaaat ttttgtattt ttagtagaga cagggtttca   18060
ctgtgttagc caggatggtc tcgatctcct gacctcgtga tccgcccacc tcagcctctc   18120
aaagtgctgg gattacaggc gtgagacact gtgcccagcc atcttcactt ttcttgtgaa   18180
atgatgactc taaatgtttg gcaaacattt ggtgattgtt catctgattt ccactatcca   18240
ggtctcagag aatataattt atctctgaaa gcttattgac ccaggaaaca agatctcttc   18300
caatctgagt acatcaggct ttattcttgt cattttgtct tttgagaatt tcaaatggaa   18360
attcatggaa tgttggctca tattcacata ttagtaaagt acgctgagac atcttaagat   18420
tgatttgtgg ttcatatttgc catattaaat caaaataata actgttaatg gttttctttt   18480
tttttttttt tttttttgag acggagtctt gctctgtcgc ccaggccgga gtgcagtggc   18540
ccgatctcag ctcactgcaa gctccgcctc ccgggtttat gccattctcc tcctcagcc   18600
tcccgagtag ctgggactac aggcgcccgc tacctcgccc agctagtttt ttgtattttt   18660
ttttagtaga cacggggttt cgccgtgtt agccaggatg gtctcgatct cctgagctcg   18720
tgatccgccc gtctcggcct cccaaagtgc tgggattgag ccaccgcgcc cggcctgtta   18780
atggttttca cattagtctg tctcttgtttt ttatggagta atgctgagag ttcattatgc   18840
```

```
ttcttgttct acagaagagc atgttaaaag gattttttgg gatcagagag gttatccatg   18900
gtttcatagg atactctgta ctttgcaggg atttcagggt atatagccaa aggtgatatt   18960
ttatataaat atgttttatg gaaacttact gannnnnnnn nnnnnnnnnn nnnnnnnnnn   19020
nnnnnnnnnn nnnnnnnnnn nnnnnnnnnn nnnnnnnnnn nnnnnnnnnn nnnnnnnnnn   19080
nnnnnnnnnn nnnnnnnnnn nnnnnnnnnn nnnnnnnnnn nnnnnnnnnn nnnnnnnnnn   19140
nnnnnnnnnn nnnnnnnnnn nnnnnnnnnn nnnnnnnnnn nnnnnnnnnn nnnnnnnnnn   19200
nnnnnnnnnn nnnnnnnnnn nnnnnnnnnn nnnnnnnnnn nnnnnnnnnn nnnnnnnnnn   19260
nnnnnnnnnn nnnnnnnnnn nnnnnnnnnn nnnnnnnnnn nnnnnnnnnn nnnnnnnnnn   19320
nnnnnnnnnn nnnnnnnnnn nnnnnnnnnn nnnnnnnnnn nnnnccctgt agtcccagct actcagaagg   19380
ctgaggcagg agaatagcgt gaacccggga ggcagagctt gcagtgagcc gagatcgccc   19440
cactgcactc cagcctaggt gacagagtga gactctgtct caaaaaaaaa aaaaaacaaa   19500
aaaacaaaaa aaccaaaacc ttatgtatat tgtgaaaatg tagtctgctt taagctctct   19560
aaagaggtct aagttactgg ttcctaagta tggatgagca tcaaaatcat ctggaaaatt   19620
tgttaaaaat acaataatga aggtacctca ctgtcctttt tcccaaacac acttctgcat   19680
tctgtttgag taggtagggc ctacacattt ttcacaagta ttctcttggg aatacccagg   19740
aatgctcact tgagcaacct cttactaata ccatatactt tgataaagtg gctaggtaaa   19800
aataaatata taaaaatcca tcaatctccc atatattagc ataaatcagc tagaaaacag   19860
taatgtttaa agatctagtt cacagtagca ctgaagtatt gaattccaag aaattgataa   19920
gaaatatgca gaaactttat aaaaacttct gttaatgttt ctgaaagata taggtgacca   19980
ctttctagac aggaagattt tatcattaa agttgacttt tctctaaatt aacacagaaa   20040
tttaaaataa tcttgattaa aattctagta gaggtatttt tgaacttgtt cactgtaaga   20100
ataaatacat aactgcaaag aatatcttaa aatcatcact aggcccggtg tggtggccca   20160
cgcctgtaat cccagcactt ttggaggcca aggcaagcgg atcacctgag gtcaggagtt   20220
tgagcccagc ctgaccaatg tggtgaaacc ctgtctctac taaaaataca aaaattagct   20280
gggtgtggtg tgcatgcct gtagtcccag ctacttggga ggctgaggca ggagaatcgc   20340
ttgaatccag gaggtggagg ttgtgtgtaag cctagatgcc accatgcac cactgcctgg   20400
gtgacgagca aaattgtgtc tcaaaaaaaa aaaaaaaaaa gaaaaaaaga aaagaaatc   20460
aacgctaata tggtgagact tgatatatgt gacattaaaa tagtgattgg acattagaac   20520
aggtatagaa cagaaagaag agtgtgtgta tctgtgtgga tttatgatgg gtgtagcata   20580
ttgtattagt agggaaatga gggaaatgat atatttcttt gactttggga caacattata   20640
tctctacctc atattgcaaa caagcataaa attctgatta attacctaaa tgtgaaaaaa   20700
tgaaatactt tcttcaaaaa atgtaatctt agtttgagga agactaacat tatgaaggaa   20760
aaacctgttt tgactggaat atagttcaat atgtcaaaat ccaccttcaa caaaattgaa   20820
agtaaattga acttgggaa agtattgata gcatgtagat caaaggttac tagcctgtgt   20880
aaagagcaat tataaatcat taagaaaaga ctgtcaaccc gtcggcacct tgttctccga   20940
ctcccagcct ccagaactgt gacgagtaag tgcctgttgt ttaaaacacc tagtctatat   21000
gtactatttt gttatagcaa ctcaagctga ttaggaccct agtaatcagt agactgagac   21060
taaaacaaaa ataagaacct tttttacctg tcaagttggc aaacattaag aatatgcaga   21120
tttttgtcag aggtgataca acctttaaga aggcaatttg ggaaaacata aagcttttaga   21180
ttattaatgt gtctgatcta gggcacttac cctaggaaag tgtgtaatga tattggtgca   21240
ctgctgttca tcccattaga aaataaaaat aaccttaata gcttaccact aaaagggggga   21300
ttgaaaaatt aagatacatt tatttattta tttattgaga cagagtcttg cactgttgcc   21360
tgggccggaa tgcaatggtg cgatctcagc tcactgctac ctccgcctcc tgggttcaca   21420
tgattctcct gcctcagcct cccgagtagc tgggaataca ggctcacacc tccacaccca   21480
gctaattttt tgtattttta gtagagatgg ggtttcactg tgttaccag actggtctcg   21540
aactcctgac cttgtgatcc atcccctcg gcctcccaaa gtgtcaggat tagaggcgtg   21600
agccattgta cctggccaga tacattata caagagagtg ttagttaaca ttcatagatt   21660
ttttttttct tgtttacttt ttattaaaaa aattttttt tagagacagg gtcttactct   21720
gtcacccagg ctgaatgcag ttgcacaatc gtagcccact gcagcctgaa ctcctgggcg   21780
gaagtgatcc ttctgcctca gcctttgag tacctggggg actttaggca gtgctgctat   21840
atataacctgg ctaagtttta aatgtttat agatgggatc ttgctatgtt gcccaggctg   21900
gtctagaatt cctgggccca agcaatcctc ccaccttggc ctcccaaagc actgagatta   21960
caggcattga gccaccactt ctgatcaata gatatttata tttgtgactg gaaaatatat   22020
taacaatgtg ttaaaaatt cagttaaaaa ataatgaaag atttttgctt ctagctaaga   22080
tagaataaca aggacagcat ttatcttctt gccttgaaat agttgaaaat ggataaaata   22140
tatgtaacag tggttttcaa gttattgggc attaggcaaa gaagagtagt tatcacagga   22200
aaattaatgt ggagagccct acaatttcct tacattgctg cctggccatg gcaagaggaa   22260
aaactgaaag gaaactgagg ctgagccagt ggtttgctgg gttgaggagg cagagctggg   22320
agtccagaga tgcaaggtgg ctagagcccg tatggaaaaa taccagggaa gagagctgca   22380
gagggagctc cggagaactg cacagtaccc tctcatgtgt gtagctgagt attgatgagc   22440
acatgctggt gaggaaatga cccagggctg caggtagaac cacttaaaag gattagaagg   22500
aacaattgct gcaactcaca cagggccagg aagaatttct ttttttttt ttttttttt   22560
gtattttag tagagatggg gtttcaccat gttagccagg atggtctcga tctcctgacc   22620
tcgtgatccg cccgtctcgg cctcccaaag tgctgggatt acaggcgtga gccaccgcc   22680
ccggccaaag ggccaggaag aatttctaat cacacaagtc ggagtggaaa acctcggctc   22740
tcatagagca gcaggtagag tactcagaag ggtttgcctg cctagcccca gactaagttt   22800
cgttactctg acccgcctaa tattaaaa aagattaatt aaattaattg tttgcaacaa   22860
aagtaatata tttcagtgtt tataacgtgt agaagtgaat tgtatgacaa tagcataaag   22920
gctggaagag cagaaattga catgtatttg tgctggacag aataatgttc ccctcttttc   22980
ccaaaagata tcgagtccta atccctgaaa cctgtaaatg ttactttata aggaaaatgg   23040
tttcatggtg tgattaaatt caggatcttg agatgagggg gctgtcttgg atgatttggg   23100
taggcactaa atgcaatcac atgtgtatgc aaaggaggca gagggagatt ttacatacac   23160
agagaaggcc atgtgaagat agaacagaaa gatttgaagg tgctggcctt gaaaattgga   23220
gtgatgaagc tataagccaa ggaatgcagt agccaccaaa gctgaaagag gtaggacgaa   23280
ttctccttca gagcctactc cagagggaac gtggtgctgc cagttcctta atttcagctc   23340
agtgatacta attttggact ctggtctctg aaactgtgaa agaataaatt ttttttgttt   23400
gtttgtttaa gccacacagt ttgtggtaat ttgttacagc agctgcagga aactaattta   23460
tgctgcatgt gaaatggcat aatatcatta agatagatt tgataaaggt acatagtata   23520
aacaattaag caacaactaa aagcacaaca aggagttata gctaatgaac caaaaaagga   23580
```

```
gattagaatc ataaaaatag tgaatcccaa agaagccaga aataggggaa gaggcaaata  23640
aaggaaagaa agagcttgat ggtagattta aacctagtta tgtcaaaaag gacattaaat  23700
gtaaaagata ttttttcggat tgaatggaaa agtaagaccc agtatatgct gctgcctgca  23760
agaaacatat tctaaatgta aaggcaaaaa tagcctacaa gtaacagaac agaaagaagt  23820
tcaccgtgct tacaagaatt agatgcaagc tagactggtt ctgttaatat cagacaaagt  23880
ggatttcaga gcaaaggcta ttgcctagga tgagatggtc gtttcataat aacgaagggg  23940
attcgttcat cagccgcaca taacaaactg aaatatttat gcacctgact acggagctaa  24000
aatacacgaa gcaaagccta acaactacga gtagacacag gcaaatccac agtgagagag  24060
atttcagtgg cttctctcag tgatttgtag aacacgtagc cataatatct ggatctagaa  24120
cagttgaaca acactgtccc tatgcaacct gattggcttt tacaggacac tccacccggc  24180
accagcagaa gagacactct ctcaagtgct cacagaatgt ctgccaagat agagcagatg  24240
ctgggccata aaacaagtct ctaaattaaa cgcattcaaa ttattcagag tacgttttcc  24300
gacctcagta tcattaagtt ggaatatatt ataggaagat aacctggaaa agcctcagat  24360
atgtggaaaa actcatttct aagtggccca tgggtcagaa gtgaagtcaa aagggaaaac  24420
tgaaaatctt ttggattgac tgatatgaaa acaatagatg tctatacttg tggggtgctg  24480
ttacagtata gtaaagggaa atttctagca ttaaatgcct gttttagtaa agaaagattt  24540
caaatcaatg acctcagctt ctaccttggg aaacttgaaa atgacaagca aatggaatcc  24600
agagttacca gaaaggccag gtacagtggc tcatgcctgc aattctgcca ctttgggagg  24660
ccaaggcagg cggattgttt gagactggca gttcaagacc agcctgggca gcataggag  24720
actccatatc tacaaaaaac acagaaaatt agccaggtgt ggtggcatgt gcctgtagtc  24780
ccagctaacc aggagtctaa ggtgggagga ttgcttgagc ctgggaggtt gaggctgcag  24840
tgaactgtga ttgtgccact gcgctccacc ctgggcaaca gaatgagacc ctgtctcaaa  24900
aacaaaaaca gttactagaa gaatggacat catagagata agagcagaag tcagtaaaat  24960
agaaaacaaa aatacataga aaatcaataa aaccaaaagc tagttcatca agaacatcaa  25020
taaattggtg agactaatag gaaaaaaagt gaagtcacat attatcaata tcaggaatga  25080
gggagatgac agtagtatag attatataga tattaaaagg gctatatgag gcaggtgcgg  25140
tggctcacgc ctgtaatccc agcactttgg aaggccgagg tggacagatc acctgaggtc  25200
aggagtttga gaccagcctg cccaacatgg tgaaactccg tctctactaa aaatacaaaa  25260
attagctggt catggtgcca tgcgcctgta gtcccagcta ctcgggaggc tgaggcagga  25320
gaattgcttg aacctgagag gcagaggttg cagtgagctg agatgcgcc attgtgctcc  25380
agcctgggtg acagagtgag actccgtctc aaaaaataat aataataaaa aggactatat  25440
gggaatatta tgaacaactt tatgccaata aatttgataa cttatagatt aaatggataa  25500
gttccttgaa agacacacaa actattaaag ctctctcaag aagaaataga taaactgatt  25560
agccctatat ctatttttatt aaatttaaat gtaaaaatca atatttagtt actggaaaac  25620
ttttaagtgt ggttggaaat ggtatatgaa ctttttcaac tgaattttat gaaggctaat  25680
cacaggtaaa ggttttctga tgaaaaattta gtgtctgaat tgagatgtgc tgtaaaaaat  25740
gttgttatgt atcttaatca tttcttcaca ttaattacat gttgaaataa tactttgggt  25800
gtattgggtt aaatgaaata ttatgaaaat cttgcctgtt ttcttttttac ttttgatgtg  25860
tcacctggga aataaaaaag tgtgacttac attctgtttc tgttgacagt actgctttgg  25920
agtgcagtgt tggaatgatc tagcatttcg aagacctttc ctcccttcgt tattcagggc  25980
tgtattccac atagataagt ctgaaatact gctaagtggc acgttttgtt ttgtgctttt  26040
gtaagttttgt tgatcgttac tgatgtggac cttttggtgcc tcttaggctc atggctatct  26100
tccaaccatt gtttgcaatt tttacctaga gataaagaaa aaaaagagatt tggtttcaga  26160
gtaagttaga ttgagatcat gaaagagcaa tctcatttg atgcttcaaa aatagcacat  26220
cccccgtatt actgggattt gctattcttg ggcttacttc aagaacatcc ttgtgttgct  26280
ggtttggatg cttccgaatg ctgtgaagtc agtttcatgg acgtggctca tcagtttagc  26340
tctcttggct ttgtttaggc agttggagca tgatagcctg aacagcttct ctcaattaaa  26400
catttacaaa tcgtttacga atagtaaaca aactccaggt tttgtgactc tttgatagtt  26460
catctagcac aacaaaaaca caatgtgacc atgatcacct ggcatcttag ggtgaaatac  26520
tttggccagc actgaaagca aaattaaaaaa ggggcaagag agatatactg ctgaactgat  26580
tttcaaggtt ccaagaatat cataggttaa gagtaaaagt aaacttttga cagagagcag  26640
cgggttttct gggattgaag tatctgaagt tttcaaacga aaattttaaaa agaaaaaatg  26700
agaattgcct tataagtaca atctcttctt ttttaaaaaa taaactttat tttgaaatag  26760
ttttaggttt atcgaaaaaa attagggtag agagttttca tatacccctac atccggttac  26820
cccagttatt tcttaatta agtgtgagac attttcatgt ttaatgaatc agtatcgata  26880
tgctgttaac taaagtgcag acttttattaa gattttctta atttctatgt aatgtccttt  26940
ttctgttcca gaattccgtg caggacaccg gataccctcat tacatttcat tgtcatgtca  27000
ccttaggctc ctcttgacag tttctcttct tttttgctta gaaattctcc agaatttcag  27060
aaacttctgg gcatcgctat ggaactttttt ctgctgtgca gtgatgacgc agagtcggat  27120
gtcagaatgg tggctgatga atgcctcaac aaagttatca aagtaagagc cgtgtgatg  27180
gtgttctcag aaatgtcatt gttgtaggct aagagaagca gccatcgttg agtgttcttc  27240
tgtttggagc ccctgaggat gtctgcactt ttttcctttc tggtgtgtgg tttgaggtg  27300
ctctggtatc tgcccgcatt gcttgccaca cctgcctggt cagaaggaac tgtgttgacc  27360
cttgtgcctg catggtgcct aggtcaatga agggaaccaa tggtgaccac tggatgctcc  27420
tgggaaaatg tcactacagg taccagaaa gccagagcta tgcccacatt ttttttttt   27480
tttttttgag acggagtctc actctgtcgc ccaggctgga gtgcagtggc gcgatctcag  27540
ctcactgcaa gctccgcctc ctgggttcac gccattctcc tgcctcagcc tcccgagcag  27600
gtgggactac aggcacctgc caccgcgccc ggttaatttt ttgtatttt agtagagaca  27660
gggtttcact atggtctcga tctcctgacc tcgtgatccg cccgcctcag cctcccaaag  27720
tgctgggatt acaggcgtga gccaccgcgc ccggcgctat gcccacattt ctatgagtct  27780
cagttttctt aactataaaa tgggatcaaa gttttgtgtgg catgcgtatg agtgtgtgtc  27840
tgtgtgagga ttaaatgcac taattgccac taccggatcc tcaaagtggt aagaagtatt  27900
cttattaatc atgcatcct cacacttcta tgcagcaaga ttgatgggtg tggcactgct  27960
tctcttttc catcacatgt atccatgct ccaggggaatc tttccctttgt  28020
ggccagcact tgttgtttg gctcatcacg ctttctgtgg gcaggacgct ggcttctctg  28080
gagtcttggg attctagctc cctctcttgt ccctagagtg gtcactgtct tctctctctg  28140
cttgcaattc ttgctttgct cgcatctcac tcatgcggtg acctgtatca gtttcacctt  28200
gttctccgtg cctgctggtc gttggcacca cttgcctgtg gatggcatcc catagcgtat  28260
ttagggcctg cttccccagt taagcttgct tttccacagg cctgaatatc cttgcttgct  28320
```

```
tctgttattc ccactggcag gaccacggcg gtcttttttg gatgagacag ggtcttgctc  28380
agtcacccag gctggagtgc agtggctgat cacggctcac tgcagccttg agctactggg  28440
ctcaagctat catcctggcc tggcttcttg agtagctggg actacaggcg tgcaccacca  28500
tgcccagcta attttaaaaa ttatttgtag atatgggatc tcgccaggtt gcccaggctg  28560
gtcttgaaca cctgggctca agtaatcctc cctccttggt ttcacaaagt gccgggatca  28620
caggtgtgag ccactgtgcc tggcccttga tgtttcagtt cttgatattt gatcctcaga  28680
gtcagaaagt ctaaaaagag gactatccca ggttgccttg gttcacggca aatgggacgt  28740
taagagggca gagaaaacaa tatgaccaga aacgcttcta atattggtca tttaacgtgt  28800
aagtattgtt cttttttaaa cctccttcat cttttttctag ggattgctgg acacagtggc  28860
ttggtgtgtc tgagggctgt aggccatggc cctgggttgt ggttttaggt ctcaggtgct  28920
cttcctggtt gtctccttgc ttctttccca tttcctcttc tttgtttcca gccatttctc  28980
cctttttgctt aagtttggtg cagcaggggtt tggctgctct cagattgctg cttcctcaga  29040
tgatgcagtt gccaggccca gtgggctggc agtgggatca ggatctgact aggtttgctc  29100
tcactgtggc agaggagggg caggcgtggg agagcacgtg tgaccccagg ccaggtgtag  29160
ggagcccagg catggtcact tagccttcag gtcctagact ttgtcttctc atgagtgtgg  29220
ctgtgtgtgt atggtgagaa ccaggttcta cgtagcccaa gaaaatgtag agaaatgcac  29280
tgggtatctg acatagcctg gcagcacgcc tccctcaagt aggttagtct caggcggtga  29340
agcatgtatg tccagcaaga acttcatatg tggcataaag tctccgttct gtgccggcact  29400
gacaaatcac caccgtcagg aggctgaagt aatttctgtc tagggaggca gggaaggctt  29460
cctggagaca gtagccaata ggtgaaaggg tagattggag accttcttaa tcatcaccgc  29520
ctcttggttc gaggggtgcc aggaagctgt ggaggctgag aggaggggga acccatctta  29580
tgctgccaga gagtgggaca ccctgagggt caggtcaggg ggttgtacct tgttgggtgg  29640
agaattaggg gctcttgaag acttttgatg tggtcagggg agtgtatcat ttaggaagag  29700
tgacctggta aggacgtggg atagaggagg acagaggtgg gagggagtct aggtgggagt  29760
gagtgggccc agcaggagtg cagggcctcg agccaggatg gtggcagggc tgtgaggaga  29820
ggcagccacc tgtgtgtctg cggaagcagg ggcaagagag aagaggccag cggcgcgcag  29880
ccatcacccca gcaactggcg tagattgtga gagcccattc cctgcttta ggaggggccg  29940
agttttagtt ttctcttata aaataaactt ggtatttgtt tacaaaacat ttgtaaagct  30000
aaatcaaggt ttgataaggc ttctagtttt atttaagaag taatgtttaa ataaatgtcc  30060
aattcgcttt gcttatttaa ggactttcag tacaaacttc aacaacagga tcaggattta  30120
aacatttctg agatgttatt accccctcaga atttcccaga acgtgatctg gttttgattt  30180
tcaagcttgc tgacccagta ggttaaccca caaattttac taagatacac ctcagtccat  30240
ttatatcgac tgcccatgtc acggtcaaag agatcatcga ctgatgtttg gcacagcttc  30300
ctccctcttg ggtgggcaag catttggaag agaaggctcc catgggtgag agtggggcac  30360
cagagtcttc cccgtcctgt ccctggcctt gagaaaccct tctctaatgt ggactttgtg  30420
ccgttagcat cgttactggc ttgaagttga ccatgtggac ataatttctg gtttagcctc  30480
acaagtgagc aaggagggtt gagagatgtg ctgtgaggaa catggggccc ccgctggccg  30540
tgggctctgg gtcaggggggg caggggacca tgggcatacc tgacagtgag gaggggccac  30600
acctgcagaa agcatgcggg actcggcnna nnnnnnnnnn nnnnnnnnnn nnnnnnnnnn  30660
nnnnnnnnnn nnnnnnnnnn nnnnnnnnnn nnnnnnnnnn nnnnnnnnnn nnnnnnnnnn  30720
nnnnnnnnnn nnnnnnnnnn nnnnnnnnnn nnnnnnnnnn nnnnnnnnnn nnnnnnnnnn  30780
nnnnnnnnnn nnnnnnnnnn nnnnnnnnnn nnnnnnnnnn nnnnnnnnnn nnnnnnnnnn  30840
nnnnnnnnnn nnnnnnnnnn nnnnnnnnnn nnnnnnnnnn nnnnnnnnnn nnnnnnnnnn  30900
nnnnnnnnnn nnnnnnnnnn nnnnnnnnnn nnnnnnnnnn nnnnnnnnnn nnnnnnnnnn  30960
nnnnnnnnnn nnnnnnnnnn nnnnnnnnnn nnnnnnnnnn nnnnnnnnnn nnnnnnnnnn  31020
nnnnnnnnnn nnnnnnnnnn nnnnnnnnnn nnnnnnnnnn nnnnnnnnnn nnnnnnnnnn  31080
nnnnnnnnnn nnnnnnnnnn nnnnnnnnnn nnnnnnnnnn nnnnnnnnnn nnnnnnnnnn  31140
nnnnnnnnnn nnnnnnnnnn nnnnnnnnnn nnnnnnnnnn nnnnnnnnnn nnnnnnnnnn  31200
nnnnnnnnnn nnnnnnnnnn nnnnnnnnnn nnnnnnnnnn nnnnnnnnnn nnnnnnnnnn  31260
nnnnnnnnnn nnnnnnnnnn nnnnnnnnnn nnnnnnnnnn nnnnnnnnnn nnnnnnnnnn  31320
nnnnnnnnnn nnnnnnnnnn nnnnnnnnnn nnnnnnnnnn nnnnnnnnnn nnnnnnnnnn  31380
nnnnnnnnnn nnnnnnnnnn nnnnnnnnnn nnnnnnnnnn nnnnnnnnnn nnnnnnnnnn  31440
nnnnnnnnnn nnnnnnnnnn nnnnnnnnnn nnnnnnnnnn nnnnnnnnnn nnnnnnnnnn  31500
nnnnnnnnnn nnnnnnnnnn nnnnnnnnnn nnnnnnnnnn nnnnnnnnnn nnnnnnnnnn  31560
nnnnnnnnnn nnnnnnnnnn nnnnnnnnnn nnnnnnnnnn nnnnnnnnnn nnnnnnnnnn  31620
nnnnnnnnnn nnnnnnnnnn nnnnnnnnnn nnnnnnnnnn nnnnnnnnnn nnnnnnnnnn  31680
nnnnnnnnnn nnnnnnnnnn nnnnnnnnnn nnnnnnnnnn nnnnnnnnnn nnnnnnnnnn  31740
nnnnnnnnnn nnnnnnnnnn nnnnnnnnnn nnnnnnnnnn nnnnnnnnnn nnnnnnnnnn  31800
nnnnnnnnnn nnnnnnnnnn nnnnnnnnnn nnnnnnnnnn nnnnnnnnnn nnnnnnnnnn  31860
nnnnnnnnnn nnnnnnnnnn nnnnnnnnnn nnnnnnnnnn nnnnnnnnnn nnnnnnnnnn  31920
nnnnnnnnnn nnnnnnnnnn nnnnnnnnnn nnnnnnnnnn nnnnnnnnnn nnnnnnnnnn  31980
nnnnnnnnnn nnnnnnnnnn nnnnnnnnnn nnnnnnnnnn nnnnnnnnnn nnnnnnnnnn  32040
nnnnnnnnnn nnnnnnnnnn nnnnnnnnnn nnnnnnnnnn nnnnnnnnnn nnnnnnnnnn  32100
nnnnnnnnnn nnnnnnnnnn nnnnnnnnnn nnnnnnnnnn nnnnggtggg agaatcactt  32160
gaacctgggc ggtggaggtt gccttgagcc gtgatcacgc cactgcactc cagcctgggc  32220
aacaaagtga gacttcgtct caaaaaataa aaataaaaat gaaataaaat cagtccgggt  32280
gtggtggctc gtacctgtag ccccagcact tcaggaagct gaggcaggtg gattgcttga  32340
gaccaggagt ttgagaccag cataggcacc atggcaaaac gctgtctgta cagaaatgag  32400
ctaggtgcgg tggtgcacaa ctatagtccc agttacttgc gaggtggagg tgggaggata  32460
aatggagcct ggaaggttga atctacagtg agctgagatt gtaccactgc ccttcagcct  32520
gggcgagcaa gtaagaccct gtctcaaaaa aaaaaattat tgactatatc ttattgtcta  32580
taatccctcc tctgtgctat tgaataccag gttttgggcc cttatttcca tcactgaaca  32640
aacttcactc tattgagcag catgtgtgga atttcatctt tattcaataa ttaacagcta  32700
ggaggaaatg ctgttttgcta gactattgct ttactttttt tcaaaaggtt actcttttatt  32760
agatgagatg ggaattaaaa atggtaactt actttatgtc tttataattg aagcccgcta  32820
gatcttaaag tagttaccag atgttttatg catttaaatg gccttttctc taaaaataga  32880
aagtaacaat gaaagaaaat gcttcgtttc tatgcaaccc tcttggtgac tagtgtgtgt  32940
gactcttaat gtgacactca ttgcaccccc tcagaatggt gcccctcgga gtttgcgtgc  33000
tgccctgtgg aggtttgccg agctggctca cctggttcgg cctcagaaat gcaggtaagt  33060
```

```
tgtacattct ggatgttgat ttttgttggg ggccagctgc tactgatcct ttatgtctca    33120
gctcagatgt catttcagaa atctgctctg cccttccaa attgcagtcg accttgccct     33180
gtttatgttt ccgtcatagc actaatccgt gtcagaaagt gtcacgtaca gtctgtgtgc    33240
ttgttcattt tctatcccac cctcccccaa gagacttatg ggatgtgtgc cccaggacag    33300
caggggtctt actgtcttat gctctgttgc agcctaaaca gcagtaacag tgtctgcaca    33360
tagtacttgc ttaaatgatt cttgccaaat tgttgaaggt tgaggtacca gtttcattat    33420
tgctgactat aggagttaca gcaaaatatc catttgtcta ttacatgagt taaaaatatg    33480
gttgtttcac tatgaatagt tttgtctagt caaaacagtt gtgtcttaac ggattgagaa    33540
acaaaagcag gaccacttt catcagctcc ctcctcctta acctgcagta tacgctgatg     33600
ctgatgtcct gtagaccctc agctccatcc tgagtcactg ggaacgtggt ctaaaccctc    33660
attattagta tgaactgagt ttcaataaga atctcacatg ggtcgggtgt agtggctgat    33720
acctgtaacc ccagcacttc aggaggccaa ggcaggtgaa tggcttgatc cagactaggc    33780
aatatggtga aaccccgcct ctacaaaaaa tacaaaaatt agctgggcat ggtggtgcgt    33840
gcctgtaatc acagctactg gagaggctga ggtgggagga tcagttgagc ctgggaggtg    33900
gaggtcgtgt tgagccaaga tcacatcact gcactccagc ctgggcaaca gagtgagacc    33960
tgtctcaaaa aacaaaaaa caagaaaca aaaaaagct tatatgggtg cagaggtata       34020
atcactaagg aaatttcttt ttgtgtagtc ttttttcttt tactgtcatt tcaaaaaatg    34080
tgttatattt ctgaagtaac acatccaggt tctcccacata gcagccaaag tgaccttaaa   34140
gaacataatt gggtcttgtc attcccttat ttaaactctt gtgcccgttt cccagtgccg    34200
tttagattga ttccagactg gtaactggct ccgtcacctc agacactctg cattgactca    34260
ttagcctgat cagttcttca gatgagtcag gttttcttc ctcctgatgg tttgtttgtt    34320
ttgtttattc ccctcagttc tcagcaaaac agtcatttcc ttaggagggt ttccctagcc    34380
tccctgtctt tccctgtccc aggagcctgg tggtgtggtc actgccctct gaggccctgc    34440
ttgttgccag gctctgccac tagagggcag ggctgcacca ctcctggcac ctcacacctg    34500
gcctgccctg tcagtgtttg ttgggtgaat tcctgtgatc tgtgactcac tgctctgtgt    34560
cctacacatt ctgcttttct tctccccctca caataccatt tataattctc cttttttcagg  34620
aaagctttat ttccattaaa acattttgt tttaaaatg gtattttctt acactattat      34680
tttctaatta aaaatgagtg ttttggcagg gcgtggtggc tcacccctgt aatcctagca    34740
ctttgggagg cccagatggg cggatcacaa ggtcaggaga tagagaccat cctggctaac    34800
atggtgaaac cccgtctcta ctaaaaatac aaaaaaaaat taggcgagtg tggtggtggg    34860
cgcctgtagt cccagctacg tgggaggctg aagcaggaga atggtgtgaa cccgggaggt    34920
ggagcttgca gtgagccgag atcacgccac tgcactccag cctgggcgac agagcgagac    34980
tccgtctcaa aaaaaataa aaataaaaaa aaaaaaataa ataaaaagta aaaaaaaaa      35040
agagtatttt aagaagtatt acgatttact gcaaataatt tttaaaccca gccttttaga   35100
tcctctgtga tcataagaga aatgaaggat gtctcccgac acttgagctt catccacatt   35160
tcattctctc gttctttcag ctgagctttg cccatcccca ttagggaccg tttggcatat   35220
gaaactggct tttccctaac agggaatgaa ttgcttctat ttctcctgaa ggagagctgg   35280
aggaatgact tgcgttcttt tgcatacaca ggccttacct ggtgaacctt ctgccgtgcc   35340
taagtcgaac aagcaagaga cccgaggaat cagtccagga gaccttggct gcagctgttc   35400
ccaaaattat ggcttctttc ggcaattttg caaatgacaa tgaaattaag gtacgattat   35460
tgcctcagat cacaaacatg tgagtgacgc tgtgagtgag tctgtggagg ttacggcttt   35520
ctgagcaggg agtcatgtgg gagcgcttct tagagtatgt tgtatgtcgt aatttagact   35580
accgtcattt gtgttatttt tgaggcacct aaagacttct ttccacttct gatttcttac   35640
tgtggggtga agagttgaat tgggagatgg tttatagatg cacattcaaa aggcatattt   35700
ccagagcaga ttggttttca gtgtattaga gtgactgttt aacctagctg tggaaagatg   35760
gctgtgccag gactgcaggt aggagaaagc tcactgacga ggccttgtgg gtctgaacat   35820
cctgcagcta tcagggcctg ttggctccct gttgtgcatt ccaacaaacc accttcaaac   35880
ccactttagt gtttgtttat aatgtccaga aatagtgacc ctgtcacatg ctctacagat   35940
tacaggattc ctagcctctt ccttttggt gggtcagtcc tgggtttgag cccaagtggc    36000
cctcttggaa ggtgatgata cacagtgggt agagtggaat cagatggact tggattagaa   36060
ttctgtccgc tttactggtt cttttcctct aggcaaacta tccaacagct ctaagctatt   36120
tccttcgtat tctgaaaact aagccttaat gggacccata tcgggcaatt ctgagagtga   36180
aataaatgaa tatgtgttag cgtgtagcat agtcgcccac aggaagggct tagatgttag   36240
ctgctactgc tcttattagc tgaatgactt ggaataaagt gttagcctct ctcatgtttt   36300
tttctctgag ctttgaagtt ttcttgttaa tactaaggag atattcaaac tagtcatggg   36360
gttttggaat gacgaaggga gatcatgaat ctaaagaatt tagtgtggta attcatcatg   36420
ctcagtaaat ggtagctgct gcttgctgtt atttttatta ccatctcttt ggagtgggag   36480
taggtctcct ttgtggtcag aggctgtgag agctccgcag cgccagtctg cccgtcagta   36540
caccgggctc tgatgaaggc agttccctct gtggtatctc tggctgtcag agctcagatg   36600
atagatggtg tttttgtact ctcagttctc atcattttca tgatttcgat cactatttga   36660
gtatgatgat gctaacactt tgttgaacat agagtccatt aattacttcc ttcctgaacc   36720
ttaggtatttt aaaaaaatct attctgctac ctctctgctc atttatgatt attcagattt  36780
attatcaaga gcctggtaca gtggcttgtg cctataattg tagctacatg ggaagctgag   36840
gtagggaggat tgctggaggc caggagtttg agaccagcct ggtaacatg gtgagaccct    36900
atcgctaaaa aatgaaaaaa gttagctggg catgatggca cgtgcctgtg gtcctagcta   36960
ctcaggagac tgaggcagga ggattgcttg agcccaggag ttggagttcg aggctatact   37020
gagctgtgat tgtgccacca cactctggga tgggtggcaa aagaagatgc catttcttca   37080
aaacaaaaca aaacaaaaaa aggtattatc ggtgaaattc aatagtacca acaggattat   37140
aaacaaagat agttctcttc ctactttttc tcttaatcct tgtgtctcag aggcaaacat   37200
aactcttagt gttttcttcca atatttactt cgannnnnnn nnnnnnnnn nnnnnnnnn    37260
nnnnnnnnn nnnnnnnnn nnnnnnnnn nnnnnnnnn nnnnnnnnn nnnnnnnnn         37320
nnnnnnnnn nnnnnnnnn nnnnnnnnn nnnnnnnnn nnnnnnnnn nnnnnnnnn          37380
nnnnnnnnn nnnnnnnnn nnnnnnnnn nnnnnnnnn nnnnnnnnn nnnnnnnnn          37440
nnnnnnnnn nnnnnnnnn nnnnnnnnn nnnnnnnnn nnnnnnnnn nnnnnnnnn          37500
nnnnnnnnn nnnnnnnnn nnnnnnnnn nnnnnnnnn nnnnnnnnn nnnnnnnnn          37560
nnnnnnnnn nnnnnnnnn nnnnnnnnn nnnnnnnnn nnnnnnnnn nnnnnnnnn          37620
nnnnnnnnn nnnnnnnnn nggagtacaa tgacatgatc ttggctcacc acaacctccg     37680
cctcccgggt tcaagcgatt ctcctgcctc aatctcctga gtagctggga ttacaggcac   37740
gcaccaccat gctcggctaa ttttgtattt ttagtagaga cggggtttct ccagattggt   37800
```

```
caggctggtc tcaaactcct gacctcaggt tatccaccca cttcagcctc ccaaagtgct  37860
gggattacag gcatgagcca ctgcacccgg caacttccac atttctcagt aacatgcttc  37920
tactgctttt tttttttttt tttttcaat tttagacatt ttttactttc acactataat  37980
tctatcagaa ttcagtatgt acattattat acctaagtaa atagtcatgg ttggttgtgt  38040
attatatttc tttgtatttc ttatttgatg agagagctgt gttttttgct gtggggttgaa 38100
actgtggaga gaggacatgg ggaggggaag gaagacagat gaagttggtg actgtaccttt 38160
cctggccata gctgggttct cagcaccctg ggatctgctg atcacctgct cgtaggccaa  38220
gcccctagcg aagttctagg tgacccagtg ctggggatgg ggggtcacc tgcaaggtct   38280
agtcatggag gtgggggcta cagtgttggc ttgtgctggg gccagcatcc ttaggaatgc  38340
atcttggagg aggaggagac agccacccac ttcttgactg gggccttcag cagtgccagc  38400
ttcttgggca gactggtgct ggctttcatc accacatcgt gttcaatctt cttccagatc  38460
ctgacttcta ggttcacctt tccttagacc ccggttcctt tcagaggctg tcgctctgcc  38520
ttgctctttg ctggcttgtg ccttgattat atgtctttgt acaacttttt gttttcctgg  38580
agttaatcct cacatctgtt ttcctagagt gaattgttac ctttatatca cttgcttatt  38640
attctttgac ctttttttct tctcacacct tccaactct ttgtaaaatg tgtttagtac    38700
aattttttcat gacaggtaat ttaccaaatc agttttttccc cagtgcagtc atccatcttg 38760
agttacccag ctcgctgccc cagtctgggc ggattgctct tcaggtctgt tgtacacttg  38820
tatcctagga cttctctttg ccatcagcct ggaatttcct ttgcagttct cctgttggat  38880
gcccagttcc tacatgccat atgtttatct ttctatcctc tagtagcttt gtgagagaag  38940
atgaatggga ggtaaattgt ttggagtttt gcattcataa aaatgccatt ttttctcgcg  39000
tacacttggc tgagtatagt gttctggggt agaaatcatt tttcctcaga aatgtgaagt  39060
ctttccccgt tgtcttaaag tctccaacat aacccaattc cttaacccat gaatgtgctt  39120
ttctctggaa gctttccatt tttggggagg tgaagtgcta ggtacttagt aggccttttta 39180
ttttttattt ttatttgttt tttgaggcgg agtctcactt tgtcgccgag gctggagtgc  39240
agtggcatga tctcggctca ctacaagctc tgcctcccag gttcacgcca ttctcctgcc  39300
tcagcctcca agtagctggg actacaggcg cacaccacca cctccggcta gtttttttttt 39360
tgtattttta gtggagacgg ggtttcaccg tgttagccag gatggtctcg atctcctgac  39420
ctcgtaatcc gcctgcctcg gcctcccaaa gtgctgggat tacaggcgtg agccaccgcg  39480
cccagccagt aggccttta atttggaaac ttatatactt cagttctggg aaaattttct   39540
tacattctc tgataaattc ttgccttta tttctgtgt tctctccttc tgaaattagt     39600
tagttggatg ttggtcctcc tgggttgact cacatcttac ctttttcttt ttctggtact  39660
ttttagatat ccatctcaaa ctcttctatt cagtgttatg ttttaacttt ctttcttttc  39720
tttgtctctt gatgggtct tgctttgttg cccaggttga ggtgcagtgg tgcaatcata   39780
gctcactgca gcctccaact cctgggctca agcaaccgtt ctgccttagc ctcccaagta  39840
gttgggacta caggtatgca ccaccatgtc cagctatttt ctttactttc tttctttttt  39900
tttttttttt ttgagatgga gtgctgctct gttacccagg ctggagtgca gtgatgcgat  39960
tttggctcac ttaagcctct gcctcccagg ttcaagcaat tctcctgcct cagcctccta  40020
agtagctggg attataggtg tgcaccacca cgcccggcta attttttgtat ttttagtaga  40080
gacggggttt cgccatgttg gccaggctgg tctcaaacac ctgacctcag gtgatccacc  40140
tgcctcagcc tcccacagtt ctgggattac aggcgtgagc ccatcattaa atctttaaat  40200
actagtatct gtaagtcttt tcctcttgag tcagccagta tccctggaag gaaattcctc  40260
attttcctgc ttggagacta taagcttggc tgtgtttatc ctgcaaccgg ggactggaag  40320
gggatgaag gggactgaca ctgttgctgg tcagggcgcc ctcttttttgt ttctgtatg   40380
catctcacat ctgtcctcag ttatgtaaac acctcttgag attatccctc tcagtctttg  40440
ctggaggtgg ggaagggggct gcttcctggg ctgccttgga ttgaggggga gacctcaggc  40500
gagtgggtgg gaatttgccc aaggagccat gagacaagcc actgttccac cctctccgtc  40560
cctccacttt cagatgtatg tggtgcctcc aaagcccgag tgcttcttgg agttctgtgg  40620
cttgaataag cttgctttttc actggtatcc ctcataccttt ctccccccatc cccagcaaag 40680
cttgcatttg aacttcttcc catgggctaa caaatcagtc agttatgtag cccttgttac  40740
tttttagctt ccgaagtttt gttgacacac gtagtctgct agtgtccctg ttctgttctt  40800
tctgtccgtg tacatttatg ctttatacaa cttctttaca tgattttttgt ggggtttttg  40860
ggtagcagag cttcacatgt tcaatccagc atgttggatt agaagtctcc caccctctgg  40920
tgtattctca ttctcagaat tacctgccaa acaccgatac tcccttgttt ttcctttttcc  40980
tgacaggaaa tgtacatacc agacaggaca gaaatcatta gtgtatccct tggtaataa    41040
ccacaaagtg atcttaccct cgtaaccacc acccaggtca agacagagta ttaccagcac  41100
tcagaagcct caccccccatc ctcccatcac tgcttcttcc ttcctcccca aggtcatgac  41160
tgtcctggct tctaatgcca gagtctgttt ttaaattctg tgtacataga ccatatagta  41220
tgtattcttt ttgtctggtt tcttttgctc gacagtaatt tcttaagagt cttctatatt  41280
atcgtgtgta ttagtagttc ctgtagtttt aggagcttca tagcattcca ttgtaggtat  41340
ataccacagt ttattcattg tgttatcact gggttgtttc tagttcttgg ctattgtgag  41400
caatgctact gtgaccactc tcaggtgttt tttttggagc acatgtgcag gtttccatca  41460
tgcgcagcta gaggtggagt tgttgggtga tagggtgtat gcatgtcagc tgcagcagaa  41520
actgccaaat agctttcctg agtgcttgta ccagctcacc ctttggttgc tgcgtatggg  41580
gactccggga gctctggtcc tcgctagcac ttggaattgc tgatgctttt acttttagcc  41640
ttcctgatgg gtattttctg gaatcacatt atgattttaa tttccgttcc ttaaagtacc  41700
cttgactctg aagtttaatg attaatgcat ctcttccttt ttgaagtact ctgaaaggta  41760
tgttgtgcat gtgttgaaaa ctggagctat ctagtctaaa atacagtgta cctcctcccc  41820
gtttgaaaag ttgtagcatg gcctcggggc ctcctgttag gtgccttgga gaagggattc  41880
ttgggattgt agagattaga cctgaggagg ccccttggag ttcagact aaatttgtt      41940
ctttattatt ccaaactatt taagctcacc gtgtgctgac tcatcataat aatgagtagc  42000
tctcattgtg cttgtatatt tggaccaata gaatgatttt tttttttga gacatagtct   42060
tgctctgtca cctaggctgg agtgcaatgg cacaatcttg gctcactgca gcctctgcct  42120
cccaggttca agcgattctt gtgcctcagc ttctcgagta gctgggactg caggtgtgta  42180
ccaccatgcc tggctaatgt ttgtatttttt agtagaaacg gggtttcacc atgttggcca  42240
agttggtctc aaactcctga cctcaagtga tctaccgct taagcctccc aaagtgctgg   42300
gattacaggc gtgagccgct cgcgttgcc aaagtagttt tttaagatgt gaatatcttt   42360
tcttgcagct aaaaaagttt gtcagagata attctacttt attctccagg tggttttttca 42420
gggagaaatt ggaggcagta aaccacgggg ggagtcctgt ggcttggtgg gtgggtgggg  42480
gaggtgtggc tggggtgggg agaagtcctg tggctcgctg ggtttggggg gagctgtggc  42540
```

```
tggggtgggg agaagtctag tggctggggt ggggagaagt cctatggctc ggtgggtggt    42600
ggggagctg tggctggggt ggggagaagt cctgtggctc ggtgggtggt ggggagctg     42660
tggctggggt ggggagaagt cctgtggctc ggtgggtggt ggggagctg tggctggggt    42720
ggggagaagt cctgtggctc ggtgggtggt ggggagctg tggctggggt ggggagaagt    42780
cttgtgactg gggtggggg cagtcctgtg gctggtgtct catcatgtgc ctaacagtgt    42840
ccagaggtct cgtgtaaatt ccctgggagt cgataagcct ctgagaaaca gatgatgcta   42900
accacgctgt ggaagagaaa cttgttata aatcagatgt ccgttactgg tttactgctt    42960
gtttgcccag gcatagctcc gacagagtcc ccgactcata gtgattgctc agtgcgtgct   43020
gaacaatgat tggaatcaag tcatggctca gagcatagtt ttgaataatg ggaaattgat   43080
gttcttaagt aacatagtca ccaagataat gcaactagat gagtcacccc ttttcaattt   43140
taggatattt ttatcaagat ttaagtggtc atcattagaa ttatagcagt ttctcctttg   43200
gattgttcta gaggcccagt gagaaagtat tccctaattt ctcaggagaa cagttgtggg   43260
tagtgtgctg tcatgtccag ttaaattgca gacgtttccg gttgaagata ttccagtcct   43320
gagaactttg tgacattagc aggactttta caagccatct cttagggtgg ggcattactg   43380
tagttggctg gtactctttt ctccttaact ttgtcatttg ttgatttttt tttttaact    43440
gtccccaaac actgtgggca gacagtatct agaattgagg cctccacccc tgcagagagg   43500
acgtggatgc tgagcagtcc ccgagtgaag attataaaga agcaaataga gtacacgtgt   43560
ctgtgaactg ttcttgagtc tcccaaattc ggggtacttc tgttcagcta taggaaaagc   43620
ctcaaactgt ttatactttg caagaattgg aaacttctaa ttcaagttaa gttttacgga   43680
atgcatggta agcttcatag gagcttcatc ttttatctgc ttggactttt gcttctatag   43740
gttttgttaa aggccttcat agcgaacctg aagtcaagct ccccactat tcggcggaca    43800
gctgctggat cagcagtgag catctgccag cactcaagaa ggacacagta tttctatagc   43860
tggctactaa atgtgctctt aggtaaggtg gaggcataca ggtggaaggg tctccagcat   43920
gtattcatga tagaccttg aaataattaa aatcagatga tccctcagct tctagaccag    43980
gctatttggc actggttgac tgaatgtgaa ctgcattggg actgctgtga gcacgcatgg   44040
gtctctgtga ccctgcagat gcagccatgc ccagggacac ctagctgggc agtgggtgtg   44100
ggctggtgtg agccctgcct gccacccagg gcctggtcct ccgtctgtgc cggccctgac   44160
tacggtgagt ctgtgaggct tgagactgtg ccttgggtcc ctgtgggttc tctgtaggtc   44220
agttgacagt ttctcctgtt gtttgggtaa ctgtggaaat gaacactggc aagtgctgaa   44280
gtgagcactg gacgcgtgat atggaccctg ccaagccagg gatatgggtg tgtagccact   44340
cccagtgggc ctcatggtgt actcgttcac ggtcatgttt gtgccatatt gatctcttgg   44400
gatctcttct tttttaacaa attaagcggg gaatctccaa acagtgagtt ggatgttaag   44460
atatcttgct gctgccccca caggcttact ggttcctgtc gaggaggagc actccaccct   44520
gctgattctt ggcgtgctgc tcaccctgag gtatttggtg ccctgctgc agcagcaggt    44580
caaggataca agcctgaaag gcagcttcgg agtgacacgg aaagaaatgg aggtctctcc   44640
ttctgcagag cagcttgtcc aggtaggagc acagggttta ctctaggcct ggcatgtgaa   44700
caactgacat ttgaagaact gattactttg aagagaagc ggcagaaccg aggggttagag   44760
gtgtggactc tggagctgtg ctgctcggtt ccgaccctag gtgctgacct ctaggtgcct   44820
tccttctgta tgccattgtc accgtgagtc agatgcaggt gatgcctctt caggtgccac   44880
tctgtttcta aaaccagagg tcacgatatg tgttcataca cccagtaaat actgattgag   44940
cacccactgt gtgctcgggt ctggggtagg tgctgggggt cctgtggtga atatttccgc   45000
tgcagcctct gccctgtgga gcctgtgcc tggtgcactg gtcgaggcag ggtggtatgc    45060
cccctcaggg aggtggggac gtggtccttc gggtgtcag aacaaaatgt tggaacttct    45120
ctttccaatg cagagaaacc ctgcagtaat tctaatgtac tgtgattggc agttgacttc   45180
agttctttgt agcgtgctta ctcaggttat tttcactaac tgtgtaacag tgcagcctca   45240
ttttaagcaa ttgaatttt tgaacttac ttaaaatatt aggtcagggt ttttattgtg     45300
cttaacatgt gccatttagc taaattttgt aggatataaa attgtaagtg acttaaaatg   45360
attcttgcat agaatcatga attgaagata atgctaataa tttaagcact gagttaggta   45420
gtgtttgtga agtgcttaga atgcttcctg gcacatgtga aggccatgta agtgctgctt   45480
attgataaac agctgagcaa gagtgaactc taagaaatga atggggctga gagttctatt   45540
ccacccagtc gccctttggt tattttacag aataaaagca gagtctcatg ggatatgaca   45600
tttaattata tttccttcac aaaaaaacact gctgaatatt ttgtggagta aaaagggtgt   45660
agccatggca ataatacatt taaaaatatag tttatttcat ctttacctta cctgtttttt   45720
tttttttaagc tagctttata ttgagaattg catacatgca aaagtatcaa gtcatgacca   45780
gttacatttc attttataatc ctacttctcc cttttttttt ttattatttg gaagcaaacc   45840
acaatcatcc tcttacttca tctataggta tttcagtatc tctatagatg aggactcttt   45900
tttatttta aaacttaatg atggtcaggc gcagtggctc atgcctgtag tcccagaact    45960
tgggaggcc aaggcgggca gatcacttga gcctaggagt ttgagaccaa cctgggaaac    46020
atggtgaaac cccatgtctt taaaaaaaaa aaacaaagtc agccaagtgt ggtgatgcat   46080
gcctgtagtc ccagctactt gggaggctga gatgggagga tcacatgagc ctggaaggtc   46140
gaggctgcag taagccatga ttgtaccact gcactccagc ctggttgatg gagcaagatt   46200
ctgtctcaag aaaacaaaac gaaactccaa aacaatgtca caaaacagtg ccattgttag   46260
acctgaaaat attaaacatt tcctacatca aatacccact aactcattgt caattttct    46320
ctctactctt ttggaatcag catataaata aaattgattg ataaggattg taaatctctt   46380
tgatcaactg gttctcctcc atccgaattt ttttttccct ttagagttca tttattgaga   46440
aaccagatta tttgtcttct aagttttcct gtggtctgat atactgctta catctccatt   46500
gtgtaaatta acacctttt ctgttctctg tatttcctgt acatcaataa ttggaggaaa    46560
aacctggtca gatttagtgt atattttata tctgagttca gtatttcgta tataatattt   46620
taaggtaaga tgtatctctt ttaaaaagtg ttgagactat atgctcaatt tttttttaaca   46680
gatgcttttg aaaaggctgc ttgatcataa aagtttagag accattggtc tgttgggaga   46740
agcaaataat tacgaaacag tttagcaagg ttaaggtgca catggtaggg cctggagagg   46800
ttcagtcgtg agccgtcact gatgggcacg tggaatctga cccggcacag agagctggga   46860
gaagacagga gctttataga cagaaaacgt ggtcttttgcc aagtcccggg agtgaaagag   46920
tgagagaatg ctcacagcac atgatgtgg gtgcgtagac agacaacgg tgggtcctga    46980
aaaggcctcc aggcttttctc atagattagc aagagtgttg gttatgaggg tcagaaggag   47040
gtcgaaactg tgttaaattg ggattgcagt aatcctggaa ggacagagat agagggtgaa   47100
ggggaaaaaa gggtatggat gtgagactta attgctgatt tcttaatac ctttctccaa    47160
agtaaataaa tgatatggca catttttgaa ctagcaaact ctagatatga ttatctgtat   47220
aacatatctt actccatctt cttttgacta ataactgttc ttaattaaat tactgtgaga   47280
```

```
tgttcaattc agcaaatgta gtttggctaa ctatatttaa ttagaattta atataatcct  47340
aggcctggcc aaactattaa gcaagtgtgg gcaaaatatt gataatttta gatatgcagg  47400
agctcagttt ctttctatgt gtgcttttg aaaaagaaag aaattgaaaa atagaggaag   47460
ccctgaaatc caagaaacaa agtctctcat ctaggcatgc aataaaagca attctaggat  47520
gattgttgtt cggcatgtag tttgttagaa aacattcttc ttgaataaat agtatgccta  47580
agaaagtggg cagagggaag gcatatgcat atattattaa caaggaggga gaaaaaggca  47640
attagtaacc atccatagga gagccagcaa gatttataaa ggaaatttgt gatccaagta  47700
tgaagcaaaa taagatgcat aataaatttt aagcaagtaa tagattacag taagagaacc  47760
catttgacca ttaattttgg ggcattttct ttcaaatgat aggagtagt aatgaaatat   47820
ttctttcttt ctgagtctag gttattgtga ctggactcag aaagaaagat ttcattattg  47880
cagtgaataa cattttgaa cattattcat aaattatgca gtaataaca tttatgaaca    47940
catgatacat aagatacata ctgtttattt ttaattaagt ttttcagctc aacttctcgg  48000
cagggaacat taaatgtaaa tagtgttacc tagtagcatg taaatggaaa tctccatagt  48060
atgaaagcag tgctgttgct aacagaattt aggaggcgac agatgaggtg aaggaaatgt  48120
gggtgccgat ttccttatta cattgagagg agccaggaga ttctttgttc aaaatagatg  48180
gcttaagaag tcaaggtata agctgattac ctagagcagg tacccacaaa tgttttgtgt  48240
aaggggccag atagtaaata ttttcagtct tgcaggccat tccaagtctg tggcaactag  48300
gccccactac cttcgtagca cgaaagcagc cacaggcagc ccataaacgt ggctgtgttc  48360
cagtgaaact ttatgtacaa aagcaggtgc gggccagacc tgacctgtgt actgtggttt  48420
gatgacctgg gattcagggg tataggagtt accatcagag gagctgaaag tgagactttt  48480
tactttatac tcttctacac tgtctgattt tttaaaaaag aaacatatgt attttataat  48540
attgagatg gggttggcaa atagcaaata aaaatacagg atgccagtga aatttgaact   48600
tcagataaat tatgagtaat tttatgatgt aagtatattc caaatcctgt gggacataca  48660
ctacaaaatt atttgttgtt tctttacaat ttaaatttaa ctgggtgccc ttgtcttta   48720
tctggcaact ctaattaaag ggaaaagaa taaattcatt atgttcatat aatgtgatac   48780
agcagggtc cccagccccc acgctgcgga gcggtattgg tccatggcct gttaggaact   48840
aggctgccca gcaggaggtg agcagcaggt gagctggcat tcccacctga gctccgcctc  48900
ctgtcagatc agtggcagca tttgattctc ctagtgcaaa cccctattgtg aacagcacat 48960
gtaagggatc tagattgtgt gctccttatg agagtctact gcctgatgat ctgaggtaga  49020
acagtctcat cttgaaacca tcccctggcc ctgtgaaaa attgtctccc atgaaaccag  49080
tctctggtgc cagaaaggtt ggggagcact gtgatatagt attgaaagtg ctgataaatg  49140
tggctactgc ctttaaaatg tctggtagct cttttctcagt ggcactcata atagtgtttt  49200
ttgattttta aatgtgtgtc aagctaactc tcccctcagt gtatgctgga ctttattttc  49260
cctttcctag tcaccagttt tgggaaatag agatcttcat tctcatgctg cttctctagt  49320
ggaagtgctc catttatttt taaggaatga atataacaat gaaaaaatca tgggaattca  49380
gaaaacaaca tggaagtaa cgatcacatt ggtagaagtg ataggaaat atttaggggg   49440
agaaattaag gtgtaaactt tgccaacgaa gtcctgttaa aaaaaaaaa gtgaagctta   49500
ggatgcattt tataaactct gaccagaaca cctgtgtttc tctgttttcta ggtttatgaa  49560
ctgacgttac atcatacaca gcaccaagac cacaatgttg tgaccggagc cctggagctg  49620
ttgcagcagc tcttcagaac gcctccccccc gagcttctgc aagccctgac cacagtgggg  49680
ggcattgggc agctcaccgc cgctaaggag gagtctggtg gccgaagccg tagtgggagt  49740
attgtggaac ttataggcaa gttattagta aggtctactc ttacagttaa cttttcagtg  49800
atactagtta ccctctattg atgatgggcc tgccctgtgc taagcagtct gcattgcatc  49860
ttccttgcca aaacttataa tacagatttc atctttattt tataaatagg ggagttgggc  49920
tgggtgtggt ggctcaggcc tgaaatttca gcactttgga aggatcactt cagcccagga  49980
gtttgagaca gcctggccaa gtgagaccct gtctctccaa aaaaaaaaa aaaaacaaaa   50040
actgggcatg gcggcacgtg cctgtagtcc cagctgcttt ggaggctgag gtggtaggat  50100
tgcttaagcc caaaaggttg aggctgcagt gagttgtgat ggcagctgca ctgcagcctg  50160
gtgaccgagc aagatgctgt ctcaacaaaa tttaaaaatc aaagaagaga attaaagttt  50220
agaaggttag gtgcaaaat gaggccacac atttaaagcc cctcctcctg attctttctc   50280
taccttgact gcctcctgtg gtggttcagt tgctgagaaa tgaaaacagt agggaaggcc  50340
gggtgcggtg gctcaagcct gtaatcccag cactttggga ggccgagacg gcggatcac   50400
gaggtcagga gatcgagacc atcctggcta acaccgtgaa accccgtctc tactaaaaaa  50460
tacaaaaaac tagccgggcg ccgtggcggg cgcctgtagt cccagctact cgggaggctg  50520
aggcaggaga atggcgtaaa cctgggaggc ggagcttgca gtgagctgag atccggccac  50580
tgcactccag ccggggcaac agagcgagac tccgtctcaa aaaataaaa acaaaacaaa   50640
acaaaaaaaa aaaaaaaag aaatccatc tgtccccagc tctgcatctg cctccactgc    50700
ccagtctgct cctctccatg cgcttgggc tgggccctgt cccaccatgc agtgctgccc   50760
tggagcagtg agcttagtgg gtcctttctg gcatgagagc tgcctttggg agctggagtg  50820
ggtgggaatc tctgaatccc agcctctacc gctgggtctg gtgcctagca ggctatggat  50880
aagcttttgc tgactctagc ctcccctagg ccactgcagc gtggtcggtg tagtgcactg  50940
cgtgtgcagc atgccttta ctcacagcct ccacattaga gagaatctga ctgaagtctc   51000
gttgctgcct cgtgtgagca taaatgtttg ccggaaccat gagcaggaaa tattaatctg  51060
ccttgtttcc tgtcctttac actgaagaat cttttctgtt atgggatgca tgccttacaa  51120
ataatgagtg gaaatactca tcgctaatga aaagttatac ctgattgtta gtctaccaaa  51180
taatctgaga tttctaatac ttttaatttg gcttttaaaa tgcaatttat cttagctttt  51240
ttgacttctt aggtcatatc tttagaacta tgtatttgaa tgttaatgta attttcatat  51300
tgaaattaaa atgttgaact gtgatgttaa gtgcttcctg tggaaataca ttcacatttg  51360
attcaacttt gaatcaagct gtttgaagat tttcacattt cttctagatt ttatcagctt  51420
gttactttat ctgtcacttt ctgtgattta cagctggagg gggttcctca tgcagccctg  51480
tccttttcaag aaaacaaaaa ggtgattatt tcagaaatca gagtcttgtg ttgaatctta  51540
ctgatttcct tgtatttctg taatgtaatg tatcttgtat tcttgtaat actgtattgg   51600
actctgtgta tgtatatatc ttctcagtgg agtgattgta tgtgtgaatg ttgctggaat  51660
acaa ctgataacaa ggcctgaata gttttatagg gtggcttta acagttactt tcatatcaga  51720
attgctttgt catacatttt gaatgcatca taaatttcta atgttcgggg tcagcagact  51780
ttttctgtaa agggacagag tgcaaacatc ttagctttat gagccatatg gtctcttttg  51840
caaccattca gctctgccct gtggcaggaa tgcagttgca gacaatacac gagctactgg  51900
ccagccatgt tccagtagaa cttttacttac aggaacaggg aggctgtagt ttgcccatac  51960
ctgccttagg gaatgtgttg ttatatttta tgaagttaac ttaccttccc agtgaatttt  52020
```

```
gtttagcatt agtcaggaat attattaagt agcttctttt ccagcctggg caatgtcatg   52080
agacccggtc tctaccaaaa caagaccaaa caaaaaaaca gccaggcatg gtggcatgtg   52140
cctgtagcct cagctgctgt tctggaggct gaggcaagag gattgtttga gcccaggagt   52200
ttgaggtcac agtgagctgt gatcatgcca ctgcactcca gcctgggcaa cagaatgaga   52260
cctcgtgtcg ttaaaaaaaa caacaaaaaa agtttccttt gttggactgt tttaatttgg   52320
acctggttat catttttcag ccatatctaa ctttgtacat atcagaatgt tctgataaag   52380
cttaactttt attaaagtgt ttctgatagt tttggtacac attatcattt gcaatgccag   52440
ttattttctt ttccagtggg gatttgcata ggaaaaaaat tgctgtcact ttctattttg   52500
aaatcttaaa agactgatcc tttttgtgt catgatttga gtgtttaatt gagagcctaa   52560
tgcctaatat tatttgcagt attgaatggg atcttaacag gaataacatt ctagccttca   52620
ttgaattaag taaacatttc ttgaaagaac tggaatcta taatatttgg gtcatcacag   52680
tatgagatac ttaatcaaat ttgagatttt agtgaaacat tgttgaaaag ccaaaaagat   52740
tctaggaaaa attcatctct atattcttga attaggagag attttcggac ctgtgactaa   52800
gttactctga cacttgtttg tttcttagtc actcttccca gtggcagtga aaaagaagat   52860
gactggttca cattgttgag attagtttat cctcttctgg ctaggacatg ggatatatcc   52920
tgtctctttt aagccctttt ggtattttt cccccattta gagctgtgtc ttcaaactgt    52980
tttgttatag ctggaaaatc ctttttttaa gtgaaatctg cccaaattat aagacagatg   53040
aaagtagagt tgtgttggat ataggattag ggtgcaagtg gcgggggtgt cctggagcct   53100
ctcttctgag ggcagcctag cgcttgtgcc tttgaggaaa ttaccctggg gatggtctat   53160
ggaacatatt tgcaaaccac tgatttgaaa gatagagatg gcttttgtta agatctgaat   53220
tcacctttt ggcattttat ttgatttctc aaggggaaga acttattttg taataaagtt    53280
tcctttattt tagtagataag gccaagttgc tgtgttaatt taacctagag tttgggtttc   53340
ctttgctaat tttttttcacc tttaatgtca catcattgta aatttgtgga agttatactt   53400
ctgacttatt cttttgaagag cagaaattag aaatttccaa taattatttt gatagtgtca   53460
tttaatgaca ttaatatgta atgtagccac aaagatttaa tgagttcagt taagtcatat   53520
taagactgtt ggtttcattt gttttcatta atgtaattct gaagatgaac aataaaatgt   53580
atttttagaa ctttcaagtg aaatattatt tcatccttcc agatcatata atgcttgagt   53640
tctgattgtt aatcataaag tcaagaaaat taaaagataa taaatgaaa gtgacttta    53700
ggtgttagag ttttatgtac aaattctggt gtgtcattgg agctatcaca tgaatatttc   53760
aaaggccaat agcattgggt cttttacagtt aaaacttact attttttaagt ttaagtagta  53820
ctatagatta tttaataatc gaaatcaata aatattaatt attaaaatgt tttgtgggtat   53880
actttgagaa tcattgcttt taactttttc catataggtt tattaacttt aatagcattc   53940
taaacataac atctctacat tctttgtgtt taatactgta gaggtataaa aatacttata   54000
tatgatgata aaccatatta gagtaaatta aatattctta tgagttttcat tttagagtgc   54060
atttacttaa ttttgaaatc cttattttta gcaaactaaa ggaatgttgg tacattattt   54120
actaggcaaa gtgctcttag gagaagaaga agccttggag gatgactctg aatcgagatc   54180
ggatgtcagc agctctgcct ttgcaggtag ttctcactag ttagccactg atgtggacct   54240
tcactctctg ccgtccaccc catgcccttc ctgcctgtcc ccctgcacct ggtggacagc   54300
gccttctggg ttccagccgt tctcctacct cagcctccca gtagctggg actacaggtg    54360
cccgtcacca cggctggcta agttttgtag gacgagggtt accatgttg                54420
accaggctgg tcttgaagtc ctgacttcaa gtgatccgcc tgtctcagcc tcccacagtg   54900
ctgggattac aggcgtgagc cactgtgcct ggccagttac agacagttat ctaatgaaat   54960
tctctgtgta ctttataaaa gataaggatt aacttaaggt actaataact ggattatatg   55020
agggtggttt tgggttgtata atcctatcta aaagaattat ttagctgtaa ctgaaagtaa   55080
gacttaaata tttagggagg aaaatctgaa taattctagt agtaattatt tacaaaataa   55140
aaatagattt tatttttgat tacacaaatt aaacaacaat aaaacatcac agcgatctag   55200
actagtataa aggtcacacg cttaccaacc caaccgcccc aggagtgacc actgccaaca   55260
gcttcgtgtt gaccttttg ccatgatttc tatatagtct tttttgtttt taaatggtaa    55320
ttaaaaaagt caactaggaa aatgtgttaa agtttatct tccaggagaa taataggact    55380
gggtcgaga tcttgaacgt ggcttggaag aaggcaagcc caccccagag agattacagt    55440
tgttcgggac cactgcttgc ttagaggacc tgcgtgtctg ggaccgccta gttttgtgcc   55500
cctgactagg ctgccccta attacgaacg tcttttaaaa ttgccctagc cagggcttgg    55560
agtagttggt taagaacttg aacttcagtt tttgcagtga aacaccgttt gagaatatta   55620
ccttctgata agccttattt tattaagatg ggtactgtag cgagaggcag tgtgagtggt   55680
acatgaggga tgcactgctg tcctgcattt cactgtcttc aggatgctat gcagtgatga   55740
catttggaaa catttcatca aacattccat caaatgaaaa cattggatga cagtggaact   55800
ttgtgttatt ttgcaagcct ttgattccat attgaatgtt ttctctcgaa atttgacaaa   55860
tgagtgtttc tctgtcttca gcctcagtga aggatgatat cagtggagag ctggctactt   55920
cttcagggct ttccactcca gggtcagcag gtcacgacat catcacggag cagccacggt   55980
cacagcacac gctgcaggcg gactcagtgg atctggccag ctgtgacttg acaagctctg   56040
ccacggatgg ggatgaggag gatatccttga gccacagctc cagccaggtc agcgccgtcc   56100
catctgaccc tgccatggac ctgaatgatg ggacccaggc ctcctcgccc atcagcgaca   56160
gctcccagac caccaccgaa gggcctgatt cagctgtcac cccttcagac agttctgaaa   56220
ttgtaagtgt gcggagggc ctgccatctt ttatttttta tttgagacag agtctcactc     56280
tatagtgcag tggaggccgg gcacagtggc tcacgcctgt aatcctagca ctttgggagg   56340
ccgaggtggg cagatcnnnn nnnnnnnnnn nnnnnnnnnn nnnnnnnnnn nnnnnnnnnn   56400
nnnnnnnnnn nnnnnnnnnn nnnnnnnnnn nnnnnnnnnn nnnnnnnnnn nnnnnnnnnn   56460
nnnnnnnnnn nnnnnnnnnn nnnnnnnnnn nnnnnnnnnn nnnnnnnnnn nnnnnnnnnn   56520
nnnnnnnnnn nnnnnnnnnn nnnnnnnnnn nnnnnnnnnn nnnnnnnnnn nnnnnnnnnn   56580
nnnnnnnnnn nnnnnnnnnn nnccacccat cttggcctcc taaagtattg ggattatatt   56640
tgtgagctac catgccaac cctactgtct gccatctttt gagctcttcc ctggagaccc     56700
agacctgaac cctcctgctt gttctcttct tgtctaatac ccctaatgac agcgcagctt   56760
```

```
agatcactag tggagagctt gacctcatct gataccttca ctgaaggaa cagcttagtg   56820
tcttttccac tgaacactga ggtaaaaaat tggaatagtt gattatgtga actctgctaa   56880
aattgagtgc attttacatt ttttaaggcc tttttaggcc ctggttaaat aattattttt   56940
aaaaatcctg aaggagccta ttataaacag atctgtggtc ttaatgaaat gtgattaata   57000
ctgtgcatta ttttaagaac ttttgacttt tcaaaaaact tttacaacat ttcccatttt   57060
atagcagcat aggtgtaagt acctctcatc cctgagttag tggacaagaa accctcatgg   57120
atagtctaat aacgtttggt acaagtctat gttgttttat actccatttt attttcagtt   57180
ttaaaaactg gttaaatatg tgtaacataa aatctacctt cttaaccatt ttttacgtat   57240
gcagcttgct ggaataaaata attaaataat gtcatggaat catcgctcca cccatctgtg   57300
taaccttttg atcatgtgac actgaagctc tgttcccatt gaactctcta ttcctccttc   57360
cccgccaagt ccctggcaac caccattctt ctttctgtct tctgaatttg actactttag   57420
gttctcatat actttagggt cacaccgtat ttgttttagt tagcataacg tccgcaaagc   57480
tcatgcatat tgtagcctgt gttgaacttc ctaatgtttc aggccaaatg ctattccatt   57540
gtatggatag gccacatttt gctttttccat ttctctgtcc atggacactt gtattgcttt   57600
catgctttag ctattgtgaa tcgtgctgtt atgaacatgc gtgtacaaat gtctcctgga   57660
gactctgctt tccatttttt tggctaaata cccagaattg gagttgcttt tacattctga   57720
ttttaattta aaacatttat atcattgagt gttttactta atagtataat agttagcaaa   57780
ctaatatttt ggtaataatt tgctggtagt tttagagtcc attgctcagt ttttttaggt   57840
aaattacaca ggacatttca agtggacgtg gaacaacttg tgatatggaa tcatgcccca   57900
agctgatggc taaacatacg aaataccatg ccctaaattt agtagattta gtctttgcaa   57960
tttaggagat aacctgttat attgttaggt ttttgtctaa aagcttttgtc ctcatatttc   58020
caacttgctg taaaattttgt tcgtgaagac aaatatttt gtatgggttt tttctttttt   58080
atattaaaaa gaaatgtcca cattggaatt tttttggagt ttttagagct aatagagctt   58140
ttcataatgt agtgggaatg agtgatcagt aagctcttag cagttccat gcacacattt   58200
ctgtgcattg aaataaatga cagatgagta catttgtgtt ctgtgtgtaa aacgtgctct   58260
ttcttcgttg catttccatg ttggagggct tgtctcttgg tgatcacact tcaaaattct   58320
cacagccccc cttgaaccgt ttaggtgtta gacggtaccg acaaccagta tttgggcctg   58380
cagattggac agcccagga tgaagatgag gaagccacag gtgttcttcc tgacaaagcc   58440
tcggaggcct tcaggaactc ttccatgggt atgtggacca caggtgacgc gctacaaagt   58500
ggtcttgtat tcaggcctgg acatcttaat tatatctttg ctctcaagaa gaaatccttt   58560
gatattgttt tctgagttct gaatagctga tgaaaatgac caattgagga ataatcatac   58620
tttttcttca tctaaatctt acgctttga gttatcttag cataaatgta taattgtatt   58680
ttaagtggaa atttgtcact taatcttgat ttctctgttt ttaaagccct tcaacaagca   58740
catttattga aaaacatgag tcacagcagg cagccttctg acagcagtgt tgataaattt   58800
gtgttgagag atgaagctac tgaaccgggt gatcaagaaa acaaggtgag ggacataggc   58860
ttgagacaac ttggtgtttc tgagcttgtg tgaggattta aaatcgccct ggctactatc   58920
tactttattg cttttcccatc cctgggcctt taaatttccc ctttaaatac cagctcttcc   58980
caggcctgtt gttttccgcc tttcaggtgc tactgacagc gttaagaatt gcctgagttc   59040
tgcctccttt gagagtgtgc cccagagaaa tctattctgt actgagtgtt tccttgtctg   59100
atttcttggg ccattcattt gatggctgcg tatggccttg caccatgttt tggttctatt   59160
gaactgtttt aaaagtctct gtttatatta cctttttaca tgtaaatgta actgtcttca   59220
cttttaattg ctcaagggca aggaatagcg tttcacagtt tctcccagca atcagaatta   59280
cagcctttgg catctccctg tctaccaggc ccagttcgtc ttagcttttgg gcttccccag   59340
gctgttacct ttccctgagt agcttctgct tgtcctgtag aagaccactc atgctttgct   59400
tccagagcag ccttttctga atgcctggtg tcaggtgcct tcttactgtg cccaccctcc   59460
ctgcatgctg catttatccc ctgccacagc cctgggaccc tgtgtccagc tgcctctgac   59520
ttgtctgttt ctgcttggtc atggtctctg tgaggtcagg tgtgcatatg agcacagacc   59580
agggcatctc tttatcccca gcacccagtg taagtgctac tctaggacta tttgttgaat   59640
gaactaatgc atgaatgtat tggttgagta tgagacaaac aagtgtcact gtctcctttc   59700
tagccttgcc gcatcaaagg tgacatcgga cagtccactg atgatgattc tgcacctctt   59760
gtccattgtg tccgcctttt atctgcttcg tttttgctaa caggggggaaa aaatggtagg   59820
tacaaaaggg gacgtgcaga gttgaaggaa ataactaggg ttcagaggtc aacttggtgc   59880
ccgtttagta ctgtgtgtag cagaggcagt agaatctgag gatgagtttg gttttcacta   59940
gccaaggggga agggaggaaa tgatgggagc aggtaggtta ctgggtctgg ttttgttcat   60000
ttgaaaacaa tctgttgttt gaggctgaag gtggcttggg tgatttctt gcagtgctgg   60060
ttccggaccg ggatgtgagg gtcagcgtga aggccctggc cctcagctgt gtggggacag   60120
ctgtggctct ccaccagaa tctttcttca gcaaactcta taaagttcct cttgacacca   60180
cagaatccc tggtatgtta aaagttcaca tcttatttc tcagatttaa tcattattgt   60240
aaaaacgatt tcagtattga ctattttagt tttagacgg tgttttggt ttatttggga   60300
tttttttttt tttttgagac ggagtctcac gctgttgccc aggctggagt gcagtggcgc   60360
gatctcggct cactgcaagc tccgcctcct gggttcacgc cattctcctg cctcagcctc   60420
ctgagtagct aggactacag gcgccccgcca ctgcgcccgg ctaattttt gtattttag   60480
tagagatggg gtttcactgt ggtctcgatc tcctgacctt gtgatccgcc cgccttggcc   60540
tcccaaagtg ctgggattac aggcgtgagc caccgcaccc ggcctatttg ggatatttga   60600
cccgcgttgt agctcttcag aaaacacatg aatagtgaag ttctttgttt catggtttct   60660
ctttagatga aatccgtaga ggaaaaaaat agaaacctca gcacgtaaga gccaacttat   60720
atacgcatcg gatttaaacc taaagcacaa attgtgcatg gtcacggtgg cgctgagtca   60780
cactcagcca ggccaggcat tcacactcag ggtgagtggg caccaggact ggctgaggca   60840
gcagtggacc cgtgtctgca ccctgcccat gcttattgtg gagcctctc gctcgctctc   60900
tttctttggg tgagggggta cacttgtgtt tttgaattta tatgaggtaa gggttttat   60960
ataggttttt ttctaatctt ttttttaagtg gaatctggaa ttttaatcag atttactatc   61020
tgacagccta gaattataat ccagaaagtc tgtggtattg aggacatatt ggcaatatga   61080
tgaatctgta atccttaaat cctgaaactt ttttttttt ttaatcactt aggggttatta   61140
tagtgaagtc atttctgaat ttggatcttc tcttcatacc tcttttttct ttcctgaga   61200
attaagcttt tgtttttgagt tagaaagttg atagtaggaa attgttccat ggctgggcaa   61260
tttatctcca cagaggaaca atatgtctca gatatcttga actacatcga tcatgggagac   61320
ccacaggttc gaggagccac tgccattctc tgtgggaccc tcatctgctc catcctcagc   61380
aggtcccgct tccacgtggg agattggatg gcgccattta gaaccctgac aggtagtggc   61440
cagttttttca gctgtgttttt ttctagatat ccttactaag gtttccgttt ccatgacgat   61500
```

```
gtttgtttct gttcttctgt caggaaacac attttcttg gcggattgca ttccttgct     61560
gcggaaaaca ctgaaggacg agtcttctgt cacttgcaag ctggcctgta cagctgtgag    61620
ggtgagcgcg atctctgtgg agccattgct tcacttagtg ggcatttat cattgctgca     61680
attacaattg gagcttaata ggaaatattt ccatacactc taaagctgta accagtaata    61740
tccaccatgt atccatctct tagctttaga aagaaaacat tgccagtaga gttaatgctt    61800
cataaacttc agtttaagtt ttaattctca gaatatttgt ttgaaataga cttcttccta    61860
aaggatatat ttagaaataa cctatcatta catgtaaagt ctgttgaata tgctgggcac    61920
ggtgactcat gcctgtaaac tgagcacttt gggaggccaa ggtggaagga ttgcttgagc    61980
ccaggagttc aagactatgg gcaacatggt tgatcctgtc tctacagaaa attaaaaga    62040
aaaaaaaaaa ttaactgggc gtggtggtgc atacctgtag tctcagctac tcgggaggct    62100
gaggtggggg gattacttga gccccggaga tgaaggctgc agtgaggcat ggctgcatca    62160
ctgccctcta gcctgggcaa cagagtgaga ctgtctcaaa ataatagta ataataatcc     62220
gttgaattaa aaaaaacccc aaaaaccact gtgttaggcc catggtgtag taagagttaa    62280
agtgagccctt agggattatt tactcaacct ctgtgttttgt atgaagtgga atggcccag    62340
ttcttaagt gatagcatgt tgaacctttc cataccagct ggctcgtaag tcacaactgg      62400
ccagtcaaca agagtcaaaa ttaactagta aaaatcaaag caaaaaactt agaattgtcg    62460
aatttgtgcg atacctcccc cttttaaat gtcatgcctg acagtaattt ttccctagtt     62520
tccaggtttt gtttcagtca attgtctg tcttgagcag aaggaagcgt gctaacagct      62580
cagtctcatg gctagctggg ggtctatgtg tcagccatgc atgtgatggt gcccctgggt    62640
gcctgaggct gcaggggagg ggtacagcag taggggcctg ttctgttctc ccgtgccttg    62700
gagtacatag tgatatagtg gggtggtcct tggtgtaggg ccctcgttcc taccctgggt    62760
ctgcgattta tttagaagtg gtgtttgggagc tgtgcggcag gcccctttg aactgatcaa    62820
tgtttgtgaa gttgccgttt gagaattgaa accatgacat aagcagaaat ggaagaaaag    62880
aaccagttat ttgaaaggga cacattcact tttaagcttg tatttactga gataaaatat    62940
ataccatcag tgttcttgag aggtgtggga aaagtgcaac atcctggttg cagttaaacc    63000
cagaacgttg tgtgttgaag actgacagtt ctcaaaccgt caagacgtgg gtactgagtg    63060
ggactaacct gctgccctct tgcctcggac cttgtgttcc agcattgtgt catgagtctc    63120
tgcagcagca gctacagtga gttaggactg cagctgatca tcgatgtgct gactctgagg    63180
aacagttcct attggctggt gaggacagag cttctgaaaa cccttgcgga gattgacttc    63240
aggtaagtga gtcacgtcca ttagatttca tgaactaagc tcaattgaaa gtcctggggt    63300
cacttggtat aaggaatgat gttatcaagt accctgccca tcagaaatct gagcggttta    63360
ggtagatgac agtgattttc tcccccagt ggcttttgc tgaacctcgc cctatgcgtg       63420
gattttattt tattttatta tttatttaga gacatgatct tgctctgttg cccaggcttg    63480
gatgcagtag cacagtcata gctcactgta gctttgaact ccaggactcg agtgtcctc    63540
ctgcctcaga ctcccggtta gctaggacaa taggtgtgtg ccatcacact ggctaatatt    63600
ttattttttg tagaaatggg gtcttgctct gttgcccagg ctagtctcat ctcctgagct    63660
caattgatcc tccaatcatg gcctcccaaa gtgctgggat tacaggcatg agccactgtg    63720
cctggcctag aattttaaaa gataaataga agagtagttt tttttttttt tttggatagt    63780
cctagtcatt taagtgttct ggatagtagg aataaaagag cttagaattt ttcatctttg    63840
tcttaaactt tttaaaaaat gtagcttatg ttaattctgc ttgtttaaa agaatatact     63900
catcattata ctgaacctag gtaagacagc tggtttatat tttgttgcaa ttaaaaatg     63960
tgagctgtgg ttgcagtgag ccaagatcgt ggccattgca cttcagcctg gcgacagagc    64020
gagactccgt ctcaaaaaaa aaacaaacca aaaaacgtga gctgtgttgg aactttcatt    64080
ttctaagagt aaagttttgg caggagaagt tttctgtcag tactttattt tagaagggaa    64140
attttttataa ttcaggtgtt tgttttttgt ttttgttttt ccccccaagc caccttttat    64200
agagcccttg tgggttattt tatttaatcc ttagaatgtt tataaatctg ggactgttct    64260
cggctccacc cacagatagg ggcgctgagc atgcgtgagt gggcagcaaa atagcaggtt    64320
atggagggcc cagctcgccc cttcgtggt ttgagccagt tctgtacggg acttacagag     64380
tgttttgaaa tagtatttat tttgaagaaa aagaaaaaca gttactgag tgctatctta     64440
ttgagtctga agttgtgaga ggaatgccac ccctatttgt ttgaagccat cggcttttc    64500
tgttgtcttg agtaagtgct gcccaagggc cttccagggc gcctgactga gcctgctgctg   64560
aagcaagctg gcggaaagtg tttactgagt aactaaatga tttcattgtt aaatgtgctc    64620
ttttgttagg ctggtgagct ttttggaggc aaaagcagaa aacttacaca gaggggctca    64680
tcattataca gggtaagcg gcttatttt gtgagatact gtttaccttt aaggaggtga      64740
aagtgaggct ttccttgtgg aatttctcta aatgcattca tcgtatttta gatctgttta    64800
tttcacagtt tatatcatga aagttataat tgtgtcacat ggatttaagt ctagcaatgt    64860
tgagttcttt ctcactagct ttccaaaata tcttacctaa aatttagtca aatacaagat    64920
tatgtttatt tttattatcc ttctctctaa agcttttaaa gctgcaagaa cgagtgctca    64980
ataatgttgt catccatttg cttggggatg aagaccccag ggtgcgacat gttgctgcag    65040
catcattaat taggtatttta ccagtattt atctcttta cttttttggt tgaagtacta     65100
aaaggtatga acatggaaag agagggaaga attcaaagga tgtagagcag tattcctgaa    65160
tctgagctca tttcagctat tctgttctta aactatcaag aaaaaaaaaat ccaaaaaagt    65220
ctaaaattat aattaaaaaa acaaaatact aaccatccat tgtaaaagt aatgcattt      65280
cattgtaaaa atttggacta tagagaatag cactaaagaa aaaaaaaatc accttcaatt    65340
ctgctaccac ctggaagtaa tcgctgttaa tattttgctg tatactttt atgagtttct     65400
tattcaaaat ggggtcaaaa ttacatgcaa ttgtgtaacc taattttcac tgaatatttt    65460
attagcattt ttctgttatg aaacagtaat tttagttatg ggtcattgtt ttactatgtg    65520
attgtgataa aattttacat aaattttttt tggaaattaa ctattgtaca taaatgtgta    65580
taattttctt tttccgagaa ttcctggaag ttgagttagc agcccaggct ttgaattttt    65640
tttttttttt gagacagagt cttgttcgtt tgcctaagcg cgatctcggc tcactgcaac    65700
ctccgcctcc caagctattc tcctgcctca gcccccgag tagccgggat tacaggtgca     65760
caccaccaca cccagctaat ttttgtattt ttagtagaga cagggtttca ccagattggc    65820
caggctggtc tcaaactcct gacccatgaa tccacctgcc tcggcctccc aaagtgctgg    65880
gattacaggc gtgaaccacc atgcctggcc aggcttttga tttaaaaaa atttctaat     65940
agctttatgg cggtataatt tacatttctt gaaacctact cgttttgagt gtatagtaaa    66000
cttcaatttt atcacatttc tatcacccca aaggtccttg ggcccattgc agtaacctcc    66060
ggttcccgcc cccattccta ggcagccact catctatttt ctgtcccta agatttgtgt     66120
tttcgtcagg cacggtggct cacgccttta ctcccaccac tttgggaggc cgaggcaggt    66180
ggatcatggg gtcaggagtt tgagaccnnn nnnnnnnnnn nnnnnnnnnn nnnnnnnnnn    66240
```

```
nnnnnnnnnn nnnnnnnnnn nnnnnnnnnn nnnnaccct gtctgtacta acaatacaaa    66300
aattagtcag gtgtggtggc gggcatctgt aatcctagct acttgggagg ctgaggcagg    66360
agaatcgctt gaacgtggga ggcgaagttg acagtgagca gagatcgtgc cactgcattc    66420
cagcctgggc agcagagaga gactctgtct gaaaacaaag atttgtattt tctggacatt    66480
ttatagaact ggggtcatag tataaatgga cttttgcatt tggcttcttt cacttaattt    66540
tgagattggg tcttgtagca tgtatccgta gtttgttcat ttttattggt gagagtatta    66600
tatgaataat accatatttt atctatccat cagatggata ttattgagtt catgttttgg    66660
ccaatttatg aattatggta ctgtgaacat ttgcctacaa gatttgtata ggcatgtttt    66720
catttctctt gagtggataa cctagaagtg gattttttaaa taattttttgg tacttactgt    66780
gaaactgctc ttcagaaaca taccatcgtt tgtcctttct ttcttgtctt tctctttctt    66840
tctttctttc tttctttctt tctctttcttt tttctttctt tctttctttc tttctttctt    66900
tctttctaca tagacacatt ttaagaaaaa tttcagtagt ttttgggggta caagtggttt    66960
ttggttacat ggctgaattt tggttgcatg gtgaagtctg agattttagt atacttgtca    67020
cccaagtagt gtatcttgta cccaaatatgt agttttcgtt ccctcaccctt cctcccagcc    67080
tcccgccttg tgagtctcca atgtgcatta taccactctg tatgcccttg cgtactcaca    67140
gcccagctcc cacttctgag aacatactgc agaaacatac caaaggatac tcccactgcc    67200
agaatgtgat tgtgcctgat tcttctcacc aataaatatt tcaaaaaaag ttaaatatat    67260
atcagttttt tgggcagaag ttgatacttc tctttatttt ttattttttt ttgagatagg    67320
gtctcactct atgatgccca gactggagtg cggtggtgcc atctagctta ctgcagtctc    67380
tgcctcccag gttcaagtga ttctcccacc tcagcctccc aagaagctgg aattacaggg    67440
gagagccact actgccagct aattttttgta ttttttggta gagatggggt ttcaccatgt    67500
tggccagact ggtctcaaac tcctgacctc aagtgatcca cctgccttgg cctcccaaag    67560
tgctgggatt acaggcgtga gctaccacac ccggctgata tttctttttta aaataactta    67620
ccttcttttg aaagtaatac atgttaaatg aacaaaattt aaggaaaata taaaaaagga    67680
aataatctttt ataatgaaac tactgaaaga aaaccaaaat tacattttgg tgcatattct    67740
ttttcgttttt catcattgta atttgcattt cttttgattac ttgtgagaca cacttttcat    67800
ttacttaaag gttcgtatga cttgcctgtt cagaaatttt gcagctttac cattttctgc    67860
aaatgatagc aacttctttt tatttttta tttttatttt tattttttatt tttttttttg    67920
agacggagtc tcgctctgtc gcccaggctg gagtgcagtg gctggatctc agctcactgc    67980
aagctccgcc tgctgggttc acgccattct cctgcctcag cctcccgagt agctgggact    68040
acaggcgccg ccacctcgcc cggctagttt ttgtattttt tagtagagac ggggttttcac    68100
cgtgttagcc aggatggtct cgatctcctg acctcgtgat ccaaccgtct cagcctccca    68160
aagtgctggg attacaggct tgagccaccg cgcccggccg caacttcttt ttatttgttt    68220
gtttgtggtg acagagtctc gctctgtcac ccaggctgga gtgcagtggt ggaatcttgg    68280
ctcattgcaa ctattgcctc ctgggttcaa gcgattttcc tgcctcagcc ccccaggtag    68340
ctgggattac aggaatgtac caccatgccc ggccaatttt tatatctta gtagagatgg    68400
ggtttcgcca tgttggccag gctggtcttg aactcctggt ctcaagcggt tcccctgtct    68460
cggcttccca aagtgctggg attacaggtg tgagccaccc tacccagcca atagttactt    68520
cttatattcc agaaaaaatt gtactcatga tcaagtctcc atgaggaaaa agactttaat    68580
taaagatatt gcagtttgca gaccaatatg ataaaatagt tgattgtttc taaaagtatt    68640
actgagtaat gatggcagat ataagccctt ttgttttttgt aggaaaatgt tacccatgtt    68700
ctgcatttga attcagttta gatttgttag gaatctcagc ttaagctttg ccatctggga    68760
gtgtttgggga caattttgca gacagaattg caaaagtgcc taagggatgc aactggcact    68820
cagacctgct ccttgctcag tactctgtgg acagatgttc agcgcttgtt gatgttgatt    68880
aaaaggttta gaaagagaac tttcaaagtt ggttttttaaat taaagcattt aatagtgtga    68940
ataaaaaggg acttaatttt atgacagaca aagaaagta cagcacctgg cggggcgcgg    69000
gggctcacgc ctgtaatccc agcactttgg gaggctgagg caggtggatc atgaagtcag    69060
gagttcaaga gttcaagacc agcctggcca aggtggtgaa accccgtctc tactaaaaact    69120
acaaaaatta gccaggtgcg ttggcaggca cctgtaatcc cgctactcag gaggctgaga    69180
caggagaatc acttgaacct ggatggcaga ggttgcagtg agccaagatt gtgccactgc    69240
actccagcct gggcaacaga gtgagagtct atctcaaaaa agaaaaaaaag aaaatacagc    69300
acccagttat gtcagagtgg gtgcatcaga gagtgaccct gagattggag acgatgctgt    69360
cacgtgcttg aagaatgcta cctgagaaag ggggcgagaa gtggtgtttg ctggtaacca    69420
gaggtgttgg cttagccacc tgcagggagg gtggtctatc acaggtgagt ttcatctact    69480
ttcttaagca aatcaacctt acttttgtgt taggcttgtc ccaaagctgt tttataaatg    69540
tgaccaagga caagctgacc cagtagtggc cgtggcaaga gatcaaagca gtgtttacct    69600
gaaacttctc atgcatgaga cgcagcctcc atctccatttc tccgtcagca caataaccag    69660
gtatgctgac ccagtggcgt cctcacattg ttgggaaaat gcccttttcct gatgcctttc    69720
tttaggctttt aattgaaaac atttttatttt ctagaaaaaa gctttagctc aggatgtttg    69780
agtgtaggtc attcctttga taggatattg tcattctgag gattgaccac accacctctg    69840
tatttaagcc ctgccacaat cacacagctg tgacactata aatctttaa tcgtttatta    69900
catttaatgt gctgacagtt atattttgt gtgtgacact tacgtattat ctgttaaaaa    69960
atttttcactt tagttgtgtt acccttttaaag aggattgtat tctatcatgc ctgttgattt    70020
gtaggtgagc gggtattaa agtcagtgtt atttagggct atccactagt tctgtgattt    70080
gcaatgactc tccttcacat ttgttgtgga gcttttgaat atagcgtcaa atggccacat    70140
atatcccatg cttacctgat tcttaggtga gtaggacaga gtgctttaat gaagctataa    70200
tcttcagaat tctagcttgc aaaggagatt gcagaaggat aagacttgtg cttttcaatt    70260
ttgtctttta aatgttattt taaaaattgg ctttatatga tactctttt ctgctgagta    70320
acggtattttt acagaacttg gactagatga cttctaagct taaatgatca cttgatgctt    70380
ttttttctgaa ttaggaactc agcttacaca tttcaaagtc ataattcctg aatacataac    70440
atcttttttt catgtaaaga ctgctttaaa aaacacatgg aaggtcgggc gtggcggctc    70500
acacctgtaa tcctagcact tgggaggcc caggcgggca ggttgcctga gttcaagagt    70560
tcaagaccac cctggacaac atggcaaaac ctgcctctac taaaacataa aaaattagcc    70620
gggcgtggtg gtgggcacct gtaatcccag ctacttggga agctggggag tgagaatcac    70680
ttgagccctg gaggcagagg ttgcagtgag ccaagatggt gccattgcac tccagcttgg    70740
gctacagagt gagactgtgt ctcaaaaaaa aaaaaaaaa aaaaaaaag ccacaaaaca    70800
acaacaacaa aaacacacgg aaacatttta tttggccacc ttagtatttc ccttcagat    70860
aattcctttg tttaaactca gaactggcat tttctctctt tgaaagatt caggacaaat    70920
actcctttaa gataagcaga aacagtgaaa gagtatttga ttatcaggaa tttgataggc    70980
```

```
ttagaataaa ttgttgcttc ttaatgtcat ttcagaagat gaatattaat agatgccaac   71040
tgagatatca ttaaaattgg ttactactac tttgaaaagt ttcccagttc caaacttcag   71100
caggcctctt cacaattcaa cagtgcttaa ttgggacttg tgtgatagat acgattccca   71160
attgtgtagc agagtgtgct gcttagctac ctattctgtt agcattcgtg tgttaactta   71220
aaatcataat ctccttagtt ttgttgagtg tctctgtgga tgagacactg tgagggatac   71280
aaaatcagat tggctttatt caaaccattg gggtattatt tttatttttt gccttttttc   71340
catgtgttct aaaggaatta gagtttgaat ataactataa tgggggatag aaatttacat   71400
gtgccatgaa gggaatgcag aaaagtgcca tgggagctca gaagtggaga aaggaatttt   71460
ttttcttgga agcaggagta acttcatgaa gcatttattt caacttagag atagtaggca   71520
atgctgtaag gggagtgtgg ctgcagcgaa agtgtttggg gcagactggg aggaagggag   71580
ggaataaatt cagccattgt tatggcataa tgatcaaaat ttattttcag ccctctttc    71640
acttaaaagt tgagactgct taacttcttt taatctttaa tcttaaactt ttaaatgcca   71700
tttgatcttt aaaaagatat gttttaatag tatattttaa gtctctgtat ttttcttatt   71760
agaatataca gaggctataa cctactgcca agcataacag atgtcactat ggaaaataac   71820
ctttcaagag ttattgcagc agtttctcat gaactgatca catcaaccac gagagcactc   71880
actgtaagtc tctttcttga ttggtcttaa tgaaattata ataattttc gtgacttgta     71940
tggccagtta gtttttatggt catcttatgg tgaggtgctt gtattagagc tcttacttat   72000
ctgtgggggct tgctaagaaa ttgtgtttct gtgaaaagga tcttagctta ctccaggaat   72060
gtaaataact attttttttct gattattaaa gtaatacatg ccaaaagtta aaaaattcag   72120
ccaatttagg aagacataaa aatgaaaata agccaggcgt ggtggctcac acctgtaatc   72180
ccagcacttt gggaagccga ggtgggggggc tcacttgatg tcaggagttc gagaccagcc   72240
tggccaacat ggtgaaaccc atctctactg aaaatacaaa aattagctgg gcatggtggc   72300
gggcgcctgt aatcccagct actcggggagg ccgaggcagg agaatcactt gaacgtggca   72360
ggcagagctt gcagtgagcc gagatcgagc cactgcactc cagcctgtgc aacagagcga   72420
gactttgttt ccaaaaaaaa aaaagagaaa gaaaactact gtcacctgca tnnnnnnnnn   72480
nnnnnnnnnn nnnnnnnnnn nnnnnnnnnn nnnnnnnnnn nnnnnnnnnn nnnnnnnnnn   72540
nnnnnnnnnn nnnnnnnnnn nnnnnnnnnn nnnnnnnnnn nnnnnnnnnn nnnnnnnnnn   72600
nnnnnnnnnn nnnnnnnnnn nnnnnnnnnn nnnnnnnnnn nnnnnnnnnn nnnnnnnnnn   72660
nnnnnnnnnn nnnnnnnnnn nnnnnnnnnn nnnnnnnnnn nnnnnnnnnn nnnnnnnnnn   72720
nnnnnnnnnn nnnnnnnnnn nnnnnnttta gtagagatgg ggtttctcca                72780
tgttggtcag gctggtctca aactcctgac ctcaggtgat ccaccgcct tggtcaccca     72840
aagtgctggg attacaggcg tgagccacca caccgtctt tacatttta taataataat     72900
ttatgttgct gatattagaa aagaaccata atatccaaga attcaagaac aattaaatta   72960
tgtacatatg ctagtgtata gtgtgatgct ttggagaatt tttaacaatg tggagatata   73020
taatctgaat tgtagtattg agtgaaaaaa ggcagaatac aaacctagta gggggtatag   73080
tcggatttca gttaagaaaa ataatattta catatataca ttcctcacat tggcagataa   73140
tcaccaagat acatttttggg attgtggatg attttttgtgt tctttatatt tttcaggtat   73200
tctcaaattt tctaaaatga gcaagtataa cttttgtcat cagaaaaaat aatatgcaaa   73260
agtaatgtta atttgttggt gaccaggtta aaccttttta tttttattat tattttttga   73320
gatagagtct cgctctgttg cccaggctgg aacgcagtgg tgtgatcttg gctcactgca   73380
gcctctgctt cccgggttca acgattctc cagcccagc ctcctgagtg gctggaatta    73440
caggtgcagg gcaccacacc tggctaattt ttgtattttt agtagaggtg gggtttcacc   73500
aggttgtca ggctggcctc gaactcctga cctcgtgatc cacccctcctg ccctcccaa   73560
agtgctggga ttacaggtgt gagccgctgc acccagccaa acctttttat ttatttgac   73620
aaaagaaata cttgcatgtt atagaaaact aaatatgtgtt tgggctgtct gcagtatggt   73680
cttctcttga tttgttcaaa atattgtaaa ctttgatttt ttcaaaatat tgtaaactt    73740
gcttattttt tttgtttcttc ccttgctttg ttcaaaatat tgtaaacttt acttattttt   73800
ttttgttctt ccccttggttt gttcaaaata ttgtaaactt tgcttattta tttttattgt   73860
ggctgacatg tgtcagacac tgttgtaggc ctgggatgta aaaacaggat tcctgcccctt   73920
acggtctctg gaggctggtc agggagtga tgtggtcagc tggagctccg ctcctaaggt    73980
tgtgcaggggg cagttgagg gcggaagggt gggacagcat ttcaaggtgt gggcagcaca   74040
ggagtctctc ttcattggga tataattgcc attccgataa catgtatttg agttgtctaa    74100
agtaggaagt tgtaccatgg tgggacagat atctcatggt tatcatacac agatctcagt    74160
tctcattgtt tgtactttt ataaaggta aaaggagata taattcaata aacctttgtg     74220
gtgtttgggt tgatttttat tgtttcttttg ttctatagtt tggatgctgt gaagctttgt   74280
gtcttcttttc cactgccttc ccagtttgca tttggagtttt aggttggcac tgtgggtatg   74340
tattttcctc agtatgtatt aatagttgtc tacaacagta taatataaac gtagttatta   74400
ggatgccctt tttctttctt tttaagtctt ttatcagttt ggcttttgca aaaatatctg    74460
atagaatact tgtttctgct gtattagttg tgtgagacta gtgacaggag ctgtcgggaat   74520
tgaatgccaa atgttcttag gcatttttgg gaatttgagg gtgtgatctt caagttcatc    74580
tagggggaatt ttcatatgct ggcaaaatac ttttctcatt agcttgattc tttccagaat   74640
tatttgctgc atattagaag tttaggaacc ttttttcact taaatgtgat ctaacatatg    74700
aaaatggtgat gatttaggaa ctactgtact tacattaaca gcttttactt aaaaatgatt   74760
ttcccccagt agatgaccct actcacatct gggaaataat ttcaagtctt ctccagcatt    74820
caggaataag ctttcattct gtgtatcaat tactgagaat gatttggtg actcacatca    74880
catttgagaa gtaaacctgt agatttcttg tgtgtgtcag tgaataacca gctgacattt    74940
gcttgaagtg gattacattc tctgctctag aatgattgct ttcccgcctt cctcacatat    75000
agactgagca actatggttt ctagtcatag gtccggcact agactttgact tctgagcaac   75060
tttggcattg gagtaaaatg tattaattta aagaaagcta aaaattcatt caagtaaaca   75120
tacagttcta atacttttta aagtttaaaa tatagatagg tttaagtgat aaaaaaatat    75180
gagtagacac cataatcctc atttctgtat ctgttcacaa ggggttgata tttatgagtt   75240
ctattctcca tacccattct gtgttctctt aatcctcagt cagcacctca ggtggttggg    75300
attcagttct tggtagtttg acttatactc tcttttctag gggattgagc cctgggtagt    75360
cctccttata tgagttgca atttgtcttc caataactt tactacaaga tatgggtat     75420
taaaggatgc cattgggaa ccaagataat attagtatca ggaaaactaa ccacgtcaga    75480
cctgcccat tgggtatcaa gtatactatt tttccatagt aataaagagc tcaccccagc    75540
caattctctt ttattttgga cctgtttatt caatggcatt aagatgccca aatgtctggg    75600
tagctatctc atctccaatt cagcagaacc attgtcatat gccctagtgg aagcattcct    75660
tcattggaca cttaggcccc agtactttta ttcagatcta ctacctgatt tcatttctca   75720
```

```
aatgattttt atggagcttt aatttatagg aaagttgtta gttgattaac agtaaaacag   75780
tttctgagct ggtataaaac atattgtgac acgcttttct cttggaattg caagagaaag   75840
gaagactgtt gtttgcttga aattttttcta taatttgacc ttgcaaatgt ctgcttccag   75900
agtgcctcca ctgagcgcct ccgatgagtc taggaagagc tgtaccgttg ggatggccac   75960
gatgattctg accctgctct cgtcagcttg gttcccattg gatctctcag cccatcaaga   76020
tgctttgatt ttggccggaa acttgcttgc aggtactgag ttgaagcagg gactccgagg   76080
cttggatttt gatttcctta gggggaatgg gggtggtgag catatgaggg gaaaatacta   76140
aaaggtcatc gccagtgatg gcttgtccct ttagtcaaat ttcagatgtt acctatatgc   76200
acaaacacat gcagctgttc tgtgctgagt attttaaagt ggcctcttcc cagtatggcc   76260
cctcagttaa ctacaaataa actcattttg aatttcatct tagtgggcac catatgccag   76320
tactgcctca ggcactggga tggtaagaaa gtataaagta tggactccat tctcaagttg   76380
gttttagatt agaggggata catgtaaaca gaagtgcagt ggtcacacag agtggccatg   76440
atcactctcc ttgggcagat ttatgggctg ataggaaagg gcacaacagg gagagggtgc   76500
agcaccgtgg cgatgataat ggaggatgtg gccagcaagg aagacgcagt ccattgaaat   76560
tgattttggg agaagttgcc aatctccatg aaagaatcgg gacctgtgtt ctttgcttta   76620
ggaggctata ggagagtttc gtgaaaggga ctaaagatgg agtatttaa taagatcatt   76680
cagccaactt gaatgtgggc tggaggagaa ggtagagaga ctcaggagat taatgttgac   76740
gctaaggcaa gagatgggga tgctaaacca agataatgcc tttgggattg tagggaagac   76800
actgatcgta agagaatgaa ggaggcagaa ttgccaggcc tgggtcacca actgaacttc   76860
ggttgtgaag accaagaaac ctgggatgac ttcacatcct gggcaggtgt gtggtagtga   76920
cagtcatgga aattgggaac acagatttgt ggggaagaca tcagtttgag tttgagtttg   76980
agtttgagtt tggcttatcc gttgaatatc agacacagat gtctggccaa ctctcaacat   77040
agattagggt cttaaatgac ttcagttccc caagcaattt gtccttccca tactgttggg   77100
ctagagaggt aatatctatg cccatatcac agccagtgct cctaaatctc tgagaagttc   77160
atgggcctct gaagaagaag ccaacccagc agccaccaag caagaggagg tctggccagc   77220
cctggggggac cgggccttgg tgcccatggt ggagcagctc ttctcccacc tgctgaaggt   77280
gatcaacatt tgtgcacatg tcctggacga cgtggctcct ggaccggcaa taaaggtaat   77340
gtcccactta ggtgctggat taatatagcc ttaatgactg tgggtttcca gactatcttt   77400
atttagtaat ctgtctcttc tttattctct tttactttaa atgaacaaaa ttgctcagat   77460
tgtgacacta aatttaacat caaaatgtga ccatgtgcca gggtgcagtg gctcatgcct   77520
gttattccag tactttggga gactgaggtg ggcagatcac ttgaggccaa gagttcaaga   77580
ccagcctggc caacatcaca aaaccccatc tctactaaaa atacaaaaaa attagttggg   77640
cgtggtggca catgcctgta gtcccagcta cttgggaggc tgaggcaaga gaattgcttg   77700
aacctgagag gtggagtttg cagtgaacct tgattgtgcc actgcattcc agcctggatg   77760
acagagtcag gctctgtctc aaaagaaaaa aaaaatgtga ccatgtgttt tacagctcct   77820
ttggtatcat cagtcactgt taccctaagg agggaaatac atagctttag ttttaggttt   77880
ccatcattag ccaagaaagc tcagaattgg tttcctggc taaagtacct cattgctgtc   77940
tccttaaatc ttagttaatg gctactgtcc tggctagcat agttatagag catgtccatg   78000
gttgtagaat gttctgccaa tctcagggac agtttttgct ttctgtgaag caataaaatc   78060
aacttcaaaa caaatgttaa ctgtttgcac aatggattta agatagacca gttcacatac   78120
ttttttttttt ttttgagacg gagtttcact cttgttgcct aggctggagt gcaatggtgc   78180
gatctcaggt cactgcaact tctgcctcct gggttcaaac gattctcctg cctcagtctc   78240
tagagtagct gggattacag gcatgcacca ccacacccag ctaattttt tgtatttta   78300
gtagagacgg ggtttcacca tgttggtcag gctggtctca aactcctgac ctaaagtgac   78360
ctaccccgcct tggcctccca aagcgttgag attacgggca tgagccacca cgcccagcct   78420
aagatagacc agttcactta ctgttatatc tgttactct ctctttgctg tgtcttctac   78480
cttaaaat ctccccacta acttcccatt ctccttagg tgccatcagt cacttccctt   78540
ctctgcaaac atctctggag agtctcagcc tcagcccaca gagcttccca ctgctctgag   78600
gtggaccttg tttgtaagac ttcttggccc tcttggcctg gaccctgtct actacttcag   78660
ccatccttcc ttaaccatcg ctagtggttt ttgttgccac cctccatagc agcgtttccc   78720
ttccagatca tgtctttaca tctctcagtca ctgctctggt cctgcctgcc tttccctctc   78780
tgtaccctgc aggccgctgc cgccatcttg agtgtcctct tcacttggct ttcagagggc   78840
ccacagagtt tcccactgct ctgaggtggg ccttgttttgc aatacttctt ggccctcttg   78900
gattactgca ctagcctttt gttttggaaa cagcattttt aaaaaaattt aattttattt   78960
ttttgagata ggatgtcact ctgttgccca ggctggagtg cagtgtcatg atcgtagctc   79020
gctgtggcct tgatctccca ggctcaagtg atccttctgc ctcagcctcc tcagtagttg   79080
ggagtacagg tgtgcaccac catgcccagc tagttttttg atttttttc tttttttctt   79140
tttttgaga cagagtctca cactgtcgcc cggactggca caatcttggc tcactgcaac   79200
aacctccacc tcccaggttc aaggtgattct cctgcctcag cctcctgagt agtgggatt   79260
acaggcgcct gccaccacaa ctttttgtat ttttaggag gacgggggtt caccatgttg   79320
gccagtctgg tctcgaactc ctgatctcgt gattcgccta cctcagcctc ccaaagtgct   79380
gggattacag gcatgagcca ctgctcccag ccaggaaaca gcattcttga gataattcat   79440
ataattcacc catttaaagt atataattca ttctctttag tatgcccaca gagttgtgca   79500
gccatcacca gaatcagttt tagaacccac aaaggaactc tgtaccctc acccaaaatc   79560
ttccatgccc ccagctgcag gcagccactg acctaccttc tgtctctgtg actctgcatc   79620
ttctggacat tactgtggat gggctcatac agtcagtgag cttgtgactg gtgccttcta   79680
ccaagcaggg ttttcagtgc agtagccttt cttttctttt tttttttta aattgagacg   79740
gagcttctgc ctcccaggtt caagcgattc tcctgcctca gcctcccaag tagctgggac   79800
tacaggccca tgccaccatg tgccggctaat tttttttttt tttttgtatt tttagtagag   79860
atgggtttc accatgttag ccaggatggt cttgatctcc tgacctcatg atccgcccac   79920
cttggcctgc caaaatgctg gaattacagg cgtgaaccac cacacctggc taacctctca   79980
tgtactgtct gcggttcttc cctgatgcct tccagtccat gcaccgatt gtagccctc   80040
atcctattat ggttaaggt gactgtctta gtcaccatgg gttgccataa caaaatacca   80100
gggaaactg tagcctggaa caca aacagaattta cttctcacga ttctagaggt taggaagttc   80160
aagatctagg actttcacct tgccctcaca tggtgagggg gtgagggagc tctctggtgc   80220
ctcttatatg tggacgctaa tctcattcat gagggtctgc cctcatgccc cagtcacctc   80280
tcaaaggccc cacctcctaa taccatcacc ctggtaatta agtttcagtg tatgaatttg   80340
ggggactata gacattgaaa ccataacaag cacttttcta aaagatcagg gagtgagtaa   80400
gtaccagagc taggaccca attccacctc tcggtcatct tgccttcact ctgctccatg   80460
```

```
atggctgcct cctagagtga tgggagcctc catgttttat attctctcat gtgttgtgta   80520
ttggagagag ttcagacttt atgaatacat ctggatttgt tgacttctag ctttgctggt   80580
aaccagctgt gaccttgagt aaattacttc atctctgagc ctgtttcctc tttttgaaaa   80640
gggagtttaa aatgctgttt tgggttgggc atggtggctc atgcctgtaa ttccagcact   80700
ttgggaggct gagatgggag gatcacttga gcttggagtt cgagaccagc ctgtgcatca   80760
tagtgtgaga tcctgtctcc tcaagaaatt aaaaaattaa ctgggtgagg taacgtgtgc   80820
ctgtgggccc atctactctg gaggctgagg tgggaggatt acttgagcct gggaggttga   80880
ggctgcagtg aactatgatt gcgcccatc ccgggtggcg agtgagaccc tatctcaaaa    80940
aaaagaaaaa aaaatgctgc tttgcacccc tttctcatgt catggtgtca tggctaacat   81000
cgaatgccct ggttgtttgc tgttggaagg cgtgggccta ggggctccct gaggactcct   81060
tccatcttca attcgttctc tgtgtacctg ttagcaagtt gtgggccagt ccctgccatg   81120
taccattgtg tgggtaaaag taaataaaat gtgtacagtg tctgaactgt acatataggg   81180
gtccaagaac aaaatgaatg acatgggtta gctcttttcta ataaatggta aaaccaaata   81240
ttctaatttt cagttttgtt atacttccat cacatgtttt tgttttttttg ttttgttttt   81300
ctattttagg cagccttgcc ttctctaaca aacccccctt ctcaagtcc catccgacga    81360
aaggggaagg agaaagaacc aggagagcaa gcatctgtac cgttgagtcc caagaaaggc   81420
agtgaggcca gtgcaggtag gaaacagtgt ggggaaggga gggacaggag tgcagcatct   81480
gtcatgtagc aacataggat ttaagtaact tggtgtttta gagaaatata atacacatca   81540
gtaaagtgag agaaggtttc tccaggtgcg gttcaagata ttagaaacta atgactaata   81600
tacacagacc accttttggt ctgaagcatc tctaagtgcc acctgctgac acgcagcccc   81660
tgcagcctcc aggcttccag ccccagcacg gagcctcact ctcctgtgct tccctggttg   81720
cgggtgaggc ctggagaggc ctcctgattt tcagtaaggg aagtggtgta gatgcttagg   81780
aatagatata gtgagtgaaa aaattgattc tgatatgtca aaattctga ttggaaatgt    81840
aatatttaca tttggaagaa ctaaaggaga gagaaagtgg ggataaagtc atctgagttg   81900
gaggagctta aaccatgcac aagtttggag gaccttttt taacccatga aaaggtcaga   81960
acagaagggg ctaggattta gttgtgactg cagtttttcg aattcccatc catactgctc   82020
ttggagggca gtggcagggg caggagagga gcctggcaaa gcatgaagtg actgctgctg   82080
cctctgctat ctgggtcgcc tggctgcctg tctgtacagt ctccctccaa acccattctc   82140
tcgctgtctc ttggtgccca ggggccagtg atggttctcc cgtttgtttt gtgtatatag   82200
catttatatc aaggctattt attatttag agacagagtc ttgctctgtc gcccaggctg   82260
gagtgtagtg gtgcaatctc ggctcattgc aagctccgcc tcccaggttc aagcaattct   82320
cttgcctcag cctcccaagt agctgggact acaggtgtgc accactacac ctggctaatt   82380
ttttgtattt tttttagtag agacagggtt tcaccatgtt ggccaggatg gtcttgatct   82440
cctgaccttg tgatccacca acctcagcct ctcaaagtgc tggaattaca ggcatgagcc   82500
actgcacctg gcctatttat ttatttttaa ttgacaaaat tgtatatgtc tgtagtatac   82560
aacatgatgt ttgaaaatatg tatacattgg ccaggcgcag tggctcannn nnnnnnnnn    82620
nnnnnnnnnn nnnnnnnnnn nnnnnnnnnn nnnnnnnnnn nnnnnnnnnn nnnnnnnnnn   82680
nnnnnnnnnn nnnnnnnnnn nnnnnnnnnn nnnnnnnnnn nnnnnnnnnn nnnnnnnnnn   82740
nnnnnnnnnn nnnnnnnnnn nnnnnnnnnn nnnnnnnnnn nnnnnnnnnn nnnnnnnnnn   82800
nnnnnnnnnn nnnnnnnnnn nnnnnnnnnn nnnnnnnnnn nnnnnnnnnn nnnnnnnnnn   82860
nnnnnnnnnn nnnnnnnnnn nnnnnnnnnn nnnnnnnnnn nnnnnnnnnn nnnnnnnnnn   82920
nnnnnnnnnn nnnnnnnnnn nnnnnnnnnn nnnnnnnnnn nnnnnnnnnn nnnnnnnnnn   82980
nnnnnnnnnn nnnnnnnnnn nnnnnnnnnn nnnnnnnnnn nnnnnnnnnn nnnnnnnnnn   83040
nnnnnnnnnn nnnnnnnnnn nnnnnnnnnn nnnnnnnnnn nnnnnnnnnn nnnnnnnnnn   83100
nnnnnnnnnn nnnnnnnnnn nnnnnnnnnn nnnnnnnnnn nnnnnnnnnn nnnnnnnnnn   83160
nnnnnnnnnn nnnnnnnnnn nnnnnnnnnn nnnnnnnnnn nnnnnnnnnn nnnnnnnnnn   83220
nnnnnnnnnn nnnnnnnnnn nnnnnnnnnn nnnnnnnnnn nnnnnnnnnn nnnnnnnnnn   83280
nnnnnnnnnn nnnnnnnnnn nnnnnnnnnn nnngcactt taatatttag tatcggttta    83340
atgataatgt ttgtgccctt actgtcttta aaacattttt acgtcatccc tgtttgatta   83400
cttggtgtgc tcatgaagtt gttggccact agggaatctt aggctcagag aggttctgga   83460
attggtcagt ggtccttgaa ttagccgctc ctatgattct ctaactgatt tctcaaaaag   83520
caaacaagca accacagcaa aacagctgtg cacaccactc ttcttatttt gttattgttt   83580
tagtacttag gccgtactta tgtttgttag tcagtttctc attacttcta gttaatcaaa   83640
agatcagagg caatatttga gtattttcat actagaatgc tttaaaaaaa gtcattattg   83700
gccaggcgcg gtggctcaag cctgtaatcc cagcactttg ggaggccgac acgggtggat   83760
cacgaggtca ggagatcgag accatcctgg cgaacacggt gaaacccgt ctctactaaa    83820
aaatacaaaa aactagccgg gcgagatggc gggcgcctgt agtcccagtt acttgggagg   83880
ctgaggcagg agaatggcgt aaacccggga ggcggagctt gcagtgagct gagatccggc   83940
cactgcactc cagcccgggc gacagagcga gactccatct caaaaaaaaa aaaaaaaaaa   84000
aaaaagtcat tatttccagt aatctcttta aaacttggca agttattttg atctaaaagt   84060
ttatcttttg tgtgcacatt tttaaagctt ctagacaatc tgatacctca ggtcctgtta   84120
caacaagtaa atcctcatca ctggggagtt tctatcatct tccttcatac ctcaaactgc   84180
atgatgtcct gaaagctacg cacgctaact acaaggtatg ggcctctgca tcttttgaaa   84240
atatatatgc ccacatactt atgtctaatg gatcgttgat gttttttctta tgattttgtag   84300
gacgtataag cccttttgaga tatgagttac aattcgtgtt ttcaagtttg tctttcagct   84360
ttgtttatga tagcatctgt catacaggtg ttttggattt tcatattgtt tgtactcaca   84420
gctaagatta ttacgtgag agagctagga tgtgcagcca ggttattggg ggaagtggcc    84480
tcggtggagt ctggagggat ctgtgtacag gcttccttcc ctcctgtgag gtcacacaa    84540
aaatcagca acctgctggt cctgcaggtc ccctctgcct aacatgagcc acaattccag   84600
actcacagaa gcaggcgttc agcataaacc acgtgtttca aatagtctgg gcgttgtgag   84660
ccacttgtta tcagctaggg aaagttttta tgtcagtgta aggaactgtt gaccagataa   84720
ccccaagagc cggcctttct gtctagggat gttttagttt tctagttcat ttttttttt    84780
ttaactttaa aattttctat tcatctgcaa tttgttagat atgaagtacg catctaattt   84840
aatttttggt tggttgtcc caatgctgtt tacagaaga atttttttgc actaattggg    84900
ttaagttact tacattctca tagttctcta gtttcatttg ccattttgtt atatcaatct   84960
atctgtctgc tcatctatta gaagcatcct tttttttcctg ttgtagacag tctcgctctg   85020
tccccaggct ggagtgcagt ggtgcaacca tgcctcactg cagtctcaac ctccaggct    85080
caagtgatcc tcccacctca gctcctgggt acctgggact acaggcatgt gccaccatag   85140
ccagctgctt tttacatttt ttgtagagac agggtctccc taagttgcct gggctggtct   85200
```

```
caagttcctg gcttaagtaa tccttcctcc ttggcctccc aaagtgctgg gattacaggc   85260
gtgagcaact gcacctggct agaagtatac ttcttagtta ttatagcttc atggtattta   85320
tgatgggatc agttctcctg ttctttagaa ttttctggat attcttcttt gttgattttg   85380
ggatgtgaac aatagaatca acttctactt gtaggttgat ttagggagaa cttataccatc  85440
agatgttaag ttaccctgtc cagaatgtgg gatgcttttcc tatttgttca aaacgtttta  85500
aattacctca gaagcacatg aaatttaaag gatttttaaaa aaaactttaa agattatttc   85560
acatagctct tgcacatttc ttggtaaatg aatcctcagg tgttcttctg tttttgttac   85620
taatagatac ttctcatggt tgttttttttt ttttttttcc tgaaaatcat ttgtcaaact   85680
tatgtggctt cttttctgaa ggatgtttga taattttgga agatataaaa gtcttcatat   85740
tttacaaggt ttggagtctc tttaagctgc gtggttctca cgtcagctcc caaagcagaa   85800
gacggcatgt cgaaaaatgc catagagaag ctacttctttt tccacctgtt ttcagctcat   85860
atcatcttga atttcgggggc acctttctat gctcctagtg cttgctgtct gtttattatt   85920
ttccttcctg aatccctga actccagcat gttctgctgt aattctggcc tccctggcgt   85980
cttggactcc tgtttccttt gctctgtcat ccccacggtc agctcctgct gcgcagcttc   86040
tcagctgaac tgtttggagt ggctggcggg tcttgctgga tctttgagta ttgcctctgg   86100
tttccttggt tccttctgct gagttgctca gcgtctccac tccccatttc tcgtgtggcc   86160
cttcctgctc tcctctgatt cctttttgtct tccctggttt cttgctttgg ttttcagtct   86220
ccgcagaact tttgccactc ttctgaaaac ccggaggctt tttcatccta attctcattt   86280
catgacctct tttccccttat ttgagaggta gaccttccca tggtgagctt ctctttccag   86340
aattccatgt cttcttttcc ctcccactta cctgttgtcc aggagaggtc agattgctgt   86400
gcgcattgga gaagaaccct ttcttccctg ggctcttcat ttcacatgac atcaccacat   86460
cacctcatcc cttggaccct cagtggtggc actgctggat ttttctttcc tttggctggc   86520
cttgggggcac acccaggttg acccctagctt agtcatggat tttagatcaa ctcacatttt   86580
cagtttctgt gtctgtctct tgcctgcttc tgactttgcc cagagaaagc ttttttcacaa  86640
gggttcttag atttacgagc accttctttc ctgaggcagt gttttttgcca atatttattt   86700
tcctagtcag tctcgcctta cctttcttgt tatacatgat gtctttgtc ctgacccatt   86760
ctctgagtct gtaaaataga attgctgtat aatttaatta catgaaatcc tttagaatct   86820
taatacatct tacaccaggt gtaacatttt atgatatcca aattgaacaa ccctgtgtga   86880
atttgacagt gatttctccc agggatccta atgtataagg aataggactt tgtatttct    86940
atttttttgat ataccacata ccagatactg acatttaacc cttttttct                87000
cattaggaaa gaaagttagg aattacatct ttcagtagtg ccagtgtgac ctgaaagatg   87060
cctttgaaag agtagtttttt gtatagctat ctgaaaggaa tttcttttcca agatattttc   87120
ccagtgctga caacaaacac gcagacacgc cctacaaggt caatgtacag cgccgcacag   87180
tggaggcgtc tgccgcagcc gttaatgttt gtatctttg ttgtacttta cgagatcttg    87240
acggggccag taaccgtgtg ttctctcctt caccttctca aggtcacctt ggatcttcag   87300
aacagcacgg aaaaatttgg aggggtttctt cgctcagcct tggacgttct ctctcagatt   87360
ctagagctgg ccacactgca ggacattggg aaggtctgtg tcttgttttg acgtgcgtcc   87420
tctgggctga gttcatctag gatggagtcc ggttctccag ggtgcctccg ggagactcct   87480
ccctgccgca cggacttgca tcacaggacc ccgagtctgac tctgccttag ccatgaagtt   87540
tgggggggaag gttctatttg tattctgttt ttgtctgttat tcacgtatta gcttagaccc   87600
agtttagttt agaaaattgg tgggtttaaa aatgtgttta tagagtccttt tatttcttaa   87660
tttgacccttt tcaagtggaa agggggcaaaa cagacagatg agggggcggg gcgggaggtg   87720
tgacttgctc ttttgtgcct gaggaagtaa cagagctggg gttgacagtt atattctctg   87780
gttttatgtc caggaatttc ccctgccgca cccctagttg atagcgaaaa tgttcaaaac   87840
tatgagaaag ttagaatgct gtggtaaaca ctctattatg tacacacaac ccagcttctg   87900
cagttgtttg cgtttggcta cgtttccttt ctatgtatat agccatctct ccatttacca   87960
gtacatctta ctttataatg catttaaaa ggagtgacag atgcctccct ccaccaaatg    88020
tgtgtcttca cgtgaaatac agtatgtctg atgcacttca tttgttctta tgtctttgaa   88080
tcttttttatc tggacatgga cacaaggtta cctagttta atcgttacat atgttagtgc    88140
ttcttctctg ttattcctca tgttttttccc atgtatctat ttagtgtgcg cagttgtcat   88200
ttttaatggc tatctagtgt cctgctgtgt tgatactcca tcgttccctt agagtaaaac   88260
ttgttgagac ttcagtaatg tcacctgctc agtgagactt tcctggccat cctttcaaaa   88320
cttgcttctc tctgtactct cttttcctgt tcatttttct ctttgaccca tagcatcgtc   88380
taacagtcaa ccttaaaata aataaataaa taaagacttc agagaaatgt ccaaatacat   88440
ggagtcagtt tgggaatgag aaatgaggat tataatccgg gatgcacggc atgtccggct   88500
gccagtgcct ctggtgaagg aagggggaagg ggaagctgtt attgtcagaa agggagagaa   88560
tcacataggc tccctggaag cagagttcgt tggctccaga ggctgaaagc cagagttgtc   88620
gtcattcact ggtggaattg taggcaccgg gcaggtgttc agttgagagt atttttaactg   88680
aattgctgca gtcctccaga atggctagtg ataaatctgg tcatagaaac atgtattcac   88740
gtggaacatg caagccatgc acagcagata tgtaaaggat gtacgggaag ggttcttct    88800
agggttgttg gaaagtcttt ggaaacagct ctaacctggg gcacataagc atgaacccca   88860
tctcccttttg tgctttccta gtccaatttt gtctgggtct gacaaagtga tttgatccct   88920
gtatctgcaa ctttcacaaa acatactatt tatttatttt acttccttgt cttttcagtg   88980
cctatagcag tgcctggaag attgtggaat ttagtgaaca tttgttgaat gaatagatgt   89040
tcttgttaaa aatgagttttt agtgtctcat ttatcttaca tccacactgt ggtggagcca   89100
tattagccca tttcacgcca taactggaag ctgaaagatg tgacattctt ggggccagat   89160
aagtcagtgg cagagcctga gttaagtctc atagatttt ttttttcttt ttcgtttttg     89220
gtggctagct ttggttttat ttttatttat ttattttattt ttattatact ttaagttgtt   89280
ggttacatgt gcagaacgtg cagttttgtt atataggtat acatgtgcca tgatgtttg    89340
ctgcacccat caacctgtca cctacattag gtatttctcc taatgttatc ccttccctag   89400
tcccctcacc ccgatgggcc ccggtatgtg atgttccct ccctgtgtcc atgtgctctc    89460
attgttcaac tcccacttgt gagtgacaac atgcagtgtt tggttttctg atcttgtgat   89520
agtttgctga gaatgatggt ttctggcttc atccatatcc ctgcaaagga cattaactca   89580
tcctttttta tggctgtata gtattccatg gtgtatatgt ggccacatttc ttaatccagt   89640
ctatcatcga tggacatttg ggttggttcc aagtcttgtc tgttgggact agtgccacaa   89700
taaacatacg tgtgcatttg tctttattgt agaatgatat aatcctttgg gtatatgccc   89760
agtaatggga ttgctgggtc aaatggtatt tctagttcta gatctttgag gaattgccac   89820
actatcttcc acaatggttg aactaattta cactcccacc aacagtgtaa aagtgttcct   89880
attttttccac aacctctcca gcatctgttg tttcattaat ttttaatgat cgccattcta   89940
```

```
gctggtgtga gatggtatct cattgtgatt ttgatttgca tttctgtaat gaacagtgac  90000
gatgagcatt tattcatatg tctgttgact gcataagtgt cttcttttga gaagtgtctg  90060
ttcatatcct ttgtccattt ttagatgggg ttgtttgctt ttttttttt tttgtaaatt   90120
tgtttaagtt ctttgtagat tctggatatt agccctttgt cagatggtta gattgcaaaa  90180
attttctccc attctgtaag ttgcctgttt actctgatga tagtttcttt tgctgtgcag  90240
aagctcttta gtttaattag atcccatttg tcaattttgg cttttgttgc cattgctttt  90300
ggtgttttag acattaagtc tttgcccatg cctatggcct gaatgttatt gcccaggttt  90360
tcttctagga ttttttatagt cctaggtctt atgtttaagt ctttgatcca tcttgagttg  90420
attttgtat aaggtgtaag gaaggggtcc agtttcagtt ttcagcatgt ggctagcagg   90480
ttttcccaac actatttatt aaataggga tcttttcccc attgcttatg tgtgtcagat   90540
ttgtcaaaga tcagatgctg gtagatgtgt ggtgttattt ctgaagcctc tgttctgttc  90600
cattggtcta tatatctgtt ttggtaccat gctgttttgg ttactgtagc cttgtagtat  90660
agtttgaagt caggtagcgt gatgcctcca gctttgttct tcttgcccag gattgtcttg  90720
gctatgcagg ctctttttg gttccatatg aagtttaaag tagttttttc caattctgtg   90780
aagaaagtca gtggtagctt gatggggata gcattgaatc tataaattac tttgggtagt  90840
aaggccattt tcacaatatt ggttcttcct atccatgaac atggaatgtt tttccatttg  90900
tttgtgtcct ctcttatttc cttgagcagt ggtttgtagt tctccttgaa gaggtccttc  90960
acatctctta caagttgtat tcccaggtat tttattctct tagtagcaat tgtgaatggg  91020
agttcactca tgatttggca caatctcagc ccactgcaac ctttgcctcc tgggttcaag  91080
gaattctcct gcctcagcct ccagagcagc tgggattaca ggcacctgcc accatacctg  91140
gctaattttt tgtattttta gtggaaacgg ggttttacca cattggccgg gctagtctcg  91200
aactcctgac ctcgtgatcc acccacctca gcctcccaga gctgcggat tacaggcttc   91260
agcaactgcg cccagccaga ttttcagatc tccctctctt tgccctaaac cactgtgctt  91320
aataagaatt cttagtggc cagcagtctc catgtgtaac acattgtagc aaaatggaaa   91380
atattacatg ttttaaattt gagtgtgaga tatactgaaa taaaaatcat ctaaatgaga  91440
ttcttaaat aataagattt tctttttttgt atgtgggttt ttttttaaca ttattattat  91500
gactgtcgta tatagaaatg gctgttttca actacagtca gtgaatgtat caaatgctgc  91560
cttatccaaa taataaaagt aaatgattaa caagtcacaa tttagtgaag attgatgtta  91620
gttgatcttt atattcctga attagccaca tggttgtgtg tgtgtatata tgtttagagg  91680
tacatataga taataagctc atctctgaaa attttttcat ttggcataag aataactgga  91740
taattaagca tcttattctc tggcctgtgt ctttacagtt aaaggtagat ttactcacct  91800
ctcctttttt gtttttctca gttcatcttt tttgctatt catgacggag gcccattta   91860
cctttctcgt atatcctttt gtttgtactt tggaagcctc acctgcttaa ttgttgagtt  91920
tttaatctgt ggtcttttag aggaggatgt gtagggtaga agctttcaca ggttcttctt  91980
tgcacttggc ccttggctgt tttgaggaat ctcccctcact aactcacagc atagcaaggt  92040
ttgagatctc ttctgccaca cagcagttcc caggcagctg gaaagatatg cagatgctca  92100
gattgtcagg ccagccttga gatatacaaa ctactgagcc ttatctgtga ccttgcttag  92160
gtgaaggcat cagagcccct gcaccgacat gtgtaggcct ctggatgtgt gcgggctgg   92220
gtgttgggt ctgagcacaa gtgtagctgg agaggtgagc ttgttgtggt gacgggtatg   92280
agcaagtttt cttcagactt ctgtgagttt acctcgttcc aggatttaaa ggcacagaga  92340
ccttagaatt aaaatagaat cattttcttt ttctaaatag caacactagg aataaaaaat  92400
aataattcca cattctttac aggtaatgtt ttgttttct tgtcttctaa tccttattta   92460
ttctgtactt attttttatac gtatttgaaa tgtattatgt gttggagttt tcttttttgca 92520
ttatattata cacggttttt catgtaactc cttactgttc cattttatat gttttgtctg  92580
gtttatttta agactttatc agcaaatcgg gaaccgtct ctacaaaaac aaaaacaaaa   92640
gcaaaaatag ttggccacag tggcatgcgt ctgtggtccc agctactcgg ggctgaggtg  92700
ggaggattgc ctgagcccgg gaggttgagg ctgcagacaa ccatggctgt gtcactgcac  92760
tccagcgtgg gtgacagact ttatactgtc tgtttggggt gatttggtaa tgatatgccc  92820
tgatgtagtt ttttttatatc ttgtgtttct tgtgcctggg tttattgagc ttgggtctgt 92880
ggcttcatag tattttaaa gtttggaaaa ttttagggca ttatttcccc aaagattttt   92940
ttctgccctg ttcccctcct ttttttcctc tcttaaaggg gctgtgattt cctgaatgat  93000
tgcttagtgt tgtcccatag cttattgatg ctcttttcag tgttttttgt gttttctgtt  93060
ttctatagtt tctattattg tatttgcaag ttctctaact tttcttctac gatgtctaat  93120
gtgttgttta tctgttaatc tattgttaat cctgtccagt attttttttt tttttttgaa  93180
acagtctcac tctgttgccc atgctggagt ttagtggtac aatctcggct cactgcaacc  93240
tccacctccc aggctcaagc aattgttctg cctcagcctc ccaagtagct gggactacag  93300
gcacgtgcca ccacacctag ctaatttttg tattttatt agagatgggg tttccccatg   93360
ttggccagac tggccttgaa ctctgatctc aggtgattca tccacctcgg cctcccaaag  93420
tgctgggatt ataggcatga gctaccttga ctggccccctg ttcagtgtat atcactaatt 93480
gtgtttttat ctatataagt ttgatttagg tcttttaaaa atttctccct gtgtctctac  93540
ttagcttgt gaacacagtt gtaataactg ttttaatatc tttctctgct agttctaaga   93600
tcttctaata acttcctggt tctcggtgtt tttgattggt ctattgatgc tccttgttgt  93660
ggattgtgct ttcctgcctc tttgcatcgc tgccaatttt tggttggatg cccaacattg  93720
tgaattttac tttgctggat gctagacatt tttgtgttca cagagatctt cttgagtttt  93780
gctctgaggt tagttgagtt acatgtagat ggttactct tttgggtctt gctttataat   93840
gagtactcta cctaatgaac cagaaagttc gggttttcca gtctgcctgc tgagaacggt  93900
gactgtttct agccctgtgt gagtgcccga gcgccgctcc ctctgatcct ttctgatgct  93960
tccctctgtg gcctcaggga gtttcctcac acacacagtt ctgctgagta ctcgagggt   94020
ccttccccga tctccaaggc tctctctgtc ttgttctctc ttctctggtg ctctgtccta  94080
taaactgtgg ctatcttggt ctccttagat tctcagcacc tcttcaattc agagggttgc  94140
ctgtccctcc tccttgtgcc acagcctagg aactctctta aagaagtgag gtggggcagc  94200
tgtgggctc actttgtctc tcgtctccca gggatcactg tccttcatgg ctgatgtcca  94260
atgtcttaag gactctggat tttgtctgtt tgtttttgt gttggctttg tttgttttcaa  94320
acaggagggt aaacccagtt cctcactctc attgtgctca gactggaag tctcgctctg   94380
ttatattgga tattagtatt tgtagcagag ccctggttcc ctggtacttg gggagctctt  94440
gaaaggccag aaacagcatg cttttctcacc tttcccaggg cttccgtttc tggtgcacac  94500
aaagcattcc atacacattt gttaaagttc tttgttagac aaatagtgat tcacaggctc  94560
tatttgtaat ttttcagta agcatgtatt agatatctgc tgggagctag tagaaacaaa   94620
aagtgacatg tgacaaattc aattctgaca agaacaacct taaacattta gaatataatt  94680
```

```
tgagtaaatc agaattttaa aaatgtgtgg cccttgaata tttgaaacca acaagaatct   94740
attgcttatt agtagaggat attttgttga acaagtggag agagaggcat tttcagtcta   94800
actggtgttg gcttttagca gctgttggaa accggttcat gattagccag gcagtggtga   94860
aacaggctgt gcattctgaa tgcctagatt ggtggcactc ttcgagttag catcttcttc   94920
tttcttcttt tttttgagat ggactttcac tcttgttgcc caggtaacaa ctccagtgca   94980
atggtgccat ctcggctcac tgcaacctct gcctcccggg ttcaagcgat tctcctgcct   95040
cagcctccca agtagctggg attacaggtg tgcgccacca tgcctgacta attttgtgtt   95100
tttagtagag atgggttttc actatattgg tcagactggt cttgaactcc tgacctcaag   95160
tgatccacct gcctcgacct cccaaaatgc tgggattaca ggtgtgaacc actgctccca   95220
gccccttctt gattcttgta aaggacattg ggtgctgtac accttgttat agatgttgat   95280
aaaaattctt gtgagaatag taacgttaag gtagttgttt ggtcattttt gtctatcagt   95340
ataagataat tctaggactg atttgtggta aatcacacat tgctgtatca tagttgtgtt   95400
cactgaacat attcaggggc tttacagatg cagggctctt agctgctttg cgcacttctg   95460
aattcctgcc ctgagaacag gactggatac ctagtagacg ataggtattt gataacagtt   95520
taatgaatta atgagtgaat gaacagatac gtaggtatgt gaaagaatgg ttgtaatgta   95580
tgtaacttgg atttcaagac ttactctgtt caaataagaa atggaaaact ttcctctgat   95640
tttgctctac tatttacact cttaaatgg aagttatctt gtacctttga tttctgtcta   95700
ggattcgtac aataatgggt catctctgag tcacttacgg tctcactgtt cttccacag   95760
tgtgttgagg agatcctagg atacctgaaa tcctgcttta gtcgagaacc aatgatggca   95820
actgtttgtg ttcaacaagt aagagcttca ttctttttcct attctgttaa gactttcagg   95880
tatgacgaca aaatgctgct actccttaag cagcaggtgc tggtggcgta atcagctggg   95940
aggattgtgg ggtccagcat agcacttttc ggctcattcc atgattgagc caagaggccg   96000
accttcccgt cattcccag gaggacgagg tctgtcattg tggagagcaa aggacatcag   96060
aagctcccct gcatcctcac tcgttaactt ccagtccctc ggggtttttg tttagcgtgc   96120
tcaatctcat ttagaatcgc aaggaaaccc aaaactctta tttaaggtac aaacagcact   96180
tcatacaata tctcgccgag gtaataatag tgattcacag gaagaatttc acattgtgaa   96240
tctttgctaa tgtatccagt tatttacaga tggatttgat atttgtgtgg gagattctta   96300
aagtgttgtt catgccacgt tgtttgtgct tcaattttt cactatagtt gttgaagact   96360
ctctttggga caaacttggc ctcccagttt gacggcttat catccaaccc cagcaagtca   96420
caaggccgag cacagcgcct tggctcctcc agtgtgaggc caggcttgta ccactactgg   96480
ttcatggccc cgtacaccca cttcacccag gccctcgctg acgccagcct gaggaacatg   96540
gtgcaggcgg agcaggagca cgacacctcg gggtaacagt tgtggcaaga atgctgtcgt   96600
tggtggaagc acaaaagagc aagcaggaaa tactttgtaa aagaataaaa acgaaaaatg   96660
ttagccaaca tcttctaata gtctgctgta ttcaaagaat tcctaggaaat atggttgatg   96720
caaagatgat ttaaggcata gcccggcctt tcaagaagtg tgtggccagt gagtgagatg   96780
ggcttgggac ttacacatct cagaggtggg ggtagaggag gaggaacact gagtgggctg   96840
agaagcagcc agctttcatt gccaaagtgt gtcagcaaac cagaaggcag ttcataatgt   96900
ccccaccgt tcaaagcaca ggcctgtag agtggtgtgg catgtgttgg tggcactttt   96960
caggcctgta acaaggatga aagaacagct tcattgcagc acagtagtgc tggtattcag   97020
aggtatatga aggtcatgga agcatcttgg atatgttacc ttgtgttttg tcaactttat   97080
gactagaaat ctcttttttac ttaaattat gtttgtgtct ttaatgcctg aatacagga   97140
cttcttaaat tgccataagt atcaacaggt attgagtta ctaatctgta tagtagcaat   97200
aataagaatcc cttgttttc cttttataaa tgtaatgact aaattgaaaca   97260
ctagagtcag gagtcaagga aaatacccat gttccaggct gtatgttagt gatgtactca   97320
ctgtgtattc cagtttcagg aataagtctg tttcaatgct ttctgtaacc atttggggta   97380
ttaataagca agtgagtgta tgcatgtttg ggttaattc atatatgtgt cttagaaagg   97440
atatcattga tgtaaatatt ttcaaggctt atcctccaaa aaatcctgt gatttcttct   97500
aaattactga tcttttaaat gaccttcacc tttctctcaa gtctcactta agactgggct   97560
gagtagtcag tttcctgtag cagtaaaaag ctcagacttg agtagccttc cacaggtgac   97620
gagacttgat ggctgtcagg cagctgtaaa ctgtaaatag agtgtcatta tctcgagagg   97680
gtgatgctgc cacactgagt ggcctttcaa gttgtttctc agtctgacat gttctgatcg   97740
tgtgaatgtg aaattggttt gaacaggagt atatctgagt gcagaggaga ttatttaaag   97800
atattctcat tgtctgcttc ccttctattc ccatttggca gatggttga tgtcctccag   97860
aaagtgtcta cccagttgaa gacgaacctc acaagtgtca caaagaaccg tgcagataag   97920
gtaaatggtg ccgtttgtgg cgtgtgaact caggcgtgtc agtgctagag atgaaactgg   97980
agctgagact tcccaggtat tttgcttgaa gcttttggtt gaaggctcac ttacggattc   98040
tttctttctt tctttttgttt ttttatagaa tgctattcat aatcacattc gtttgtttga   98100
acctcttgtt ataaaagctt taaacagta cacgacaaca acatcgtgc agttacagaa   98160
gcaggtttta gatttgctgg cgcagtcggt tcagttacgg gttaattact gtcttctgga   98220
ttcagatcag gtttgtcgct tttaatcttt catccatcat acctgtacct aatttagtac   98280
aaattaccct gaaagacact gaaatctact ttaaagaaat gtgaactgtg tttccccacc   98340
ccccatcaat tgctgctgct tatgtttttc atgcacttag ctagtacaag gcccgggca   98400
tagccagcct cagcaagtcg gcatccttgc cccagctccc tggactcaag gctaacctgg   98460
ggttgctgt tagggatttc caaaggtttg tcccatccac tcgcctcccc tccaaaataa   98520
gtttgaattt aaaattgtgag atttaattaa gatttattgt ttggggaaca tttttgcaaa   98580
atctagagag ttagttaaa tggattatca attatgacta taattgatca tctgcagttt   98640
caggctatct aacaggttag cttacctctt taaaaggaa tggaatttag ccggacagta   98700
actgagaccc acgctcctgg agtccacgtg ggagccgcgt ggctctgcac aaacaagcat   98760
ttgcactctt cccctcttgg ctgcgttgcc ctcctcgtg agttgctgtg ggcactagat   98820
tctggctagt catgtccctt catgatgcac agtttcctca agattcgtgc cagttaaatc   98880
actgcctttt catagtcaaa atttaactgt catctttgac ccatgatctt gggctacttc   98940
cttatgtggg gtaggaatat ttttgagata gaaatattac acttctctgt ttccttctag   99000
acaaaaatct gttaattctg ttagtaccgt gactcatctg aaagggtctg tttccctagg   99060
agaactgagg gcacgtggtc aacactgatt tcccaccatg ggattgagg tgggctctgg   99120
ttttttttgt tttgtctttt tttttttgag acggagtctt gctctgtcgc ccaggctgga   99180
gtgcaatagt gccatctcag ctcactgcaa cctccacctc ccgggttcac gccattctcc   99240
tgcctcagcc tcccaagtag ctgggactac aggcacccac cacttcgcct ggcttatttt   99300
ttgtagagac cgggtttcac catgttagcc aggatggtct ctatctcctg acctcatgat   99360
ccacctgcct cggcctccca aagtgctagg attacaggcg tgagccaccg tgcccggcct   99420
```

```
ggggtctgct tttaatgaaa gaggcatcta ggggtgggct ttgccttggc ttgatgcttt    99480
gaacctttgt tcacaaaacc tatctgaaga aaatctgtct cagtgggcca ttgctctcct    99540
caggaaacat gcattgggaa cttctttttcg tttcctttga cactaggagg ctgcctgggg   99600
agaagccctg gtctatggct atgggcaagc aggggctgag aggagcaggc tctcagtggg    99660
gcagggtacc ccaagggaag ccagaaccct gatttgttcc attctagtga gaacaaagac    99720
tacagtctac cttttcttca gaatttccca gttctaactg ggcatggtgg cacacctctg    99780
tagtcctagt tactgaggag gctgaggcgg gaggatcact tgagtccagg agtttgagtc    99840
cagcctgcac aacatggcaa ggcctgtctc taaaataata gtaataatca taatctctag    99900
ttctagccgg gcacagtggc tcatgcctgt aatcccagca ctttgagagg ccgaggcagg    99960
taaatcattt gagctcagga gtttgagaac agcctggcca acatgatgaa acccccatctt  100020
tactaaaagt acaaaaatat tagctgggtg tggtggcagg tgcctgtaat cccagttact   100080
tgggaggctg aggcaggaga atcacttgaa cccgggagat ggaggttgca gtcagctgag   100140
attgtgccac tgtcctccag cctgggcgag acagagcgag actgtgtctc aaaataataa   100200
taacaacctg tggttctgac tcgtcatggg taggaactga ttttctcatg tggtagttac   100260
agactatggt ctccttgggc ctgtctttag tagggaaaaa aggcaactcc ccactctaac   100320
ataaaatggg tggacttgaa tgttttatca aattctttct ttagtcgttc tactggagct   100380
ttttcttcaa tgtagaatat tctgttgctt tattatattt gtctgcaatc tccatgtgat   100440
atttccatgt tgagggagga cagccttgag gctcccccgt gctgcctgcg gccctgcagg   100500
catgtggaat tcatctttgg cctgtgcttt cttctgggtc ccggtgcccc tgcccgcgag   100560
gctcatgtcc agctgcccct ttgtggtggt gtgaggtcat tcctgctgtg agcgctctgg   100620
tttcatgttt gttccgattg cctttcatca gccgatcccc tttctcccag ttcttaagat   100680
tcaatacagt gacagtttta tgaacaagaa tagaactaga acagacaagc cattgaactc   100740
tatgctgata atgatttacc gagcacctgc tgtatgtttg cattccgcgc agaggctctg   100800
agaaagccgg gccatgtgct ccatgcttta tcggtggaag ctcctcatca ggtttgggaaa  100860
gctgacagct gcgtagaata ccagtgtgac acaaagctgg ctcccgtgcg gcccttgcgt   100920
gttgcctctc agatggtggg aggaagaagg tcgactcctt tggggatctt actaccaaac   100980
cagtttcagg gaatctgcta ccctgtctgc cattaatgag aacagatgag tccccaaggt   101040
gtacttctgg gtattgtctg atgtcgcttg gaatttatta cttgtttttc caatgaggtt   101100
tcacctcagt gtgtagtaaa gttgttgagg ggattcctgg aggtgttcta cagttatcta   101160
ggctgatttc agaatagagt tatgcttata gtccaattca tcagctgtca agaaattcat   101220
ttaaaatttg tgcagataag caggaggaaa agaaacctgg tttttacgtt ttaatcctat   101280
tattgatgta aaattttact ttccttcccg taggtgttta ttggctttgt attgaaacag   101340
ttcgaataca ttgaagtggg ccagttcagg taatagcatt ttgttatttt agagtttttt   101400
ctccttcttg tgtacttaca tgtaatttag gttattaaga tgaatgttta aactactgtt   101460
aggcattttt gctgttttct ttaaatggaa atctgattaa catgctgtgc attttttgctt  101520
ctcttaaaaa ttaatgtata tctcaagact tgtttggaag tagttacata tctgaaaatt   101580
ccatatgttg tcagttttca ttgcacattt caaagcattt aattatgttg acagatggcg   101640
gaatgaaatc ttgtggtgga gcactagttt ttaaatcttc ttagagaaag cagttttttat  101700
ataaggttgt cttttagtaat tattatgcac ttgtattctc tgcagctttt ttttgctaga   101760
tgttgaggtt ttaatacttc ttgctagtcc attacaggtt tataatgatt gaaagttaaa   101820
attctttagt acctgaaata cttaataaat actgtagtta ggaaaactta gtgcagaagg   101880
aaagtgttcc cagattccct ggggtctgga agcatagcgt ttgttctaat cacgtgacac   101940
ctccactgtg ttttggggca agttactttt tctcttttga gtttcaattt ctacaagagc   102000
aaaggggcag agagagctag ggagattgta gctgctgtgc ctctgtgccg tcaggtgcct   102060
tctacctgct ccctctgaac cttttacacct gtcccggctc tgcacaaggg cacagatggg   102120
atgcactgtg gcagggatgg gcttagagta gatcactgac acctgttagc ttcatgtgcc   102180
ctcatgatt attttatgtt gcttatattg atatgtatct taattttaaa agaaaggtct   102240
aaatggatgt ttttgtttct agggaatcag aggcaatcat tccaaacatc ttttttcttct  102300
tggtattact gtcttatgaa cgctatcatt caaaacagat cattggaatt cctaaaatca   102360
ttcagctctg tgatggcatc atggccagtg aaggaaggc tgtgacacac ggtaatggga    102420
cacatctttc actgtcgtct tcagtgtcac gatgtgcttg gcagtgttcg tttctttttt   102480
tttgttgttg ttgtttttt tttttgaga cggagtctcg ctgtgtctcc caggctggag     102540
tgcagtggcg tgatctcggc tcactgcaag ctccgcctcc cgggttcacg ccattctccc   102600
gcctcagcct cccaagtagc tgagactaca ggcgccgcc accacgcccg gctagttttt    102660
tgtattttta gtagagacgg ggtttcacca tgttagccag gatagtcctg ac           102720
ctcgtgatcc acccgcctcg gcctcccaaa gtgctgggat tacaggcttg agccaccgcg   102780
cccggccggc agtgttcgtt ttcatacacc cactttcaac tttgtcagtg gcggccgtgt   102840
gcgtctcagg ctctgcatat gtgtctgtgt gtctgtgtat gtgaatgtac tggttagaga   102900
cgtttcaaaa gagaaggaga catattcttt actctcagca atttgtaatc ttctcaggga   102960
aaaaagttc aagaaacagt aagatagcct aaggtacaga tagattctga atataaagtt    103020
cctgttcatt cacacgaaac actaaaagtt cttcacctga tcttagccca aaggccgaga   103080
agcgatgaaa cactaaaaat tcttcagtcg aacttgctgt gaattaaatt ttgatctctc   103140
atccaggtgg tattggagat acagtttgac ttgggttcag ggctttctgt tttgcctgat   103200
gattattttg ctggagctta aataaagaca gggctccagg agatggccag ctgtgcaagc   103260
ccccagcctg tggaaggagc tagcctggtt ttatgaatga gctgtaaatc tttctttgag   103320
ctttttgaac tggtcttcca gcattgccct attgacccct ccctgactcc tttgctggaa   103380
tccgtaggct tttgaacttt gacagggaca catcctaaga cccttgcaaa cccctagatg   103440
tgagaatggc actactacat agagtctttt ccactcagcg tgtgtgcaga agaacatcaa   103500
ccatgctgtg tggcgaggca gggccttggc tgacctctca gtcaaggcct tagctttaca   103560
gagctaagcc agttagtctt tgccatggct tcacaatggc ttcaggttca cactgccaaa   103620
gtatagatta ttaaaggcat aggtgtttgg tttcctgcac ttgagggtc tttggacaga    103680
aaatcagtag gcagccaaag ccagtacttt gcgctgggaa gcttggtcgt ctgtgagagg   103740
gtcagagagg atacccatgt gtgcgcacca ccgaagggtc agtgagtctc agggctctgc   103800
gtgcatgtct caggggctgga gagatgtgt cactgagagg tcagtgttgt tgtgcgtgtg   103860
tgtcaaagag ggttgcagtg tgcccttcac tgaggggtca gagggtgcct cacgtgtgtg   103920
tatgtgtgtg tgtcactggg tcagtgagtg ttctctgtgtg tgcatgtcac tgagaggtca   103980
gagggtgcct ttgtgtgtgt gtgctcatgt gtgtgtgcgt gtcactgagg ggtcagtgtt   104040
cctgtgtgca catgacattg agggtcagag tgtgcctctg tgtgcgtgtg ctcgtgtgtg   104100
catgcgtgac acctccactg tgttttgggg caagttactt tttctctttc tcttttactt   104160
```

```
ggtcatctgt gagagggtca gagaggatat ggtcctgtgt gcgcatgaca ctggggcaga    104220
gtgtgcctct gtgtgtgtgt gtgctcctgt gtgtgtacgt gtcactgagg ggtcagtgtt    104280
cctgtgtgcg cgtgacactg aggggcagag tgtgcctctg tgtgtgtgtg tgtgctcctg    104340
tgtgtgtacg tgtcactgag gggtcagtgt tcctgtgtgc gcgtgacact gagggggcaga    104400
gtgtacccgt gtgccaatga aaggcatttc ttatttttt ttatatgtgg tcacagtaga    104460
ccaattaatt tattttgact cctgttttag accaaaataa gacctgggggg aaagtccctt    104520
atctatctaa tgagagagtg agtttactta aaaaagcata ataatccagt ggctttgact    104580
aaatgtatta cgtggaagtt tttattgtct tttcagatga atcaaataga ttattctcga    104640
gaccaggaat ggtgctgttt tggttatttg ggaagtttta tcattttcaa attgaccttt    104700
gaatttgagt cacctttttt cagaagtggt gttaaattac aggagcccta ggttttttttt    104760
ccttttttag aagccatcac aaaatgatcg gtgttcagag gaaaagcttt gatcttccac    104820
aatggtataa tgattgataa ccttaattca tctcttacca taaaccaagt atgtgtaagg    104880
gttttctta tttcttgata tcattttgta gatgttgaga gcagttttcc aaatgtaatt    104940
tccatgaaat gcctgatgag ggtacccttt tgtccccaca gccataccgg ctctgcagcc    105000
catagtccat gaccttttttg tattaagagg aacaaataaa gctgatgcag gaaaagagct    105060
tgaaacccaa aaagaagtgg tggtatcaat gttactgaga ctcatccagt accatcaggt    105120
aagaggaatg tgtgttggaa ctgtcgtgga tactttattg acccgtacag atggaaggaa    105180
gtgccatgtg gtaacactca ctgttaaccg tgctacttg aactaggttt gagcttttctg    105240
aggcctgggg agatgctggg gcagcggcgg gtgcaggggg aggtggggggc ggggacagg    105300
cgtggtggca ggaggtatca ttggtgttta tccttccttt tttttttttttt ttttgagat    105360
ggagtctcac tccgttgccc aggctggagt gcggtggcat gatcttggct cactgtaagc    105420
tccatctccc gggtttaagc gattctcctg cctcccacct ccgagtagct gggattacag    105480
acatgcacca ccatgcccag ctaatttttt ttttttttttt tttgtatttt tagtagagat    105540
ggggtttcac catgatggcc aagctggttt caaactcctg acctcaagtg atccgcctgc    105600
ctcggcctcc caaagtgctg ggattacagg cgtgagccac cgcgcccggc ctggtgttta    105660
tctttaaagt gggtacagcc acagggggtt aacctgactcc tggtctgaga gtcacaaagt    105720
cgttcaagat agtgaggccc tctttttccaa aacaaggacc aaaaatcagt tgacagtgtt    105780
ggtcaagatg gtagaaacct aaaatgatag aaatctcaac tctgaaataa aaacttttat    105840
tgcatattta tttaccacta ttttgacata gggctaaggt ccttttttcttt gagctagttt    105900
ctggtttttgt tttcttaagg tggcataaga attcaaagac attttgagga aaactgagtg    105960
tagaaatctc tcttttttaa tgacttctct tttcttcag cttgtactgt tgtgtagccc    106020
tcgcttattt tgtcaattct ttttagctgt ttgtctttga atctttatga agccatagct    106080
tttctcataa gaagcagcac tttctttgtt cattcatatt ttaattaact cctgtagtat    106140
ttaaatactt aatgcctaat taaatcacat aattgcaatg caaaagtaca tgtatcataa    106200
agaggtctga aaatgagcaa ctggcaagca ggtggctgca ggcagagctg gctgggtggg    106260
tgggtgtcct ggagaagagc tcatcagctg catgttcagt gagctctgga tatctctgtg    106320
taaaaatgat cactaataaa cttgtgctca actgtgcaca cttccggaaa ggagatgctg    106380
ttcagtagat tgcctctgca gagaacacag aattgaaggg aatttccaca aaggcggtga    106440
gccgcctgca gaatagttta gtcaaggctg tgtttgaata ttgccaaaga ttaatataca    106500
tttattttt tcatgctgtg ccttttctct gattgtgaaa tattataaat tctatccaaa    106560
taacaatgat ggcaagtcct cctgagcaaa gtgtgcagct tgcatgtgtc ctagaggaac    106620
tcgtgtttcg ttctgattcc cctgcatttc tcatgtcata gagtggggat tgcatccgtg    106680
tcccctgtc ctcgtgggga tcacatctgt ttggatccta gagtcttcaa gctgagctgg    106740
gacaagtgta acagatggac catgggggt ggaaaggcgc tctaggcag cagactctct    106800
aattgtgcac actcttatag gtgttggaga tgttcattct cgtcctgcag cagtgccaca    106860
aggagaatga agacaagtgg aagcgactgt ctcgacagat agctgacatc atcctcccaa    106920
tgttagccaa acagcaggtt tgtccccgca gccttgcctc gttgttgcat agtgatggta    106980
gcttaaggtc cttgtgaaag gtgggtggct ggaatcagct cttccttcaa tcctaatctg    107040
tgctttgata gcagttctcc atgctagtca tgggcaact gacttcattt cttctcataa    107100
tgccatctca ggttggtatt gcccacctcc tttacggggg gaactcatga ctcagagagg    107160
ttatggaggc gatcaggcag cacacagctt tagagtgctg gggtgagggc gggccaagtc    107220
tgactctaaa gcccgaaccc ttacctccta tactgcctcc tgcattctgg tcaacgcagt    107280
gttttatttg gtggttacat ttttgttttt gttaccttac tacttgtaat ttagcagttt    107340
tcctttcctt tccttttccct tccttttcctt tttccttctt tctttccttt ctgacaggggt    107400
ctcgctctgt cactcaggct agagtgcagt gtgtaatct cactgcaact tccgcctccc    107460
aggttcaagc aattctccca cctcagtctc ccgagtagca aggaccacag gtgtgcacca    107520
ctacacctgg ctagtttttt gtattttag tagaggcgag gtcttgctgt gttgcccagg    107580
ctggttttag actcctgggt gcaagtgatc caccaacctt ggcctcccaa agtgctggca    107640
ttacaggtgt gagccacctc acctggccta ttcatcacta atcagaattt ctatgatcaa    107700
atgacatgaa ttgttgttctt cacacaatgca gtggaaggaa atggcctggc agtaccaatt    107760
ttggaagcaa caggccccca gtcaggcaca ggacactgtg ccccccagtgt agcagcatct    107820
ctatctcaca gagaaggtgg tgcgtcctcc tcaaggcagc tccgcagaa aatctcatga    107880
gcggcctggc acggcttgag gttgccttttt aaatggactc agcaaataca tgtttgttca    107940
tcttgattat acacaataaa caactactct gtatagtaca attgtccgt ggtttttttgc    108000
atttgattta aaccagagac atgtgatatt gatggttact gccttcatga ctgcacccccc    108060
atcctgatttt cataatagaa tgttatcctg agaccagtta gacaatggaa cagggatctt    108120
ggcttctggt gagactgaca gcagtttagg cgtggtcagg gtctccctgc ccacagatgg    108180
tgttagaatg gtgctctgga agctttattc cattatcttc tgtgcataat ctgagtagag    108240
tggagattga aggcctgaat agaacctaaa tatctgactt aatttctgcc ggccaggtag    108300
ttgtgcgata aacatttat gaaatgcgta gcacagcccc ggccaggtag ctcagcacag    108360
gagcctgttg cattcagaag tagtgctaga tactatcctg ttactggcag tacatacatc    108420
agtgatcaga gcagattcaa gaaagaccc ctgccttctt ggagtgaagg ttttgttggg    108480
atggggtgag gggacagaca atagaaaaac cagtgagtga agtctctacc atggcagctg    108540
atcaggacg ctgtacagaa gaatcccgga gggaagagga ttagttggtt tcggcgggtgg    108600
agtggcattg ttcagttggt gatgagaaac gttgtggtga tctggtgaca tttgagtgaa    108660
tttgcagaaa ggaaagatac aagcctagga gatacctggg ggaggagcat tccaagaaga    108720
gcaaacagct gcaaaggccc tggggggaac gctgttag ggtaaaagca atggggtgg    108780
aggagtgggg cagctatgcg gagggaaggg agcgaggcct ggtgggggtga ggccagcatg    108840
gaggagcctg agaggnnnnn nnnnnnnnnn nnnnctcccc aaagtgctgg gattacaggt    108900
```

```
gtgagccact gcaccccggc ctgttttttt tagagacgga gtcttgctct gtcgcccagg  108960
ctggagtata gtggtgcgat ctcggctcac tgcagcctcc gcctcccgga ttcaagcgat  109020
tctcctgcct cagcctcctg agtagctggg actacaggcg tgtgccactg tgcctggcta  109080
attttttgta gagacggagt ttcaccgtgt tagccaggat ggtctcaatc tcctgacctt  109140
gtgatccgcc cgtctcagcc tcccaaagtt tacaggtgga ttacaggtgg ctcccacacc  109200
gagccaagag tttgcatttt taacaaattc ccaggtgata ctaatgctgc ttttctggga  109260
ccacactttg agactcagtg atagaaagat ttattggtag gatagtaaaa taggagtaat  109320
ttttttttc cacaaaattg gcaattgggg gaaatttaat cttccttttt tctttagcta  109380
tgacttattt attctgttta ttttaggcat ctgtgagcac tgttcaactg tggatatcag  109440
gaattctggc cattttgagg gttctgattt cccagtcaac tgaagatatt gttctttctc  109500
gtattcagga gctctctttc tctccatatt taatctcctg tccagtaatt aataggctaa  109560
gagatgggga cagtaattca gcactagaag aacacagtga agggaaacaa ataaagaatt  109620
tgccagaaga aacattttca aggtatgctt tctatctgag cctgtaacta acccatgcct  109680
tttgggaagt cacttggtat ttcatgatca gttaagtctg gaataaccac tggtctcgct  109740
tcagttctga gctgggtaaa gaagtctgta tcagtgtaat tttctaatcc atcctggctt  109800
atctgtggct cctgtttcat acctctcttg aggttctgtc atgttctgtc tcttgtcctc  109860
agcagagatg ctacagcagt ggcttgctca ggtaggacag ggcagtgggg tggctgtcct  109920
ggggcaggc agtaggcgtg cattgccttc agggaagtta aaacccaaga gaagccacag  109980
aaagtgaatc ttatattctc accatgtgcc ggcagtttta cacgctgtca gtaataaaat  110040
acttctccct gcaaggcaga ctgcctccag taaatacctg tagtatcaaa tcctgtcttc  110100
cctcataaat tgttgggaag ctccctcagg acagtggtca ggcactcgta aatgcttgct  110160
gcctagatgg gtccctctcc acctctgctg gattctgagc attcactgag ttagagctgc  110220
tgctgcaaat gtgctacttc tgcctgagtg gctgtgactt catgcagccg tcatttggtt  110280
tgtcgtcagt gaagatgccc tgtgttgtcg atggagataa gcccagtaag cctgctgggc  110340
accttttgt ttgcgggttc agcaggcagc ccgtggcttt ccctctgttg cattgaagca  110400
gctggctaaa actgcatggta cattaaaattc ctatgacaga tgatcagctt gtatttgtgt  110460
aatggtgtac agtttacaaa gcttaaaaaa atactacctg ccatttcatc ctcagcgagg  110520
aaggtgatac acagagagga aaagtgactg tatccaaggc gatggtgtta cgcgtttcac  110580
tttaacggtt taatgtactt tacttctatt tttactttat atttaccaca tatattttca  110640
tatatacttg gcataagtgc tttatagtag tcacctaatt cactgtcacc ctttttgttt  110700
cttggaaggt ttctattaca actggtgggt attcttttag aagacattgt tacaaaacag  110760
ctgaaggtgg aaatgagtga gcagcaacat acttttctatt gccaagaact aggcactctg  110820
ctaatgtgtc tgatccacat cttcaagtct ggtaggtaaa tcacattagt cttcctcgag  110880
tatctcaatt ccccattctg cactgtacgc tcttagagtg taggagctat gctgcccggt  110940
agaaactctg tcttgcccag agtgccagtt gaaaatgttt gttgctataa gagtcagcct  111000
gatccatatg acccagcagt tctactcttg ggtatgtacc caaagaatg gaacgcaggg  111060
tggtgaaaag atgtttgcat gccagcgttc atagcagcgt tattcacagc agctaaaatg  111120
tggaagcaac tgaagtgtcc attgatggac gaatggataa gcaaaactg gtgtatactt  111180
agagtggaat attattgaac cttaatattc aataacctta aaggacattc tgacacgtgc  111240
tacaacatgg gtgaccccta aggacattat gctaaatgaa ataagccagt cacaaaagga  111300
caaatactat gtgattcctc ttatatgagg gacctggagt acttaattca tagatacgga  111360
cagtagagtg gtggttgcca ggggctgcgg gggagggag ttgttttttac aagatgaaaa  111420
gagttattct agaaacgaat ggtgggatg gttgtataac gtttaatgc tatttaatgc  111480
tactgaactc tacagttaaa aatagttaag atgagccagg tgtaatggct catgcctgta  111540
atccaagcac tttgagaggc caaggcagga ggactgcttg agccaaggag tttgagacca  111600
gcctcagcaa catggcaaga ccccatctgt acaaacagac tagccaggga tagtggtgtg  111660
cctgtggtcc caactactca ggacactgag gctggtgac gccttgagct caggaggtca  111720
aggctctagt gaagtatgtt catgcctctg cactccagcc tcgactacag agtaagaccc  111780
tgcctcaaaa aaacaaagca agacaagacc caaaaatggt taagacgggc caatcacact  111840
ggcttactcc tgtaatccca cacttcgggg gggtcaaggt ggaaggatca cttgaagcca  111900
ggagcttgaa accagcctga gcaacatagt gagacccca tctctacaaa gaaaataaaa  111960
aactagctag gtatggtagg cacatgcctg tagtcccagc tacttgggag gccgaggcgg  112020
gatgatcgct tgagcttgag accagcctgg aaaacatagg aagagactcc atctccacaa  112080
aaataaaaaa aataaaaaaa ttatccaggg gtagtgacgt gagcctgagc ccaggaggtc  112140
aagctgtagt gagccacgat cgtgccactg cactccaacc tgggcgagag atcgagacca  112200
tgtctctaaa gaaagaaaat tacaaggaca gtgaacccaa gaaagtcagt tgtgcagcaa  112260
gcatagaaag caaccagtcc aaattaggac agtgtgtttt ccaagaagaa cgatcatttg  112320
tcatgagaat gctttgcttt aaataaatga gtaaataggt agaagactag ttctagggga  112380
taggcacgtc tttcttctct caacaagaaa aagaaaggc aattctaatc tctaggaaaa  112440
gcaaatagca ttaagtcatg gtccaaatat gaggcaaacc aaaatatggc ttgattttc   112500
agcagttgat ctgttggaag cccttgatat taaaaaggtt ctcctttaag cagtttaggg  112560
gtcatgatca aagacccata gaaagagatg ccatcctttt aggatccttg gctctcttgg  112620
gaactgtatt cacgtagtca taatgtaagt attgcttgag ctttcatttt tggaatcaat  112680
atgtgactga aacactgaag acttactgac ttaattatga tttcagaaca gaataaaaat  112740
gtcttcagtt ctgatgaata taaaaggaaa actaaccaag ttaatttggc aagtagatgc  112800
tagagatggg gtgggaatgg aaggggcact aaaatcctta cctagcattg ttggagttac  112860
atgattacat catctgaagt tgacagacca aaatatagag gcttcaaagg tatccagata  112920
gagctaaaca tgtaactcag attgttagga ggtagtataa atgagccaaa tctcctcttt  112980
attaccgtag agttaatggg taatgtctaa agttgtctga agtctgtaaa tcatgcaaaa  113040
ttatgatgtg gtgattgtat tcaacagtct ttcagttgca gggataaaac cccaatttaa  113100
actagagtaa gagaaagaat ttgttggttt gagctcctgg aaagtgcagg caagggtagt  113160
tggtaggact gcatcagtg ttataattct atggtctgca ttgtatattt atgcatatca    113220
gctctgctttt cttctcttaa tttgtatact tttaaaattt tatttaaag atagggtctc  113280
actttgtcg ctacgctgaa gtgcagtggt gtgaagtgca gtgcgaggct cgctctgcc    113340
tcgaactcct gggctctaga gttcttcctg cctcagcctt ctaaggagct gagacaatag  113400
gcattcacca ccatgctgg ataggtttta aaattctttt gtagaaatgg aggccttgtt   113460
atgttgccca ggctggtctt taactcctag cttcaggcga tcctcctgcc tctgcttccc  113520
aaaatgctga ggttataggt gtgagccacc gcgcccagtc tcatctctgc ttcctgtctt  113580
agcccctcaa gtaggcatgt gattggcctt gcataagtca tatgggtgac cataaaccgc  113640
```

```
tgaatgctct ggtccacctg ggccaaatgg gagactggac agcattccat tgacgaggag    113700
gtggggcttg tctccgggag taagggagag gagcgcatgc agtaactgat ggtctgctgc    113760
acgggatagc ggcgcatcag ttagaatttt gaaggtaact accagaactg aaaacagaaa    113820
agataacaag tagttgcctt aaaaaggat ggggcagggt gcttttgtga tcagaaactc     113880
cttctctta ttggatttt gtacacattt tgccgacata cccttagagt aaagataatt      113940
agcattttca gccttggtcc atttgaggag tggcccgcct ccctgctagc aggctctggg    114000
tctgctaggt tcagttgagc atcctggctc ttgcctgcat ggaacttaca gtcagtgcgt    114060
cagtatcaca agtcttaata tttcctatga aggaaaacaa tagtgcagtg acagacaaaa    114120
tgggtgggcg ggcagaggca ggatttccga gggggagaag tagctagctt tttgcagaga    114180
aatgttccgg cacccgagag agcagctgag agtgcaggca ggcaggaggc gagtggggcc    114240
tggccgcaca gcgtcacaga gtcccagaga aaggggcctc ttcatggcca ctgcattcag    114300
ctgctgtcac cctccacaca agccatggcc aaaatttaat tttgataatg gactctagtt    114360
tttgagcctt acttgctatt attgaaagaa ttttcttgtt tcttttaaa gatcttcaga    114420
ttatgcttca ctgaccactg taaaagttt aagttgaga aaatatgcct tgttaatgaa     114480
tgataggtca attttagtat attggtcatt ttaatatttt gccaccagtt ggtttgaatc    114540
tgatgccagg aggagacagc ctcatttctt tttttttttt tgagacggag tctcgctctg    114600
ccgcccaggc tggagtgcag gggccggatc tcagctcact gcaagctccg cctcccgggt    114660
tcacgccgtt ctcctgcctc agccgcccga gtagatggga ctgcaggtgc ccaccatctc    114720
gcccggctag ttttttgtat ttttttcagta gagacggggt ttcaccgtgt tcgccaggat    114780
ggtctcgatc tcctgacctc gtgatgcgcc cgtctcggcc tcccaaagtg ctgggattac    114840
agacttgagc taccgcgccc ggccgagaca gcctcatttc taaggactag tcttgccttt    114900
gtgggataag ggtggtgtgt tctgtgtctt tctacatgtc cgagcgatct ctgcagctca    114960
aaggtgttca ctgtcttatt gtgctgattt cctcttcttc catctcaaaa ttgaggcaaa    115020
atactttcac tattgaagtg ttgtccagta gaacttccag cagagacggg atgtctgcac    115080
tgtctaattt agttgccttt agccacgtgt ggtgttccat acctgaaatg tggctggtct    115140
gattgggtag cttaattat aattttattt aagtttgaac agctctgtgt                115200
ggatagtggc tcctgtatga aactgcaggt ctgttgagaa gcatctttac tggagagagt    115260
ggagggcttg gaggggggcac atgggtttcc tgctgctatc tttgaccta tttaattggc    115320
ccaacatttg caagtaagtt gtctgtgcgt gtatatataa atgtctgttt ctgtcttctt    115380
gtttcgtttg actgcattta tttgaaagac actaggtggc agaattactg tatttggttg    115440
gtttaaagat aagagttgaa gtaatccgtc ttgtgttttt atatcggtaa ggtgtgttta    115500
gcatgtaaaa ttggtaattc gtattcacgt actgcttaaa caaaggctaa gaattccacc    115560
catacactga aaatggagac ctttgaattt gtccatttca ggcattactt cttaaacaat    115620
acctggttca ggaactagtc agaatggcac ccttgactt tagtttcctg ctttttccttt    115680
tgttggggga ggagggtatt tagctcaaag gtgtgtgcct atttcagatt ccatctagga    115740
gaagcagaat agccaagaca gatacctgtc ctcctgttta caacatttgg ggtaaccagc    115800
atccctctcc tttggtccaa gatagacggg tttagaaaca gatgatgta ccagaggccc     115860
cggggggtgga agcatcagct ttgtttgttg tccatgtggc tggattagag ctgtctggct    115920
ttgtagcctc aacacggccg tccagcttg ctcagtatga tttttcaagga cacatcttg      115980
gcccttccct gcctgccatc cagaccatac ccagtcaggg tggcaggaac tgctgcccct    116040
tcctccctga gtcctggtcg tgggtggtgg agaggtacca tgaccctcac ggaggcctgc    116100
tcaccctttcc tctgcggcag aggcgatggc tgcacgacag ctctttccct gtccttttcca   116160
aagcgtccat ggttccactt gatggggcaa agcaggaata ctggaagaga aagtggtcct    116220
ttctatagta ataaagttga cattgattca agttcaccct tggggaaagg acagggccac    116280
taacaattat aatgctggaa gcagtggaat tttctcatgg gtatatagta ggtttaattt    116340
taattatccc agttaattct tagaacagct ctgtgaagta tttccccctt tctgcttgag    116400
ttctaaaaga tcctatgcca aaaccaagaa tgaaaaccca agcattcttt cttgctcatc    116460
gatcttttctc tcatcgggcc acttcttggg ttgttagtgg tgaatgtagc cgctggcaat    116520
tgcagaatac ccaccatggg ccccagtcac tgtgtggcgt ggattagagg tggttctctc    116580
catgtcatag ccgaacaagc ccagcccaga gaggtttctg ccctaggagc tcttgatggt    116640
ggaattggga tgcgatccca catcctgcct gtgttttgaa agcagcattc ttcattttcca    116700
gttcctgctt ccgttgttcc ttttagtatt tctttgttta actcacgaaa tcaggacttg    116760
gggagctgct gcgtgcagct gtagctgttt ctctgggtgc agcctgcatc caccttcctg    116820
cccccctcct tactgccatc gtggtctctg ggcacttggt cccttttctct tccccccgagt   116880
cccttttggct ccctgtgcc accttgtga tccacaggct cctgccttctt tctgctgag     116940
actgctgctc atcactaccc gggaccttag gaagggaggt tcctccgaga agcatcttct    117000
aatctcagcc acgttctcaa tgccgctgtt ggctttgtta aataatggta gctactgtaa    117060
caaataaacc aacatttcca tggcttcaca ccagagaagg ttgtttcttg gtttatgac    117120
aatgtgttga gggtgtttct ggttcacgga tggttttcct ccatgtggga attcgggag     117180
ccaggctcct ttccttcttt tggttctctt ctctgggcct ccacatcctc tgtgtctagt    117240
tggggacaag gagagggaag gtagagaaga aggctctgtg gccttggaca agtgacatgc    117300
atgcctttgc tggtgttctc tgctggtggt gggtcacagc cccaccccgt acgagggggac   117360
tgggagacgt cgtcctgctg cctcccagca gcaagcagca ctgtggtctc tgatgtgttt    117420
tctatgagga taaaaacagg cgattccagg atgagtaaga tcagggaaac ccttggaagg    117480
aggtgaccag gcaggtgtca ccatgggatt agtggtggct tcagaatgag ccgccaagag    117540
tgcagtgcct tctaaagctt ttgctattct gatatgccca caccatgccc agcaggtgtc    117600
tgccttgctc tccgcagaga gagtgatgaa tccttctcgt gaacctctgt cccgttcttc    117660
ctccctccac ctggaaggga ccctgggttc cttgaaacat cccggtggaa caggggacct    117720
tctgtcctgt ccctaagctc agcctcatcc tcctgccagc ttcccaaccc ctcttatgtc    117780
tgcttcctca cgccacatcc ttctggattc tctggaattca aatttttgcct tgatgcttta  117840
tttaaaaata tccattcag gccaggtatg gtggctcaca cctgtaatcc tgtgcacttt     117900
gggaagccaa ggcgggcaga ttgcttgaac ccaggagtct gagattagcc tgagcaacat    117960
ggtgaaatcc tgtttataga gaatacaaac agggcatggt ggcgcacacc tatactccca    118020
gctagacagg atcgactgag cctggaggcc cctggaggcc gaagctgcag tgggctgtga    118080
tcgtgccact gtattccgt ctgggcaaca gagtgagacc ctgtctttaa aaaaaaaaaa    118140
aaatccattg catacttcac cacagtgaaa cgtgtgtctt atcttccttt tccggcctgt    118200
agctgctctt ttgcacttat agccgcacta agtcaacctt aaattaaaag caaaccagca    118260
cttcctgtgc tcttctgctt ccttcatgag ggtccctccc tctgtgtacg ctccattctc    118320
attgcccgg tgggtttgttt ccctcttggt tctcaagctg tggcagcctg cctcttatca    118380
```

```
tctttactga aaagtcctttt gcagaggctg cctgtgttct ttctttctcg gtccctctca 118440
tcctgggccc cccagcttga tgctgtgggg ctgccctctc ctcactcagt agcttgcagg 118500
gtcttctctg tctagccact taattggttg tgttccccga gttgctgtcc gtggtctctc 118560
gtcactgttt tctctgtgtc tctgcctctc tcctcggcct tggtaggtct ctccccttttg 118620
tgaccctgac tgttgctctc gtggacaact ttctcttgct ggtccgcgta gtcctggcat 118680
ccagcttctc aacatgggac ttgtcctgcc agtacctcag acttacgctg aaaattgaac 118740
tagcaccact gtcactctcc aggacctctt cttgttaatt aggtcattag ggatgttcga 118800
aatcccagca tcattgtcca ttcctcctcc tgccagccca gggaccctga ccttacctcc 118860
tcctctccat ctaccgggag gtggctctca gagtccgtct catcttccac ccgaacttcc 118920
ctacagactc cccgctgccg cccaggggc tgagcacttc ctccgtgcct cgtgcagcgc 118980
tgagcccttt acctgggttc tcctgtttgc tccttattgc aaccctgtgg acagatactg 119040
ctcttaattc catcttaaac ctgaggaagc tgaggcccca ggtaaggtgc atccaaggtc 119100
actcaggtag taaactgtag agccacgatc cgaaccaggc agtctgattc ggagcctgtg 119160
ttgacactca gccacctaga acacagctca gattgtgggt ttctattacg tgttcaaaac 119220
cgccacatcc cgggtctgtc cctgcacgtg ccctgtggcc tggctgcatc ttcttgaagg 119280
cagcgcatgc gtcttcactc aaggggccca tgcaggaaag agggcccac agaaggacga 119340
ggccagtgca gaatgggctg gaggggacga tgctgactgt gaagcaagtg tagagaaatc 119400
ccaggaaacc tggaggaacc agagacaggg cattagaact catcgttgtg acctggtctg 119460
tattctctga gtgtgctgct gcttttagct cgcttcctta gtctcaggtt gtagtttaag 119520
gcattgtgga gccctaaaaa gcctctactc tgttttttgcc tgtttcggga cccttttcact 119580
tcggggatgt gttgaatttt ttgttttttgt ttttttaattt tttgagatag agtcttgctc 119640
cattgcctag gctggagtgc aatggcacaa tcttggccca ctgcagcccc tgcctcctgg 119700
gttcaagcga ttcttgtgcc tctgcctccc aagtacctgg gattacaggc gcccgccacc 119760
acgcctgacc aatttttata ttttttagtgg agacagagtt ttgccatgtt ggccaagctg 119820
gtctcgaact cctgacctca gtgatccac ccacctcggc ctcccaaagt gctgggatta 119880
taggcatgag ccaccatgcc cggcctgaaa tttaatcaga aataaaattt tgacccccaac 119940
aatgatgcta ggaggcccag atctggggga gagggcaacc ttggccagat gggcctgtct 120000
ctgtttccca agtcttgctg cctctccctg ctgtgctttg cagcctgtgc atgtctctgt 120060
gcctctgatc ttgttcatcc agaggagagg atagaatcaa gtcatgattc ctggagcccct 120120
gagaagaatg ctgtggagaa acttgcaggt agactctaac tgagtgtgtg gctgaggtgc 120180
cagcattgtg tgtggggagg ctgaccgctt ggcctgccca ggcccaggat gctccatggc 120240
cgggcacaga ggcaacttgg ctgtcaggtg tcaggagcct gcagagagca cacagcctgg 120300
accgcagggc gctgcccatg ttcttccagc acctgtcctg cttgctcacc tggcctctta 120360
cagcatttct gtccctcagt tcttagcaag cccaggagct gttcaggttg gcaggtgccg 120420
agtgctgttc ctgcctctgt agctgtggct cagtcctgtg gggggccccg ctgtggcctg 120480
agtgcagtga ttcgaggtgc cgagtgttcc ctgactcgtt ctgcaggagc tgtgttcaga 120540
cttttcacagc tcttggcttg gagcttctgg agggcttggc attgccaacc agtgcagggg 120600
tggacagtgg gagaggagga atgctagctt tcttgaccag tccattaaat aaatgggata 120660
ttggccgggc acggtggctc acgcctgtaat cccagcactt tgggaggctg aggcgggtgg 120720
atcacgaagt caggagttcg agaccagcct ggccaacatg gggaaacccc ctctattcta 120780
aaaatacaaa aattagctgg gcgtggtggc agacaccctgt aatcctagct actcgggaga 120840
ctgaggcagg agaataggtt gaaaccagaa ggcggaggtt gcagtgagcc aagatcatgc 120900
cactgtactc ccaccctggg aacaagagtg aaactcctca tcacaaaaaa aaaagcagaa 120960
tgtctgtttc tgcttagaaa aatcagaatt ttctaaatgc caggtgctttt gaatatgtaa 121020
gtatgggaaa caactcagcc tgtttcattt ttatgtaaaa tctccacgta gccatgtggc 121080
actgaccga gatgaaagca aagacatttc tccttctgaa ctttgtttct aggaatgttc 121140
cggagaatca cagcagctgc cactagactg ttccgcagta atggctgtgg cggcagtttc 121200
tacaccctgg acagcttgaa tttgcgggct cgttccatga tcaccaccca cccggccctg 121260
gtgctgctct ggtgtcagat cctgctgctt gtcaaccaca ccgactaccg ctggtgggca 121320
gaagtgcagc agaccccgaa gtaggttcat aatgcccaca gcccagggcg ctggcccagc 121380
actctgtcct gagactccca gtaacctgag atttgggccac cgttacagca ttttcattttt 121440
ccattttttg tgagggcttg taaaattttct gctgcatatt aatattcctt tcatggacag 121500
catattgtag agacaaacat gcggtccagc caaaggcatt cagaatagca attgctttct 121560
aaatgtgatt ttcttttggca agttctttga caccattcca tcttgtggat tatgcttgtc 121620
atgctgtgtg gctcctacta agttctagtc ctttcagtttg ttccatagcc agacatgttg 121680
caatgtctta acttcattat aaaattaaatg tggttctggt tattcttaga taatggagta 121740
acgatttagc aaatttcaaa acctcttgga aatattattt gaccattcaa aaagacttac 121800
taagtctctc attatgggtg gccctctttt tgtaaaaggt tttcaggctt aagctccatt 121860
tctaggtgct ccaacactct gttatttgta tacacgtgga aataaaagct gtgacatccc 121920
cgccctagct gaatcctcag cacagtgttt ctggaaggct caagatccca cactgggaa 121980
aagaagttcc agagagaaaa gagggcaggt gctgccgtgc ctctctgctc agtatgggata 122040
ctgggccatg tgcggccagg gcttcagta gggccagttc atggcactca gctggaaagt 122100
ccactgttgg cgggcattcg taaccatcca ctctgtgccg tatgtagtgg ggtgtggcat 122160
ccaagtatt gaaatcagcc gcgtgcagag aaatcagcc cggatgcagc agatcactct 122220
ttttctgaca ggcctgctca ctctgatgtt atatcagaaa gctctgaatc tgggaattgt 122280
gttccctgaa ttggaataac agaaatgctt agatgatcag tgtttaaaag aaataaacca 122340
aagtaaatt tagtttggaa ttcagcaagc gtcttcattc agccctctga gggcaaacta 122400
cagcttttca taaatgtagg taaattctct gtttcttgac cccttctgac ccagtttctc 122460
tttataacct tctgtattgt tccattatcc tgaaataaca ttaatagatt aggctgggtg 122520
tggtggctca tgcctataat cccagcacct tgggaggcca aggcgggagg atcacctgag 122580
gccaggactt cgagaccagc ccagcctggc aacatggtg aaaccctgtc tctactgaaa 122640
ataacaaaaa ttagccaagc gtggtgacag gtgcctgtag tcccagctac tcagaaggct 122700
gaggcaggag aattgcttga acccaggagg caaaggttgc agcgagctga gatcacgcca 122760
ctgcactcca gcctgggtga cagagtgaga ctccatctca aaaaaaaaaa aaaaattaa 122820
tggatcaatg gattttttaac ctaatagtta aattaaaaaa atatcattct ttaatggtaa 122880
tgtaaagta aaattaagag aagataatat gtaacaagca tttagtatg tgagtgtcca 122940
aggtctccct gtggtggaag gaaaaaataa atccccataa gtgtccacga tgctcataga 123000
gagcagagct gttccggttt aaaccgctgc tcttaggact gtgttttttcc agctatgggt 123060
ggtgggggat gagtaccttt ttatttccat gagatgagaa aaatgaatta ctagaagtat 123120
```

```
gaagcacaaa acacagctgc tcttttttta tctggactca gcagctataa aattgctcta    123180
tccagttgca gaagttcctg ctgcttaccc ttgatgcccc ctcggttagt gtgcatctcc    123240
tttcaggctg gctcccagat gggagctggc tccaggcgac actgggtgct ctgctccagg    123300
aggtccttgt gtgggcccta ccccggccta gcccctctct tatggactct gtcaccatgg    123360
gtttgattca ctcaatctgt cttacctttt ggtgagctgt tagagtcctg cctatacttc    123420
agcacttgtg ggtgtgttgt ggtacacatg acatgttggt cacttcccag ctcatcttgt    123480
tctgagtcac cctggatttg gtacgttcat tcgccactag tagctggcgg tatatggcct    123540
gcgatttgga ggacttgtgc tgctacaaat tggggctgaa tttgagttga cactggccct    123600
tctttatgtc tactgctaat atttgaattg caaatgctgc ctcttctctt tcagaggctc    123660
attaccctat agctgtatta ttgcaaagta cataattaca gcttgagtgt aagtcacgct    123720
gggctggcag gacagccaac tgagaaaggg caagttcct gttagttttc acattgacac    123780
ataatttaca atacagtaga atgtactttt gtatcaactg tagtcagtaa cagccccctc    123840
ccccaaccac ataagatata gagcagtgct gtcgcttcac atagttccct cttcctctgc    123900
catgtcccgc cctcccagg tctaaccacc aatccgtgct ctattcagcc cattgcagag    123960
ggtcatagaa atagaatcta caggctgggg gtggtggctc atgcctgtaa tcccagtgct    124020
ttgagaggct gaagtggaag gatcacttga ggctaggagt tcgagactag cctgggctac    124080
ctagcaagac cccatctcca gaaaaaaaa atttgaaaat tacaagcatg tccctgtagt    124140
tccagctgct tgggaagctg aggcgggagg atctcttgtt gaggttacag tgagctatga    124200
tcgtgccact gtgctccagc ctgggtgaca cagcaagacc ttgtctttgg gaaaaaaatt    124260
aagaaagaga tggaaccaca cagtgtgcag ccttttgagt ctggcccctt gcagtgagcg    124320
gtgtctaccg tcatgcgttg cacacgtgtt ggtggctggc ttcttgtgac tgctgagcat    124380
tatatgctg ggctgtagat tgctttcact tcaccagttg ggaaacagag aaaaggcagt    124440
ttttaaaaag tttaaatctg tagaattttg gttttacca gttctcttct aaatcctgag    124500
ggattacagg aaaagttgtt gtatttcaga atattcttag cttgatgtga cctctctccc    124560
tgttaaggcc ctttgctgca atgggaagga cgtcgtcctc ggtcagaccc tgaaggtcag    124620
aggggcactt tgggagtgtg tcaacatttt aactgtatgg actagagcca aggtgtcaa    124680
gatttataat tcccacctat tcaaaaagaa aaaataataa taataaagtg agaagaagtc    124740
aatgtaaagt gaaataaacct gtgttggtgg ggaagaagtg ttttttaaaca gaatttccat    124800
aatgtatacc ctgaacgtgt ttagagtggt gatgtttcat tgggaaacga acagtaaaac    124860
atgaaagcag ggagattttc tttctgcag ttggcaactt tcatggcaga tgggaattt    124920
gaaaagcaat tgctcaatta tcaaacatag ccagtgtgaa ttctgaaata aaggtgctga    124980
ttgaatgtgc agctttatgg tggattttgt cattcaggca agcattttaa ttttctgcct    125040
gttaaattct gttttcttta gtttttcata tgtggttat tgtagcttgg aatagataa    125100
ctgagagtat atattacaca tacaacattc tgatatggca atatttaaac caacttgtct    125160
gttttagaac tagaattaaa cataatcatc ttcagtattt tgcaaataag ctcactgcca    125220
tccagaaaca ttgtcaatgc atctgttgct ccttctagaa gacacagtct gtccagcaca    125280
aagttactta gtcccagat gtctggagaa gaggaggatt ctgacttggc agccaaactt    125340
ggaatgtgca atagagaaat agtacgaaga ggggctctca ttctcttctg tgattatgtc    125400
gtaagtttga aatgcctgta aacggggttg agggaggtgg ggaccgggag aacatccgta    125460
gtagatgaca cttgcctgga ccctctgaa cccagactgc ccagtgtcct gccagctcca    125520
tcaaaactaa atctggaatg aatgtttact tctgctctga catataattg gagaccgggc    125580
ctggccttcc agtcactgga ttctaagctg gactgtgaga gttgatgcag ctgactcatt    125640
tatcaaatgc ccagctattg gcttcacgcc tacacgatgc tgggcatatt tgttaattca    125700
agggaagcaa tggaataata ataactaatg atttgaaaaa caagataagt gcattgacta    125760
tagtggggtt ctgattttaa attttttaaa aagtaatac caggagcagt ggcttacgcc    125820
taaattctag caactcgaga ggctgaggtg gaaagatcac ttgagcccag gagtttgaga    125880
caagcctggg ctacggtgta agaccccat ctctaaaaaa ataaaaatg aaaaattatc    125940
caagtgtggt ggctcgtgcc tgcaatcaca gcttcttgag aagctgaggc cagaggatgg    126000
ctagagcgtg ggagttcgag accagcctgg caacacagag aaaccctgcc cctaccgaaa    126060
gaaagaaaaa ttagcctgat ggtggtgcgt gcctgtggtc ccagctacct gagagactga    126120
gaagggagga ttgcttgagc ccagaagttt gaggctgagc tgagccgtga ctgtgtcact    126180
gcactttagc ctgggtgaca aggcgagacc cctgctctaa aaaacaattt ttttaagtta    126240
atttgtagaa aaggtgttag atgttcattg ccgtatttta tgatggattc ctgtttaaat    126300
gccattctct taaaaaaaaa aaaataactt gtaggagttt ttaaccgtaa aattagcatc    126360
acatgtttac catggagaat ttacaaaaaa caaacagagg aaaataaaac ctctgtaatc    126420
atactactca gagataactt gctgttagat ttcggtgtag atctaatact ttttctgtat    126480
ttatattaaa aatacttaaa acatatacat ttctttgtta caaacatggt atcttataga    126540
tagtgctgtc acatagcaaa acagtgttaa atattctgaa tcagaaaagg aagccgactc    126600
tccaactgaa agaggtgtta tcctagagac tttttctggt gatggcaatt tgttaatatt    126660
cactttttgc tttacattct gtattgaaat agttttttctg ttttgttcta cttttaagga    126720
taatataatt gtatcatgct gtttttcaca gaaatgtaag aaaaaaagat attaattttg    126780
taagttaata gaggttgagc atcccaaatc caaaaatctg aaatcccaga tgctccaaat    126840
tctgaagctt tttgagtgct gacattatgt tcaaaggaaa tgttcattgg aagatttcag    126900
attttttgat ttagggagct caacaaataa gtataatgca catattccaa aacctgaaaa    126960
aaatcctaca ttcagaatac ttctgatccc aaacattca gataagggtt attcaacctt    127020
tactgtcaga tgatcccaaa tgaaaatat taatcgttaa ccaaatgtca aggaattgat    127080
cacattttac agtttctgcc taggattatg aatcaagatg aaaaggctct gcgtgtttaa    127140
aaatatatat attttttattt tcttataaat cttaaatgta tcaacactta agatgtattt    127200
gatatgtgaa atccattcat attttggatt aaacatttgt gtcaagaccg tggcagtgat    127260
agaggatttt ttttttcccac tgaactatca caaaattgga aaaagagtaa ttggagaacc    127320
ccactggctt ggccagctcg aagccccgga ggggcaggc agtgctgtgg atgggagcgt    127380
cgcagtacca cgctgcccct cctgccatg gatctctgag gcctgccttt gtcctttgac    127440
ccttggccat ttgttagtgt ctctgagagc tggactgctg taccctactt ccccaggggg    127500
gcctgacttc acacagccttc tgctgcagtg cgtggttgga ggcaggtgcc ttggtaaatc    127560
cagtttcctg cctcctcaat tatttgtgct catacactgt atatttttta gtgaggttta    127620
tatttgagat gtgttttctc cttcttaccc tttctggcct ttctatggat taatacctgg    127680
tctcttcttg tgtacttgaa agtgaatctc tcatcgtatt tttccttagt gtcagaacct    127740
ccatgactcc gagcacttaa cgtggctcat tgtaaatcac attcaagatc tgatcagcct    127800
ttcccacgag ccctccagtac aggacttcat cagtgctgtt catcggaact ccgctgccag    127860
```

```
cggcctcttc atccaggcaa ttcagtctcg ttgtgaaaac ctttcaactg tacgtcttca    127920
tcctgccaac aattgccagt tgcagttttc tctgccttaa aaatggagta ttgaattttt    127980
taactttaat ttctgactgg caaaatagtc atcttttgtt cttttccttc tcgctgttag    128040
ccaaccactc tgaagaaaac tcttcagtgc ttggagggga tccatctcag ccagtcggga    128100
gctgtgctca cgttgtatgt ggacaggctg ctgtgcaccc ctttccgtgt gctggctcgc    128160
atggtcgaca tccttgcttg tcgccggta gaaatgcttc tggctgcaaa tttacaggta    128220
ttgggaaaag aaaccctgat attgatttat attgaaaatt tagcaggcca agcaaaacag    128280
gtggctgcct ttttcctcca taggtgtggt cttgacacgg tcaccaatag aaacatggaa    128340
atatctgcaa acttgccatt cctcgtgtgt ctgatctgtt tcttgaactt ttttctagtc    128400
tgtccttact aggatgaact gtacacatca gtttatcctt tttaaatgag catgaggtta    128460
ttttgggttg tacagtgtca caaacacact aatgtgtttt tgtctattag agcagcatgg    128520
cccagttgcc aatggaagaa ctcaacagaa tccaggaata ccttcagagc agcgggctcg    128580
ctcagaggta atgctggaaa cacaggtcat ccttgtgtta ggagaaccca ggatataaaa    128640
gatatagatt tgtgcgggaa taaattcaca ggacaagaaa ttgatgtgcg ttataggtgg    128700
gtttgctgca gaagtgccat aatagaaagc ttcctacttt taaaacaacc agatctcact    128760
ttatatggag taaaggacaa ccagcaggat cacgtctatg acatgagtgg aggcagtttg    128820
cactccttt ggctgtttga gaggtagtat ttagaatgcc tgtattcact gtcctgtgat    128880
gagtgggaaa ataggttatc agctttatct tagcaaaatc aaagcatatc atctaattgc    128940
taaacaagag ttggcaaatc tgaaagacat tactgaatcc ttggcatgca ggacttacat    129000
ctgcatcccg ttgccatttt ttctcttcaa agcatttaat cacttagttg tgtttgcaaa    129060
gtcttttaga agccttatc agaaatcctt acatctccta tgtgagtgta tttccatgac    129120
tgcaaaataa gttaaacttt tacctttttt cttcccttgg tggggggcgga aattgtgtgt    129180
gtgaaaggga aagagagaca gcagagaagg agaatataat tatcatgctg tgtccttttga   129240
gctgaaattg caaaaaagaa aacacacaca cacatgcttt gatttcagtc ttaagagtac    129300
cttgttgatg gtgtttttaa atgggattgg gcacaattag gtggacagtt tggggcgatt    129360
ttcggtctg tagggccaag ctgttttgta atttgcttta taagtttgtc actctcatag    129420
catatggtgg cagataaact attattactt tttgaccccta gacttagtct tcagtccaga   129480
tgagggagat taaaagatta taaatatctt gtgccagatg aggtgatttt attttgaaat    129540
gaccataaat tcctatcagt tgtcttactg ggatatttga tagtggagtt tgtgcatttg    129600
agtcttagat gatctgttt acgtttatta agaaagcctt tattagcttt tataccatgt    129660
atggactgtt gcaatgtttg agtataaatg aaatttctgg acaatattaa tggagtacaa    129720
actgtgatac cttagaagta aactagggcc tgcgtttata tcatgacctg tttgagtgtt    129780
gatgagaaaa tagctgtgaa gaaaagttt taaacaagtt tcattttcct ttaagaagcc    129840
actaatagtg catccttagg gtgtatattt ctagaatcct agtgtgcaga gtttagacta    129900
agactaaaaa aaaaattgca ctgtaatttc ctttttgttt gtattttaga caccagaggc    129960
tctattccct gctggacagg tttcgtctct ccaccatgca agactcactt agtccctctc    130020
ccccagtctc ttcccacccg ctggacgggg atgggcacgt gtcactgaa acagtgagtc    130080
cggacaaagt aagtgtccag cgtgtctgca tgcgaggcac agggcagagt gcctctgtca    130140
cctgaggcag atacagagag tgcagaggag gtgcggtgga cccaaggagt gctggcgctc    130200
tgctcggctc aatgaagccg tggttagaga cctgggggga ccatcaatgt ccgagggagc    130260
aaagcagtgc tgatgtggga ccgtttcggt aggagtgcga ggtgagtcgt tagtgggtga    130320
ctcaaggaa agtcaattgt ggcctgcagg cccctgactg cacaggcctt caagcacatg    130380
tcagtgcatt tagcctcct ccatcgcctc ataccttctg gccacctgtg agttgcactg    130440
ccactgccag ccatactggt atgttgtcag cacctccact gctcatacct caccgttagg    130500
gaccacttgg ggccttggta gagccttggt actctacttt cctggagaga gttcagctta    130560
tgaatatgaa tttagatttc aaaaaccagc agcccaagta taagaaagcg aaggttcagt    130620
cctgccgcct taggctctat ttgctaagca tctgccctgc cctgccctg ttgctgggaa    130680
gagatgagca aagcagacag cccaggagag gatggcaaag gggccgctaa cccttagtag    130740
tttagctata tttggaagga ctattagaaa ttcaccaggt gaaggggag gccgtgagag    130800
tacccaggta ggtaacagaa gtccaaagag gaagacctgt ggtgtggtga gctgtatagc    130860
cacaacatgc cggccggagg ccctctcagt tagcctagta cagtgttccc aagcactggc    130920
ctaggcctgt agctccaggg atgtgaagtc cccttgaacg ccaccatca tgttcccctt    130980
attcatcttt tccttccag gactggtaca ttcatcttgt caaatcccag tgttggacca    131040
ggtcagattc tgcgctgctg gaaggtgcag agctggtgaa tcggattcct gctgaagata    131100
tgagtgcctt catgatgaac tcggtacggg gggagcagcg gaagcaagga atcctcagct    131160
tttcttgtga cttccaagtg ggatttgtct cctcatgtga cccacttgtt gacaacacat    131220
gttgaggact ccactctgga tggggacggg atgacggaga gactccactc tgaatggggc    131280
tgggaactgg ggaggactcc atttcagggg gccgggacat gggggatatg ctgatcgaga    131340
ttgtttcagc cacattagaa tccaaggagg caagtcgatt tcactcaacc tttcatgcat    131400
ttaaagaaaa tggaggtggt cttagattac agtcatttca ctggttgtt ctcatgcag    131460
tgaggaaggg tattgggatt ggtgtctgtc ttaattcagg atctttgaga agatggagag    131520
cactccctca gggattagga gagactcgag atggaaatga agattttact acttacaggt    131580
cctgcgggt acatggcatg cccagaggcc cctcacacgt ggaagttggg ggcatgtgag    131640
ggaatgaagt gtggtcctgg gcactagggt gggggaccts agcggnnnnn nnnnnnnnnn    131700
nnnnnnnnnn nnnnnnnnnn nnnnnnnnnn nnnnnnnnnn nnnnnnnnnn nnnnnnnnnn    131760
nnnnnnnnnn nnnnnnnnnn nnnnnnnnnn nnnnnnnnnn nnnnnnnnnn nnnnnnnnnn    131820
nnnnnnnnnn nnnnnnnnnn nnnnnnnnnn nnnnnnnnnn nnnnnnnnnn nnnnnnnnnn    131880
nnnnnnnnnn nnnnnnnnnn nnnnnnnnnn nnnnnnnnnn nnnnnnnnnn nnnnnnnnnn    131940
nnnnnnnnnn nnnnnnnnnn nnnnnnnnnn nnnnnnnnnn nnnnnnnnnn nnnnnnnnnn    132000
nnnnnnnnnn nnnnnnnnnn nnnnnnnnnn nnnnnnnnnn nnnnnnnnnn nnnnnnnnnn    132060
nnnnnnnnnn nnnnnnnnnn nnnnnnnnnn nnnnnnnnnn nnnnnnnnnn nnnnnnnnnn    132120
nnnnnnnnnn nnnnnnnnnn nnnnnnnnnn nnnnnnnnnn nnnnnnnnnn nnnnnnnnnn    132180
nnnnnnnnnn nnnnnnnnnn nnnnnnnnnn nnnnnnnnnn nnnnnnnnnn nnnnnnnnnn    132240
nnnnnnnnnn nnnnnnnnnn nnnnnnnnnn nnnngagaa acctcctggt gcttagccg    132300
tgcgttgata cacagcagat gggagggaag tgggcacccg ggaggacaaa tgcatgtaga    132360
ggctgggggt ggaggcaggt gttcatgaaa agagaccta cagggagggc aacacaacag    132420
tgtgttctga tgtactgaag agctagactg aaaagaacag gagaattcac ccaaaatcca    132480
tttactaaaa ttgtttatcc tttttttttt tgagacgaag tctcgctctt gtcccccagg    132540
ctggagtgcg atggtagatc ttggctcact gcaacctctg cctcctggat ttaaacaatt    132600
```

```
ctcctgcctc agcctcccga gtacaggcat gcgcccacca cgcccggcta attttttgtat    132660
ttttagtaga gacgcggttt caccgtgttg gccaggcttg tcttaaactc ctgacctcag    132720
gtgatctccc tgcctcagcc tcccaaagtg ctgggattac aggcctgagc cactgcgccc    132780
ggcctaaaat tgtttatctt aagattcatg cagtgaaaac taacttactg agtgataaat    132840
ttgcttagtg atctgtttat taggttttct aaatttgcta attgggcttt gaacagctgt    132900
aaaagttctg actgtaaaag aaagctgcaa cttttggcat tcatgatgct tttctgaata    132960
ttaaactaag atagatgttt tacctgaaga attggccccc aatcttataa atggctaaac    133020
aaaaaaggtt gctaaaacat aatccaaatt gtcataggaa ataccatttt tccaaccaaa    133080
attttgtcat tcatatgct acttttactt atttcagctg catttgacca tcttttttcaa    133140
acttcaggga tggctggtgt atcaccgaga tcttggatga cactttagct ttgattttct    133200
gtttttatga attaaaattg tcataccaaa attttttactt caagcaaatc caagagcata    133260
aaaaattaaa atatcactta aagtaccaag agagaacaga aatatatttt actaagcgta    133320
cgttgaatga agttgttcaa atatttgtaa caggcataga gtagaattt cttaaaaaca    133380
ttttgatgg tataccaatc tgtgttttct cagaaacatt tgccttattc ttttttctgt    133440
tgtgttttc ttacctgatt gaaagctcct aatctgttgt tattgtttgt ttaacccttta    133500
atgctctgat tcaggagtt caacctaagc ctgctagctc catgcttaag cctagggatg    133560
agtgaaattt ctggtggcca gaagagtccg cttttttgaag cagcctgtga ggtgactctg    133620
gcccgcgtga gcagcaccgt gcagcagctc cctgctgtcc accacgtctt ccagtccgac    133680
ctgcctgcag agccggcggc ctactggagc aagttgaatg atctattgg taattaaaat    133740
taaaatttat cttattttta gaaaggttcc agggccagta tagtactttg caccaagtaa    133800
atatacaata aaggcggtgg atctaataca gcgaaagcgt ttacagaggc agctaaagag    133860
cagcactggt ggcctcagcg cagaaatttct tcctgcgtgt ttgccactt gccgttcatt    133920
gacgtggtca cggacatagg gctctaagcc cttgaggaag ctgggccag acctcagggg    133980
agatgcagcc ccaaactaca tgcagtcatg tggatggatg cgtagatgtg ccattgagga    134040
gcaatgtctt gtgctttcat cagattctca aagaattgct tgactgcctt tcgaaggtgt    134100
tgcatctgtg ctcatgtttg cacccaccca cgagggcctt ctgtttcagg ggatgctgcg    134160
ctgtatcagt ccctgaccac tctgccccgg gccctggcac agtacctggt ggcggtctcc    134220
aaactgccca gtcacttgca ccttcctcct gagaaagaga aggacaccat gaaattcgtg    134280
gtggcaaccc ttgaggtaag aggcagctcc ggagctcatt gttgctgtgg gaggggacac    134340
ggggctgaca ctggagaggg taaagcagtt ttatttgaaa agcaaagagct ctgaccaatc    134400
cagtcactat tctgtctcag cctggcagta agtcttgtca ccgtcaagtt attgtagcca    134460
gccttcaccc ttgcctcgcc actcctcacg gtggcctgtg aggtcagcca ggtccccttc    134520
tcatctgcac ctccagtgtt atgtggatcg taattttaga gacttgaaaa ataaccatct    134580
gtaggtactt tgtgtcttaa gttggcctgg acatgtcagc caaggaatac ttggtttgtg    134640
ttagtgcttg taattagccc ccaaaacatg tacacattct ggatgcatta aactcaggcc    134700
tgtatccta aagggccatc tctgtgctgc ctgccctcag cagggacaca ctttgcagac    134760
ccacagaggc tccgcctcca cctcacacca aagaaaggga ggagtccaaa gggcatcagt    134820
gccgttactc acaaaatgat aaatacaccc ttattcgaa ccaggtggag tcagatggtt    134880
tgtgatccct gtccttttagg tttcagctta gtgggggaagt gggaaagcca gcgtgtgatc    134940
acagcacagg gtgattgctg ccgattatat tatgtgcctg ctgtgtgcag gacaacatac    135000
tttacacgca tcatcttatt tgactctcac aactcccgt gagataggct ctgttactcc    135060
catttgacag gtgaggagag caaggcttag agaatttcag tgacttgccc aggtccactg    135120
agctaggaag tagccattct ggcgtttgaa ctcaaaggcct gctatcccta gaacccacgc    135180
tctcaaattc aacctctgag gctatgccaa aggcaagccc cagtgctgtg ggcgccccag    135240
ggaagaacct ctggcctggt ggccacgtag cccaggagag atgctacag gagcccacag    135300
cgctgaagga gagaagggca gcagagtta gggggcattc tggcagagag gggactggca    135360
ccttgggggaa tagctgggtc aggactgaat gtcatggagt caggtcagag ctgtccttct    135420
ggaggggcaag ggcatctgga cctgcttccc ctcaatgctt tggacggttc caccacaact    135480
gattcacacg gcctccccaa atgaaggtac acgagcgggc attctgtgac ttggtacttc    135540
cctttaggcc ctgtcctggc atttgatcca tgagcagatt ccgctgagtc tggatctcca    135600
ggcagggctg gactgctgct gcctggccct gcagctgccc ggcctctgga gcgtggtctc    135660
ctccgcagag tttgtgaccc acgcctgctc cctcatccac tgtgtgcact tcatcctgga    135720
ggccggtgag tccccatccg tgaacaatgg gttcctatcc tagttcctgt ctagttcacc    135780
atgtttatat tttgtgctgc ctgtttgcca ggtactaagc taggaattgg ggatggagag    135840
gtagataaaa tacgcattag gaaggggctgg gctccatcct ttttttttttt ttttttttt    135900
tgagacggag tctcgctctg tcgcccaggc tggagtgcag tggccagatc tcagctcact    135960
gcaagctccg cctcccgggt tcacgccatt ctcttgcctc agcctcccga gtagctggga    136020
ctacaggtgc ccgccacctc gcccagctag tttttcgtat ttttttagtag acgggggtt    136080
tcaccgtgtt agccaggatg gtctcgatct cctgacctcg tgatccgccc gtctcggcct    136140
cccaaagtgc tgggattaca ggcttgagcc accgcgcccg gccggctcca tctcttactc    136200
tccaatatat tggagtctac actggaattt aacttgaatt tgctttttta gtcattttat    136260
ttagattttg gaattcagc tttcatcaaa attacttcta aatttatgt ctctgtgatc    136320
tttggtctta gctgactgtt ttatgcatttt agtcttatat gatcgaaagg ttagtaagat    136380
tacgttcaga agattgtttt ctgttcaaat gcttgttttct atactgcact ataattataa    136440
cgtactgtaa aataaaagtg gctattcttt ttcaaggaac agtatcctca acaagggtta    136500
ttagccacaa ttttttaaaaa attggacatc atggtttaca tgttggaggg catttttgaag    136560
cttttgtattt tcaaattaaa cattatagag tgatgttttg atgtttcata attgttttca    136620
tctgtgcatt tgtggccagc ttgaaaacaa agatccaggg attaatactt aaaagccaga    136680
cttcttgggg gttatagaga tgattttggt agtaatgaat cttgagccgt ctgataataa    136740
cctcggggtg agagatggcc aacaggagag agtcgaggga cttacaaatc tgaatgaaat    136800
ctgaagtaca aatcttcaga catatgccac taaccaagag attggtacct cagtctaata    136860
ttgtctgttt gtctaaaatt ggttctaaga aatctaggct catctgtcta tcccttgaa    136920
cttttgtgag gctgcacaaa tgtaaatttt tgaatgaaaa gcactgatgg aagtctgtgg    136980
aaattcttct gtttgttctg ttgtaatttt agttgcagtg cagcctggag agcagcttct    137040
tagtccagaa agaaggacaa ataccccaaa agtcatcaga gaggaggagg aggaaataga    137100
tcctaacaca cagagtaagt ctcaggaccc attcttcttt acatgtggtt cctccaagac    137160
ttaaaagtca ttcacagaga cgtgcgccgt ggtgagtgtg cactcctgga agcgcaccgt    137220
agctcggctg tgtcctgctg ctcctccctc gccgtgggag gctttagtcc attgctttgc    137280
cacactcttt tgtttcaccg tatccctgtg catgcggctg tttctgaccc tacagagcag    137340
```

```
ctgggatgcc tctggggag cccttccccg ctccagcact tccacatgcg gttactctgg   137400
gctcctggag ggcagggagc aggtttgtct tctctgtgtt ctcagaaatt aatgcttggc   137460
ccctggtcag caagcagcaa ccttttgttg agtgatactg aataaataca tgtttcccac   137520
atgagtattc agtaacctca gtgtcaggtt caggcatctg ttttggtgga tatttaaaag   137580
aaaattccac ttttcctaca gaaaaaaaaa aataaataaa tctaaatccc agtgatttaa   137640
gccagttata gacttagaca tatactacgg cttttcatgc cctttcctcc cagttctaga   137700
gtagtatttt actaggaaaa tggtggcaat gcctgttgag aggaaaagtt tttggccaag   137760
tgtctttcgt tcttgccagg ggccctaggc tgctggggct acttcagttt ctttagccca   137820
gtgtctggca gggaatgctc cctgtagcct gtcccacaga ggcaggggtg cctcacctgg   137880
ggcctgtcca cgcattttac acagcaccct tacttggagc atcaggcatc ttttccgcgt   137940
tccgtggctc aggaaacaca ccttttcaat catgagttcg ccagtgcttt tgggcttttt   138000
ctcccagctt ttgtgcaatc ctagttatgg atggagtttt cctgccttta gtcttctgca   138060
tagtacttt ttcttctggt tcccggttcg aggttttgta attaaagaat gacccagaag   138120
cagtggcatt ttcttttctt ttctttcttt tttttttttg agacagagtc tggctctgtc   138180
gtccaggctg gagtgcagtg gccggatctc agctcactgc aagctccgcc tcccgggttc   138240
acgccattct cccgcctcag cctcccgagt agctgggact acaggcgccc gccacctcgc   138300
ccggctagtt ttttgtattt tttagtagag acggggtttc accgtgttag ccaggatggt   138360
ctcgatctcc tgacctcgtg attcaccggt cttggcctcc caaagtgctg ggattacagg   138420
cttgagccac cacgcctggc cagcagtggc attttcatac acagccaagg tcttctctga   138480
attttatct cgaacctctg tgggtccttc aggcttcagt ttgtgatttc atgatttctt   138540
gttgctacct aaggaatatg aaaacaccca cctcccact ctgcgtcttc cagccgatgg   138600
cacctcaggc tcttggtcct gtgcttctgt ggcgaggata agaatagtgc caaccatgtg   138660
gattgagata gatcagttag tccatccatg tcaagcacct ggaatggatg acagtcttgt   138720
tgtgaatact caacagatgc taccatgact ttagttagat ttccattgct ttgaaacagt   138780
tgagacatct cagagctttg agccagagca gtgggccctg atgcaggttc tgtttggttg   138840
aagatgattg tgcttattcc ctgtggccct tgtagaccgg agtgggaagc ttgcttgatt   138900
ttaatcacct cgataggatc ttacttctta aaggtcatcc aataaataat gagccaactc   138960
attagcctgg ggcttaattg cttaagtcca atgagaagtc attctctatc ctaggaagtt   139020
gcccaaactg tagaatctcg tggcctgtgg gtagtagcca cttactacac attcactgac   139080
tcaacgaatc atatttttag tagatacaat atttctagact caagacacca tgatgtggat   139140
cttcccaggg gtgtgacgtg ttcctcggcg tctgccttgg gagtttccat ttccatcaga   139200
accatgcccc agggccctca aacactctga tctaggaaag ccagtgaagc aaggatgaca   139260
gcgtggccct ttgataccag ctgagggaca gacacaggtc ctgggagacc agagaaagac   139320
aaggggcaga ggaagtgtcc tagagggtgg gccagagggc tgggaacgaa ggccagagcc   139380
caggttcagg accattccag caatcccagc agaaaatggg gaggattgta tggtataggc   139440
ggatatgaag gaggtagact ctgcaagctt tcagtggcca actcattcta ggtgattcca   139500
caattacagc ttgagcagct gcttgtcggt catgcttctt acactgggca agtagaatgt   139560
gtttttaaa aagtcttctc ttaaccattg cttgtttaga tccgaagtat atcaccgcag   139620
cctgtgagat ggtggcagaa atggtggagt ctctgcagtc ggtgttggct ttgggtcata   139680
aaaggaatag tggcgtgccg gcgtttctca cgtcagtgct caggaacatc gtcgtcagcc   139740
tggcccgcct gccccttgtc aacagctaca cacgtgtgcc cccactggtg agtctggtcg   139800
ttccgtgtag aagaccaagt acggtgaaac gcatgggtaa gccctgggct gggcacaccg   139860
gagagggcag ggcagagtcc ccgcggccca gaggctgcca gctgtggttc tggtgccagc   139920
tgtggttctg gtgccagctg tggttctggt gccagctgtg gttctcgtgc caggctgctt   139980
tcctcaggca ccgtatgtgg aggtcgctag tagaaatact gggttttcta aaatgaagtg   140040
aggccccaca tccctaagag attagtgtta gacttgattc taaagcaact agaccacttt   140100
gcttactggt agaccagaaa ccacactccc tcgagtgagt gagattttcc tttgaaaata   140160
attcatgttt ttctacacaa ttttgctgtt gtcttcagaa tcggtttaaa gtaggtgtta   140220
ttgctgggca cagtaactca tgcctgtaat cccagcactt tgggaagcca aggcgggcag   140280
atcacttgag gtcaggagtt tgagaccagc ctggccaaca tggtgaaacc ccgtctctac   140340
taaaaataca aaaattagcc aggtgtggtg gtgtgcacct gtaatcccag ctactcagga   140400
gactgagaca ggagaatggc ttgaacccag gaggcggagg ttgcagtgag ccgagatcac   140460
gctactgcac tccagcctgg gcaacagagc aatattttgt ttcaaaaaaa aaaaaaaaa   140520
aaaaaaaaa aaagtaggtg ttattgatca ggatgcttgt ttcagataac gaagagctta   140580
gcttgaggag agtgagggtt gatggaaggg gactggcttc tgctcagtga aatggcatca   140640
tccccccacca gcctgctgaa gtaagatgat gggacctgtt ccttagggac tgcagcatcc   140700
tcaggcaaga aagaaaggcc gaccggcagg gtgtgagcca gcaggtatag gtcagtgaca   140760
atggagctgg gtcccaggga agaggcttgt ggctgcttga aagggcgcg tgcccgtctg   140820
cgtgcgcgtg tgtgtatgta cgctggagag tctggggagg cttgctccaa ggacacagta   140880
tttgatcctg agacatgagg aggtttctgc cgcaggcgat gaaggtattc agatggagag   140940
ctcattcgga agaagaggcc agggcctggt ggtgctggca gcagttgcag aacagggagt   141000
tgtaagcttt cctaggaaga gcagcaggag tgctggagaa gcaggccacc cttgctgcat   141060
gggggttgct cttggcccca ctcttggtgc acggcgagtc actgtgagtt cgttagcatc   141120
tggttctgaa acagtaactg ctcctttgga ggggctcggg gagaccatgt aggagggcac   141180
agtcaagagg tcatgctatc tggaacacac ttgaggatat gccaggacgg actgcatgct   141240
gtagataaaa ttcctctagc aagctcttaa ccggcattga ggattccct gagtgcggtc   141300
atctggaagg cagctgtgaa aggcactgca gtctcccccc gggcaggtac caggagcaca   141360
gggagcaga actgatttaa agagagggct ttcctgtggt gaggtgagag atgagctggt   141420
cattatcata gaaccctct gcctgtgtgc agatgcgctg tgggaatcct aggggttcct   141480
tgggtcctct gtcacctcac tgaaggcatg tcagctgagc tggccagacc ttcagctgat   141540
cctgccactt gaacagcatc aagcctgcct ctggattctt ctgtgcacgg tgcttgtcta   141600
atcacctcat gcacagagaa ctgtacttca gagtttacag aaataagctg tatggttcat   141660
tttcgtgcct gcttgccaac aaacatatct gagctgaact tcattgaacg cctgccttta   141720
ttctaacaca tccatctgtc tttgtgggcg aggggtgctg tctctaactc ctgcctgcct   141780
ctcccagcat ccctgagtgg ggtgtgccag cagcctcagg gtgaggacag gaagtgggag   141840
ggcagagcag atttggaagg gccacttgat ggggaaggaa gtcccaggaa gcagttggag   141900
ctgttttctg ggggagaagg tgccagcttg ggacagtgt tgtagtgagg aggaagccca   141960
gtggagagaa gtggggcttc ctgcttcctc acagtgtgtc tgtcctgact cagctcgggt   142020
gatgtcactt ccttttcatc ttctcaggtg tggaagcttg gatggtcacc caaacccgga   142080
```

```
ggggattttg gcacagcatt ccctgagatc cccgtggagt tcctccagga aaaggaagtc   142140
tttaaggagt tcatctaccg catcaacacg ctaggtactc ttggggcctc tttcaggtca   142200
ccatcgtcgg gcatgtaccg ggaggaaatc cagagcccca gtactgggat cttctcattt   142260
gactccagaa aagatttaag catgataata atacaaacct gtgtgaatac attttgcagt   142320
gtcagcaaaa ctccttttac tgagaaaata gatcccagtt cctgtgtttt gtggcttgaa   142380
tcccagcttt ttatattctg ggcttgtttt aagtcaggaa agattcatgt gtaacagaca   142440
acgtgaggcc aaattctgcc ttcgattttg catttaggct caacagtggc agcgcttgtc   142500
tcggagtgtg ttctcgtgtt caccagtctg atcctgttgt gtctcactgg tgcgttttct   142560
cacatgggaa caagcagacg ggagcagatg gagtcaagtc tcttagcact cgccttcctc   142620
agagcctaga ggcagcatgg ggagaaagcg ggcttgggc tcagacagtc ctggtctgct    142680
tccagccctc tgtagctgag cagcgcggaa caagtcctc taacctctag agaccctcag    142740
ttttgtcaaa tgtaaaatgg gagtcacgtc tatttcatag aattgttgca gatttagaaa   142800
ttacatttct tttttttttt tgagacggag tctcggctct gtcacccagg ctggagtgca   142860
gtggcgcgat ctcggctcac tccaaactcc gcctcctggg ttcacgccat tctcctgcct   142920
cagcctcccg agtagctggg actacaggcg cccgctgcca cgcctggcta atttttttgta  142980
tttttagtag agacagggtt tcattgtatt aaccaggatg gtctcgatct cctgacctcg   143040
tgatccgccc acctcggtct cccaaagtgc tgggattaca ggagtgagcc accgtgcctg   143100
gcctagaaat tgcatttcta aacaagtgtt agccctttat tctaaataag tgtcgaaatg   143160
aataagtcac cactttcgcc cctatttgat ggcaagaggt gtgatcttgt ggtgggattg   143220
taatcagtca gtcctcagtg actgtgccct gctgtggtgt ttcctggaaa gttcttgtct   143280
tgtcctagaa agtctggcag gggcaccctg tctccactgt ccagtcttct ccccaggccc   143340
ttcaggcttc tgcaaatttg aggcttgttt tcatcccaga aggttctggc agcagacgcc   143400
ttgcgtctac tgtccccttt agttaattag ataattcaat gtccaaaggg aaccctgagc   143460
aggaacctca agccagctgc ctcacggagc tcctcctctt cctcactgtg aagattggtg   143520
tcagtggcct cctggtctcc cccttgccta acacgagctc ctttgcttac ttgggtgccc   143580
ttgccttga actccccggc agacgtgcgt gacccaagac tgtgctacag tccttgtttt   143640
tgttcatgct catcttcttc ttggttcatt gttttccctg taatgtcaat tgtttttattt  143700
gtctgtatct gtgtctgaat cagtcctgca cgctctcctt ctctctgtct tttgttcttt   143760
ctttacccag tttatcacag ggaccccga tgtccatttc tctagttctc ctgtcctaag    143820
caccccatcc tgtctttctg gccttatcac aagtggcgtg tctgcctcag acatcatgat   143880
ggggcatga agcacagctg tcagaaacaa ctgttcgtta ggtacactcg aattcagctc    143940
atcaatagga atgagggtc tatcagatgt gttttcactg aatccctgtt cnnnnnnnnn    144000
nnnnnnnnnn nnnnnnnnnn nnnnnnnnnn nnnnnnnnnn nnnnnnnnnn nnnnnnnnnn   144060
nnnnnnnnnn nnnnnnnnnn nnnnnnnnnn nnnnnnnnnn nnnnnnnnnn nnnnnnnnnn   144120
nnnnnnnnnn nnnnnnnnnn nnnnnnnnnn nnnnnnnnnn nnnnnnnnnn nnnnnnnnnn   144180
nnnnnnnnnn nnnnnnnnnn nnnnnnnnnn nnnnnnnnnn nnnnnnnnnn nnnnnnnnnn   144240
nnnnnnnnnn nnnnnnnnnn nnnnnnnnnn nnnnnnnnnn nnnnnnnnnn nnnnnnnnnn   144300
nnnnnnnnnn nnnnnnnnnn nnnnnnnnnn nnnnnnnnnn nnnnnnnnnn nnnnnnnnnn   144360
nnnnnnnnnn nnnnnnnnnn nnnnnnnnnn nnnnnnnnnn nnnnnnnnnn nnnnnnnnnn   144420
nnnnnnnnnn nnnnnnnnnn nnnnnnnnnn nnnnnnnnnn nnnnnnnnnn nnnnnnnnnn   144480
nnnnnnnnnn nnnnnnnnnn nnnnnnnnnn nnnnnnnnnn nnnnnnnnnn nnnnnnnnnn   144540
nnnnnnnnnn nnnnnnnnnn nnnnnnnnnn nnnnnnnnnn nnnnnnnnnn nnnnnnnnnn   144600
nnnnnnnnnn nnnnnnnnnn nnnnnnnnnn nnnnnnnnnn nnnnnnnnnn nnnnnnnnnn   144660
nnnnnnnnnn nnnnnnnnnn nnnnnnnnnn nnnnnnnnnn nnnnnnnnnn nnnnnnnnnn   144720
nnnnnnnnnn nnnnnnnnnn nnnnnnnnnn nnnnnnnnnn nnnnnnnnnn nnnnnnnnnn   144780
nnnnnnnnnn nnnnnnnnnn nnnnnnnnnn nnnnnnnnnn nnnnnnnnnn nnnnnnnnnn   144840
nnnnnnnnnn nnnnnnnnnn nnnnnnnnnn nnnnnnnnnn nnnnnnnnnn nnnnnnnnnn   144900
nnnnnnnnnn nnnnnnnnnn nnnnnnnnnn nnnnnnnnnn nnnnnnnnnn nnnnnnnnnn   144960
nnnnnnnnnn nnnnnnnnnn nnnnnnnnnn nnnnnnnnnn nnnnnnnnnn nnnnnnnnnn   145020
nnnnnnnnnn nnnnnnnnnn nnnnnnnnnn nnnnnnnnnn nnnnnnnnnn nnnnnnnnnn   145080
nnnnnnnnnn nnnnnnnnnn nnnnnnnnnn nnnnnnnnnn nnnnnnnnnn nnnnnnnnnn   145140
nnnnnnnnnn nnnnnnnnnn nnnagaaaat aaggcagcag actggtgttt ctttcttttt   145200
ttttttctc ctaccttatt ttgagagagt agccagatgg tgtcttgact gatattccag     145260
agcagggaca aagcccactg aggtttgggg gctgcaatta ccaatggctg gaatgcattt    145320
gattacggtg cgttccatgt taaggatcaa ttagattgtg ctctttctgg aaagtatctt   145380
ttagttttat ttattggtat tcagaggagt gtaggttgaa ttaaaatgaa aaggcatttt   145440
ataaaggccg tgagtagtac atggtttcat ttttctaatg tcttgcagag attttattag   145500
gcttctcgaa gtgttcacgt acattacgtt aatgtgatac taagagtaac tgtactctgg   145560
cacagcgaag ccagcagaat gggaagttgt ggaatgcagg cccttgattc tgatagaagg   145620
tgtggtatga actcgcagaa atgacagttt ggagggtaga catatgtcac aagtcatcaa   145680
gattgtctttt aaattcatcc atagaagcta acaggttgtc ataagcaaag cctctaaaat   145740
gtatgaggga attcaaggat aatttatcaa aaagtaattc atgtttggag ttttgtgccc   145800
aaaggagtcc ttgatttgaa aaatgggtgt ttgcccatca gattgtttca gggtccgtat   145860
gtgcagagc cgtgcctcgt gccccgtgag ctcagcctga cagaagtccc ttggtagcac    145920
ttagggactt ggttagcact tcttcccttt gaggcagggt ggactctggg ttctgcattc   145980
agagctggct gtgggtgtct tgctgttctt gttgaccgt gggctctcct tccaggaaga    146040
cacagagagg acgcagatca acgtcctggc cgtgcaggcc atcacctcac tggtgctcag   146100
tgcaatgacc gtgcctgtgg ccggcaaccc agctgtgagc tgctggagc agcagcctcg    146160
gaacaagcct ctgaaagctc tggacaccag gtttgcctga attcccacgt gtctccagga   146220
catcatgggt gctgcggaca gtgggtccc cgctgaagca tccagcagct tcccccaggc    146280
tgttttcctt tgttgctaga attgaaaacg ctgtccatgt ggcctgtgca ggaggtgcag   146340
acccaaaggt ggcctcttgg ccattgagga gctgaaacg cgacgggaac tgacatgggg    146400
ttattgggca tttaggggta acattagca gagcaagaat gagcgggcaa gtggtagaac    146460
acccacctaa gggctcatgg acaggtgctc acttaggaag tgagtttcgt ttggtattac   146520
accaggttcc tttaggcagg gcggaggaa agttctggcg tttttcactt gtaagatttt    146580
gaaggaaaca aaacactctt tacctttttt ctgaaatgta ggtttgggag aagctgagc    146640
attatcagag ggattgtaga gcaagagatt caagcaatgg tttcaaagag agaacatc    146700
gccacccatc atttatacca ggcgtgggat cctgtccctc tctgtccccc ggctaccaca   146760
ggtacctgag ggagagggtg gggggtggct gtacttgggc tgggatgaga aaagactggc   146820
```

```
gtgctcacca caccagttat gcaggaagac ctgagtgtgg tttgagttgg aggctgtggt    146880
gctaaatagc tgccccattc ataagcagga gtcttattca ggcccaggga ggaaataaaa    146940
tctggaaatg aattaggagc attatctcct gccagtcaat tctccacggc tgtaagaaca    147000
gcaggattta aaagttgaat gagttcctta tgttaagaac tcaaccgagt tcatctacac    147060
aagctgaatc tccagctttt cctaagaaac caggtgtgca agtggctgca gggcggggca    147120
cagctgggcc tgagcacccc gctccctgca cctctcccct ccctgggccc tgtctgtcgg    147180
tgcccactct cccaccaagc ctgccagttg tgtgcctgcc ctatcacagg catcagagtt    147240
tgtcacctgg tttaaaagaa gggagttgtg tagggatctg gggatgcaca ttttcactg     147300
aacagtatt tagcataagag gtttgtgatt ccctggttat ttaggagttt aagcaccta     147360
aaggctttaa ttgcagaaag gtctatgtgg acatgcaatg tgttatacgc agtgtctatg    147420
accctcaaat gtttattagg gtattgaaat aaactgagca cttggagggc catggatcca    147480
gcttcaagga gttcataggt caggaggacc caggagcaat gacctgtcgt agacggcaga    147540
aaagaggggc acagaggtgg gttggggggca tacacaggca gctcctggag ctccaaggag    147600
agcaagtgct tccagggaag gggggtgtgga ggctccttgg gaggaggcga gttgatgctg    147660
gggtctggca gagggttagc tgggggacatt cggctggagg ctgttgtctg ggaattgggg    147720
ggatgcccag cagaaagaca tgcggaggtt gtttggcctg gggcgtgggg ggtgtgagag    147780
gtcgagtggg ggcattatcc tgctcccgct cctgctggct gtatctggtc agcctgggca    147840
ccgaggcggg ttctggaaag cactgttcac agatgcttat ctgagtcccc cagannnnnn    147900
nnnnnnnnnn nnnnnnnnnn nnnnnnnnnn nnnnnnnnnn nnnnnnnnnn nnnnnnnnnn    147960
nnnnnnnnnn nnnnnnnnnn nnnnnnnnnn nnnnnnnnnn nnnnnnnnnn nnnnnnnnnn    148020
nnnnnnnnnn nnnnnnnnnn nnnnnnnnnn nnnnnnnnnn nnnnnnnnnn nnnnnnnnnn    148080
nnnnnnnnnn nnnnnnnnnn nnnnnnnnnn nnnnnnnnnn nnnnnnnnnn nnnnnnnnnn    148140
nnnnnnnnnn nnnnnnnnnn nnnnnnnnnn nnnnnnnnnn nnnnnnnnnn nnnnnnnnnn    148200
nnnnnnnnnn nnnnnnnnnn nnnnnnnnnn nnnnnnnnnn nnnnnnnnnn nnnnnnnnnn    148260
nnnnnnnnnn nnnnnnnnnn nnnnnnnnnn nnnnnnnnnn nnnnnnnnnn nnnnnnnnnn    148320
nnnnnnnnnn nnnnnnnnnn nnnnnnnnnn nnnnnnnnnn nnnnnnnnnn nnnnnnnnnn    148380
nnnnnnnntt gcagtgagcc aagatcacgc cattgcactc cagcctgggc ggcagagcga    148440
gactctgttt caaaaaaaaa aaaaaaaaaa aaaaatcttt taatgttcat tgtttttgtc    148500
cttttattc ctaggtccca caagcagaga aaatattact tttgttttta tttatgttct     148560
ttattctaga aagtagttaa gagacctcac atgtagtgat agagatgtat ataagagaca    148620
gtgagagggc ctgagctgga cttaagcaag gaccgtgaga caccaaaagg ggtgaggaca    148680
gagtggagtt agctgagatg ctcaggagga agtagatgcc atgaagggct ctgttgtggg    148740
gggctgcagg cttggccctg agtgtccctg tggccagttg ttggggggggg cccagtgtgc    148800
aggcagacag ctcggccact ttgtggcagg tcacgttggt ctgtgcttct gtttcctcct    148860
caggtaagtg aagggattta aggggtccagg tgtggtggct cacacctgta atgtataaca    148920
ttttaggagg ctgaggccgg aggctcacct gagctcaggc ggttgaggct gcagtgagcc    148980
atgattgcac cactgcactc cagcctgggc aacagaccaa tactctgtca cttaaaaaaa    149040
gtgtaaacag aaacacaggg ccattacat atgatggcac atggcaggag cccacaggt     149100
gtatgctcag gggaggggccc agctttgctg gctgacttgc acctatcct ccaccctgtg    149160
ctgtgtcttt cgctcactgg gttcctggtt tagtgaaacc agttgtgcag gacggttccc    149220
ttggtagctt ttgttgcagt ggaaatgggt caggatatgg tgtgtagaag cacttatgag    149280
ctctgagagt ttcctcttat gacttcctgg cctgcagcct tcacagcaga aaccccatga    149340
tgtcacacgc ctgttttcgt tcctgctct gtgcctgta ctgtcctgtt ctgtgcctgc      149400
tggtttcagt gacaggaggc agggagctgc tggaccagcc tgtattttc tagacatagt     149460
tggaaaaaga agtcacgctc ttctgtcctc tcaccttga cagatgttc cacctcaaga      149520
taagtggaca tggccaatag gacgcactgt acttttcctg gatgtgttc tgaagggcag     149580
gctgagagtg agaggcctgg agctcactgg gtgcctgtgg ccttgtcctg ccccggggga    149640
cactggtctg tgcccgagat actcccatt ccccacgccc cactgcattt gcccacatcc     149700
ttcgatgttt gccctgtgtc caatgtcgc aaaccgactg tcatgggatt atactggggc     149760
tgaagtatag tgccaccct gccctgtcgg ggacgttcag ccccagatgc cactggactg     149820
agccactgct tgcttttagg aaaggggggtg ggggttatgg gtctgggctt ggggagcaca   149880
ggggctgctc cttggcctga gaattgttca tacagactcg ctgcccactc cctgcagggg    149940
tgctgggtcc cagggggggaa atgggccctt gtgccaagaa cgtgagttgg gcctagggcc   150000
agtgatgatg gagaacagct tttttatggc acacagccca tagcactgtg ccaagtgctc    150060
gaggctccca gagaagcagg cagaaaggag gacagtcgag gtgtgctgag cacgtggtgg    150120
ctgtgtgatc tggagcgcgg gtcacagagg cgcggggacg ctctggcctg gggttacca    150180
caatgactgc cagtggcgga gatcggaaaa gaaatctcac gcgttggttc cgtgttttgg   150240
ggggttccgt gttttggggg gttccgtgtt ttgggggggtt ccgtgttttg gggactgcat    150300
tgagatctca cttacgagtg agagcgtggc cttcgtagag cctctttctg tgtcgcctcc    150360
tcagccgctc ctgggggctgg ctgactcctg atccaggcc ttagcgtgtg ctggagcttc    150420
ccagcagcag tccagcccc accccaccct ctctgtggac tcccttgcct gtaagctggg    150480
gtgtctgaac gaccccttgca aaggggcaga ctgttcaacg gtaggcatgt gctgagtccc    150540
ggcggccgca cccgcccacc aggagcctgg cactgtggct gcagcgctga gcagcaccct    150600
gtttctgtgg caggtgtcca tacactctgt gtggctgggc aacagcatca caccccctaag   150660
ggaggaggaa tgggacgagg aggaggagga ggaggccgac gccctgcac cttcatcacc     150720
acccacgtct ccagtcaact ccaggttttc caatggcctt tttctttct acagaaattt     150780
gaaatttctt atcagtcatt tgatttgttt gaggtgcttc ttgaaatgag cctctcatct   150840
tctgtaccca gaaaacaccc atcttgcata ttctacagga aacaccgggc tggagttgac    150900
atccattcct gttcgcagtt tttactcgag ttgtacagcc gctggatcct gccatccaac    150960
tcagccagga ggaccccggc catcctgatc agtgaggtgg ttcgatccgt aagtgagcct    151020
tcccattccc ctcacactgg cacatgccac acgaccacca cacgctgcac acacagacac    151080
gccacaccac acgtaccaca tgcaccacac acacgtcaca tcacacatac cccacatgca    151140
cggaacacac acacgccaca tgcacacgta ccccacatgc atgcaccaca cacacacacc    151200
acatgcaca gtaccccaaa tcacgcccc atacacctca catgcacaca taccccacat     151260
gcacacaaca cacacatgcc acatgcacac gtacccgca tgcacacaac acacacatgc    151320
cacatgcaca catacccccac atgcacacaa cacacacacg ccacacgtgc acacatac     151380
accacatgcc ccacgcacag cacacatgcc acacgcacac acacaccaca cacccccac    151440
acagcccata caccactttc atgcaacaca ccacacacac aatgccacac tcgccacatg    151500
cacacacacc acatgtacat accacacaca tgccacacgc accacacaca tgccacatgc    151560
```

```
accacacaca tgccacacca cacacaccac acacaatgcc acactcacca catgcacaca    151620
caccacatgt acataccaca cacatgccac atgcaccaca cacatgccac atgcaccaca    151680
cacaccacac acatcacata catgcaccac gtgtactatg tacacacaca gacacaccac    151740
acgcgtacac cacacacaga cgcacacacg cgtcccgcgc agtcatgtct cttaggtgta    151800
agaacacgac ttgccagtag cggcgttctg gatgtgttgc ctggattcta actgcgctac    151860
tctcccttg  ctttcctggt gttccacatc tccagcttct ggtggtctca gacttgttca    151920
ctgagcgcaa ccagtttgag ctgatgtatg tgacgctgac agaactgcga agggtgcatc    151980
cttcagaaga cgagatcctc gctcagtacc tggtgcccgc cacctgcaag gcagctgccg    152040
tccttgggat ggtaagtgac aggtggtaca gaggttcctg tcctgaagcc atgtgggcc     152100
atctgccttg ggacctggtg ttggccagag gtgccaggtg cggctgcctc cttccaagag    152160
ttgacccgag ccggactcca cagcccacgt gagctgcagt gcttctcagc tggaggggt     152220
tcagcgacgg tcagtgccat ccacaggcca ccgtgatgtg ggtcgtggcg gccaagccat    152280
ggtttggggt cccgtgtccc tgggcttgtg acatcattgt agtagcccat ccccacagaa    152340
ccatggtgtg tggtagcact gaagcatcgt agatggtgga aacgcgactg gcttcccat     152400
gctctgccct gaggcctgac tgcctcactc cccctcagtt atgttccagg cccccgaac     152460
ttcctgactg gacagcttct ctcctggggg ccattttgtc acagtgaccc tgcgtttcca    152520
gtcccaagtc tgggtgctat agtgtcttct tagcatggtg ttttctcttag tctatttcgg   152580
ctgctaccac aaggtacctt agactgggtg atttataaac agtggaaatt cacttctcat    152640
agttctgggg gctggaagtt catggtcaag gtgccaacag atttggtgtt tggtgagggc    152700
tgctctctgc ttcatagatg gcatgttctc actgggtcct cacggtgaaa ggagtgaaca    152760
agctccctca ggcctttcaa aagggcccca atccacaagg gctcacccct catgacttca    152820
tcaccaccg  aggccccacc ttctagtact gtggcactgc aaattagttg tcagtgtaag    152880
agtttcgggg gggatacatt cattcagacc atcccaaggg tcaagtgttc atcctcttga    152940
gctcctcctt attctgcttc tggtttatca ggattcagcc cgtgcagcac ggtacctgtg    153000
ttctgtgggc acatcaccac atggcatttc ccaagcatcc atcagctgta cacatgaaat    153060
cgctacctgt gggcccgac  tgctggcaaa gcctattcaa ggatgtcaga actgtcagag    153120
ctggagcctc tgggtctttg tcatgtggca ttacctagta atccatttta tgatagcaat    153180
agaaacgcgt gtcttcaaca aacacctcag tggctgccgt gtgccagccg tctgagccc     153240
ttggtgagaa tggcatggta gtgcccatca gggcctgctt accccatgct ctggatgggc    153300
tcctgtcagt aacaacgctg tcgtgacagt gatgatgttt ttttgccgtc actccagctg    153360
ctaacatttg cggagctctt cctcctgcac cccacctgac aaaggcaccc taggcggcca    153420
gcgtcagagg ttagctggct tgtctgggtc acacaaaatg cggcagaggt gggactgagc    153480
ccatgtctgt gacctgaagc ctgactccct gcgagtcttg actactcttg cctggactct    153540
gtcctccccg agcccaaact ccagtcatct tcccttgtgg gtggccgtca gctcggtgcc    153600
gtgctggtga cttggcagcc atccagggag tggaaacaat gaacgcgtgg gctccctgtg    153660
tgggcatctc tcttcactgc gagcaccctc tgggtgttgc ccacatgatg tcaaagcggc    153720
tctcggaagg ggtccttctc ctttatgggg agtttcagct gctgggctaa cttgaattgt    153780
aatgtggttt tgtgctcagg cccagagctc cttaggcaag tgttgtgcca tcagtaatca    153840
aatgagaaat aatcattttg aaaagcagat cctaaggcag gatggtcatg ggcactaatt    153900
cccagctctg tgcatctttc ttgaagacgg tgatcctctg tgaaggtttt cagcatgtca    153960
tgcttggtac cagcgtatcc agagcatgtc attttgaggt atttgcctcc tgttgtgaaa    154020
tccgtgccac ctgagagcag gtcctgatgt gggactttca gaggtgggac caggggccgt    154080
gggagcgcag tccttaggga ggtgccgcgt ggcgttgtgt gtatgagggg atagcacagg    154140
gtgaggtggg ggcccaagaa ggaagtgatc caccaaagaa cagcctcttt cggtcctcat    154200
tcctgggatg ggtgggagcg gcttctgtgt cttccggtca tttccccctgc ggagaagctc   154260
ctgccactgc caagaacctc atcttgttcc acaacaagaa gaggctgcct ggccatccag    154320
cgctccatgg gaattctgtg tccccatagt cttgggctga aagagagcga cataccttgg    154380
tgacttctgc aggggtctcc tcactgttaa agagcagatt gaaagtgaag aatgtgggct    154440
aagtgtttag gtcgatattt aaccccatta ggttttggat actaagtgaa attgaggcca    154500
ttttggttga aggttggcat aaactactat cagggatccc caagactacc cccaggcttt    154560
tctagaagga ctctcagcta agatgtaata cagtaaaagc acacaaaaca caatcagcaa    154620
accaaatcag caagggcaga ggccatggg gcgtgtccc  gaggaaacca ggcccgagct    154680
tccagaatcc tctcccggcg gggtcgtgca ggacacactg agctccccca gagtgagccg    154740
tgacagcgtg tgcagtgtcg tcaccaggct caagcttcca gaatcctctc ccagtggggt    154800
cgtgcaggac gcactgagct cccccagagt gagctgtgac agtgtgtgca gtgttgtcac    154860
cagggaagcc cactagagac tcggtgccag ggttttgact gcgggctggg cacgtgggca    154920
ccttctgcct gcttcgtgcc catactctgg actcccagag ggaaggcaga ttctcagcac    154980
aaacaccgtt gcccacacaa gcagctgagc acagagagcc cctcctcagt gaggatggtg    155040
ggcaccgtcc cgacaccagc caggggccag ccttgcacac agcctctca ggatggtctt     155100
gggccgtgca cacaagcatg agggcagcgc accgccccg  ccctcctgg gctgtgggga    155160
ggagccactg gggcgtgagc tctggtggca tcagcagctt ttgtctgtgt gtgtctagga    155220
caaggtcgtg gcggagcctg tcagccgcct gctggagagc acactcagga gcagccacct    155280
gcccagcagg gtcggagccc tgcacggcat cctctatgtc ctggagtgcg acctgctgga    155340
cgatactgcc aagcagctca tcccagtcat cagtgactat ctcctctcca acctgaaagg    155400
gatcgcccag tgagtgggag cctggctggg gctaggacga gggtctcgga atgagctgcg    155460
aaggaagcag catcaccctc tccaagtgcc caggtccctg ccagatggca ggcaggtgt     155520
cagtgggaac ccaggtgggc gccatggctg aggttggtga gacgcaaggg cacaggtgtg    155580
tcctagagggc ttcctcgggc acccccagtg agctagagct cctgcctctg ctgctgtctc   155640
atgtggcgct gagcacatt  cccccatgtgc ccattcctga tctctgctcgc gaggccagcg  155700
gttctcattc tctgctctca gaaccctctc ctcattaccc aggccagcct cctctctgca    155760
ccttccccgc cctggcccag caactccctc ctgtttccac tgtgactccg acctcacttt    155820
atcttaaagc tgctgggcgg caggttctgc acagatgtgt ccttgacaaa gcacggctgg    155880
tgccacaacc ccttaacgag caagtcaagc tcttcacaac gatgtcttgt gagtgcgag     155940
ggctcgtga  caccctggtc tcacctccgc tctcccgaag tcgcagaggc tttagcagag    156000
atgggcccag cctctctgag tcacaggctt tagagctgtc tgtagaggga gggtagaatt    156060
tcatcagcca cccacatggg ggagttgagg gcaagaattt ggagcaaaga tgggaaaggg    156120
gctgggaaga atgccagtg  atcccctttg acaagtgggc aggagatggg ggcccggtca    156180
aagttgagtg gaagacttgg agggagatgg gaagatctct gtaggcacag ttcagacagg    156240
agggaggtgt gagccagggc actggctggt ggctgtctgc caggatttgg gacatcctgg    156300
```

```
agcagggaca gtggctcaac aggggccatt gccctcatcc aggccagagt ggcacaagct    156360
tgtggggagg cccttctcgt ctgtcatcct tgctgggcgg tgggtgctgt gctagcagga    156420
cgcaggacag gcggacagct ggcaactgtc tctgcatccc tggagcctgg catagggcaa    156480
gtcacacggg ggacacaggc ctgcaaatca ggcacatgcg ttggtgcagc gaggtgattt    156540
tgggggcgag ccccacaaca ggccccaggc acaggccaaa gccctggctg tgctggcgtg    156600
ttgggccgtc tatggctctt gctgtgggca tggaggactc aggaaaggag agttgaggtg    156660
gcccaggagt tgcgtttggg atgcagagag cttgtggcat ccaggtagaa atggtgtgtg    156720
gggctggcct cagtgccatg ggcacgggct gtgtcacatg cctccgaggt agaggtggga    156780
ccacgtggtg atggatataa gcatcactgg gcacatttct gtgggtggag gggggcatct    156840
tactggctcc tctgttcaca gtggccactc attcagtccc tggctaccgg gtccccattg    156900
tgccatgggg aaggcaggtg ctgtcggggg atcacacaag gcagcacgtc atggtggaat    156960
gtgccacgaa ggaaaagcac agggcactca ggaagtagag gggactggcc tggggtgtgg    157020
gaatccaggg cctctttgag ggacagagag aggaagtctg tggtgccag tatggaggtg    157080
gccacagggg aggctgggcc aggccgagag ggcaggggct ggaggaggta gacgggctca    157140
gctatccagg gaggggtcga gcagaggctg aagggtcagg ccaggttaca ggggcctggg    157200
gagccacaca gggtaggtgc ttccgggagc cagcctggcc cgcagctctt cactcccgcg    157260
tggggccggg catgctgcga agccctctct acgttggatg gggcggctg agcctggctg    157320
ctgtctcccg ttttcagctg cgtgaacatt cacagccagc agcacgtact ggtcatgtgt    157380
gccactgcgt tttacctgat tgagaactat cctctggacg tagggccaga attttcagca    157440
tcaataatac aggtgagtgg gccctggctg tcttcctctg cacacgggga gtgggcttcc    157500
cttctctttt ccttgcggga tcataccagt gggccagttt tgacttggtg gggaggaggc    157560
atgaacacct gagaccatgc agcgaacgaa acctttctcc ctgtgcagat gtgtggggtg    157620
atgctgtccg gaagtgagga gtccaccccc tctatcattt accactgtgc cctcagaggc    157680
ctggagcgcc tcctgctctc tgagcagctc tcccgcctgg atgcagaatc cctggtcaag    157740
ctgagtgtgt acagagtgaa cgtgcacagc ccgcaccgcg ccatggcggc tctgggcttg    157800
atgctcacct gcatgtacac aggtgagcag gtacacagtg cccgcaaggc cagcccaagt    157860
cctgttcaag ggagacagga gcatgctcgc tcaaggaacc tagactaggt gtcctctgat    157920
ttgacacttt tagtgttgcc ccaagctggc cccatcacct tgcaagagag gctctggagc    157980
ccccagggct ggagtacctg gtcagggttg accacccctc tggtcactca tcccatgtgg    158040
ctgagctgtg ctgggtcctg ggctagcgag gggctcacat cacctgctgt caggtcttct    158100
ccagtgattc attggactcc tgtgtacaaa gcactatcta cagagcctgt tgggttgtat    158160
agatgtaacc ttcgtactga acactttat tacaggaaag gagaaagtca gtccgggtag    158220
aacttcgac cctaatcctg cagccccaga cagcgagtcg gtgattgttg ctatggagcg    158280
ggtgtctgtt cttttttgata ggtaagaaac gaagccccat ccctcagccg ttagcttctc    158340
tagaattttg gcctgaagct gagcgtttgt gtgtgtttggc tgatccctg gcgctgttgc    158400
tggagtcccg ccagtgattc ctgaccacag cctgaccgtg ggctgccttg gctcagggtt    158460
ccactggcga gctggtggtc cttggacccc agcgctcagg tgtagtgttg accagttcca    158520
aggttgtccc agcgcctgcc catctctcct gagggctcag gcaccgcacc tggccgtgtg    158580
gggtatggca gggggcagga atgaccagtc tctgggaggg tgcggcagaa gcctgcgcag    158640
tgatgaggag ttggctcagc ctggctgcct gtcgtgagag gggagcccac ggggtgtctgt    158700
gggagggggt ccatggtgcc tgtgagcagg gtgaggggca gcagcaggag gaggaaggtg    158760
aaacccacac atgcatcttt gagacccgtg tggtcagtgg cttctcctcg ctaccctcc    158820
gccccactgc tgtgcgtgaa ttggtgttga gaattggctt cgctccccctg tctgggaagt    158880
gggttaggag cttcgtaggg cttttttctca aggacaaggc tccctgattg ctctcaggcc    158940
tcagtcctgg cgacatggcg gatctggggc gttgttgtgc tgccttgcct gtgctctcca    159000
atcagggtgt cccagtcctg cgacatggc ggatctgggg cgttgttgca ctgccttgcc    159060
tgtgctctcc aatcagggtg tccagtgggg agccattttg cttttctcaa gagcatactc    159120
aggtggactt tgctctattc tttggccaga tgaggtgttc tgaacagctg agcctgtgct    159180
tgtctgtttt catgtttttt tttttttttg agatggagtt ttgcccttgt cacccaggct    159240
ggagtgcaat ggcgcgatct cggctcactg caacctccac ctcccgggtt caagcgattc    159300
tcctgcctca gcctcccaag tagctgggat tacaggcacg tgccaccacg cccagctaat    159360
ttttgtgttt ttagtagaga cagtgcttca ccgtgttggc cgaactggtc tcgaacttct    159420
gaactcaagt gatccaccct cctcggcctc ccaaagtgct gggattgcag gcatgagcca    159480
ccgtgcctgg cccccatgtc gatttttaaaa cgcacctctg catcattctt cagttccac    159540
atgctcactg agcaccacca cagctggcag acggacacag ggaggcgcca cgaccagtcc    159600
tggccttcaa ggggcttgtg gtctagtgga cccagtgcta ggtggcgagt gctccagaga    159660
gcgtggtgta tgccttccgc tctaccgccc tccagacgcc gcaggaggc accttggagc    159720
tgaccacaga tctccctccg tggagcactg tcttcagcgc agccgccatg ccactgctgg    159780
gcgagggtct gcgggcgggt agagccagga gcacctctga gaaagtgcac tgccgtttct    159840
tggctgcttc ctgtgcatct cagttacaca cagctggcat gtgtgcactg atgacagag    159900
aacatgatgg ttgctttca gcactaaaaa ggatactgct caggggggcgt gtttcaggat    159960
ctggttaggg aaaaagcagc gagagcacag atggggccct gtttggtaac aagaaaaaag    160020
tcccggttga caacagtgct acaaagtgtt agaaacacata gaaatgttta tggagcattt    160080
ggatgtggaa agcagcaaaa acataatgag aagggttct tttgttagga ttttaaaaa    160140
tctcttttgt aacatccttc cggctgcacc atttctgcat attcttttat gtagctttca    160200
gactcttagg atttctggtc actgcagggc gtggagcca gacagagcct atgcctagca    160260
gcctgtcttc acgagctgga cagaggagga gctgggtttt tgccttttta gcctcaaatt    160320
tcatactcca gttgcttagg ctctgacttt ccccacttgg aaagtccctc acggccaagg    160380
gtacctccca gccctgattt cacatcagca tttttcccag agccaaggcc ctccgcgggc    160440
aggtggggca gctgtgggag ctggtgccag gctctgacct gtgtccctcc tccaggatc    160500
aggaaaggct ttccttgtga agccagagtg gtggcgagga tcctgcccca gtttctagac    160560
gacttcttcc cacccccagga catcatgaac aaagtcatcg gagagtttct gtccaaccag    160620
cagccatacc cccagttcat ggccaccgtg gtgtataagg tgaggttgca tgtgggatgg    160680
ggatggagtg gggaagcctg gaggtggaat tgaccccgac ttgccagcag attcgccaga    160740
agaacccagc tcctccccctt taaagcagca atgcctctgg cccccacccc accccacca    160800
cccgggcaca gcaggtgctt cccgccccccc agccctgaca ctcaggcgcc cgcttgctcc    160860
tggcaggtgt tcagactct gcacagcacc gggcagtcat ccatggtccg ggactgggtc    160920
atgctgtccc tctccaactt cacacagagg acccagtcg ccatgccac atggagcctc    160980
tcctgcttct tcgtcagcgc gtccaccagc ccatgggttg cggcgatgta tcctctctgg    161040
```

```
gtccctggtg ctggccccgt ttccctcgtc aacaccgagg ctcatgtttc atgataaagt   161100
tttgaaacct aacctttgca aaagccccac agatgccaag gtgacaggcc ctcagcccca   161160
gggaagtaca atgctgacag ggatacagaa aggagcacat ccagacattt gctgaccagg   161220
gcctctcaga ggggcccgtg tatggcagaa gggtcgaagc tgctaagggg cccttctgtg   161280
gagggcctgg gtgaggggag cgagggtggg cggcggtctc tgcagacctc ccgcccactc   161340
gcgggctctg tgtggctggg cttctcctga cactgcttct cattagcttt ggtcattgtg   161400
cctcgatcac cctctcgggg aaaggcttaa gtaaagatcc agttcccacc cccagatgct   161460
ggctgccagg agtttccctt tccacagccc tcccccaaga cagaccacaa gagcctccga   161520
gcagcacggt tgtcctggtg ctgacagcac agcctcgccc agtgtgcctg gcgtggctcc   161580
gcccgcactg tactggagca gggctcgtgg gggccagcag gacagcagga gcatcggcca   161640
ccagcgctac acaggagcca ggccaggtga gtgctgccga gtgggtgcct gcctgcaggc   161700
ctcctgcttc cttggccagc tctgcccagc tcacttctgc cctgctgcc ttccagcagg    161760
gtgtccagcc agccaagggt tgcaggaatg aaggtggagg cgctgctgca gctggagcca   161820
tccaggtagc ccttccgggg ctctgctggc tctccagcct ccctgggcc cttcgtaggc    161880
tgtttcagga gaggagctcc caggtgagga cagggaggca gcattcccct catttgccgg   161940
cctttttcct taactcctgc accagcctcc cacatgtcat cagcaggatg ggaaagctgg   162000
agcaggtgga cgtcaacctt ttctgcctgg ttgccacaga cttttacaga caccagatag   162060
aggaggagct cgaccgcagg gccttccagt ctgtgtttga ggtggttgca gctccaggaa   162120
gcccatatca ccggctgctg acttgtttac gaaatgtcca caaggtcacc acctgctgag   162180
cgccatggtg ggagagactg tgaggcggca gctgggctg gagcctccag aaatctgcgc    162240
cctgtgccct gcctccaccg agccagcttg gtccctgtgg gcttccgcac atgccgcggg   162300
cggccaggca acgtgcgtgt ctctgccata tggcagaagt gctctttgtg gtacagtgga   162360
caggcaagga gtatctgcag tcccggtggg gctgagcctg aggccttccg gagagcagga   162420
gcagctgtgc tgcacgccat gtgggtgacc aggtcctttc tcctgatgct cacctgttgg   162480
gtgttgccag gctgcagctg ctcttgcatc tgggccggaa gtcctccctc ctgcaggctg   162540
gctgtgggcc cctctgctgt cctgcagtag aagtgcgt gagcaggctt tgggaacact     162600
ggcctgtgtc ttcctggtgg ggtgtgcatg ccacgccctg tgtctgtatg cacagatgcc   162660
atggcatgtg ctgggccagt ggctgggggt gctagacacc cagcaccatt ctcccttctc   162720
tcttttcttc tcaggattta aaatttaatt atatcagtaa agagattaat tttaacgtaa   162780
ctctttctat gcccgtgtaa agtatgtgaa ttgcaaggcc tgtgctgcat gcagacagtgt 162840
tcggggaggt gggcagggcc cctggccacg ctccctctcc tgtagccact ggcatagcct   162900
tcctgagcac ccgctgacat ttccgttgta catgttcctg tttatgcatt cacaaggtga   162960
ctgggatgta gagaggcgct agtgtgcagg tggccacagc aggactaagg acaggccccc   163020
actgtcctag gggcatgctc gcctgcagcc cctccttctt gggcacagac aactgttgtt   163080
ctccacccac attagggaca gcagcctccc tatcagctga gaaggccagc cctccctggc   163140
tgtgagcagc ctccgctgtg tccagagaca tgggcctccc actcctgttc cttgctagcc   163200
ctggggcggt gtctgcccag gagctggctg gccggtgatg ggatctgccg ttccatggat   163260
gcatgcccca agggtgtcac tgagctgtgt tttgtctgag cctctcttgg tcaacagcaa   163320
agcttggcgt cttggcactg ttagtgacag agcctggcat ccctttctgcc ccgttccag   163380
ctgacatctt gcacgggac ccctttagt caggagagtg cagatctgcc ttcattggag     163440
actgccccac tgcccctgtca gagccgccac tcctatcccc aggccaggtc cctggaccag  163500
cctcttgttt gcaggcccag aggagccaag tcattaaaat ggaagtggat tctggatggc   163560
cggctgctgc tgacatagga gctggatttg ggagctctga gatggggcag gagctctgct   163620
tcctcagccc ttgaggcgag ccaggcgagg ttggcgactg tcatgggct tggtttgctc    163680
atgcctgttg atgttttggg tattgaatat ggtaagtgga ggaaatgctt ttctggagtc   163740
tgtgcaggtg ctgccttgag accctcaagc ttccacctgt ccctctccta tgtggcagct   163800
gaggagcagc tgacatgtgg acttgtgtgc tgcccacata catgagggg cgctgaaagg    163860
gagcccctgc tcaaaggag ccctcctct gagcagcctt tgacaggcct gtatgaggct    163920
tttcccacca gctcccaaca gaggcctccc ccagccagga ccacctcgtc ctcgtggcag   163980
ggcagcagga gcggtagaaa ggggtctgat gtttgaggag gcccttaagg gaagctactg   164040
aattttaaca agaaagccac cattcttccg tattggttgg gggctcctgt ttctcatcct   164100
agcttcttcc tggaaagcct gctagaagct ttgggaatga ggggaaagtt ctcagaaccc   164160
ttgctgctcc ccacccacct cccctgcagt aagttatgtc aacagctcgg agacagaagt   164220
atcacaggcc agatgttgtt ctgctagatg tttacatttg taagaaataa cactgtgaat   164280
gtaaaacgga gccattcccc ttggaatgca tatcgctggg ctcaacacag agtttgtctt   164340
cctttgtttt acgacgtgat ctaaaacagt ccttagcaag gggctcagaa caccccgctc   164400
tggcagtggg tgtcccccac tcccaaaggc ctgcctgtgt gctccagaga tgaatatgag   164460
ctcattagta aaatgacttt acccatgcgt aagtcaagta cacgtgcacg tgcatatgga   164520
cacatctgta gttttataca cgcacatctc aagacagaga tgcatggcct ccaagagtgc   164580
ccgtgtcggt tcttcctgga agttgacttt cctcagacct gccaggtaaa gttagctgtg   164640
tgacgggcgt ccaggcgcgg ggcttggtca gagcagggct cattcatggc tcactaggat   164700
cccaccggag aaaacggtct ccatatcaac tctgccgaag ggaggaagac tttgtcgcgt   164760
tcctaaaaaa cctatggcaa gcaccaatca tattatccaa attgtgttga aaatgtgatt   164820
aatttggttg tcaagttttg ggggtgagct gcggggagac tgcttttgtt ttgctgctgg   164880
taatatcagg aaagacttta atgaaaccag ggtagaattg tttggcaatg cactgaagcg   164940
cgtttctgtc ccaaaacgtg cctccttcc gctgcgggcc cagctgagtc tgtgtaggtg    165000
acgtttccgg ctgccaagcg ctctttgtta ctgtccaccc ccatttctgc cagcacacgt   165060
gtcctttcag gaggaaaatg tgaagctgaa acccctccag acacccagaa tgtagcatct   165120
gagaaggccc tgtgccctaa aggacacccc cgcccccacc ttcatggagg ggtcattcca   165180
gagccctcgg agccgatgaa cagctcgtcc tcttgggagct gagctgagcc cccacggag   165240
ctcgggacgt atagtaaaca gcaataactc ggtctgtggc tgcctggcag gtggaagttc   165300
ctccccctga ggggcggagt gaggttagtt ctgtgtgtct gtgggtgga gtcagcctgc    165360
tcctgctacc tgtgagcatc ctgcccagca gacatcctca cccggctttg tccctcccca   165420
cttcctccct ctgcggggag gacccaggac cacgctgcct ggcagggta ggcttggagc    165480
tgtgctccga aggggccacc tgtgggagcg agaagaagga agatcttgag agctgccgag   165540
gcacctggag gagctcagga tggtccaggc gagaagagga cactcgctcg ccaggcctgg   165600
gcctcctggg aaggagggag ccgctcagag cgccgcatga caactgaagg caacctggaa   165660
ggttcagagg ccactcttcc cccgtgtgcc tgtcacgctc tggtgcagtc caaggaacgc   165720
cttcccctca gttgtttcca aaagcagagt ctcccgctgc aatctgggtg gtgattgcca   165780
```

```
gccttggagg attgtggcca acgtggacct gcctacggag ggtgggctct gacccacgtg   165840
gggcctcctt gtccaggtct cattgctttg tgctgtggtc agagggactg tcagctgagc   165900
ctgagctccc ctggagccag cagggctgtg atgggcgagt cccggagccc acccagacc    165960
tgactgcttc tgagagcaaa gggaaggact gacgagagat gtatatttaa ttttttttaac  166020
tgctgcaaac attgtacatc caaattaaag gaaaaacatt gaaaccatca gttgttgctg   166080
tgtgaggctt gctttacttc atgagaacct agaccttgct gagctggagt cttaggaaac   166140
tgtctcctaa gtgcttatcc agcagggca gaaactgtcc caccagctaa catctgacat    166200
tacgagggt cccgcaggca gctgccagca aggacaagcc ctgtgttttc tgtagccagg    166260
gatgaggaag tggccccagg ggcctggctg ggtgctgctt caagggcctt cgcaaaccac   166320
agtacaggtg gtcttcctgc actgcagatg ggagctgctgg gagctgctgg atccttcatg  166380
gtcaagtgac atcataagct tatatgacac acacaagcct caggacttgg cccatggcac   166440
tggagcaggt catcaggccc agcagactag agctgtgttc tcacagggcc catgacccctt 166500
ctagctcctt ggccattgaa acctgtgtcc ctgacccagc tgctcccagg tacccccaa    166560
agcagctggc acatcccacc tctggtgtgg cctgggctgc tgtgtgtccg cagggcctgg   166620
cccgtctgtt ctagcttgtt tctcctgtct gaaccagcgc ctactccaag aaggctctgc   166680
tcagcccagc ggggatgctt ctaagctcgg cccagcctct gggaagcctt ggtggtcggt   166740
ggtgtagtca tcctgggatg cagaacgaaa acctgcaaga acaaaactgt ggcttcgtct   166800
ggtgcagggt atttagttac tgtttgctga ggtcctgtct ggttctggcg aatgggcagg   166860
ggtcgcccac ccattctttc cctgctctgc tgtccgtgcc aggagagacg ggggcctgtt   166920
ggccaagggg gcagctcctg ctgcctgctg tccttaggca cgtgcaggga ccccctttct   166980
ctgagcagga tggggatcag tctgccagag ggatgtggtg gacaggccca gccgggtaaa   167040
aaattccccc agttgctcaa agcatttggg gcggggcagg ccacttgagc tccttaaatc   167100
tgtctcatag gtgacaccgc tccagggcgc cccaggggcc tctcccttca gagctaccaa   167160
agttctggtc acttcagaaa aatgagcac ccccttctcc ctggtccaga tgtggacagc    167220
cagacccttg gcacacctag cacacctggc atggctggta atttcagaaa gaaaagggggc 167280
cggggtccag tgggaagcag tggcgaaccc ctcatgccgtg ggcttttgcga tcccctcccc 167340
tgccacggca gagctgccct cagcacagcc ttcctcttcc tcatcggaga gcacaccctg   167400
tcccccttgcc ggggctgtgc tctgtgcctg cagtggtatt tggttttggc tgctactggc  167460
tttgttccaa agaggatctg gaagtcgctt ccctgtgtg gagcgtggag cactgtgagt    167520
cagatgaggg aagtagccag ggggaggtga gtacccggca ggccgccac agaaaggact    167580
gggtaggggg ccttgcctcc acgtgatgtg acacggccag ccgaggacag aggaagcccc   167640
gttcctgggg gtgtggggtg caccccctcag ggaagcctgc agtgggggcc aaggaaaggc  167700
gttctctgcg agcccacgag tctgctctgt gggcaccgtg acaatgcccg tgggcagagg   167760
tgggcccggc cttgtgtcgt caccaggacc tctttgggga aaccatgtgg gcatcccttg   167820
cgggtccccc aggttctgca gtcccgacgg cctggctgcc tgttgggcac atggcttgag   167880
ccgcccagag ggcccagccc tgttggcagc cacatcctct ggaggcctg ccggtggggc    167940
tggctttctc taccccacac caggcctcca agtatactgg tcggggtgt ctgggccctg    168000
gg                                                                  168002
```

SEQ ID NO: 5        moltype = DNA  length = 10295
FEATURE               Location/Qualifiers
source                1..10295
                        mol_type = genomic DNA
                        organism = Rattus norvegicus
SEQUENCE: 5

```
gcactcgccg cgagggttgc cgggacgggc ccaagatggc tgggagcttt ggttccgctt   60
cggtctacct cgtagagccc cattcattac cttgctgtca agtggcgctg cgtagtgcga   120
ataggctcca agccttcagg gtctgtcctg tcgggcagga ggccgtcatg gcaaccctg    180
aaaaactgat gaaggctttc gagtcgctca agtcgttcca gcagcaacag cagcagcagc   240
agccgccgcc gcaggcgccg ccaccaccgc cgccgccgcc gctcaaccc ctcagccgc     300
cgcctcaggg gcagccgccg ccaccaccgc cgctgccagg tccggccgag gagccgctga   360
accgaccaaa gaaggaactc tcagccacca agaaggaccg tgtgaatcac tgtctaacaa   420
tatgtgaaaa cattgtggca cagtctctca gaaattctcc agaatttcag aaactcttgg   480
gcattgctat ggaactgttt ctgctgtgca gcgacgatgc ggagtcagac gtcagaatgg   540
tggctgatga gtgcctcaac aaagtcatca aagctttgat ggactctaat cttccaaggc   600
tacagttaga actctataag gaaattaaaa agaatggtgc tcctcgaagt ttgcgtgcag   660
ctctgtggag gtttgctgag ctggctcacc tggttcgacc tcagaagtgc aggccttatc   720
tggtgaatct tcttccatgt ttgacccgaa caagcaaacg accggaggag tcagttcagg   780
agactttggc tgcagcttgt tcctaaaatta tggcctcttt tggcaatttc gcgaatgaca   840
atgaaattaa ggttctattg aaagctttca tagcaaatct gaagtcaagc tctcccactg   900
tgcggcggac agcagctggg tcagcagtga gtatctgcca gcactctagg aggacacagt   960
acttctacaa ctggctcctg aatgtgctcc taggtttgct ggttcccatg gaggaagacc   1020
accccactct cctgatcctt ggtgtgttgc tcacactgag gtgtctagtg cccttgctcc   1080
agcagcaggt caaggacaca agtctaaagg cgcagctttg ggtaacacgg aaagaaattgg  1140
aagtctctcc ttctgcagag cagcttgtcc aggtttatga actgactttg catcacacac   1200
agcaccaaga cataatgtg gtgacagggg cattggagct cctgcagcag ctcttccgta    1260
cccctccacc tgagctgctg caagcactga ccacaccagg agggtgcggg cagctcactc   1320
tggttcgaga ggaagccggg ggccgaggcc gcagcggag tcgtggag cttttagctg      1380
gaggggttc ctcatgcagc cctgttctct caagaaagca aaaggcaaa gtgctcttag     1440
gagaggaaga agccttggag gatgactcgg agtccaggtc agatgtcagc agctcagcct   1500
ttgcagcctc tgtgaagagt gagattggtg gagagctcgc tgcttcttct tcgggtgtct   1560
ccactcccgg ttctgtaggt cacgacatca tcactgagca gcctcgatcc cagcacacac   1620
ttcaagcaga ctctgtggat ttgtcaggct gtgacttgac cagtgctgct actgatggag   1680
atgaggaaga catcttgagc cacacgctcca caggttcag tggcgacccctg 1740
ccatggacct gaatgatggg acccaggcct cctcacccat cagtgacagt tctcagacca   1800
ccactgaagg acctgattca gctgtgactc cttctgacag ttctgaaatt gtcttagatg   1860
gtgctgacag ccagtattta ggcgtgcaga taggacagcc acaggaggaa gacgaggagg   1920
aagctgcagg tgttctttct ggtgaagtct cagacgtttt cagaaactct tctctggccc   1980
ttcagcaggc acacttgttg gaaagaatgg gtcatagccg gcagccttct gacagcagtg   2040
```

```
ttgataagtt tgtttcaaaa gatgaggttg ctgaagctgg ggacccagaa agcaagcctt   2100
gccgaatcaa aggtgacata ggacagccta atgatgatga ttctgctcct ctggtacatt   2160
gtgtccgtct tttatccgct tcctttttgt taactggcga aaagaaagca ctggttccag   2220
acagagatgt gagagtcagt gtgaaggccc tggccctcag ctgtattggt gcagctgtgg   2280
cccttcatcc agagtcgttc ttcagcaaac tctacaaagt acctctcagt accatggaaa   2340
gtactgagga acagtatgtc tctgacatcc tgaactacat cgatcatgga gaccctcagg   2400
tgcgaggagc tactgccatt ctctgtggga cccttgtcta ctccatcctc agcaggtccc   2460
gtctccgtgt tggtgactgg ctgggcacca tcagggccct gacaggaaat acattttctc   2520
tggtggactg cattccttta ctgcagaaaa cttttgaagga tgaatcttct gttacttgca   2580
agttggcttg tacagctgtg aggcactgtg tcctgagtct ttgcagcagc agctacagtg   2640
acttgggatt acaactgctt attgacatgc tgcctctgaa gaacagctcc tactggctgg   2700
tgaggactga actgctggaa acttcagcag agattgattt caggctggtg agttttttgg   2760
aggcaaaagc agaaagttta caccgagggg ctcatcatta tacagggttt ctaaaactac   2820
aagaacgagt actcaataat gtggtcattt atttgcttgg agatgaagac cccagggttc   2880
gacatgttgc tgcgacgaca ttgacaagac ttgtcccaaa gctgttttat aagtgtgacc   2940
aaggacaggc tgacccagtc gtggctgtag caagagatca agtagtgtt  tacctgaagc   3000
tcctcatgca tgagacccag ccaccatccc acttctccgt cagcaccata accagaatct   3060
atagagccta cagcttacta ccaagtgtaa cagatgtcac catggaaaac aacctctcaa   3120
gagtcgttgc cgcagtttct catgaactca ttacgtcaac tacacgggca ctcacatttg   3180
ggtgctgtga agccttgtgt gttctttcag ccgcctttcc agtttgcact ggagtctag    3240
gatggcactg tggagtgccc ccactgagtg cctctgatga gtccaggaag agctgcactg   3300
tgggatggcc ctccatgatt ctcaccttgc tttcatcagc ttggttccca ctggatctct   3360
cagcccatca ggatgccttg attttggctg gaaacttgct agcagcgagt gcccccaagt   3420
ctctgagaag ctcatgggcc tcggaagaag aaggcagctc agcagccacc agacaggagg   3480
agatctggcc tgccctgggg gatcggactc tggtgcccat ggtggagcag cttttctccc   3540
acctgctgaa ggtgatcaat atctgtgctc atgtcttgga tgacgtgact cctggaccag   3600
caatcaaggc agctttgcct tctctcacaa accccccttc tctaagtcct attcgacgga   3660
aagggaagga gaaagagccc ggagaacaaa catccactcc gatgagtccc aagaaaggtg   3720
gagaggccag tacagcctct cgacagtcag acacctcagg acctgtcaca gcgagtaaat   3780
catcttcact tgggagtttc taccatctcc cttcctacct cagactgact gatgtcctga   3840
aagccactca cgccaactat aaggtcacct tagatcttca gaacagcact gaaaagtttg   3900
ggggggttcct gcgctctgcc ttggacgtcc tttctcagat tctagagctg gcgcactgc   3960
aggacattgg aaagtgtgtt gaagaggtcc ttggatactt gaaatcctgc tttagtcgag   4020
aaccaatgat ggcgactgtc tgtgttcagc agctattgaa gactctcttt gggacaaact   4080
tagcctcaca gtttgatggc ttatcttcca accccagcaa gtctcagtgc cgagcacagc   4140
gccttggctc ttccagtgtg aggcccggct tatatcacta ctgcttcatg gcaccataca   4200
cgcacttcac gcaggctttg gctgatgcca gcctgaggaa catggtacag gcggaccagg   4260
agcacgatgc ctcagggtgg tttgatgtac tccagaaagt gtctgctcag ttgaagacga   4320
accttacaag tgtcacaaag aaccgtgcag ataagaacgc tattcataac cacattaggt   4380
tatttgagcc tcttgttata aaagcattga agcagtacac cacgacaaca tcagtacaac   4440
tgcagaagca ggttttggat ttgctggcac agctggttca gctacgggtc aattactgtc   4500
tactggattc agatcaggtg ttcatcgggt ttgtgctgaa gcagtttgag tacattgaag   4560
tgggccagtt cagggaatca gaggcaatta ttccaaatat attttcttc ctggtactat   4620
tatcttatga gcgctaccat tcaaaacaga tcattggaat tcctaaaatc atccagctgt   4680
gtgatggcat catggccagt ggaaggaagg ctgtcacaca tgctattcct gcgctgcagc   4740
ccattgtcca tgacctcttt gtgttaagag gaacaaataa agctgatgca gggaaagagc   4800
ttgaaaccca gaaggaggtg gtggtctcaa tgctgttcag actcatccag taccatcagg   4860
tgctagagat gttcatcctc gtcctgcagc agtgccacaa agagaatgag gacaagtgga   4920
aacggctctc tcggcaggtc gcagacatca tcctgcccat gttagccaag cagcagatgc   4980
atattgactc tcatgaagcc cttggagtat aaaataccct gtttgagatt ttggctcctt   5040
cctccctacg tcctgtggac atgctttttgc ggagtatgtt catcactcca agcacaatgg   5100
catctgtaag cactgtgcag ctgtggatat ctggaatcct agccattctg agggttctca   5160
tttcccagtc aaccgaagac attgttcttt ctcgtattca ggagctctcc ttctctccat   5220
atttaatttc ctgtccagta attaacaggt taagggatgg agacagtaat ccaacactag   5280
gagaacgcag tgaagggaaa caagtaaaga atttgccaga agatacattc tcaaggtttc   5340
tcttacagct ggttggtatt cttctgaag  acattgttac aaaacagctc aaagtggaca   5400
tgagtgaaca gcagcataca ttctattgcc aagagctcgg cacactgctc atgtgtctga   5460
tccacatatt caaatctgga atgttccgga gaatcacagc cgctgccact agactcttca   5520
ccagtgatgg ctgtgaaggc agcttctata tctctagatag cctgaatgca cgggtgcgag   5580
ccatggtgcc cacacaccca gctctggtac tgctctggtg tcagatccta ctgctcatca   5640
accacactga ccaccgatgg tgggccgagg tgcagcagac gcccaagaga cacagtctgt   5700
cctgcacgaa gtcactaaac ccccagatat ctgctgaaga ggattctggc tcagcagctc   5760
agcttggaat gtgcaataga gaaatagtac gaagaggggc ccttattctc ttctgtgatt   5820
atgtctgtca gaatctccat gactcagaac acttaacatg gtccattgtg aatcacattc   5880
aagatctgat cagcttgtcc cacgagcctc cagttcaaga ctttattagt gccattcatc   5940
gtaattctgc agctagtggt cttttttatcc aggcaattca gtctcgctgt gaaaatcttt   6000
caactccaac cactctgaag aaaacacttc agtgcttgga aggcatccat ctcagccagt   6060
ctggtgctgt gctcacactg tatgtggaca ggctactggg caccccttc cgtcgcgtgg   6120
ctcgcatggt cgacaccctg gcctgtcgcc gagtagaaat gcttttggct gcaaatttac   6180
agagcagcat ggcccagttg ccagaggagg aactgaacag aatccaggaa cacctccaga   6240
acactgggct tgcacaaaga caccaaaggc tctattcact gctggacaga ttccgactct   6300
ctactgtgca ggactcactt agccccttgc cccagtcac  ttcccaccct ctggatgggg   6360
atgggcacac atccctggaa acagtgaatc cggacaaaga ctggtacctc cagcttgtca   6420
gatcccagtg ttggaccagg tcagattctg cactgctgga aggtgcagag ctggtgaacc   6480
gtatccctg tgaagatatg agtgacttca tgatgagctc ggagttcaac ctaagccttt   6540
tggctccctg cttaagcctt ggcatgagcg agattgctaa tggccaaaag agtcccttt   6600
ttgaagcggc tcgtagggtg actctggacc gggtgaccaa tgtggttcag cagctgcctg   6660
cagtccatca agtcttccag ccttttcctgc ctacagaacc cacagcctac tggagcaagc   6720
tgaatgatct cttttggtgat accacatcat accagtctct gaccacactt gccgtgtgccc   6780
```

```
tggcacagta cctggtggtg ctctccaaag tgcctgctcc tttgcacctt cctcctgaga   6840
aggagggca cacggtgaag tttgtggtaa tgacacttga ggccctgtca tggcatttga    6900
tccatgagca gatcccactg agtctggacc tccaagccgg cctagactgc tgctgcctgg   6960
cactgcaggt gcctggcctc tggggggtgc tgtcctcccc agagtacgtg actcatactt   7020
gctcccttat ccactgtgtg cgattcatcc tggaagcat tgcagtacaa cctggagacc    7080
aacttcttgg tccggaaagc aggtcacata ctccaagggc tgtcagaaag gaggaagtag   7140
actcagatat acaaaacctc agtcacatca cttcggcctg cgagatggtg gcagacatgg   7200
tggaatccct gcagtcggtg ctggccctgg gccacaagag gaacagcacc ctaccttcat   7260
ttctcacagc tgtgctgaag aacattgttg tcagtctggc ccgcctcccc ctcgttaaca   7320
gctatactcg tgtgcctcct ctggtatgga aactcggtg gtcacccaag cctggagggg    7380
atttcggcac agtgtttcct gagatccctg tagttcct ccaggagaag gaggtcctca     7440
aggagttcat ctaccgcatc aacacccctag ggtggaccag tcgtactcaa ttcgaagaaa   7500
cttgggccac cctccttggt gtcctggtga ctcagcccctt ggtgatgaa caggaagaga    7560
gccaccaga ggaagacacc gaaaggaccc agatccctgct cctggctgta caggccatca    7620
cctctctagt gctcagcgca atggctgtgc ctgtggctgg caatccagct gtaagctgct    7680
tggagcaaca gccccggaac aagccactga aggctctcga taccagattt ggaagaaagt    7740
tgagcatgat cagagggatt gtagaacaag aaatccaaga gatggtttcc caaagagaga    7800
atactgccac tcatcattct caccaggcat gggatcctgt cccttctctg ttaccagcta    7860
ctacaggtgc tcttatcagc catgacaagc tgctgctgca gatcaactca gagcgggagc    7920
caggcaacat gagctacaag ctgggccagg tgtccataca ctccgtgtgg ctggggaaca    7980
acatcacacc cctgagagag gaggaatggg atgaggagga ggaggaagaa gcggatgccc    8040
ctgcgccaac atcaccacct gtgtctccaa tcaattccaa aaaacaccgt gctgggggttg    8100
atattcactc ctgttcgcag tttctgcttt aattatacag ccgttggatc ctgccatcca    8160
gtgcagccag aaggaccct gtcatcctga tcagtgaagt ggttcgatct cttcttgtgg     8220
tgtcagactt attcactgaa cgtacccagt ttgaaatgat gtatctgacg ctgacagaac     8280
tacggagagt gcaccttca gaagatgaca tcctcattca atacctggtg cctgccacct      8340
gtaaggcagc tgctgttctt ggaatggaca aaactgtggc agagccggtc agccgcctac      8400
tggagagcac actcaggagc acccacctgc ccagccagat cggagccctg catggcatcc     8460
tctatgtgtt ggagtgtgac ctcttggatg acactgtaaa gcagctcatt ccagttgtta     8520
gtgactatct gctgtccaac ctcaaaggaa tagcccactg cgtgaacatt cacagccagc     8580
agcatgtgct ggtgatgtgt gccactgcat tctacctgat ggaaaactac cctctgatg     8640
tggggccaga attctcagca tctgtgatac agatgtgtgg agtaatgctg tctgaagtg      8700
aggagtccac cccctccatc atttaccact gtgccctccg gggtctggaa cggctcctgc     8760
tgtctgagca gctctctcgg ctagacacgg agtccttggt caagctaagt gtggacagag     8820
tgaatgtaca aagcccacac agggccatgg cagccctagg cctgatgctt acctgcatgt     8880
acacaggaaa ggaaaagcc agtccaggca gagcttctga ccccagccct gctaccctg      8940
acagcgagtc tgtgattgta gctatggagc gagtgtctgt gctcttgac aggatccgca     9000
aggatttcc ctgtgaagcc agggtcgtgg caaggatcct gcctcagttt ctagatgact      9060
tcttccacc tcaagatgtc atgaacaaag tcattgagaa gttcctgtcc aaccagcagc     9120
catacccaca gttcatggcc actgtagtat acaaggtttt tcagactctg cacagtgctg     9180
ggcagtcatc catggtccgg gactgggtta tgctgtctct gtccaacttc acacaaagaa     9240
ctccagttgc catggccatg tggagcctct cctgcttcct tgtcagtgca tctaccagcc     9300
ctcatgggtttc tgcaatcctt ccacacgtca tcagcaggat gggcaaactg agcaggttgg   9360
atgtgaacct tttctgcctg gttgccacag acttctacag acaccagata gaggaggaat    9420
tcgaccgcag ggcttccag tctgtgtttg aggtggtggc agcaccagga agtccatacc      9480
acaggctgct tgcttgtttg caaaatgttc acaaggtcac cgcctgctga gtagtacctg     9540
tggaacaaga ggctgagagg aggcaactgc tgtggctaca gcctccaggg gcctgcacca    9600
agcttctgct aaggctgcct tggacgtgca ggcttccact tgtgtcaagt ggacagccag    9660
gcaatggcag gagtgctttg caatgagagc tatgcaggga acatgcacta tgttggggtt   9720
gagcctgagt cctgggtcct ggcatcactg cagctggtgg cagtgctagg ttgaccaggt   9780
gtttgtcttt ttcttagtgt tgccctggcc atagttgaca ggttgcagct ggcctggtat   9840
gtggaacaga atccgagctc ttgtaagatg gttctgagcc ccctgtccc actgggctga    9900
agagctccct cccacattta cccagcaggt gtacctgcca caccagtgtc tggacacaaa    9960
gtgaatggtg tgggctgg gaactgggac tgccaggtgt ccagcatcat tttccctttc    10020
tctgttttct tctcaggagt taaaatttaa ttatatcagt aaagagatta attttaatgt    10080
aactcttcct atgcccgtgt aaagtgtgtg acttggcaag gcctgtgctg catgtgacaa    10140
agtttatgga agtggatgcg ccttctggcc accactctct ctcctgtagc tactcagtct    10200
agtcgggcag gtccctcatg tagccctccc aacaccctat ggcacttgca cttcacacgg    10260
ctccttttttc ttatgcattc catttgacta gcaca                             10295

SEQ ID NO: 6          moltype = DNA   length = 20
FEATURE               Location/Qualifiers
misc_feature          1..20
                      note = Synthetic oligonucleotide
source                1..20
                      mol_type = other DNA
                      organism = synthetic construct
SEQUENCE: 6
tagcattctt atctgcacgg                                                  20

SEQ ID NO: 7          moltype = DNA   length = 20
FEATURE               Location/Qualifiers
misc_feature          1..20
                      note = Synthetic oligonucleotide
source                1..20
                      mol_type = other DNA
                      organism = synthetic construct
SEQUENCE: 7
acccgtaact gaaccagctg                                                  20
```

```
SEQ ID NO: 8            moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 8
ttccctgaac tggcccactt                                                      20

SEQ ID NO: 9            moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 9
ctctgattcc ctgaactggc                                                      20

SEQ ID NO: 10           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 10
gcctctgatt ccctgaactg                                                      20

SEQ ID NO: 11           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 11
tgcctctgat tccctgaact                                                      20

SEQ ID NO: 12           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 12
ttgcctctga ttccctgaac                                                      20

SEQ ID NO: 13           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 13
attgcctctg attccctgaa                                                      20

SEQ ID NO: 14           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 14
tggaatgatt gcctctgatt                                                      20

SEQ ID NO: 15           moltype = DNA   length = 18
FEATURE                 Location/Qualifiers
misc_feature            1..18
                        note = Synthetic oligonucleotide
source                  1..18
                        mol_type = other DNA
                        organism = synthetic construct
SEQUENCE: 15
```

```
gtttggaatg attgcctc                                                18

SEQ ID NO: 16           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 16
ccaatgatct gttttgaatg                                              20

SEQ ID NO: 17           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 17
gccttccttc cactggccat                                              20

SEQ ID NO: 18           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 18
ctgcatcagc tttatttgtt                                              20

SEQ ID NO: 19           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 19
cctgcatcag ctttatttgt                                              20

SEQ ID NO: 20           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 20
agctcttttc ctgcatcagc                                              20

SEQ ID NO: 21           moltype = DNA  length = 18
FEATURE                 Location/Qualifiers
misc_feature            1..18
                        note = Synthetic oligonucleotide
source                  1..18
                        mol_type = other DNA
                        organism = synthetic construct
SEQUENCE: 21
gtaacattga caccacca                                                18

SEQ ID NO: 22           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 22
ctcagtaaca ttgacaccac                                              20

SEQ ID NO: 23           moltype = DNA  length = 20
FEATURE                 Location/Qualifiers
misc_feature            1..20
                        note = Synthetic oligonucleotide
source                  1..20
                        mol_type = other DNA
                        organism = synthetic construct
```

```
SEQUENCE: 23
atgagtctca gtaacattga                                               20

SEQ ID NO: 24           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 24
tccttgtggc actgctgcag                                               20

SEQ ID NO: 25           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 25
ttctccttgt ggcactgctg                                               20

SEQ ID NO: 26           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 26
tcattctcct tgtggcactg                                               20

SEQ ID NO: 27           moltype = DNA  length = 18
FEATURE                 Location/Qualifiers
misc_feature            1..18
                        note = Synthetic oligonucleotide
source                  1..18
                        mol_type = other DNA
                        organism = synthetic construct
SEQUENCE: 27
attctccttg tggcactg                                                 18

SEQ ID NO: 28           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 28
cgagacagtc gcttccactt                                               20

SEQ ID NO: 29           moltype = DNA  length = 18
FEATURE                 Location/Qualifiers
misc_feature            1..18
                        note = Synthetic oligonucleotide
source                  1..18
                        mol_type = other DNA
                        organism = synthetic construct
SEQUENCE: 29
tgtcgagaca gtcgcttc                                                 18

SEQ ID NO: 30           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 30
ttgcacattc caagtttggc                                               20

SEQ ID NO: 31           moltype = DNA  length = 20
FEATURE                 Location/Qualifiers
misc_feature            1..20
                        note = Synthetic oligonucleotide
source                  1..20
                        mol_type = other DNA
```

```
                       organism = synthetic construct
SEQUENCE: 31
tctctattgc acattccaag                                                    20

SEQ ID NO: 32          moltype = DNA   length = 20
FEATURE                Location/Qualifiers
misc_feature           1..20
                       note = Synthetic oligonucleotide
source                 1..20
                       mol_type = other DNA
                       organism = synthetic construct
SEQUENCE: 32
tttctctatt gcacattcca                                                    20

SEQ ID NO: 33          moltype = DNA   length = 18
FEATURE                Location/Qualifiers
misc_feature           1..18
                       note = Synthetic oligonucleotide
source                 1..18
                       mol_type = other DNA
                       organism = synthetic construct
SEQUENCE: 33
tctctattgc acattcca                                                      18

SEQ ID NO: 34          moltype = DNA   length = 20
FEATURE                Location/Qualifiers
misc_feature           1..20
                       note = Synthetic oligonucleotide
source                 1..20
                       mol_type = other DNA
                       organism = synthetic construct
SEQUENCE: 34
gcagggttac cgccatcccc                                                    20

SEQ ID NO: 35          moltype = DNA   length = 18
FEATURE                Location/Qualifiers
misc_feature           1..18
                       note = Synthetic oligonucleotide
source                 1..18
                       mol_type = other DNA
                       organism = synthetic construct
SEQUENCE: 35
accttatctg cacggttc                                                      18

SEQ ID NO: 36          moltype = DNA   length = 20
FEATURE                Location/Qualifiers
misc_feature           1..20
                       note = Synthetic oligonucleotide
source                 1..20
                       mol_type = other DNA
                       organism = synthetic construct
SEQUENCE: 36
ctctctgtgt atcaccttcc                                                    20

SEQ ID NO: 37          moltype = DNA   length = 20
FEATURE                Location/Qualifiers
misc_feature           1..20
                       note = Primer
source                 1..20
                       mol_type = other DNA
                       organism = synthetic construct
SEQUENCE: 37
ctccgtccgg tagacatgct                                                    20

SEQ ID NO: 38          moltype = DNA   length = 23
FEATURE                Location/Qualifiers
misc_feature           1..23
                       note = Primer
source                 1..23
                       mol_type = other DNA
                       organism = synthetic construct
SEQUENCE: 38
ggaaatcaga accctcaaaa tgg                                                23

SEQ ID NO: 39          moltype = DNA   length = 29
FEATURE                Location/Qualifiers
misc_feature           1..29
                       note = Probe
source                 1..29
```

```
                              mol_type = other DNA
                              organism = synthetic construct
SEQUENCE: 39
tgagcactgt tcaactgtgg atatcggga                                          29

SEQ ID NO: 40            moltype = DNA   length = 21
FEATURE                  Location/Qualifiers
misc_feature             1..21
                         note = Primer
source                   1..21
                         mol_type = other DNA
                         organism = synthetic construct
SEQUENCE: 40
gtctgagcct ctctcggtca a                                                  21

SEQ ID NO: 41            moltype = DNA   length = 19
FEATURE                  Location/Qualifiers
misc_feature             1..19
                         note = Primer
source                   1..19
                         mol_type = other DNA
                         organism = synthetic construct
SEQUENCE: 41
aagggatgct gggctctgt                                                     19

SEQ ID NO: 42            moltype = DNA   length = 30
FEATURE                  Location/Qualifiers
misc_feature             1..30
                         note = Probe
source                   1..30
                         mol_type = other DNA
                         organism = synthetic construct
SEQUENCE: 42
agcaaagctt ggtgtcttgg cactgttagt                                         30

SEQ ID NO: 43            moltype = DNA   length = 21
FEATURE                  Location/Qualifiers
misc_feature             1..21
                         note = Primer
source                   1..21
                         mol_type = other DNA
                         organism = synthetic construct
SEQUENCE: 43
cagagctggt caaccgtatc c                                                  21

SEQ ID NO: 44            moltype = DNA   length = 21
FEATURE                  Location/Qualifiers
misc_feature             1..21
                         note = Primer
source                   1..21
                         mol_type = other DNA
                         organism = synthetic construct
SEQUENCE: 44
ggcttaaaca gggagccaaa a                                                  21

SEQ ID NO: 45            moltype = DNA   length = 26
FEATURE                  Location/Qualifiers
misc_feature             1..26
                         note = Probe
source                   1..26
                         mol_type = other DNA
                         organism = synthetic construct
SEQUENCE: 45
acttcatgat gagctcggag ttcaac                                             26

SEQ ID NO: 46            moltype = DNA   length = 25
FEATURE                  Location/Qualifiers
misc_feature             1..25
                         note = Primer
source                   1..25
                         mol_type = other DNA
                         organism = synthetic construct
SEQUENCE: 46
aggagaaaaa caaagaacac cagaa                                              25

SEQ ID NO: 47            moltype = DNA   length = 25
FEATURE                  Location/Qualifiers
misc_feature             1..25
                         note = Primer
```

```
                               -continued source                  1..25
                        mol_type = other DNA
                        organism = synthetic construct
SEQUENCE: 47
caattagggc aactcagaaa tagct                                        25

SEQ ID NO: 48           moltype = DNA  length = 22
FEATURE                 Location/Qualifiers
misc_feature            1..22
                        note = Probe
source                  1..22
                        mol_type = other DNA
                        organism = synthetic construct
SEQUENCE: 48
ccaactggtc ccccagccaa ga                                           22

SEQ ID NO: 49           moltype = DNA  length = 21
FEATURE                 Location/Qualifiers
misc_feature            1..21
                        note = Primer
source                  1..21
                        mol_type = other DNA
                        organism = synthetic construct
SEQUENCE: 49
cagagctggt gaaccgtatc c                                            21

SEQ ID NO: 50           moltype = DNA  length = 21
FEATURE                 Location/Qualifiers
misc_feature            1..21
                        note = Primer
source                  1..21
                        mol_type = other DNA
                        organism = synthetic construct
SEQUENCE: 50
ggcttaagca gggagccaaa a                                            21

SEQ ID NO: 51           moltype = DNA  length = 26
FEATURE                 Location/Qualifiers
misc_feature            1..26
                        note = Probe
source                  1..26
                        mol_type = other DNA
                        organism = synthetic construct
SEQUENCE: 51
acttcatgat gagctcggag ttcaac                                       26

SEQ ID NO: 52           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 52
tcctagtgtt acattaccgc                                              20

SEQ ID NO: 53           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 53
ctcgactaaa gcaggatttc                                              20

SEQ ID NO: 54           moltype = DNA  length = 17
FEATURE                 Location/Qualifiers
misc_feature            1..17
                        note = Primer
source                  1..17
                        mol_type = other DNA
                        organism = synthetic construct
SEQUENCE: 54
tggtcccca gccaaga                                                  17

SEQ ID NO: 55           moltype = DNA  length = 18
FEATURE                 Location/Qualifiers
misc_feature            1..18
```

-continued

```
                        note = Primer
source                  1..18
                        mol_type = other DNA
                        organism = synthetic construct
SEQUENCE: 55
cccaccgtgt gacatcca                                                     18

SEQ ID NO: 56           moltype = DNA  length = 26
FEATURE                 Location/Qualifiers
misc_feature            1..26
                        note = Probe
source                  1..26
                        mol_type = other DNA
                        organism = synthetic construct
SEQUENCE: 56
agctatctcc gagctgccct gattgg                                            26
```